US011173179B2

(12) United States Patent
Ma et al.

(10) Patent No.: US 11,173,179 B2
(45) Date of Patent: Nov. 16, 2021

(54) CHIMERIC ANTIGEN RECEPTOR (CAR) TARGETING MULTIPLE ANTIGENS, COMPOSITIONS AND METHODS OF USE THEREOF

(71) Applicant: iCell Gene Therapeutics LLC, Stony Brook, NY (US)

(72) Inventors: Yupo Ma, Stony Brook, NY (US); Kevin Pinz, Stony Brook, NY (US); Xun Jiang, Stony Brook, NY (US); Masayuki Wada, Stony Brook, NY (US); Kevin Chen, Stony Brook, NY (US)

(73) Assignee: ICELL GENE THERAPEUTICS LLC, Stony Brook, NY (US)

( * ) Notice: Subject to any disclaimer, the term of this patent is extended or adjusted under 35 U.S.C. 154(b) by 348 days.

(21) Appl. No.: 15/893,629

(22) Filed: Feb. 10, 2018

(65) Prior Publication Data

US 2019/0255108 A1 Aug. 22, 2019

Related U.S. Application Data

(63) Continuation-in-part of application No. 15/739,596, filed as application No. PCT/US2016/039306 on Jun. 24, 2016.

(60) Provisional application No. 62/184,321, filed on Jun. 25, 2015, provisional application No. 62/235,840, filed on Oct. 1, 2015, provisional application No. 62/244,435, filed on Oct. 21, 2015.

(51) Int. Cl.
| | |
|---|---|
| *C07K 14/705* | (2006.01) |
| *A61K 35/17* | (2015.01) |
| *A61P 35/02* | (2006.01) |
| *C07K 14/47* | (2006.01) |
| *C07K 14/54* | (2006.01) |

(52) U.S. Cl.
CPC .............. *A61K 35/17* (2013.01); *A61P 35/02* (2018.01); *C07K 14/4748* (2013.01); *C07K 14/5443* (2013.01); *C07K 14/70596* (2013.01)

(58) Field of Classification Search
None
See application file for complete search history.

(56) References Cited

U.S. PATENT DOCUMENTS

| | | | |
|---|---|---|---|
| 8,399,645 B2 | 3/2013 | Campana et al. | |
| 9,328,156 B2 | 5/2016 | June et al. | |
| 10,196,444 B2 * | 2/2019 | Jarjour | C07K 16/2803 |
| 10,287,354 B2 * | 5/2019 | Brogdon | C07K 14/71 |
| 10,457,731 B2 * | 10/2019 | Jarjour | A61P 37/02 |
| 2002/0009449 A1 | 1/2002 | Wallner et al. | |
| 2003/0147865 A1 | 8/2003 | Salomon et al. | |
| 2004/0265315 A1 | 12/2004 | Dingivan et al. | |
| 2005/0277587 A1 | 12/2005 | Chen et al. | |
| 2008/0254027 A1 | 10/2008 | Bernett et al. | |
| 2008/0254512 A1 | 10/2008 | Capon | |
| 2008/0299042 A1 | 12/2008 | Bechtel et al. | |
| 2009/0081157 A1 | 3/2009 | Kornbluth et al. | |
| 2009/0238791 A1 | 9/2009 | Jacques et al. | |
| 2009/0325188 A1 | 12/2009 | Glass | |
| 2012/0058082 A1 | 3/2012 | Kaplan et al. | |
| 2012/0070408 A1 | 3/2012 | Kaplan et al. | |
| 2012/0134970 A1 | 5/2012 | Yang et al. | |
| 2012/0258494 A1 | 10/2012 | Stitz | |
| 2013/0058936 A1 | 3/2013 | Bruenker et al. | |
| 2013/0259876 A1 | 10/2013 | Murphy et al. | |
| 2013/0287748 A1 | 10/2013 | June et al. | |
| 2013/0287752 A1 | 10/2013 | Davila et al. | |
| 2014/0099309 A1 | 4/2014 | Powell, Jr. et al. | |
| 2014/0106449 A1 | 4/2014 | June et al. | |
| 2014/0286918 A1 | 9/2014 | Dao | |
| 2014/0322183 A1 | 10/2014 | Milone et al. | |
| 2015/0038684 A1 | 2/2015 | Jensen | |
| 2015/0133640 A1 | 5/2015 | Blein et al. | |
| 2015/0307623 A1 | 10/2015 | Abbot et al. | |
| 2015/0342993 A1 | 12/2015 | Kloss et al. | |
| 2016/0207989 A1 | 7/2016 | Short | |
| 2016/0250258 A1 | 9/2016 | Delaney et al. | |
| 2016/0340406 A1 | 11/2016 | Zhao et al. | |
| 2017/0145108 A1 | 5/2017 | Schreiber et al. | |
| 2017/0267742 A1 | 9/2017 | Jensen et al. | |
| 2020/0071399 A1* | 3/2020 | Jarjour | C07K 16/40 |

FOREIGN PATENT DOCUMENTS

| | | |
|---|---|---|
| WO | 2009091826 A1 | 7/2009 |
| WO | 2012079000 A1 | 6/2012 |
| WO | WO2013126712 A1 | 8/2013 |

(Continued)

OTHER PUBLICATIONS

Zhang et al Neoplasia vol. 20, No. 1, Jan. 2018 pp. 1-11, GO Improves Induction Chemotherapy in AML Models.*
Leong et al ., An anti-CD3/anti-CLL-1 bispecific antibody for the treatment of acute myeloid leukemia Blood. 2017;129(5):609-618.*
Milone et al Chimeric Receptors Containing CD137 Signal Transduction Domains Mediate Enhanced Survival of T Cells and Increased Antileukemic Efficacy In Vivo Molecular Therapy vol. 17 No. 8, 1453-1464 Aug. 2009.*
Leong et al An anti-CD3/anti-CLL-1 bispecific antibody for the treatment of acute myeloid leukemia ; Blood pp. 609-618.*

(Continued)

*Primary Examiner* — Maria G Leavitt
(74) *Attorney, Agent, or Firm* — Hoffmann & Baron, LLP

(57) ABSTRACT

The present disclosure relates to compositions and methods relating to chimeric antigen receptor (CAR) polypeptides and methods relating thereto. In one embodiment, the present disclosure relates to engineered cells having chimeric antigen receptor polypeptides directed to at least two targets. In another embodiment, the present disclosure relates to engineered cells having chimeric antigen receptor polypeptides and an enhancer moiety.

1 Claim, 170 Drawing Sheets
(156 of 170 Drawing Sheet(s) Filed in Color)
Specification includes a Sequence Listing.

(56) References Cited

FOREIGN PATENT DOCUMENTS

| | | |
|---|---|---|
| WO | WO2014055668 A1 | 4/2014 |
| WO | WO2014100385 A1 | 6/2014 |
| WO | WO2014127261 A1 | 8/2014 |
| WO | WO2014184143 A1 | 11/2014 |
| WO | WO2015018529 A1 | 2/2015 |
| WO | WO2015075468 A1 | 5/2015 |
| WO | WO2015075469 A1 | 5/2015 |
| WO | WO2015075470 A1 | 5/2015 |
| WO | WO2015120180 A1 | 8/2015 |
| WO | WO2015121454 A1 | 8/2015 |
| WO | WO2015157399 A9 | 10/2015 |
| WO | WO2015168613 A2 | 11/2015 |
| WO | WO2015172339 A1 | 11/2015 |
| WO | WO2016014553 A1 | 1/2016 |
| WO | WO2016102965 A1 | 6/2016 |
| WO | WO2016210293 A1 | 12/2016 |
| WO | WO2017068361 A1 | 4/2017 |

OTHER PUBLICATIONS

John, Liza B., et al., "Anti-PD-1 Antibody Therapy Potently Enhances the Eradication of Established Tumors by Gene-Modified T Cells", Clin Cancer Res; 19(20) Oct. 15, 2013.
Rowley, Jesse, et al., "Expression of IL-15RA or an IL-15/IL-15RA fusion on CD8+ T cells modifies adoptively transferred T-cell function in cis", Eur. J. Immunol. 2009: 491-506.
Gill, Saar, MD, PhD, "Chimeric antigen receptor T-cell therapy in AML: How close are we?", Best Pract Res Clin Haematol. Dec. 2016; 29(4): 329-333. doi:10.1016/j.beha.2016.10.004.
Chen, KH, et al., "A compound chimeric antigen receptor strategy for targeting multiple myeloma", Leukemia (2018) 32, 402-412.
Petrov, Jessica C., et al., "Compound CAR T-cells as a double-pronged approach for treating acute myeloid leukemia", Leukemia (2018) 32: 1317-1326.
Hamieh, Mohamad, et al., "CAR T cell trogocytosis and cooperative killing regulate tumour antigen escape", Nature 568, 112-116 (2019).
Qin, Haiying, et al., "Novel CD19/CD22 Bicistronic Chimeric Antigen Receptors Outperform Single or Bivalent Cars in Eradicating CD19+CD22+, CD19−, and CD22− Pre-B Leukemia", Blood 2017, 130:810.
Curran, Kevin, et al., "Chimeric Antigen Receptors for T Cell Immunotherapy: Current Understanding and Future Directions." The Journal of Gene Medicine, 14.(6), pp. 405-415, Jun. 2012.
Shirasu, N., et al., "Functional Design of Chimeric T-Cell Antigen Receptors for Adoptive Immunotherapy of Cancer: Architecture and Outcomes", Anticancer Research, 32(6), pp. 2377-2384, 2012.
Bridgeman, J.S., et al., "CD 3ζ-Based Chimeric Antigen Receptors Mediate T Cell Activation Via Cis-and Trans-Signalling Mechanisms: Implications for Optimization of Receptor Structure for Adoptive Cell Therapy", Clinical & Experimental Immunology, 175(2), pp. 258-267, 2013.
Kaiser, A.D., et al., "Towards a Commercial Process for the Manufacture of Genetically Modified T Cells for Therapy", Cancer Gene Therapy, 22(2), pp. 72-78, Jan. 2015.
Sentman, C.L., "Challenges of Creating Effective CARs for Cancer Therapy", Immunotherapy, 5(8), pp. 783-785, 2013.
Brown et al., "Novel Treatments for Chronic Lymphocytic Leukemia and Moving Forward", American Society of Clinical Oncology Educational Book, vol. 34, 2014, pp. e317-e325, XP055201368.
Leavitt et al., Concordant Modulation of Neutralization Resistance and High Infectivity of the Primary Human Immunodeficiency Virus Type 1 MN Strain and Definition of a Potential gp41 Binding Site in gp120 Journal of Virology, Jan. 2003, p. 560-570.
Marzo et al., Fully Functional Memory CDS T Cells in the Absence of CD4 T Cells J Immunol 2004; 173:969-975.
Moeller et al., Sustained Antigen-Specific Antitumor Recall Response Mediated by Gene-Modified CD4+ T Helper-1 and CDS+ T Cells Cancer Res 2007; 67: (23). Dec. 1 pp. 11428-11437.
Moeller et al Adoptive transfer of gene-engineered CD4 helper T cells induces potent primary and secondary tumor rejection Blood, Nov. 1, 2005 vol. 106, No. 9; pp. 2995-3003.
Gibson et al Risk of non-Hodgkin lymphoma subtypes in HIV-infected people during the HAART era: a population-based study AIDS. Sep. 24, 2014; 28(15): 2313-2318.
Beard et al., "Multiple chimeric antigen receptors successfully target chondroitin sulfate proteoglycan 4 in several different cancer histologies and cancer stem cells," Journal for ImmunoTherapy of Cancer 2014; 2(25), pp. 1-11.
Imboden et al., "Stimulation of CDS Enhances Signal Transduction by the T Cell Antigen Receptor," J. Clin. Invest. 1990; 85:130-134.
Rabinowich et al., "Signaling via CD7 molecules on human NK cells. Induction of tyrosine phosphorylation and beta 1 integrin-mediated adhesion to fibronectin," J. Immunol. 1994; 153:3504-3513.
Inoue et al., "Mechanisms of NK cell activation stimulated by CD2; granzyme B is released by CD2 crosslinking-stimulation on NK92 cell," J Osaka Dent Univ Oct. 2012; 46(2): 229-235.
McNerney et al., "The CD2 family of natural killer cell receptors," Curr Top Microbiol Immuhnol 2006; 298:91-120.
Rabinowich et al., "Expression and function of CD7 molecule on human natural killer cells," J Immunol 1994; 152: 517-526.
Liu et al., "Critical Role of CD2 Co-stimulation in Adaptive Natural Killer Cell Responses Revealed in NKG2CDeficient Humans," Cell Reports 2016; 15, 1088-1099.
Muyldermans et al., "Recognition of antigens by single domain antibody fragments: the superfluous luxury of paired domains", Trends in Biochemical Sciences, vol. 26,No. 4, Apr. 2001: pp. 230-235.
Wilkie et al., "Dual Targeting of ErbB2 and MUC1 in Breast Cancer using Chimeric Antigen Receptors Engineered to Provide Complementary Signaling", J Clin Immunol (2012) 32: 1059-1070.
Dotti et al., "Design and Development of Therapies using Chimeric Antigen Receptor-Expressing T Cells", Immunol Rev. Jan. 2014; 257(1); pp. 1-35.
Muyldermans et al., "Single domain camel antibodies: current status", Reviews in Molecular Biotechnology 74 (2001), 277-302.
Lai et al., International Scholarly Research Network 2011; pp. 1-6.
Liu et al., Molecular Therapy vol. 23, Supplement 1, May 2015 Abstract 512.
Grupp et al., "Chimeric Antigen Receptor-Modified T Cells for Acute Lymphoid Leukemia," New England Journal of Medicine, Apr. 18, 2013, vol. 368, No. 16, pp. 1509-1518.
Rowley et al., "Expression of IL-15RA or an IL-15/IL-15RA fusion on CD8+ T cells modifies adoptively transferred T-cell function in cis," Eur J Immunol, Jan. 29, 2009, vol. 39, No. 2, pp. 491-506.
John et al., "Anti-PD-1 Antibody Therapy Potently Enhances the Eradication of Established Tumors By Gene-Modified T Cells," Clin Cancer Res, Oct. 15, 2013, vol. 19, No. 20, pp. 5636-5646.
Penney et al., "Greater frequency of CD5-negative CD8(+) T cells against human immunodeficiency virus type 1 than other viruses is consistent with adaptation to antigenic variation," AIDS Res Ther, Sep. 15, 2014, vol. 11, No. 30, pp. 1-10.
Maus et al., "Antibody-modified T cells: CARs take the front seat for hematologic malignancies," Blood, Apr. 24, 2014, vol. 123, No. 17, pp. 2625-2635.
D'Amore et al., "Phase II trial of zanolimumab (HuMax-CD4) in relapsed or refractory non-cutaneous peripheral T cell lymphoma," Br J Haematol 2010, 150: 565-573.
Shenghui et al., "Elevated frequencies of CD4+CD25+CD127lo regulatory T cells is associated to poor prognosis in patients with acute myeloid leukemia," Int. J. Cancer 2011, 129: 1373-1381.
Ehninger et al., "Distribution and levels of cell surface expression of CD33 and CD123 in acute myeloid leukemia," Blood Cancer Journal 2014, vol. 4, pp. 1-10.
Liu et al., "Tumor_Associated Macrophages Via Up-Regulation of PD1 Ligands Protect Neuroblastoma from Immunotherapy With NKT Cells Expressing GD2-Specific Chimeric Antigen Receptor," Molecular Therapy, vol. 23, Supp. 1, May 2015, Abstract 512. p. S205.
Rouce et al., "Equal opportunity CAR T cells," Blood 2017, 129:3275-3277.

(56) References Cited

OTHER PUBLICATIONS

Lai et al., "The Roles of CD4+ T Cells in Tumor Immunity," ISRN Immunology, vol. 2011, Article ID 497397, 6 pages, doi:10.5402/2011/497397.
Kebriaei et al., "Phase I trials using Sleeping Beauty to generate CD19-specific CAR T cells," The Journal of Clinical Investigation, vol. 126, No. 9, Sep. 2016, pp. 3363-3376 and Supplemental Tables.
Schreiber et al., "Cancer Immunoediting: Integrating Immunity's Roles in Cancer Suppression and Promotion", Science, vol. 331, Issue 6024, pp. 1565-1570 (Mar. 25, 2011).
Liu, Fang, et al. "First-in-Human CLL1-CD33 Compound CAR T Cell Therapy Induces Complete Remission in Patients with Refractory Acute Myeloid Leukemia: Update on Phase 1 Clinical Trial", Blood, vol. 132, Supp. 1, pp. 901 (Nov. 29, 2019).

\* cited by examiner

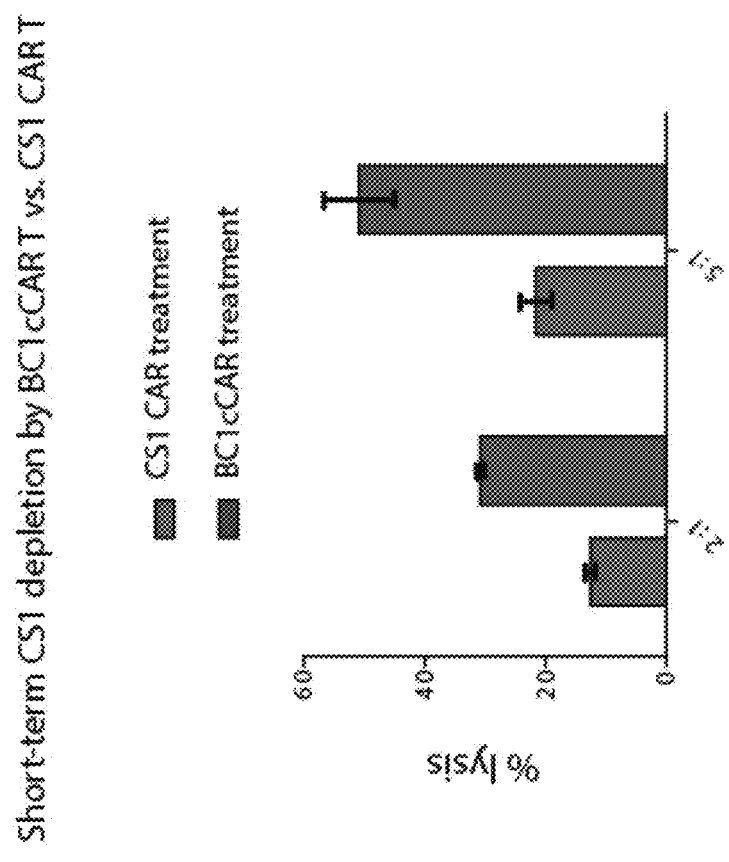
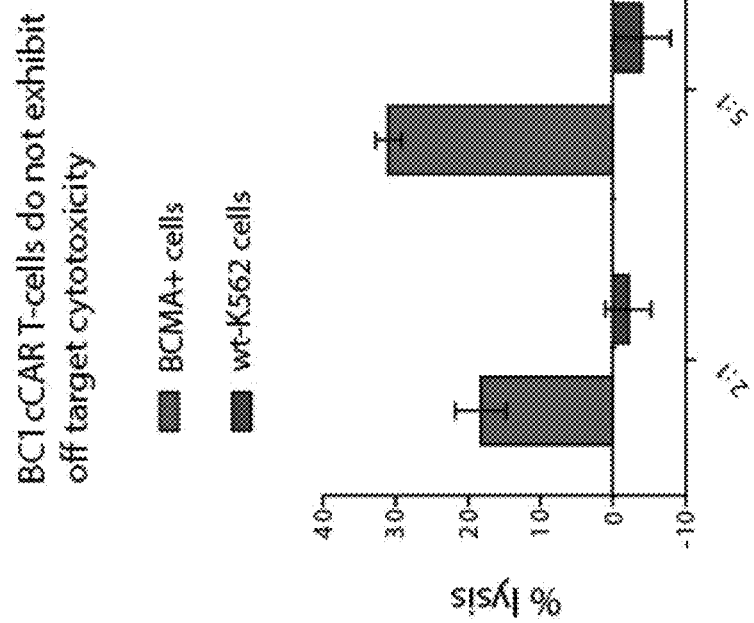
Figure 5B

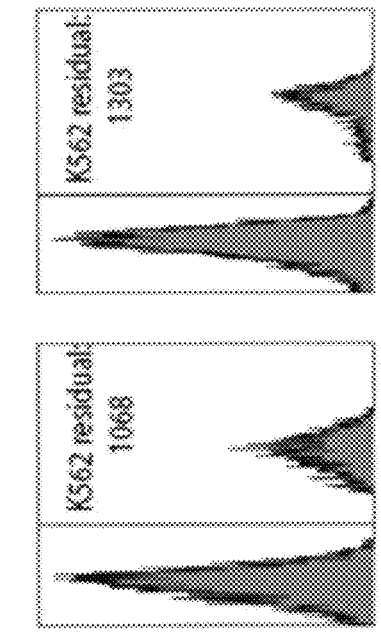
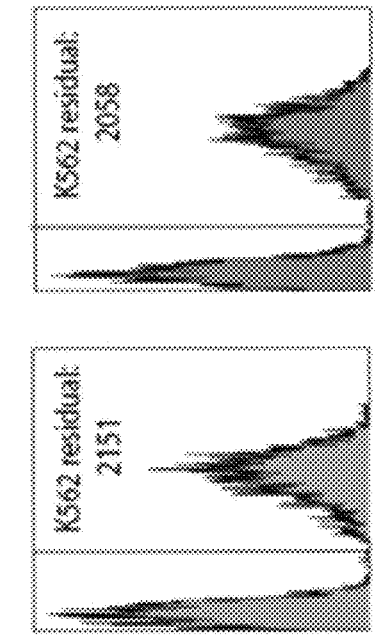
Figure 9A

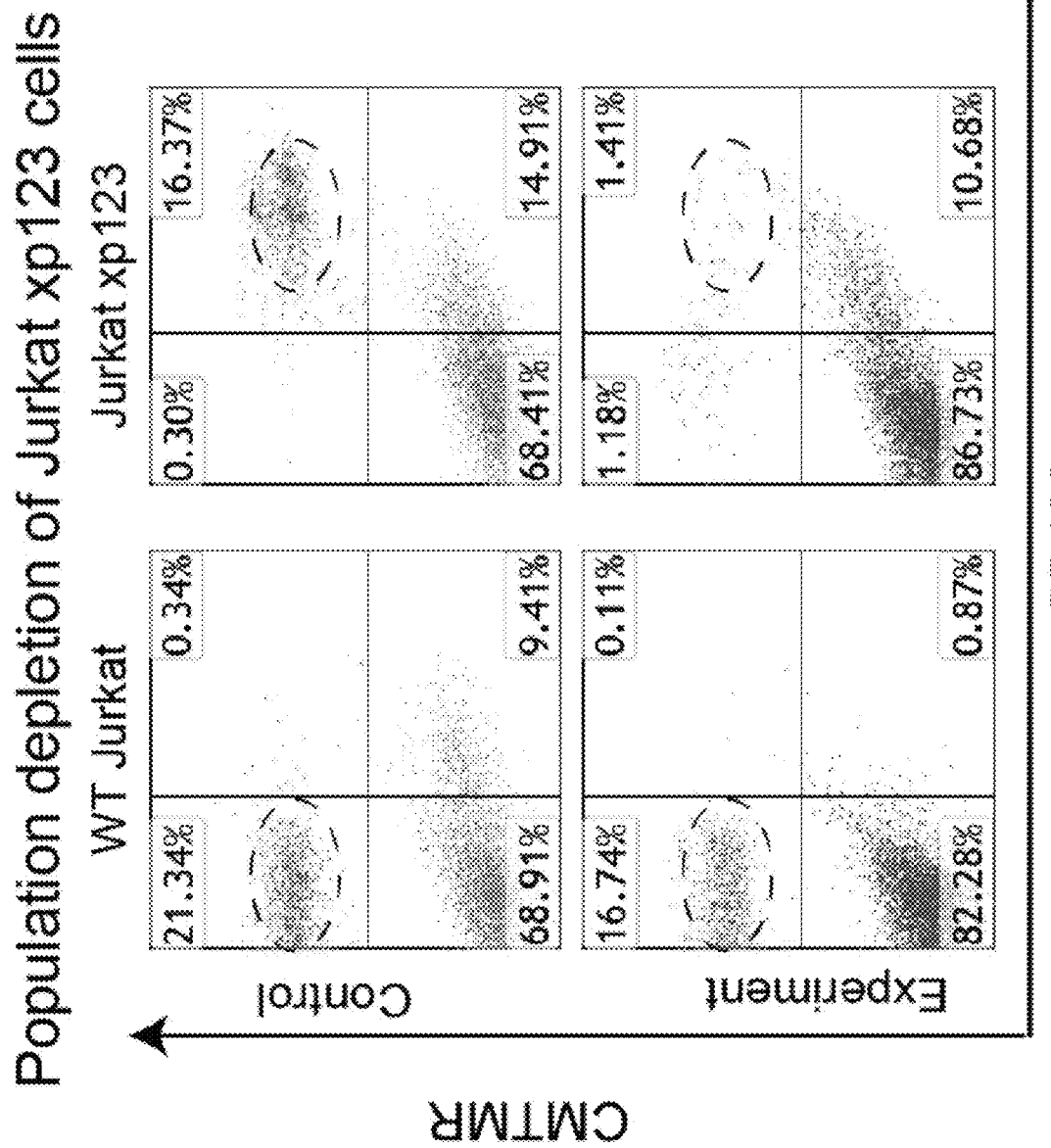

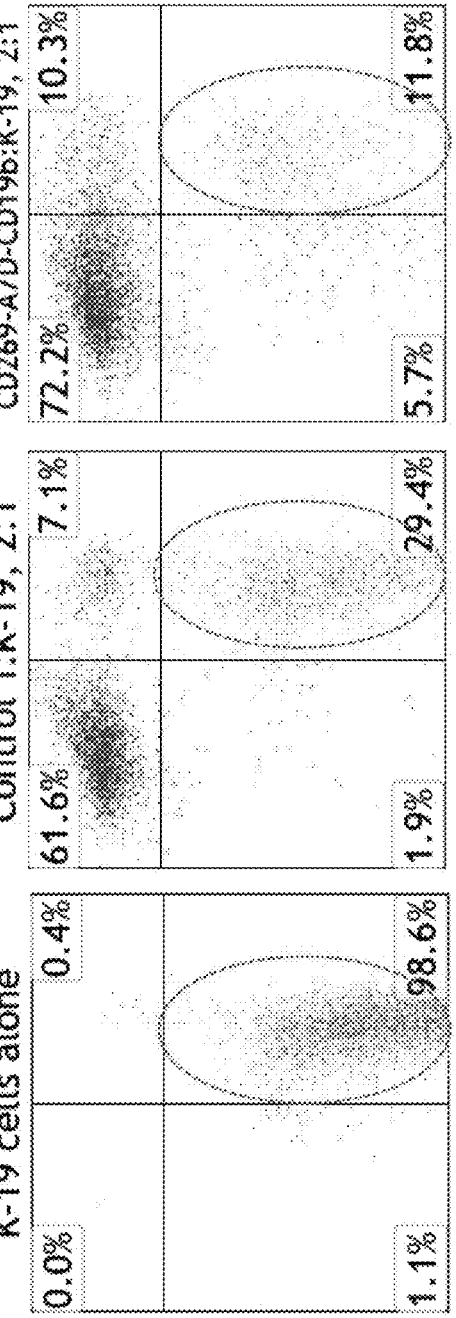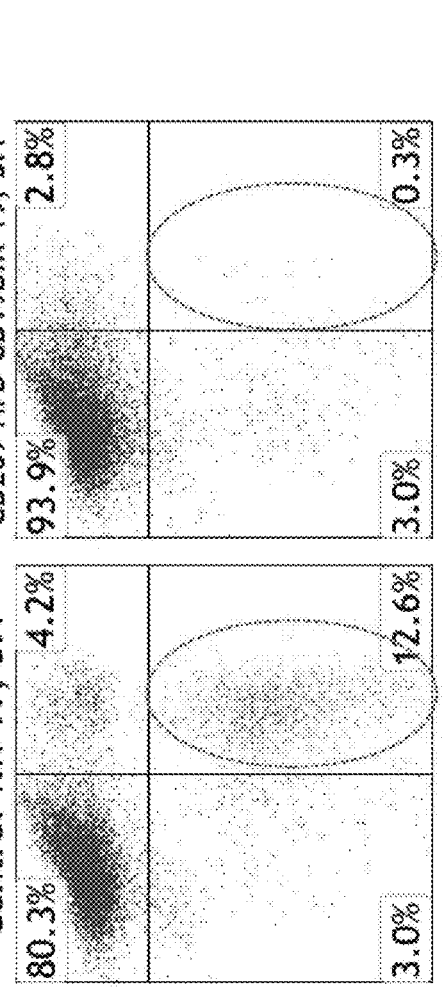
Figure 29A

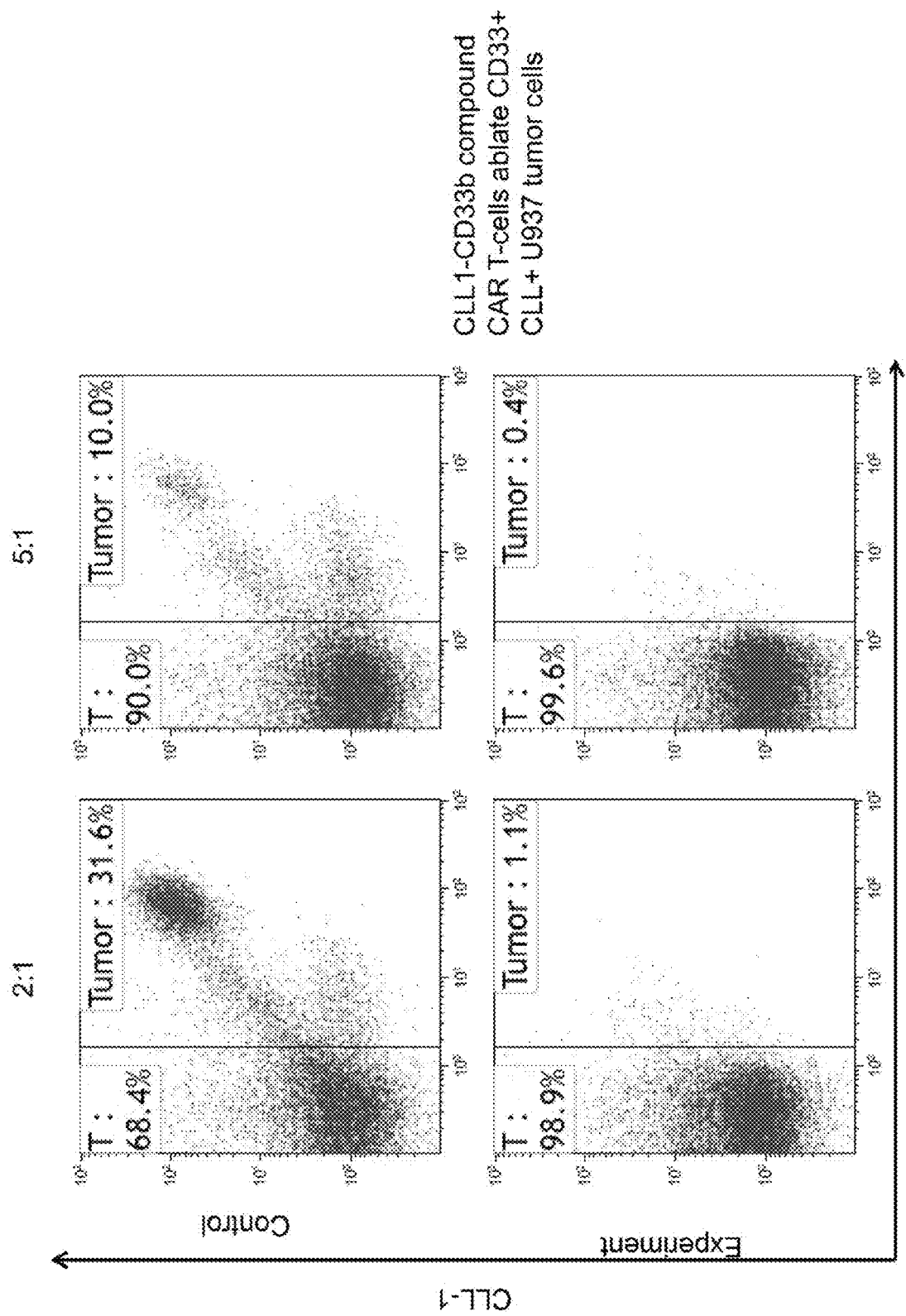

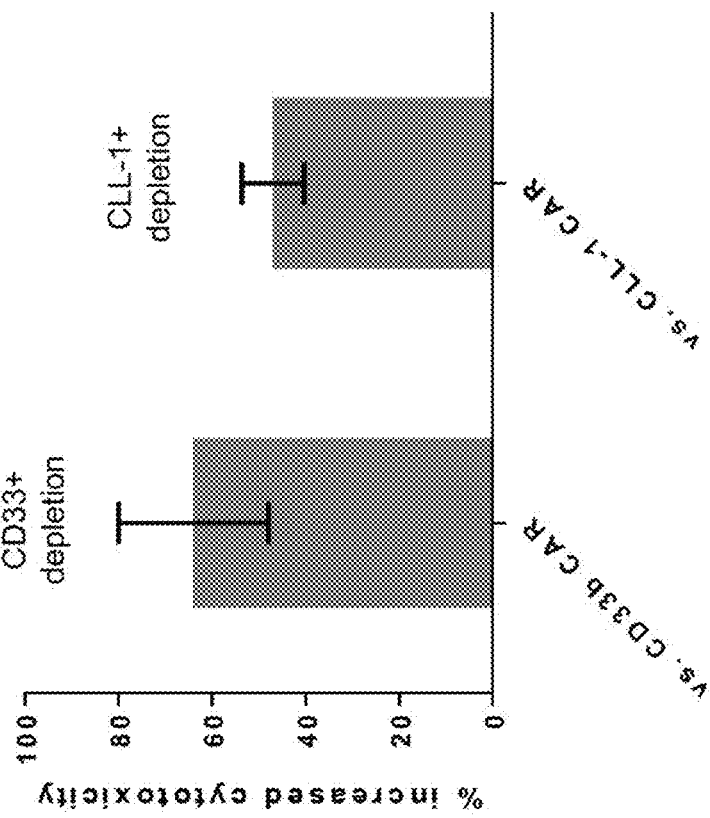
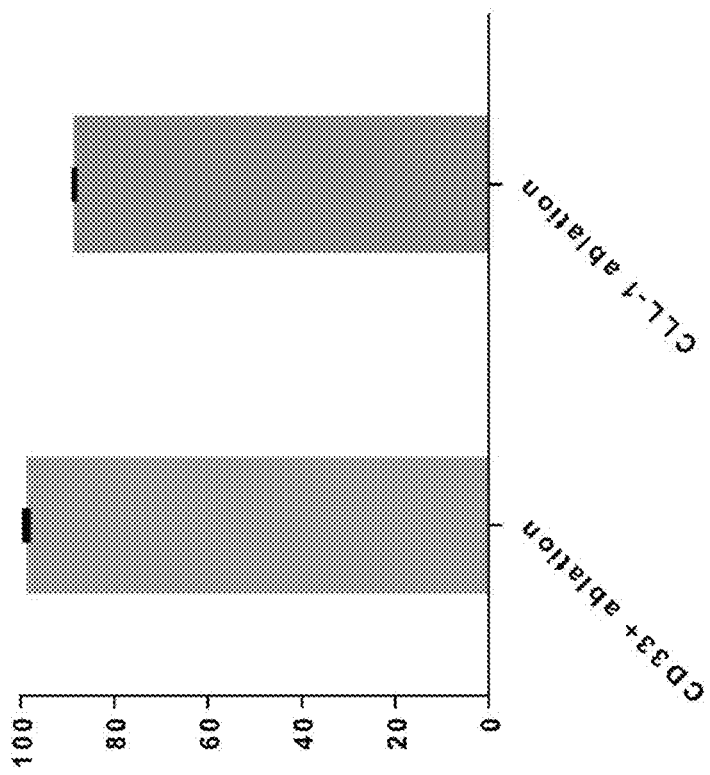
Figure 32L

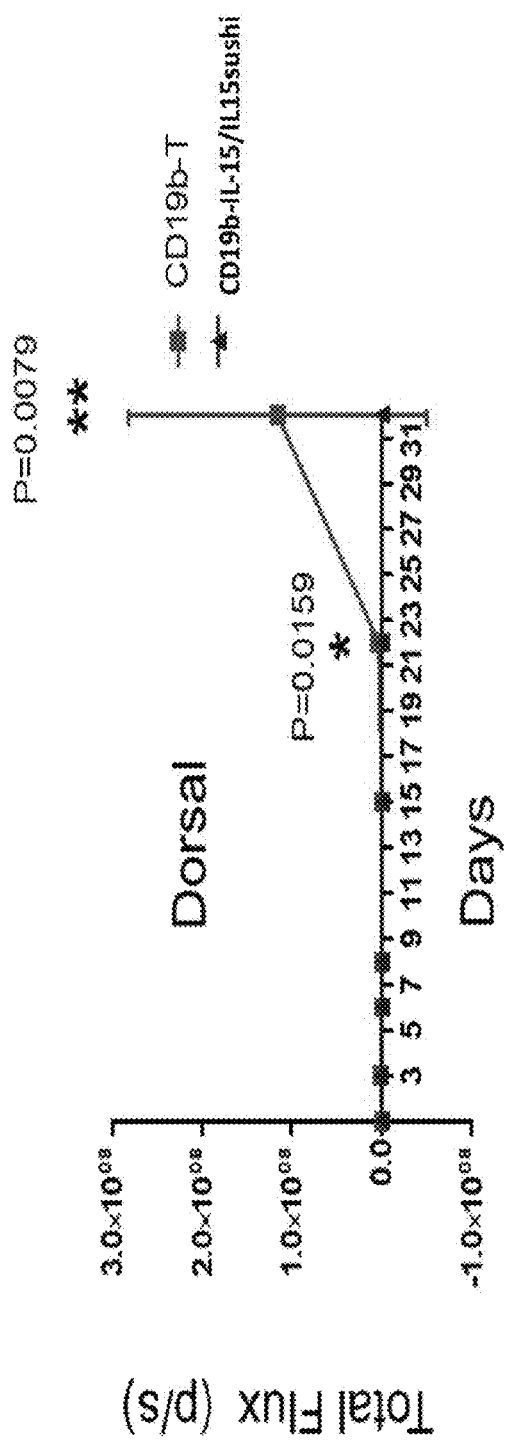
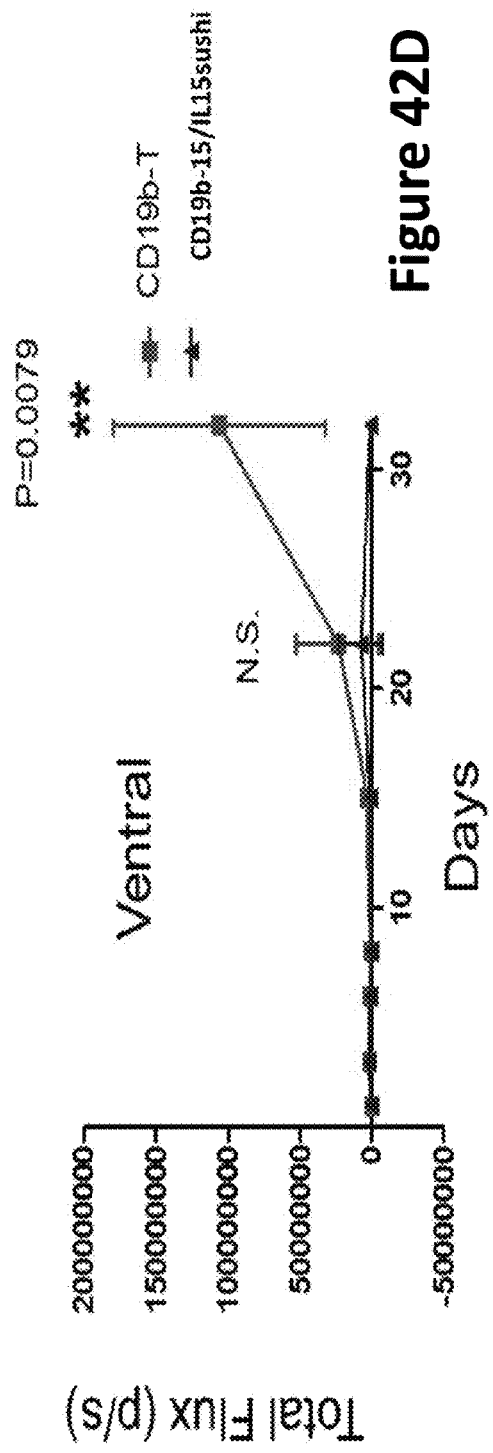
Figure 42D

No tumor cells and no T cells were detected

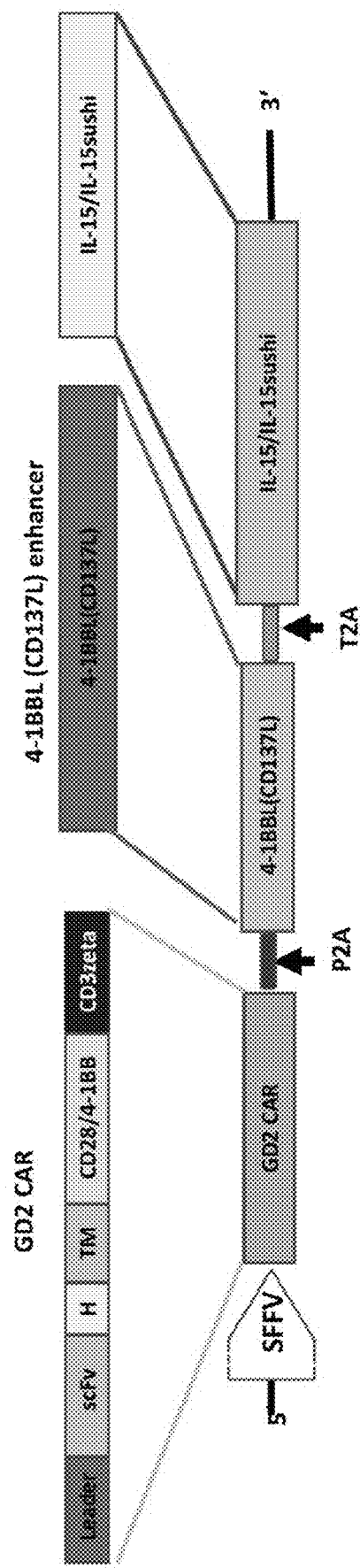

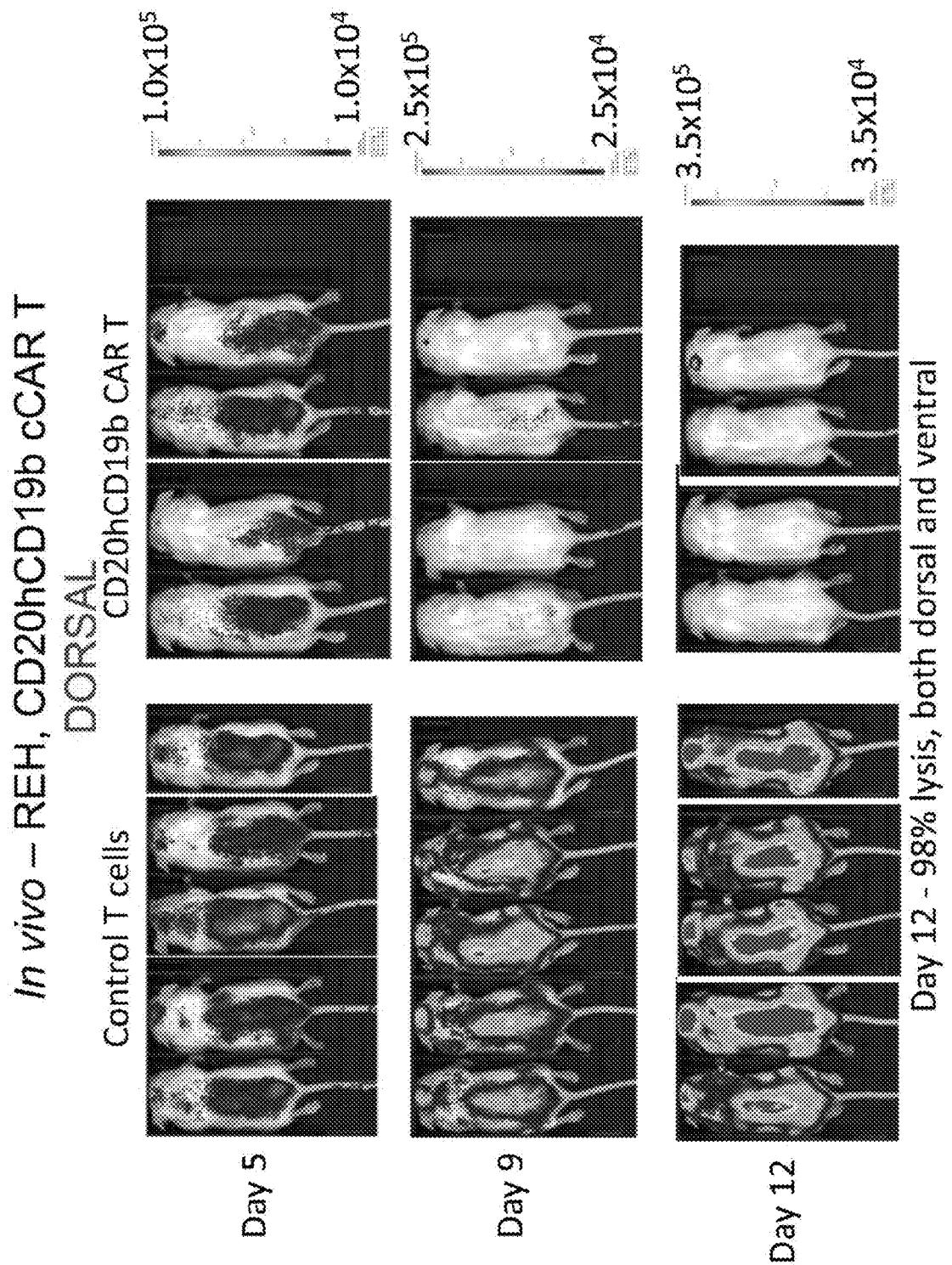

Strategy for IL-15/IL-15sushi secreting CAR T therapy

Step 1 — Treatment of subjects with a lower dose of CAR T cells, at ¼, 1/3, 1/5, 1/10, or 1/20 of the normal dose, where 1/5 of the normal dose is preferred.

Step 2 — If cytokine storm (CRS) is severe, administer Campath, or any other reagent that can reduce or eliminate T cells.

Step 3 — Subjects will be monitored by imaging or biopsy for resistant disease, and can again be administered the lower dose of CAR T cells, as a split dose.

This strategy can be applied for any cytokine release related CAR.

Figure 55

Mice given lower dose of CD269-A7D-IL15/IL15sushi, CAR T cells lyse tumor cells equally as well as fully-dosed mice by Day 15

Figure 56

SEQUENCE LISTING

```
<160> NUMBER OF SEQ ID NOS: 47

<210> SEQ ID NO 1
<211> LENGTH: 734
<212> TYPE: PRT
<213> ORGANISM: Artificial Sequence
<220> FEATURE:
<223> OTHER INFORMATION: synthetic sequence

<400> SEQUENCE: 1

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
```

```
            225                 230                 235                 240

Glu Ala Glu Asp Val Gly Val Tyr Tyr Cys Met Gln His Leu Glu Tyr
                        245                 250                 255

Pro Phe Thr Phe Gly Ala Gly Thr Lys Leu Glu Leu Lys Arg Thr Thr
                        260                 265                 270

Thr Pro Ala Pro Arg Pro Pro Thr Pro Ala Pro Thr Ile Ala Ser Gln
                        275                 280                 285

Pro Leu Ser Leu Arg Pro Glu Ala Cys Arg Pro Ala Ala Gly Gly Ala
                        290                 295                 300

Val His Thr Arg Gly Leu Asp Phe Ala Cys Asp Ile Tyr Ile Trp Ala
        305                 310                 315                 320

Pro Leu Ala Gly Thr Cys Gly Val Leu Leu Leu Ser Leu Val Ile Thr
                        325                 330                 335

Leu Tyr Cys Arg Ser Lys Arg Ser Arg Leu Leu His Ser Asp Tyr Met
                        340                 345                 350

Asn Met Thr Pro Arg Arg Pro Gly Pro Thr Arg Lys His Tyr Gln Pro
                        355                 360                 365

Tyr Ala Pro Pro Arg Asp Phe Ala Ala Tyr Arg Ser Arg Val Lys Phe
                        370                 375                 380

Ser Arg Ser Ala Asp Ala Pro Ala Tyr Gln Gln Gly Gln Asn Gln Leu
        385                 390                 395                 400

Tyr Asn Glu Leu Asn Leu Gly Arg Arg Glu Glu Tyr Asp Val Leu Asp
                        405                 410                 415

Lys Arg Arg Gly Arg Asp Pro Glu Met Gly Gly Lys Pro Gln Arg Arg
                        420                 425                 430

Lys Asn Pro Gln Glu Gly Leu Tyr Asn Glu Leu Gln Lys Asp Lys Met
                        435                 440                 445

Ala Glu Ala Tyr Ser Glu Ile Gly Met Lys Gly Glu Arg Arg Arg Gly
                        450                 455                 460

Lys Gly His Asp Gly Leu Tyr Gln Gly Leu Ser Thr Ala Thr Lys Asp
        465                 470                 475                 480

Thr Tyr Asp Ala Leu His Met Gln Ala Leu Pro Pro Arg Gly Ser Gly
                        485                 490                 495

Glu Gly Arg Gly Ser Leu Leu Thr Cys Gly Asp Val Glu Glu Asn Pro
                        500                 505                 510

Gly Pro Met Tyr Arg Met Gln Leu Leu Ser Cys Ile Ala Leu Ser Leu
                        515                 520                 525

Ala Leu Val Thr Asn Ser Gln Gly Gln Asp Arg His Met Ile Arg Met
                        530                 535                 540

Arg Gln Leu Ile Asp Ile Val Asp Gln Leu Lys Asn Tyr Val Asn Asp
        545                 550                 555                 560

Leu Val Pro Glu Phe Leu Pro Ala Pro Glu Asp Val Glu Thr Asn Cys
                        565                 570                 575

Glu Trp Ser Ala Phe Ser Cys Phe Gln Lys Ala Gln Leu Lys Ser Ala
                        580                 585                 590

Asn Thr Gly Asn Asn Glu Arg Ile Ile Asn Val Ser Ile Lys Lys Leu
                        595                 600                 605

Lys Arg Lys Pro Pro Ser Thr Asn Ala Gly Arg Arg Gln Lys His Arg
                        610                 615                 620

Leu Thr Cys Pro Ser Cys Asp Ser Tyr Glu Lys Lys Pro Pro Lys Glu
        625                 630                 635                 640

Phe Leu Glu Arg Phe Lys Ser Leu Leu Gln Lys Met Ile His Gln His
                        645                 650                 655
```

```
Leu Ser Ser Arg Thr His Gly Ser Glu Asp Ser Thr Thr Pro Ala
            660                 665                 670

Pro Arg Pro Pro Thr Pro Ala Pro Thr Ile Ala Ser Gln Pro Leu Ser
    675                 680                 685

Leu Arg Pro Glu Ala Cys Arg Pro Ala Ala Gly Gly Ala Val His Thr
    690                 695                 700

Arg Gly Leu Asp Phe Ala Cys Asp Val Ala Ile Ser Thr Ser Thr Val
705                 710                 715                 720

Leu Leu Cys Gly Leu Ser Ala Val Ser Leu Leu Ala Cys Tyr
                725                 730

<210> SEQ ID NO 2
<211> LENGTH: 2221
<212> TYPE: DNA
<213> ORGANISM: Artificial Sequence
<220> FEATURE:
<223> OTHER INFORMATION: synthetic sequence

<400> SEQUENCE: 2
```

| | | | | | |
|---|---|---|---|---|---|
| gcgatcgcat | ggccttacca | gtgaccgcct | tgctcctgcc | gctggccttg | ctgctccacg | 60 |
| ccgccaggcc | ggaggtccag | ctgcagcagt | ctggacctga | gctgataaag | cctggggctt | 120 |
| cagtgaagat | gtcctgcaag | gcttctggat | acacattcac | tagctatgtt | atgcactggg | 180 |
| tgaagcagaa | gcctgggcag | ggccttgagt | ggattggata | tattaatcct | acaatgatg | 240 |
| gtactaagta | caatgagaag | ttcaaaggca | aggccacact | gacttcagac | aaatcctcca | 300 |
| gcacagccta | catggagctc | agcagcctga | cctctgagga | ctctgcggtc | tattactgtg | 360 |
| caagagggac | ttattactac | ggtagtaggg | tatttgacta | ctggggccaa | ggcaccactc | 420 |
| tcacagtctc | ctcaggtgga | gggggctcag | gcggaggtgg | ctctggggt | ggaggctcgg | 480 |
| acattgtgat | gactcaggct | gcaccctcta | tacctgtcac | tcctggagag | tcagtatcca | 540 |
| tctcctgcag | gtctagtaag | agtctcctga | atagtaatgg | caacacttac | ttgtattggt | 600 |
| tcctgcagag | gccaggccag | tctcctcagc | tcctgatata | tcggatgtcc | aaccttgcct | 660 |
| caggagtccc | agacaggttc | agtggcagtg | ggtcaggaac | tgctttcaca | ctgagaatca | 720 |
| gtagagtgga | ggctgaggat | gtgggtgttt | attactgtat | gcaacatcta | gaatatccgt | 780 |
| tcacgttcgg | tgctgggacc | aagctggagc | tgaaacggac | cacgacgcca | gcgccgcgac | 840 |
| caccaacacc | ggcgcccacc | atcgcgtcgc | agcccctgtc | cctgcgccca | gaggcgtgcc | 900 |
| ggccagcggc | ggggggcgca | gtgcacacga | ggggctgga | cttcgcctgt | gatatctaca | 960 |
| tctgggcgcc | cttggccggg | acttgtgggg | tccttctcct | gtcactggtt | atcacccttt | 1020 |
| actgcaggag | taagaggagc | aggctcctgc | acagtgacta | catgaacatg | actccccgcc | 1080 |
| gccccgggcc | cacccgcaag | cattaccagc | cctatgcccc | accacgcgac | ttcgcagcct | 1140 |
| atcgctccag | agtgaagttc | agcaggagcg | cagacgcccc | cgcgtaccag | cagggccaga | 1200 |
| accagctcta | taacgagctc | aatctaggac | gaagagagga | gtacgatgtt | ttggacaaga | 1260 |
| gacgtggccg | ggaccctgag | atggggggaa | agccgcagag | aaggaagaac | cctcaggaag | 1320 |
| gcctgtacaa | tgaactgcag | aaagataaga | tggcggaggc | ctacagtgag | attgggatga | 1380 |
| aaggcgagcg | ccggaggggc | aagggcacg | atggcctta | ccagggtctc | agtacagcca | 1440 |
| ccaaggacac | ctacgacgcc | cttcacatgc | aggcccctgcc | cctcgcggc | agcggcgaag | 1500 |
| gccgcggcag | cctgctgacc | tgcggcgatg | tggaagaaaa | ccccggcccc | atgtacagaa | 1560 |
| tgcagctgct | gagctgcatc | gccctgagcc | tggcctggt | gaccaacagc | cagggccagg | 1620 |

-continued

```
acaggcacat gatcaggatg aggcagctga tcgacatcgt ggaccagctg aagaactacg    1680
tgaacgacct ggtgcccgag ttcctgcccg cccccgagga cgtggagacc aactgcgagt    1740
ggagcgcctt cagctgcttc cagaaggccc agctgaagag cgccaacacc ggcaacaacg    1800
agaggatcat caacgtgagc atcaagaagc tgaagaggaa gccccccagc accaacgccg    1860
gcaggaggca gaagcacagg ctgacctgcc ccagctgcga cagctacgag aagaagcccc    1920
ccaaggagtt cctggagagg ttcaagagcc tgctgcagaa gatgatccac cagcacctga    1980
gcagcaggac ccacggcagc gaggacagca ccaccacccc cgcccccagg cccccaccc     2040 ccgcccccac catcgccagc cagccctga gcctgaggcc cgaggcctgc aggcccgccg     2100
ccggcggcgc cgtgcacacc aggggcctgg acttcgcctg cgacgtggct atctccacgt    2160
ccactgtcct gctgtgtggg ctgagcgctg tgtctctcct ggcatgctac taagtttaaa    2220
c                                                                    2221
```

<210> SEQ ID NO 3
<211> LENGTH: 997
<212> TYPE: PRT
<213> ORGANISM: Artificial Sequence
<220> FEATURE:
<223> OTHER INFORMATION: synthetic sequence

<400> SEQUENCE: 3

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
```

-continued

```
                245                 250                 255
Gln Gly Thr Leu Val Thr Val Ser Ala Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
                355                 360                 365

Asp Phe Ala Ala Tyr Arg Ser Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Ala
                500                 505                 510

Leu Pro Val Thr Ala Leu Leu Leu Pro Leu Ala Leu Leu Leu His Ala
            515                 520                 525

Ala Arg Pro Asp Ile Val Leu Thr Gln Ser Pro Pro Ser Leu Ala Met
            530                 535                 540

Ser Leu Gly Lys Arg Ala Thr Ile Ser Cys Arg Ala Ser Glu Ser Val
545                 550                 555                 560

Thr Ile Leu Gly Ser His Leu Ile His Trp Tyr Gln Gln Lys Pro Gly
                565                 570                 575

Gln Pro Pro Thr Leu Leu Ile Gln Leu Ala Ser Asn Val Gln Thr Gly
            580                 585                 590

Val Pro Ala Arg Phe Ser Gly Ser Gly Ser Arg Thr Asp Phe Thr Leu
            595                 600                 605

Thr Ile Asp Pro Val Glu Glu Asp Asp Val Ala Val Tyr Tyr Cys Leu
610                 615                 620

Gln Ser Arg Thr Ile Pro Arg Thr Phe Gly Gly Gly Thr Lys Leu Glu
625                 630                 635                 640

Ile Lys Gly Gly Gly Gly Ser Gly Gly Gly Gly Ser Gly Gly Gly Gly
                645                 650                 655

Ser Gln Ile Gln Leu Val Gln Ser Gly Pro Glu Leu Lys Lys Pro Gly
                660                 665                 670
```

```
Glu Thr Val Lys Ile Ser Cys Lys Ala Ser Gly Tyr Thr Phe Thr Asp
            675                 680                 685

Tyr Ser Ile Asn Trp Val Lys Arg Ala Pro Gly Lys Gly Leu Lys Trp
        690                 695                 700

Met Gly Trp Ile Asn Thr Glu Thr Arg Glu Pro Ala Tyr Ala Tyr Asp
705                 710                 715                 720

Phe Arg Gly Arg Phe Ala Phe Ser Leu Glu Thr Ser Ala Ser Thr Ala
                725                 730                 735

Tyr Leu Gln Ile Asn Asn Leu Lys Tyr Glu Asp Thr Ala Thr Tyr Phe
            740                 745                 750

Cys Ala Leu Asp Tyr Ser Tyr Ala Met Asp Tyr Trp Gly Gln Gly Thr
        755                 760                 765

Ser Val Thr Val Ser Ser Thr Thr Thr Pro Ala Pro Arg Pro Pro Thr
770                 775                 780

Pro Ala Pro Thr Ile Ala Ser Gln Pro Leu Ser Leu Arg Pro Glu Ala
785                 790                 795                 800

Cys Arg Pro Ala Ala Gly Gly Ala Val His Thr Arg Gly Leu Asp Phe
                805                 810                 815

Ala Cys Asp Ile Tyr Ile Trp Ala Pro Leu Ala Gly Thr Cys Gly Val
            820                 825                 830

Leu Leu Leu Ser Leu Val Ile Thr Leu Tyr Cys Arg Ser Lys Arg Ser
        835                 840                 845

Arg Leu Leu His Ser Asp Tyr Met Asn Met Thr Pro Arg Arg Pro Gly
850                 855                 860

Pro Thr Arg Lys His Tyr Gln Pro Tyr Ala Pro Pro Arg Asp Phe Ala
865                 870                 875                 880

Ala Tyr Arg Ser Arg Val Lys Phe Ser Arg Ser Ala Asp Ala Pro Ala
                885                 890                 895

Tyr Gln Gln Gly Gln Asn Gln Leu Tyr Asn Glu Leu Asn Leu Gly Arg
            900                 905                 910

Arg Glu Glu Tyr Asp Val Leu Asp Lys Arg Arg Gly Arg Asp Pro Glu
        915                 920                 925

Met Gly Gly Lys Pro Gln Arg Arg Lys Asn Pro Gln Glu Gly Leu Tyr
930                 935                 940

Asn Glu Leu Gln Lys Asp Lys Met Ala Glu Ala Tyr Ser Glu Ile Gly
945                 950                 955                 960

Met Lys Gly Glu Arg Arg Arg Gly Lys Gly His Asp Gly Leu Tyr Gln
                965                 970                 975

Gly Leu Ser Thr Ala Thr Lys Asp Thr Tyr Asp Ala Leu His Met Gln
            980                 985                 990

Ala Leu Pro Pro Arg
        995

<210> SEQ ID NO 4
<211> LENGTH: 3013
<212> TYPE: DNA
<213> ORGANISM: Artificial Sequence
<220> FEATURE:
<223> OTHER INFORMATION: synthetic sequence

<400> SEQUENCE: 4
ggcgatcgca ccatggcctt accagtgacc gccttgctcc tgccgctggc cttgctgctc    60
cacgccgcca ggccggacgt ggtgatgacc cagaccacag ttcatgagc  accagcgtgg    120 gcgacagggt gagcatcacc tgcagggcca gccaggacgt gaacaccgcc gtgagctggt   180
```

```
accagcagaa gcccggccag agccccaagc tgctgatctt cagcgccagc tacaggtaca   240
ccggcgtgcc cgacaggttc accggcagcg gcagcggcgc cgacttcacc ctgaccatca   300
gcagcgtgca ggccgaggac ctggccgtgt actactgcca gcagcactac agcaccccct   360
ggaccttcgg cggcggcacc aagctggaca tcaaggaggg ggggggatcc ggggaggag    420 gctccggcgg aggcggaagc cagatccagc tggtgcagag cggccccgac ctgaagaagc   480
ccggcgagac cgtgaagctg agctgcaagg ccagcggcta caccttcacc aacttcggca   540
tgaactgggt gaagcaggcc cccggcaagg gcttcaagtg gatggcctgg atcaacacct   600
acaccggcga gagctacttc gccgacgact caagggcag gttcgccttc agcgtggaga    660
ccagcgccac caccgcctac ctgcagatca acaacctgaa gaccgaggac accgccacct   720
acttctgcgc caggggcgag atctactacg gctacgacgg cggcttcgcc tactggggcc   780
agggcaccct ggtgaccgtg agcgccacca cgacgccagc gccgcgacca ccaacaccgg   840
cgcccaccat cgcgtcgcag cccctgtccc tgcgcccaga ggcgtgccgg ccagcggcgg   900
ggggcgcagt gcacacgagg gggctggact cgcctgtga tatctacatc tgggcgccct    960
tggccgggac ttgtggggtc cttctcctgt cactggttat cacccttta ctgcaggagta   1020 agaggagcag gctcctgcac agtgactaca tgaacatgac tccccgccgc cccgggccca   1080
cccgcaagca ttaccagccc tatgccccac acgcgacttt cgcagcctat cgctccagag   1140
tgaagttcag caggagcgca gacgcccccg cgtaccagca gggccagaac cagctctata   1200
acgagctcaa tctaggacga agagaggagt acgatgtttt ggacaagaga cgtggccggg   1260
accctgagat gggggaaag ccgcagagaa ggaagaaccc tcaggaaggc ctgtacaatg    1320
aactgcagaa agataagatg gcggaggcct acagtgagat tgggatgaaa ggcgagcgcc   1380
ggaggggcaa ggggcacgat ggcctttacc agggtctcag tacagccacc aaggacacct   1440
acgacgccct tcacatgcag gccctgcccc ctcgcggaag cggagccacc aacttcagcc   1500
tgctgaagca ggccggcgac gtggaggaga accccggccc catggcctta ccagtgaccg   1560
ccttgctcct gccgctggcc ttgctgctcc acgccgccag gccggacatc gtgctgaccc   1620
agagcccccc cagcctggcc atgagcctgg gcaagagggc caccatcagc tgcagggcca   1680
gcgagagcgt gaccatcctg ggcagccacc tgatccactg gtaccagcag aagcccggcc   1740
agccccccac cctgctgatc cagctggcca gcaacgtgca gaccggcgtg cccgccaggt   1800
tcagcggcag cggcagcagg accgacttca ccctgaccat cgaccccgtg gaggaggacg   1860
acgtggccgt gtactactgc ctgcagagca ggaccatccc caggaccttc ggcggcggca   1920
ccaagctgga gatcaaggga gggggggat ccggggagg aggctccggc ggaggcggaa    1980
gccagatcca gctggtgcag agcggccccg agctgaagaa gcccggcgag accgtgaaga   2040
tcagctgcaa ggccagcggc tacaccttca ccgactacag catcaactgg gtgaagaggg   2100
cccccggcaa gggcctgaag tggatggct ggatcaacac cgagaccagg agcccgcct    2160 acgcctacga cttcagggc aggttcgcct tcagcctgga gaccagcgcc agcaccgcct   2220
acctgcagat caacaacctg aagtacgagg acaccgccac ctacttctgc gccctggact   2280
acagctacgc catggactac tggggccagg gcaccagcgt gaccgtgagc agcaccacga   2340
cgccagcgcc gcgaccacca acaccggcgc ccaccatcgc gtcgcagccc ctgtccctgc   2400
gcccagaggc gtgccggcca gcggcggggg gcgcagtgca cacgaggggg ctggacttcg   2460
cctgtgatat ctacatctgg gcgccttgg ccgggacttg tggggtcctt ctcctgtcac   2520
```

```
tggttatcac cctttactgc aggagtaaga ggagcaggct cctgcacagt gactacatga    2580
acatgactcc ccgccgcccc gggcccaccc gcaagcatta ccagccctat gccccaccac    2640
gcgacttcgc agcctatcgc tccagagtga agttcagcag gagcgcagac gcccccgcgt    2700
accagcaggg ccagaaccag ctctataacg agctcaatct aggacgaaga gaggagtacg    2760
atgttttgga caagagacgt ggccgggacc ctgagatggg gggaaagccg cagagaagga    2820
agaaccctca ggaaggcctg tacaatgaac tgcagaaaga taagatggcg gaggcctaca    2880
gtgagattgg gatgaaaggc gagcgccgga ggggcaaggg gcacgatggc ctttaccagg    2940
gtctcagtac agccaccaag gacacctacg acgcccttca catgcaggcc ctgccccctc    3000
gctaagttta aac                                                      3013
```

<210> SEQ ID NO 5
<211> LENGTH: 1005
<212> TYPE: PRT
<213> ORGANISM: Artificial Sequence
<220> FEATURE:
<223> OTHER INFORMATION: synthetic sequence

<400> SEQUENCE: 5

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
            260                 265                 270
```

-continued

```
Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Leu Pro Val Thr Ala Leu Leu Leu Pro Leu Ala Leu Leu Leu His Ala
        515                 520                 525

Ala Arg Pro Asp Ile Val Met Thr Gln Ser Pro Leu Ser Leu Pro Val
530                 535                 540

Thr Pro Gly Glu Pro Ala Ser Ile Ser Cys Arg Ser Ser Gln Ser Leu
545                 550                 555                 560

Leu Phe Ile Asp Gly Asn Asn Tyr Leu Asn Trp Tyr Leu Gln Lys Pro
                565                 570                 575

Gly Gln Ser Pro Gln Leu Leu Ile Tyr Leu Gly Ser Asn Arg Ala Ser
            580                 585                 590

Gly Val Pro Asp Arg Phe Ser Gly Ser Gly Ser Gly Thr Asp Phe Thr
        595                 600                 605

Leu Lys Ile Ser Arg Val Glu Ala Glu Asp Val Gly Val Tyr Tyr Cys
    610                 615                 620

Gln Gln Tyr Ser Ser Lys Ser Ala Thr Phe Gly Gln Gly Thr Lys Val
625                 630                 635                 640

Glu Ile Lys Arg Thr Gly Gly Gly Ser Gly Gly Gly Gly Ser Gly
                645                 650                 655

Gly Gly Gly Ser Gln Val Gln Leu Val Gln Ser Gly Ala Glu Val Lys
            660                 665                 670

Lys Pro Gly Ala Ser Val Lys Val Ser Cys Lys Ala Ser Gly Tyr Thr
        675                 680                 685

Phe Thr Ser Tyr Ser Ile Asn Trp Val Arg Gln Ala Pro Gly Gln Gly
```

Leu Glu Trp Met Gly Tyr Ile Asp Pro Asn Arg Gly Asn Thr Asn Tyr
705                 710                 715                 720

Ala Gln Lys Phe Gln Gly Arg Val Thr Met Thr Arg Asp Thr Ser Ile
            725                 730                 735

Ser Thr Ala Tyr Met Glu Leu Ser Ser Leu Arg Ser Glu Asp Thr Ala
        740                 745                 750

Val Tyr Tyr Cys Ala Arg Glu Tyr Ile Tyr Phe Ile His Gly Met Leu
    755                 760                 765

Asp Phe Trp Gly Gln Gly Thr Leu Val Thr Val Ser Ser Thr Thr Thr
770                 775                 780

Pro Ala Pro Arg Pro Pro Thr Pro Ala Pro Thr Ile Ala Ser Gln Pro
785                 790                 795                 800

Leu Ser Leu Arg Pro Glu Ala Cys Arg Pro Ala Ala Gly Gly Ala Val
            805                 810                 815

His Thr Arg Gly Leu Asp Phe Ala Cys Asp Ile Tyr Ile Trp Ala Pro
        820                 825                 830

Leu Ala Gly Thr Cys Gly Val Leu Leu Leu Ser Leu Val Ile Thr Leu
    835                 840                 845

Tyr Cys Lys Arg Gly Arg Lys Lys Leu Leu Tyr Ile Phe Lys Gln Pro
850                 855                 860

Phe Met Arg Pro Val Gln Thr Thr Gln Glu Glu Asp Gly Cys Ser Cys
865                 870                 875                 880

Arg Phe Pro Glu Glu Glu Glu Gly Gly Cys Glu Leu Arg Val Lys Phe
            885                 890                 895

Ser Arg Ser Ala Asp Ala Pro Ala Tyr Gln Gln Gly Gln Asn Gln Leu
        900                 905                 910

Tyr Asn Glu Leu Asn Leu Gly Arg Arg Glu Glu Tyr Asp Val Leu Asp
    915                 920                 925

Lys Arg Arg Gly Arg Asp Pro Glu Met Gly Gly Lys Pro Gln Arg Arg
930                 935                 940

Lys Asn Pro Gln Glu Gly Leu Tyr Asn Glu Leu Gln Lys Asp Lys Met
945                 950                 955                 960

Ala Glu Ala Tyr Ser Glu Ile Gly Met Lys Gly Glu Arg Arg Arg Gly
            965                 970                 975

Lys Gly His Asp Gly Leu Tyr Gln Gly Leu Ser Thr Ala Thr Lys Asp
        980                 985                 990

Thr Tyr Asp Ala Leu His Met Gln Ala Leu Pro Pro Arg
    995                 1000                1005

<210> SEQ ID NO 6
<211> LENGTH: 2966
<212> TYPE: DNA
<213> ORGANISM: Artificial Sequence
<220> FEATURE:
<223> OTHER INFORMATION: synthetic sequence

<400> SEQUENCE: 6
atggccttac cagtgaccgc cttgctcctg ccgctggcct tgctgctcca cgccgccagg     60
ccggacgtgg tgatgaccca gagccacagg ttcatgagca ccagcgtggg cgacagggtg    120
agcatcacct gcagggccag ccaggacgtg aacaccgccg tgagctggta ccagcagaag    180
cccggccaga gccccaagct gctgatcttc agcgccagct acaggtacac cggcgtgccc    240
gacaggttca ccggcagcgg cagcggcgcc gacttcaccc tgaccatcag cagcgtgcag    300

```
gccgaggacc tggccgtgta ctactgccag cagcactaca gcaccccctg gaccttcggc    360
ggcggcacca agctggacat caagggaggg gggggatccg ggggaggagg ctccggcgga    420
ggcggaagcc agatccagct ggtgcagagc ggccccgacc tgaagaagcc cggcgagacc    480
gtgaagctga gctgcaaggc cagcggctac accttcacca acttcggcat gaactgggtg    540
aagcaggccc ccggcaaggg cttcaagtgg atggcctgga tcaacaccta caccggcgag    600
agctacttcg ccgacgactt caagggcagg ttcgccttca gcgtggagac cagcgccacc    660
accgcctacc tgcagatcaa caacctgaag accgaggaca ccgccaccta cttctgcgcc    720
aggggcgaga tctactacgg ctacgacggc ggcttcgcct actggggcca gggcaccctg    780
gtgaccgtga gcgccaccac gacgccagcg ccgcgaccac caacaccggc gcccaccatc    840
gcgtcgcagc cctgtccct gcccagag gcgtgccggc cagcggcggg gggcgcagtg    900
cacacgaggg ggctggactt cgcctgtgat atctacatct gggcgccctt ggccgggact    960
tgtggggtcc ttctcctgtc actggttatc acctttact gcaggagtaa gaggagcagg   1020
ctcctgcaca gtgactacat gaacatgact ccccgccgcc ccgggcccac ccgcaagcat   1080
taccagccct atgccccacc acgcgacttc gcagcctatc gctccagagt gaagttcagc   1140
aggagcgcag acgcccccgc gtaccagcag ggccagaacc agctctataa cgagctcaat   1200
ctaggacgaa gagaggagta cgatgttttg acaagagac gtggccggga ccctgagatg   1260
gggggaaagc cgcagagaag gaagaaccct caggaaggc tgtacaatga actgcagaaa   1320
gataagatgg cggaggccta cagtgagatt gggatgaaag cgagcgccg gaggggcaag   1380 gggcacgatg gcctttacca gggtctcagt acagccacca aggacaccta cgacgccctt   1440
cacatgcagg ccctgccccc tcgcggaagc ggagccacca acttcagcct gctgaagcag   1500
gccggcgacg tggaggagaa ccccggcccc atggccctgc ccgtgaccgc cctgctgctg   1560
cccctggccc tgctgctgca cgccgccagg cccgacatcg tgatgaccca gagccccctg   1620
agcctgcccg tgaccccgg cgagcccgcc agctacctgc agaagcccgg ccagagcccc   1680
cagctgctga tctacctggg cagcaacagg gccagcggcg tgcccgacag gttcagcggc   1740
agcggcagcg gcaccgactt caccctgaag atcagcaggg tggaggccga ggacgtgggc   1800
gtgtactact gccagcagta cagcagcaag agcgccacct tcggccaggg caccaaggtg   1860
gagatcaaga ggaccggcgg cggcggcagc ggcggcggcg gcagcggcgg cggcggcagc   1920
caggtgcagc tggtgcagag cggcgccgag gtgaagaagc ccggcgccag cgtgaaggtg   1980
agctgcaagg ccagcggcta caccttcacc agctacagca tcaactgggt gaggcaggcc   2040
cccggccagg gcctggagtg gatgggctac atcgacccca caggggcaa caccaactac   2100 gcccagaagt tccagggcag ggtgaccatg accaggaca ccagcatcag caccgcctac   2160
atggagctga gcagcctgag gagcgaggac accgccgtgt actactgcgc cagggagtac   2220
atctacttca tccacggcat gctggacttc tggggccagg gcaccctggt gaccgtgagc   2280
agcaccacca ccccgccc caggcccccc accccgccc ccaccatcgc cagccagccc   2340
ctgagcctga ggcccgaggc ctgcaggccc gccgccggcg gcgccgtgca caccaggggc   2400
ctggacttcg cctgcgacat ctacatctgg gccccctgg ccggcacctg cggcgtgctg   2460
ctgctgagcc tggtgatcac cctgtactgc aaacggggca gaaagaaact cctgtatata   2520
ttcaaacaac catttatgag accagtacaa actactcaag aggaagatgg ctgtagctgc   2580
cgatttccag aagaagaaga aggaggatgt gaactgaggg tgaagttcag caggagcgcc   2640
gacgcccccg cctaccagca gggccagaac cagctgtaca cgagctgaa cctgggcagg   2700
```

-continued

```
agggaggagt acgacgtgct ggacaagagg aggggcaggg accccgagat gggcggcaag    2760
ccccagagga ggaagaaccc ccaggagggc ctgtacaacg agctgcagaa ggacaagatg    2820
gccgaggcct acagcgagat cggcatgaag ggcgagagga ggaggggcaa gggccacgac    2880
ggcctgtacc agggcctgag caccgccacc aaggacacct acgacgccct gcacatgcag    2940
gccctgcccc ccaggtaagt ttaaac                                         2966
```

<210> SEQ ID NO 7
<211> LENGTH: 1001
<212> TYPE: PRT
<213> ORGANISM: Artificial Sequence
<220> FEATURE:
<223> OTHER INFORMATION: synthetic sequence

<400> SEQUENCE: 7

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
                20                  25                  30

Ser Thr Ser Val Gly Asp Arg Val Ser Ile Thr Cys Arg Ala Ser Gln
            35                  40                  45

Asp Val Asn Thr Ala Val Ser Trp Tyr Gln Gln Lys Pro Gly Gln Ser
        50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
```

```
                305                 310                 315                 320
        Cys Gly Val Leu Leu Leu Ser Leu Val Ile Thr Leu Tyr Cys Arg Ser
                        325                 330                 335

Lys Arg Ser Arg Leu Leu His Ser Asp Tyr Met Asn Met Thr Pro Arg
                        340                 345                 350

Arg Pro Gly Pro Thr Arg Lys His Tyr Gln Pro Tyr Ala Pro Pro Arg
                        355                 360                 365

Asp Phe Ala Ala Tyr Arg Ser Arg Val Lys Phe Ser Arg Ser Ala Asp
        370                 375                 380

Ala Pro Ala Tyr Gln Gln Gly Gln Asn Gln Leu Tyr Asn Glu Leu Asn
        385                 390                 395                 400

Leu Gly Arg Arg Glu Glu Tyr Asp Val Leu Asp Lys Arg Arg Gly Arg
                        405                 410                 415

Asp Pro Glu Met Gly Gly Lys Pro Gln Arg Arg Lys Asn Pro Gln Glu
                        420                 425                 430

Gly Leu Tyr Asn Glu Leu Gln Lys Asp Lys Met Ala Glu Ala Tyr Ser
                        435                 440                 445

Glu Ile Gly Met Lys Gly Glu Arg Arg Arg Gly Lys Gly His Asp Gly
                        450                 455                 460

Leu Tyr Gln Gly Leu Ser Thr Ala Thr Lys Asp Thr Tyr Asp Ala Leu
        465                 470                 475                 480

His Met Gln Ala Leu Pro Pro Arg Gly Ser Gly Ala Thr Asn Phe Ser
                        485                 490                 495

Leu Leu Lys Gln Ala Gly Asp Val Glu Glu Asn Pro Gly Pro Met Ala
                        500                 505                 510

Leu Pro Val Thr Ala Leu Leu Leu Pro Leu Ala Leu Leu Leu His Ala
                        515                 520                 525

Ala Arg Pro Asp Ile Gln Met Thr Gln Ser Pro Ser Ser Leu Ser Ala
                        530                 535                 540

Ser Val Gly Asp Arg Val Thr Ile Thr Cys Arg Ala Ser Gln Asp Ile
        545                 550                 555                 560

Ser Ala Phe Leu Asn Trp Tyr Gln Gln Lys Pro Gly Lys Ala Pro Lys
                        565                 570                 575

Leu Leu Ile Thr Lys Val Ser Asn Leu Gln Ser Gly Val Pro Ser Arg
                        580                 585                 590

Phe Ser Gly Ser Gly Ser Gly Thr Asp Phe Thr Leu Thr Ile Ser Ser
                        595                 600                 605

Leu Gln Pro Glu Asp Phe Ala Thr Tyr Tyr Cys Gln Gln Ala Tyr Ser
                        610                 615                 620

Gly Ser Ile Thr Phe Gly Gln Gly Thr Lys Val Glu Ile Lys Arg Thr
        625                 630                 635                 640

Gly Gly Gly Gly Ser Gly Gly Gly Gly Ser Gly Gly Gly Gly Ser Gln
                        645                 650                 655

Val Gln Leu Val Glu Ser Gly Gly Gly Leu Val Gln Pro Gly Gly Ser
                        660                 665                 670

Leu Arg Leu Ser Cys Ala Ala Ser Gly Phe Thr Phe Ser Asn Tyr Gly
                        675                 680                 685

Met His Trp Val Arg Gln Ala Pro Gly Lys Gly Leu Glu Trp Val Ser
                        690                 695                 700

Asn Ile Arg Ser Asp Gly Ser Trp Thr Tyr Tyr Ala Asp Ser Val Lys
        705                 710                 715                 720

Gly Arg Phe Thr Ile Ser Arg Asp Asn Ser Lys Asn Thr Leu Tyr Leu
                        725                 730                 735
```

```
Gln Met Asn Ser Leu Arg Ala Glu Asp Thr Ala Val Tyr Tyr Cys Ala
            740                 745                 750

Arg Arg Tyr Trp Ser Lys Ser His Ala Ser Val Thr Asp Tyr Trp Gly
        755                 760                 765

Gln Gly Thr Leu Val Thr Val Ser Ser Thr Thr Pro Ala Pro Arg
    770                 775                 780

Pro Pro Thr Pro Ala Pro Thr Ile Ala Ser Gln Pro Leu Ser Leu Arg
785                 790                 795                 800

Pro Glu Ala Cys Arg Pro Ala Ala Gly Gly Ala Val His Thr Arg Gly
                805                 810                 815

Leu Asp Phe Ala Cys Asp Ile Tyr Ile Trp Ala Pro Leu Ala Gly Thr
            820                 825                 830

Cys Gly Val Leu Leu Leu Ser Leu Val Ile Thr Leu Tyr Cys Lys Arg
            835                 840                 845

Gly Arg Lys Lys Leu Leu Tyr Ile Phe Lys Gln Pro Phe Met Arg Pro
    850                 855                 860

Val Gln Thr Thr Gln Glu Glu Asp Gly Cys Ser Cys Arg Phe Pro Glu
865                 870                 875                 880

Glu Glu Glu Gly Gly Cys Glu Leu Arg Val Lys Phe Ser Arg Ser Ala
                885                 890                 895

Asp Ala Pro Ala Tyr Gln Gln Gly Gln Asn Gln Leu Tyr Asn Glu Leu
            900                 905                 910

Asn Leu Gly Arg Arg Glu Glu Tyr Asp Val Leu Asp Lys Arg Arg Gly
            915                 920                 925

Arg Asp Pro Glu Met Gly Gly Lys Pro Gln Arg Arg Lys Asn Pro Gln
    930                 935                 940

Glu Gly Leu Tyr Asn Glu Leu Gln Lys Asp Lys Met Ala Glu Ala Tyr
945                 950                 955                 960

Ser Glu Ile Gly Met Lys Gly Glu Arg Arg Arg Gly Lys Gly His Asp
                965                 970                 975

Gly Leu Tyr Gln Gly Leu Ser Thr Ala Thr Lys Asp Thr Tyr Asp Ala
            980                 985                 990

Leu His Met Gln Ala Leu Pro Pro Arg
            995                 1000

<210> SEQ ID NO 8
<211> LENGTH: 3014
<212> TYPE: DNA
<213> ORGANISM: Artificial Sequence
<220> FEATURE:
<223> OTHER INFORMATION: synthetic sequence

<400> SEQUENCE: 8
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcacccctg gaccttcggc     360 ggcggcacca agctggacat caagggaggg ggggatccg ggggaggagg ctccggcgga     420
ggcggaagcc agatccagct ggtgcagagc ggccccgacc tgaagaagcc cggcgagacc     480
gtgaagctga gctgcaaggc cagcggctac accttcacca acttcggcat gaactgggtg     540
```

-continued

| | | | | |
|---|---|---|---|---|
| aagcaggccc | ccggcaaggg | cttcaagtgg | atggcctgga | tcaacaccta caccggcgag | 600 |
| agctacttcg | ccgacgactt | caagggcagg | ttcgccttca | gcgtggagac cagcgccacc | 660 |
| accgcctacc | tgcagatcaa | caacctgaag | accgaggaca | ccgccaccta cttctgcgcc | 720 |
| aggggcgaga | tctactacgg | ctacgacggc | ggcttcgcct | actggggcca gggcaccctg | 780 |
| gtgaccgtga | gcgccaccac | gacgccagcg | ccgcgaccac | caacaccggc gcccaccatc | 840 |
| gcgtcgcagc | ccctgtccct | gcgcccagag | gcgtgccggc | cagcggcggg gggcgcagtg | 900 |
| cacacgaggg | ggctggactt | cgcctgtgat | atctacatct | gggcgccctt ggccgggact | 960 |
| tgtgggtcc | ttctcctgtc | actggttatc | acccttact | gcaggagtaa gaggagcagg | 1020 |
| ctcctgcaca | gtgactacat | gaacatgact | ccccgccgcc | cgggcccac ccgcaagcat | 1080 |
| taccagcct | atgccccacc | acgcgacttc | gcagcctatc | gctccagagt gaagttcagc | 1140 |
| aggagcgcag | acgccccgc | gtaccagcag | ggccagaacc | agctctataa cgagctcaat | 1200 |
| ctaggacgaa | gagaggagta | cgatgttttg | gacaagagac | gtggccggga ccctgagatg | 1260 |
| gggggaaagc | cgcagagaag | gaagaaccct | caggaaggcc | tgtacaatga actgcagaaa | 1320 |
| gataagatgg | cggaggccta | cagtgagatt | gggatgaaag | cgagcgccg gaggggcaag | 1380 |
| gggcacgatg | gcctttacca | gggtctcagt | acagccacca | aggacaccta cgacgccctt | 1440 |
| cacatgcagg | ccctgccccc | tcgcggaagc | ggagccacca | acttcagcct gctgaagcag | 1500 |
| gccggcgacg | tggaggagaa | ccccggcccc | atggccctgc | ccgtgaccgc cctgctgctg | 1560 |
| cccctggccc | tgctgctgca | cgccgccagg | cccgacatcc | agatgaccca gagccccagc | 1620 |
| agcctgagcg | ccagcgtggg | cgacagggtg | accatcacct | gcagggccag ccaggacatc | 1680 |
| agcgccttcc | tgaactggta | ccagcagaag | cccggcaagg | ccccaagct gctgatcacc | 1740 |
| aaggtgagca | acctgcagag | cggcgtgccc | agcaggttca | gcggcagcgg cagcggcacc | 1800 |
| gacttcaccc | tgaccatcag | cagcctgcag | cccgaggact | cgccaccta ctactgccag | 1860 |
| caggcctaca | gcggcagcat | caccttcggc | cagggcacca | aggtggagat caagaggacc | 1920 |
| ggcggcggcg | gcagcggcgg | cggcggcagc | ggcggcggcg | gcagccaggt gcagctggtg | 1980 |
| gagagcggcg | gcggcctggt | gcagcccggc | ggcagcctga | ggctgagctg cgccgccagc | 2040 |
| ggcttcacct | tcagcaacta | cggcatgcac | tgggtgaggc | aggccccgg caagggcctg | 2100 |
| gagtgggtga | gcaacatcag | gagcgacggc | agctggacct | actacgccga cagcgtgaag | 2160 |
| ggcaggttca | ccatcagcag | ggacaacagc | aagaacaccc | tgtacctgca gatgaacagc | 2220 |
| ctgagggccg | aggacaccgc | cgtgtactac | tgcgccagga | ggtactggag caagagccac | 2280 |
| gccagcgtga | ccgactactg | gggccagggc | accctggtga | ccgtgagcag caccaccacc | 2340 |
| cccgccccca | ggccccccac | ccccgccccc | accatcgcca | gccagccct gagcctgagg | 2400 |
| cccgaggcct | gcaggcccgc | cgccggcggc | gccgtgcaca | ccaggggcct ggacttcgcc | 2460 |
| tgcgacatct | acatctgggc | ccccctggcc | ggcacctgcg | gcgtgctgct gctgagcctg | 2520 |
| gtgatcaccc | tgtactgcaa | acggggcaga | aagaaactcc | tgtatatatt caaacaacca | 2580 |
| tttatgagac | cagtacaaac | tactcaagag | gaagatggct | gtagctgccg atttccagaa | 2640 |
| gaagaagaag | gaggatgtga | actgaggggtg | aagttcagca | ggacgccga cgcccccgcc | 2700 |
| taccagcagg | gccagaacca | gctgtacaac | gagctgaacc | tgggcaggag ggaggagtac | 2760 |
| gacgtgctgg | acaagaggag | gggcagggac | cccgagatgg | gcggcaagcc ccagaggagg | 2820 |
| aagaaccccc | aggagggcct | gtacaacgag | ctgcagaagg | acaagatggc cgaggcctac | 2880 |

```
agcgagatcg gcatgaaggg cgagaggagg aggggcaagg gccacgacgg cctgtaccag    2940
ggcctgagca ccgccaccaa ggacacctac gacgccctgc acatgcaggc cctgcccccc    3000
aggtaagttt aaac                                                      3014
```

<210> SEQ ID NO 9
<211> LENGTH: 1004
<212> TYPE: PRT
<213> ORGANISM: Artificial Sequence
<220> FEATURE:
<223> OTHER INFORMATION: synthetic sequence

<400> SEQUENCE: 9

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
                20                  25                  30

Ser Thr Ser Val Gly Asp Arg Val Ser Ile Thr Cys Arg Ala Ser Gln
            35                  40                  45

Asp Val Asn Thr Ala Val Ser Trp Tyr Gln Gln Lys Pro Gly Gln Ser
        50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Ser Gln
130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335
```

```
Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Leu Pro Val Thr Ala Leu Leu Leu Pro Leu Ala Leu Leu Leu His Ala
            515                 520                 525

Ala Arg Pro Ala Gln Pro Ala Met Ala Lys Val Gln Leu Gln Glu Ser
530                 535                 540

Gly Pro Ser Leu Val Gln Pro Ser Gln Arg Leu Ser Ile Thr Cys Thr
545                 550                 555                 560

Val Ser Gly Phe Ser Leu Ile Ser Tyr Gly Val His Trp Val Arg Gln
                565                 570                 575

Ser Pro Gly Lys Gly Leu Glu Trp Leu Gly Val Ile Trp Arg Gly Gly
            580                 585                 590

Ser Thr Asp Tyr Asn Ala Ala Phe Met Ser Arg Leu Ser Ile Thr Lys
            595                 600                 605

Asp Asn Ser Lys Ser Gln Val Phe Phe Lys Met Asn Ser Leu Gln Ala
        610                 615                 620

Asp Asp Thr Ala Ile Tyr Phe Cys Ala Lys Thr Leu Ile Thr Thr Gly
625                 630                 635                 640

Tyr Ala Met Asp Tyr Trp Gly Gln Gly Thr Thr Val Thr Val Ser Ser
                645                 650                 655

Gly Gly Gly Gly Ser Gly Gly Gly Ser Gly Gly Gly Gly Ser Asp
                660                 665                 670

Ile Glu Leu Thr Gln Ser Pro Ser Ser Phe Ser Val Ser Leu Gly Asp
            675                 680                 685

Arg Val Thr Ile Thr Cys Lys Ala Ser Glu Asp Ile Tyr Asn Arg Leu
        690                 695                 700

Ala Trp Tyr Gln Gln Lys Pro Gly Asn Ala Pro Arg Leu Leu Ile Ser
705                 710                 715                 720

Gly Ala Thr Ser Leu Glu Thr Gly Val Pro Ser Arg Phe Ser Gly Ser
                725                 730                 735

Gly Ser Gly Lys Asp Tyr Thr Leu Ser Ile Thr Ser Leu Gln Thr Glu
            740                 745                 750

Asp Val Ala Thr Tyr Tyr Cys Gln Gln Tyr Trp Ser Thr Pro Thr Phe
```

```
                        755                 760                 765
Gly Gly Gly Thr Lys Leu Glu Ile Lys Arg Ala Ala Thr Thr Thr Pro
                770                 775                 780

Ala Pro Arg Pro Pro Thr Pro Ala Pro Thr Ile Ala Ser Gln Pro Leu
785                 790                 795                 800

Ser Leu Arg Pro Glu Ala Cys Arg Pro Ala Ala Gly Gly Ala Val His
                805                 810                 815

Thr Arg Gly Leu Asp Phe Ala Cys Asp Ile Tyr Ile Trp Ala Pro Leu
                820                 825                 830

Ala Gly Thr Cys Gly Val Leu Leu Leu Ser Leu Val Ile Thr Leu Tyr
                835                 840                 845

Cys Lys Arg Gly Arg Lys Lys Leu Leu Tyr Ile Phe Lys Gln Pro Phe
                850                 855                 860

Met Arg Pro Val Gln Thr Thr Gln Glu Glu Asp Gly Cys Ser Cys Arg
865                 870                 875                 880

Phe Pro Glu Glu Glu Glu Gly Gly Cys Glu Leu Arg Val Lys Phe Ser
                        885                 890                 895

Arg Ser Ala Asp Ala Pro Ala Tyr Gln Gln Gly Gln Asn Gln Leu Tyr
                900                 905                 910

Asn Glu Leu Asn Leu Gly Arg Arg Glu Glu Tyr Asp Val Leu Asp Lys
                915                 920                 925

Arg Arg Gly Arg Asp Pro Glu Met Gly Gly Lys Pro Gln Arg Arg Lys
                930                 935                 940

Asn Pro Gln Glu Gly Leu Tyr Asn Glu Leu Gln Lys Asp Lys Met Ala
945                 950                 955                 960

Glu Ala Tyr Ser Glu Ile Gly Met Lys Gly Glu Arg Arg Arg Gly Lys
                        965                 970                 975

Gly His Asp Gly Leu Tyr Gln Gly Leu Ser Thr Ala Thr Lys Asp Thr
                980                 985                 990

Tyr Asp Ala Leu His Met Gln Ala  Leu Pro Pro Arg
                995                 1000
```

<210> SEQ ID NO 10
<211> LENGTH: 3023
<212> TYPE: DNA
<213> ORGANISM: Artificial Sequence
<220> FEATURE:
<223> OTHER INFORMATION: synthetic sequence

<400> SEQUENCE: 10

```
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240
gacaggttca ccggcagcgg cagcggcgcc gacttcaccc tgaccatcag cagcgtgcag     300
gccgaggacc tggccgtgta ctactgccag cagcactaca gcacccctg  gaccttcggc     360 ggcggcacca gctggacat  caaggggaggg gggggatccg ggggaggagg ctccggcgga     420
ggcggaagcc agatccagct ggtgcagagc ggccccgacc tgaagaagcc cggcgagacc     480
gtgaagctga gctgcaaggc cagcggctac accttcacca acttcggcat gaactgggtg     540
aagcaggccc ccggcaaggg cttcaagtgg atggcctgga tcaacaccta caccggcgag     600
agctacttcg ccgacgactt caagggcagg ttcgccttca gcgtggagac cagcgccacc     660
```

| | |
|---|---|
| accgcctacc tgcagatcaa caacctgaag accgaggaca ccgccaccta cttctgcgcc | 720 |
| aggggcgaga tctactacgg ctacgacggc ggcttcgcct actggggcca gggcaccctg | 780 |
| gtgaccgtga gcgccaccac gacgccagcg ccgcgaccac caacaccggc gcccaccatc | 840 |
| gcgtcgcagc ccctgtccct gcgcccagag gcgtgccggc cagcggcggg gggcgcagtg | 900 |
| cacacgaggg ggctggactt cgcctgtgat atctacatct gggcgccctt ggccgggact | 960 |
| tgtggggtcc ttctcctgtc actggttatc acccttact gcaggagtaa gaggagcagg | 1020 |
| ctcctgcaca gtgactacat gaacatgact ccccgccgcc ccgggcccac ccgcaagcat | 1080 |
| taccagcccT atgccccacc acgcgacttc gcagcctatc gctccagagt gaagttcagc | 1140 |
| aggagcgcag acgccccgc gtaccagcag ggccagaacc agctctataa cgagctcaat | 1200 |
| ctaggacgaa gagaggagta cgatgttttg gacaagagac gtggccggga ccctgagatg | 1260 |
| gggggaaagc cgcagagaag gaagaaccct caggaaggcc tgtacaatga actgcagaaa | 1320 |
| gataagatgg cggaggccta cagtgagatt gggatgaaag cgagcgccg gaggggcaag | 1380 |
| gggcacgatg gcctttacca gggtctcagt acagccacca aggacaccta cgacgcccTt | 1440 |
| cacatgcagg ccctgccccc tcgcggaagc ggagccacca acttcagcct gctgaagcag | 1500 |
| gccgcgacg tggaggagaa ccccggcccc atgcccctgc ccgtgaccgc cctgctgctg | 1560 |
| cccctggccc tgctgctgca cgccgccagg cccgcccagc ccgccatggc caaggtgcag | 1620 |
| ctgcaggaga gcggccccag cctggtgcag cccagccaga ggctgagcat cacctgcacc | 1680 |
| gtgagcggct tcagcctgat cagctacggc gtgcactggg tgaggcagag ccccggcaag | 1740 |
| ggcctggagt ggctgggcgt gatctggagg ggcggcagca ccgactacaa cgccgccttc | 1800 |
| atgagcaggc tgagcatcac caaggacaac agcaagagcc aggtgttctt caagatgaac | 1860 |
| agcctgcagg ccgacgacac cgccatctac ttctgcgcca agaccctgat caccaccggc | 1920 |
| tacgccatgg actactgggg ccagggcacc accgtgaccg tgagcagcgg cggcggcggc | 1980 |
| agcggcggcg gcggcagcgg cggcggcggc agcgacatcg agctgaccca gagccccagc | 2040 |
| agcttcagcg tgagcctggg cgacagggtg accatcacct gcaaggccag cgaggacatc | 2100 |
| tacaacaggc tggcctggta ccagcagaag cccggcaacg cccccaggct gctgatcagc | 2160 |
| ggcgccacca gcctggagac cggcgtgccc agcaggttca gcggcagcgg cagcggcaag | 2220 |
| gactacaccc tgagcatcac cagcctgcag accgaggacg tggccaccta ctactgccag | 2280 |
| cagtactgga gcacccccac cttcggcggc ggcaccaagc tggagatcaa gagggccgcc | 2340 |
| accaccaccc ccgcccccag gcccccacc ccgcccccca ccatcgccag ccagcccctg | 2400 |
| agcctgaggc ccgaggcctg caggcccgcc gccggcggcg ccgtgcacac caggggcctg | 2460 |
| gacttcgcct gcgacatcta catctgggcc cccctggccg gcacctgcgg cgtgctgctg | 2520 |
| ctgagcctgg tgatcaccct gtactgcaaa cggggcagaa agaaactcct gtatatattc | 2580 |
| aaacaaccat ttatgagacc agtacaaact actcaagagg aagatggctg tagctgccga | 2640 |
| tttccagaag aagaagaagg aggatgtgaa ctgagggtga agttcagcag gagcgccgac | 2700 |
| gcccccgcct accagcaggg ccagaaccag ctgtacaacg agctgaacct gggcaggagg | 2760 |
| gaggagtacg acgtgctgga caagaggagg ggcagggacc ccgagatggg cggcaagccc | 2820 |
| cagaggagga gaacccccca ggagggcctg tacaacgagc tgcagaagga caagatggcc | 2880 |
| gaggcctaca gcgagatcgg catgaagggc gagaggagga ggggcaaggg ccacgacggc | 2940 |
| ctgtaccagg gcctgagcac cgccaccaag gacacctacg acgccctgca catgcaggcc | 3000 |
| ctgccccca ggtaagttta aac | 3023 |

<210> SEQ ID NO 11
<211> LENGTH: 687
<212> TYPE: PRT
<213> ORGANISM: Artificial Sequence
<220> FEATURE:
<223> OTHER INFORMATION: synthetic sequence

<400> SEQUENCE: 11

Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
                20                  25                  30

Ser Thr Ser Val Gly Asp Arg Val Ser Ile Thr Cys Arg Ala Ser Gln
            35                  40                  45

Asp Val Asn Thr Ala Val Ser Trp Tyr Gln Gln Lys Pro Gly Gln Ser
        50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125

Gly Gly Gly Gly Ser Gly Gly Gly Ser Gly Gly Gly Ser Gln
130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Tyr
            500                 505                 510

Arg Met Gln Leu Leu Ser Cys Ile Ala Leu Ser Leu Ala Leu Val Thr
        515                 520                 525

Asn Ser Tyr Phe Gly Lys Leu Glu Ser Lys Leu Ser Val Ile Arg Asn
    530                 535                 540

Leu Asn Asp Gln Val Leu Phe Ile Asp Gln Gly Asn Arg Pro Leu Phe
545                 550                 555                 560

Glu Asp Met Thr Asp Ser Asp Cys Arg Asp Asn Ala Pro Arg Thr Ile
                565                 570                 575

Phe Ile Ile Ser Met Tyr Lys Asp Ser Gln Pro Arg Gly Met Ala Val
            580                 585                 590

Thr Ile Ser Val Lys Cys Glu Lys Ile Ser Thr Leu Ser Cys Glu Asn
        595                 600                 605

Lys Ile Ile Ser Phe Lys Glu Met Asn Pro Pro Asp Asn Ile Lys Asp
    610                 615                 620

Thr Lys Ser Asp Ile Ile Phe Phe Gln Arg Ser Val Pro Gly His Asp
625                 630                 635                 640

Asn Lys Met Gln Phe Glu Ser Ser Ser Tyr Glu Gly Tyr Phe Leu Ala
                645                 650                 655

Cys Glu Lys Glu Arg Asp Leu Phe Lys Leu Ile Leu Lys Lys Glu Asp
            660                 665                 670

Glu Leu Gly Asp Arg Ser Ile Met Phe Thr Val Gln Asn Glu Asp
        675                 680                 685

<210> SEQ ID NO 12
<211> LENGTH: 2061
<212> TYPE: DNA
<213> ORGANISM: Artificial Sequence
<220> FEATURE:
<223> OTHER INFORMATION: synthetic sequence

<400> SEQUENCE: 12
atggccttac cagtgaccgc cttgctcctg ccgctggcct tgctgctcca cgccgccagg      60
ccggacgtgg tgatgaccca gagccacagg ttcatgagca ccagcgtggg cgacagggtg     120
agcatcacct gcagggccag ccaggacgtg aacaccgccg tgagctggta ccagcagaag     180
cccggccaga gccccaagct gctgatcttc agcgccagct acaggtacac cggcgtgccc     240

```
gacaggttca ccggcagcgg cagcggcgcc gacttcaccc tgaccatcag cagcgtgcag      300
gccgaggacc tggccgtgta ctactgccag cagcactaca gcaccccctg gaccttcggc      360
ggcggcacca agctggacat caaggagggg gggggatccg ggggaggagg ctccggcgga      420
ggcggaagcc agatccagct ggtgcagagc ggccccgacc tgaagaagcc cggcgagacc      480
gtgaagctga gctgcaaggc cagcggctac accttcacca acttcggcat gaactgggtg      540
aagcaggccc ccggcaaggg cttcaagtgg atggcctgga tcaacaccta caccggcgag      600
agctacttcg ccgacgactt caagggcagg ttcgccttca gcgtggagac cagcgccacc      660
accgcctacc tgcagatcaa caacctgaag accgaggaca ccgccaccta cttctgcgcc      720
aggggcgaga tctactacgg ctacgacggc ggcttcgcct actggggcca gggcaccctg      780
gtgaccgtga gcgccaccac gacgccagcg ccgcgaccac caacaccggc gcccaccatc      840
gcgtcgcagc ccctgtccct gcgcccagag gcgtgccggc cagcggcggg gggcgcagtg      900
cacacgaggg ggctggactt cgcctgtgat atctacatct gggcgccctt ggccgggact      960
tgtggggtcc ttctcctgtc actggttatc accctttact gcaggagtaa gaggagcagg     1020
ctcctgcaca gtgactacat gaacatgact ccccgccgcc cgggcccac ccgcaagcat     1080 taccagcccc atgccccacc acgcgacttc gcagcctatc gctccagagt gaagttcagc     1140
aggagcgcag acgccccgc gtaccagcag ggccagaacc agctctataa cgagctcaat     1200
ctaggacgaa gagaggagta cgatgttttg gacaagagac gtggccggga ccctgagatg     1260
gggggaaagc cgcagagaag gaagaaccct caggaaggcc tgtacaatga actgcagaaa     1320
gataagatgg cggaggccta cagtgagatt gggatgaaag cgagcgccg gaggggcaag     1380 gggcacgatg gcctttacca gggtctcagt acagccacca aggacaccta cgacgccctt     1440
cacatgcagg ccctgccccc tcgcggaagc ggagccacca acttcagcct gctgaagcag     1500
gccggcgacg tggaggagaa ccccggcccc atgtacagaa tgcagctgct gagctgcatc     1560
gccctgagcc tggccctggt gaccaacagc tacttcggca gctggagag caagctgagc     1620 gtgatcagga acctgaacga ccaggtgctg ttcatcgacc agggcaacag gcccctgttc     1680
gaggacatga ccgacagcga ctgcagggac aacgcccca ggaccatctt catcatcagc     1740
atgtacaagg acagccagcc caggggcatg gccgtgacca tcagcgtgaa gtgcgagaag     1800
atcagcaccc tgagctgcga aacaagatc atcagcttca aggagatgaa ccccccgac     1860 aacatcaagg acaccaagag cgacatcatc ttcttccaga ggagcgtgcc cggccacgac     1920
aacaagatgc agttcgagag cagcagctac gagggctact cctggcctg cgagaaggag     1980 agggacctgt tcaagctgat cctgaagaag gaggacgagc tgggcgacag gagcatcatg     2040
ttcaccgtgc agaacgagga c                                              2061
```

<210> SEQ ID NO 13
<211> LENGTH: 754
<212> TYPE: PRT
<213> ORGANISM: Artificial Sequence
<220> FEATURE:
<223> OTHER INFORMATION: synthetic sequence

<400> SEQUENCE: 13

Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
                20                  25                  30

Ser Thr Ser Val Gly Asp Arg Val Ser Ile Thr Cys Arg Ala Ser Gln

-continued

```
            35                  40                  45
Asp Val Asn Thr Ala Val Ser Trp Tyr Gln Gln Lys Pro Gly Gln Ser
 50                  55                  60

Pro Lys Leu Leu Ile Phe Ser Ala Ser Tyr Arg Tyr Thr Gly Val Pro
 65                  70                  75                  80

Asp Arg Phe Thr Gly Ser Gly Ser Gly Ala Asp Phe Thr Leu Thr Ile
                 85                  90                  95

Ser Ser Val Gln Ala Glu Asp Leu Ala Val Tyr Tyr Cys Gln Gln His
                100                 105                 110

Tyr Ser Thr Pro Trp Thr Phe Gly Gly Gly Thr Lys Leu Asp Ile Lys
                115                 120                 125

Gly Gly Gly Gly Ser Gly Gly Gly Ser Gly Gly Gly Ser Gln
130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
                180                 185                 190

Trp Ile Asn Thr Tyr Thr Gly Glu Ser Tyr Phe Ala Asp Asp Phe Lys
                195                 200                 205

Gly Arg Phe Ala Phe Ser Val Glu Thr Ser Ala Thr Thr Ala Tyr Leu
210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
                290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
                355                 360                 365

Asp Phe Ala Ala Tyr Arg Ser Arg Val Lys Phe Ser Arg Ser Ala Asp
                370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
                450                 455                 460
```

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Tyr
            500                 505                 510

Arg Met Gln Leu Leu Ser Cys Ile Ala Leu Ser Leu Ala Leu Val Thr
        515                 520                 525

Asn Ser Tyr Phe Gly Lys Leu Glu Ser Lys Leu Ser Val Ile Arg Asn
    530                 535                 540

Leu Asn Asp Gln Val Leu Phe Ile Asp Gln Gly Asn Arg Pro Leu Phe
545                 550                 555                 560

Glu Asp Met Thr Asp Ser Asp Cys Arg Asp Asn Ala Pro Arg Thr Ile
                565                 570                 575

Phe Ile Ile Ser Met Tyr Lys Asp Ser Gln Pro Arg Gly Met Ala Val
            580                 585                 590

Thr Ile Ser Val Lys Cys Glu Lys Ile Ser Thr Leu Ser Cys Glu Asn
        595                 600                 605

Lys Ile Ile Ser Phe Lys Glu Met Asn Pro Pro Asp Asn Ile Lys Asp
    610                 615                 620

Thr Lys Ser Asp Ile Ile Phe Phe Gln Arg Ser Val Pro Gly His Asp
625                 630                 635                 640

Asn Lys Met Gln Phe Glu Ser Ser Ser Tyr Glu Gly Tyr Phe Leu Ala
                645                 650                 655

Cys Glu Lys Glu Arg Asp Leu Phe Lys Leu Ile Leu Lys Lys Glu Asp
            660                 665                 670

Glu Leu Gly Asp Arg Ser Ile Met Phe Thr Val Gln Asn Glu Asp Thr
        675                 680                 685

Thr Thr Pro Ala Pro Arg Pro Pro Thr Pro Ala Pro Thr Ile Ala Ser
    690                 695                 700

Gln Pro Leu Ser Leu Arg Pro Glu Ala Cys Arg Pro Ala Ala Gly Gly
705                 710                 715                 720

Ala Val His Thr Arg Gly Leu Asp Phe Ala Cys Asp Val Ala Ile Ser
                725                 730                 735

Thr Ser Thr Val Leu Leu Cys Gly Leu Ser Ala Val Ser Leu Leu Ala
            740                 745                 750

Cys Tyr

<210> SEQ ID NO 14
<211> LENGTH: 2273
<212> TYPE: DNA
<213> ORGANISM: Artificial Sequence
<220> FEATURE:
<223> OTHER INFORMATION: synthetic sequence

<400> SEQUENCE: 14
atggccttac cagtgaccgc cttgctcctg ccgctggcct tgctgctcca cgccgccagg    60
ccggacgtgg tgatgaccca gagccacagg ttcatgagca ccagcgtggg cgacagggtg   120
agcatcacct gcagggccag ccaggacgtg aacaccgccg tgagctggta ccagcagaag   180
cccggccaga gccccaagct gctgatcttc agcgccagct acaggtacac cggcgtgccc   240
gacaggttca ccggcagcgg cagcggcgcc gacttcaccc tgaccatcag cagcgtgcag   300
gccgaggacc tggccgtgta ctactgccag cagcactaca gcacccctg gaccttcggc   360

```
ggcggcacca agctggacat caagggaggg ggggatccg ggggaggagg ctccggcgga      420
ggcggaagcc agatccagct ggtgcagagc ggccccgacc tgaagaagcc cggcgagacc      480
gtgaagctga gctgcaaggc cagcggctac accttcacca acttcggcat gaactgggtg      540
aagcaggccc ccggcaaggg cttcaagtgg atggcctgga tcaacaccta caccggcgag      600
agctacttcg ccgacgactt caagggcagg ttcgccttca gcgtggagac cagcgccacc      660
accgcctacc tgcagatcaa caacctgaag accgaggaca ccgccaccta cttctgcgcc      720
aggggcgaga tctactacgg ctacgacggc ggcttcgcct actggggcca gggcaccctg      780
gtgaccgtga gcgccaccac gacgccagcg ccgcgaccac caacaccggc gcccaccatc      840
gcgtcgcagc ccctgtccct gcgcccagag gcgtgccggc cagcggcggg gggcgcagtg      900
cacacgaggg ggctggactt cgcctgtgat atctacatct gggcgccctt ggccgggact      960
tgtggggtcc ttctcctgtc actggttatc acccttact gcaggagtaa gaggagcagg     1020
ctcctgcaca gtgactacat gaacatgact ccccgccgcc cgggcccac ccgcaagcat     1080
taccagccct atgccccacc acgcgacttc gcagcctatc gctccagagt gaagttcagc     1140
aggagcgcag acgccccgc gtaccagcag ggccagaacc agctctataa cgagctcaat     1200
ctaggacgaa gagaggagta cgatgttttg acaagagac gtggccggga ccctgagatg     1260
gggggaaagc cgcagagaag gaagaaccct caggaaggcc tgtacaatga actgcagaaa     1320
gataagatgg cggaggccta cagtgagatt gggatgaaag cgagcgccg gaggggcaag     1380
ggcacgatg gcctttacca gggtctcagt acagccacca aggacaccta cgacgccctt     1440
cacatgcagg ccctgccccc tcgcggaagc ggagccacca cttcagcct gctgaagcag     1500
gccggcgacg tggaggagaa ccccggcccc atgtacagaa tgcagctgct gagctgcatc     1560
gccctgagcc tggccctggt gaccaacagc tacttcggca gctggagag caagctgagc     1620
gtgatcagga acctgaacga ccaggtgctg ttcatcgacc agggcaacag gcccctgttc     1680
gaggacatga ccgacagcga ctgcagggac aacgccccca ggaccatctt catcatcagc     1740
atgtacaagg acagccagcc cagggcatg gccgtgacca tcagcgtgaa gtgcgagaag     1800
atcagcaccc tgagctgcga aacaagatc atcagcttca aggagatgaa ccccccgac     1860
aacatcaagg acaccaagag cgacatcatc ttcttccaga ggagcgtgcc cggccacgac     1920
aacaagatgc agttcgagag cagcagctac gagggctact cctggcctg cgagaaggag     1980
agggacctgt tcaagctgat cctgaagaag gaggacgagc tgggcgacag gagcatcatg     2040
ttcaccgtgc agaacgagga caccaccacc ccgcccccca gccccccac ccccgccccc     2100
accatcgcca gccagcccct gagcctgagg cccgaggcct gcaggccgc cgccggcggc     2160
gccgtgcaca ccaggggcct ggacttcgcc tgcgacgtgg ctatctccac gtccactgtc     2220
ctgctgtgtg ggctgagcgc tgtgtctctc ctggcatgct actaagttta aac           2273
```

<210> SEQ ID NO 15
<211> LENGTH: 258
<212> TYPE: PRT
<213> ORGANISM: Artificial Sequence
<220> FEATURE:
<223> OTHER INFORMATION: synthetic sequence

<400> SEQUENCE: 15

```
Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30
```

```
Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
 50                  55                  60

Gln Pro Leu Met Lys Leu Gly Thr Gln Thr Val Pro Cys Asn Lys Ile
 65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Thr Leu Leu Gly Tyr Leu Ala
                100                 105                 110

Asp Asp Leu Thr Trp Cys Gly Glu Phe Asn Thr Ser Lys Ile Asn Tyr
                115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
                180                 185                 190

Val Gln Thr Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
            210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 16
<211> LENGTH: 667
<212> TYPE: PRT
<213> ORGANISM: Artificial Sequence
<220> FEATURE:
<223> OTHER INFORMATION: synthetic sequence

<400> SEQUENCE: 16

Met Ala Leu Pro Val Thr Ala Leu Leu Leu Pro Leu Ala Leu Leu Leu
 1               5                  10                  15

His Ala Ala Arg Pro Glu Val Gln Leu Gln Gln Ser Gly Pro Glu Leu
                20                  25                  30

Ile Lys Pro Gly Ala Ser Val Lys Met Ser Cys Lys Ala Ser Gly Tyr
            35                  40                  45

Thr Phe Thr Ser Tyr Val Met His Trp Val Lys Gln Lys Pro Gly Gln
 50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
                100                 105                 110

Ala Val Tyr Tyr Cys Ala Arg Gly Thr Tyr Tyr Tyr Gly Ser Arg Val
            115                 120                 125
```

```
Phe Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
                245                 250                 255

Pro Phe Thr Phe Gly Ala Gly Thr Lys Leu Glu Leu Lys Arg Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Gln Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Ser Gly
                485                 490                 495

Glu Gly Arg Gly Ser Leu Leu Thr Cys Gly Asp Val Glu Glu Asn Pro
            500                 505                 510

Gly Pro Met Tyr Arg Met Gln Leu Leu Ser Cys Ile Ala Leu Ser Leu
        515                 520                 525

Ala Leu Val Thr Asn Ser Gln Gly Gln Asp Arg His Met Ile Arg Met
530                 535                 540

Arg Gln Leu Ile Asp Ile Val Asp Gln Leu Lys Asn Tyr Val Asn Asp
```

```
                545                 550                 555                 560
Leu Val Pro Glu Phe Leu Pro Ala Pro Glu Asp Val Glu Thr Asn Cys
                565                 570                 575

Glu Trp Ser Ala Phe Ser Cys Phe Gln Lys Ala Gln Leu Lys Ser Ala
                580                 585                 590

Asn Thr Gly Asn Asn Glu Arg Ile Ile Asn Val Ser Ile Lys Lys Leu
                595                 600                 605

Lys Arg Lys Pro Pro Ser Thr Asn Ala Gly Arg Arg Gln Lys His Arg
        610                 615                 620

Leu Thr Cys Pro Ser Cys Asp Ser Tyr Glu Lys Lys Pro Pro Lys Glu
625                 630                 635                 640

Phe Leu Glu Arg Phe Lys Ser Leu Leu Gln Lys Met Ile His Gln His
                645                 650                 655

Leu Ser Ser Arg Thr His Gly Ser Glu Asp Ser
        660                 665

<210> SEQ ID NO 17
<211> LENGTH: 2012
<212> TYPE: DNA
<213> ORGANISM: Artificial Sequence
<220> FEATURE:
<223> OTHER INFORMATION: synthetic sequence

<400> SEQUENCE: 17
```

| | | | | | |
|---|---|---|---|---|---|
| atggccttac | cagtgaccgc | cttgctcctg | ccgctggcct | tgctgctcca | cgccgccagg | 60 |
| ccggaggtcc | agctgcagca | gtctggacct | gagctgataa | agcctggggc | ttcagtgaag | 120 |
| atgtcctgca | aggcttctgg | atacacattc | actagctatg | ttatgcactg | ggtgaagcag | 180 |
| aagcctgggc | agggccttga | gtggattgga | tatattaatc | cttacaatga | tggtactaag | 240 |
| tacaatgaga | agttcaaagg | caaggccaca | ctgacttcag | acaaatcctc | cagcacagcc | 300 |
| tacatggagc | tcagcagcct | gacctctgag | gactctgcgg | tctattactg | tgcaagaggg | 360 |
| acttattact | acggtagtag | ggtatttgac | tactggggcc | aaggcaccac | tctcacagtc | 420 |
| tcctcaggtg | agggggctc | aggcggaggt | ggctctgggg | gtggaggctc | ggacattgtg | 480 |
| atgactcagg | ctgcacccte | tatacctgtc | actcctggag | agtcagtatc | catctcctgc | 540 |
| aggtctagta | agagtctcct | gaatagtaat | ggcaacactt | acttgtattg | gttcctgcag | 600 |
| aggccaggcc | agtctcctca | gctcctgata | tatcggatgt | ccaaccttgc | ctcaggagtc | 660 |
| ccagacaggt | tcagtggcag | tgggtcagga | actgctttca | cactgagaat | cagtagagtg | 720 |
| gaggctgagg | atgtgggtgt | ttattactgt | atgcaacatc | tagaatatcc | gttcacgttc | 780 |
| ggtgctggga | ccaagctgga | gctgaaacgg | accacgacgc | cagcgccgcg | accaccaaca | 840 |
| ccggcgccca | ccatcgcgtc | gcagcccctg | tccctgcgcc | cagaggcgtg | ccggccagcg | 900 |
| gcggggggcg | cagtgcacac | gagggggctg | gacttcgcct | gtgatatcta | catctgggcg | 960 |
| cccttggccg | ggacttgtgg | ggtccttctc | ctgtcactgg | ttatcaccct | ttactgcagg | 1020 |
| agtaagagga | gcaggctcct | gcacagtgac | tacatgaaca | tgactccccg | ccgccccggg | 1080 |
| cccacccgca | agcattacca | gccctatgcc | ccaccgcgcg | acttcgcagc | ctatcgctcc | 1140 |
| agagtgaagt | tcagcaggag | cgcagacgcc | cccgcgtacc | agcagggcca | gaaccagctc | 1200 |
| tataacgagc | tcaatctagg | acgaagagag | gagtacgatg | ttttggacaa | gagacgtggc | 1260 |
| cgggaccctg | agatgggggg | aaagccgcag | agaaggaaga | accctcagga | aggcctgtac | 1320 |
| aatgaactgc | agaaagataa | gatggcggag | gcctacagtg | agattgggat | gaaaggcgag | 1380 |

```
cgccggaggg gcaaggggca cgatggcctt taccagggtc tcagtacagc caccaaggac   1440
acctacgacg cccttcacat gcaggccctg cccctcgcg gcagcggcga aggccgcggc   1500
agcctgctga cctgcggcga tgtggaagaa aacccgggcc ccatgtacag aatgcagctg   1560
ctgagctgca tcgccctgag cctggccctg gtgaccaaca gccagggcca ggacaggcac   1620
atgatcagga tgaggcagct gatcgacatc gtggaccagc tgaagaacta cgtgaacgac   1680
ctggtgcccg agttcctgcc cgccccgag gacgtggaga ccaactgcga gtggagcgcc   1740
ttcagctgct tccagaaggc ccagctgaag agcgccaaca ccggcaacaa cgagaggatc   1800
atcaacgtga gcatcaagaa gctgaagagg aagcccccca gcaccaacgc cggcaggagg   1860
cagaagcaca ggctgaccctg ccccagctgc gacagctacg agaagaagcc ccccaaggag   1920
ttcctggaga ggttcaagag cctgctgcag aagatgatcc accagcacct gagcagcagg   1980
acccacggca gcgaggacag ctaagtttaa ac                                  2012
```

<210> SEQ ID NO 18
<211> LENGTH: 1000
<212> TYPE: PRT
<213> ORGANISM: Artificial Sequence
<220> FEATURE:
<223> OTHER INFORMATION: synthetic sequence

<400> SEQUENCE: 18

```
Met Ala Leu Pro Val Thr Ala Leu Leu Leu Pro Leu Ala Leu Leu Leu
1               5                   10                  15

His Ala Ala Arg Pro Asp Ile Gln Val Thr Gln Ser Pro Ser Ser Leu
            20                  25                  30

Ser Ala Ser Leu Gly Glu Arg Ile Ser Leu Thr Cys Arg Thr Ser Gln
        35                  40                  45

Asp Ile Ser Asn Tyr Leu Asn Trp Phe Gln Gln Lys Pro Asp Gly Thr
    50                  55                  60

Phe Lys Arg Leu Ile Tyr Ala Thr Ser Ser Leu Asp Ser Gly Val Pro
65                  70                  75                  80

Lys Arg Phe Ser Gly Ser Gly Ser Gly Ser Asp Tyr Ser Leu Thr Ile
                85                  90                  95

Ser Ser Leu Glu Ser Glu Asp Phe Ala Asp Tyr Tyr Cys Leu Gln Tyr
            100                 105                 110

Ala Ser Tyr Pro Phe Thr Phe Gly Ser Gly Thr Lys Leu Glu Ile Lys
        115                 120                 125

Gly Gly Gly Gly Ser Gly Gly Gly Ser Gly Gly Gly Ser Glu
    130                 135                 140

Val Gln Leu Gln Glu Ser Gly Pro Gly Leu Val Lys Pro Ser Gln Thr
145                 150                 155                 160

Leu Ser Leu Thr Cys Ser Val Thr Gly Tyr Ser Ile Thr Ser Gly Tyr
                165                 170                 175

Tyr Trp His Trp Ile Arg Gln Phe Pro Gly Asn Lys Leu Gln Trp Met
            180                 185                 190

Gly Tyr Ile Ser Tyr Ser Gly Phe Thr Asn Tyr Lys Thr Ser Leu Ile
        195                 200                 205

Asn Arg Ile Ser Ile Thr His Asp Thr Ser Glu Asn Gln Phe Phe Leu
    210                 215                 220

Asn Leu Asn Ser Val Thr Thr Glu Asp Thr Ala Thr Tyr Tyr Cys Ala
225                 230                 235                 240

Gly Asp Arg Thr Gly Ser Trp Phe Ala Tyr Trp Gly Gln Gly Thr Leu
                245                 250                 255
```

```
Val Thr Val Ser Ala Thr Thr Pro Ala Pro Arg Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
            355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
                405                 410                 415

Gly Gly Lys Pro Gln Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg Gly Ser Gly Ala Thr Asn Phe Ser Leu Leu Lys Gln
            485                 490                 495

Ala Gly Asp Val Glu Glu Asn Pro Gly Pro Met Ala Leu Pro Val Thr
            500                 505                 510

Ala Leu Leu Leu Pro Leu Ala Leu Leu Leu His Ala Ala Arg Pro Asp
        515                 520                 525

Ile Glu Leu Thr Gln Ser Pro Ser Ser Phe Ser Val Ser Leu Gly Asp
530                 535                 540

Arg Val Thr Ile Thr Cys Lys Ala Ser Glu Asp Ile Tyr Asn Arg Leu
545                 550                 555                 560

Ala Trp Tyr Gln Gln Lys Pro Gly Asn Ala Pro Arg Leu Leu Ile Ser
            565                 570                 575

Gly Ala Thr Ser Leu Glu Thr Gly Val Pro Ser Arg Phe Ser Gly Ser
            580                 585                 590

Gly Ser Gly Lys Asp Tyr Thr Leu Ser Ile Thr Ser Leu Gln Thr Glu
        595                 600                 605

Asp Val Ala Thr Tyr Tyr Cys Gln Gln Tyr Trp Ser Thr Pro Thr Phe
    610                 615                 620

Gly Gly Gly Thr Lys Leu Glu Ile Lys Arg Ala Ala Gly Gly Gly Gly
625                 630                 635                 640

Ser Gly Gly Gly Gly Ser Gly Gly Gly Ser Ala Gln Pro Ala Met
            645                 650                 655

Ala Lys Val Gln Leu Gln Glu Ser Gly Pro Ser Leu Val Gln Pro Ser
            660                 665                 670
```

| | | | | | | | | | | | |
|---|---|---|---|---|---|---|---|---|---|---|---|
|Gln|Arg|Leu|Ser|Ile|Thr|Cys|Thr|Val|Ser|Gly|Phe|Ser|Leu|Ile|Ser|
| | |675| | | |680| | | |685| |

Gln Arg Leu Ser Ile Thr Cys Thr Val Ser Gly Phe Ser Leu Ile Ser
              675                 680                 685

Tyr Gly Val His Trp Val Arg Gln Ser Pro Gly Lys Gly Leu Glu Trp
        690                 695                 700

Leu Gly Val Ile Trp Arg Gly Gly Ser Thr Asp Tyr Asn Ala Ala Phe
705                 710                 715                 720

Met Ser Arg Leu Ser Ile Thr Lys Asp Asn Ser Lys Ser Gln Val Phe
                725                 730                 735

Phe Lys Met Asn Ser Leu Gln Ala Asp Asp Thr Ala Ile Tyr Phe Cys
            740                 745                 750

Ala Lys Thr Leu Ile Thr Thr Gly Tyr Ala Met Asp Tyr Trp Gly Gln
        755                 760                 765

Gly Thr Thr Val Thr Val Ser Ser Thr Thr Thr Pro Ala Pro Arg Pro
770                 775                 780

Pro Thr Pro Ala Pro Thr Ile Ala Ser Gln Pro Leu Ser Leu Arg Pro
785                 790                 795                 800

Glu Ala Cys Arg Pro Ala Ala Gly Gly Ala Val His Thr Arg Gly Leu
                805                 810                 815

Asp Phe Ala Cys Asp Ile Tyr Ile Trp Ala Pro Leu Ala Gly Thr Cys
            820                 825                 830

Gly Val Leu Leu Leu Ser Leu Val Ile Thr Leu Tyr Cys Lys Arg Gly
        835                 840                 845

Arg Lys Lys Leu Leu Tyr Ile Phe Lys Gln Pro Phe Met Arg Pro Val
850                 855                 860

Gln Thr Thr Gln Glu Glu Asp Gly Cys Ser Cys Arg Phe Pro Glu Glu
865                 870                 875                 880

Glu Glu Gly Gly Cys Glu Leu Arg Val Lys Phe Ser Arg Ser Ala Asp
                885                 890                 895

Ala Pro Ala Tyr Gln Gln Gly Gln Asn Gln Leu Tyr Asn Glu Leu Asn
            900                 905                 910

Leu Gly Arg Arg Glu Glu Tyr Asp Val Leu Asp Lys Arg Arg Gly Arg
        915                 920                 925

Asp Pro Glu Met Gly Gly Lys Pro Gln Arg Arg Lys Asn Pro Gln Glu
930                 935                 940

Gly Leu Tyr Asn Glu Leu Gln Lys Asp Lys Met Ala Glu Ala Tyr Ser
945                 950                 955                 960

Glu Ile Gly Met Lys Gly Glu Arg Arg Arg Gly Lys Gly His Asp Gly
                965                 970                 975

Leu Tyr Gln Gly Leu Ser Thr Ala Thr Lys Asp Thr Tyr Asp Ala Leu
            980                 985                 990

His Met Gln Ala Leu Pro Pro Arg
        995                 1000

<210> SEQ ID NO 19
<211> LENGTH: 3011
<212> TYPE: DNA
<213> ORGANISM: Artificial Sequence
<220> FEATURE:
<223> OTHER INFORMATION: synthetic sequence

<400> SEQUENCE: 19 atggcttac cagtgaccgc cttgctcctg ccgctggcct tgctgctcca cgccgccagg    60
ccggacatcc aggtgaccca gagccccagc agcctgagcg ccagcctggg cgagagaatc   120
agcctgacct gcagaaccag ccaggacatc agcaactacc tgaactggtt ccagcagaag   180

```
cccgacggca ccttcaagag actgatctac gccaccagca gcctggacag cggcgtgccc      240
aagagattca gcggcagcgg cagcggcagc gactacagcc tgaccatcag cagcctggag      300
agcgaggact cgccgactac tactgcctg cagtacgcca gctaccctt caccttcggc       360 agcggcacca agctggagat caagggaggg ggggatccg ggggaggagg ctccggcgga      420
ggcggaagcg aggtgcagct gcaggagagc ggccccggcc tggtgaagcc cagccagacc      480
ctgagcctga cctgcagcgt gaccggctac agcatcacca gcggctacta ctggcactgg      540
atcagacagt tccccggcaa caagctgcag tggatgggct acatcagcta cagcggcttc      600
accaactaca agaccagcct gatcaacaga atcagcatca cccacgacac cagcgagaac      660
cagttcttcc tgaacctgaa cagcgtgacc accgaggaca ccgccaccta ctactgcgcc      720
ggcgacagaa ccggcagctg gttcgcctac tggggccagg gcaccctggt gaccgtgagc      780
gccaccacga cgccagcgcc gcgaccacca acaccggcgc caccatcgc gtcgcagccc      840 ctgtccctgc gcccagaggc gtgccggcca cggcggggg gcgcagtgca cacgaggggg      900
ctggacttcg cctgtgatat ctacatctgg gcgcccttgg ccgggacttg tggggtcctt      960
ctcctgtcac tggttatcac cctttactgc aggagtaaga ggagcaggct cctgcacagt     1020
gactacatga acatgactcc ccgccgcccc gggcccaccc gcaagcatta ccagccctat     1080
gccccaccac gcgacttcgc agcctatcgc tccagagtga agttcagcag gagcgcagac     1140
gcccccgcgt accagcaggg ccagaaccag ctctataacg agctcaatct aggacgaaga     1200
gaggagtacg atgttttgga caagagacgt ggccgggacc ctgagatggg gggaaagccg     1260
cagagaagga agaaccctca ggaaggcctg tacaatgaac tgcagaaaga taagatggcg     1320
gaggcctaca gtgagattgg gatgaaaggc gagcgccgga ggggcaaggg gcacgatggc     1380
ctttaccagg gtctcagtac agccaccaag gacacctacg acgcccttca catgcaggcc     1440 ctgcccccctc gcggaagcgg agccaccaac ttcagcctgc tgaagcaggc cggcgacgtg     1500
gaggagaacc ccgccccat ggccctgccc gtgaccgccc tgctgctgcc cctggccctg     1560
ctgctgcacg ccgccaggcc cgacatcgag ctgacccaga gccccagcag cttcagcgtg     1620
agcctgggcg acagggtgac catcacctgc aaggccagcg aggacatcta caacaggctg     1680
gcctggtacc agcagaagcc cggcaacgcc cccaggctgc tgatcagcgg cgccaccagc     1740
ctggagaccg gcgtgcccag caggttcagc ggcagcggca gcggcaagga ctacaccctg     1800
agcatcacca gcctgcagac cgaggacgtg gccacctact actgccagca gtactggagc     1860 accccccacct tcggcggcgg caccaagctg gagatcaaga gggccgccgg cggcggcggc     1920
agcggcggcg gcggcagcgg cggcggcggc agcgcccagc ccgccatggc caaggtgcag     1980
ctgcaggaga gcgccccag cctggtgcag cccagccaga ggctgagcat cacctgcacc     2040
gtgagcggct tcagcctgat cagctacggc gtgcactggg tgaggcagag ccccggcaag     2100
ggcctggagt ggctgggcgt gatctggagg ggcggcagca ccgactacaa cgccgccttc     2160
atgagcaggc tgagcatcac caaggacaac agcaagagcc aggtgttctt caagatgaac     2220
agcctgcagg ccgacgacac cgccatctac ttctgcgcca gaccctgat caccaccggc     2280 tacgccatgg actactgggg ccagggcacc accgtgaccg tgagcagcac caccaccccc     2340
gcccccaggc cccccacccc cgcccccacc atcgccagcc agcccctgag cctgaggccc     2400
gaggcctgca ggcccgccgc cggcggcgcc gtgcacacca ggggcctgga cttcgcctgc     2460
gacatctaca tctgggcccc cctggccggc acctgcggcg tgctgctgct gagcctggtg     2520
atcaccctgt actgcaaacg gggcagaaag aaactcctgt atatattcaa acaaccattt     2580
```

-continued

```
atgagaccag tacaaactac tcaagaggaa gatggctgta gctgccgatt ccagaagaa      2640 gaagaaggag gatgtgaact gagggtgaag ttcagcagga gcgccgacgc ccccgcctac      2700
cagcagggcc agaaccagct gtacaacgag ctgaacctgg gcaggaggga ggagtacgac      2760
gtgctggaca gaggaggggg cagggacccc gagatgggcg gcaagcccca gaggaggaag      2820
aacccccagg agggcctgta caacgagctg cagaaggaca gatggccga ggcctacagc      2880 gagatcggca tgaagggcga gaggaggagg ggcaagggcc acgacggcct gtaccagggc      2940
ctgagcaccg ccaccaagga cacctacgac gccctgcaca tgcaggccct gccccccagg      3000
taagtttaaa c                                                           3011
```

<210> SEQ ID NO 20
<211> LENGTH: 1001
<212> TYPE: PRT
<213> ORGANISM: Artificial Sequence
<220> FEATURE:
<223> OTHER INFORMATION: synthetic sequence

<400> SEQUENCE: 20

```
Met Ala Leu Pro Val Thr Ala Leu Leu Leu Pro Leu Ala Leu Leu Leu
1               5                   10                  15

His Ala Ala Arg Pro Asp Ile Val Leu Ser Gln Ser Pro Ala Ile Leu
            20                  25                  30

Ser Ala Ser Pro Gly Glu Lys Val Thr Met Thr Cys Arg Ala Ser Ser
        35                  40                  45

Ser Val Ser Tyr Met His Trp Tyr Gln Gln Lys Pro Gly Ser Ser Pro
    50                  55                  60

Lys Pro Trp Ile Tyr Ala Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Val Glu Ala Glu Asp Ala Ala Thr Tyr Tyr Cys Gln Gln Trp Ile
            100                 105                 110

Ser Asn Pro Pro Thr Phe Gly Ala Gly Thr Lys Gly Gly Gly Gly Ser
        115                 120                 125

Gly Gly Gly Gly Ser Gly Gly Gly Ser Leu Glu Leu Lys Gln Val
    130                 135                 140

Gln Leu Val Gln Ser Gly Ala Glu Leu Val Lys Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Gly Gln Gly Leu Glu Trp Ile Gly Ala
            180                 185                 190

Ile Tyr Pro Gly Asn Gly Asp Thr Ser Tyr Asn Gln Lys Phe Lys Gly
        195                 200                 205

Lys Ala Thr Leu Thr Ala Asp Lys Ser Ser Ser Thr Ala Tyr Met Gln
    210                 215                 220

Leu Ser Ser Leu Thr Ser Glu Asp Ser Ala Val Tyr Tyr Cys Ala Arg
225                 230                 235                 240

Ala Gln Leu Arg Pro Asn Tyr Trp Tyr Phe Asp Val Trp Gly Ala Gly
                245                 250                 255

Thr Thr Val Thr Val Ser Thr Thr Pro Ala Pro Arg Pro Pro Thr
            260                 265                 270

Pro Ala Pro Thr Ile Ala Ser Gln Pro Leu Ser Leu Arg Pro Glu Ala
```

-continued

```
            275                 280                 285
Cys Arg Pro Ala Ala Gly Gly Ala Val His Thr Arg Gly Leu Asp Phe
290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Arg Ser Lys Arg Ser
                325                 330                 335
Arg Leu Leu His Ser Asp Tyr Met Asn Met Thr Pro Arg Arg Pro Gly
                340                 345                 350
Pro Thr Arg Lys His Tyr Gln Pro Tyr Ala Pro Pro Arg Asp Phe Ala
                355                 360                 365
Ala Tyr Arg Ser Arg Val Lys Phe Ser Arg Ser Ala Asp Ala Pro Ala
370                 375                 380
Tyr Gln Gln Gly Gln Asn Gln Leu Tyr Asn Glu Leu Asn Leu Gly Arg
385                 390                 395                 400
Arg Glu Glu Tyr Asp Val Leu Asp Lys Arg Gly Arg Asp Pro Glu
                405                 410                 415
Met Gly Gly Lys Pro Gln Arg Arg Lys Asn Pro Gln Glu Gly Leu Tyr
                420                 425                 430
Asn Glu Leu Gln Lys Asp Lys Met Ala Glu Ala Tyr Ser Glu Ile Gly
                435                 440                 445
Met Lys Gly Glu Arg Arg Arg Gly Lys Gly His Asp Gly Leu Tyr Gln
450                 455                 460
Gly Leu Ser Thr Ala Thr Lys Asp Thr Tyr Asp Ala Leu His Met Gln
465                 470                 475                 480
Ala Leu Pro Pro Arg Gly Ser Gly Ala Thr Asn Phe Ser Leu Leu Lys
                485                 490                 495
Gln Ala Gly Asp Val Glu Glu Asn Pro Gly Pro Met Ala Leu Pro Val
                500                 505                 510
Thr Ala Leu Leu Leu Pro Leu Ala Leu Leu Leu His Ala Ala Arg Pro
                515                 520                 525
Glu Val Gln Leu Gln Gln Ser Gly Pro Glu Leu Ile Lys Pro Gly Ala
530                 535                 540
Ser Val Lys Met Ser Cys Lys Ala Ser Gly Tyr Thr Phe Thr Ser Tyr
545                 550                 555                 560
Val Met His Trp Val Lys Gln Lys Pro Gly Gln Gly Leu Glu Trp Ile
                565                 570                 575
Gly Tyr Ile Asn Pro Tyr Asn Asp Gly Thr Lys Tyr Asn Glu Lys Phe
                580                 585                 590
Lys Gly Lys Ala Thr Leu Thr Ser Asp Lys Ser Ser Ser Thr Ala Tyr
                595                 600                 605
Met Glu Leu Ser Ser Leu Thr Ser Glu Asp Ser Ala Val Tyr Tyr Cys
                610                 615                 620
Ala Arg Gly Thr Tyr Tyr Tyr Gly Ser Arg Val Phe Asp Tyr Trp Gly
625                 630                 635                 640
Gln Gly Thr Thr Leu Thr Val Ser Ser Gly Gly Gly Ser Gly Gly
                645                 650                 655
Gly Gly Ser Gly Gly Gly Gly Ser Asp Ile Val Met Thr Gln Ala Ala
                660                 665                 670
Pro Ser Ile Pro Val Thr Pro Gly Glu Ser Val Ser Ile Ser Cys Arg
                675                 680                 685
Ser Ser Lys Ser Leu Leu Asn Ser Asn Gly Asn Thr Tyr Leu Tyr Trp
                690                 695                 700
```

```
Phe Leu Gln Arg Pro Gly Gln Ser Pro Gln Leu Leu Ile Tyr Arg Met
705                 710                 715                 720

Ser Asn Leu Ala Ser Gly Val Pro Asp Arg Phe Ser Gly Ser Gly Ser
            725                 730                 735

Gly Thr Ala Phe Thr Leu Arg Ile Ser Arg Val Glu Ala Glu Asp Val
        740                 745                 750

Gly Val Tyr Tyr Cys Met Gln His Leu Glu Tyr Pro Phe Thr Phe Gly
    755                 760                 765

Ala Gly Thr Lys Leu Glu Leu Lys Arg Thr Thr Thr Pro Ala Pro Arg
770                 775                 780

Pro Pro Thr Pro Ala Pro Thr Ile Ala Ser Gln Pro Leu Ser Leu Arg
785                 790                 795                 800

Pro Glu Ala Cys Arg Pro Ala Ala Gly Gly Ala Val His Thr Arg Gly
            805                 810                 815

Leu Asp Phe Ala Cys Asp Ile Tyr Ile Trp Ala Pro Leu Ala Gly Thr
        820                 825                 830

Cys Gly Val Leu Leu Leu Ser Leu Val Ile Thr Leu Tyr Cys Lys Arg
    835                 840                 845

Gly Arg Lys Lys Leu Leu Tyr Ile Phe Lys Gln Pro Phe Met Arg Pro
850                 855                 860

Val Gln Thr Thr Gln Glu Glu Asp Gly Cys Ser Cys Arg Phe Pro Glu
865                 870                 875                 880

Glu Glu Glu Gly Gly Cys Glu Leu Arg Val Lys Phe Ser Arg Ser Ala
            885                 890                 895

Asp Ala Pro Ala Tyr Gln Gln Gly Gln Asn Gln Leu Tyr Asn Glu Leu
        900                 905                 910

Asn Leu Gly Arg Arg Glu Glu Tyr Asp Val Leu Asp Lys Arg Arg Gly
    915                 920                 925

Arg Asp Pro Glu Met Gly Gly Lys Pro Gln Arg Arg Lys Asn Pro Gln
930                 935                 940

Glu Gly Leu Tyr Asn Glu Leu Gln Lys Asp Lys Met Ala Glu Ala Tyr
945                 950                 955                 960

Ser Glu Ile Gly Met Lys Gly Glu Arg Arg Arg Gly Lys Gly His Asp
            965                 970                 975

Gly Leu Tyr Gln Gly Leu Ser Thr Ala Thr Lys Asp Thr Tyr Asp Ala
        980                 985                 990

Leu His Met Gln Ala Leu Pro Pro Arg
        995                 1000

<210> SEQ ID NO 21
<211> LENGTH: 3014
<212> TYPE: DNA
<213> ORGANISM: Artificial Sequence
<220> FEATURE:
<223> OTHER INFORMATION: synthetic sequence

<400> SEQUENCE: 21
atggccttac cagtgaccgc cttgctcctg ccgctggcct tgctgctcca cgccgccagg    60
ccggacatcg tgctgagcca gagccccgcc atcctgagcg ccagccccgg cgagaaggtg   120
accatgacct gcagggccag cagcagcgtg agctacatgc actggtacca gcagaagccc   180
ggcagcagcc ccaagccctg gatctacgcc accagcaacc tggccagcgg cgtgcccgcc   240
aggttcagcg gcagcggcag cggcaccagc tacagcctga ccatcagcag ggtggaggcc   300
gaggacgccg ccacctacta ctgccagcag tggatcagca cccccccac cttcggcgcc   360
```

-continued

```
ggcaccaagg gcggcggcgg cagcggcggc ggcggcagcg gcggcggcgg cagcctggag    420
ctgaagcagg tgcagctggt gcagagcggc gccgagctgg tgaagcccgg cgccagcgtg    480
aagatgagct gcaaggccag cggctacacc ttcaccagct acaacatgca ctgggtgaag    540
cagacccccg gccagggcct ggagtggatc ggcgccatct accccggcaa cggcgacacc    600
agctacaacc agaagttcaa gggcaaggcc accctgaccg ccgacaagag cagcagcacc    660
gcctacatgc agctgagcag cctgaccagc gaggacagcg ccgtgtacta ctgcgccagg    720
gcccagctga ggcccaacta ctggtacttc gacgtgtggg gcgccggcac caccgtgacc    780
gtgagcacca cgacgccagc gccgcgacca ccaacaccgg cgcccaccat cgcgtcgcag    840
cccctgtccc tgcgcccaga ggcgtgccgg ccagcggcgg ggggcgcagt gcacacgagg    900
gggctggact tcgcctgtga tatctacatc tgggcgccct tggccgggac ttgtggggtc    960
cttctcctgt cactggttat cacccttac tgcaggagta agaggagcag gctcctgcac   1020
agtgactaca tgaacatgac tccccgccgc cccgggccca cccgcaagca ttaccagccc   1080
tatgccccac cacgcgactt cgcagcctat cgctccagag tgaagttcag caggagcgca   1140
gacgcccccg cgtaccagca gggccagaac cagctctata cgagctcaa tctaggacga   1200 agagaggagt acgatgtttt ggacaagaga cgtggccggg accctgagat gggggaaag    1260 ccgcagagaa ggaagaaccc tcaggaaggc ctgtacaatg aactcagaaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgcggaag cggagccacc aacttcagcc tgctgaagca ggccggcgac   1500
gtggaggaga ccccggccc catggccctg cccgtgaccg ccctgctgct gccctggcc    1560 ctgctgctgc acgccgccag gcccgaggtc cagctgcagc agtctggacc tgagctgata   1620
aagcctgggg cttcagtgaa gatgtcctgc aaggcttctg gatacacatt cactagctat   1680
gttatgcact gggtgaagca gaagcctggg cagggccttg agtggattgg atatattaat   1740
ccttacaatg atggtactaa gtacaatgag aagttcaaag gcaaggccac actgacttca   1800
gacaaatcct ccagcacagc ctacatggag ctcagcagcc tgacctctga ggactctgcg   1860
gtctattact gtgcaagagg gacttattac tacggtagta gggtatttga ctactggggc   1920
caaggcacca ctctcacagt ctcctcaggt ggagggggct caggcggagg tggctctggg   1980
ggtggaggct cggacattgt gatgactcag gctgcaccct ctatacctgt cactcctgga   2040
gagtcagtat ccatctcctg caggtctagt aagagtctcc tgaatagtaa tggcaacact   2100
tacttgtatt ggttcctgca gaggccaggc cagtctcctc agctcctgat atatcggatg   2160
tccaaccttg cctcaggagt cccagacagg ttcagtggca gtgggtcagg aactgctttc   2220
acactgagaa tcagtagagt ggaggctgag gatgtgggtg tttattactg tatgcaacat   2280
ctagaatatc cgttcacgtt cggtgctggg accaagctgg agctgaaacg gaccaccacc   2340
cccgccccca ggccccccac cccgccccc accatcgcca gcagccccct gagcctgagg   2400
cccgaggcct gcaggcccgc cgccggcggc gccgtgcaca ccaggggcct ggacttcgcc   2460
tgcgacatct acatctgggc ccccctggcc ggcacctgcg gcgtgctgct gctgagcctg   2520
gtgatcaccc tgtactgcaa cgggcagaa agaaactcc tgtatatatt caaacaacca   2580
tttatgagac cagtacaaac tactcaagag gaagatggct gtagctgccg atttccagaa   2640
gaagaagaag aggatgtgaa actgagggtg aagttcagca ggagcgccga cgcccccgcc   2700
```

-continued

```
taccagcagg gccagaacca gctgtacaac gagctgaacc tgggcaggag ggaggagtac    2760
gacgtgctgg acaagaggag gggcagggac cccgagatgg gcggcaagcc ccagaggagg    2820
aagaaccccc aggagggcct gtacaacgag ctgcagaagg acaagatggc cgaggcctac    2880
agcgagatcg gcatgaaggg cgagaggagg aggggcaagg ccacgacgg cctgtaccag    2940 ggcctgagca ccgccaccaa ggacacctac gacgccctgc acatgcaggc cctgccccc    3000 aggtaagttt aaac                                                     3014
```

```
<210> SEQ ID NO 22
<211> LENGTH: 1003
<212> TYPE: PRT
<213> ORGANISM: Artificial Sequence
<220> FEATURE:
<223> OTHER INFORMATION: synthetic sequence

<400> SEQUENCE: 22

Met Ala Leu Pro Val Thr Ala Leu Leu Leu Pro Leu Ala Leu Leu Leu
 1               5                  10                  15

His Ala Ala Arg Pro Asp Ile Gln Leu Thr Gln Ser Pro Ser Ser Leu
                20                  25                  30

Ser Ala Ser Val Gly Asp Arg Val Thr Met Thr Cys Arg Ala Ser Ser
            35                  40                  45

Ser Val Ser Tyr Ile His Trp Phe Gln Gln Lys Pro Gly Lys Ala Pro
        50                  55                  60

Lys Pro Trp Ile Tyr Ala Thr Ser Asn Leu Ala Ser Gly Val Pro Val
 65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Thr
            100                 105                 110

Ser Asn Pro Pro Thr Phe Gly Gly Gly Thr Lys Leu Glu Ile Lys Arg
        115                 120                 125

Gly Gly Gly Gly Ser Gly Gly Gly Gly Ser Gly Gly Gly Gly Ser Gln
    130                 135                 140

Val Gln Leu Gln Gln Ser Gly Ala Glu Val Lys Lys Pro Gly Ser Ser
145                 150                 155                 160

Val Lys Val Ser Cys Lys Ala Ser Gly Tyr Thr Phe Ser Ser Tyr Asn
                165                 170                 175

Met His Trp Val Arg Gln Ala Pro Gly Gln Gly Leu Glu Trp Met Gly
            180                 185                 190

Ala Ile Tyr Pro Gly Asn Gly Asp Thr Ser Tyr Asn Gln Lys Phe Lys
        195                 200                 205

Gly Arg Ala Thr Ile Thr Ala Asp Glu Ser Thr Asn Thr Ala Tyr Met
    210                 215                 220

Glu Leu Ser Ser Leu Arg Ser Glu Asp Thr Ala Phe Tyr Phe Cys Ala
225                 230                 235                 240

Arg Ser Thr Tyr Tyr Gly Gly Asp Trp Tyr Phe Asp Val Trp Gly Gln
                245                 250                 255

Gly Thr Thr Val Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300
```

```
Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Ser Lys
            325                 330                 335

Arg Ser Arg Leu Leu His Ser Asp Tyr Met Asn Met Thr Pro Arg Arg
            340                 345                 350

Pro Gly Pro Thr Arg Lys His Tyr Gln Pro Tyr Ala Pro Pro Arg Asp
            355                 360                 365

Phe Ala Ala Tyr Arg Ser Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Gln Arg Arg Lys Asn Pro Gln Glu Gly
                420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg Gly Ser Gly Ala Thr Asn Phe Ser Leu
                485                 490                 495

Leu Lys Gln Ala Gly Asp Val Glu Glu Asn Pro Gly Pro Met Ala Leu
            500                 505                 510

Pro Val Thr Ala Leu Leu Leu Pro Leu Ala Leu Leu Leu His Ala Ala
            515                 520                 525

Arg Pro Glu Val Gln Leu Gln Gln Ser Gly Pro Glu Leu Ile Lys Pro
530                 535                 540

Gly Ala Ser Val Lys Met Ser Cys Lys Ala Ser Gly Tyr Thr Phe Thr
545                 550                 555                 560

Ser Tyr Val Met His Trp Val Lys Gln Lys Pro Gly Gln Gly Leu Glu
                565                 570                 575

Trp Ile Gly Tyr Ile Asn Pro Tyr Asn Asp Gly Thr Lys Tyr Asn Glu
            580                 585                 590

Lys Phe Lys Gly Lys Ala Thr Leu Thr Ser Asp Lys Ser Ser Ser Thr
            595                 600                 605

Ala Tyr Met Glu Leu Ser Ser Leu Thr Ser Glu Asp Ser Ala Val Tyr
610                 615                 620

Tyr Cys Ala Arg Gly Thr Tyr Tyr Gly Ser Arg Val Phe Asp Tyr
625                 630                 635                 640

Trp Gly Gln Gly Thr Thr Leu Thr Val Ser Ser Gly Gly Gly Gly Ser
                645                 650                 655

Gly Gly Gly Gly Ser Gly Gly Gly Ser Asp Ile Val Met Thr Gln
                660                 665                 670

Ala Ala Pro Ser Ile Pro Val Thr Pro Gly Glu Ser Val Ser Ile Ser
            675                 680                 685

Cys Arg Ser Ser Lys Ser Leu Leu Asn Ser Asn Gly Asn Thr Tyr Leu
            690                 695                 700

Tyr Trp Phe Leu Gln Arg Pro Gly Gln Ser Pro Gln Leu Leu Ile Tyr
705                 710                 715                 720

Arg Met Ser Asn Leu Ala Ser Gly Val Pro Asp Arg Phe Ser Gly Ser
```

-continued

```
                    725                 730                 735
Gly Ser Gly Thr Ala Phe Thr Leu Arg Ile Ser Arg Val Glu Ala Glu
                740                 745                 750
Asp Val Gly Val Tyr Tyr Cys Met Gln His Leu Glu Tyr Pro Phe Thr
                755                 760                 765
Phe Gly Ala Gly Thr Lys Leu Glu Leu Lys Arg Thr Thr Pro Ala
                770                 775                 780
Pro Arg Pro Pro Thr Pro Ala Pro Thr Ile Ala Ser Gln Pro Leu Ser
785                 790                 795                 800
Leu Arg Pro Glu Ala Cys Arg Pro Ala Ala Gly Gly Ala Val His Thr
                805                 810                 815
Arg Gly Leu Asp Phe Ala Cys Asp Ile Tyr Ile Trp Ala Pro Leu Ala
                820                 825                 830
Gly Thr Cys Gly Val Leu Leu Leu Ser Leu Val Ile Thr Leu Tyr Cys
                835                 840                 845
Lys Arg Gly Arg Lys Lys Leu Leu Tyr Ile Phe Lys Gln Pro Phe Met
                850                 855                 860
Arg Pro Val Gln Thr Thr Gln Glu Glu Asp Gly Cys Ser Cys Arg Phe
865                 870                 875                 880
Pro Glu Glu Glu Glu Gly Gly Cys Glu Leu Arg Val Lys Phe Ser Arg
                885                 890                 895
Ser Ala Asp Ala Pro Ala Tyr Gln Gln Gly Gln Asn Gln Leu Tyr Asn
                900                 905                 910
Glu Leu Asn Leu Gly Arg Arg Glu Glu Tyr Asp Val Leu Asp Lys Arg
                915                 920                 925
Arg Gly Arg Asp Pro Glu Met Gly Gly Lys Pro Gln Arg Arg Lys Asn
                930                 935                 940
Pro Gln Glu Gly Leu Tyr Asn Glu Leu Gln Lys Asp Lys Met Ala Glu
945                 950                 955                 960
Ala Tyr Ser Glu Ile Gly Met Lys Gly Glu Arg Arg Arg Gly Lys Gly
                965                 970                 975
His Asp Gly Leu Tyr Gln Gly Leu Ser Thr Ala Thr Lys Asp Thr Tyr
                980                 985                 990
Asp Ala Leu His Met Gln Ala Leu  Pro Pro Arg
                995                 1000
```

<210> SEQ ID NO 23
<211> LENGTH: 3020
<212> TYPE: DNA
<213> ORGANISM: Artificial Sequence
<220> FEATURE:
<223> OTHER INFORMATION: synthetic sequence

<400> SEQUENCE: 23

```
atggccttac cagtgaccgc cttgctcctg ccgctggcct tgctgctcca cgccgccagg      60
ccggacatcc agctgaccca gagccccagc agcctgagcg ccagcgtggg cgacagggtg     120
accatgacct gcagggccag cagcagcgtg agctacatcc actggttcca gcagaagccc     180
ggcaaggccc ccaagccctg gatctacgcc accagcaacc tggccagcgg cgtgcccgtg     240
aggttcagcg gcagcggcag cggcaccgac tacaccttca ccatcagcag cctgcagccc     300
gaggacatcg ccacctacta ctgccagcag tggaccagca accccccac cttcggcggc      360 ggcaccaagc tggagatcaa gggggcggg gcggcagcg cggcggcgg cagcggcggc         420 ggcggcagcc aggtgcagct gcagcagagc ggcgccgagg tgaagaagcc cggcagcagc     480
```

```
gtgaaggtga gctgcaaggc cagcggctac accttcagca gctacaacat gcactgggtg    540
aggcaggccc ccggccaggg cctggagtgg atgggcgcca tctacccgg caacggcgac     600 accagctaca accagaagtt caagggcagg gccaccatca ccgccgacga gagcaccaac    660
accgcctaca tggagctgag cagcctgagg agcgaggaca ccgccttcta cttctgcgcc    720
aggagcacct actacggcgg cgactggtac ttcgacgtgt ggggccaggg caccaccgtg    780
accgtgagca gcaccacgac gccagcgccg cgaccaccaa caccggcgcc caccatcgcg    840
tcgcagcccc tgtccctgcg cccagaggcg tgccggccag cggcggggg cgcagtgcac     900 acgagggggc tggacttcgc ctgtgatatc tacatctggg cgcccttggc cgggacttgt    960
ggggtccttc tcctgtcact ggttatcacc ctttactgca ggagtaagag gagcaggctc   1020
ctgcacagtg actacatgaa catgactccc cgccgcccg ggcccacccg caagcattac    1080
cagccctatg ccccaccacg cgacttcgca gcctatcgct ccagagtgaa gttcagcagg   1140
agcgcagacg ccccgcgta ccagcagggc cagaaccagc tctataacga gctcaatcta    1200
ggacgaagag aggagtacga tgttttggac aagacgtg ccgggacccc tgagatgggg     1260
ggaaagccgc agagaaggaa gaaccctcag gaaggcctgt acaatgaact gcagaaagat   1320 aagatggcg aggcctacag tgagattggg atgaaaggcg agcgccggag gggcaagggg    1380
cacgatggcc tttaccaggg tctcagtaca gccaccaagg acacctacga cgcccttcac   1440
atgcaggccc tgccccctcg cggaagcgga gccaccaact tcagcctgct gaagcaggcc   1500
ggcgacgtgg aggagaaccc cggccccatg gccctgcccg tgaccgccct gctgctgccc   1560
ctggccctgc tgctgcacgc cgccaggccc gaggtccagc tgcagcagtc tggacctgag   1620
ctgataaagc ctggggcttc agtgaagatg tcctgcaagg cttctggata cacattcact   1680
agctatgtta tgcactgggt gaagcagaag cctgggcagg ccttgagtg gattggatat   1740 attaatcctt acaatgatgg tactaagtac aatgagaagt tcaaaggcaa ggccacactg   1800
acttcagaca aatcctccag cacagcctac atggagctca gcagcctgac ctctgaggac   1860
tctgcggtct attactgtgc aagagggact tattactacg gtagtagggt atttgactac   1920
tggggccaag gcaccactct cacagtctcc tcaggtggag ggggctcagg cggaggtggc   1980
tctgggggtg gaggctcgga cattgtgatg actcaggctg caccctctat acctgtcact   2040
cctggagagt cagtatccat ctcctgcagg tctagtaaga gtctcctgaa tagtaatggc   2100
aacacttact tgtattggtt cctgcagagg ccaggccagt ctcctcagct cctgatatat   2160
cggatgtcca accttgcctc aggagtccca gacaggttca gtggcagtgg gtcaggaact   2220
gctttcacac tgagaatcag tagagtggag gctgaggatg tgggtgttta ttactgtatg   2280
caacatctag aatatccgtt cacgttcggt gctgggacca agctggagct gaaacggacc   2340 accaccccg ccccaggcc ccccaccccc gccccacca tcgccagcca gcccctgagc      2400
ctgaggcccg aggcctgcag gccgccgcc ggcggcgccg tgcacaccag gggcctggac    2460
ttcgcctgcg acatctacat ctgggccccc ctggccggca cctgcggcgt gctgctgctg   2520
agcctggtga tcaccctgta ctgcaaacgg ggcagaaaga aactcctgta tatattcaaa   2580
caaccattta tgagaccagt acaaactact caagaggaag atggctgtag ctgccgattt   2640
ccagaagaag aagaaggagg atgtgaactg agggtgaagt tcagcaggag cgccgacgcc   2700
cccgcctacc agcagggcca gaaccagctg tacaacgagc tgaacctggg caggagggag   2760
gagtacgacg tgctggacaa gaggaggggc agggacccccg agatgggcgg caagccccag   2820
aggaggaaga acccccagga gggcctgtac aacgagctgc agaaggacaa gatggccgag   2880
```

-continued

```
gcctacagcg agatcggcat gaagggcgag aggaggaggg gcaagggcca cgacggcctg    2940
taccagggcc tgagcaccgc caccaaggac acctacgacg ccctgcacat gcaggccctg    3000
ccccccaggt aagtttaaac                                                3020
```

<210> SEQ ID NO 24
<211> LENGTH: 1321
<212> TYPE: PRT
<213> ORGANISM: Artificial Sequence
<220> FEATURE:
<223> OTHER INFORMATION: synthetic sequence

<400> SEQUENCE: 24

```
Met Ala Leu Pro Val Thr Ala Leu Leu Leu Pro Leu Ala Leu Leu Leu
1               5                   10                  15

His Ala Ala Arg Pro Met Ala Asp Tyr Lys Asp Ile Val Met Thr Gln
            20                  25                  30

Ser His Lys Phe Met Ser Thr Ser Val Gly Asp Arg Val Asn Ile Thr
        35                  40                  45

Cys Lys Ala Ser Gln Asn Val Asp Ser Ala Val Ala Trp Tyr Gln Gln
    50                  55                  60

Lys Pro Gly Gln Ser Pro Lys Ala Leu Ile Tyr Ser Ala Ser Tyr Arg
65                  70                  75                  80

Tyr Ser Gly Val Pro Asp Arg Phe Thr Gly Arg Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Gln Tyr Tyr Ser Thr Pro Trp Thr Phe Gly Gly Gly Thr
        115                 120                 125

Lys Leu Glu Ile Lys Arg Gly Gly Gly Ser Gly Gly Gly Gly Ser
    130                 135                 140

Gly Gly Gly Gly Ser Gly Gly Gly Ser Glu Val Lys Leu Val Glu
145                 150                 155                 160

Ser Gly Gly Gly Leu Val Gln Pro Gly Gly Ser Leu Ser Leu Ser Cys
                165                 170                 175

Ala Ala Ser Gly Phe Thr Phe Thr Asp Tyr Tyr Met Ser Trp Val Arg
            180                 185                 190

Gln Pro Pro Gly Lys Ala Leu Glu Trp Leu Ala Leu Ile Arg Ser Lys
        195                 200                 205

Ala Asp Gly Tyr Thr Thr Glu Tyr Ser Ala Ser Val Lys Gly Arg Phe
    210                 215                 220

Thr Leu Ser Arg Asp Asp Ser Gln Ser Ile Leu Tyr Leu Gln Met Asn
225                 230                 235                 240

Ala Leu Arg Pro Glu Asp Ser Ala Thr Tyr Tyr Cys Ala Arg Asp Ala
                245                 250                 255

Ala Tyr Tyr Ser Tyr Tyr Ser Pro Glu Gly Ala Met Asp Tyr Trp Gly
            260                 265                 270

Gln Gly Thr Ser Val Thr Val Ser Ser Ala Ser Gly Ala Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335
```

-continued

```
Leu Ala Gly Thr Cys Gly Val Leu Leu Leu Ser Leu Val Ile Thr Leu
                340                 345                 350
Tyr Cys Arg Ser Lys Arg Ser Arg Leu Leu His Ser Asp Tyr Met Asn
                355                 360                 365
Met Thr Pro Arg Arg Pro Gly Pro Thr Arg Lys His Tyr Gln Pro Tyr
                370                 375                 380
Ala Pro Pro Arg Asp Phe Ala Ala Tyr Arg Ser Arg Val Lys Phe Ser
385                 390                 395                 400
Arg Ser Ala Asp Ala Pro Ala Tyr Gln Gln Gly Gln Asn Gln Leu Tyr
                405                 410                 415
Asn Glu Leu Asn Leu Gly Arg Arg Glu Glu Tyr Asp Val Leu Asp Lys
                420                 425                 430
Arg Arg Gly Arg Asp Pro Glu Met Gly Gly Lys Pro Gln Arg Arg Lys
                435                 440                 445
Asn Pro Gln Glu Gly Leu Tyr Asn Glu Leu Gln Lys Asp Lys Met Ala
        450                 455                 460
Glu Ala Tyr Ser Glu Ile Gly Met Lys Gly Glu Arg Arg Arg Gly Lys
465                 470                 475                 480
Gly His Asp Gly Leu Tyr Gln Gly Leu Ser Thr Ala Thr Lys Asp Thr
                485                 490                 495
Tyr Asp Ala Leu His Met Gln Ala Leu Pro Pro Arg Ser Gly Ala
                500                 505                 510
Thr Asn Phe Ser Leu Leu Lys Gln Ala Gly Asp Val Glu Glu Asn Pro
        515                 520                 525
Gly Pro Met Ala Leu Pro Val Thr Ala Leu Leu Leu Pro Leu Ala Leu
        530                 535                 540
Leu Leu His Ala Ala Arg Pro Met Ala Asp Tyr Lys Asp Ile Val Met
545                 550                 555                 560
Thr Gln Ser His Lys Phe Leu Leu Val Ser Val Gly Asp Arg Val Ser
                565                 570                 575
Ile Thr Cys Lys Ala Ser Gln Asp Val Ser Thr Ala Val Ala Trp Tyr
                580                 585                 590
Gln Gln Lys Pro Gly Gln Ser Pro Lys Leu Leu Ile Tyr Ser Ala Ser
                595                 600                 605
Tyr Arg Tyr Thr Gly Val Pro Asp Arg Phe Ile Gly Ser Gly Ser Gly
        610                 615                 620
Thr Asp Phe Thr Leu Thr Ile Ser Ser Val Gln Ala Glu Asp Leu Ala
625                 630                 635                 640
Asp Tyr Phe Cys Gln Gln His Tyr Ser Thr Pro Leu Thr Phe Gly Ala
                645                 650                 655
Gly Thr Lys Leu Glu Ile Lys Arg Gly Gly Gly Gly Ser Gly Gly Gly
                660                 665                 670
Gly Ser Gly Gly Gly Gly Ser Gly Gly Gly Gly Ser Glu Val Gln Leu
        675                 680                 685
Lys Glu Ser Gly Pro Gly Leu Val Ala Pro Ser Gln Ser Leu Ser Ile
        690                 695                 700
Thr Cys Thr Val Ser Gly Phe Pro Leu Thr Ser Tyr Gly Val Ser Trp
705                 710                 715                 720
Val Arg Gln Pro Pro Gly Lys Gly Leu Glu Trp Leu Gly Val Ile Trp
                725                 730                 735
Gly Asp Gly Ser Thr Asn Tyr His Ser Ala Leu Ile Ser Arg Leu Ser
                740                 745                 750
```

```
Ile Ser Lys Asp Asn Ser Lys Ser Gln Val Phe Leu Lys Leu Asn Asn
        755                 760                 765

Leu Gln Thr Asp Thr Ala Thr Tyr Tyr Cys Ala Arg Asp Thr Tyr
    770                 775                 780

Tyr Pro Tyr Tyr Ala Met Asp Tyr Trp Gly Gln Gly Thr Ser Val Thr
785                 790                 795                 800

Val Ser Ser Thr Thr Thr Pro Ala Pro Arg Pro Pro Thr Pro Ala Pro
                805                 810                 815

Thr Ile Ala Ser Gln Pro Leu Ser Leu Arg Pro Glu Ala Cys Arg Pro
        820                 825                 830

Ala Ala Gly Gly Ala Val His Thr Arg Gly Leu Asp Phe Ala Cys Asp
        835                 840                 845

Ile Tyr Ile Trp Ala Pro Leu Ala Gly Thr Cys Gly Val Leu Leu Leu
850                 855                 860

Ser Leu Val Ile Thr Leu Tyr Cys Lys Arg Gly Arg Lys Lys Leu Leu
865                 870                 875                 880

Tyr Ile Phe Lys Gln Pro Phe Met Arg Pro Val Gln Thr Thr Gln Glu
                885                 890                 895

Glu Asp Gly Cys Ser Cys Arg Phe Pro Glu Glu Glu Glu Gly Gly Cys
                900                 905                 910

Glu Leu Arg Val Lys Phe Ser Arg Ser Ala Asp Ala Pro Ala Tyr Gln
915                 920                 925

Gln Gly Gln Asn Gln Leu Tyr Asn Glu Leu Asn Leu Gly Arg Arg Glu
        930                 935                 940

Glu Tyr Asp Val Leu Asp Lys Arg Arg Gly Arg Asp Pro Glu Met Gly
945                 950                 955                 960

Gly Lys Pro Gln Arg Arg Lys Asn Pro Gln Glu Gly Leu Tyr Asn Glu
                965                 970                 975

Leu Gln Lys Asp Lys Met Ala Glu Ala Tyr Ser Glu Ile Gly Met Lys
                980                 985                 990

Gly Glu Arg Arg Arg Gly Lys Gly His Asp Gly Leu Tyr Gln Gly Leu
        995                 1000                1005

Ser Thr Ala Thr Lys Asp Thr Tyr Asp Ala Leu His Met Gln Ala
    1010                1015                1020

Leu Pro Pro Arg Gly Ser Gly Glu Gly Arg Gly Ser Leu Leu Thr
    1025                1030                1035

Cys Gly Asp Val Glu Glu Asn Pro Gly Pro Met Tyr Arg Met Gln
    1040                1045                1050

Leu Leu Ser Cys Ile Ala Leu Ser Leu Ala Leu Val Thr Asn Ser
    1055                1060                1065

Gly Ile His Val Phe Ile Leu Gly Cys Phe Ser Ala Gly Leu Pro
    1070                1075                1080

Lys Thr Glu Ala Asn Trp Val Asn Val Ile Ser Asp Leu Lys Lys
    1085                1090                1095

Ile Glu Asp Leu Ile Gln Ser Met His Ile Asp Ala Thr Leu Tyr
    1100                1105                1110

Thr Glu Ser Asp Val His Pro Ser Cys Lys Val Thr Ala Met Lys
    1115                1120                1125

Cys Phe Leu Leu Glu Leu Gln Val Ile Ser Leu Glu Ser Gly Asp
    1130                1135                1140

Ala Ser Ile His Asp Thr Val Glu Asn Leu Ile Ile Leu Ala Asn
    1145                1150                1155

Asn Ser Leu Ser Ser Asn Gly Asn Val Thr Glu Ser Gly Cys Lys
```

```
                    1160             1165             1170
Glu Cys Glu Glu Leu Glu Glu Lys Asn Ile Lys Glu Phe Leu Gln
    1175             1180             1185

Ser Phe Val His Ile Val Gln Met Phe Ile Asn Thr Ser Ser Gly
    1190             1195             1200

Gly Gly Ser Gly Gly Gly Ser Gly Gly Gly Ser Gly Gly
    1205             1210             1215

Gly Gly Ser Gly Gly Gly Ser Leu Gln Ala Pro Arg Arg Ala Arg
    1220             1225             1230

Gly Cys Arg Thr Leu Gly Leu Pro Ala Leu Leu Leu Leu Leu
    1235             1240             1245

Leu Arg Pro Pro Ala Thr Arg Gly Ile Thr Cys Pro Pro Pro Met
    1250             1255             1260

Ser Val Glu His Ala Asp Ile Trp Val Lys Ser Tyr Ser Leu Tyr
    1265             1270             1275

Ser Arg Glu Arg Tyr Ile Cys Asn Ser Gly Phe Lys Arg Lys Ala
    1280             1285             1290

Gly Thr Ser Ser Leu Thr Glu Cys Val Leu Asn Lys Ala Thr Asn
    1295             1300             1305

Val Ala His Trp Thr Thr Pro Ser Leu Lys Cys Ile Arg
    1310             1315             1320
```

<210> SEQ ID NO 25
<211> LENGTH: 3974
<212> TYPE: DNA
<213> ORGANISM: Artificial Sequence
<220> FEATURE:
<223> OTHER INFORMATION: synthetic sequence

<400> SEQUENCE: 25

```
atggccttac cagtgaccgc cttgctcctg ccgctggcct tgctgctcca cgccgccagg    60
ccgatggccg actacaagga catcgtgatg acccagagcc acaagttcat gagcaccagc   120
gtgggcgaca gggtgaacat cacctgcaag gccagccaga acgtggacag cgccgtggcc   180
tggtaccagc agaagcccgg ccagagcccc aaggccctga tctacagcgc cagctacagg   240
tacagcggcg tgcccgacag gttcaccggc aggggcagcg gcaccgactt caccctgacc   300
atcagcagcg tgcaggccga ggacctggcc gtgtactact gccagcagta ctacagcacc   360
ccctggacct tcggcggcgg caccaagctg gagatcaaga ggggcggcgg cggcagcggc   420
ggcggcggca gcggcggcgg cggcagcggc ggcggcggca gcgaggtgaa gctggtggag   480
agcggcggcg gcctggtgca gcccggcggc agcctgagcc tgagctgcgc cgccagcggc   540
ttcaccttca ccgactacta catgagctgg gtgaggcagc cccccggcaa ggccctggag   600
tggctggccc tgatcaggag caaggccgac ggctacacca ccgagtacag cgccagcgtg   660
aagggcaggt tcaccctgag cagggacgac agccagagca tcctgtacct gcagatgaac   720
gccctgaggc ccgaggacag cgccacctac tactgcgcca gggacgccgc ctactacagc   780
tactacagcc ccgagggcgc catggactac tggggccagg caccagcgt gaccgtgagc   840
agcgccagcg cgccaccac gacgccagcg ccgcgaccac caacaccggc gcccaccatc   900
gcgtcgcagc ccctgtccct gcgcccagag gcgtgccggc cagcggcggg gggcgcagtg   960
cacacgaggg ggctgactt cgcctgtgat atctacatct gggcgccctt ggccgggact  1020
tgtgggtcc ttctcctgtc actggttatc acccttact gcaggagtaa gaggagcagg  1080
ctcctgcaca gtgactacat gaacatgact ccccgccgcc ccgggcccac ccgcaagcat  1140
```

```
taccagccct atgccccacc acgcgacttc gcagcctatc gctccagagt gaagttcagc    1200
aggagcgcag acgccccgc gtaccagcag ggccagaacc agctctataa cgagctcaat    1260
ctaggacgaa gagaggagta cgatgttttg gacaagagac gtggccggga ccctgagatg    1320
gggggaaagc cgcagagaag gaagaaccct caggaaggc tgtacaatga actgcagaaa    1380
gataagatgg cggaggccta cagtgagatt gggatgaaag gcgagcgccg gaggggcaag    1440
gggcacgatg gcctttacca gggtctcagt acagccacca aggacaccta cgacgccctt    1500
cacatgcagg ccctgccccc tcgcggaagc ggagccacca acttcagcct gctgaagcag    1560
gccggcgacg tggaggagaa ccccggcccc atggccctgc ccgtgaccgc cctgctgctg    1620
cccctggccc tgctgctgca cgccgccagg cccatggccg actacaagga catcgtgatg    1680
acccagagcc acaagttcct gctggtgagc gtgggcgaca gggtgagcat cacctgcaag    1740
gccagccagg acgtgagcac cgccgtggcc tggtaccagc agaagcccgg ccagagcccc    1800
aagctgctga tctacagcgc cagctacagg tacaccggcg tgcccgacag gttcatcggc    1860
agcggcagcg gcaccgactt caccctgacc atcagcagcg tgcaggccga ggacctggcc    1920
gactacttct gccagcagca ctacagcacc cccctgacct tcggcgccgg caccaagctg    1980
gagatcaaga ggggcggcgg cggcagcggc ggcgcggca ggcggcggcgg cggcagcagc    2040 ggcggcggca gcgaggtgca gctgaaggag agcggccccg gcctggtggc cccagccag    2100 agcctgagca tcacctgcac cgtgagcggc ttccccctga ccagctacgg cgtgagctgg    2160
gtgaggcagc cccccggcaa gggcctggag tggctgggcg tgatctgggg cgacggcagc    2220
accaactacc acagcgccct gatcagcagg ctgagcatca gcaaggacaa cagcaagagc    2280
caggtgttcc tgaagctgaa caacctgcag accgacgaca ccgccaccta ctactgcgcc    2340
agggacacct actaccccta ctacgccatg gactactggg gccagggcac cagcgtgacc    2400
gtgagcagca ccaccacccc cgcccccagg ccccccaccc ccgccccca catcgccagc    2460 cagccctga gcctgaggcc cgaggcctgc aggcccgccg ccggcggcgc cgtgcacacc    2520
agggccctgg acttcgcctg cgacatctac atctgggccc cctggccggg cacctgcggc    2580
gtgctgctgc tgagcctggt gatcaccctg tactgcaaac ggggcagaaa gaaactcctg    2640
tatatattca aacaaccatt tatgagacca gtacaaacta ctcaagagga agatggctgt    2700
agctgccgat ttccagaaga agaagaagga ggatgtgaac tgagggtgaa gttcagcagg    2760
agcgccgacg cccccgccta ccagcagggc cagaaccagc tgtacaacga gctgaacctg    2820
ggcaggaggg aggagtacga cgtgctggac aagaggaggg gcaggacccc gagatgggc    2880 ggcaagcccc agaggaggaa gaaccccag gagggcctgt acaacgagct gcagaaggac    2940
aagatggccg aggcctacag cgagatcggc atgaagggcg agaggaggag gggcaagggc    3000
cacgacggcc tgtaccaggg cctgagcacc gccaccaagg acacctacga cgccctgcac    3060
atgcaggccc tgccccag ggcagcggc aaggccgcg gcagcctgct gacctgcggc    3120
gatgtggaag aaaacccggg ccccatgtac agaatgcagc tgctgagctg catcgccctg    3180
agcctggccc tggtgaccaa cagcggcatc cacgtgttca tcctgggctg cttcagcgcc    3240
ggcctgccca gaccgaggc caactgggtg aacgtgatca gcgacctgaa gaagatcgag    3300
gacctgatcc agagcatgca catcgacgcc accctgtaca ccgagagcga cgtgcacccc    3360
agctgcaagg tgaccgccat gaagtgcttc ctgctggagc tgcaggtgat cagcctggag    3420
agcggcgacg ccagcatcca cgacaccgtg gagaacctga tcatcctggc caacaacagc    3480
```

```
ctgagcagca acggcaacgt gaccgagagc ggctgcaagg agtgcgagga gctggaggag    3540
aagaacatca aggagttcct gcagagcttc gtgcacatcg tgcagatgtt catcaacacc    3600
agctccggcg gcggctccgg cggcggcggc tccggcggcg gcggctccgg cggcggcggc    3660
tccggcggcg gctccctgca ggcccccaga agagccagag gctgcagaac cctgggcctg    3720
cccgccctgc tgctgctgct gctgctgaga ccccccgcca ccagaggcat cacctgcccc    3780 cccccatga gcgtggagca cgccgacatc tgggtgaaga gctacagcct gtacagcaga    3840
gagagataca tctgcaacag cggcttcaag agaaaggccg gcaccagcag cctgaccgag    3900
tgcgtgctga acaaggccac caacgtggcc cactggacca cccccagcct gaagtgcatc    3960
agataagttt aaac                                                      3974
```

<210> SEQ ID NO 26
<211> LENGTH: 1016
<212> TYPE: PRT
<213> ORGANISM: Artificial Sequence
<220> FEATURE:
<223> OTHER INFORMATION: synthetic sequence

<400> SEQUENCE: 26

```
Met Ala Leu Pro Val Thr Ala Leu Leu Leu Pro Leu Ala Leu Leu Leu
1               5                   10                  15

His Ala Ala Arg Pro Met Ala Asp Tyr Lys Asp Ile Val Met Thr Gln
                20                  25                  30

Ser His Lys Phe Met Ser Thr Ser Val Gly Asp Arg Val Asn Ile Thr
            35                  40                  45

Cys Lys Ala Ser Gln Asn Val Asp Ser Ala Val Ala Trp Tyr Gln Gln
        50                  55                  60

Lys Pro Gly Gln Ser Pro Lys Ala Leu Ile Tyr Ser Ala Ser Tyr Arg
65                  70                  75                  80

Tyr Ser Gly Val Pro Asp Arg Phe Thr Gly Arg Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Gln Tyr Tyr Ser Thr Pro Trp Thr Phe Gly Gly Gly Thr
        115                 120                 125

Lys Leu Glu Ile Lys Arg Gly Gly Gly Gly Ser Gly Gly Gly Gly Ser
    130                 135                 140

Gly Gly Gly Gly Ser Gly Gly Gly Ser Glu Val Lys Leu Val Glu
145                 150                 155                 160

Ser Gly Gly Gly Leu Val Gln Pro Gly Gly Ser Leu Ser Leu Ser Cys
                165                 170                 175

Ala Ala Ser Gly Phe Thr Phe Thr Asp Tyr Tyr Met Ser Trp Val Arg
            180                 185                 190

Gln Pro Pro Gly Lys Ala Leu Glu Trp Leu Ala Leu Ile Arg Ser Lys
        195                 200                 205

Ala Asp Gly Tyr Thr Thr Glu Tyr Ser Ala Ser Val Lys Gly Arg Phe
    210                 215                 220

Thr Leu Ser Arg Asp Asp Ser Gln Ser Ile Leu Tyr Leu Gln Met Asn
225                 230                 235                 240

Ala Leu Arg Pro Glu Asp Ser Ala Thr Tyr Tyr Cys Ala Arg Asp Ala
                245                 250                 255

Ala Tyr Tyr Ser Tyr Tyr Ser Pro Glu Gly Ala Met Asp Tyr Trp Gly
            260                 265                 270
```

-continued

```
Gln Gly Thr Ser Val Thr Val Ser Ser Ala Ser Ala Thr Thr Thr
            275                 280                 285
Pro Ala Pro Arg Pro Pro Thr Pro Ala Pro Thr Ile Ala Ser Gln Pro
290                 295                 300
Leu Ser Leu Arg Pro Glu Ala Cys Arg Pro Ala Ala Gly Gly Ala Val
305                 310                 315                 320
His Thr Arg Gly Leu Asp Phe Ala Cys Asp Ile Tyr Ile Trp Ala Pro
                325                 330                 335
Leu Ala Gly Thr Cys Gly Val Leu Leu Leu Ser Leu Val Ile Thr Leu
            340                 345                 350
Tyr Cys Arg Ser Lys Arg Ser Arg Leu Leu His Ser Asp Tyr Met Asn
        355                 360                 365
Met Thr Pro Arg Arg Pro Gly Pro Thr Arg Lys His Tyr Gln Pro Tyr
    370                 375                 380
Ala Pro Pro Arg Asp Phe Ala Ala Tyr Arg Ser Arg Val Lys Phe Ser
385                 390                 395                 400
Arg Ser Ala Asp Ala Pro Ala Tyr Gln Gln Gly Gln Asn Gln Leu Tyr
                405                 410                 415
Asn Glu Leu Asn Leu Gly Arg Arg Glu Glu Tyr Asp Val Leu Asp Lys
            420                 425                 430
Arg Arg Gly Arg Asp Pro Glu Met Gly Gly Lys Pro Gln Arg Arg Lys
        435                 440                 445
Asn Pro Gln Glu Gly Leu Tyr Asn Glu Leu Gln Lys Asp Lys Met Ala
    450                 455                 460
Glu Ala Tyr Ser Glu Ile Gly Met Lys Gly Glu Arg Arg Arg Gly Lys
465                 470                 475                 480
Gly His Asp Gly Leu Tyr Gln Gly Leu Ser Thr Ala Thr Lys Asp Thr
                485                 490                 495
Tyr Asp Ala Leu His Met Gln Ala Leu Pro Pro Arg Gly Ser Gly Ala
            500                 505                 510
Thr Asn Phe Ser Leu Leu Lys Gln Ala Gly Asp Val Glu Glu Asn Pro
        515                 520                 525
Gly Pro Met Ala Leu Pro Val Thr Ala Leu Leu Leu Pro Leu Ala Leu
    530                 535                 540
Leu Leu His Ala Ala Arg Pro Asp Ile Gln Met Thr Gln Ser His Lys
545                 550                 555                 560
Phe Met Ser Thr Ser Val Gly Asp Arg Val Ser Ile Thr Cys Lys Ala
                565                 570                 575
Ser Gln Asp Val Ser Thr Ala Val Ala Trp Phe Gln Gln Lys Pro Gly
            580                 585                 590
Gln Ser Pro Lys Leu Leu Ile Tyr Ser Pro Ser Tyr Arg Tyr Thr Gly
        595                 600                 605
Val Pro Asp Arg Phe Thr Gly Ser Gly Ser Gly Thr Asp Phe Thr Phe
    610                 615                 620
Thr Ile Ser Ser Val Gln Ala Glu Asp Leu Ala Val Tyr Tyr Cys Gln
625                 630                 635                 640
Gln Leu Tyr Ser Thr Pro Tyr Thr Phe Gly Gly Gly Thr Lys Leu Glu
                645                 650                 655
Ile Lys Gly Gly Gly Gly Ser Gly Gly Gly Ser Gly Gly Gly Gly
            660                 665                 670
Ser Glu Val Gln Leu Gln Gln Ser Gly Pro Glu Leu Val Lys Pro Gly
        675                 680                 685
Ala Ser Val Lys Met Ser Cys Lys Ala Ser Gly Tyr Thr Phe Thr Asp
```

```
                690             695             700
Tyr Tyr Leu Asp Trp Val Lys Gln Ser His Gly Glu Ser Phe Glu Trp
705             710             715             720

Ile Gly Arg Val Asn Pro Tyr Asn Gly Gly Thr Ile Tyr Asn Gln Lys
                725             730             735

Phe Lys Gly Lys Ala Thr Leu Thr Val Asp Lys Ser Ser Ser Thr Ala
                740             745             750

Tyr Met Asp Leu Asn Ser Leu Thr Ser Glu Asp Ser Ala Val Tyr Tyr
            755             760             765

Cys Ala Arg Asp His Tyr Arg Tyr Asp Pro Leu Leu Asp Tyr Trp Gly
            770             775             780

Gln Gly Thr Thr Leu Thr Val Ser Ser Thr Thr Pro Ala Pro Arg
785             790             795             800

Pro Pro Thr Pro Ala Pro Thr Ile Ala Ser Gln Pro Leu Ser Leu Arg
                805             810             815

Pro Glu Ala Cys Arg Pro Ala Ala Gly Gly Ala Val His Thr Arg Gly
                820             825             830

Leu Asp Phe Ala Cys Asp Ile Tyr Ile Trp Ala Pro Leu Ala Gly Thr
            835             840             845

Cys Gly Val Leu Leu Leu Ser Leu Val Ile Thr Leu Tyr Cys Arg Ser
850             855             860

Lys Arg Ser Arg Leu Leu His Ser Asp Tyr Met Asn Met Thr Pro Arg
865             870             875             880

Arg Pro Gly Pro Thr Arg Lys His Tyr Gln Pro Tyr Ala Pro Pro Arg
                885             890             895

Asp Phe Ala Ala Tyr Arg Ser Arg Val Lys Phe Ser Arg Ser Ala Asp
                900             905             910

Ala Pro Ala Tyr Gln Gln Gly Gln Asn Gln Leu Tyr Asn Glu Leu Asn
            915             920             925

Leu Gly Arg Arg Glu Glu Tyr Asp Val Leu Asp Lys Arg Arg Gly Arg
            930             935             940

Asp Pro Glu Met Gly Gly Lys Pro Gln Arg Arg Lys Asn Pro Gln Glu
945             950             955             960

Gly Leu Tyr Asn Glu Leu Gln Lys Asp Lys Met Ala Glu Ala Tyr Ser
                965             970             975

Glu Ile Gly Met Lys Gly Glu Arg Arg Gly Lys Gly His Asp Gly
                980             985             990

Leu Tyr Gln Gly Leu Ser Thr Ala  Thr Lys Asp Thr Tyr  Asp Ala Leu
            995             1000            1005

His Met  Gln Ala Leu Pro Pro  Arg
    1010            1015

<210> SEQ ID NO 27
<211> LENGTH: 3051
<212> TYPE: DNA
<213> ORGANISM: Artificial Sequence
<220> FEATURE:
<223> OTHER INFORMATION: synthetic sequence

<400> SEQUENCE: 27
atggccttac cagtgaccgc cttgctcctg ccgctggcct tgctgctcca cgccgccagg      60
ccgatggccg actacaagga catcgtgatg acccagagcc acaagttcat gagcaccagc     120
gtgggcgaca gggtgaacat cacctgcaag gccagccaga acgtggacag cgccgtggcc     180
tggtaccagc agaagcccgg ccagagcccc aaggccctga tctacagcgc cagctacagg     240
```

-continued

| | |
|---|---|
| tacagcggcg tgcccgacag gttcaccggc aggggcagcg gcaccgactt caccctgacc | 300 |
| atcagcagcg tgcaggccga ggacctggcc gtgtactact gccagcagta ctacagcacc | 360 |
| ccctggacct tcggcggcgg caccaagctg gagatcaaga ggggcggcgg cggcagcggc | 420 |
| ggcggcggca gcgcggcgg cggcagcggc ggcggcggca gcgaggtgaa gctggtggag | 480 |
| agcggcggcg gcctggtgca gcccggcggc agcctgagcc tgagctgcgc cgccagcggc | 540 |
| ttcaccttca ccgactacta catgagctgg gtgaggcagc cccccggcaa ggccctggag | 600 |
| tggctggccc tgatcaggag caaggccgac ggctacacca ccgagtacag cgccagcgtg | 660 |
| aagggcaggt tcaccctgag cagggacgac agccagagca tcctgtacct gcagatgaac | 720 |
| gccctgaggc ccgaggacag cgccacctac tactgcgcca gggacgccgc ctactacagc | 780 |
| tactacagcc ccgagggcgc catggactac tggggccagg gcaccagcgt gaccgtgagc | 840 |
| agcgccagcg cgccaccac gacgccagcg ccgcgaccac caacaccggc gcccaccatc | 900 |
| gcgtcgcagc ccctgtccct gcgcccagag gcgtgccggc cagcggcggg gggcgcagtg | 960 |
| cacacgaggg ggctggactt cgcctgtgat atctacatct gggcgccctt ggccgggact | 1020 |
| tgtgggtcc ttctcctgtc actggttatc acccttact gcaggagtaa gaggagcagg | 1080 |
| ctcctgcaca gtgactacat gaacatgact ccccgccgcc ccgggcccac ccgcaagcat | 1140 |
| taccagcct atgccccacc acgcgacttc gcagcctatc gctccagagt gaagttcagc | 1200 |
| aggagcgcag acgccccgc gtaccagcag ggccagaacc agctctataa cgagctcaat | 1260 |
| ctaggacgaa gagaggagta cgatgttttg gacaagagac gtggccggga ccctgagatg | 1320 |
| gggggaaagc cgcagagaag gaagaaccct caggaaggcc tgtacaatga actgcagaaa | 1380 |
| gataagatgg cggaggccta cagtgagatt gggatgaaag cgagcgccg gaggggcaag | 1440 |
| gggcacgatg ccttttacca gggtctcagt acagccacca aggacaccta cgacgccctt | 1500 |
| cacatgcagg ccctgccccc tcgcggaagc ggagccacca acttcagcct gctgaagcag | 1560 |
| gccggcgacg tggaggagaa ccccggcccc atggccctgc ccgtgaccgc cctgctgctg | 1620 |
| cccctggccc tgctgctgca cgccgccagg cccgacatcc agatgaccca gagccacaag | 1680 |
| ttcatgagca ccagcgtggg cgacagggtg agcatcacct gcaaggccag ccaggacgtg | 1740 |
| agcaccgccg tggcctggtt ccagcagaag cccggccaga gcccaagct gctgatctac | 1800 |
| agccccagct acaggtacac cggcgtgccc gacaggttca ccggcagcgg cagcggcacc | 1860 |
| gacttcacct tcaccatcag cagcgtgcag gccgaggacc tggccgtgta ctactgccag | 1920 |
| cagctgtaca gcacccccta caccttcggc ggcggcacca gctggagat caaggggaggg | 1980 |
| gggggatccg ggggaggagg ctccggcgga ggcggaagcg aggtgcagct gcagcagagc | 2040 |
| ggccccgagc tggtgaagcc cggcgccagc gtgaagatga gctgcaaggc cagcggctac | 2100 |
| accttcaccg actactacct ggactgggtg aagcagagcc acggcgagag cttcgagtgg | 2160 |
| atcggcaggt gaaccccta caacggcggc accatctaca accagaagtt caagggcaag | 2220 |
| gccaccctga ccgtggacaa gagcagcagc accgcctaca tggacctgaa cagcctgacc | 2280 |
| agcgaggaca cgccgtgta ctactgcgcc agggaccact acaggtacga ccccctgctg | 2340 |
| gactactggg gccagggcac caccctgacc gtgagcagca ccaccacccc cgcccccagg | 2400 |
| cccccaccc ccgcccccac catcgccagc cagcccctga gcctgaggcc cgaggcctgc | 2460 |
| aggcccgccg ccggcggcgc cgtgcacacc agggggcctgg acttcgcctg cgacatctac | 2520 |
| atctgggccc ccctggccgg cacctgcggc gtgctgctgc tgagcctggt gatcaccctg | 2580 |

```
tactgcagga gtaagaggag caggctcctg cacagtgact acatgaacat gactccccgc    2640
cgccccgggc ccacccgcaa gcattaccag ccctatgccc caccacgcga cttcgcagcc    2700
tatcgctcca gggtgaagtt cagcaggagc gccgacgccc ccgcctacca gcagggccag    2760
aaccagctgt acaacgagct gaacctgggc aggagggagg agtacgacgt gctggacaag    2820
aggaggggca gggaccccga gatgggcggc aagccccaga ggaggaagaa ccccccaggag   2880 ggcctgtaca cgagctgca gaaggacaag atggccgagg cctacagcga gatcggcatg    2940
aagggcgaga ggaggagggg caagggccac gacggcctgt accagggcct gagcaccgcc    3000
accaaggaca cctacgacgc cctgcacatg caggccctgc cccccaggta a              3051

<210> SEQ ID NO 28
<211> LENGTH: 1299
<212> TYPE: PRT
<213> ORGANISM: Artificial Sequence
<220> FEATURE:
<223> OTHER INFORMATION: synthetic sequence

<400> SEQUENCE: 28
```

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser His Lys Phe Met
                20                  25                  30

Ser Thr Ser Val Gly Asp Arg Val Ser Ile Thr Cys Lys Ala Ser Gln
            35                  40                  45

Asp Val Ser Thr Ala Val Ala Trp Phe Gln Gln Lys Pro Gly Gln Ser
        50                  55                  60

Pro Lys Leu Leu Ile Tyr Ser Pro Ser Tyr Arg Tyr Thr Gly Val Pro
65                  70                  75                  80

Asp Arg Phe Thr Gly Ser Gly Ser Gly Thr Asp Phe Thr Phe Thr Ile
                85                  90                  95

Ser Ser Val Gln Ala Glu Asp Leu Ala Val Tyr Tyr Cys Gln Gln Leu
            100                 105                 110

Tyr Ser Thr Pro Tyr Thr Phe Gly Gly Gly Thr Lys Leu Glu Ile Lys
        115                 120                 125

Gly Gly Gly Gly Ser Gly Gly Gly Gly Ser Gly Gly Gly Gly Ser Glu
130                 135                 140

Val Gln Leu Gln Gln Ser Gly Pro Glu Leu Val Lys Pro Gly Ala Ser
145                 150                 155                 160

Val Lys Met Ser Cys Lys Ala Ser Gly Tyr Thr Phe Thr Asp Tyr Tyr
                165                 170                 175

Leu Asp Trp Val Lys Gln Ser His Gly Glu Ser Phe Glu Trp Ile Gly
            180                 185                 190

Arg Val Asn Pro Tyr Asn Gly Thr Ile Tyr Asn Gln Lys Phe Lys
        195                 200                 205

Gly Lys Ala Thr Leu Thr Val Asp Lys Ser Ser Thr Ala Tyr Met
        210                 215                 220

Asp Leu Asn Ser Leu Thr Ser Glu Asp Ser Ala Val Tyr Tyr Cys Ala
225                 230                 235                 240

Arg Asp His Tyr Arg Tyr Asp Pro Leu Leu Asp Tyr Trp Gly Gln Gly
                245                 250                 255

Thr Thr Leu Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

```
Ala Cys Arg Pro Ala Ala Gly Gly Ala Val His Thr Arg Gly Leu Asp
        290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Arg Ser Lys Arg
                325                 330                 335
Ser Arg Leu Leu His Ser Asp Tyr Met Asn Met Thr Pro Arg Arg Pro
            340                 345                 350
Gly Pro Thr Arg Lys His Tyr Gln Pro Tyr Ala Pro Pro Arg Asp Phe
        355                 360                 365
Ala Ala Tyr Arg Ser Arg Val Lys Phe Ser Arg Ser Ala Asp Ala Pro
370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Gln Arg Arg Lys Asn Pro Gln Glu Gly Leu
            420                 425                 430
Tyr Asn Glu Leu Gln Lys Asp Lys Met Ala Glu Ala Tyr Ser Glu Ile
        435                 440                 445
Gly Met Lys Gly Glu Arg Arg Arg Gly Lys Gly His Asp Gly Leu Tyr
450                 455                 460
Gln Gly Leu Ser Thr Ala Thr Lys Asp Thr Tyr Asp Ala Leu His Met
465                 470                 475                 480
Gln Ala Leu Pro Pro Arg Gly Ser Gly Ala Thr Asn Phe Ser Leu Leu
                485                 490                 495
Lys Gln Ala Gly Asp Val Glu Glu Asn Pro Gly Pro Met Ala Leu Pro
            500                 505                 510
Val Thr Ala Leu Leu Leu Pro Leu Ala Leu Leu Leu His Ala Ala Arg
        515                 520                 525
Pro Met Ala Asp Tyr Lys Asp Ile Val Met Thr Gln Ser His Lys Phe
530                 535                 540
Leu Leu Val Ser Val Gly Asp Arg Val Ser Ile Thr Cys Lys Ala Ser
545                 550                 555                 560
Gln Asp Val Ser Thr Ala Val Ala Trp Tyr Gln Gln Lys Pro Gly Gln
                565                 570                 575
Ser Pro Lys Leu Leu Ile Tyr Ser Ala Ser Tyr Arg Tyr Thr Gly Val
            580                 585                 590
Pro Asp Arg Phe Ile Gly Ser Gly Ser Gly Thr Asp Phe Thr Leu Thr
        595                 600                 605
Ile Ser Ser Val Gln Ala Glu Asp Leu Ala Asp Tyr Phe Cys Gln Gln
610                 615                 620
His Tyr Ser Thr Pro Leu Thr Phe Gly Ala Gly Thr Lys Leu Glu Ile
625                 630                 635                 640
Lys Arg Gly Gly Gly Gly Ser Gly Gly Gly Gly Ser Gly Gly Gly Gly
                645                 650                 655
Ser Ser Gly Gly Gly Ser Glu Val Gln Leu Lys Glu Ser Gly Pro Gly
            660                 665                 670
Leu Val Ala Pro Ser Gln Ser Leu Ser Ile Thr Cys Thr Val Ser Gly
        675                 680                 685
Phe Pro Leu Thr Ser Tyr Gly Val Ser Trp Val Arg Gln Pro Pro Gly
690                 695                 700
```

-continued

Lys Gly Leu Glu Trp Leu Gly Val Ile Trp Gly Asp Gly Ser Thr Asn
705                 710                 715                 720

Tyr His Ser Ala Leu Ile Ser Arg Leu Ser Ile Ser Lys Asp Asn Ser
            725                 730                 735

Lys Ser Gln Val Phe Leu Lys Leu Asn Asn Leu Gln Thr Asp Asp Thr
        740                 745                 750

Ala Thr Tyr Tyr Cys Ala Arg Asp Thr Tyr Pro Tyr Tyr Ala Met
            755                 760             765

Asp Tyr Trp Gly Gln Gly Thr Ser Val Thr Val Ser Ser Thr Thr Thr
    770                 775                 780

Pro Ala Pro Arg Pro Pro Thr Pro Ala Pro Thr Ile Ala Ser Gln Pro
785                 790                 795                 800

Leu Ser Leu Arg Pro Glu Ala Cys Arg Pro Ala Ala Gly Gly Ala Val
                805                 810                 815

His Thr Arg Gly Leu Asp Phe Ala Cys Asp Ile Tyr Ile Trp Ala Pro
            820                 825                 830

Leu Ala Gly Thr Cys Gly Val Leu Leu Leu Ser Leu Val Ile Thr Leu
            835                 840                 845

Tyr Cys Lys Arg Gly Arg Lys Lys Leu Leu Tyr Ile Phe Lys Gln Pro
850                 855                 860

Phe Met Arg Pro Val Gln Thr Thr Gln Glu Glu Asp Gly Cys Ser Cys
865                 870                 875                 880

Arg Phe Pro Glu Glu Glu Glu Gly Gly Cys Glu Leu Arg Val Lys Phe
                885                 890                 895

Ser Arg Ser Ala Asp Ala Pro Ala Tyr Gln Gln Gly Gln Asn Gln Leu
            900                 905                 910

Tyr Asn Glu Leu Asn Leu Gly Arg Arg Glu Glu Tyr Asp Val Leu Asp
        915                 920                 925

Lys Arg Arg Gly Arg Asp Pro Glu Met Gly Gly Lys Pro Gln Arg Arg
    930                 935                 940

Lys Asn Pro Gln Glu Gly Leu Tyr Asn Glu Leu Gln Lys Asp Lys Met
945                 950                 955                 960

Ala Glu Ala Tyr Ser Glu Ile Gly Met Lys Gly Glu Arg Arg Arg Gly
                965                 970                 975

Lys Gly His Asp Gly Leu Tyr Gln Gly Leu Ser Thr Ala Thr Lys Asp
            980                 985                 990

Thr Tyr Asp Ala Leu His Met Gln Ala Leu Pro Pro Arg Gly Ser Gly
        995                 1000                1005

Glu Gly Arg Gly Ser Leu Leu Thr Cys Gly Asp Val Glu Glu Asn
    1010                1015                1020

Pro Gly Pro Met Tyr Arg Met Gln Leu Leu Ser Cys Ile Ala Leu
    1025                1030                1035

Ser Leu Ala Leu Val Thr Asn Ser Gly Ile His Val Phe Ile Leu
    1040                1045                1050

Gly Cys Phe Ser Ala Gly Leu Pro Lys Thr Glu Ala Asn Trp Val
    1055                1060                1065

Asn Val Ile Ser Asp Leu Lys Lys Ile Glu Asp Leu Ile Gln Ser
    1070                1075                1080

Met His Ile Asp Ala Thr Leu Tyr Thr Glu Ser Asp Val His Pro
    1085                1090                1095

Ser Cys Lys Val Thr Ala Met Lys Cys Phe Leu Leu Glu Leu Gln
    1100                1105                1110

Val Ile Ser Leu Glu Ser Gly Asp Ala Ser Ile His Asp Thr Val

| | | | | | | | | | | |
|---|---|---|---|---|---|---|---|---|---|---|
| | | 1115 | | | 1120 | | | 1125 | | |
| Glu | Asn | Leu | Ile | Ile | Leu | Ala | Asn | Asn | Ser | Leu | Ser | Ser | Asn | Gly |
| | | 1130 | | | | 1135 | | | 1140 | |
| Asn | Val | Thr | Glu | Ser | Gly | Cys | Lys | Glu | Cys | Glu | Leu | Glu | Glu |
| | 1145 | | | | 1150 | | | | 1155 | |
| Lys | Asn | Ile | Lys | Glu | Phe | Leu | Gln | Ser | Phe | Val | His | Ile | Val | Gln |
| | 1160 | | | | | 1165 | | | | 1170 | |
| Met | Phe | Ile | Asn | Thr | Ser | Ser | Gly | Gly | Gly | Ser | Gly | Gly | Gly | Gly |
| | 1175 | | | | | 1180 | | | | 1185 | |
| Ser | Gly | Gly | Gly | Gly | Ser | Gly | Gly | Gly | Ser | Gly | Gly | Gly | Ser |
| | 1190 | | | | 1195 | | | | 1200 | |
| Leu | Gln | Ala | Pro | Arg | Arg | Ala | Arg | Gly | Cys | Arg | Thr | Leu | Gly | Leu |
| | 1205 | | | | | 1210 | | | | 1215 | |
| Pro | Ala | Leu | Leu | Leu | Leu | Leu | Leu | Arg | Pro | Pro | Ala | Thr | Arg |
| | 1220 | | | | 1225 | | | | 1230 | |
| Gly | Ile | Thr | Cys | Pro | Pro | Pro | Met | Ser | Val | Glu | His | Ala | Asp | Ile |
| | 1235 | | | | | 1240 | | | | 1245 | |
| Trp | Val | Lys | Ser | Tyr | Ser | Leu | Tyr | Ser | Arg | Glu | Arg | Tyr | Ile | Cys |
| | 1250 | | | | | 1255 | | | | 1260 | |
| Asn | Ser | Gly | Phe | Lys | Arg | Lys | Ala | Gly | Thr | Ser | Ser | Leu | Thr | Glu |
| | 1265 | | | | | 1270 | | | | 1275 | |
| Cys | Val | Leu | Asn | Lys | Ala | Thr | Asn | Val | Ala | His | Trp | Thr | Thr | Pro |
| | 1280 | | | | | 1285 | | | | 1290 | |
| Ser | Leu | Lys | Cys | Ile | Arg |
| | 1295 | | | |

```
<210> SEQ ID NO 29
<211> LENGTH: 3908
<212> TYPE: DNA
<213> ORGANISM: Artificial Sequence
<220> FEATURE:
<223> OTHER INFORMATION: synthetic sequence

<400> SEQUENCE: 29
```

| | | | | | |
|---|---|---|---|---|---|
| atggccctgc | ccgtgaccgc | cctgctgctg | cccctggccc | tgctgctgca | cgccgccagg | 60 |
| cccgacatcc | agatgaccca | gagccacaag | ttcatgagca | ccagcgtggg | cgacagggtg | 120 |
| agcatcacct | gcaaggccag | ccaggacgtg | agcaccgccg | tggcctggtt | ccagcagaag | 180 |
| cccggccaga | gccccaagct | gctgatctac | agccccagct | acaggtacac | cggcgtgccc | 240 |
| gacaggttca | ccggcagcgg | cagcggcacc | gacttcaccc | tcaccatcag | cagcgtgcag | 300 |
| gccgaggacc | tggccgtgta | ctactgccag | cagctgtaca | gcacccccta | caccttcggc | 360 |
| ggcggcacca | agctggagat | caaggggaggg | ggggatccg | ggggaggagg | ctccggcgga | 420 |
| ggcggaagcg | aggtgcagct | gcagcagagc | ggccccgagc | tggtgaagcc | cggcgccagc | 480 |
| gtgaagatga | gctgcaaggc | cagcggctac | accttcaccg | actactacct | ggactgggtg | 540 |
| aagcagagcc | acggcgagag | cttcgagtgg | atcggcaggg | tgaacccta | caacggcggc | 600 |
| accatctaca | accagaagtt | caagggcaag | gccaccctga | ccgtggacaa | gagcagcagc | 660 |
| accgcctaca | tggacctgaa | cagcctgacc | agcgaggaca | cgccgtgta | ctactgcgcc | 720 |
| agggaccact | acaggtacga | ccccctgctg | gactactggg | gccagggcac | caccctgacc | 780 |
| gtgagcagca | ccaccacccc | cgccccagg | ccccccaccc | cgccccac | catcgccagc | 840 |
| cagcccctga | gcctgaggcc | cgaggcctgc | aggcccgccg | ccggcggcgc | cgtgcacacc | 900 |
| aggggcctgg | acttcgcctg | cgacatctac | atctgggccc | ccctggccgg | cacctgcggc | 960 |

```
gtgctgctgc tgagcctggt gatcaccctg tactgcagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gggtgaagtt cagcaggagc    1140
gccgacgccc ccgcctacca gcagggccag aaccagctgt acaacgagct gaacctgggc    1200
aggagggagg agtacgacgt gctggacaag aggaggggca gggaccccga tgggcggc     1260 aagccccaga ggaggaagaa ccccaggag ggcctgtaca cgagctgca gaaggacaag     1320 atggccgagg cctacagcga gatcggcatg aagggcgaga ggaggagggg caagggccac    1380
gacggcctgt accagggcct gagcaccgcc accaaggaca cctacgacgc cctgcacatg    1440
caggccctgc ccccaggggg aagcggagcc accaacttca gcctgctgaa gcaggccggc    1500
gacgtggagg agaaccccgg ccccatggcc ctgcccgtga ccgccctgct gctgcccctg    1560
gccctgctgc tgcacgccgc caggcccatg gccgactaca aggacatcgt gatgacccag    1620
agccacaagt tcctgctggt gagcgtgggc gacagggtga gcatcacctg caaggccagc    1680
caggacgtga gcaccgccgt ggcctggtac cagcagaagc ccggccagag ccccaagctg    1740
ctgatctaca cgccagcta caggtacacc ggcgtgcccg acaggttcat cggcagcggc    1800
agcggcaccg acttcaccct gaccatcagc agcgtgcagg ccgaggacct ggccgactac    1860
ttctgccagc agcactacag cacccccctg accttcggcg ccggcaccaa gctggagatc    1920
aagaggggcg gcggcggcag cggcggcggc ggcagcggcg gcggcggcag cagcggcggc    1980
ggcagcgagg tgcagctgaa ggagagcggc cccggcctgg tggcccccag ccagagcctg    2040
agcatcacct gcaccgtgag cggcttcccc ctgaccagct acggcgtgag ctgggtgagg    2100
cagccccccg gcaagggcct ggagtggctg ggcgtgatct ggggcgacgg cagcaccaac    2160
taccacagcg ccctgatcag caggctgagc atcagcaagg acaacagcaa gagccaggtg    2220
ttcctgaagc tgaacaacct gcagaccgac gacaccgcca cctactactg cgccagggac    2280
acctactacc cctactacgc catggactac tggggccagg gcaccagcgt gaccgtgagc    2340
agcaccacca ccccgcccc caggccccc accccgccc ccaccatcgc cagccagccc    2400
ctgagcctga ggcccgaggc ctgcaggccc gccgccggcg gcgccgtgca caccaggggc    2460
ctggacttcg cctgcgacat ctacatctgg gcccccctgg ccggcacctg cggcgtgctg    2520
ctgctgagcc tggtgatcac cctgtactgc aaacggggca gaaagaaact cctgtatata    2580
ttcaaacaac catttatgag accagtacaa actactcaag aggaagatgg ctgtagctgc    2640
cgatttccag aagaagaaga aggaggatgt gaactgaggg tgaagttcag caggagcgcc    2700 gacgccccg cctaccagca gggccagaac cagctgtaca cgagctgaa cctgggcagg    2760 agggaggagt acgacgtgct ggacaagagg agggcaggg accccgagat gggcggcaag    2820
ccccagagga ggaagaaccc caggagggc ctgtacaacg agctgcagaa ggacaagatg    2880
gccgaggcct acagcgagat cggcatgaag ggcgagagga ggaggggcaa gggccacgac    2940
ggcctgtacc agggcctgag caccgccacc aaggacacct acgacgccct gcacatgcag    3000
gccctgcccc caggggcag cggcgaaggc cgcggcagcc tgctgacctg cggcgatgtg    3060
gaagaaaacc cgggccccat gtacagaatg cagctgctga ctgcatcgc cctgagcctg    3120 gccctggtga ccaacagcgg catccacgtg ttcatcctgg gctgcttcag cgccggcctg    3180
cccaagaccg aggccaactg ggtgaacgtg atcagcgacc tgaagaagat cgaggacctg    3240
atccagagca tgcacatcga cgccaccctg tacaccgaga gcgacgtgca ccccagctgc    3300
```

```
aaggtgaccg ccatgaagtg cttcctgctg gagctgcagg tgatcagcct ggagagcggc    3360
gacgccagca tccacgacac cgtggagaac ctgatcatcc tggccaacaa cagcctgagc    3420
agcaacggca acgtgaccga gagcggctgc aaggagtgcg aggagctgga ggagaagaac    3480
atcaaggagt cctgcagag cttcgtgcac atcgtgcaga tgttcatcaa caccagctcc    3540
ggcggcggct ccggcggcgg cggctccggc ggcggcggct ccggcggcgg cggctccggc    3600
ggcggctccc tgcaggcccc cagaagagcc agaggctgca gaaccctggg cctgcccgcc    3660
ctgctgctgc tgctgctgct gagaccccccc gccaccagag gcatcacctg ccccccccc    3720 atgagcgtgg agcacgccga catctgggtg aagagctaca gcctgtacag cagagagaga    3780
tacatctgca acagcggctt caagagaaag gccggcacca gcagcctgac cgagtgcgtg    3840
ctgaacaagg ccaccaacgt ggcccactgg accacccca gcctgaagtg catcagataa    3900
gtttaaac                                                            3908
```

<210> SEQ ID NO 30
<211> LENGTH: 1009
<212> TYPE: PRT
<213> ORGANISM: Artificial Sequence
<220> FEATURE:
<223> OTHER INFORMATION: synthetic sequence

<400> SEQUENCE: 30

```
Met Ala Leu Pro Val Thr Ala Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Ile Lys Pro Gly Ala Ser Val Lys Met Ser Cys Lys Ala Ser Gly Tyr
            35                  40                  45

Thr Phe Thr Ser Tyr Val Met His Trp Val Lys Gln Lys Pro Gly Gln
        50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
                245                 250                 255
```

Pro Phe Thr Phe Gly Ala Gly Thr Lys Leu Glu Leu Lys Arg Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                    325                 330                 335

Leu Tyr Cys Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
            405                 410                 415

Lys Arg Arg Gly Arg Asp Pro Glu Met Gly Gly Lys Pro Gln Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Ser Gly
            485                 490                 495

Ala Thr Asn Phe Ser Leu Leu Lys Gln Ala Gly Asp Val Glu Glu Asn
            500                 505                 510

Pro Gly Pro Met Ala Leu Pro Val Thr Ala Leu Leu Leu Pro Leu Ala
            515                 520                 525

Leu Leu Leu His Ala Ala Arg Pro Asp Ile Glu Leu Thr Gln Ser Pro
            530                 535                 540

Ser Ser Phe Ser Val Ser Leu Gly Asp Arg Val Thr Ile Thr Cys Lys
545                 550                 555                 560

Ala Ser Glu Asp Ile Tyr Asn Arg Leu Ala Trp Tyr Gln Gln Lys Pro
            565                 570                 575

Gly Asn Ala Pro Arg Leu Leu Ile Ser Gly Ala Thr Ser Leu Glu Thr
            580                 585                 590

Gly Val Pro Ser Arg Phe Ser Gly Ser Gly Ser Gly Lys Asp Tyr Thr
            595                 600                 605

Leu Ser Ile Thr Ser Leu Gln Thr Glu Asp Val Ala Thr Tyr Tyr Cys
            610                 615                 620

Gln Gln Tyr Trp Ser Thr Pro Thr Phe Gly Gly Gly Thr Lys Leu Glu
625                 630                 635                 640

Ile Lys Arg Ala Ala Gly Gly Gly Ser Gly Gly Gly Gly Ser Gly
            645                 650                 655

Gly Gly Gly Ser Ala Gln Pro Ala Met Ala Lys Val Gln Leu Gln Glu
            660                 665                 670

Ser Gly Pro Ser Leu Val Gln Pro Ser Gln Arg Leu Ser Ile Thr Cys
            675                 680                 685

Thr Val Ser Gly Phe Ser Leu Ile Ser Tyr Gly Val His Trp Val Arg
        690                 695                 700

Gln Ser Pro Gly Lys Gly Leu Glu Trp Leu Gly Val Ile Trp Arg Gly
705                 710                 715                 720

Gly Ser Thr Asp Tyr Asn Ala Ala Phe Met Ser Arg Leu Ser Ile Thr
                725                 730                 735

Lys Asp Asn Ser Lys Ser Gln Val Phe Phe Lys Met Asn Ser Leu Gln
            740                 745                 750

Ala Asp Asp Thr Ala Ile Tyr Phe Cys Ala Lys Thr Leu Ile Thr Thr
        755                 760                 765

Gly Tyr Ala Met Asp Tyr Trp Gly Gln Gly Thr Thr Val Thr Val Ser
770                 775                 780

Ser Thr Thr Thr Pro Ala Pro Arg Pro Pro Thr Pro Ala Pro Thr Ile
785                 790                 795                 800

Ala Ser Gln Pro Leu Ser Leu Arg Pro Glu Ala Cys Arg Pro Ala Ala
            805                 810                 815

Gly Gly Ala Val His Thr Arg Gly Leu Asp Phe Ala Cys Asp Ile Tyr
        820                 825                 830

Ile Trp Ala Pro Leu Ala Gly Thr Cys Gly Val Leu Leu Leu Ser Leu
        835                 840                 845

Val Ile Thr Leu Tyr Cys Lys Arg Gly Arg Lys Lys Leu Leu Tyr Ile
        850                 855                 860

Phe Lys Gln Pro Phe Met Arg Pro Val Gln Thr Thr Gln Glu Glu Asp
865                 870                 875                 880

Gly Cys Ser Cys Arg Phe Pro Glu Glu Glu Glu Gly Gly Cys Glu Leu
                885                 890                 895

Arg Val Lys Phe Ser Arg Ser Ala Asp Ala Pro Ala Tyr Gln Gln Gly
            900                 905                 910

Gln Asn Gln Leu Tyr Asn Glu Leu Asn Leu Gly Arg Arg Glu Glu Tyr
        915                 920                 925

Asp Val Leu Asp Lys Arg Arg Gly Arg Asp Pro Glu Met Gly Gly Lys
930                 935                 940

Pro Gln Arg Arg Lys Asn Pro Gln Glu Gly Leu Tyr Asn Glu Leu Gln
945                 950                 955                 960

Lys Asp Lys Met Ala Glu Ala Tyr Ser Glu Ile Gly Met Lys Gly Glu
                965                 970                 975

Arg Arg Arg Gly Lys Gly His Asp Gly Leu Tyr Gln Gly Leu Ser Thr
            980                 985                 990

Ala Thr Lys Asp Thr Tyr Asp Ala Leu His Met Gln Ala Leu Pro Pro
        995                 1000                1005

Arg

<210> SEQ ID NO 31
<211> LENGTH: 3038
<212> TYPE: DNA
<213> ORGANISM: Artificial Sequence
<220> FEATURE:
<223> OTHER INFORMATION: synthetic sequence

<400> SEQUENCE: 31 atggcttac cagtgaccgc cttgctcctg ccgctggcct tgctgctcca cgccgccagg    60
ccggaggtcc agctgcagca gtctggacct gagctgataa agcctggggc ttcagtgaag   120

```
atgtcctgca aggcttctgg atacacattc actagctatg ttatgcactg ggtgaagcag    180
aagcctgggc agggccttga gtggattgga tatattaatc cttacaatga tggtactaag    240
tacaatgaga agttcaaagg caaggccaca ctgacttcag acaaatcctc cagcacagcc    300
tacatggagc tcagcagcct gacctctgag gactctgcgg tctattactg tgcaagaggg    360
acttattact acggtagtag ggtatttgac tactggggcc aaggcaccac tctcacagtc    420
tcctcaggtg gagggggctc aggcggaggt ggctctgggg gtggaggctc ggacattgtg    480
atgactcagg ctgcaccctc tatacctgtc actcctggag agtcagtatc catctcctgc    540
aggtctagta agagtctcct gaatagtaat ggcaacactt acttgtattg gttcctgcag    600
aggccaggcc agtctcctca gctcctgata tatcggatgt ccaaccttgc ctcaggagtc    660
ccagacaggt tcagtggcag tgggtcagga actgctttca cactgagaat cagtagagtg    720
gaggctgagg atgtgggtgt ttattactgt atgcaacatc tagaatatcc gttcacgttc    780
ggtgctggga ccaagctgga gctgaaacgg accacgacgc cagcgccgcg accaccaaca    840
ccggcgccca ccatcgcgtc gcagcccctg tccctgcgcc cagaggcgtg ccggccagcg    900
gcggggggcg cagtgcacac gagggggctg gacttcgcct gtgatatcta catctgggcg    960
cccttggccg ggacttgtgg ggtccttctc ctgtcactgg ttatcaccct ttactgcagg   1020
agtaagagga gcaggctcct gcacagtgac tacatgaaca tgactccccg ccgccccggg   1080
cccacccgca agcattacca gccctatgcc ccaccacgcg acttcgcagc ctatcgctcc   1140
agagtgaagt tcagcaggag cgcagacgcc cccgcgtacc agcagggcca gaaccagctc   1200
tataacgagc tcaatctagg acgaagagag gagtacgatg ttttggacaa gagacgtggc   1260
cgggaccctg agatgggggg aaagccgcag agaaggaaga accctcagga aggcctgtac   1320
aatgaactgc agaaagataa gatggcggag gcctacagtg agattgggat gaaaggcgag   1380
cgccggaggg gcaaggggca cgatggcctt taccagggtc tcagtacagc caccaaggac   1440
acctacgacg cccttcacat gcaggccctg ccccctcgcg aagcggagc accaacttc    1500
agcctgctga agcaggccgg cgacgtggag gagaaccccg gccccatggc cctgccgtg    1560
accgccctgc tgctgccccct ggccctgctg ctgcacgccg ccaggcccga catcgagctg   1620
acccagagcc ccagcagctt cagcgtgagc ctgggcgaca gggtgaccat cacctgcaag   1680
gccagcgagg acatctacaa caggctggcc tggtaccagc agaagcccgg caacgccccc   1740
aggctgctga tcagcggcgc caccagcctg agaccggcg tgcccagcag gttcagcggc    1800
agcggcagcg gcaaggacta cacccctgagc atcaccagcc tgcagaccga ggacgtggcc   1860
acctactact gccagcagta ctggagcacc cccaccttcg gcggcggcac caagctggag   1920
atcaagaggg gccgccggcg cggcggcagc ggcggcggcg gcagcggcgg cggcggcagc   1980
gcccagcccg ccatggccaa ggtgcagctg caggagagcg gccccagcct ggtgcagccc   2040
agccagaggc tgagcatcac ctgcaccgtg agcggcttca gcctgatcag ctacggcgtg   2100
cactgggtga ggcagagccc cggcaagggc ctggagtggc tgggcgtgat ctggagggc   2160
ggcagcaccg actacaacgc cgccttcatg agcaggctga gcatcaccaa ggacaacagc   2220
aagagccagg tgttcttcaa gatgaacagc ctgcaggccg acgacaccgc catctacttc   2280
tgcgccaaga ccctgatcac caccggctac gccatggact actggggcca gggcaccacc   2340
gtgaccgtga gcagcaccac caccccccgcc ccaggccccc caccccgc cccccaccatc   2400
gccagccagc cctgagcct gaggcccgag gcctgcaggc cgccgccgg cggcgccgtg   2460
cacaccaggg gcctggactt cgcctgcgac atctacatct gggcccccct ggccggcacc   2520
```

-continued

```
tgcggcgtgc tgctgctgag cctggtgatc accctgtact gcaaacgggg cagaaagaaa    2580
ctcctgtata tattcaaaca accatttatg agaccagtac aaaactactca agaggaagat    2640 ggctgtagct gccgatttcc agaagaagaa gaaggaggat gtgaactgag ggtgaagttc    2700
agcaggagcg ccgacgcccc cgcctaccag cagggccaga accagctgta caacgagctg    2760
aacctgggca ggagggagga gtacgacgtg ctggacaaga ggaggggcag ggaccccgag    2820
atgggcggca agccccagag gaggaagaac ccccaggagg gcctgtacaa cgagctgcag    2880
aaggacaaga tggccgaggc ctacagcgag atcggcatga agggcgagag gaggagggc    2940 aagggccacg acggcctgta ccagggcctg agcaccgcca ccaaggacac ctacgacgcc    3000
ctgcacatgc aggccctgcc ccccaggtaa gtttaaac                            3038
```

<210> SEQ ID NO 32
<211> LENGTH: 478
<212> TYPE: PRT
<213> ORGANISM: Artificial Sequence
<220> FEATURE:
<223> OTHER INFORMATION: synthetic sequence

<400> SEQUENCE: 32

```
Met Ala Leu Pro Val Thr Ala Leu Leu Leu Pro Leu Ala Leu Leu Leu
1               5                   10                  15

His Ala Ala Arg Pro Asn Ser Cys Glu Leu Thr Asn Ile Thr Ile Ala
            20                  25                  30

Ile Glu Lys Glu Glu Cys Arg Phe Cys Ile Ser Ile Asn Thr Thr Trp
        35                  40                  45

Cys Ala Gly Tyr Cys Tyr Thr Arg Asp Leu Val Tyr Lys Asp Pro Ala
    50                  55                  60

Arg Pro Lys Ile Gln Lys Thr Cys Thr Phe Lys Glu Leu Val Tyr Glu
65                  70                  75                  80

Thr Val Arg Val Pro Gly Cys Ala His His Ala Asp Ser Leu Tyr Thr
                85                  90                  95

Tyr Pro Val Ala Thr Gln Cys His Cys Gly Lys Cys Asp Ser Asp Ser
            100                 105                 110

Thr Asp Cys Thr Val Arg Gly Leu Gly Pro Ser Tyr Cys Ser Phe Gly
        115                 120                 125

Glu Met Lys Glu Phe Gln Asp Ser Ser Ser Lys Ala Pro Pro Pro
    130                 135                 140

Ser Leu Pro Ser Pro Ser Arg Leu Pro Gly Pro Ser Asp Thr Pro Ile
145                 150                 155                 160

Leu Pro Gln Ala Pro Asp Val Gln Asp Cys Pro Glu Cys Thr Leu Gln
                165                 170                 175

Glu Asn Pro Phe Phe Ser Gln Pro Gly Ala Pro Ile Leu Gln Cys Met
            180                 185                 190

Gly Cys Cys Phe Ser Arg Ala Tyr Pro Thr Pro Leu Arg Ser Lys Lys
        195                 200                 205

Thr Met Leu Val Gln Lys Asn Val Thr Ser Glu Ser Thr Cys Cys Val
    210                 215                 220

Ala Lys Ser Tyr Asn Arg Val Thr Val Met Gly Gly Phe Lys Val Glu
225                 230                 235                 240

Asn His Thr Ala Cys His Cys Ser Thr Cys Tyr Tyr His Lys Ser Thr
                245                 250                 255

Thr Thr Pro Ala Pro Arg Pro Thr Pro Ala Pro Thr Ile Ala Ser
            260                 265                 270
```

Gln Pro Leu Ser Leu Arg Pro Glu Ala Cys Arg Pro Ala Gly Gly
            275                 280                 285

Ala Val His Thr Arg Gly Leu Asp Phe Ala Cys Asp Ile Tyr Ile Trp
290                 295                 300

Ala Pro Leu Ala Gly Thr Cys Gly Val Leu Leu Ser Leu Val Ile
305                 310                 315                 320

Thr Leu Tyr Cys Arg Ser Lys Arg Ser Arg Leu Leu His Ser Asp Tyr
                325                 330                 335

Met Asn Met Thr Pro Arg Arg Pro Gly Pro Thr Arg Lys His Tyr Gln
            340                 345                 350

Pro Tyr Ala Pro Pro Arg Asp Phe Ala Ala Tyr Arg Ser Arg Val Lys
        355                 360                 365

Phe Ser Arg Ser Ala Asp Ala Pro Ala Tyr Gln Gln Gly Gln Asn Gln
370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Gln Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 33
<211> LENGTH: 1445
<212> TYPE: DNA
<213> ORGANISM: Artificial Sequence
<220> FEATURE:
<223> OTHER INFORMATION: synthetic sequence

<400> SEQUENCE: 33
atggccttac cagtgaccgc cttgctcctg ccgctggcct tgctgctcca cgccgccagg    60
ccgaacagct gcgagctgac caacatcacc atcgccatcg agaaggagga gtgcaggttc   120
tgcatcagca tcaacaccac ctggtgcgcc ggctactgct acaccaggga cctggtgtac   180
aaggaccccg ccaggcccaa gatccagaag acctgcacct tcaaggagct ggtgtacgag   240
accgtgaggg tgcccggctg cgcccaccac gccgacagcc tgtacaccta ccccgtggcc   300
acccagtgcc actgcggcaa gtgcgacagc gacagcaccg actgcaccgt gagggggctg   360
ggccccagct actgcagctt cggcgagatg aaggagttcc aggacagcag cagcagcaag   420 gcccccccc ccagcctgcc cagccccagc aggctgcccg gccccagcga cccccccatc   480
ctgccccagg cccccgacgt gcaggactgc cccgagtgca ccctgcagga gaacccccttc   540 ttcagccagc ccggcgcccc catcctgcag tgcatgggct gctgcttcag cagggcctac   600
cccacccccc tgaggagcaa gaagaccatg ctggtgcaga agaacgtgac cagcgagagc   660
acctgctgcg tggccaagag ctacaacagg gtgaccgtga tgggcggctt caaggtggag   720
aaccacaccg cctgccactg cagcacctgc tactaccaca gagcaccac gacgccagcg   780 ccgcgaccac caacaccggc gcccaccatc gcgtcgcagc cctgtccct gcgcccagag   840 gcgtgccggc cagcggcggg gggcgcagtg cacacgaggg ggctggactt cgcctgtgat   900

```
atctacatct gggcgcccett ggccgggact tgtggggtcc ttctcctgtc actggttatc    960 acccttact gcaggagtaa gaggagcagg ctcctgcaca gtgactacat gaacatgact     1020
ccccgccgcc ccgggcccac ccgcaagcat taccagccct atgccccacc acgcgacttc    1080
gcagcctatc gctccagagt gaagttcagc aggagcgcag acgccccgc gtaccagcag     1140 ggccagaacc agctctataa cgagctcaat ctaggacgaa gagaggagta cgatgttttg    1200
gacaagagac gtggccggga ccctgagatg ggggaaagc cgcagagaag gaagaaccct     1260
caggaaggcc tgtacaatga actgcagaaa gataagatgg cggaggccta cagtgagatt    1320
gggatgaaag gcgagcgccg gaggggcaag ggcacgatg gcctttacca gggtctcagt     1380
acagccacca aggacaccta cgacgccctt cacatgcagg ccctgccccc tcgctaagtt    1440
taaac                                                                1445
```

<210> SEQ ID NO 34
<211> LENGTH: 3155
<212> TYPE: DNA
<213> ORGANISM: Artificial Sequence
<220> FEATURE:
<223> OTHER INFORMATION: synthetic sequence

<400> SEQUENCE: 34

```
atggccttac cagtgaccgc cttgctcctg ccgctggcct tgctgctcca cgccgccagg     60
ccgaacagct gcgagctgac caacatcacc atcgccatcg agaaggagga gtgcaggttc    120
tgcatcagca tcaacaccac ctggtgcgcc ggctactgct acaccaggga cctggtgtac    180
aaggaccccg ccaggcccaa gatccagaag acctgcacct tcaaggagct ggtgtacgag    240
accgtgaggg tgcccggctg cgcccaccac gccgacagcc tgtacaccta ccccgtggcc    300
acccagtgcc actgcggcaa gtgcgacagc gacagcaccg actgcaccgt gaggggcctg    360
ggcccccagc tactgcagct tcggcgagatg aaggagttcc aggacagcag cagcagcaag    420 gcccccccc ccagcctgcc cagccccagc aggctgcccg gccccagcga cacccccatc    480
ctgccccagg cccccgacgt gcaggactgc cccgagtgca ccctgcagga gaacccccttc    540 ttcagccagc ccggcgcccc catcctgcag tgcatgggct gctgcttcag cagggcctac    600
cccacccccc tgaggagcaa gaagaccatg ctggtgcaga gaacgtgac cagcgagagc    660 acctgctgcg tggccaagag ctacaacagg gtgaccgtga tgggcggctt caagcgtggag    720 aaccacaccg cctgccactg cagcacctgc tactaccaca gagcaccac gacgccagcg    780 ccgcgaccac caacaccggc gcccaccatc gcgtcgcagc ccctgtccct gcgcccagag    840
gcgtgccggc cagcggcggg gggcgcagtg cacacgaggg gctggacttc gcctgtgat    900 atctacatct gggcgcccett ggccgggact tgtggggtcc ttctcctgtc actggttatc    960 acccttact gcaggagtaa gaggagcagg ctcctgcaca gtgactacat gaacatgact     1020
ccccgccgcc ccgggcccac ccgcaagcat taccagccct atgccccacc acgcgacttc    1080
gcagcctatc gctccagagt gaagttcagc aggagcgcag acgccccgc gtaccagcag     1140 ggccagaacc agctctataa cgagctcaat ctaggacgaa gagaggagta cgatgttttg    1200
gacaagagac gtggccggga ccctgagatg ggggaaagc cgcagagaag gaagaaccct     1260
caggaaggcc tgtacaatga actgcagaaa gataagatgg cggaggccta cagtgagatt    1320
gggatgaaag gcgagcgccg gaggggcaag ggcacgatg gcctttacca gggtctcagt     1380
acagccacca aggacaccta cgacgccctt cacatgcagg ccctgccccc tcgcggcagc    1440
```

```
ggcgaaggcc gcggcagcct gctgacctgc ggcgatgtgg aagaaaaccc gggccccatg    1500
gaatacgcct ctgacgcttc actggacccc gaagccccgt ggcctcccgc gccccgcgct    1560
cgcgcctgcc gcgtactgcc ttgggccctg gtcgcggggc tgctgctgct gctgctgctc    1620
gctgccgcct cgccgtcttc cctcgcctgc cctggccg   tgtccggggc tcgcgcctcg    1680
cccggctccg cggccagccc gagactccgc gagggtcccg agctttcgcc cgacgatccc    1740 gccgcctct tggacctgcg gcagggcatg tttgcgcagc tggtggccca aaatgttctg    1800
ctgatcgatg ggcccctgag ctggtacagt gacccaggcc tggcaggcgt gtccctgacg    1860
gggggcctga gctacaaaga ggacacgaag gagctggtgg tggccaaggc tggagtctac    1920
tatgtcttct tcaactaga gctgcggcgc gtggtggccg gcgagggctc aggctccgtt    1980
tcacttgcgc tgcacctgca gccactgcgc tctgctgctg gggccgccgc cctggctttg    2040
accgtggacc tgccacccgc ctcctccgag gctcggaact cggccttcgg tttccagggc    2100
cgcttgctgc acctgagtgc cggccagcgc ctgggcgtcc atcttcacac tgaggccagg    2160
gcacgccatg cctggcagct acccagggc gccacagtct tgggactctt ccgggtgacc    2220
cccgaaatcc cagccggact cccttcaccg aggtcggaag gaagcggagc tactaacttc    2280
agcctgctga agcaggctgg agacgtggag gagaaccctg acctatgta cagaatgcag    2340 ctgctgagct gcatcgccct gagcctggcc ctggtgacca acagcggcat ccacgtgttc    2400
atcctgggct gcttcagcgc cggcctgccc aagaccgagg ccaactgggt gaacgtgatc    2460
agcgacctga agaagatcga ggacctgatc cagagcatgc acatcgacgc caccctgtac    2520
accgagagcg acgtgcaccc cagctgcaag gtgaccgcca tgaagtgctt cctgctggag    2580
ctgcaggtga tcagcctgga gagcggcgac gccagcatcc acgacaccgt ggagaacctg    2640
atcatcctgg ccaacaacag cctgagcagc aacggcaacg tgaccgagag cggctgcaag    2700
gagtgcgagg agctggagga aagaacatc aaggagttcc tgcagagctt cgtgcacatc    2760
gtgcagatgt tcatcaacac cagctccggc ggcggctccg cggcggcgg ctccggcggc    2820 ggcggctccg gcggcggcgg ctccggcggc ggctccctgc aggcccccag aagagccaga    2880
ggctgcagaa ccctgggcct gccgccctg ctgctgctgc tgctgctgag acccccgcc    2940 accagaggca tcacctgccc ccccccatg agcgtggagc acgccgacat ctgggtgaag    3000
agctacagcc tgtacagcag agagagatac atctgcaaca gcggcttcaa gagaaaggcc    3060
ggcaccagca gcctgaccga gtgcgtgctg aacaaggcca ccaacgtggc ccactggacc    3120
acccccagcc tgaagtgcat cagataagtt taaac                              3155
```

<210> SEQ ID NO 35
<211> LENGTH: 1048
<212> TYPE: PRT
<213> ORGANISM: Artificial Sequence
<220> FEATURE:
<223> OTHER INFORMATION: synthetic sequence

<400> SEQUENCE: 35

```
Met Ala Leu Pro Val Thr Ala Leu Leu Leu Pro Leu Ala Leu Leu Leu
1               5                   10                  15

His Ala Ala Arg Pro Asn Ser Cys Glu Leu Thr Asn Ile Thr Ile Ala
                20                  25                  30

Ile Glu Lys Glu Glu Cys Arg Phe Cys Ile Ser Ile Asn Thr Thr Trp
            35                  40                  45

Cys Ala Gly Tyr Cys Tyr Thr Arg Asp Leu Val Tyr Lys Asp Pro Ala
        50                  55                  60
```

```
Arg Pro Lys Ile Gln Lys Thr Cys Thr Phe Lys Glu Leu Val Tyr Glu
 65                  70                  75                  80

Thr Val Arg Val Pro Gly Cys Ala His His Ala Asp Ser Leu Tyr Thr
             85                  90                  95

Tyr Pro Val Ala Thr Gln Cys His Cys Gly Lys Cys Asp Ser Asp Ser
            100                 105                 110

Thr Asp Cys Thr Val Arg Gly Leu Gly Pro Ser Tyr Cys Ser Phe Gly
            115                 120                 125

Glu Met Lys Glu Phe Gln Asp Ser Ser Ser Lys Ala Pro Pro
130                 135                 140

Ser Leu Pro Ser Pro Ser Arg Leu Pro Gly Pro Ser Asp Thr Pro Ile
145                 150                 155                 160

Leu Pro Gln Ala Pro Asp Val Gln Asp Cys Pro Glu Cys Thr Leu Gln
                165                 170                 175

Glu Asn Pro Phe Phe Ser Gln Pro Gly Ala Pro Ile Leu Gln Cys Met
            180                 185                 190

Gly Cys Cys Phe Ser Arg Ala Tyr Pro Thr Pro Leu Arg Ser Lys Lys
        195                 200                 205

Thr Met Leu Val Gln Lys Asn Val Thr Ser Glu Ser Thr Cys Cys Val
210                 215                 220

Ala Lys Ser Tyr Asn Arg Val Thr Val Met Gly Gly Phe Lys Val Glu
225                 230                 235                 240

Asn His Thr Ala Cys His Cys Ser Thr Cys Tyr Tyr His Lys Ser Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
            275                 280                 285

Ala Val His Thr Arg Gly Leu Asp Phe Ala Cys Asp Ile Tyr Ile Trp
290                 295                 300

Ala Pro Leu Ala Gly Thr Cys Gly Val Leu Leu Leu Ser Leu Val Ile
305                 310                 315                 320

Thr Leu Tyr Cys Arg Ser Lys Arg Ser Arg Leu Leu His Ser Asp Tyr
            325                 330                 335

Met Asn Met Thr Pro Arg Arg Pro Gly Pro Thr Arg Lys His Tyr Gln
            340                 345                 350

Pro Tyr Ala Pro Pro Arg Asp Phe Ala Ala Tyr Arg Ser Arg Val Lys
            355                 360                 365

Phe Ser Arg Ser Ala Asp Ala Pro Ala Tyr Gln Gln Gly Gln Asn Gln
            370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Gln Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg Arg
                435                 440                 445

Gly Lys Gly His Asp Gly Leu Tyr Gln Gly Leu Ser Thr Ala Thr Lys
        450                 455                 460

Asp Thr Tyr Asp Ala Leu His Met Gln Ala Leu Pro Pro Arg Gly Ser
465                 470                 475                 480
```

```
Gly Glu Gly Arg Gly Ser Leu Leu Thr Cys Gly Asp Val Glu Glu Asn
            485                 490                 495
Pro Gly Pro Met Glu Tyr Ala Ser Asp Ala Ser Leu Asp Pro Glu Ala
        500                 505                 510
Pro Trp Pro Ala Pro Arg Ala Arg Ala Cys Arg Val Leu Pro Trp
        515                 520                 525
Ala Leu Val Ala Gly Leu Leu Leu Leu Leu Leu Ala Ala Cys
        530                 535                 540
Ala Val Phe Leu Ala Cys Pro Trp Ala Val Ser Gly Ala Arg Ala Ser
545                 550                 555                 560
Pro Gly Ser Ala Ala Ser Pro Arg Leu Arg Glu Gly Pro Glu Leu Ser
                565                 570                 575
Pro Asp Asp Pro Ala Gly Leu Leu Asp Leu Arg Gln Gly Met Phe Ala
            580                 585                 590
Gln Leu Val Ala Gln Asn Val Leu Leu Ile Asp Gly Pro Leu Ser Trp
        595                 600                 605
Tyr Ser Asp Pro Gly Leu Ala Gly Val Ser Leu Thr Gly Gly Leu Ser
        610                 615                 620
Tyr Lys Glu Asp Thr Lys Glu Leu Val Val Ala Lys Ala Gly Val Tyr
625                 630                 635                 640
Tyr Val Phe Phe Gln Leu Glu Leu Arg Arg Val Val Ala Gly Glu Gly
                645                 650                 655
Ser Gly Ser Val Ser Leu Ala Leu His Leu Gln Pro Leu Arg Ser Ala
            660                 665                 670
Ala Gly Ala Ala Ala Leu Ala Leu Thr Val Asp Leu Pro Pro Ala Ser
            675                 680                 685
Ser Glu Ala Arg Asn Ser Ala Phe Gly Phe Gln Gly Arg Leu Leu His
        690                 695                 700
Leu Ser Ala Gly Gln Arg Leu Gly Val His Leu His Thr Glu Ala Arg
705                 710                 715                 720
Ala Arg His Ala Trp Gln Leu Thr Gln Gly Ala Thr Val Leu Gly Leu
                725                 730                 735
Phe Arg Val Thr Pro Glu Ile Pro Ala Gly Leu Pro Ser Pro Arg Ser
            740                 745                 750
Glu Gly Ser Gly Ala Thr Asn Phe Ser Leu Leu Lys Gln Ala Gly Asp
        755                 760                 765
Val Glu Glu Asn Pro Gly Pro Met Tyr Arg Met Gln Leu Leu Ser Cys
        770                 775                 780
Ile Ala Leu Ser Leu Ala Leu Val Thr Asn Ser Gly Ile His Val Phe
785                 790                 795                 800
Ile Leu Gly Cys Phe Ser Ala Gly Leu Pro Lys Thr Glu Ala Asn Trp
                805                 810                 815
Val Asn Val Ile Ser Asp Leu Lys Lys Ile Glu Asp Leu Ile Gln Ser
            820                 825                 830
Met His Ile Asp Ala Thr Leu Tyr Thr Glu Ser Asp Val His Pro Ser
        835                 840                 845
Cys Lys Val Thr Ala Met Lys Cys Phe Leu Leu Glu Leu Gln Val Ile
        850                 855                 860
Ser Leu Glu Ser Gly Asp Ala Ser Ile His Asp Thr Val Glu Asn Leu
865                 870                 875                 880
Ile Ile Leu Ala Asn Asn Ser Leu Ser Ser Asn Gly Asn Val Thr Glu
                885                 890                 895
Ser Gly Cys Lys Glu Cys Glu Glu Leu Glu Glu Lys Asn Ile Lys Glu
```

```
                   900                 905                  910
Phe Leu Gln Ser Phe Val His Ile Val Gln Met Phe Ile Asn Thr Ser
            915                 920                 925
Ser Gly Gly Gly Ser Gly Gly Gly Gly Ser Gly Gly Gly Gly Ser Gly
        930                 935                 940
Gly Gly Gly Ser Gly Gly Gly Ser Leu Gln Ala Pro Arg Arg Ala Arg
945                 950                 955                 960
Gly Cys Arg Thr Leu Gly Leu Pro Ala Leu Leu Leu Leu Leu Leu Leu
            965                 970                 975
Arg Pro Pro Ala Thr Arg Gly Ile Thr Cys Pro Pro Met Ser Val
                980                 985                 990
Glu His Ala Asp Ile Trp Val Lys Ser Tyr Ser Leu Tyr Ser Arg Glu
            995                 1000                1005
Arg Tyr Ile Cys Asn Ser Gly Phe Lys Arg Lys Ala Gly Thr Ser
        1010                1015                1020
Ser Leu Thr Glu Cys Val Leu Asn Lys Ala Thr Asn Val Ala His
        1025                1030                1035
Trp Thr Thr Pro Ser Leu Lys Cys Ile Arg
        1040                1045
```

```
<210> SEQ ID NO 36
<211> LENGTH: 483
<212> TYPE: PRT
<213> ORGANISM: Artificial Sequence
<220> FEATURE:
<223> OTHER INFORMATION: synthetic sequence

<400> SEQUENCE: 36

Met Ala Leu Pro Val Thr Ala Leu Leu Leu Pro Leu Ala Leu Leu Leu
1               5                   10                  15
His Ala Ala Arg Pro Asp Ile Gln Met Thr Gln Ser Pro Ser Ser Leu
                20                  25                  30
Ser Ala Ser Val Gly Asp Arg Val Thr Ile Thr Cys Arg Ala Ser Gln
            35                  40                  45
Ser Ile Ser Ser Tyr Leu Asn Trp Tyr Gln Gln Lys Pro Gly Lys Ala
        50                  55                  60
Pro Lys Leu Leu Ile Tyr Ala Ala Ser Met Leu Gln Ser Gly Val Pro
65                  70                  75                  80
Ser Arg Phe Ser Gly Ser Gly Ser Gly Thr Asp Phe Thr Leu Thr Ile
                85                  90                  95
Ser Ser Leu Gln Pro Glu Asp Phe Ala Thr Tyr Tyr Cys Gln Gln Asn
                100                 105                 110
Arg Gly Phe Pro Leu Thr Phe Gly Gln Gly Thr Lys Val Glu Ile Lys
            115                 120                 125
Gly Gly Gly Gly Ser Gly Gly Gly Ser Gly Gly Gly Gly Ser Gln
        130                 135                 140
Val Gln Leu Val Gln Ser Gly Gly Gly Leu Val Gln Pro Gly Gly Ser
145                 150                 155                 160
Leu Arg Leu Ser Cys Ala Ala Ser Tyr Phe Asp Phe Asp Ser Tyr Glu
                165                 170                 175
Met Ser Trp Val Arg Gln Ala Pro Gly Lys Gly Leu Glu Trp Ile Gly
                180                 185                 190
Ser Ile Tyr His Ser Gly Ser Thr Tyr Tyr Asn Pro Ser Leu Lys Ser
            195                 200                 205
Arg Val Thr Ile Ser Arg Asp Asn Ser Lys Asn Thr Leu Tyr Leu Gln
```

```
                   210                 215                  220
Met Asn Thr Leu Arg Ala Glu Asp Thr Ala Thr Tyr Tyr Cys Ala Arg
225                 230                  235                 240

Val Asn Met Asp Arg Phe Asp Tyr Trp Gly Gln Gly Thr Leu Val Thr
                245                  250                 255

Val Ser Ser Ser Thr Thr Thr Pro Ala Pro Arg Pro Pro Thr Pro Ala
            260                  265                 270

Pro Thr Ile Ala Ser Gln Pro Leu Ser Leu Arg Pro Glu Ala Cys Arg
        275                  280                 285

Pro Ala Ala Gly Gly Ala Val His Thr Arg Gly Leu Asp Phe Ala Cys
    290                  295                 300

Asp Ile Tyr Ile Trp Ala Pro Leu Ala Gly Thr Cys Gly Val Leu Leu
305                 310                  315                 320

Leu Ser Leu Val Ile Thr Leu Tyr Cys Arg Ser Lys Arg Ser Arg Leu
                325                  330                 335

Leu His Ser Asp Tyr Met Asn Met Thr Pro Arg Arg Pro Gly Pro Thr
            340                  345                 350

Arg Lys His Tyr Gln Pro Tyr Ala Pro Pro Arg Asp Phe Ala Ala Tyr
        355                  360                 365

Arg Ser Arg Val Lys Phe Ser Arg Ser Ala Asp Ala Pro Ala Tyr Gln
    370                  375                 380

Gln Gly Gln Asn Gln Leu Tyr Asn Glu Leu Asn Leu Gly Arg Arg Glu
385                 390                  395                 400

Glu Tyr Asp Val Leu Asp Lys Arg Arg Gly Arg Asp Pro Glu Met Gly
                405                  410                 415

Gly Lys Pro Gln Arg Arg Lys Asn Pro Gln Glu Gly Leu Tyr Asn Glu
            420                  425                 430

Leu Gln Lys Asp Lys Met Ala Glu Ala Tyr Ser Glu Ile Gly Met Lys
        435                  440                 445

Gly Glu Arg Arg Arg Gly Lys Gly His Asp Gly Leu Tyr Gln Gly Leu
    450                  455                 460

Ser Thr Ala Thr Lys Asp Thr Tyr Asp Ala Leu His Met Gln Ala Leu
465                 470                  475                 480

Pro Pro Arg

<210> SEQ ID NO 37
<211> LENGTH: 1452
<212> TYPE: DNA
<213> ORGANISM: Artificial Sequence
<220> FEATURE:
<223> OTHER INFORMATION: synthetic sequence

<400> SEQUENCE: 37
atggccttac cagtgaccgc cttgctcctg ccgctggcct tgctgctcca cgccgccagg      60
ccggacatcc agatgaccca gtctccatcc tccctgtctg catctgtagg agacagagtc    120
accatcactt gccgggcaag tcagagcatt agcagctatt taaattggta tcagcagaaa    180
ccagggaaag cccctaagct cctgatctat gctgcatcca tgttgcaaag tggggtccca    240
tcaaggttca gtggcagtgg atctgggaca gatttcactc tcaccatcag cagtctgcaa    300
cctgaagatt ttgcaactta ctactgtcaa cagaatcggg ttttcctct gacgttcggc     360 caagggacca aggtggaaat caaaggaggg ggggatccg ggggaggagg ctccggcgga     420
ggcggaagcc aggtgcagct ggtgcagtct ggggaggct tggtacagcc tggagggtcc     480
ctgagactct cctgtgcagc ctcttatttc gatttcgatt cttatgaaat gagctgggtc    540
```

```
cgccaggctc agggaaggg cctagagtgg attgggagta tctatcatag tgggagcacc      600
tactacaacc cgtccctcaa gagtcgagtc accatctcca gagacaattc caagaacacg      660
ctgtatctgc aaatgaacac cctgagagcc gaggacacag ccacgtatta ctgtgcgaga      720
gtaaatatgg accgatttga ctactggggc cagggaaccc tggtcaccgt ctcctcaagt      780
accacgacgc cagcgccgcg accaccaaca ccggcgccca ccatcgcgtc cagcccctg       840
tccctgcgcc cagaggcgtg ccggccagcg cggggggcg cagtgcacac gagggggctg       900
gacttcgcct gtgatatcta catctgggcg cccttggccg ggacttgtgg ggtccttctc      960
ctgtcactgg ttatcaccct ttactgcagg agtaagagga gcaggctcct gcacagtgac    1020
tacatgaaca tgactccccg ccgccccggg cccacccgca agcattacca gccctatgcc    1080
ccaccacgcg acttcgcagc ctatcgctcc agagtgaagt tcagcaggag cgcagacgcc    1140
cccgcgtacc agcagggcca gaaccagctc tataacgagc tcaatctagg acgaagagag    1200
gagtacgatg ttttggacaa gagacgtggc cgggaccctg agatgggggg aaagccgcag    1260
agaaggaaga accctcagga aggcctgtac aatgaactgc agaaagataa gatggcggag    1320
gcctacagtg agattgggat gaaaggcgag cgccggaggg gcaaggggca cgatggcctt    1380
taccagggtc tcagtacagc caccaaggac acctacgacg cccttcacat gcaggccctg    1440
ccccctcgct aa                                                        1452

<210> SEQ ID NO 38
<211> LENGTH: 777
<212> TYPE: PRT
<213> ORGANISM: Artificial Sequence
<220> FEATURE:
<223> OTHER INFORMATION: synthetic sequence

<400> SEQUENCE: 38

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Ile Ser Ser Tyr Leu Asn Trp Tyr Gln Gln Lys Pro Gly Lys Ala
    50                  55                  60

Pro Lys Leu Leu Ile Tyr Ala Ala Ser Met Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Asn
            100                 105                 110

Arg Gly Phe Pro Leu Thr Phe Gly Gln Gly Thr Lys Val Glu Ile Lys
        115                 120                 125

Gly Gly Gly Gly Ser Gly Gly Gly Ser Gly Gly Gly Gly Ser Gln
    130                 135                 140

Val Gln Leu Val Gln Ser Gly Gly Gly Leu Val Gln Pro Gly Gly Ser
145                 150                 155                 160

Leu Arg Leu Ser Cys Ala Ala Ser Tyr Phe Asp Phe Asp Ser Tyr Glu
                165                 170                 175

Met Ser Trp Val Arg Gln Ala Pro Gly Lys Gly Leu Glu Trp Ile Gly
            180                 185                 190
```

Ser Ile Tyr His Ser Gly Ser Thr Tyr Tyr Asn Pro Ser Leu Lys Ser
            195                 200                 205

Arg Val Thr Ile Ser Arg Asp Asn Ser Lys Asn Thr Leu Tyr Leu Gln
    210                 215                 220

Met Asn Thr Leu Arg Ala Glu Asp Thr Ala Thr Tyr Tyr Cys Ala Arg
225                 230                 235                 240

Val Asn Met Asp Arg Phe Asp Tyr Trp Gly Gln Gly Thr Leu Val Thr
                245                 250                 255

Val Ser Ser Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Gln Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg Gly Ser Gly Glu Gly Arg Gly Ser Leu Leu Thr Cys Gly
                485                 490                 495

Asp Val Glu Glu Asn Pro Gly Pro Met Tyr Arg Met Gln Leu Leu Ser
            500                 505                 510

Cys Ile Ala Leu Ser Leu Ala Leu Val Thr Asn Ser Gly Ile His Val
        515                 520                 525

Phe Ile Leu Gly Cys Phe Ser Ala Gly Leu Pro Lys Thr Glu Ala Asn
        530                 535                 540

Trp Val Asn Val Ile Ser Asp Leu Lys Lys Ile Glu Asp Leu Ile Gln
545                 550                 555                 560

Ser Met His Ile Asp Ala Thr Leu Tyr Thr Glu Ser Asp Val His Pro
                565                 570                 575

Ser Cys Lys Val Thr Ala Met Lys Cys Phe Leu Leu Glu Leu Gln Val
            580                 585                 590

Ile Ser Leu Glu Ser Gly Asp Ala Ser Ile His Asp Thr Val Glu Asn
        595                 600                 605

Leu Ile Ile Leu Ala Asn Asn Ser Leu Ser Ser Asn Gly Asn Val Thr

Glu Ser Gly Cys Lys Glu Cys Glu Leu Glu Glu Lys Asn Ile Lys
625             630                 635                 640

Glu Phe Leu Gln Ser Phe Val His Ile Val Gln Met Phe Ile Asn Thr
            645                 650                 655

Ser Ser Gly Gly Gly Ser Gly Gly Gly Ser Gly Gly Gly Ser
            660                 665                 670

Gly Gly Gly Gly Ser Gly Gly Gly Ser Leu Gln Ala Pro Arg Arg Ala
            675                 680                 685

Arg Gly Cys Arg Thr Leu Gly Leu Pro Ala Leu Leu Leu Leu Leu
        690             695                 700

Leu Arg Pro Pro Ala Thr Arg Gly Ile Thr Cys Pro Pro Pro Met Ser
705             710                 715                 720

Val Glu His Ala Asp Ile Trp Val Lys Ser Tyr Ser Leu Tyr Ser Arg
                725                 730                 735

Glu Arg Tyr Ile Cys Asn Ser Gly Phe Lys Arg Lys Ala Gly Thr Ser
                740                 745                 750

Ser Leu Thr Glu Cys Val Leu Asn Lys Ala Thr Asn Val Ala His Trp
            755                 760                 765

Thr Thr Pro Ser Leu Lys Cys Ile Arg
        770             775

<210> SEQ ID NO 39
<211> LENGTH: 2342
<212> TYPE: DNA
<213> ORGANISM: Artificial Sequence
<220> FEATURE:
<223> OTHER INFORMATION: synthetic sequence

<400> SEQUENCE: 39

```
atggccttac cagtgaccgc cttgctcctg ccgctggcct tgctgctcca cgccgccagg     60
ccggacatcc agatgaccca gtctccatcc tccctgtctg catctgtagg agacagagtc    120
accatcactt gccgggcaag tcagagcatt agcagctatt taaattggta tcagcagaaa    180
ccagggaaag cccctaagct cctgatctat gctgcatcca gtttgcaaag tggggtccca    240
tcaaggttca gtggcagtgg atctgggaca gatttcactc tcaccatcag cagtctgcaa    300
cctgaagatt ttgcaactta ctactgtcaa cagaatcggg gttttcctct gacgttcggc    360
caagggacca aggtggaaat caaaggaggg gggggatccg ggggaggagg ctccggcgga    420
ggcggaagcc aggtgcagct ggtgcagtct ggggaggct tggtacagcc tggagggtcc     480
ctgagactct cctgtgcagc tcttatttc gatttcgatt cttatgaaat gagctgggtc     540
cgccaggctc cagggaaggg cctagagtgg attgggagta tctatcatag tgggagcacc    600
tactacaacc cgtccctcaa gagtcgagtc accatctcca gagacaattc caagaacacg    660
ctgtatctgc aaatgaacac cctgagagcc gaggacacag ccacgtatta ctgtgcgaga    720
gtaaatatgg accgatttga ctactggggc caggaacccc tggtcaccgt ctcctcaagt    780
accacgacgc cagcgccgcg accaccaaca ccggcgccca ccatcgcgtc gcagccctg    840
tccctgcgcc cagaggcgtg ccggccagcg gcgggggcg cagtgcacac gagggggctg    900
gacttcgcct gtgatatcta catctgggcg cccttggccg gacttgtgg ggtccttctc    960
ctgtcactgg ttatcaccct ttactgcagg agtaagagga caggctcct gcacagtgac   1020
tacatgaaca tgactccccg ccgccccggg cccacccgca agcattacca gcccatgcc   1080
ccaccacgcg acttcgcagc ctatcgctcc agagtgaagt tcagcaggag cgcagacgcc   1140
```

| cccgcgtacc agcagggcca gaaccagctc tataacgagc tcaatctagg acgaagagag | 1200 |
| gagtacgatg tttttggacaa gagacgtggc cgggaccctg agatggggggg aaagccgcag | 1260 |
| agaaggaaga accctcagga aggcctgtac aatgaactgc agaaagataa gatggcggag | 1320 |
| gcctacagtg agattgggat gaaaggcgag cgccggaggg gcaaggggca cgatggcctt | 1380 |
| taccagggtc tcagtacagc caccaaggac acctacgacg cccttcacat gcaggccctg | 1440 |
| ccccctcgcg gcagcggcga aggccgcggc agcctgctga cctgcggcga tgtggaagaa | 1500 |
| aacccgggcc ccatgtacag aatgcagctg ctgagctgca tcgccctgag cctggccctg | 1560 |
| gtgaccaaca gcggcatcca cgtgttcatc ctgggctgct tcagcgccgg cctgcccaag | 1620 |
| accgaggcca actgggtgaa cgtgatcagc gacctgaaga agatcgagga cctgatccag | 1680 |
| agcatgcaca tcgacgccac cctgtacacc gagagcgacg tgcacccccag ctgcaaggtg | 1740 |
| accgccatga agtgcttcct gctggagctg caggtgatca gcctggagag cggcgacgcc | 1800 |
| agcatccacg acaccgtgga gaacctgatc atcctggcca acaacagcct gagcagcaac | 1860 |
| ggcaacgtga ccgagagcgg ctgcaaggag tgcgaggagc tggaggagaa gaacatcaag | 1920 |
| gagttcctgc agagcttcgt gcacatcgtg cagatgttca tcaacaccag ctccggcggc | 1980 |
| ggctccggcg gcggcggctc cggcggcggc ggctccggcg gcggcggctc cggcggcggc | 2040 |
| tccctgcagg cccccagaag agccagaggc tgcagaaccc tgggcctgcc cgccctgctg | 2100 |
| ctgctgctgc tgctgagacc ccccgccacc agaggcatca cctgccccccc ccccatgagc | 2160 |
| gtggagcacg ccgacatctg ggtgaagagc tacagcctgt acagcagaga gagatacatc | 2220 |
| tgcaacagcg gcttcaagag aaaggccggc accagcagcc tgaccgagtg cgtgctgaac | 2280 |
| aaggccacca acgtgcccca ctggaccacc cccagcctga agtgcatcag ataagtttaa | 2340 |
| ac | 2342 |

<210> SEQ ID NO 40
<211> LENGTH: 1053
<212> TYPE: PRT
<213> ORGANISM: Artificial Sequence
<220> FEATURE:
<223> OTHER INFORMATION: synthetic sequence
<400> SEQUENCE: 40

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Ile Ser Ser Tyr Leu Asn Trp Tyr Gln Gln Lys Pro Gly Lys Ala
    50                  55                  60

Pro Lys Leu Leu Ile Tyr Ala Ala Ser Met Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Asn
            100                 105                 110

Arg Gly Phe Pro Leu Thr Phe Gly Gln Gly Thr Lys Val Glu Ile Lys
        115                 120                 125

Gly Gly Gly Gly Ser Gly Gly Gly Ser Gly Gly Gly Gly Ser Gln
    130                 135                 140
```

```
Val Gln Leu Val Gln Ser Gly Gly Gly Leu Val Gln Pro Gly Gly Ser
145                 150                 155                 160

Leu Arg Leu Ser Cys Ala Ala Ser Tyr Phe Asp Phe Asp Ser Tyr Glu
                165                 170                 175

Met Ser Trp Val Arg Gln Ala Pro Gly Lys Gly Leu Glu Trp Ile Gly
            180                 185                 190

Ser Ile Tyr His Ser Gly Ser Thr Tyr Tyr Asn Pro Ser Leu Lys Ser
        195                 200                 205

Arg Val Thr Ile Ser Arg Asp Asn Ser Lys Asn Thr Leu Tyr Leu Gln
    210                 215                 220

Met Asn Thr Leu Arg Ala Glu Asp Thr Ala Thr Tyr Tyr Cys Ala Arg
225                 230                 235                 240

Val Asn Met Asp Arg Phe Asp Tyr Trp Gly Gln Gly Thr Leu Val Thr
                245                 250                 255

Val Ser Ser Ser Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Gln Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg Gly Ser Gly Glu Gly Arg Gly Ser Leu Leu Thr Cys Gly
                485                 490                 495

Asp Val Glu Glu Asn Pro Gly Pro Met Glu Tyr Ala Ser Asp Ala Ser
                500                 505                 510

Leu Asp Pro Glu Ala Pro Trp Pro Pro Ala Pro Arg Ala Arg Ala Cys
        515                 520                 525

Arg Val Leu Pro Trp Ala Leu Val Ala Gly Leu Leu Leu Leu Leu Leu
    530                 535                 540

Leu Ala Ala Ala Cys Ala Val Phe Leu Ala Cys Pro Trp Ala Val Ser
545                 550                 555                 560
```

```
Gly Ala Arg Ala Ser Pro Gly Ser Ala Ser Pro Arg Leu Arg Glu
                565                 570                 575

Gly Pro Glu Leu Ser Pro Asp Pro Ala Gly Leu Leu Asp Leu Arg
            580                 585                 590

Gln Gly Met Phe Ala Gln Leu Val Ala Gln Asn Val Leu Leu Ile Asp
        595                 600                 605

Gly Pro Leu Ser Trp Tyr Ser Asp Pro Gly Leu Ala Gly Val Ser Leu
            610                 615                 620

Thr Gly Gly Leu Ser Tyr Lys Glu Asp Thr Lys Glu Leu Val Val Ala
625                 630                 635                 640

Lys Ala Gly Val Tyr Tyr Val Phe Phe Gln Leu Glu Leu Arg Arg Val
                645                 650                 655

Val Ala Gly Glu Gly Ser Gly Ser Val Ser Leu Ala Leu His Leu Gln
            660                 665                 670

Pro Leu Arg Ser Ala Ala Gly Ala Ala Ala Leu Ala Leu Thr Val Asp
        675                 680                 685

Leu Pro Pro Ala Ser Ser Glu Ala Arg Asn Ser Ala Phe Gly Phe Gln
        690                 695                 700

Gly Arg Leu Leu His Leu Ser Ala Gly Gln Arg Leu Gly Val His Leu
705                 710                 715                 720

His Thr Glu Ala Arg Ala Arg His Ala Trp Gln Leu Thr Gln Gly Ala
                725                 730                 735

Thr Val Leu Gly Leu Phe Arg Val Thr Pro Glu Ile Pro Ala Gly Leu
            740                 745                 750

Pro Ser Pro Arg Ser Glu Gly Ser Gly Ala Thr Asn Phe Ser Leu Leu
        755                 760                 765

Lys Gln Ala Gly Asp Val Glu Glu Asn Pro Gly Pro Met Tyr Arg Met
        770                 775                 780

Gln Leu Leu Ser Cys Ile Ala Leu Ser Leu Ala Leu Val Thr Asn Ser
785                 790                 795                 800

Gly Ile His Val Phe Ile Leu Gly Cys Phe Ser Ala Gly Leu Pro Lys
                805                 810                 815

Thr Glu Ala Asn Trp Val Asn Val Ile Ser Asp Leu Lys Lys Ile Glu
            820                 825                 830

Asp Leu Ile Gln Ser Met His Ile Asp Ala Thr Leu Tyr Thr Glu Ser
        835                 840                 845

Asp Val His Pro Ser Cys Lys Val Thr Ala Met Lys Cys Phe Leu Leu
        850                 855                 860

Glu Leu Gln Val Ile Ser Leu Glu Ser Gly Asp Ala Ser Ile His Asp
865                 870                 875                 880

Thr Val Glu Asn Leu Ile Ile Leu Ala Asn Asn Ser Leu Ser Ser Asn
                885                 890                 895

Gly Asn Val Thr Glu Ser Gly Cys Lys Glu Cys Glu Glu Leu Glu Glu
            900                 905                 910

Lys Asn Ile Lys Glu Phe Leu Gln Ser Phe Val His Ile Val Gln Met
        915                 920                 925

Phe Ile Asn Thr Ser Ser Gly Gly Ser Gly Gly Gly Ser Gly
        930                 935                 940

Gly Gly Gly Ser Gly Gly Gly Gly Ser Gly Gly Ser Leu Gln Ala
945                 950                 955                 960

Pro Arg Arg Ala Arg Gly Cys Arg Thr Leu Gly Leu Pro Ala Leu Leu
                965                 970                 975

Leu Leu Leu Leu Leu Arg Pro Pro Ala Thr Arg Gly Ile Thr Cys Pro
```

```
                  980            985             990
Pro Pro Met Ser Val Glu His Ala Asp Ile Trp Val Lys Ser Tyr Ser
            995             1000            1005

Leu Tyr Ser Arg Glu Arg Tyr Ile Cys Asn Ser Gly Phe Lys Arg
    1010            1015            1020

Lys Ala Gly Thr Ser Ser Leu Thr Glu Cys Val Leu Asn Lys Ala
    1025            1030            1035

Thr Asn Val Ala His Trp Thr Pro Ser Leu Lys Cys Ile Arg
    1040            1045            1050

<210> SEQ ID NO 41
<211> LENGTH: 3170
<212> TYPE: DNA
<213> ORGANISM: Artificial Sequence
<220> FEATURE:
<223> OTHER INFORMATION: synthetic sequence

<400> SEQUENCE: 41
```

| | | | | | |
|---|---|---|---|---|---|
| atggccttac | cagtgaccgc | cttgctcctg | ccgctggcct | tgctgctcca | cgccgccagg | 60 |
| ccggacatcc | agatgaccca | gtctccatcc | tccctgtctg | catctgtagg | agacagagtc | 120 |
| accatcactt | gccgggcaag | tcagagcatt | agcagctatt | taaattggta | tcagcagaaa | 180 |
| ccagggaaag | cccctaagct | cctgatctat | gctgcatcca | gtttgcaaag | tggggtccca | 240 |
| tcaaggttca | gtggcagtgg | atctgggaca | gatttcactc | tcaccatcag | cagtctgcaa | 300 |
| cctgaagatt | ttgcaactta | ctactgtcaa | cagaatcggg | gttttcctct | gacgttcggc | 360 |
| caagggacca | aggtggaaat | caaaggaggg | ggggatccg | gggaggagg | ctccggcgga | 420 |
| ggcggaagcc | aggtgcagct | ggtgcagtct | ggggaggct | tggtacagcc | tggagggtcc | 480 |
| ctgagactct | cctgtgcagc | ctcttatttc | gatttcgatt | cttatgaaat | gagctgggtc | 540 |
| cgccaggctc | cagggaaggg | cctagagtgg | attgggagta | tctatcatag | tgggagcacc | 600 |
| tactacaacc | cgtccctcaa | gagtcgagtc | accatctcca | gagacaattc | caagaacacg | 660 |
| ctgtatctgc | aaatgaacac | cctgagagcc | gaggacacag | ccacgtatta | ctgtgcgaga | 720 |
| gtaaatatgg | accgatttga | ctactggggc | cagggaaccc | tggtcaccgt | ctcctcaagt | 780 |
| accacgacgc | cagcgccgcg | accaccaaca | ccggcgccca | ccatcgcgtc | gcagcccctg | 840 |
| tccctgcgcc | cagaggcgtg | ccggccagc | gcgggggcg | cagtgcacac | gagggggctg | 900 |
| gacttcgcct | gtgatatcta | catctgggcg | cccttggccg | gacttgtgg | ggtccttctc | 960 |
| ctgtcactgg | ttatcaccct | ttactgcagg | agtaagagga | gcaggctcct | gcacagtgac | 1020 |
| tacatgaaca | tgactccccg | ccgccccggg | cccacccgca | agcattacca | gcccctatgcc | 1080 |
| ccaccacgcg | acttcgcagc | ctatcgctcc | agagtgaagt | tcagcaggag | cgcagacgcc | 1140 |
| cccgcgtacc | agcagggcca | gaaccagctc | tataacgagc | tcaatctagg | acgaagagag | 1200 |
| gagtacgatg | ttttggacaa | gagacgtggc | cgggaccctg | agatgggggg | aaagccgcag | 1260 |
| agaaggaaga | accctcagga | aggcctgtac | aatgaactgc | agaaagataa | gatggcggag | 1320 |
| gcctacagtg | agattgggat | gaaaggcgag | cgccggaggg | gcaaggggca | cgatggcctt | 1380 |
| taccagggtc | tcagtacagc | caccaaggac | acctacgacg | cccttcacat | gcaggccctg | 1440 |
| cccctcgcg | gcagcggcga | aggccgcggc | agcctgctga | cctgcggcga | tgtggaagaa | 1500 |
| aacccgggcc | ccatggaata | cgcctctgac | gcttcactgg | accccgaagc | cccgtggcct | 1560 |
| cccgcgcccc | gcgctcgcgc | ctgccgcgta | ctgccttggg | ccctggtcgc | ggggctgctg | 1620 |
| ctgctgctgc | tgctcgctgc | cgcctgcgcc | gtcttcctcg | cctgccccctg | ggccgtgtcc | 1680 |

```
ggggctcgcg cctcgcccgg ctccgcggcc agcccgagac tccgcgaggg tcccgagctt    1740
tcgcccgacg atcccgccgg cctcttggac ctgcggcagg gcatgtttgc gcagctggtg    1800
gcccaaaatg ttctgctgat cgatgggccc ctgagctggt acagtgaccc aggcctggca    1860
ggcgtgtccc tgacgggggg cctgagctac aaagaggaca cgaaggagct ggtggtggcc    1920
aaggctggag tctactatgt cttctttcaa ctagagctgc ggcgcgtggt ggccggcgag    1980
ggctcaggct ccgtttcact gcgctgcac ctgcagccac tgcgtctgc tgctggggcc     2040 gccgccctgg ctttgaccgt ggacctgcca cccgcctcct ccgaggctcg gaactcggcc    2100
ttcggtttcc agggccgctt gctgcacctg agtgccggcc agcgcctggg cgtccatctt    2160
cacactgagg ccagggcacg ccatgcctgg cagcttaccc agggcgccac agtcttggga    2220
ctcttccggg tgaccccga atcccagcc ggactccctt caccgaggtc ggaaggaagc      2280
ggagctacta acttcagcct gctgaagcag gctggagacg tggaggagaa ccctggacct    2340
atgtacagaa tgcagctgct gagctgcatc gccctgagcc tggccctggt gaccaacagc    2400
ggcatccacg tgttcatcct gggctgcttc agcgccggcc tgcccaagac cgaggccaac    2460
tgggtgaacg tgatcagcga cctgaagaag atcgaggacc tgatccagag catgcacatc    2520
gacgccaccc tgtacaccga gagcgacgtg caccccagct gcaaggtgac cgccatgaag    2580
tgcttcctgc tggagctgca ggtgatcagc ctggagagcg gcgacgccag catccacgac    2640
accgtggaga acctgatcat cctggccaac aacagcctga gcagcaacgg caacgtgacc    2700
gagagcggct gcaaggagtg cgaggagctg gaggagaaga acatcaagga gttcctgcag    2760
agcttcgtgc acatcgtgca gatgttcatc aacaccagct ccgccggcgg ctccggcggc    2820
ggcggctccg gcggcggcgg ctccggcggc ggcggctccg gcggcggctc cctgcaggcc    2880
cccagaagag ccagaggctg cagaaccctg ggcctgcccg ccctgctgct gctgctgctg    2940
ctgagacccc ccgccaccag aggcatcacc tgccccccc ccatgagcgt ggagcacgcc    3000
gacatctggg tgaagagcta cagcctgtac agcagagaga gatacatctg caacagcggc    3060
ttcaagagaa aggccggcac cagcagcctg accgagtgcg tgctgaacaa ggccaccaac    3120
gtggcccact ggaccacccc cagcctgaag tgcatcagat aagtttaaac                3170
```

<210> SEQ ID NO 42
<211> LENGTH: 486
<212> TYPE: PRT
<213> ORGANISM: Artificial Sequence
<220> FEATURE:
<223> OTHER INFORMATION: synthetic sequence

<400> SEQUENCE: 42

```
Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
                20                  25                  30

Pro Val Ser Leu Gly Asp Gln Ala Ser Ile Ser Cys Arg Ser Ser Gln
            35                  40                  45

Ser Leu Val His Ser Asn Gly Asn Thr Tyr Leu His Trp Tyr Leu Gln
        50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95
```

Phe Thr Leu Lys Ile Ser Arg Val Glu Ala Glu Asp Leu Gly Val Tyr
            100                 105                 110

Phe Cys Ser Gln Asn Thr His Val Pro Pro Thr Phe Gly Ser Gly Thr
        115                 120                 125

Lys Leu Glu Ile Lys Gly Gly Gly Gly Ser Gly Gly Gly Gly Ser Gly
    130                 135                 140

Gly Gly Ser Gln Val Gln Leu Gln Gln Ser Gly Ala Glu Leu Val
145                 150                 155                 160

Arg Pro Gly Ala Ser Val Lys Leu Ser Cys Lys Ala Ser Gly Tyr Thr
                165                 170                 175

Phe Thr Asp Tyr Glu Met His Trp Val Lys Gln Thr Pro Val His Gly
            180                 185                 190

Leu Lys Trp Ile Gly Ala Leu Asp Pro Lys Thr Gly Asp Thr Ala Tyr
        195                 200                 205

Ser Gln Lys Phe Lys Gly Lys Ala Thr Leu Thr Ala Asp Lys Ser Ser
    210                 215                 220

Ser Thr Ala Tyr Met Glu Leu Arg Ser Leu Thr Ser Glu Asp Ser Ala
225                 230                 235                 240

Val Tyr Tyr Cys Thr Arg Phe Tyr Ser Tyr Thr Tyr Trp Gly Gln Gly
                245                 250                 255

Thr Leu Val Thr Val Ser Ala Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Gly Arg Asp Pro
                405                 410                 415

Glu Met Gly Gly Lys Pro Gln Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 43
<211> LENGTH: 1469
<212> TYPE: DNA

<213> ORGANISM: Artificial Sequence
<220> FEATURE:
<223> OTHER INFORMATION: synthetic sequence

<400> SEQUENCE: 43

```
atggccttac cagtgaccgc cttgctcctg ccgctggcct tgctgctcca cgccgccagg      60
ccggacgtgg tgatgaccca gaccccctg agcctgcccg tgagcctggg cgaccaggcc     120
agcatcagct gcaggagcag ccagagcctg gtgcacagca cggcaacac ctacctgcac     180
tggtacctgc agaagcccgg ccagagcccc aagctgctga tctacaaggt gagcaacagg     240
ttcagcggcg tgcccgacag gttcagcggc agcggcagcg gcaccgactt caccctgaag     300
atcagcaggg tggaggccga ggacctgggc gtgtacttct gcagccagaa cacccacgtg     360
ccccccacct tcggcagcgg caccaagctg gagatcaagg gaggggggg atccggggga     420
ggaggctccg gcggaggcgg aagccaggtg cagctgcagc agagcggcgc cgagctggtg     480
aggcccggcg ccagcgtgaa gctgagctgc aaggccagcg gctacacctt caccgactac     540
gagatgcact gggtgaagca gacccccgtg cacggcctga gtggatcgg cgccctggac     600
cccaagaccg gcgacaccgc ctacagccag aagttcaagg gcaaggccac cctgaccgcc     660
gacaagagca gcagcaccgc ctacatggag ctgaggagcc tgaccagcga ggacagcgcc     720
gtgtactact gcaccaggtt ctacagctac acctactggg ccagggcac cctggtgacc     780
gtgagcgcca ccacgacgcc agcgccgcga ccaccaacac cggcgcccac catcgcgtcg     840
cagcccctgt ccctgcgccc agaggcgtgc cggccagcgg cggggggcgc agtgcacacg     900
agggggctgg acttcgcctg tgatatctac atctgggcgc ccttggccgg acttgtgggg     960
gtccttctcc tgtcactggt tatcaccctt tactgcagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tgggggga    1260
aagccgcaga gaaggaagaa ccctcaggaa ggcctgtaca tgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcta gtttaaac                                        1469
```

<210> SEQ ID NO 44
<211> LENGTH: 777
<212> TYPE: PRT
<213> ORGANISM: Artificial Sequence
<220> FEATURE:
<223> OTHER INFORMATION: synthetic sequence

<400> SEQUENCE: 44

```
Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
```

```
            65                  70                  75                  80
        Phe Ser Gly Val Pro Asp Arg Phe Ser Gly Ser Gly Ser Gly Thr Asp
                         85                  90                  95
        Phe Thr Leu Lys Ile Ser Arg Val Glu Ala Glu Asp Leu Gly Val Tyr
                        100                 105                 110
        Phe Cys Ser Gln Asn Thr His Val Pro Pro Thr Phe Gly Ser Gly Thr
                        115                 120                 125
        Lys Leu Glu Ile Lys Gly Gly Gly Gly Ser Gly Gly Gly Gly Ser Gly
        130                 135                 140
        Gly Gly Ser Gln Val Gln Leu Gln Gln Ser Gly Ala Glu Leu Val
        145                 150                 155                 160
        Arg Pro Gly Ala Ser Val Lys Leu Ser Cys Lys Ala Ser Gly Tyr Thr
                        165                 170                 175
        Phe Thr Asp Tyr Glu Met His Trp Val Lys Gln Thr Pro Val His Gly
                        180                 185                 190
        Leu Lys Trp Ile Gly Ala Leu Asp Pro Lys Thr Gly Asp Thr Ala Tyr
                        195                 200                 205
        Ser Gln Lys Phe Lys Gly Lys Ala Thr Leu Thr Ala Asp Lys Ser Ser
                        210                 215                 220
        Ser Thr Ala Tyr Met Glu Leu Arg Ser Leu Thr Ser Glu Asp Ser Ala
        225                 230                 235                 240
        Val Tyr Tyr Cys Thr Arg Phe Tyr Ser Tyr Thr Tyr Trp Gly Gln Gly
                        245                 250                 255
        Thr Leu Val Thr Val Ser Ala Thr Thr Thr Pro Ala Pro Arg Pro Pro
                        260                 265                 270
        Thr Pro Ala Pro Thr Ile Ala Ser Gln Pro Leu Ser Leu Arg Pro Glu
                        275                 280                 285
        Ala Cys Arg Pro Ala Ala Gly Gly Ala Val His Thr Arg Gly Leu Asp
                        290                 295                 300
        Phe Ala Cys Asp Ile Tyr Ile Trp Ala Pro Leu Ala Gly Thr Cys Gly
        305                 310                 315                 320
        Val Leu Leu Leu Ser Leu Val Ile Thr Leu Tyr Cys Arg Ser Lys Arg
                        325                 330                 335
        Ser Arg Leu Leu His Ser Asp Tyr Met Asn Met Thr Pro Arg Arg Pro
                        340                 345                 350
        Gly Pro Thr Arg Lys His Tyr Gln Pro Tyr Ala Pro Pro Arg Asp Phe
                        355                 360                 365
        Ala Ala Tyr Arg Ser Arg Val Lys Phe Ser Arg Ser Ala Asp Ala Pro
                        370                 375                 380
        Ala Tyr Gln Gln Gly Gln Asn Gln Leu Tyr Asn Glu Leu Asn Leu Gly
        385                 390                 395                 400
        Arg Arg Glu Glu Tyr Asp Val Leu Asp Lys Arg Gly Arg Asp Pro
                        405                 410                 415
        Glu Met Gly Gly Lys Pro Gln Arg Arg Lys Asn Pro Gln Glu Gly Leu
                        420                 425                 430
        Tyr Asn Glu Leu Gln Lys Asp Lys Met Ala Glu Ala Tyr Ser Glu Ile
                        435                 440                 445
        Gly Met Lys Gly Glu Arg Arg Arg Gly Lys Gly His Asp Gly Leu Tyr
                        450                 455                 460
        Gln Gly Leu Ser Thr Ala Thr Lys Asp Thr Tyr Asp Ala Leu His Met
        465                 470                 475                 480
        Gln Ala Leu Pro Pro Arg Gly Ser Gly Glu Gly Arg Gly Ser Leu Leu
                        485                 490                 495
```

Thr Cys Gly Asp Val Glu Glu Asn Pro Gly Pro Met Tyr Arg Met Gln
            500                 505                 510

Leu Leu Ser Cys Ile Ala Leu Ser Leu Ala Leu Val Thr Asn Ser Gly
            515                 520                 525

Ile His Val Phe Ile Leu Gly Cys Phe Ser Ala Gly Leu Pro Lys Thr
        530                 535                 540

Glu Ala Asn Trp Val Asn Val Ile Ser Asp Leu Lys Lys Ile Glu Asp
545                 550                 555                 560

Leu Ile Gln Ser Met His Ile Asp Ala Thr Leu Tyr Thr Glu Ser Asp
                565                 570                 575

Val His Pro Ser Cys Lys Val Thr Ala Met Lys Cys Phe Leu Leu Glu
            580                 585                 590

Leu Gln Val Ile Ser Leu Glu Ser Gly Asp Ala Ser Ile His Asp Thr
        595                 600                 605

Val Glu Asn Leu Ile Ile Leu Ala Asn Asn Ser Leu Ser Ser Asn Gly
    610                 615                 620

Asn Val Thr Glu Ser Gly Cys Lys Glu Cys Glu Glu Leu Glu Glu Lys
625                 630                 635                 640

Asn Ile Lys Glu Phe Leu Gln Ser Phe Val His Ile Val Gln Met Phe
                645                 650                 655

Ile Asn Thr Ser Ser Gly Gly Ser Gly Gly Gly Ser Gly Gly
            660                 665                 670

Gly Gly Ser Gly Gly Gly Ser Gly Gly Gly Ser Leu Gln Ala Pro
        675                 680                 685

Arg Arg Ala Arg Gly Cys Arg Thr Leu Gly Leu Pro Ala Leu Leu Leu
    690                 695                 700

Leu Leu Leu Leu Arg Pro Pro Ala Thr Arg Gly Ile Thr Cys Pro Pro
705                 710                 715                 720

Pro Met Ser Val Glu His Ala Asp Ile Trp Val Lys Ser Tyr Ser Leu
                725                 730                 735

Tyr Ser Arg Glu Arg Tyr Ile Cys Asn Ser Gly Phe Lys Arg Lys Ala
            740                 745                 750

Gly Thr Ser Ser Leu Thr Glu Cys Val Leu Asn Lys Ala Thr Asn Val
        755                 760                 765

Ala His Trp Thr Thr Pro Ser Leu Lys
    770                 775

<210> SEQ ID NO 45
<211> LENGTH: 2351
<212> TYPE: DNA
<213> ORGANISM: Artificial Sequence
<220> FEATURE:
<223> OTHER INFORMATION: synthetic sequence

<400> SEQUENCE: 45
atggccttac cagtgaccgc cttgctcctg ccgctggcct tgctgctcca cgccgccagg    60
ccggacgtgg tgatgaccca gacccccctg agcctgcccg tgagcctggg cgaccaggcc   120
agcatcagct gcaggagcag ccagagcctg gtgcacagca acggcaacac ctacctgcac   180
tggtacctgc agaagcccgg ccagagcccc aagctgctga tctacaaggt gagcaacagg   240
ttcagcggcg tgcccgacag gttcagcggc agcggcagcg gcaccgactt cacctgaag   300 atcagcaggg tggaggccga ggacctgggc gtgtacttct gcagccagaa cacccacgtg   360 cccccccacct tcggcagcgg caccaagctg gagatcaagg gagggggggg atccggggga   420

```
ggaggctccg gcggaggcgg aagccaggtg cagctgcagc agagcggcgc cgagctggtg    480
aggcccggcg ccagcgtgaa gctgagctgc aaggccagcg gctacacctt caccgactac    540
gagatgcact gggtgaagca gacccccgtg cacggcctga gtggatcgg cgccctggac     600
cccaagaccg cgacaccgc ctacagccag aagttcaagg gcaaggccac cctgaccgcc    660
gacaagagca gcagcaccgc ctacatggag ctgaggagcc tgaccagcga ggacagcgcc    720
gtgtactact gcaccaggtt ctacagctac acctactggg gccagggcac cctggtgacc    780
gtgagcgcca ccacgacgcc agcgccgcga ccaccaacac cggcgcccac catcgcgtcg    840
cagcccctgt ccctgcgccc agaggcgtgc cggccagcgg cggggggcgc agtgcacacg    900
aggggggctgg acttcgcctg tgatatctac atctgggcgc ccttggccgg acttgtggg    960
gtccttctcc tgtcactggt tatcacccttt tactgcagga gtaagaggag caggctcctg   1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tgggggga     1260
aagccgcaga gaaggaagaa ccctcaggaa ggcctgtaca atgaactgca gaaagataag    1320
atggcggagg cctacagtga gattgggatg aaaggcgagc gccggagggg caaggggcac   1380
gatggccttt accagggtct cagtacagcc accaaggaca cctacgacgc ccttcacatg    1440
caggccctgc cccctcgcgg cagcggcgaa ggccgcggca gcctgctgac ctgcggcgat   1500
gtggaagaaa acccggggcc catgtacaga atgcagctgc tgagctgcat cgccctgagc   1560
ctggccctgg tgaccaacag cggcatccac gtgttcatcc tgggctgctt cagcgccggc   1620
ctgcccaaga ccgaggccaa ctgggtgaac gtgatcagcg acctgaagaa gatcgaggac   1680
ctgatccaga gcatgcacat cgacgccacc ctgtacaccg agagcgacgt gcaccccagc    1740
tgcaaggtga ccgccatgaa gtgcttcctg ctggagctgc aggtgatcag cctggagagc    1800
ggcgacgcca gcatccacga caccgtggag aacctgatca tcctggccaa caacagcctg    1860
agcagcaacg gcaacgtgac cgagagcggc tgcaaggagt cgcaggagct ggaggagaag    1920
aacatcaagg agttcctgca gagcttcgtg cacatcgtgc agatgttcat caacaccagc   1980
tccggcggcg gctccggcgg cggcggctcc ggcggcggcg gctccggcgg cggcggctcc    2040
ggcggcggct ccctgcaggc ccccagaaga gccagaggct gcagaaccct gggcctgccc    2100
gccctgctgc tgctgctgct gctgagaccc ccgccaccag aggcatcac ctgccccccc   2160
cccatgagcg tggagcacgc cgacatctgg gtgaagagct acagcctgta cagcagagag    2220
agatacatct gcaacagcgg cttcaagaga aaggccggca ccagcagcct gaccgagtgc    2280
gtgctgaaca aggccaccaa cgtggcccac tggaccaccc cagcctgaa gtgcatcaga    2340
taagtttaaa c                                                         2351
```

<210> SEQ ID NO 46
<211> LENGTH: 1056
<212> TYPE: PRT
<213> ORGANISM: Artificial Sequence
<220> FEATURE:
<223> OTHER INFORMATION: synthetic sequence

<400> SEQUENCE: 46

```
Met Ala Leu Pro Val Thr Ala Leu Leu Leu Pro Leu Ala Leu Leu Leu
1               5                   10                  15
```

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Asn Thr His Val Pro Pro Thr Phe Gly Ser Gly Thr
        115                 120                 125

Lys Leu Glu Ile Lys Gly Gly Gly Gly Ser Gly Gly Gly Gly Ser Gly
    130                 135                 140

Gly Gly Ser Gln Val Gln Leu Gln Gln Ser Gly Ala Glu Leu Val
145                 150                 155                 160

Arg Pro Gly Ala Ser Val Lys Leu Ser Cys Lys Ala Ser Gly Tyr Thr
                165                 170                 175

Phe Thr Asp Tyr Glu Met His Trp Val Lys Gln Thr Pro Val His Gly
            180                 185                 190

Leu Lys Trp Ile Gly Ala Leu Asp Pro Lys Thr Gly Asp Thr Ala Tyr
        195                 200                 205

Ser Gln Lys Phe Lys Gly Lys Ala Thr Leu Thr Ala Asp Lys Ser Ser
    210                 215                 220

Ser Thr Ala Tyr Met Glu Leu Arg Ser Leu Thr Ser Glu Asp Ser Ala
225                 230                 235                 240

Val Tyr Tyr Cys Thr Arg Phe Tyr Ser Tyr Thr Tyr Trp Gly Gln Gly
                245                 250                 255

Thr Leu Val Thr Val Ser Ala Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Gly Arg Asp Pro
                405                 410                 415

Glu Met Gly Gly Lys Pro Gln Arg Arg Lys Asn Pro Gln Glu Gly Leu
            420                 425                 430

Tyr Asn Glu Leu Gln Lys Asp Lys Met Ala Glu Ala Tyr Ser Glu Ile

```
            435                 440                 445
Gly Met Lys Gly Glu Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Gly Glu Gly Arg Gly Ser Leu Leu
                485                 490                 495

Thr Cys Gly Asp Val Glu Glu Asn Pro Gly Pro Met Glu Tyr Ala Ser
            500                 505                 510

Asp Ala Ser Leu Asp Pro Glu Ala Pro Trp Pro Pro Ala Pro Arg Ala
        515                 520                 525

Arg Ala Cys Arg Val Leu Pro Trp Ala Leu Val Ala Gly Leu Leu Leu
    530                 535                 540

Leu Leu Leu Leu Ala Ala Ala Cys Ala Val Phe Leu Ala Cys Pro Trp
545                 550                 555                 560

Ala Val Ser Gly Ala Arg Ala Ser Pro Gly Ser Ala Ala Ser Pro Arg
                565                 570                 575

Leu Arg Glu Gly Pro Glu Leu Ser Pro Asp Asp Pro Ala Gly Leu Leu
            580                 585                 590

Asp Leu Arg Gln Gly Met Phe Ala Gln Leu Val Ala Gln Asn Val Leu
        595                 600                 605

Leu Ile Asp Gly Pro Leu Ser Trp Tyr Ser Asp Pro Gly Leu Ala Gly
    610                 615                 620

Val Ser Leu Thr Gly Gly Leu Ser Tyr Lys Glu Asp Thr Lys Glu Leu
625                 630                 635                 640

Val Val Ala Lys Ala Gly Val Tyr Tyr Val Phe Phe Gln Leu Glu Leu
                645                 650                 655

Arg Arg Val Val Ala Gly Glu Gly Ser Gly Ser Val Ser Leu Ala Leu
            660                 665                 670

His Leu Gln Pro Leu Arg Ser Ala Ala Gly Ala Ala Ala Leu Ala Leu
        675                 680                 685

Thr Val Asp Leu Pro Pro Ala Ser Ser Glu Ala Arg Asn Ser Ala Phe
    690                 695                 700

Gly Phe Gln Gly Arg Leu Leu His Leu Ser Ala Gly Gln Arg Leu Gly
705                 710                 715                 720

Val His Leu His Thr Glu Ala Arg Ala Arg His Ala Trp Gln Leu Thr
                725                 730                 735

Gln Gly Ala Thr Val Leu Gly Leu Phe Arg Val Thr Pro Glu Ile Pro
            740                 745                 750

Ala Gly Leu Pro Ser Pro Arg Ser Glu Gly Ser Gly Ala Thr Asn Phe
        755                 760                 765

Ser Leu Leu Lys Gln Ala Gly Asp Val Glu Glu Asn Pro Gly Pro Met
    770                 775                 780

Tyr Arg Met Gln Leu Leu Ser Cys Ile Ala Leu Ser Leu Ala Leu Val
785                 790                 795                 800

Thr Asn Ser Gly Ile His Val Phe Ile Leu Gly Cys Phe Ser Ala Gly
                805                 810                 815

Leu Pro Lys Thr Glu Ala Asn Trp Val Asn Val Ile Ser Asp Leu Lys
            820                 825                 830

Lys Ile Glu Asp Leu Ile Gln Ser Met His Ile Asp Ala Thr Leu Tyr
        835                 840                 845

Thr Glu Ser Asp Val His Pro Ser Cys Lys Val Thr Ala Met Lys Cys
    850                 855                 860
```

Phe Leu Leu Glu Leu Gln Val Ile Ser Leu Glu Ser Gly Asp Ala Ser
865                 870                 875                 880

Ile His Asp Thr Val Glu Asn Leu Ile Ile Leu Ala Asn Asn Ser Leu
            885                 890                 895

Ser Ser Asn Gly Asn Val Thr Glu Ser Gly Cys Lys Glu Cys Glu Glu
        900                 905                 910

Leu Glu Glu Lys Asn Ile Lys Glu Phe Leu Gln Ser Phe Val His Ile
            915                 920                 925

Val Gln Met Phe Ile Asn Thr Ser Ser Gly Gly Ser Gly Gly Gly
    930                 935                 940

Gly Ser Gly Gly Gly Gly Ser Gly Gly Gly Ser Gly Gly Gly Ser
945                 950                 955                 960

Leu Gln Ala Pro Arg Arg Ala Arg Gly Cys Arg Thr Leu Gly Leu Pro
                965                 970                 975

Ala Leu Leu Leu Leu Leu Leu Arg Pro Pro Ala Thr Arg Gly Ile
            980                 985                 990

Thr Cys Pro Pro Pro Met Ser Val Glu His Ala Asp Ile Trp Val Lys
        995                 1000                1005

Ser Tyr Ser Leu Tyr Ser Arg Glu Arg Tyr Ile Cys Asn Ser Gly
    1010                1015                1020

Phe Lys Arg Lys Ala Gly Thr Ser Ser Leu Thr Glu Cys Val Leu
    1025                1030                1035

Asn Lys Ala Thr Asn Val Ala His Trp Thr Thr Pro Ser Leu Lys
    1040                1045                1050

Cys Ile Arg
    1055

<210> SEQ ID NO 47
<211> LENGTH: 3179
<212> TYPE: DNA
<213> ORGANISM: Artificial Sequence
<220> FEATURE:
<223> OTHER INFORMATION: synthetic sequence

<400> SEQUENCE: 47
atggccttac cagtgaccgc cttgctcctg ccgctggcct tgctgctcca cgccgccagg      60
ccggacgtgg tgatgaccca gaccccctg agcctgcccg tgagcctggg cgaccaggcc     120
agcatcagct gcaggagcag ccagagcctg gtgcacagca cggcaacac ctacctgcac     180 tggtacctgc agaagcccgg ccagagcccc aagctgctga tctacaaggt gagcaacagg     240
ttcagcggcg tgcccgacag gttcagcggc agcggcagcg gcaccgactt caccctgaag     300
atcagcaggg tggaggccga ggacctgggc gtgtacttct gcagccagaa cacccacgtg     360
ccccccacct tcggcagcgg caccaagctg gagatcaagg agggggggg atccggggga     420 ggaggctccg gcggaggcgg aagccaggtg cagctgcagc agagcggcgc cgagctggtg     480
aggcccggcg ccagcgtgaa gctgagctgc aaggccagcg gctacacctt caccgactac     540
gagatgcact gggtgaagca gaccccgtg cacggcctga gtggatcgg cgccctggac     600 cccaagaccg gcgacaccgc ctacagccag aagttcaagg gcaaggccac cctgaccgcc     660
gacaagagca gcagcaccgc ctacatggag ctgaggagcc tgaccagcga ggacagcgcc     720
gtgtactact gcaccaggtt ctacagctac acctactggg gccagggcac cctggtgacc     780
gtgagcgcca ccacgacgcc agcgccgcga ccaccaacac cggcgcccac catcgcgtcg     840 cagccctgt ccctgcgccc agaggcgtgc cggccagcgg cggggggcgc agtgcacacg     900

```
aggggggctgg acttcgcctg tgatatctac atctgggcgc ccttggccgg gacttgtggg    960
gtccttctcc tgtcactggt tatcaccctt tactgcagga gtaagaggag caggctcctg    1020
cacagtgact acatgaacat gactccccgc cgccccgggc ccaccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga gatggggga    1260
aagccgcaga gaaggaagaa ccctcaggaa ggcctgtaca atgaactgca gaaagataag    1320
atggcggagc cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg cagcggcgaa ggccgcggca gctgctgac ctgcggcgat    1500
gtggaagaaa cccgggcccc catggaatac gcctctgacg cttcactgga ccccgaagcc    1560
ccgtggcctc ccgcgcccg cgctcgcgcc tgccgcgtac tgccttgggc cctggtcgcg    1620
gggctgctgc tgctgctgct gctcgctgcc gcctgcgccg tcttcctcgc ctgccctgg    1680
gccgtgtccg gggctcgcgc ctcgcccggc tccgcggcca gcccgagact ccgcgagggt    1740
cccgagcttt cgcccgacga tcccgccggc ctcttggacc tgcggcaggg catgtttgcg    1800
cagctggtgg cccaaaatgt tctgctgatc gatgggcccc tgagctggta cagtgaccca    1860
ggcctggcag gcgtgtccct gacgggggc ctgagctaca aagaggacac gaaggagctg    1920
gtggtggcca aggctggagt ctactatgtc ttctttcaac tagagctgcg gcgcgtggtg    1980
gccggcgagg gctcaggctc cgtttcactt gcgctgcacc tgcagccact gcgctctgct    2040
gctggggccg ccgccctggc tttgaccgtg gacctgccac ccgcctcctc cgaggctcgg    2100
aactcggcct tcggttttcca gggccgcttg ctgcacctga gtgccggcca gcgcctgggc    2160
gtccatcttc acactgaggc cagggcacgc catgcctggc agcttaccca gggcgccaca    2220
gtcttgggac tcttccgggt gaccccgaa atcccagccg gactcccttc accgaggtcg    2280
gaaggaagcg gagctactaa cttcagcctg ctgaagcagg ctggagacgt ggaggagaac    2340
cctggaccta tgtacagaat gcagctgctg agctgcatcg ccctgagcct ggccctggtg    2400
accaacagcg gcatccacgt gttcatcctg gctgcttca gcgccggcct gcccaagacc    2460
gaggccaact gggtgaacgt gatcagcgac ctgaagaaga tcgaggacct gatccagagc    2520
atgcacatcg acgccaccct gtacaccgag agcgacgtgc accccagctg caaggtgacc    2580
gccatgaagt gcttcctgct ggagctgcag gtgatcagcc tggagagcgg cgacgccagc    2640
atccacgaca ccgtggagaa cctgatcatc ctggccaaca acagcctgag cagcaacggc    2700
aacgtgaccg agagcggctg caaggagtgc gaggagctgg aggagaagaa catcaaggag    2760
ttcctgcaga gcttcgtgca catcgtgcag atgttcatca acaccagctc cggcggcggc    2820
tccggcggcg gcggctccgg cggcggcggc tccggcggcg gcggctccgg cggcggctcc    2880
ctgcaggccc ccagaagagc cagaggctgc agaacccctgg gcctgcccgc cctgctgctg    2940
ctgctgctgc tgagaccccc cgccaccaga ggcatcacct gccccccccc catgagcgtg    3000
gagcacgccg acatctgggt gaagagctac agcctgtaca gcagagaga atacatctgc    3060
aacagcggct tcaagagaaa ggccggcacc agcagcctga ccgagtgcgt gctgaacaag    3120
gccaccaacg tggcccactg gaccacccc agcctgaagt gcatcagata agtttaaac    3179
```

CHIMERIC ANTIGEN RECEPTOR (CAR) TARGETING MULTIPLE ANTIGENS, COMPOSITIONS AND METHODS OF USE THEREOF

CROSS-REFERENCE TO RELATED APPLICATIONS

This application is a continuation-in-part application of application Ser. No. 15/739,596, filed Dec. 22, 2017, which is a national stage filing under 35 USC § 371 of international application number PCT/US2016/039306, filed on Jun. 24, 2016, which claims the benefit of U.S. Provisional Application No. 62/184,321, filed on Jun. 25, 2015, U.S. Provisional Application No. 62/235,840, filed on Oct. 1, 2015, and U.S. Provisional Application No. 62/244,435, filed on Oct. 21, 2015. All of which are incorporated by reference herein in their entirety.

The application is a continuation-in part application of application Ser. No. 15/538,620, filed Jun. 21, 2017, which is a continuation of PCT/US2016/068349, filed Dec. 22, 2016, which is a continuation of PCT/US2016/039306, filed Jun. 24, 2016, and claims the benefit of U.S. Provisional Application No. 62/369,004, filed on Jul. 29, 2016. All of which are incorporated by reference herein in their entirety.

BACKGROUND

T cells, a type of lymphocyte, play a central role in cell-mediated immunity. They are distinguished from other lymphocytes, such as B cells and natural killer cells (NK cells), by the presence of a T-cell receptor (TCR) on the cell surface. T helper cells, also called CD4+ T or CD4 T cells, express CD4 glycoprotein on their surface. Helper T cells are activated when exposed to peptide antigens presented by MHC (major histocompatibility complex) class II molecules. Once activated, these cells proliferate rapidly and secrete cytokines that regulate immune response. Cytotoxic T cells, also known as CD8+ T cells or CD8 T cells, express CD8 glycoprotein on the cell surface. The CD8+ T cells are activated when exposed to peptide antigens presented by MHC class I molecules. Memory T cells, a subset of T cells, persist long term and respond to their cognate antigen, thus providing the immune system with "memory" against past infections and/or tumor cells.

T cells can be genetically engineered to produce special receptors on their surface called chimeric antigen receptors (CARs). CARs are proteins that allow the T cells to recognize a specific protein (antigen) on tumor cells. These engineered CAR T cells are then grown in the laboratory until they number in the billions. The expanded population of CAR T cells is then infused into the patient.

Clinical trials to date have shown chimeric antigen receptor (CAR) T cells to have great promise in hematologic malignancies resistant to standard chemotherapies. Most notably, CD19-specific CAR (CD19CAR) T-cell therapies have had remarkable results including long-term remissions in B-cell malignancies (Kochenderfer, Wilson et al. 2010, Kalos, Levine et al. 2011, Porter, Levine et al. 2011, Davila, Riviere et al. 2013, Grupp, Frey et al. 2013, Grupp, Kalos et al. 2013, Kalos, Nazimuddin et al. 2013, Kochenderfer, Dudley et al. 2013, Kochenderfer, Dudley et al. 2013, Lee, Shah et al. 2013, Park, Riviere et al. 2013, Maude, Frey et al. 2014).

Despite the success of CAR therapy in B-cell leukemia and lymphoma, the application of CAR therapy to soft tissue tumors has not yet been well established. Given that malignant soft tissue tumor are associated with dramatically poorer outcomes compared to those of B-cell malignancies (Abramson, Feldman et al. 2014), CAR therapy in this respect has the potential to further address a great clinical need.

There are some roadblocks that hinder the broader adoption of CAR therapeutic approach. Among the most general challenges are: (1) selection of antigen target and chimeric antigen receptor(s); (2) CAR design; (3) tumor heterogeneity, particularly the variance in the surface expression of tumor antigens. Targeting single antigen carries the risk of immune escape and this could be overcome by targeting multiple desired antigens.

Most CAR chimeric antigen receptors are scFvs derived from monoclonal antibodies and some of these monoclonal antibodies have been used in the clinical trials or treatment for diseases. However, they have limited efficacy, which suggests that alternative and more potent targeting approaches, such as CARs are required.

Target discovery and selection are the initial step as there are no general rules to ensure or guide CAR design that are efficacious.

scFvs are the most commonly used chimeric antigen receptor for CARs. However, CAR affinity binding and locations of the recognized epitope on the antigen could affect the function. Additionally the level of the surface CAR expression on the T cells or NK cells is affected by an appropriate leader sequence and promoter. However, overexpressed CAR proteins could be toxic to cells.

Therefore, there remains a need for improved chimeric antigen receptor-based therapies that allow for more effective, safe, and efficient targeting of T-cell associated malignancies Furthermore, CAR targeting neuroblastoma is quite challenging because of the presence of heterogeneous tumor populations as well the presence of tumor micro-environment suppression. Antigen-specific immunotherapies for neuroblastoma have long been pursued to improve the patient treatment outcomes but success thus far has been limited as many these therapies have either been ineffective in the clinic or have an uncertain impact on patient outcomes. The ideal target(s) in neuroblastoma or other soft tissue tumors (such as sarcomas), diseases of great antigenic diversity, has not been established. The identification of appropriate target (s) is an important step for the CAR design and the CAR design is required to address tumor heterogeneity, CAR persistency and tumor microenvironment suppression. There is no general rule that CAR design is efficacious and safe.

Therefore, there remains a need for improved chimeric antigen receptor-based therapies that allow for more effective, safe, and efficient targeting of soft tissue tumors.

SUMMARY OF THE INVENTION

In one embodiment, the present disclosure provides an engineered cell having a first chimeric antigen receptor polypeptide including a first antigen recognition domain, a first signal peptide, a first hinge region, a first transmembrane domain, a first co-stimulatory domain, and a first signaling domain; and a second chimeric antigen receptor polypeptide including a second antigen recognition domain, a second signal peptide, a second hinge region, a second transmembrane domain, a second co-stimulatory domain, and a second signaling domain; wherein the first antigen recognition domain is different than the second antigen recognition domain, and the first antigen recognition domain and second antigen rejection domain are selected from the group consisting of interleukin 6 receptor, NY-ESO-1, alpha fetoprotein (AFP), glypican-3 (GPC3), BAFF-R, BAFF, APRIL, BCMA, TACI, LeY, CD5, CD13, CD14, CD15 CD19, CD20, CD22, CD33, CD30, CD41, CD45, CD61, CD64, CD68, CD117, CD123, CD138, CD267, CD269, CD38, MMG49 epitope, Flt3 receptor, CD4, CLL-1 and CS1(SLAMF7).

In another embodiment, the present disclosure provides an engineered polypeptide including a chimeric antigen receptor and an enhancer.

In another embodiment, the present disclosure provides a method of reducing the number of target cells including the steps of (i.) contacting said target cells with an effective amount of an engineered cell having at least one chimeric antigen receptor polypeptide, for engineered cells having multiple chimeric antigen receptor polypeptides, each chimeric antigen receptor polypeptide is independent; and (ii.) optionally, assaying for the reduction in the number of said cells. The target cells include at least one cell surface antigen selected from the group consisting of GD2, GD3, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, MMG49 epitope, EGFRvIII, CD33, CD123, CLL-1, immunoglobin kappa and lambda, CD38, CD52, CD47, CD200, CD70, CD19, CD20, CD22, CD38, BCMA, CS1, NKG2D receptor, April receptor, BAFF receptor, TACI, CD3, CD4, CD8, CD5, CD7, CD2, and CD138. The target antigens can also include viral or fungal antigens, such as E6 and E7 from the human papillomavirus (HPV) or EBV (Epstein Barr virus) antigens.

In another embodiment, the present disclosure provides methods for treating B-cell lymphoma, T-cell lymphoma, multiple myeloma, chronic myeloid leukemia, acute myeloma leukemia, myelodysplastic syndromes, chronic myeloproliferative neoplasms, B-cell acute lymphoblastic leukemia (B-ALL), and cell proliferative diseases by administering any of the engineered cells described above to a patient in need thereof.

In another embodiment, the present disclosure provides a method of treating an autoimmune disease, said method including administering an engineered cell according to claim 1 to a patient in need thereof; wherein said autoimmune disease comprises systemic lupus erythematosus (SLE), multiple sclerosis (MS), Inflammatory bowel disease (IBD), Rheumatoid arthritis, Sjogren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis), or eosinophilic granulomatosis with polyangiitis (EGPA, Churg-Strauss syndrome) and TTP (thrombotic thrombocytopenic purpura)

The present disclosure provides chimeric antigen receptors (CARS) targeting non-hematologic malignancies, compositions and methods of use thereof.

In one embodiment, the present disclosure provides an engineered cell having a first chimeric antigen receptor polypeptide including a first antigen recognition domain, a first signal peptide, a first hinge region, a first transmembrane domain, a first co-stimulatory domain, and a first signaling domain; and a second chimeric antigen receptor polypeptide including a second antigen recognition domain, a second signal peptide, a second hinge region, a second transmembrane domain, a second co-stimulatory domain, and a second signaling domain; wherein the first antigen recognition domain is different than the second antigen recognition domain.

In another embodiment, the present disclosure provides an engineered polypeptide including a chimeric antigen receptor and an enhancer (s). In a further embodiment, an enhancer can be selected from at least one of the group including, but not limited, IL-2, IL-7, IL-12, IL-15, IL-15/IL-15sush, IL-15/IL-15sushi anchor, IL-15/IL-15RA, IL-18, IL-21, IL-21 anchor, PD-1, PD-L1, CSF1R, CTAL-4, TIM-3, cytoplasmic domain of IL-15 receptor alpha, 4-1BBL, IL-21, IL-21 anchor and TGFR beta, receptors.

In some embodiments, CAR having an antigen recognition domain (s) is part of an expression cassette. In a preferred embodiment, the expressing gene or the cassette may include an accessory gene or a tag or a part thereof. The accessory gene may be an inducible suicide gene or a part thereof, including, but not limited to, caspase 9 gene. The "suicide gene" ablation approach improves safety of the gene therapy and kills cells only when activated by a specific compound or a molecule. In some embodiments, the epitope tag is a c-myc tag, CD52, streptavidin-binding peptide (SBP), truncated EGFR gene (EGFRt) or a part or a combination thereof.

In some embodiments, CAR cells can be ablated by administrating an anti-CD52 monoclonal antibody (CAMPATH) to a subject.

In another embodiment, the present disclosure provides methods for treating soft tissue tumors, carcinoma, sarcomas, leukemia, and cell proliferative diseases by administering any of the engineered cells described above to a patient in need thereof.

BRIEF DESCRIPTION OF DRAWINGS

The patent or patent application contains at least one drawing executed in color. Copies of this patent or patent application publication with color drawing(s) will be provided by the U.S. Patent and Trademark Office upon request and payment of the necessary fee.

Primary cells were assayed by FACS for BCMA and CS1 expression. Density plots represent major antigen populations.

FIGS. 4A-4D: Characterization of BC1cCAR T-cell antitumor activity against primary myeloma tumor cells.

(4A) Co-cultures against $BCMA^+CS1^+$ primary myeloma cells (MM7-G) were carried out over 24 hours and target cells pre-stained with CMTMR. Populations were gated by BCMA and CS1, along with CMTMR, and flow cytometry plots show target tumor populations in red (left). Bar graph summarizing in vitro cytotoxicity (right). (4B) Co-cultures with MM10-G primary cells were conducted under similar conditions. $BCMA^+CS1^+$ double positive populations (purple) and $CS1^+$ only populations (dark blue) by FACS. Specific cytotoxicity summarized (below). (4C) $BCMA^{dim}CS1^{dim}$ primary cells (MM11-G) show BC1cCAR anti-tumor activity over a range of E:T dosages. (4D) Summary panel graph showing results of BC1cCAR in vitro screening.

Figure 5A:
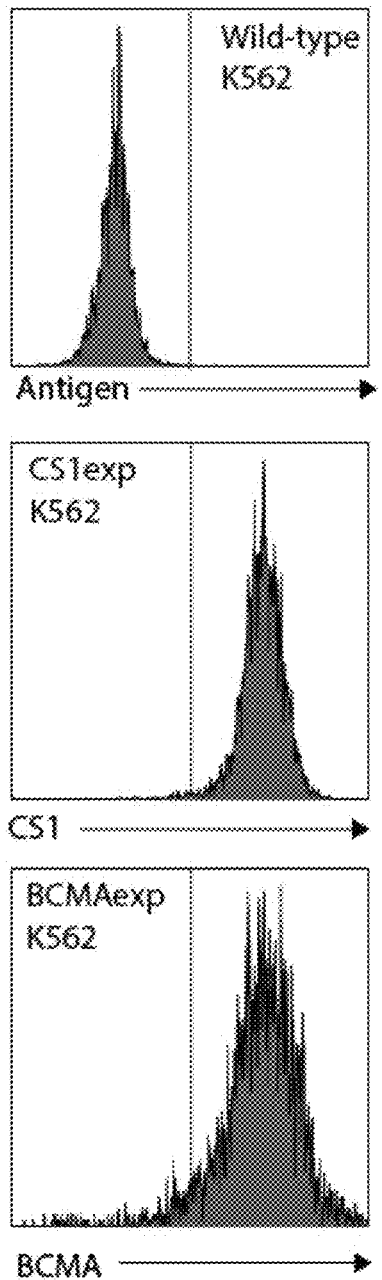
Figure 5C:
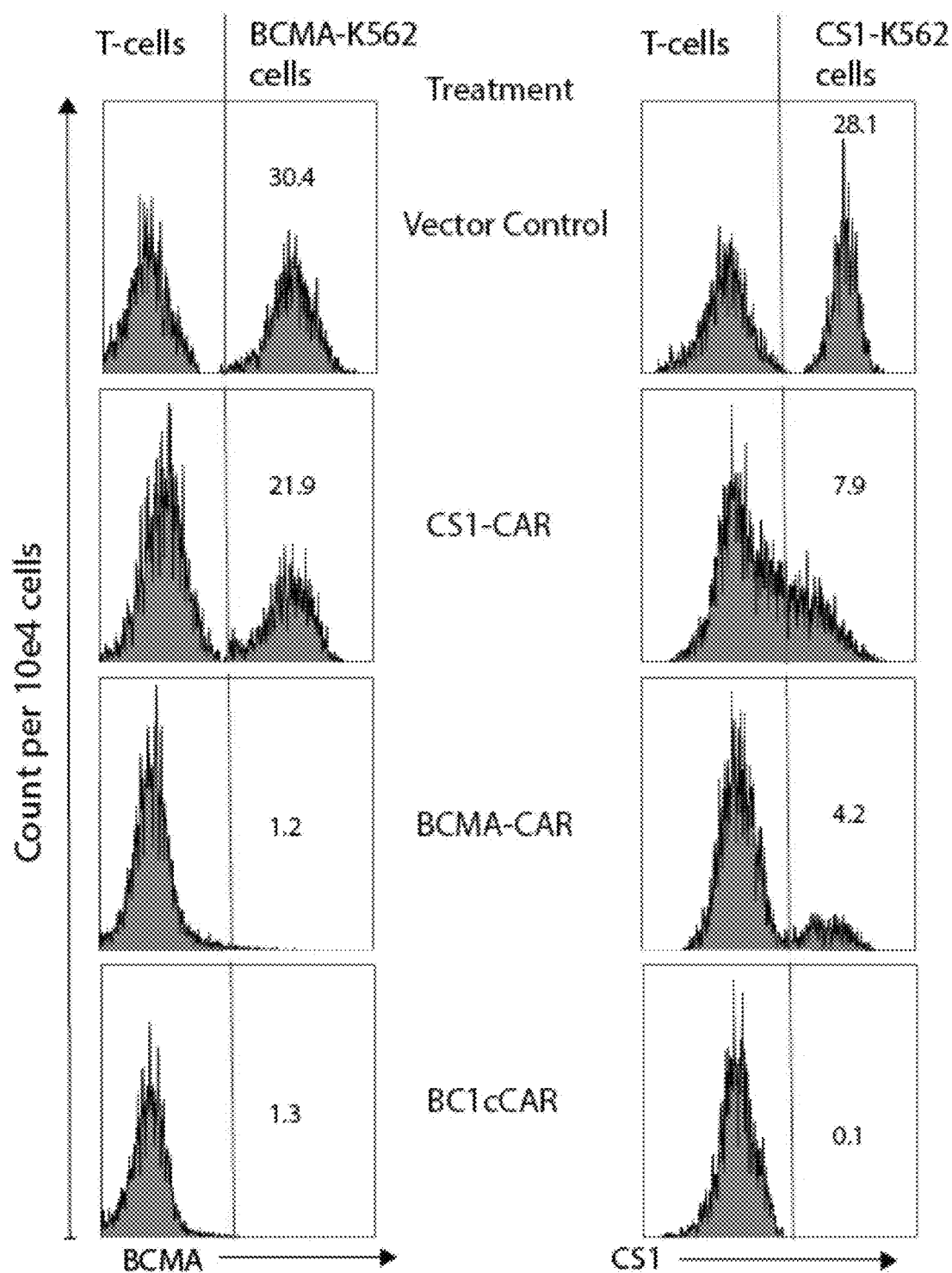

FIGS. 5A-5C: Functional validation of BC1cCAR antigen specificity.

(5A) A CML cell line (K562) was transduced to stably express either BCMA or CS1. Histogram population shifts in their respective antigen expression ranges show expression. (5B) Short term (4 hour-8 hour) cultures of BC1cCAR T-cells against either BCMA-K562 or CS1-K562 show antigen specific cytotoxicity correlating with E:T dosage increase. Wild-type K562 cells were used as a negative control. A CS1 single CAR (red bar) was generated to compare efficacy with BC1cCAR against CS1-K562 cells. (5C) Long-term cultures (48 hours) conducted with a 1:1 mixture of BCMA-K562 cells and CS1-K562 cells. BC1cCAR, CS1-CAR, BCMA-CAR, and control T-cells were added at a 5:1 E:T ratio to each treatment well. Histogram plots showing residual populations (% gated) of BCMA or CS1 cells are shown per treatment condition, with red lines demarcating T-cell or target tumor populations.

Figure 6A:
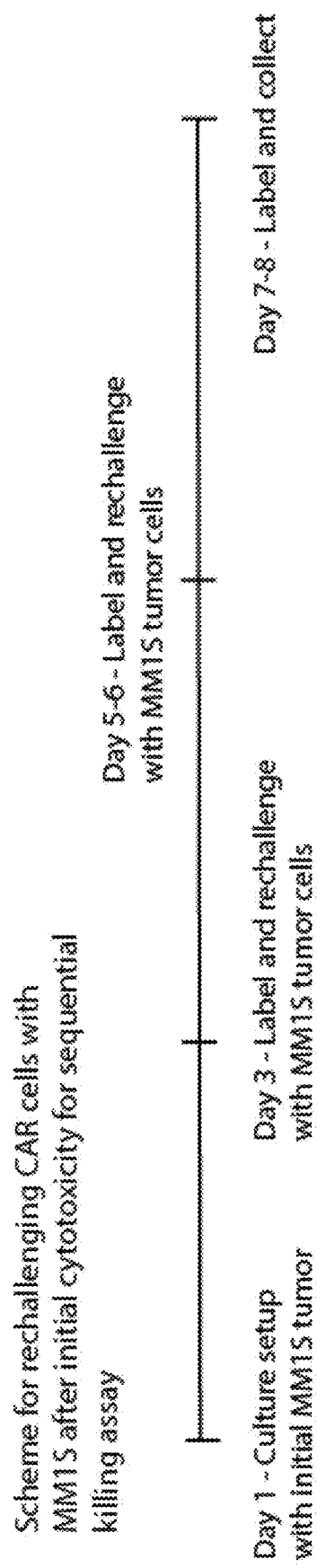
Figure 6B:
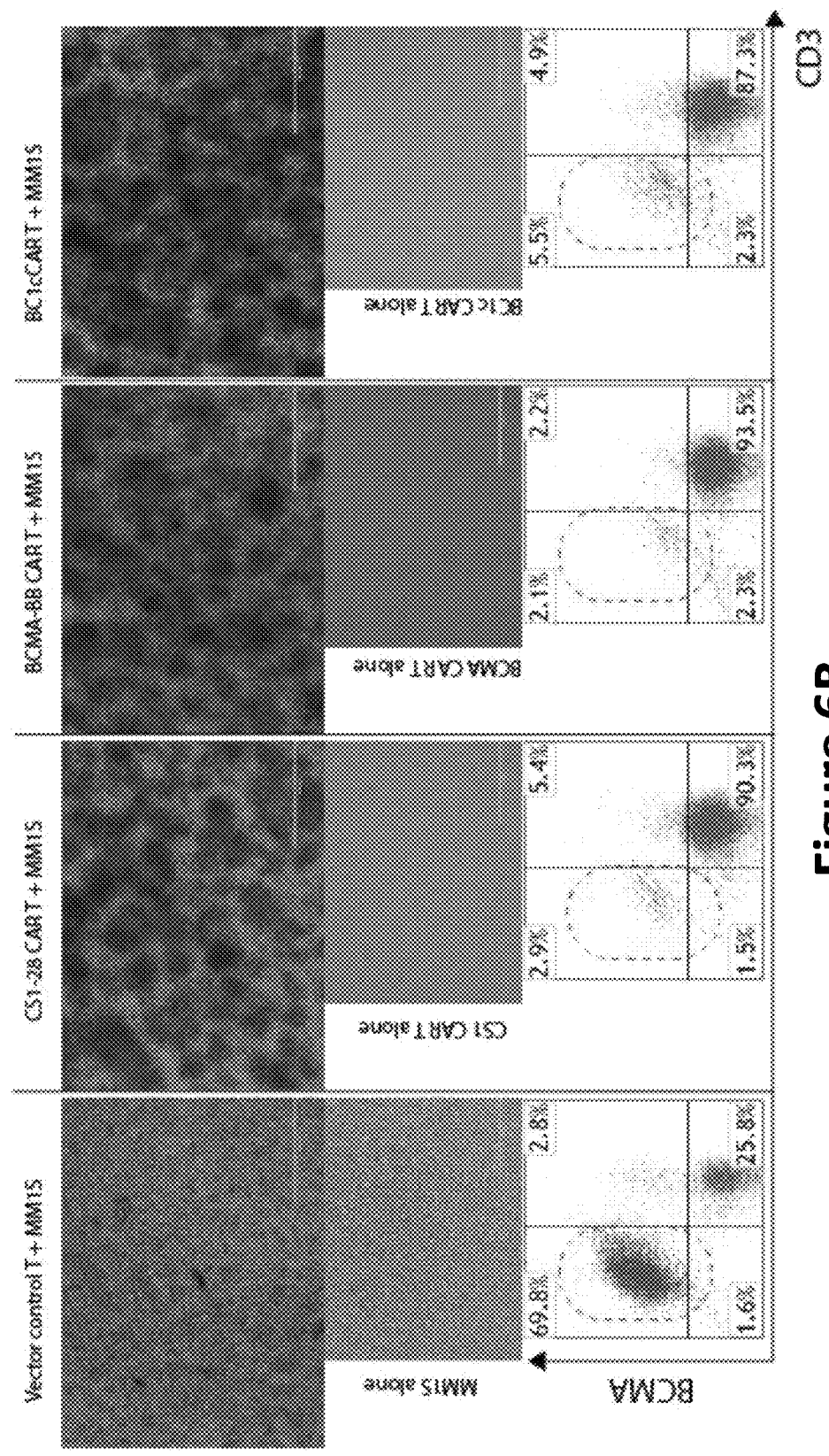
Figure 6C:
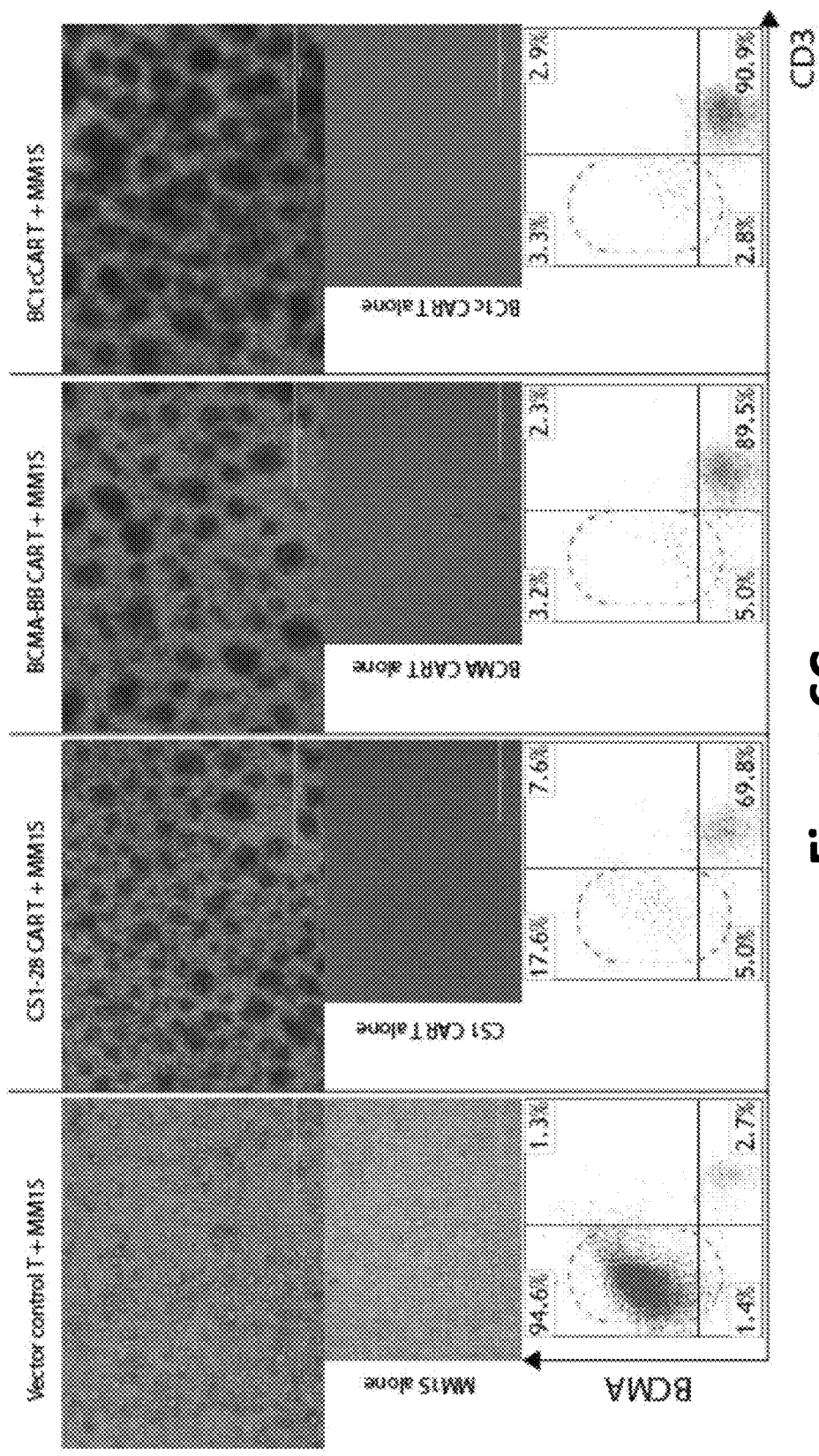

FIGS. 6A-6C: Long-term sequential killing assay and tumor re-challenge.

(6A) Assay was conducted over a period of 168 hours without exogenous cytokines and initial culture was performed using a 1:1 E:T ratio of CAR cells or control cells mixed with $BCMA^+CS1^+$ MM1S cells. After 48 hours, flow cytometry analysis was acquired for a small sample collection and MM1S cells were re-introduced into each treatment well. Repeated through the 168 hour time-point. (6B) T-cell proliferation and response after 48 hours. Images were taken on the day of flow cytometry acquisition and cells were stained with anti-BCMA, anti-CS1, and anti-CD3 antibodies, MM1S cells (circled, blue). (6C) Similar image acquisition and FACS analysis was performed at the 108 hour time mark.

Figure 7A:
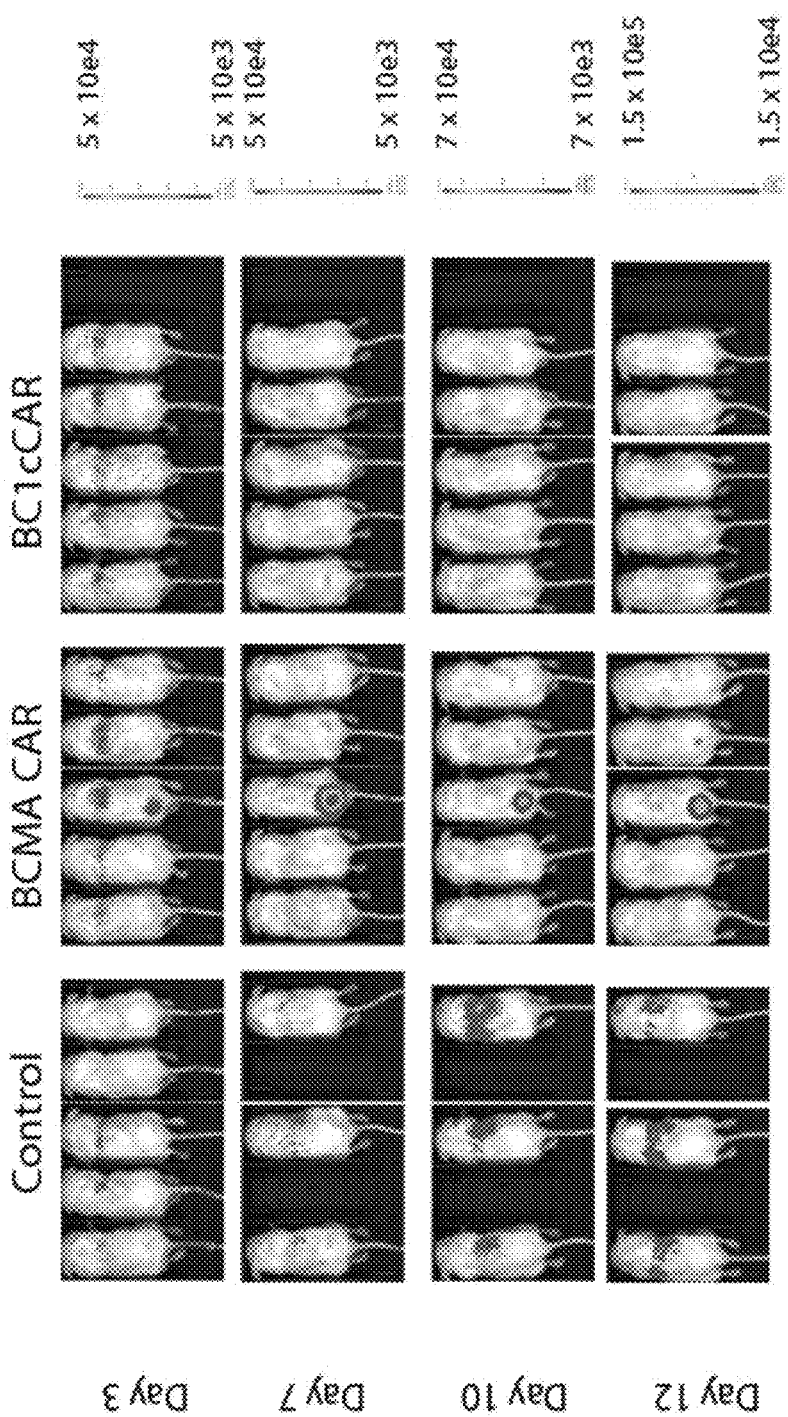
Figure 7B:
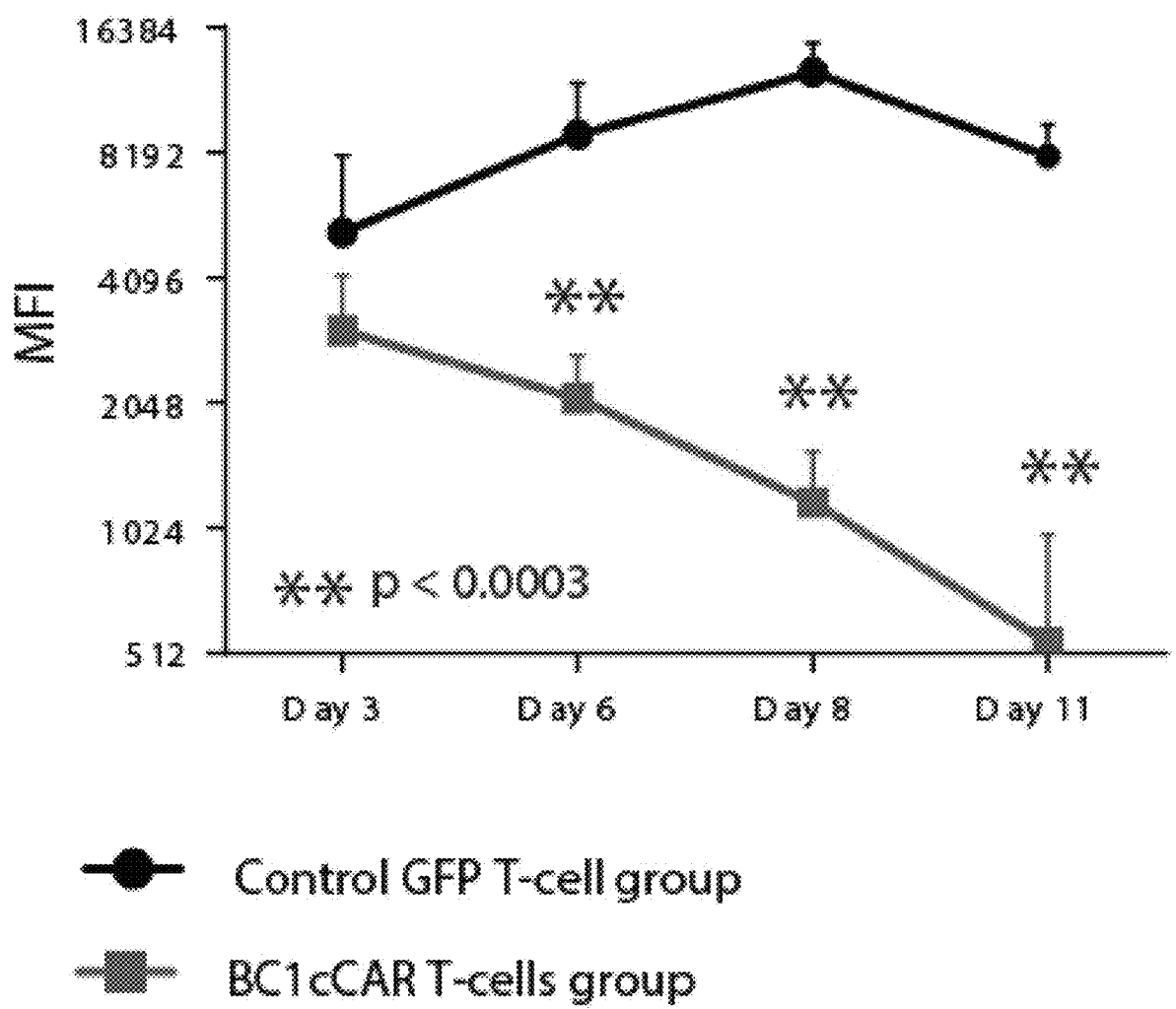
Figure 7C:
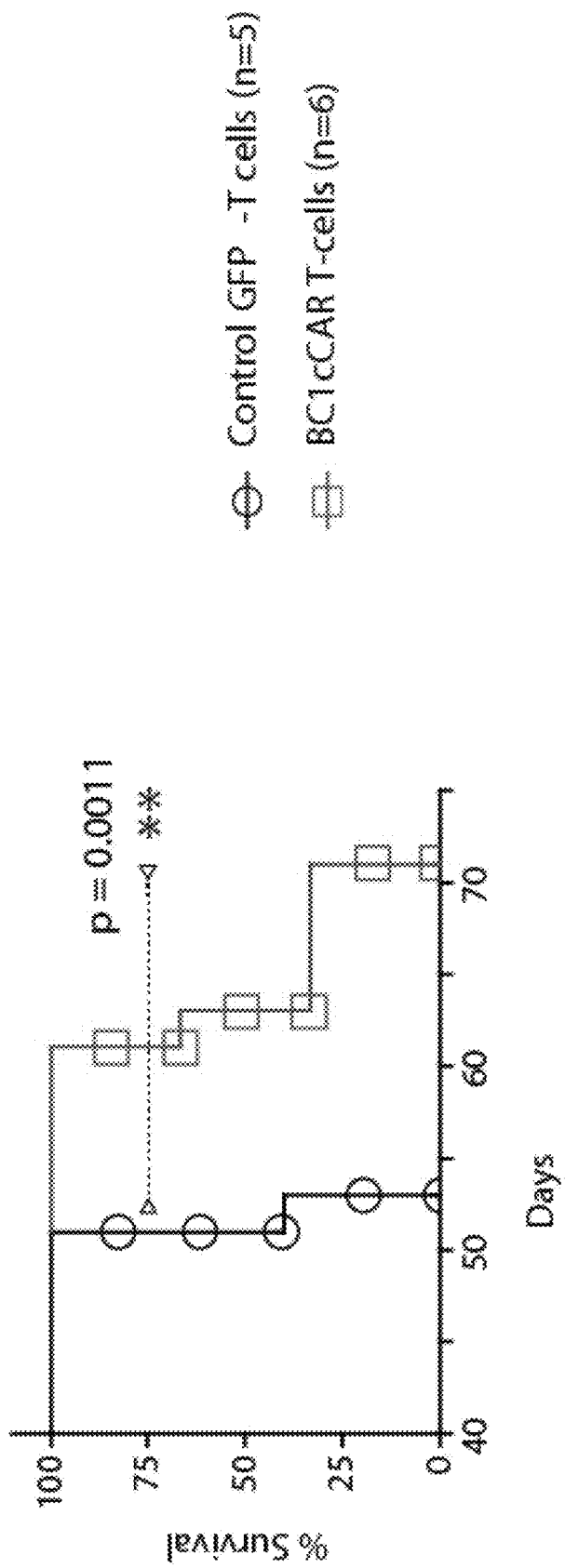

FIGS. 7A-7C: BC1cCAR T-cells demonstrate anti-leukemic effects in vivo.

(7A) MM1S model tumor generated by injection of $1.0 \times 10^6$ luciferase$^+$ cells per mouse. Mice treated with either BC1cCAR T-cells (right) or control T-cells (left) and IVIS image acquisition. (7B) Average light intensity measured for BC1cCAR T-cell treated mice (red) compared to control T-cell treated mice (black). (7C) Survival outcomes for BC1cCAR (red) and control (black) groups.

Figure 8A:
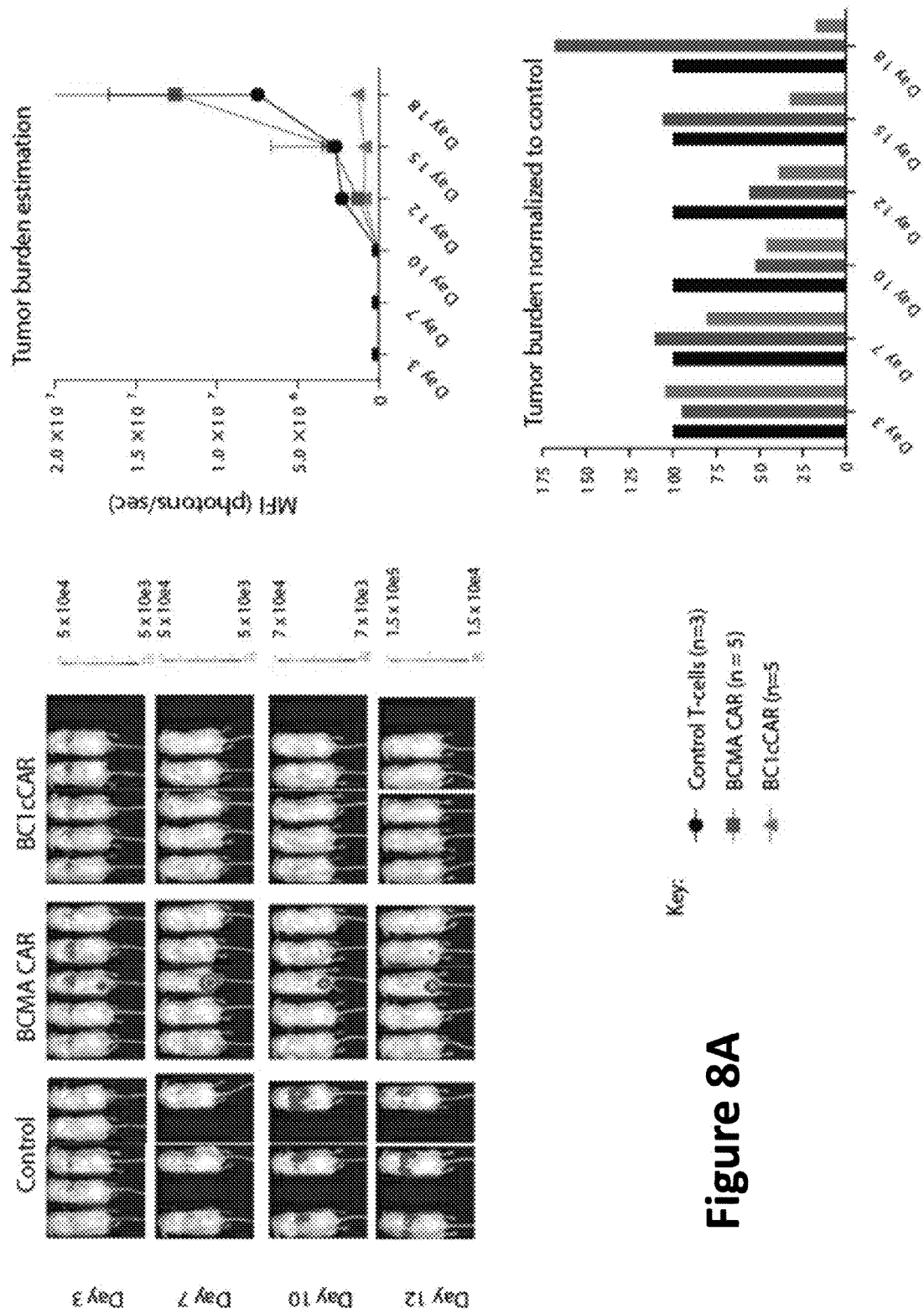
Figure 8B:
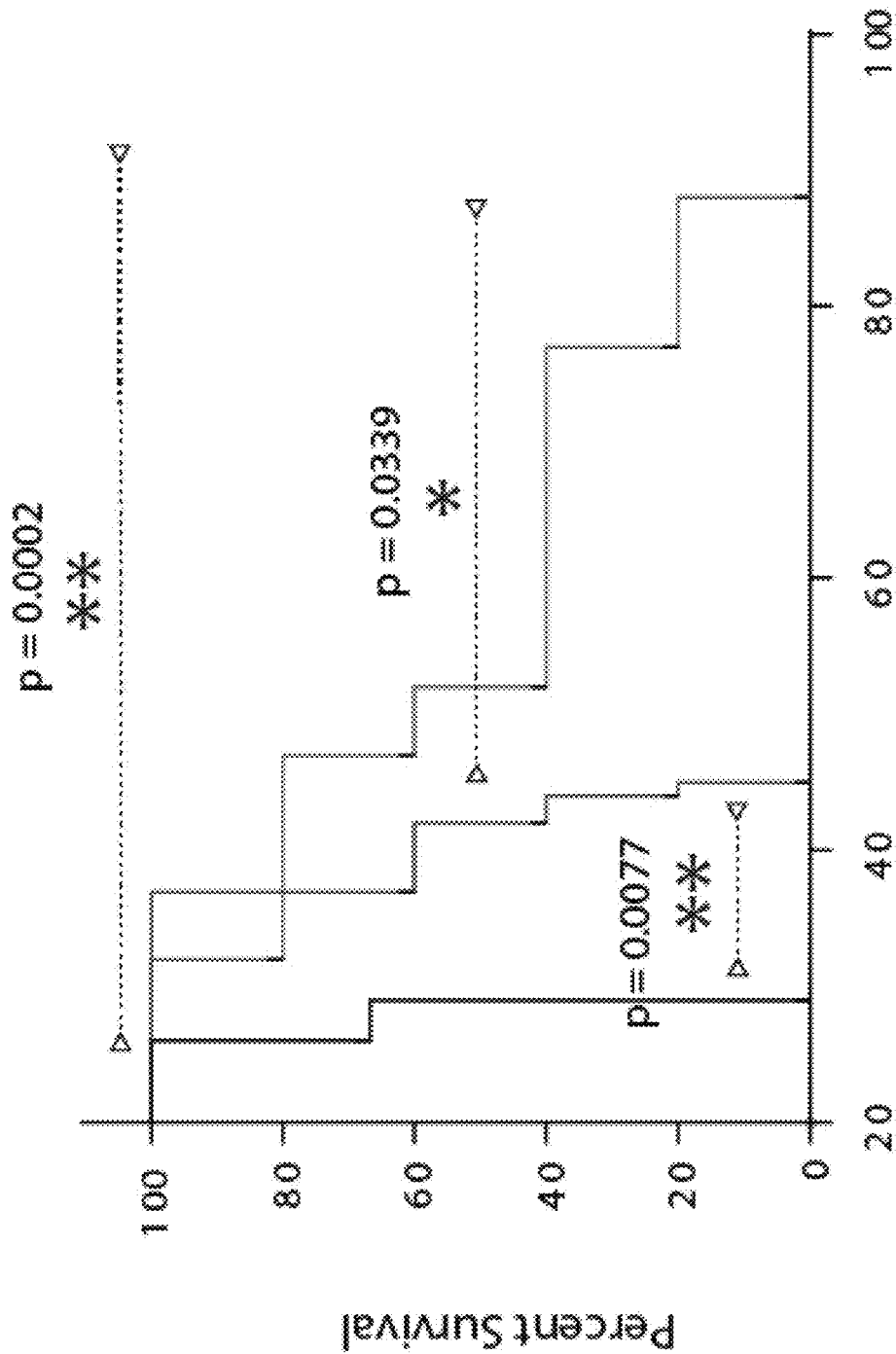

FIGS. 8A-8B: BC1cCAR T-cells exhibit improved cytotoxic effect in a mixed antigen xenogeneic mouse model.

(8A) Mouse model injected with BCMA and CS1 expressing K562 cells in a ratio of 4:1 BCMA:CS1 K562 cells (n=5 for each group). Mice were treated with either BC1cCAR T-cells, control T-cells, or a BCMA-specific CAR. Tumor burden was visualized by IVIS and plotted as a function of fluorescence intensity (right) for all groups. (8B) Survival outcomes for control treated (black), BCMA-CAR treated (blue), and BC1cCAR (red) treated mice.

Figure 9B:
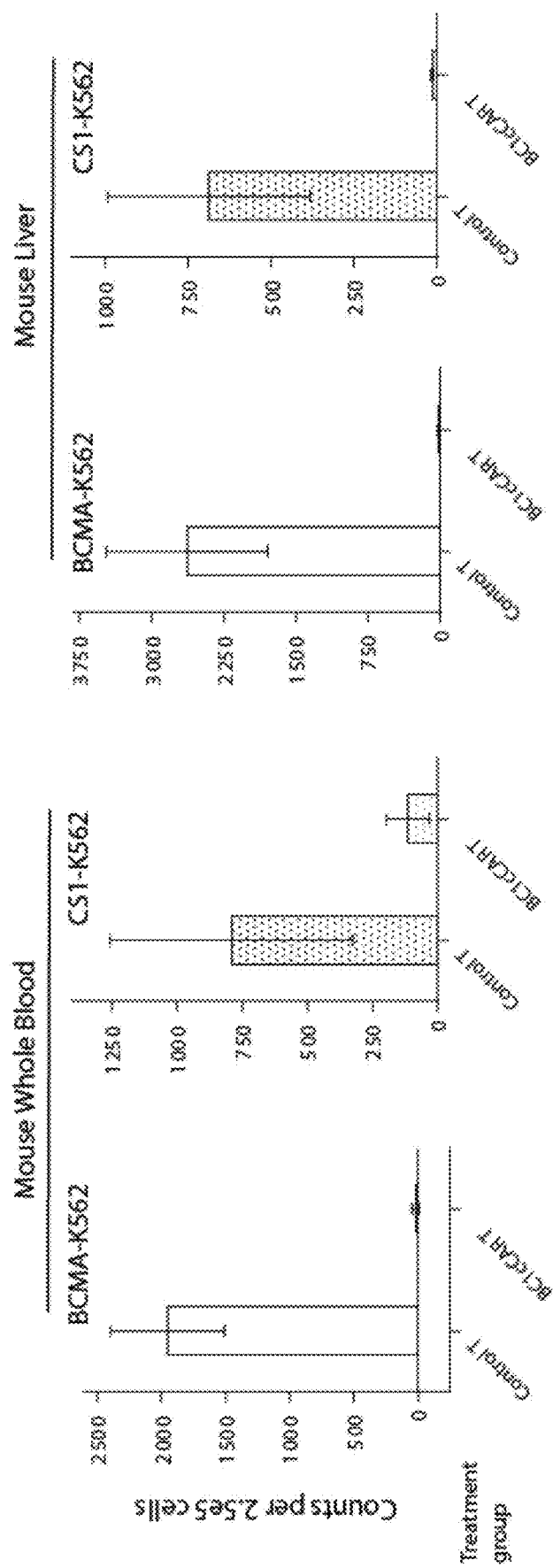
Figure 9C:
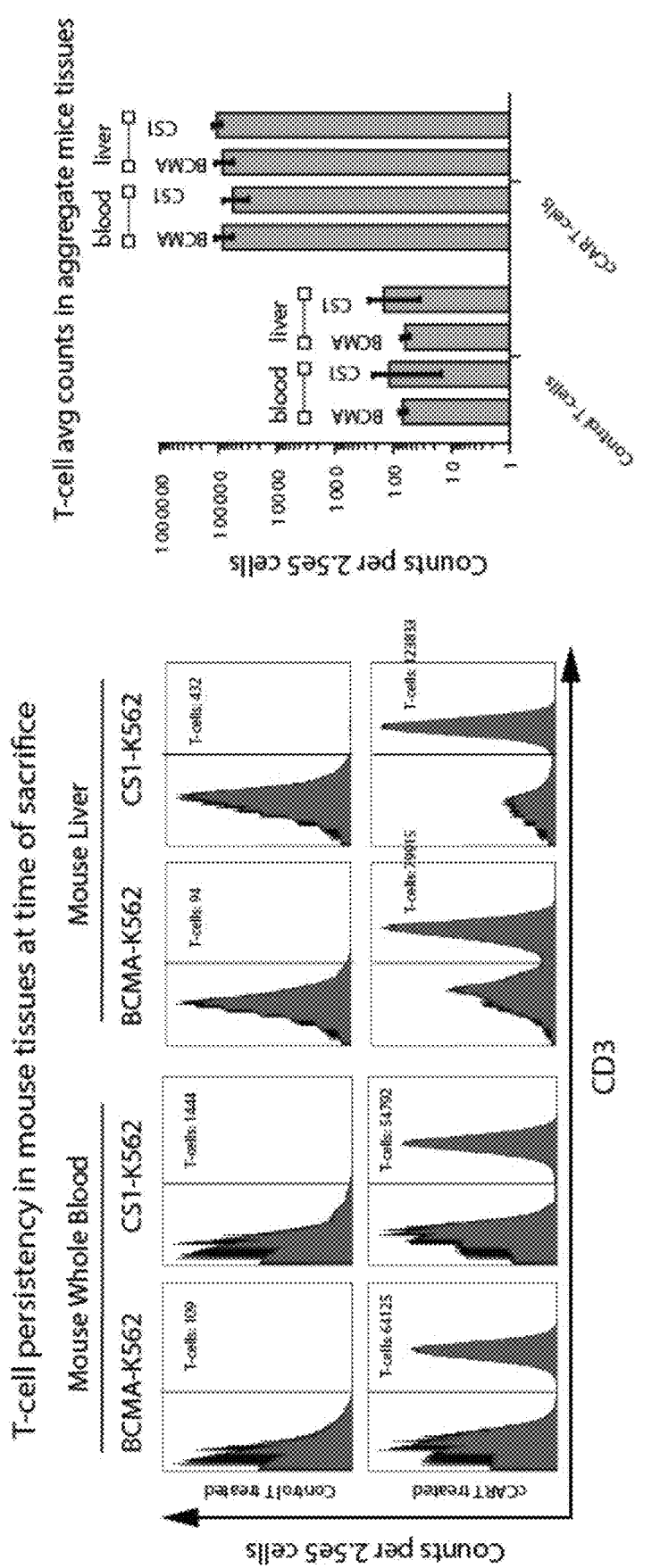
Figure 10A:
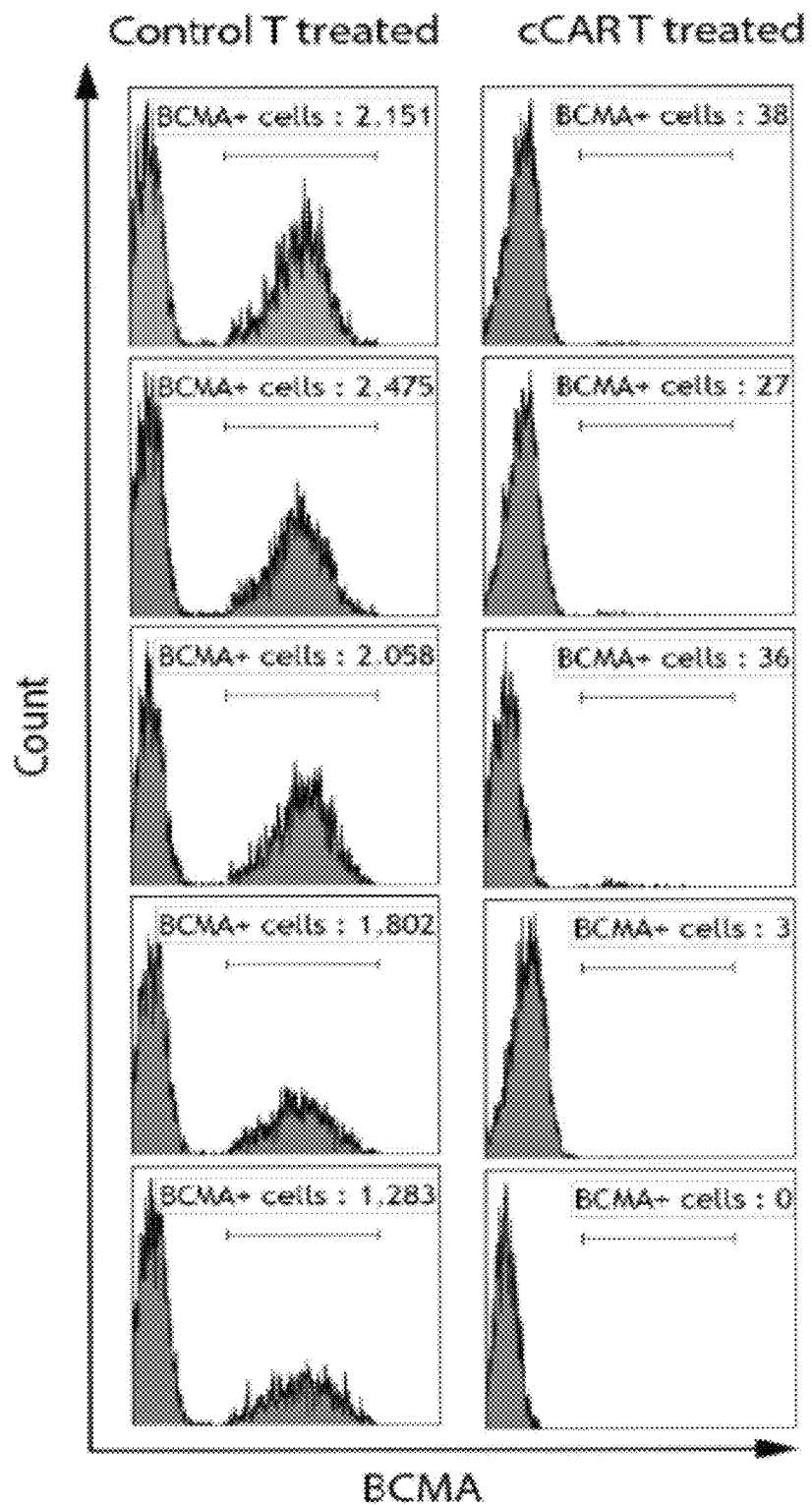
Figure 10B:
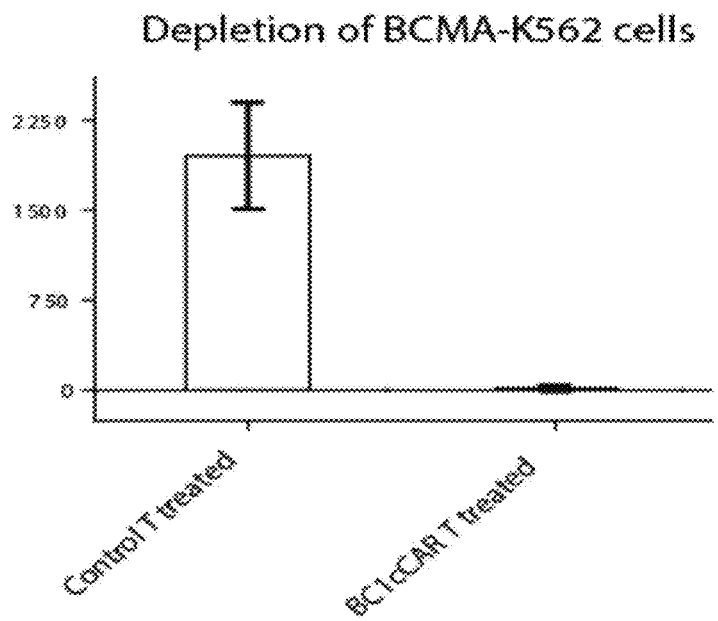
Figure 10C:
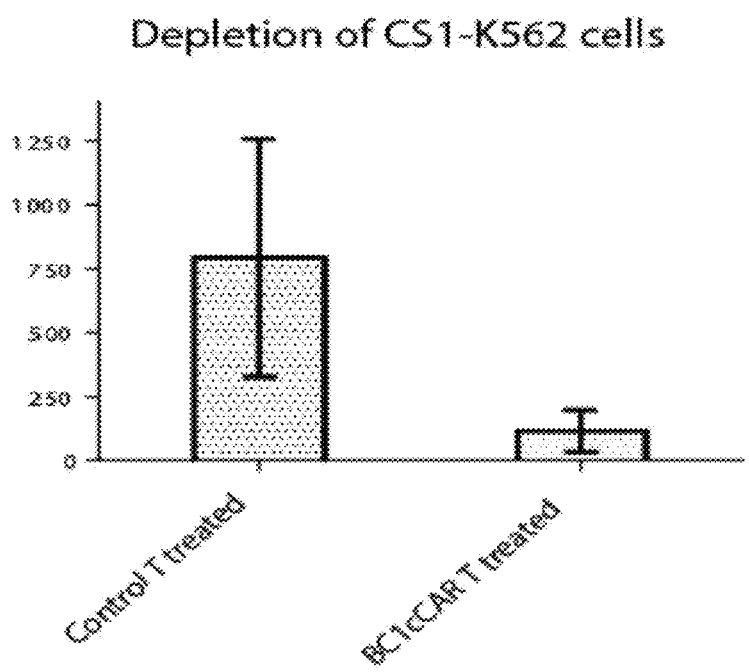
Figure 10D:
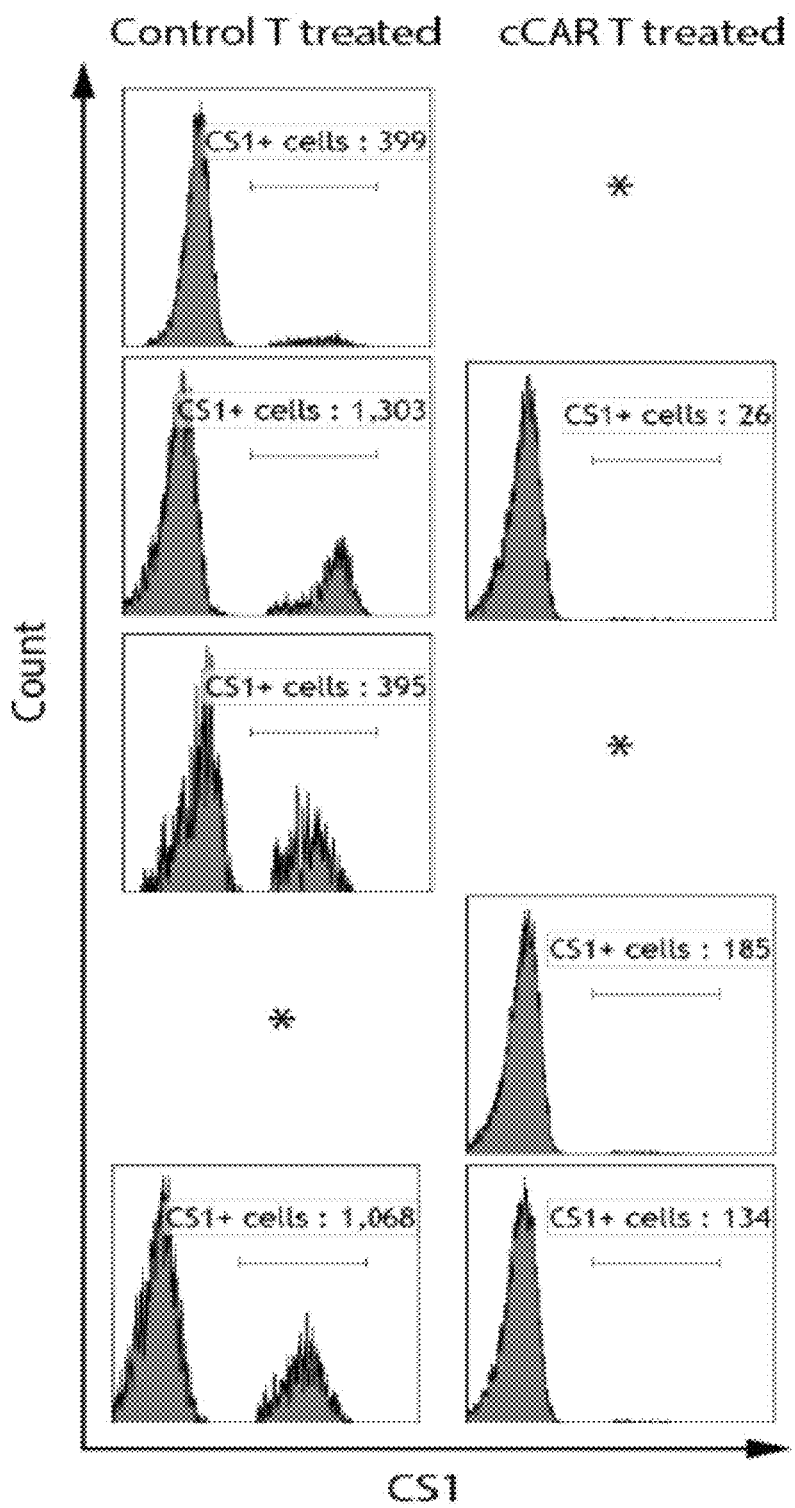
Figure 11A:
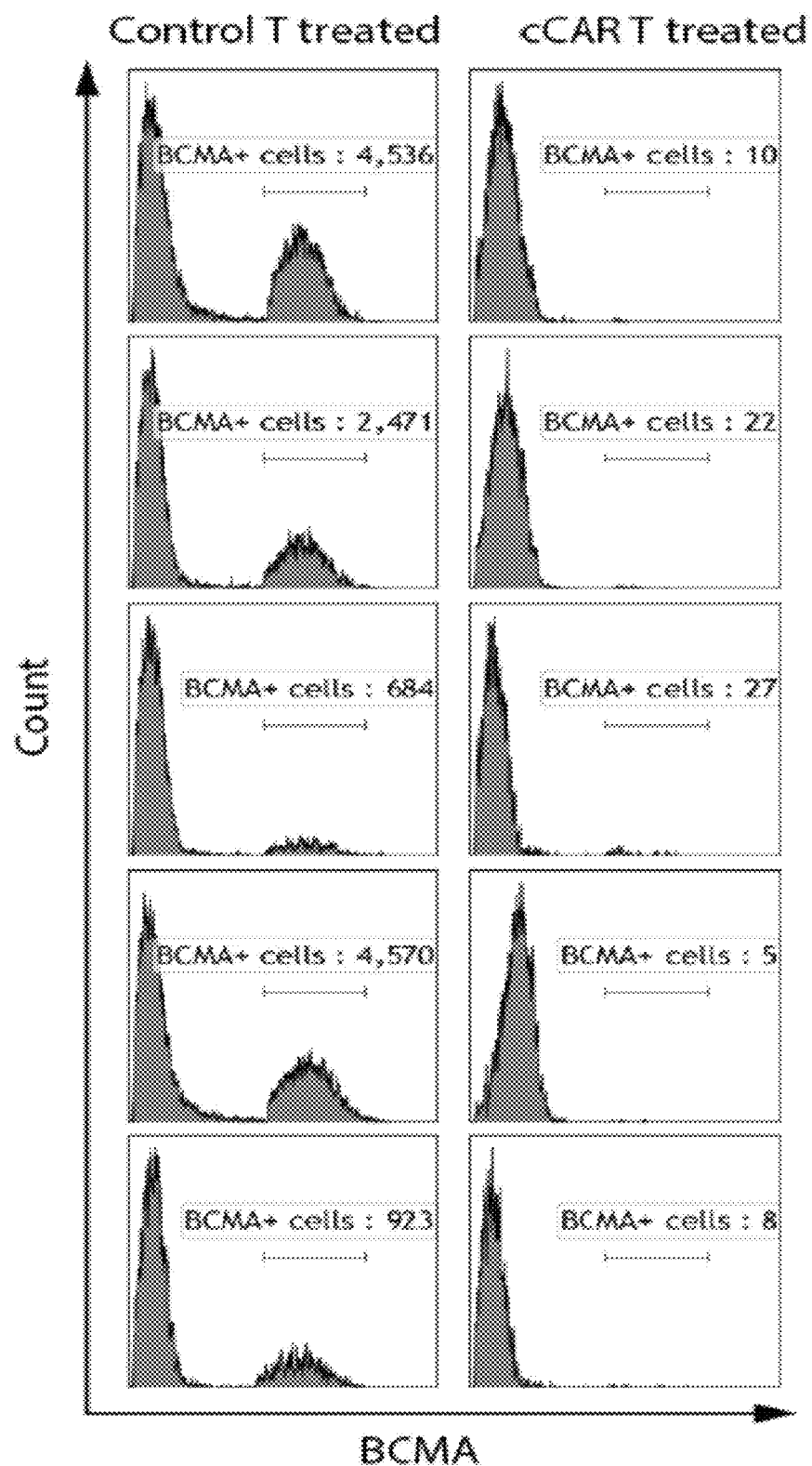
Figure 11B:
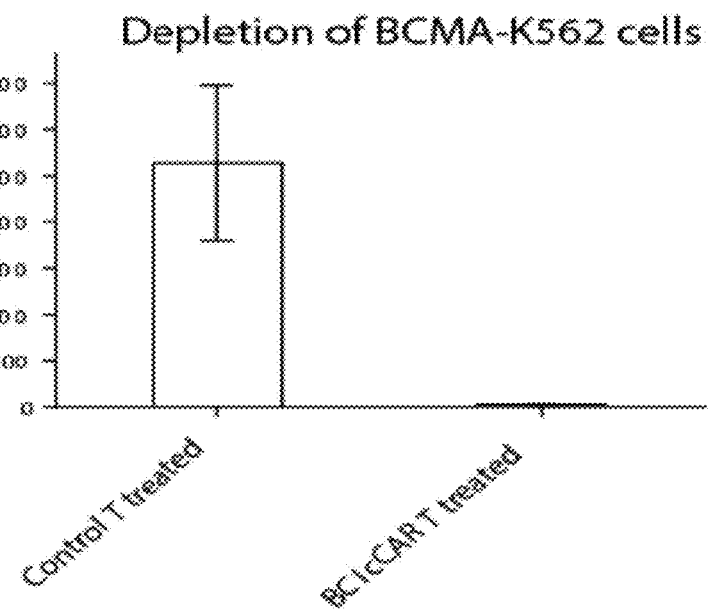
Figure 11C:
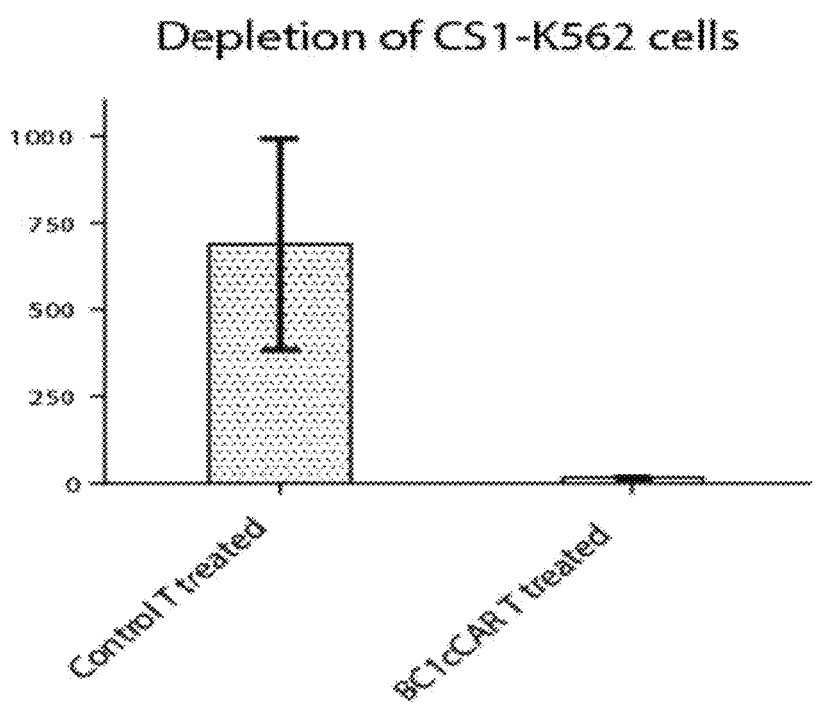
Figure 11D:
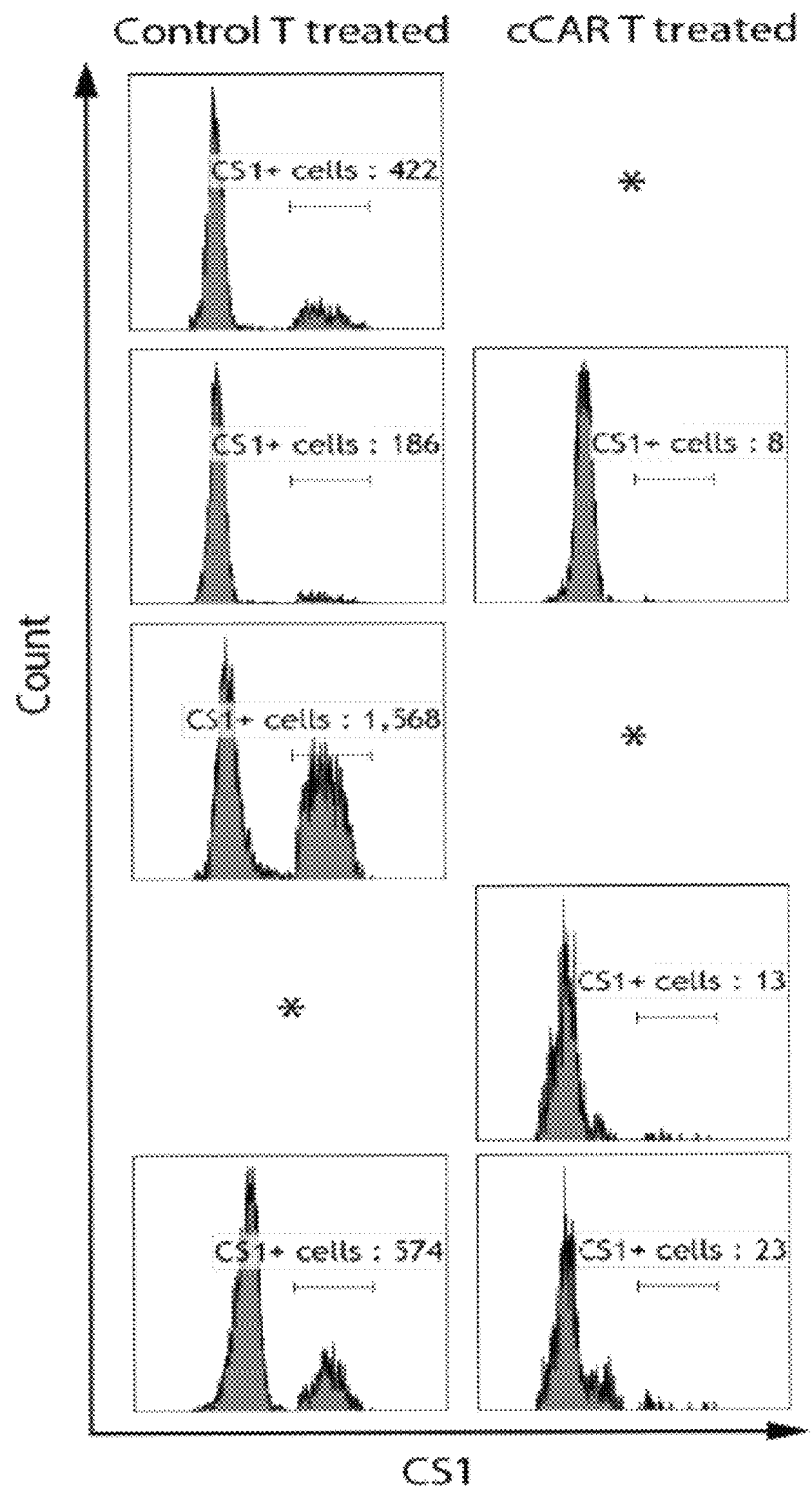

FIGS. 9A-9C: Improved BC1cCAR T-cell persistency and maintenance of tumor suppression in separate antigen models.

(9A) Whole blood samples from mice injected with either BCMA-K562 or CS1-K562 tumor cells (n=5 per group) were taken at time of sacrifice. Histogram population of BCMA or CS1 positive peaks represent tumor presence. (9B) Aggregate tissue analysis of both whole blood and liver samples across sacrificed mice are summarized. Mice tumor cell counts were established by FACS of antigen positive cells per 250000 cells collected per sample and averaged across all mice per treatment group. (9C) Whole blood and liver tissues were also analyzed for T-cell persistency by CD3 expression at time of sacrifice, summarized across all sacrificed mice (right).

FIGS. 10A-10D: Analysis of mouse whole blood from separately injected BCMA-K562 or CS1-K562 injected mice.

At times of sacrifice (various), mice whole blood was collected and labeled with antibodies against CD3, CD45, BCMA (10A), and CS1 (10D). Histograms were constructed to visualize presence of tumor and counts were averaged across 250000 events to generate graphical summaries. Some mice died before sacrifice, and were unusable for sample collection.

FIGS. 11A-11D: Analysis of mouse liver from separately injected BCMA-K562 or CS1-K562 injected mice.

At times of sacrifice (various), mice liver samples were collected and labeled with antibodies against CD3, CD45, BCMA, and CS1. Histograms were constructed to visualize presence of tumor and counts were averaged across 250000 events to generate graphical summaries. Some mice died before sacrifice, and were unusable for sample collection.

Figure 12A:
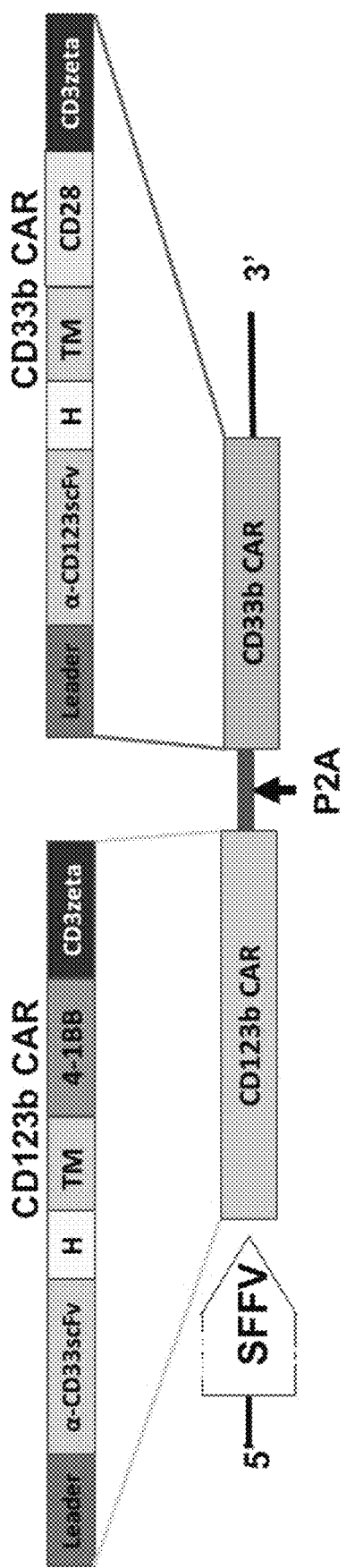
Figure 12B:
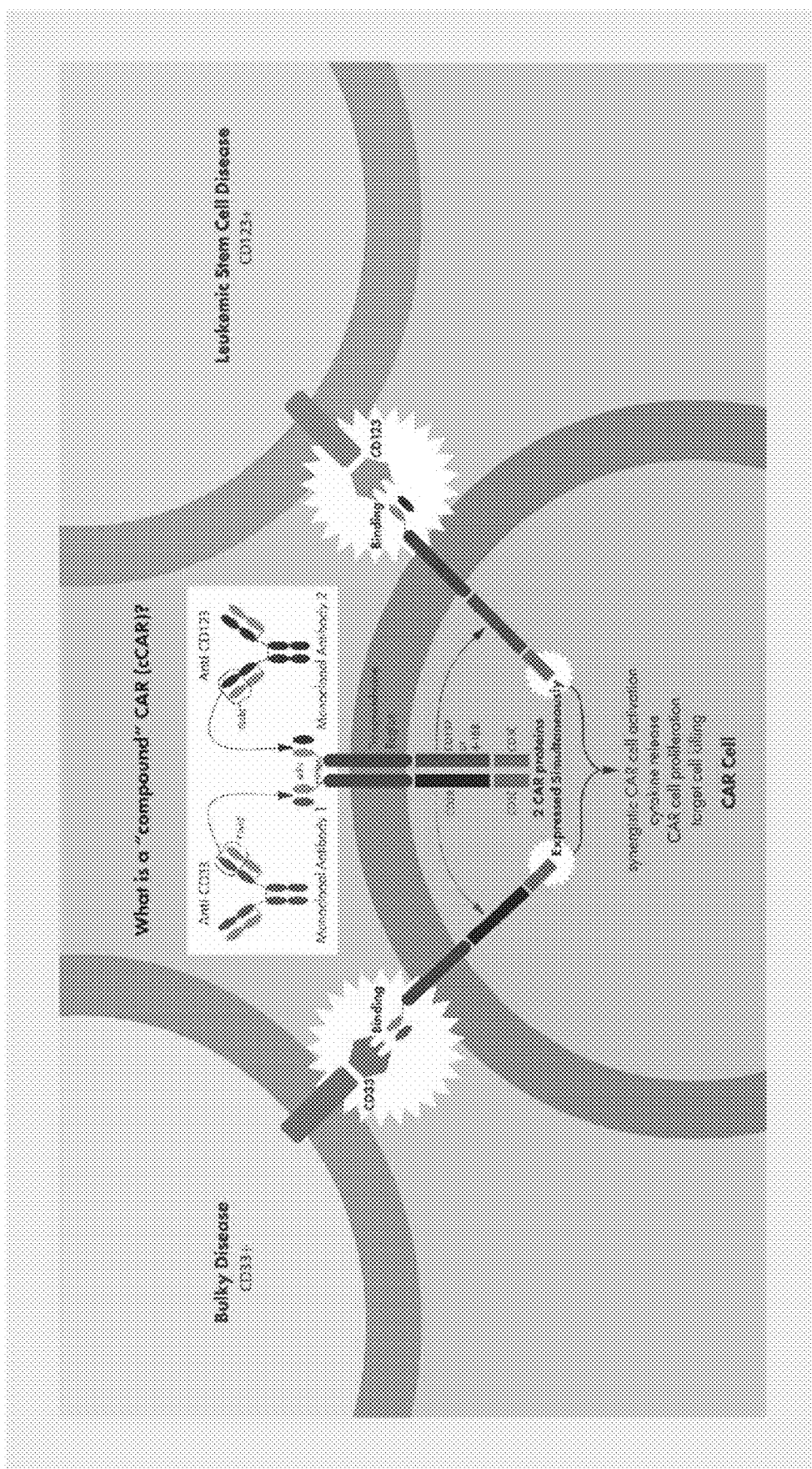

FIGS. 12A-12B: Genetic structure and function of CD123b-CD33b cCar.

(12A) Representation of CD123-CD33cCAR. (12B) CD123b-CD33b cCAR T-cells are created by the viral transduction of patient donor T-cells with the CD123b-CD33b cCAR gene construct. The translated CD123 and CD33 CAR proteins are then expressed on the surface of the CAR T-cells, where they can recognize and bind the CD123 and CD33 target proteins on the surface of leukemic cells. The pharmacologic effect and mechanism of CD123b-CD33b cCAR T-cells is mediated by CD123b-CD33b cCAR recognition of the antigen, which triggers CD3zeta/Zap70 canonical cytotoxic T-cell activity further enhanced by the incorporation of CD28 or 4-1BB co-activation domains in the construct, creating a "second generation" CAR.

Figure 13:
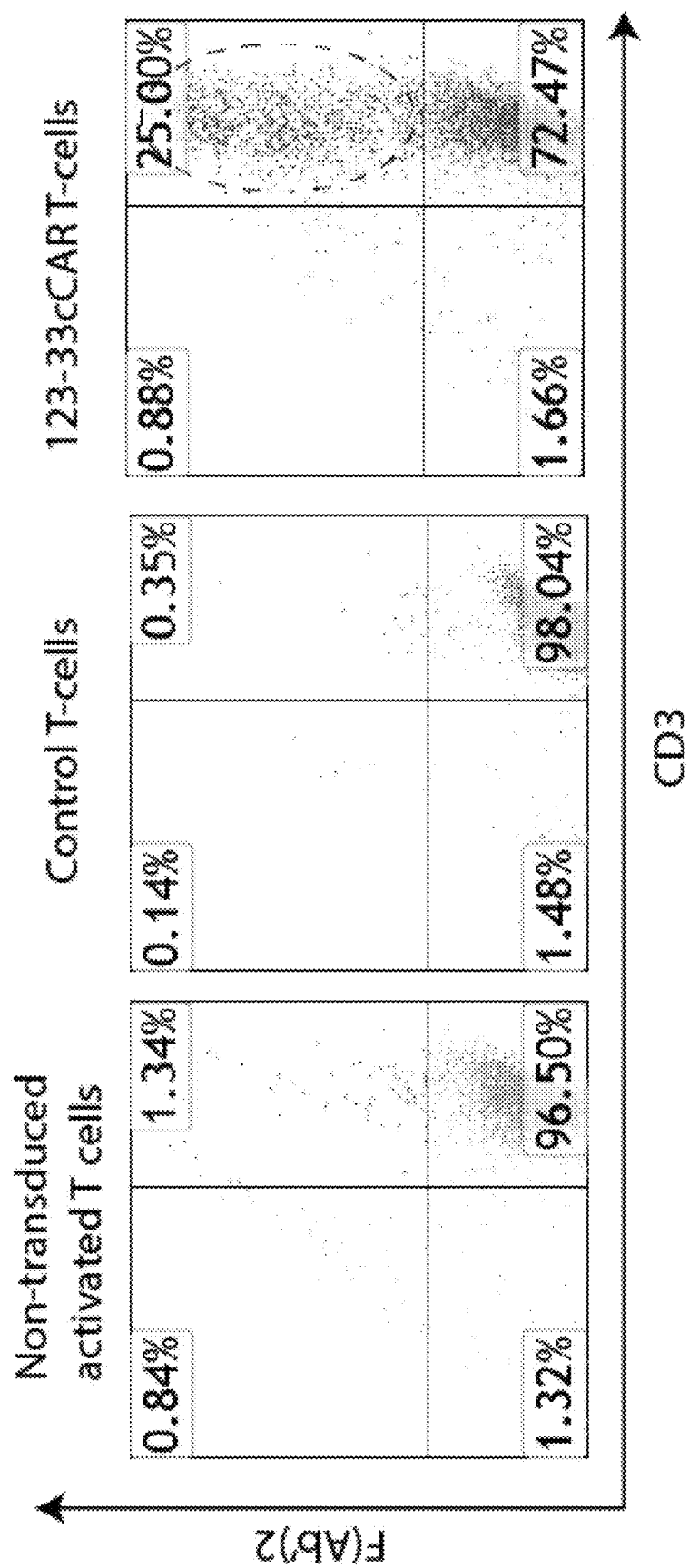

FIG. 13: CD123b-CD33b cCAR Transduction Efficiency.

Flow cytometry was used to determine CD123b-CD33b cCAR expression levels on the T-cell surface after transduction.

FIGS. 14A-14D: CD123b-CD33b cCAR T-cells demonstrate targeted lysis of MOLM13 and U937 tumor cells lines.

(14A) Flow cytometry analysis of control T-cells and CD123b-CD33b cCAR T-cells against MOLM13 (an AML cell line) tumor target cells at 2:1 and 5:1 E:T ratios. The target cell population is encircled. (14B) Flow cytometry analysis of control T-cells and CD123b-CD33b cCAR T-cells against U937 tumor target cells at 2:1 and 5:1 E:T ratios. The target cell population is encircled. (14C) MOLM13 tumor cells (CD123+CD33+) and U937 cells (CD123−CD33+) alone stained for markers and their percent lysis summary at both E:T ratios. (14D) Dose-dependent cultures performed with HL60 (CD123dimCD33+) and KG1a (CD123dimCD33+) cells display high cCAR killing efficiency at E:T ratios ranging from 0.25:1 to 10:1.

FIGS. 15A-15E: CD123b−CD33b cCAR T-cells demonstrate targeted lysis of primary patient tumor cells.

(15A) Flow cytometry analysis of control T-cells and CD123b−CD33b cCAR T-cells against PT1 tumor target cells at 2:1 and 5:1 E:T ratios. The target cell population is encircled. (15B) Flow cytometry analysis of control T-cells and CD123b−CD33b cCAR T-cells against PT2 tumor target cells at 2:1 and 5:1 E:T ratios. The target cell population is encircled. (15C) Flow cytometry analysis of control T-cells and CD123b−CD33b cCAR T-cells against PT3 tumor target cells at 2:1 and 5:1 E:T ratios. The target cell population (CD123+CD34+) is encircled and further broken down by CD38 expression to display LSC (CD123+CD34+CD38−) elimination. (15D) Flow cytometry analysis of control T-cells and CD123b−CD33b cCAR T-cells against PT4 tumor target cells at 2:1 and 5:1 E:T ratios. The target cell population (CD33+ bulk disease) is encircled. (15E) Percent lysis summary of CD123b−CD33b cCAR T-cells against all four patient samples at both 2:1 and 5:1 E:T ratios.

Figure 16B:
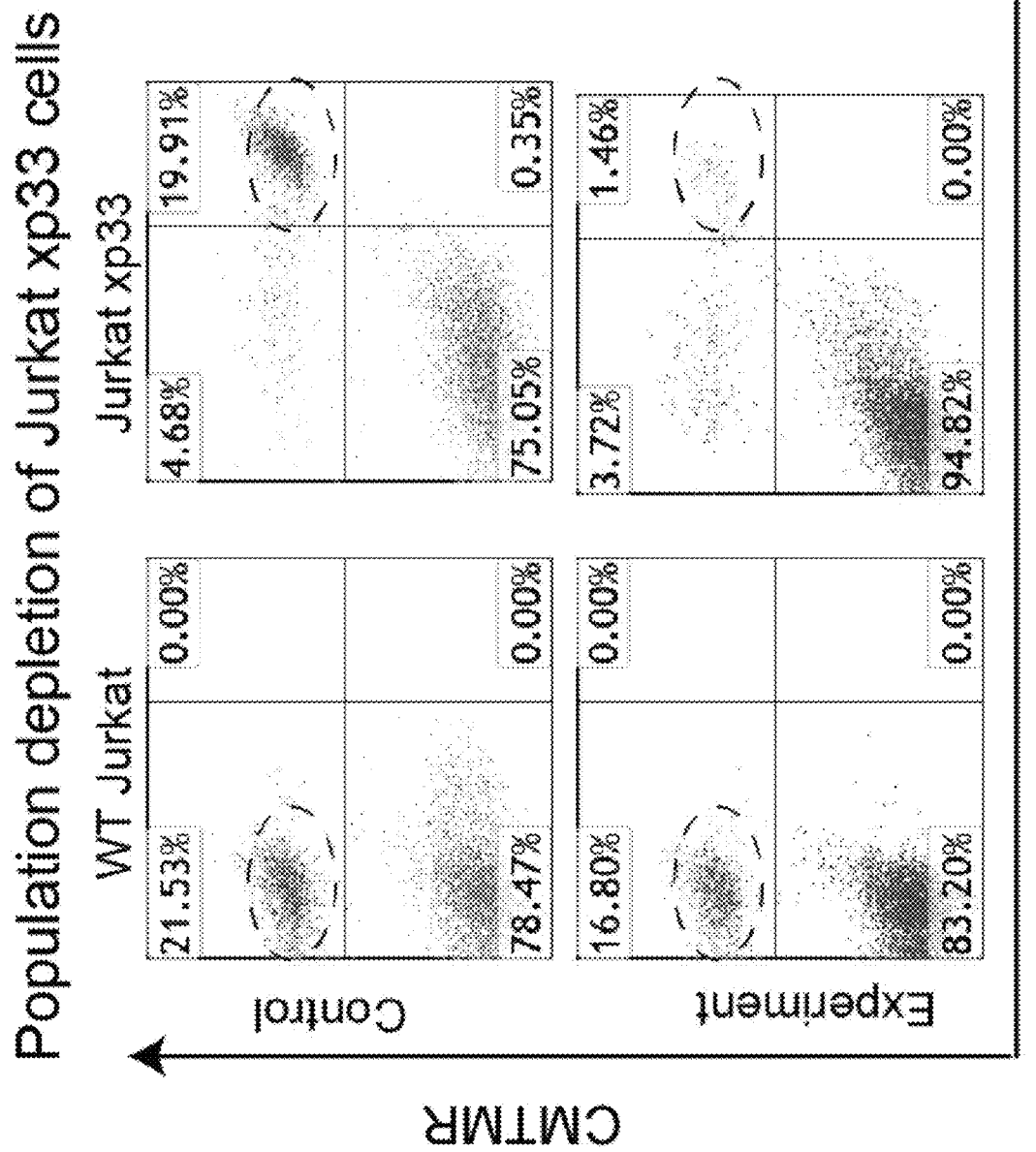
Figure 16C:
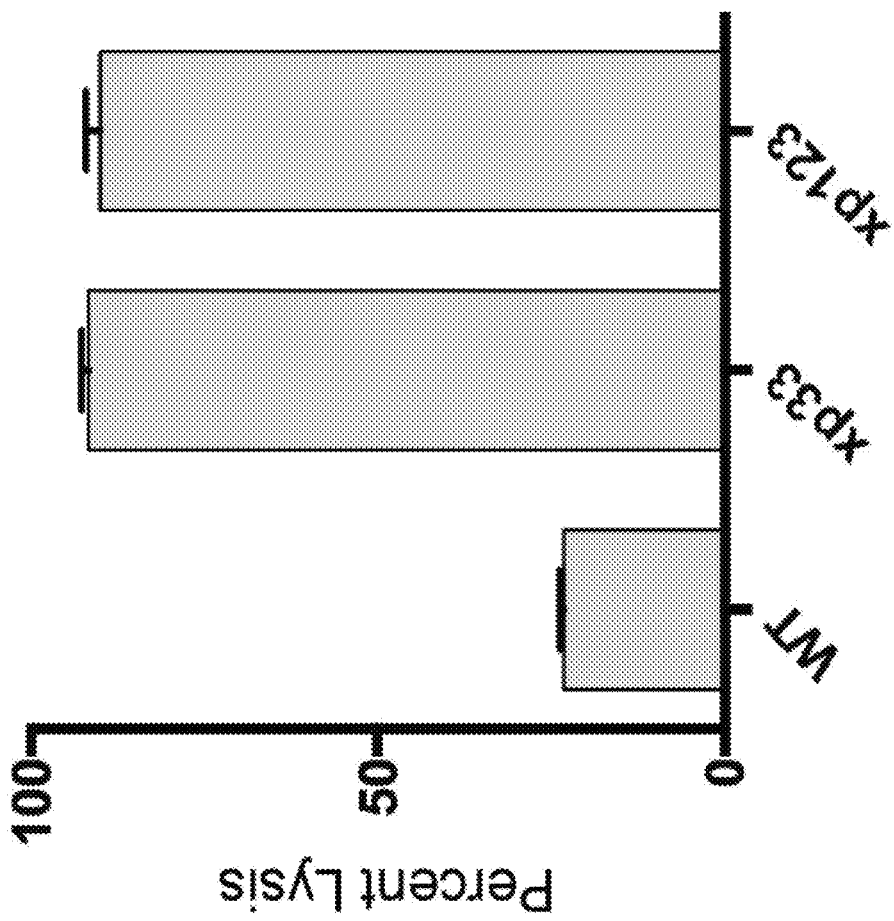

FIGS. 16A-16C: CD123b−CD33b cCAR T-cells ablate cells expressing either the CD33 or CD123 antigen with high efficacy.

(16A) Flow cytometry analysis of control T-cells and CD123b−CD33b cCAR T-cells against wild-type (WT) Jurkat tumor cells and Jurkat cells expressing CD123 (Jurkatxp123) at a 2:1 E:T ratio. The target cell population is encircled. (16B) Flow cytometry analysis of control T-cells and CD123b−CD33b cCAR T-cells against wild-type (WT) Jurkat tumor cells and Jurkat cells expressing CD33 (Jurkatxp33) at a 2:1 E:T ratio. The target cell population is encircled. (16C) Percent lysis summary of CD123b−CD33b cCAR T-cells against WT Jurkat cells, Jurkat xp33, and Jurkat xp123 cells at a 2:1 E:T ratio.

Figure 17A:
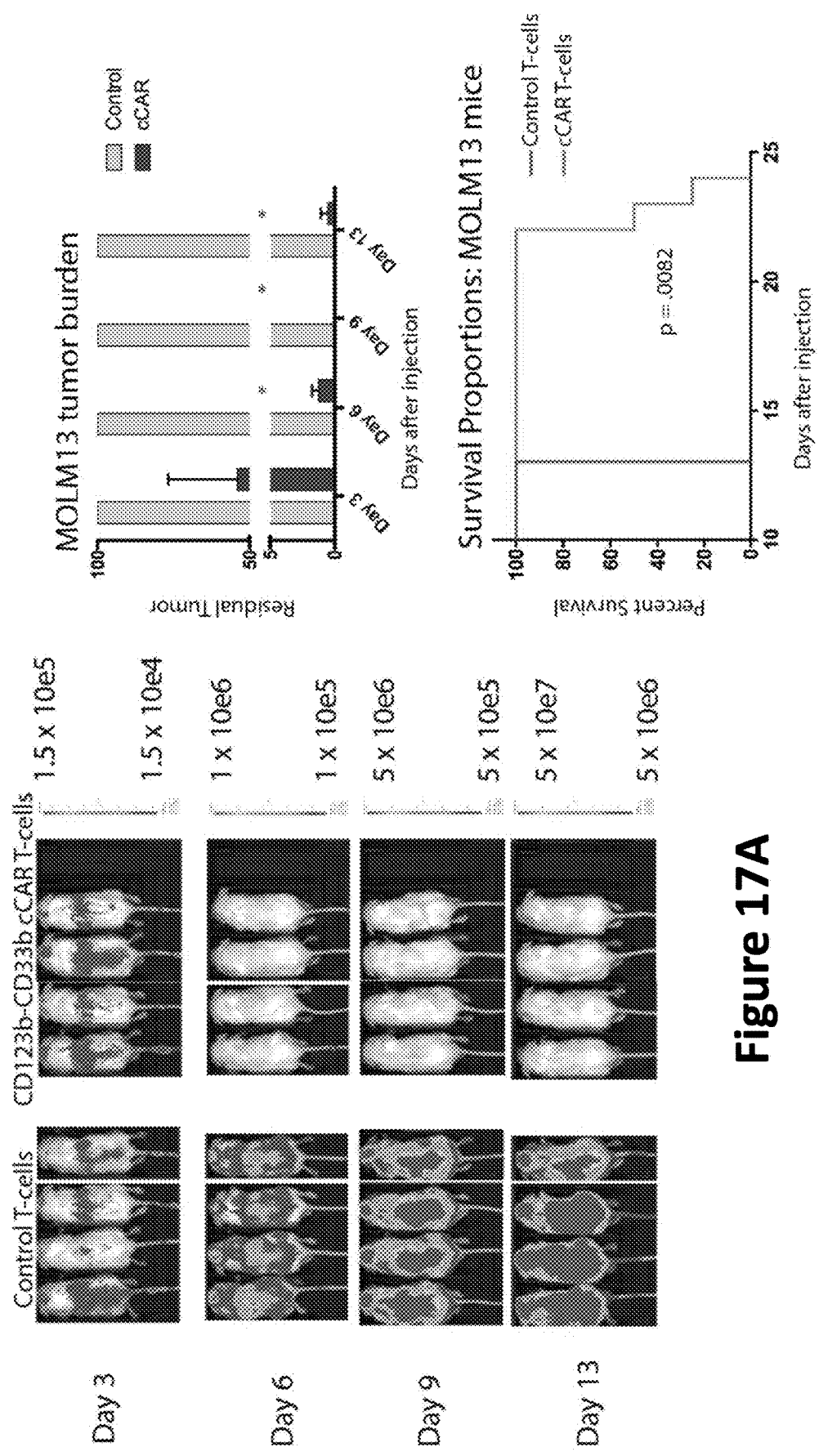
Figure 17B:
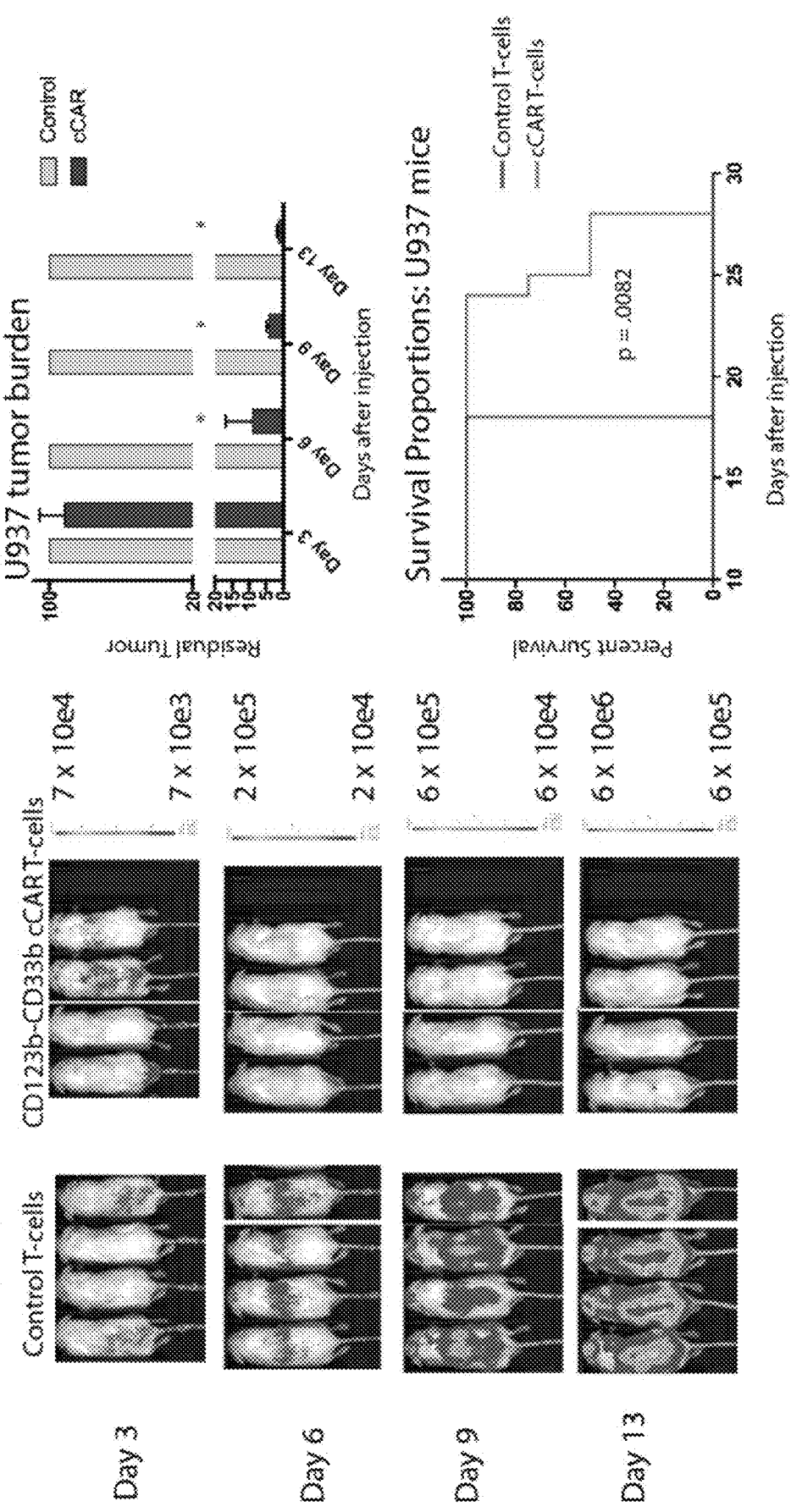
Figure 17C:
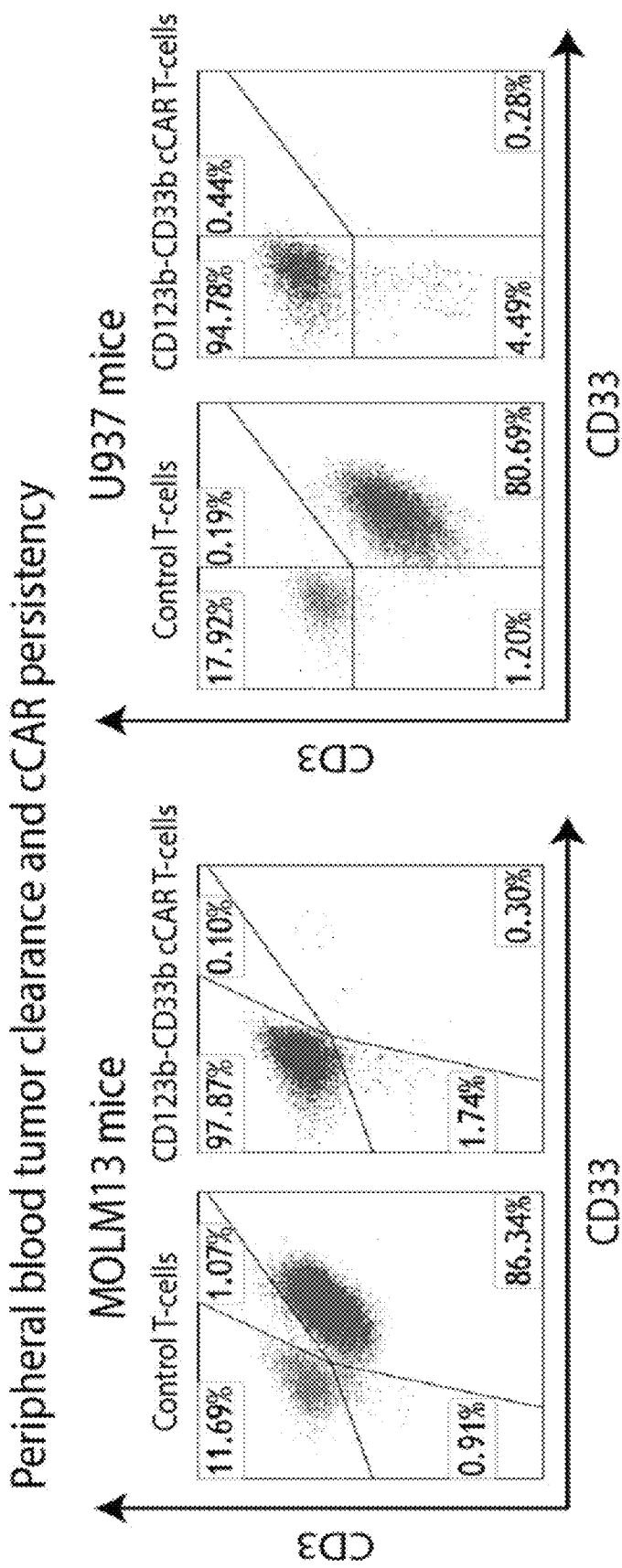

FIGS. 17A-17C: CD123b−CD33b cCAR T-cells demonstrate a profound anti-leukemic effect against MOLM13 and U937 cell lines in two in vivo xenograft mouse models.

(17A) IVIS imaging of luciferase-expressing MOLM13 cells on days 3, 6, 9, and 13 allowing tumor burden visualization (n=8 for each group). Graphical representation of tumor burden comparison between CD123b−CD33b cCAR T-cell and control T-cell treated mice over time. Tumor reduction is statistically significant from day 6 onward. Kaplan-Meier survival analysis curve represents survival outcomes (Mantel-Cox log-rank test p=0.0082). (17B) IVIS imaging of luciferase-expressing U937 cells on days 3, 6, 9, and 13 allowing tumor burden visualization (n=8 for each group). Graphical representation of tumor burden comparison between CD123b−CD33b cCAR T-cell and control T-cell treated mice over time. Tumor reduction is statistically significant from day 6 onward. Kaplan-Meier survival analysis curve represents survival outcomes (Mantel-Cox log-rank test p=0.0082). (17C) Peripheral blood of MOLM13 and U937 mice tumor models. Flow cytometry allowed visualization of CD45+CD3+ T-cells and CD45+CD33+ tumor cells.

Figure 18A:
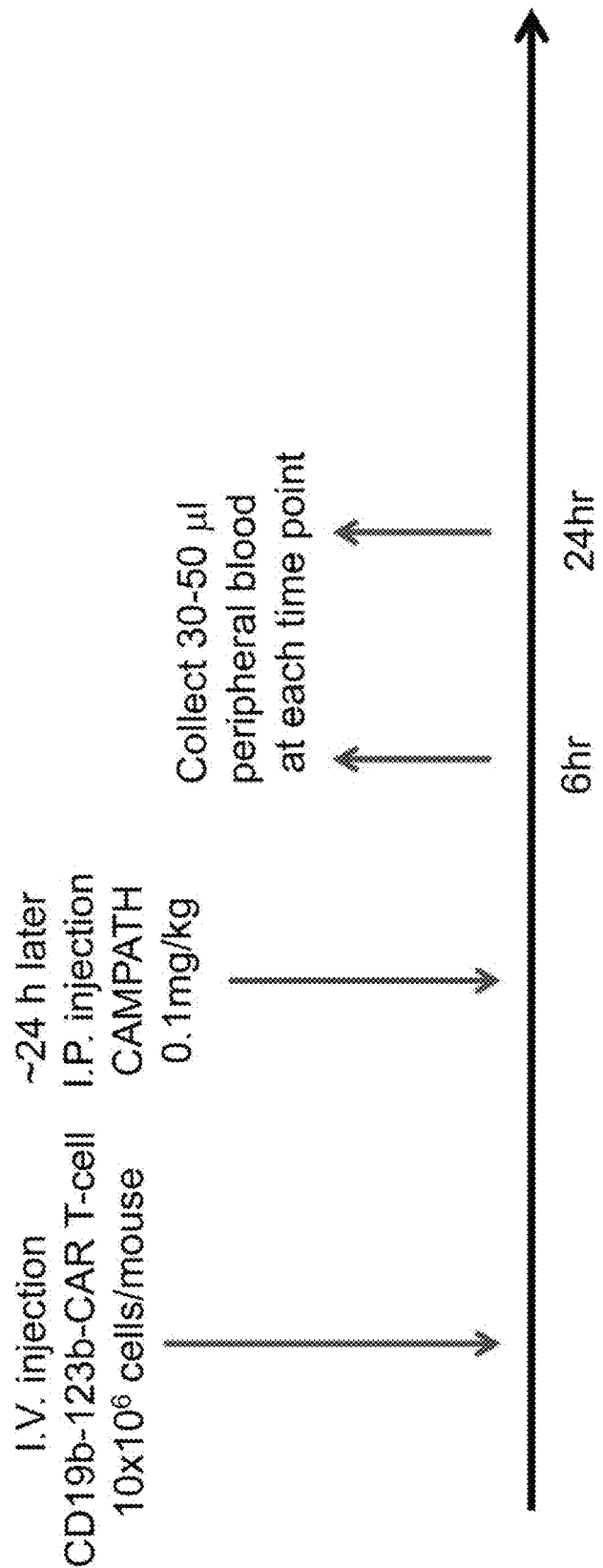
Figure 18B:
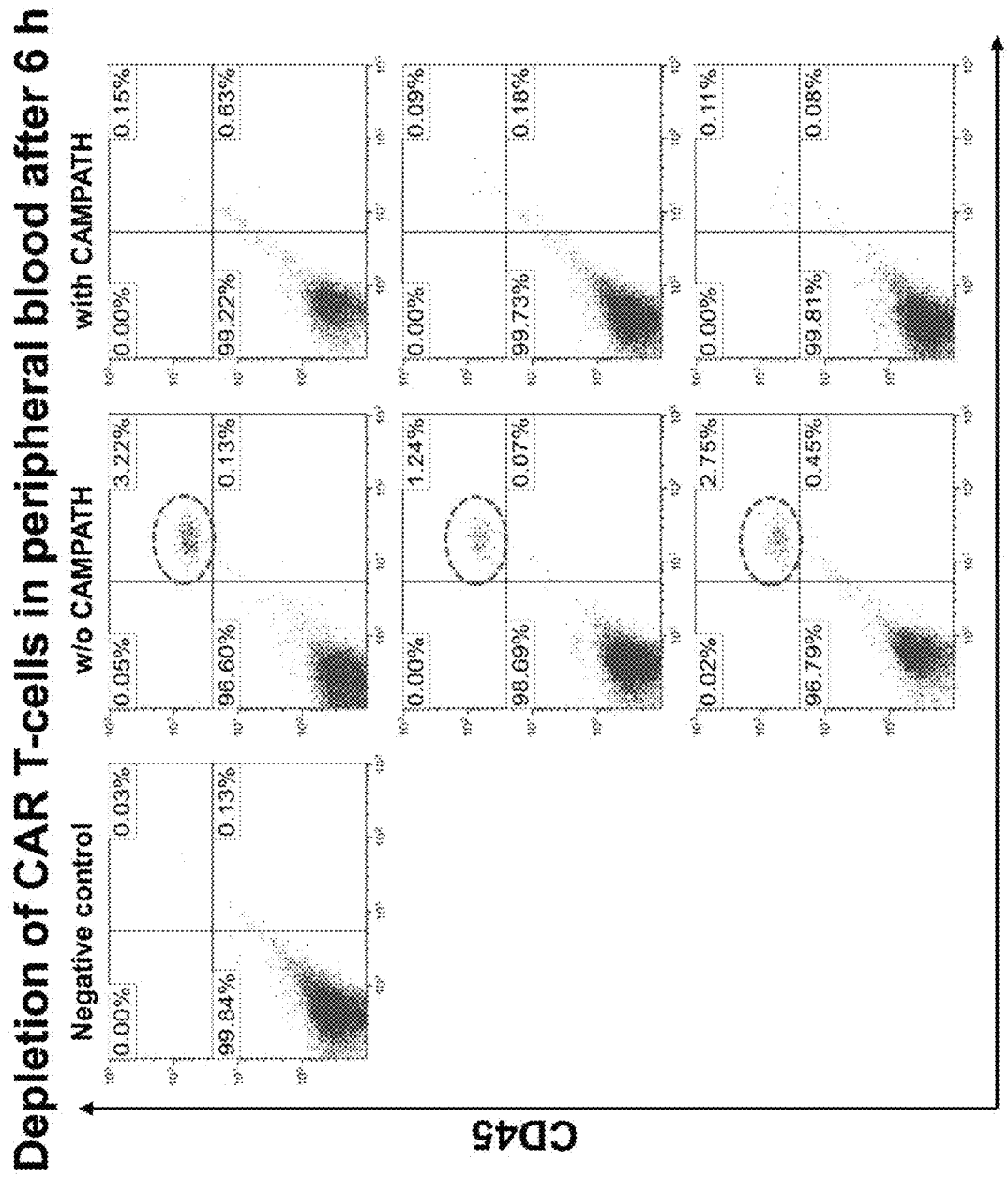
Figure 18C:
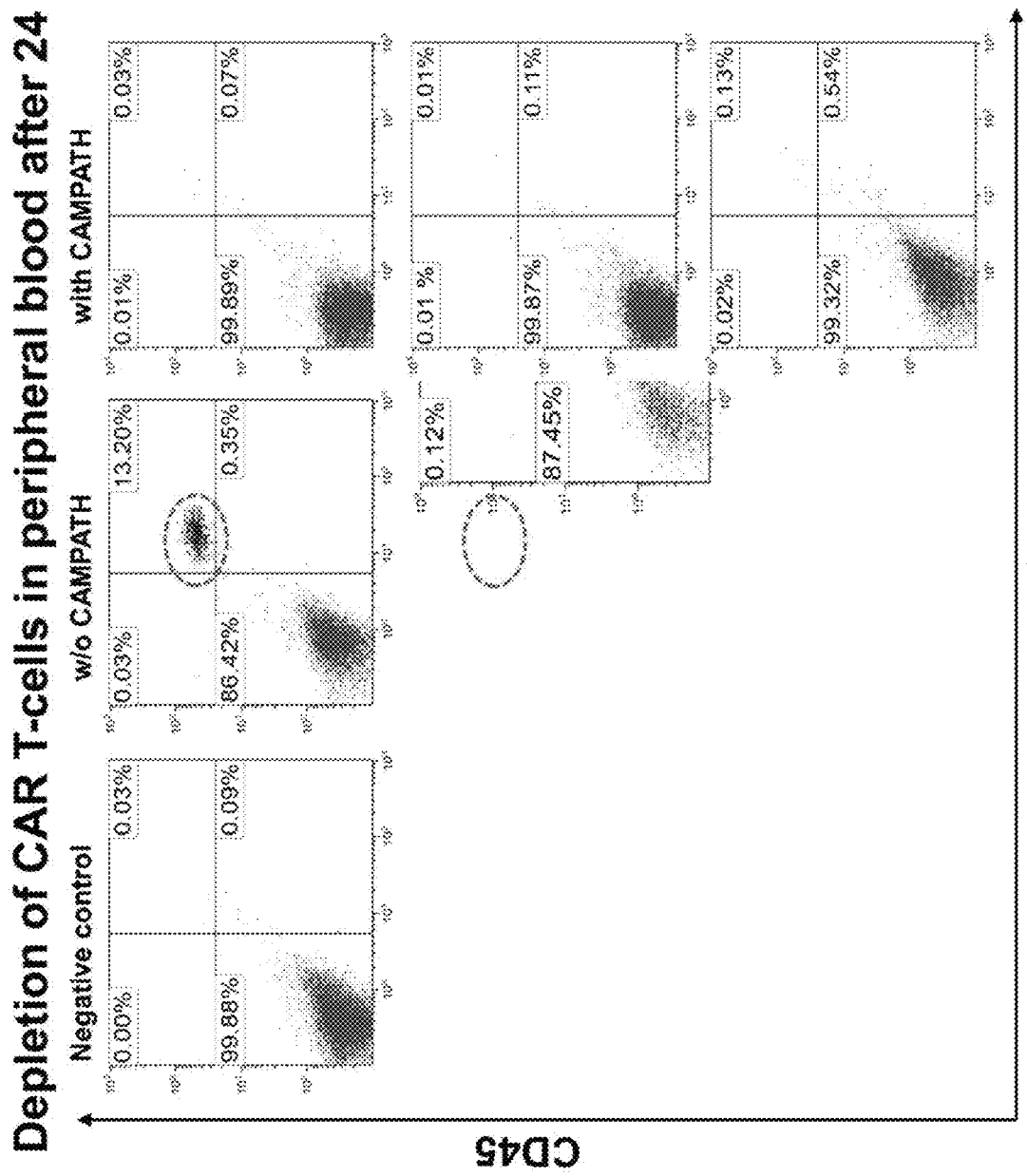

FIGS. 18A-18C: Depletion of infused CD123b−CD33b cCAR T-cells following treatment with CAMPATH.

(18A) Experimental schema to evaluate the effect of CAMPATH administration after CD19b−CD123 cCAR T-cell infusion into NGS mice. $10 \times 10^6$ CD19b−CD123 cCAR T-cells were injected intravenously into sublethally irradiated mice (n=6) and ~24 hours later, CAMPATH (0.1 mg/kg) or PBS were intraperitoneally injected (n=3 of each, except for hour 6 where n=2 for control group). 6 and 24 hour later, peripheral blood was collected to determine the persistence of CAR T-cells. (18B) Representation of persistence of infused CD19b−CD123 cCART-cells in peripheral blood 6 hours later with or without CAMPATH treatment. Presence of CD19b−CD123 cCART-cells was detected by flow cytometry. (18C) Representation of persistence of infused CD19b−CD123 cCART-cells in peripheral blood 24 hours later with or without CAMPATH treatment. Presence of CD19b−CD123 cCAR T-cells was detected by flow cytometry.

Figure 19:
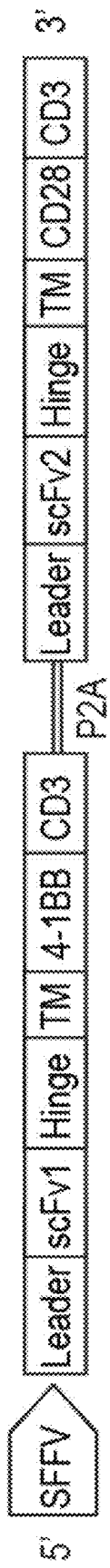

FIG. 19: Structure organization of CD19b−CD123 cCAR.

A schematic representation of cCAR-T construct (CD19b−CD123cCAR). The construct comprises a SFFV promoter driving the expression of-multiple modular units of CARs linked by a P2A peptide. Upon cleavage of the linker, the cCARs split and engage upon targets expressing CD19b CAR and CD123 CAR targeting CD19 and CD123 antigen respectively. As a novel cCAR construct, the activation domains of the construct may include, but is not limited to, 4-1BB on the CD19b CAR segment and a CD28 region on the CD123 CAR. A hinge domain (H), a transmembrane domain (TM), a co-stimulatory domain (CD28 or 4-1BB) and the intracellular signaling domain CD3 zeta (CD3).

Figure 20:
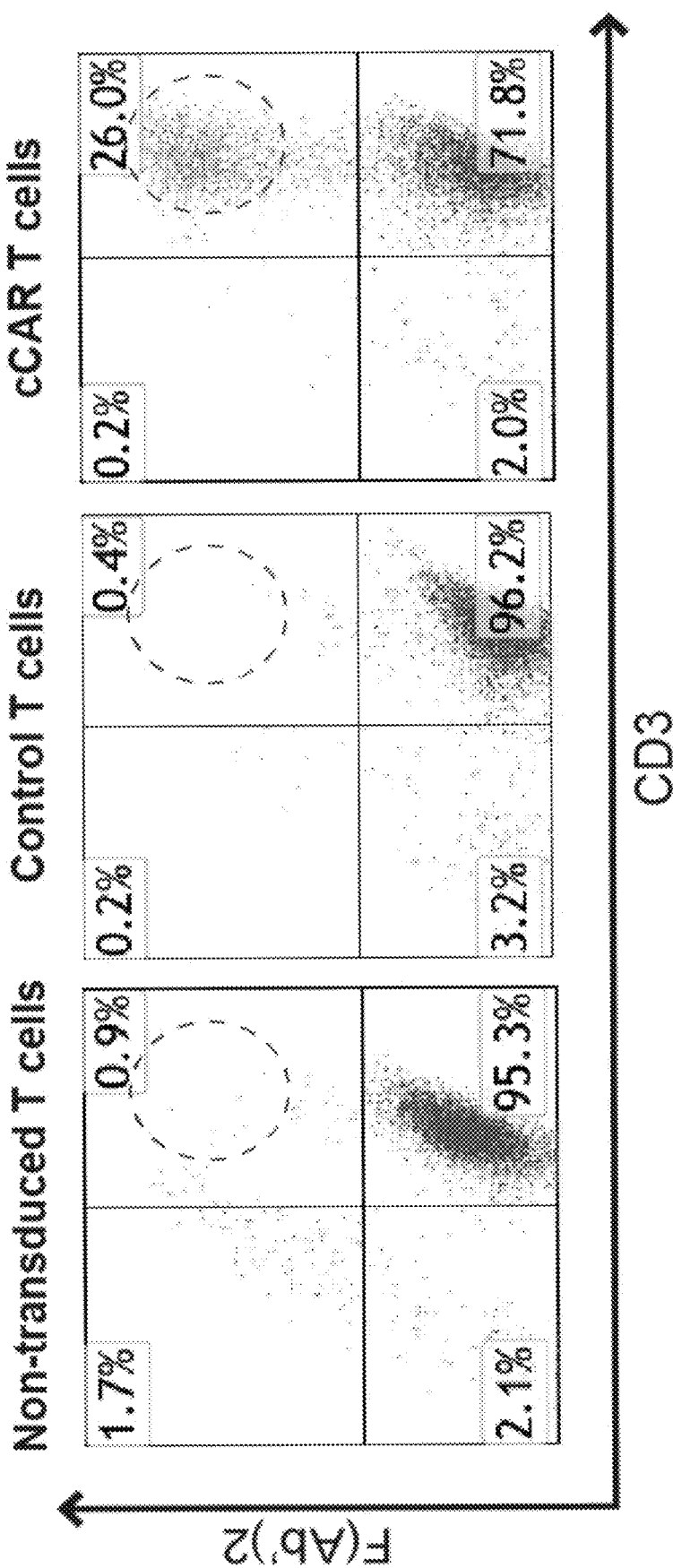

FIG. 20: Transduction efficiency of CD19b−CD123 cCAR.

Activated T cells were transduced with thawed lentivirus expressing CD19b−CD123 cCAR on retronectin-coated plates. After transduction, cells are washed and expanded; flow analysis (F(Ab')2 labeling) is done to confirm CAR efficiency.

FIGS. 21A-21D: CD19b−CD123 cCAR T cells demonstrate specific and efficacious lysis of CD19+ and CD123+ leukemia/lymphoma cell lines.

(21A) Flow cytometry analysis of control T-cells and CD19b−CD123 cCAR T-cells against artificially-induced CD19+ K562 cells and control K562 cells at 5:1 E:T ratios at 16 and 48 hours. The target cell population is depicted in red. Non-transduced CD19− cells are depicted in dark yellow. (21B) Flow cytometry analysis of control T-cells and CD19b−CD123 cCAR T-cells against artificially-induced CD19+ K562 cells and control K562 cells at 5:1 E:T ratios at 16 hours. The target cell population is depicted in red. Non-transduced CD123− Jurkat cells are depicted in purple. (21C) Flow cytometry analysis of KG1a tumor cells (CD123+CD19−) and SP53 cells (CD123−CD19+) at 5:1 E:T ratio, at 16 and 48 hours. (21D) Summary graph of tumor cell percent lysis.

FIGS. 22A-22D: CD19b−CD123 cCAR T cells demonstrate targeted lysis of primary patient cells.

(22A) Flow cytometry analysis of PT1 and PT2 tumor cell phenotypes. (22B) Flow cytometry analysis of control T-cells and CD19b−CD123 cCAR T-cells against PT1 tumor target cells a 5:1 E:T ratio, at 24 hours. The target cell population is depicted in red. (22C) Flow cytometry analysis of control T-cells and CD19b−CD123 cCAR T-cells against PT2 tumor target cells a 5:1 E:T ratio, at 24 and 48 hours. The target cell population is depicted in red. (22D) Percent lysis summary of CD19b−CD123 cCAR T-cells against patient samples at a 5:1 E:T ratio at 24 and 48 hours.

FIGS. 23A-23F: CD19b−CD123 cCAR T-cells demonstrate a profound anti-leukemic effect against MOLM13 and REH cell lines in two in vivo xenograft mouse models.

(23A) IVIS imaging of luciferase-expressing MOLM13 cells on days 3, 6, 8, and 11 allowing tumor burden visualization (represented mice for each group). (23B) Graphical representation of tumor burden comparison between CD19b–CD123 cCAR T-cell and control T-cell treated mice over time, tumor burden was measured both dorsally and ventrally. Tumor reduction is statistically significant from day 6 onward. (23C) Kaplan-Meier survival analysis curve represents survival outcomes (Mantel-Cox log-rank test p=0.0031). (23D) IVIS imaging of luciferase-expressing REH cells on day 16, allowing for tumor burden visualization (n=5 for each group). (23E) Graphical representation of tumor burden comparison between CD19b–CD123 cCAR T-cell and control T-cell treated mice over time. Tumor reduction is statistically significant. Tumor burden was measured dorsally and ventrally. (23F) Kaplan-Meier survival analysis curve represents survival outcomes (Mantel-Cox log-rank test p=0.0016).

Figure 24:
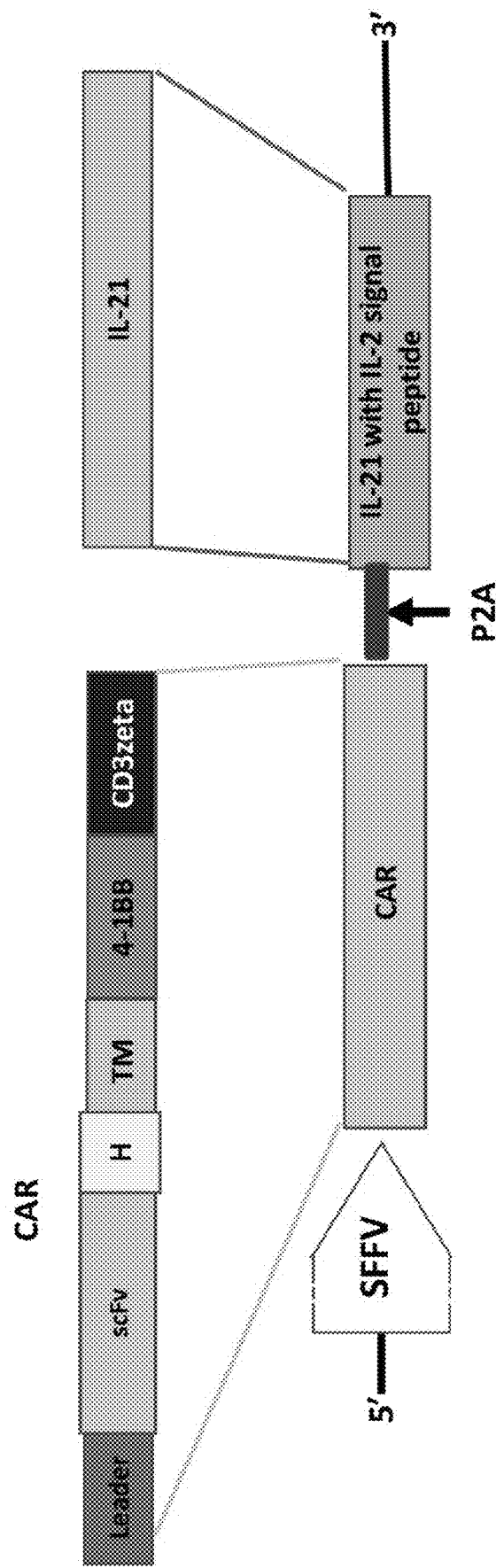

FIG. 24. A Link by P2A schematic showing CAR, 4-1BB and IL-21 in a single construct (CAR co-expressing IL-21) and its expression in T or NK cells.

The construct consists of a SFFV promoter driving the expression of CAR with costimulatory domain, 4-1BB). Upon cleavage of the linkers, a CAR and IL-21 split and engage upon targets expressing antigen. CAR T cells received not only costimulation through the 4-1BB or CD28 but also 4-1BB ligand (4-1BBL or CD137L) or IL-21. The CD3-zeta signaling domain complete the assembly of this CAR-T. The IL-21 signal peptide is replaced with IL-2 signal peptide for a better secretion of IL-21. H, CD8a hinge region, TM, CD8a transmembrane domain. Example of CAR with IL-21 can be CD19-IL-21 CAR, BCMA-IL-21 CAR, CD4-IL-21 CAR and CD45-IL-21 CAR.

Figure 25:
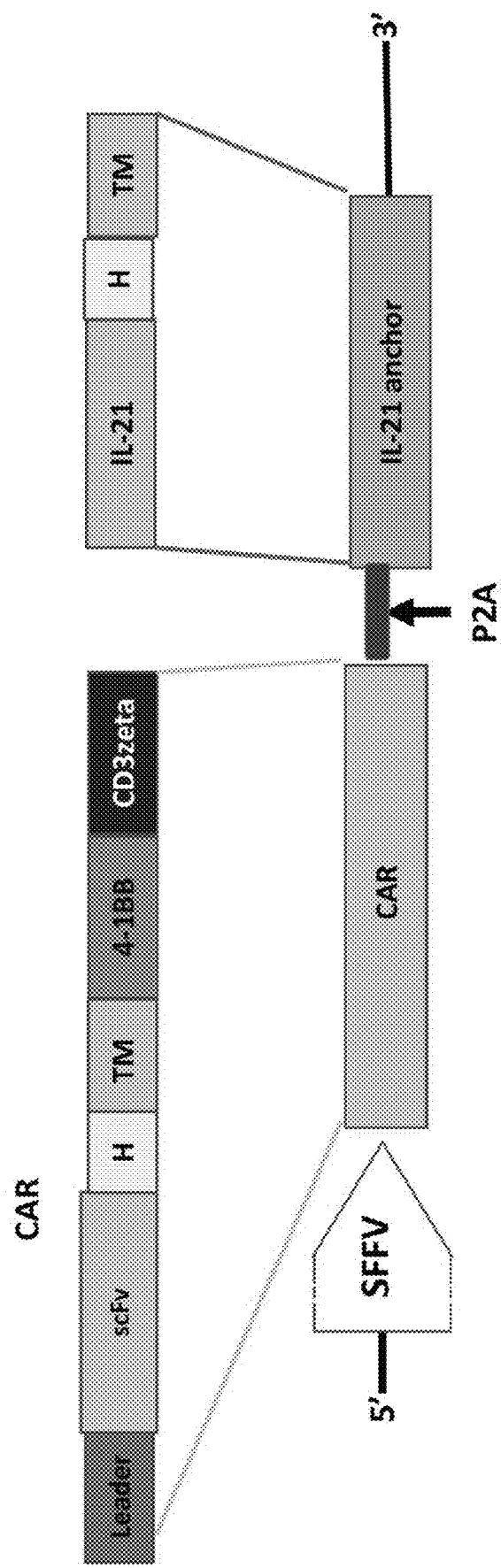

FIG. 25. Schematic diagram to elucidate the construct (CAR co-expressing IL-21 anchor) and its expression in T or NK cells.

A CAR with IL-21anchor is linked with the P2A self-cleaving sequence. The IL-21 anchor fusion is composed of IL-2 signal peptide fused to IL-21, and linked to CD8 hinge region and CD8 transmembrane domain. The combination of CAR and IL-21 fusion is assembled on an expression vector and their expression is driven by the SFFV promoter. The IL-21 signal peptide is replaced with IL-2 signal peptide for a better secretion of IL-21 and anchoring on the cell surface. Example of CAR with IL-21 anchor can be CD19-IL-21 anchor CAR, BCMA-IL-21 anchor CAR, CD4-IL-21 anchor CAR and CD45-IL-21 anchor CAR.

Figure 26:
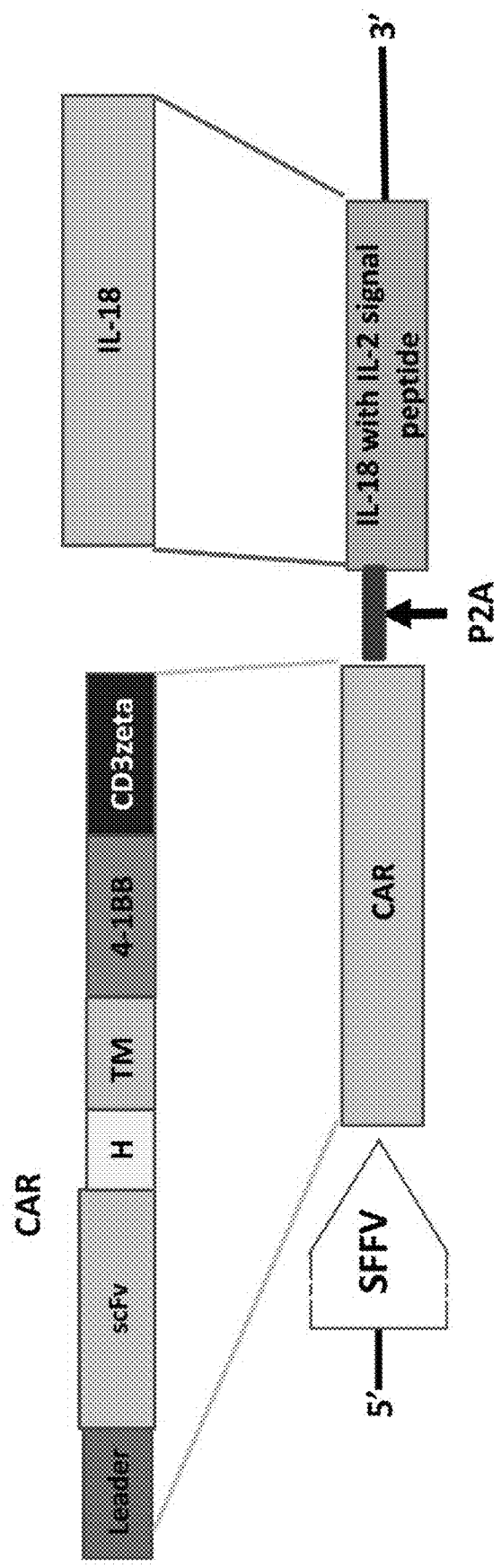

FIG. 26. A Link by P2A schematic showing CAR, 4-1BB and IL-18 in a single construct (CAR co-expressing IL-18) and its expression in T or NK cells.

The construct consists of a SFFV promoter driving the expression of CAR with costimulatory domain, 4-1BB). Upon cleavage of the linkers, a CAR and IL-18 split and engage upon targets expressing antigen. CAR T cells received not only costimulation through the 4-1BB or CD28 but also 4-1BB ligand (4-1BBL or CD137L) or IL-21. The CD3-zeta signaling domain complete the assembly of this CAR-T. The IL-21 signal peptide is replaced with IL-2 signal peptide for a better secretion of IL-18. H, CD8a hinge region, TM, CD8a transmembrane domain. The CD3-zeta signaling domain complete the assembly of this CAR-T. Example of CAR with IL-18 can be CD19-IL-18 CAR, BCMA-IL-18 CAR, CD4-IL-18 CAR and CD45-IL-18 CAR.

Figure 27:
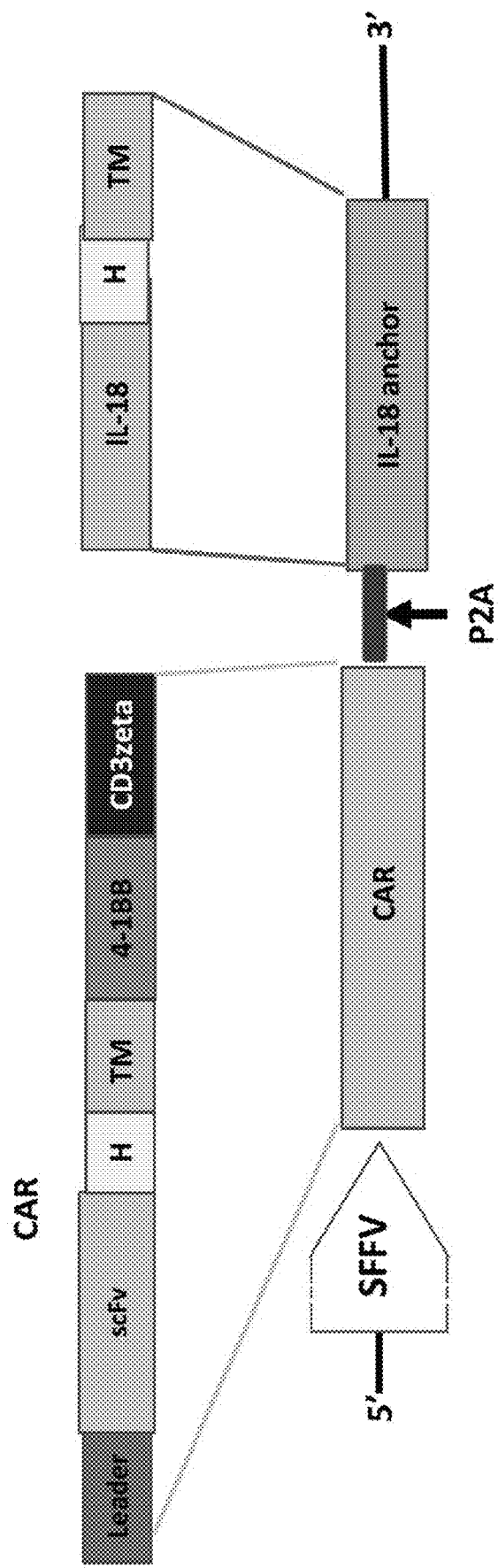

FIG. 27. Schematic diagram to elucidate the construct (CAR co-expressing IL-18 anchor) and its expression in T or NK cells.

A CAR with IL-18 anchor is linked with the P2A self-cleaving sequence. The IL-18 anchor fusion is composed of IL-2 signal peptide fused to IL-18 and linked to CD8 hinge region and CD8 transmembrane domain. The combination of CAR and IL-18 anchor fusion is assembled on an expression vector without CD3 zeta chain, and their expression is driven by the SFFV promoter. The IL-18 signal peptide is replaced with IL-2 signal peptide for a better secretion of IL-18 and then anchoring on the cell surface. Example of CAR with IL-18 anchor can be CD19-IL-18 anchor CAR, BCMA-IL-18 anchor CAR, CD4-IL-18 anchor CAR and CD45-IL-18 anchor CAR.

Figure 28A:
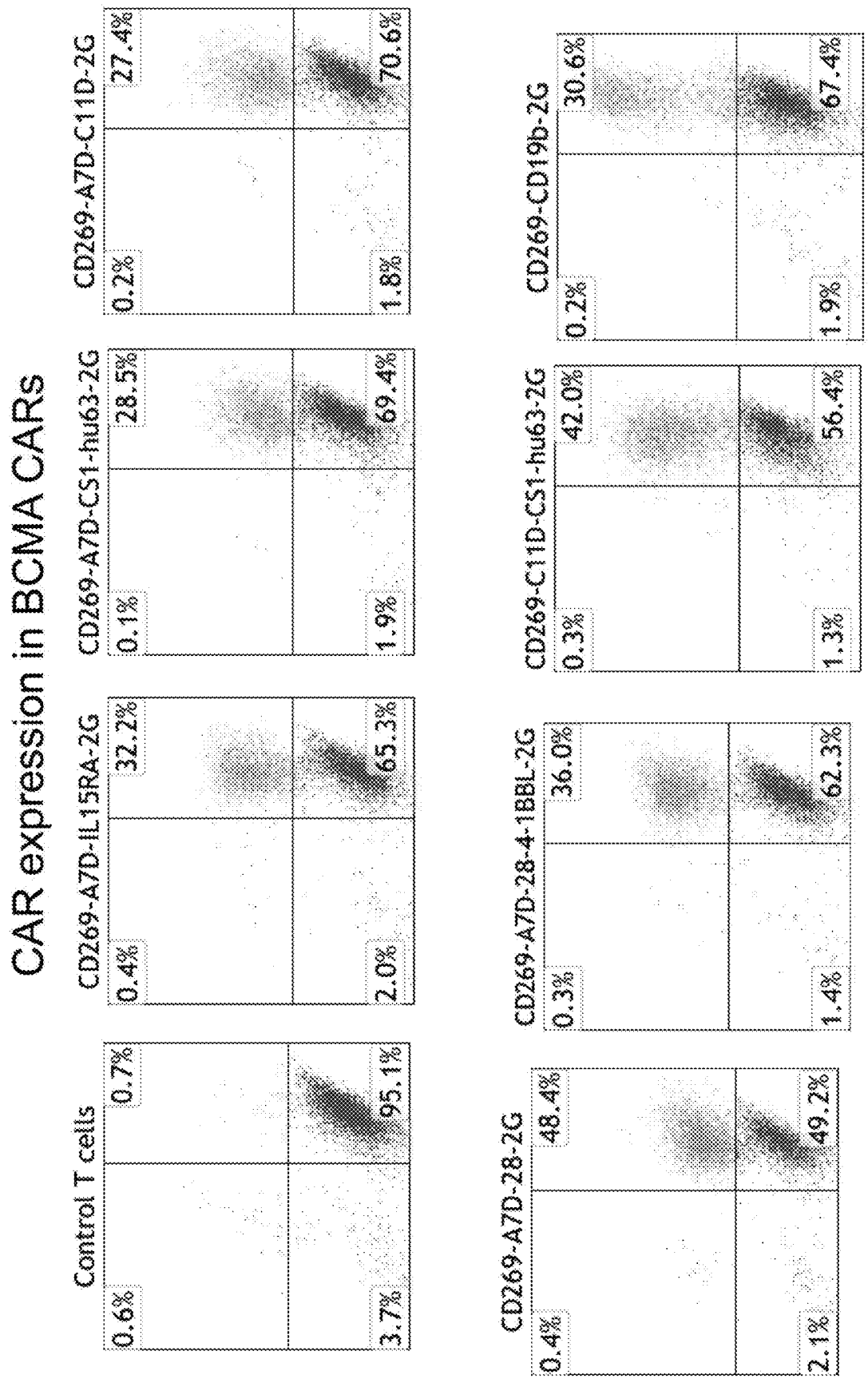

FIG. 28A. Expression of different versions of anti-BCMA CAR or cCAR T cells. Buffy coat cells were activated 3 days with anti-CD3 antibody.

Cells were transduced with either control vector (top left) or various CD269 CAR lentiviral supernatants. After 3 days of incubation, cells were harvested and labeled for flow cytometry.

Figure 28B:
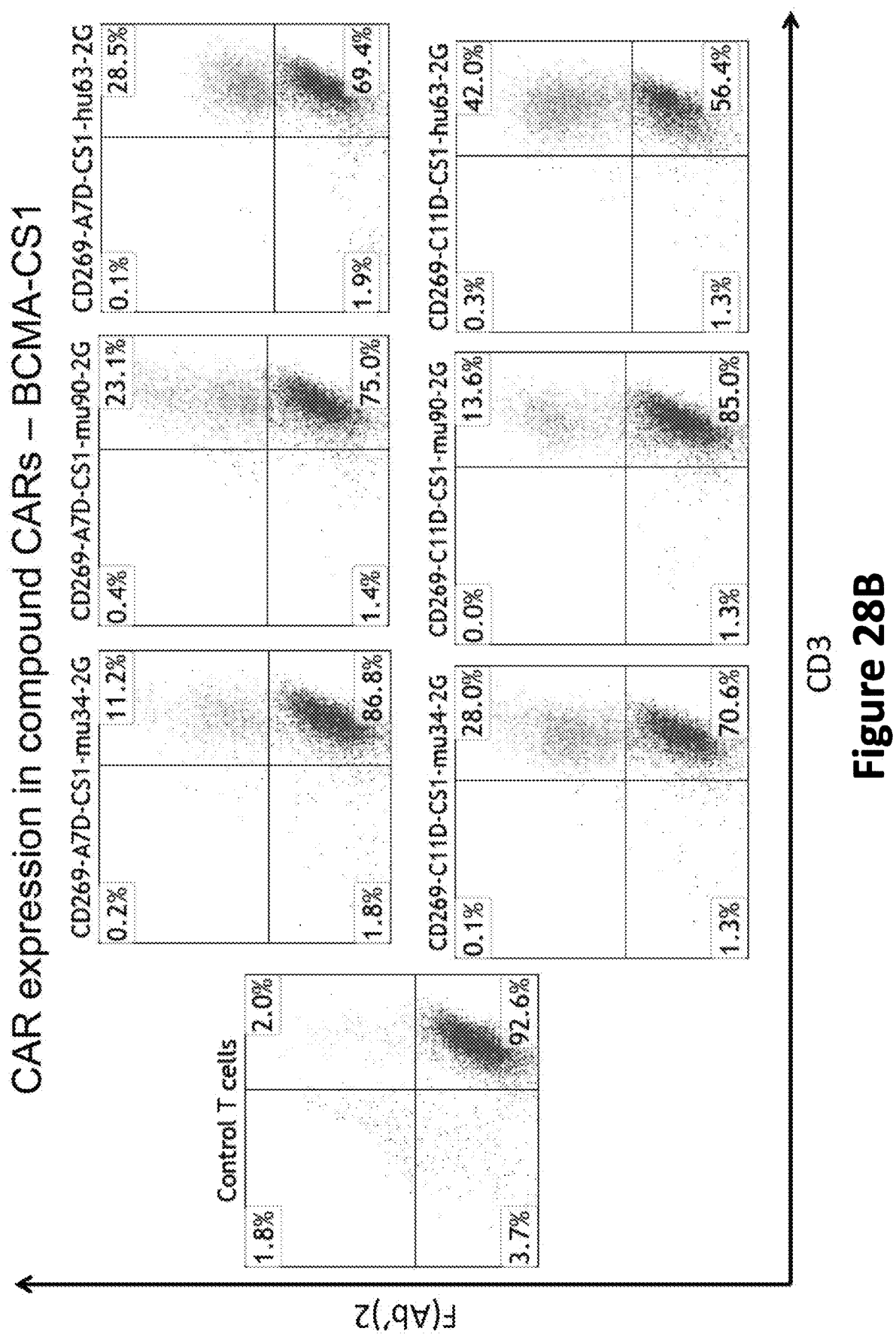

FIG. 28B. Expression of different versions of BCMA–CS1 cCAR T cells.

Buffy coat cells were activated 3 days with anti-CD3 antibody. Cells were transduced with either control vector (top left) or various CD269 cCAR lentiviral supernatants. After 3 days of incubation, cells were harvested and labeled for flow cytometry.

FIG. 29A. CD269-A7D-CD19b CAR T cells specifically lyse the K562 tumor cell line, which is synthetically expressing CD19 surface antigen (K-19), in co-culture assays. Co-culture experiments were performed at an effector to target ratio of 2:1 or 5:1 for 18 hours and were directly analyzed by flow cytometry for CD19 and CD3. Each assay consists of K-19 target cells alone (left), control T cells (center panels) and CD269-A7D-CD19b CAR T cells (right panels). K-19 cells are circled.

Figure 29B:
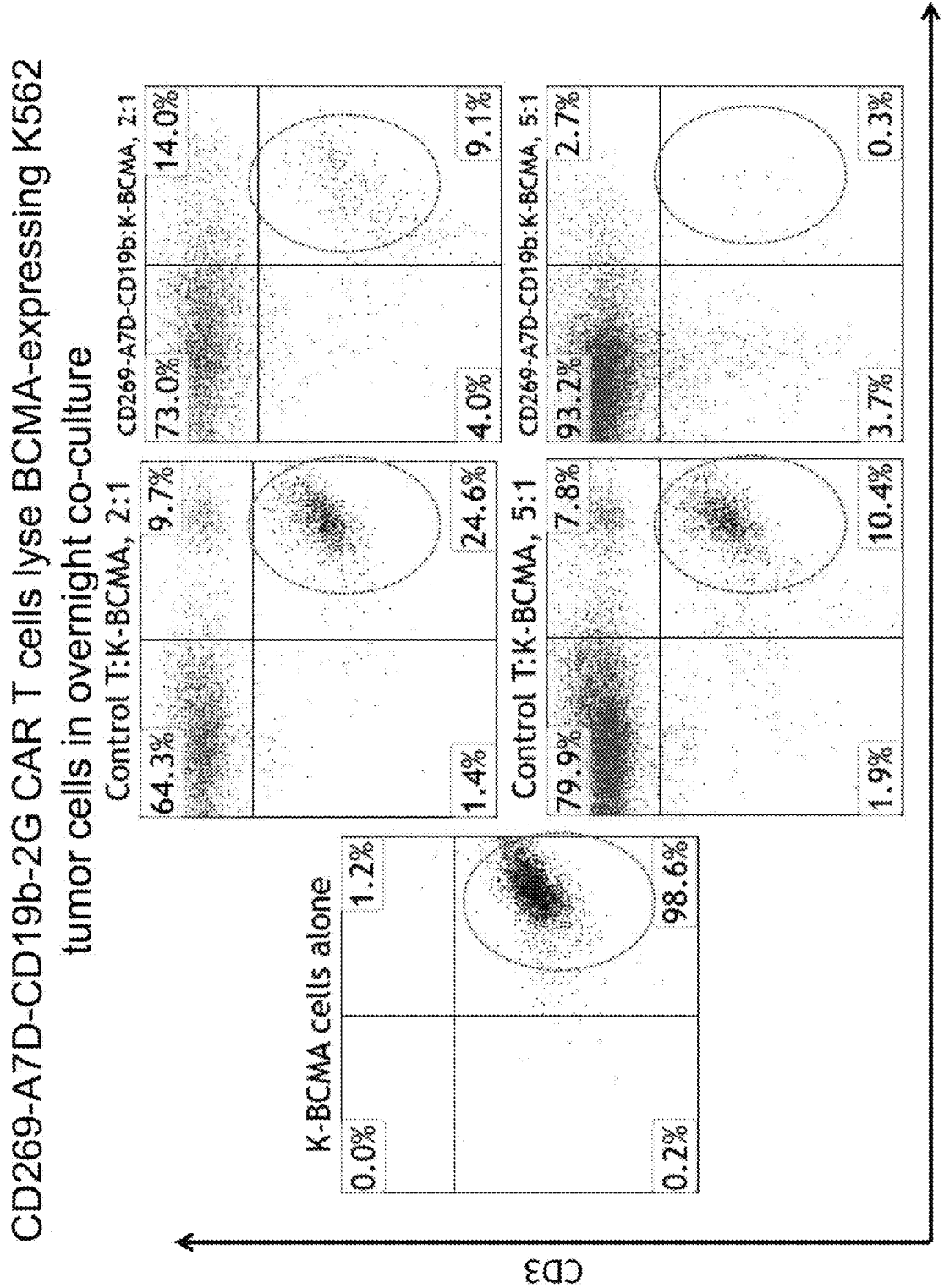

FIG. 29B. CD269-A7D-CD19b CAR T cells specifically lyse the K562 tumor cell line, which is synthetically expressing BCMA surface antigen (K-BCMA), in co-culture assays.

Co-culture experiments were performed at an effector to target ratio of 2:1 or 5:1 for 18 hours and were directly analyzed by flow cytometry for CD269 and CD3. Each assay consists of K-BCMA target cells alone (left), control T cells (center panels) and CD269-A7D-CD19b CAR T cells (right panels). K-BCMA cells are circled.

Figure 30A:
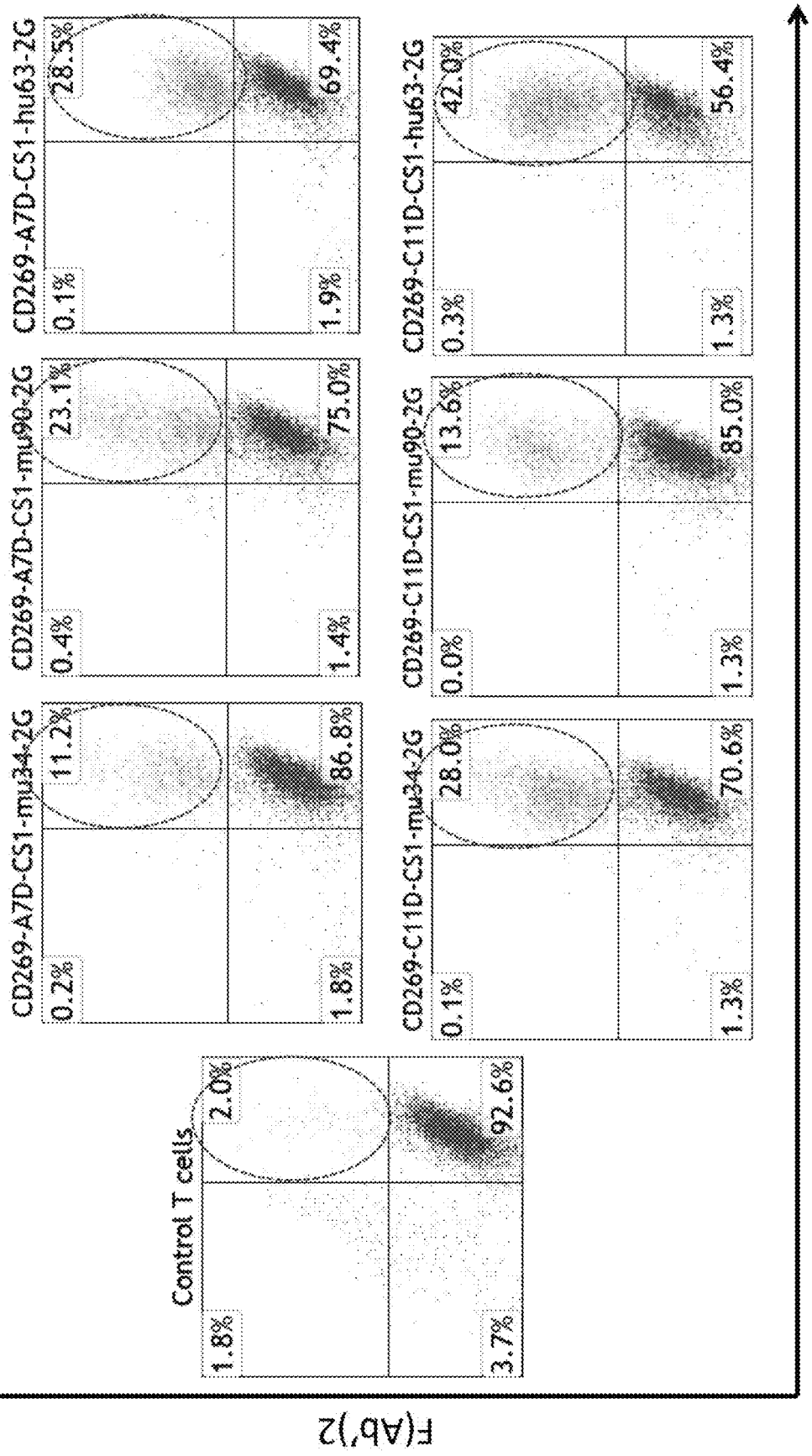

FIG. 30A. Expression of different versions of BCMA–CS1 cCAR T cells.

Buffy coat cells were activated 3 days with anti-CD3 antibody. Cells were transduced with either control vector (top left) or various CD269 (BCMA) cCAR lentiviral supernatants. After 3 days of incubation, cells were harvested and labeled for flow cytometry.

Figure 30B:
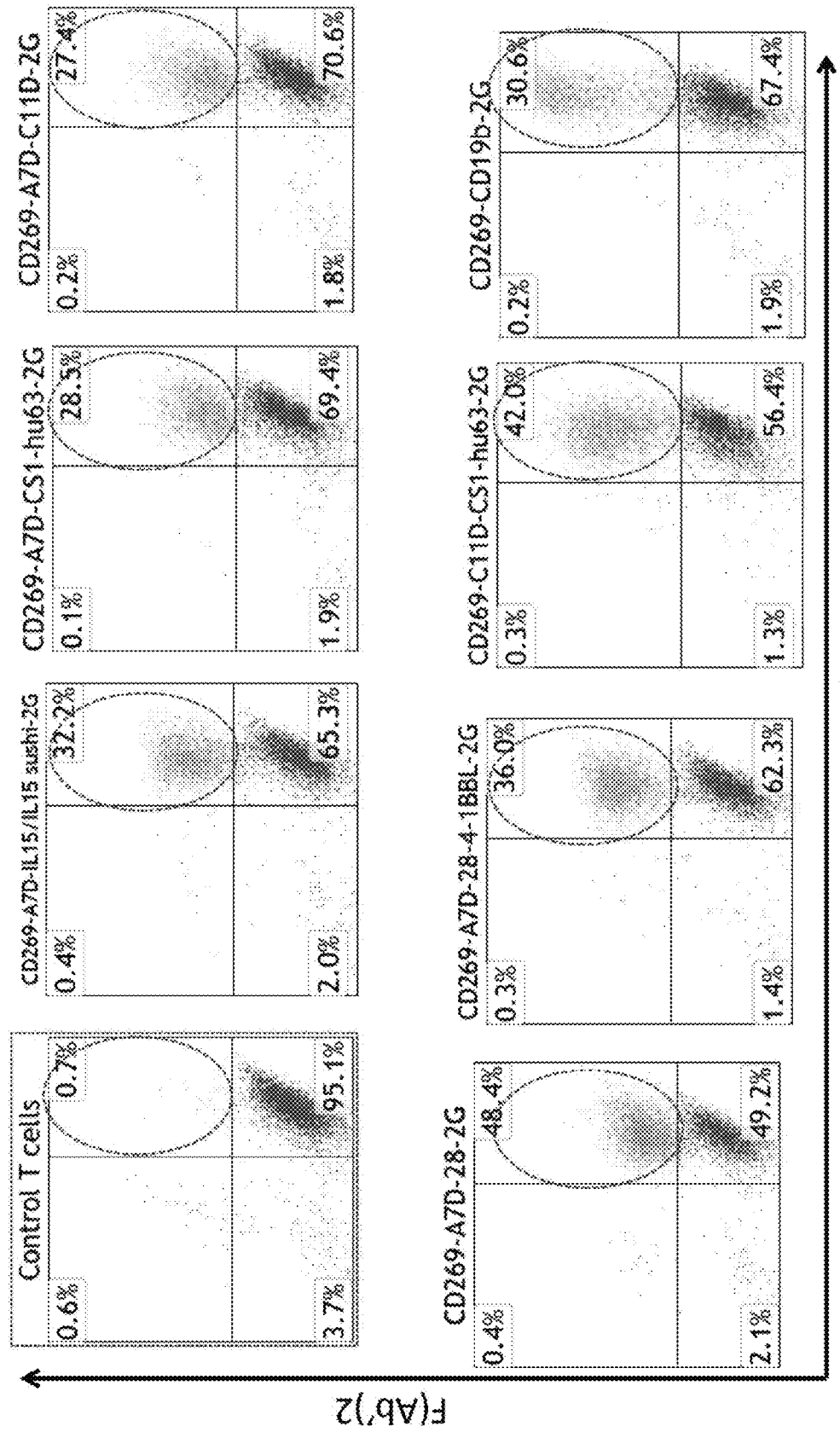

FIG. 30B. Expression of different versions of BCMA–CS1 cCAR T cells or enhanced BCMA CAR T cells.

Buffy coat cells were activated 3 days with anti-CD3 antibody. Cells were transduced with either control vector (top left) or various CD269 (BCMA) CAR lentiviral supernatants. After 3 days of incubation, cells were harvested and labeled for flow cytometry.

Figure 30C:
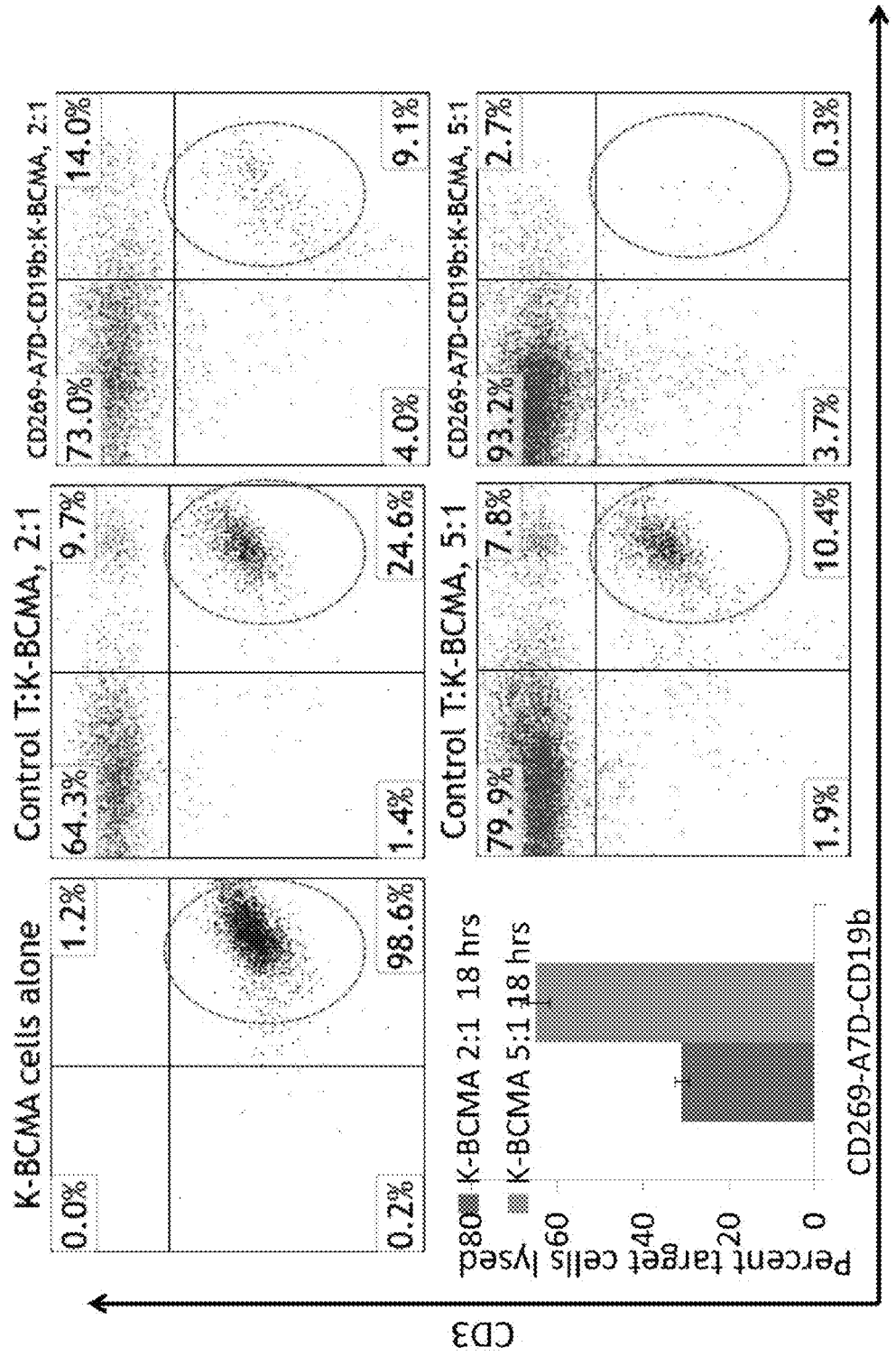

FIG. 30C. CD269-A7D-CD19b CAR T cells specifically lyse the K562 tumor cell line, which is synthetically expressing BCMA surface antigen (K-BCMA), in co-culture assays.

Co-culture experiments were performed at an effector to target ratio of 2:1 or 5:1 for 18 hours and were directly analyzed by flow cytometry for CD269 and CD3. Each assay consists of K-BCMA target cells alone (left), control T cells (center panels) and CD269-A7D-CD19b CAR T cells (right panels). K-BCMA cells are circled.

Figure 30D:
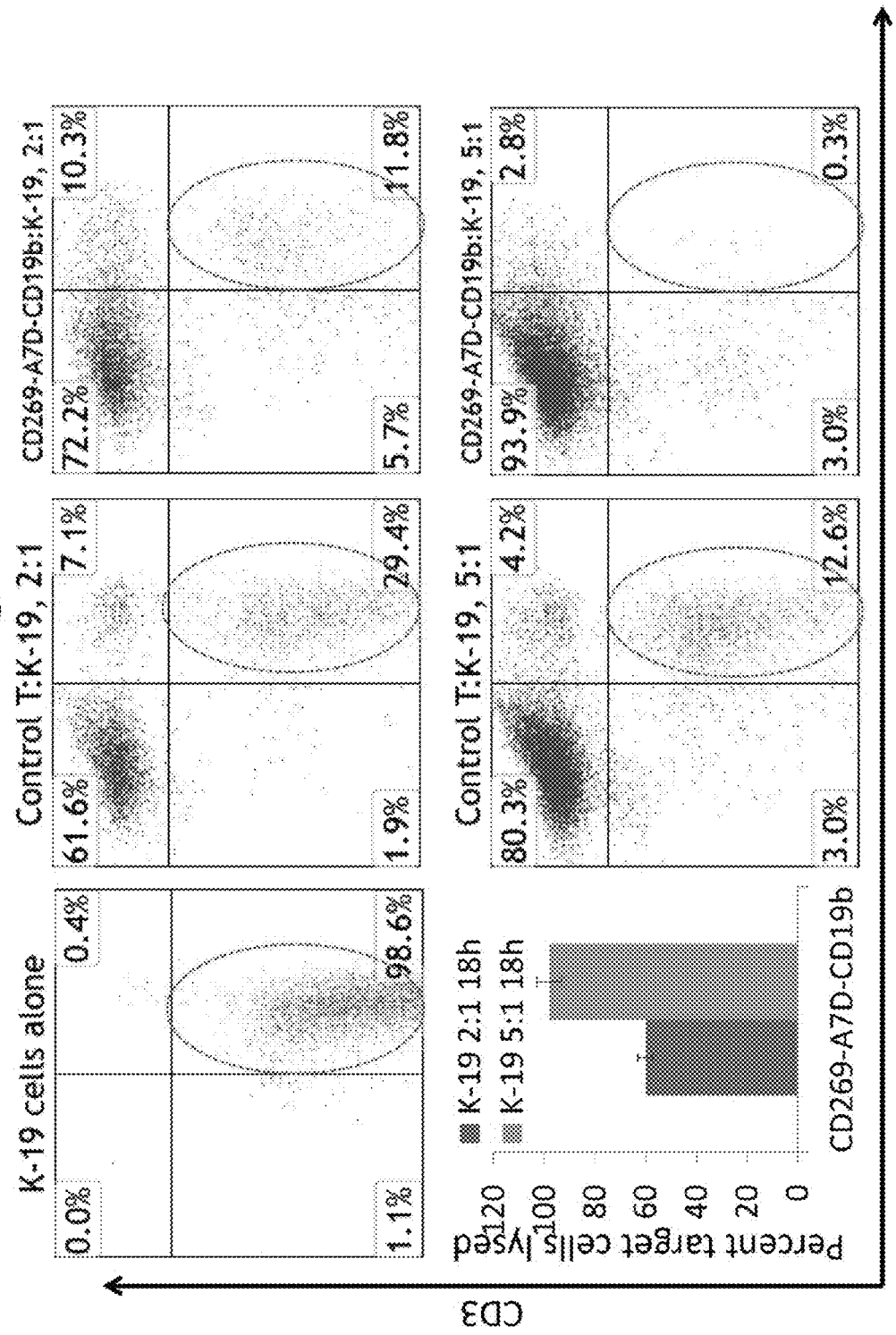

FIG. 30D. CD269-A7D-CD19b CAR T cells specifically lyse the K562 tumor cell line, which is synthetically expressing CD19 surface antigen (K-19), in co-culture assays.

Co-culture experiments were performed at an effector to target ratio of 2:1 or 5:1 for 18 hours and were directly analyzed by flow cytometry for CD19 and CD3. Each assay consists of K-19 target cells alone (left), control T cells (center panels) and CD269-A7D-CD19b CAR T cells (right panels). K-19 cells are circled. Results are summarized in the graph in the lower left. (N=2).

Figure 30E:
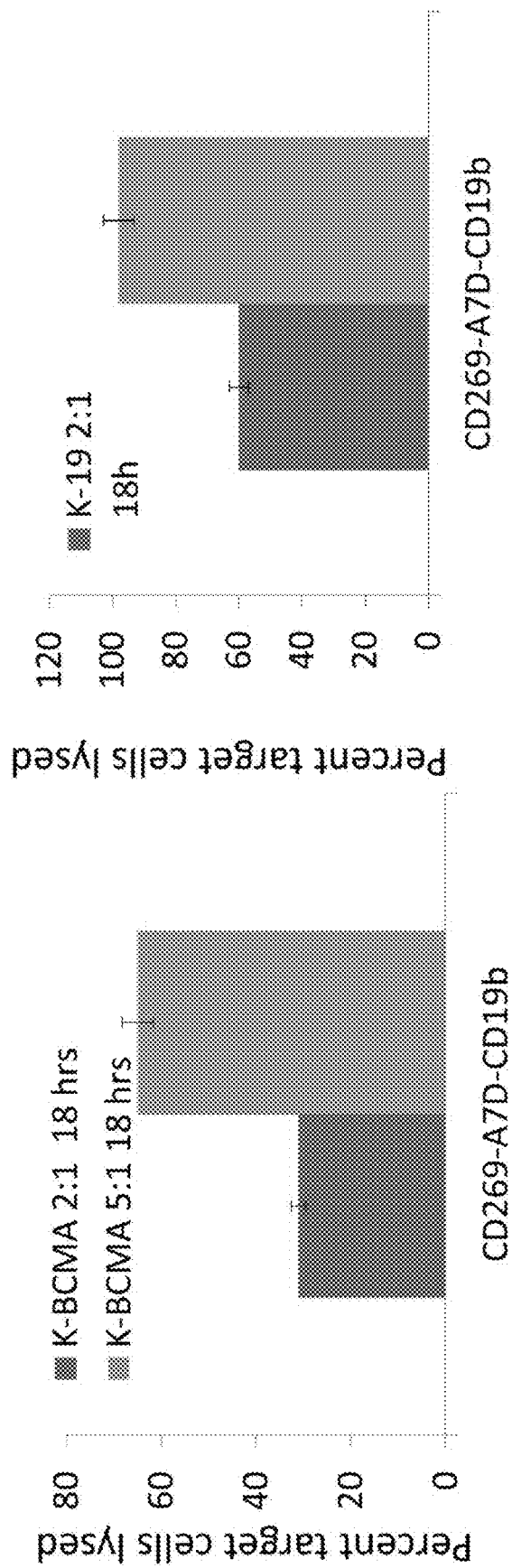

FIG. 30E. Summary lysis of K562-BCMA (K-BCMA) and K562-CD19 (K-19) cells by CD269-A-7D-CD19b cCAR T cells.

Figure 30F:
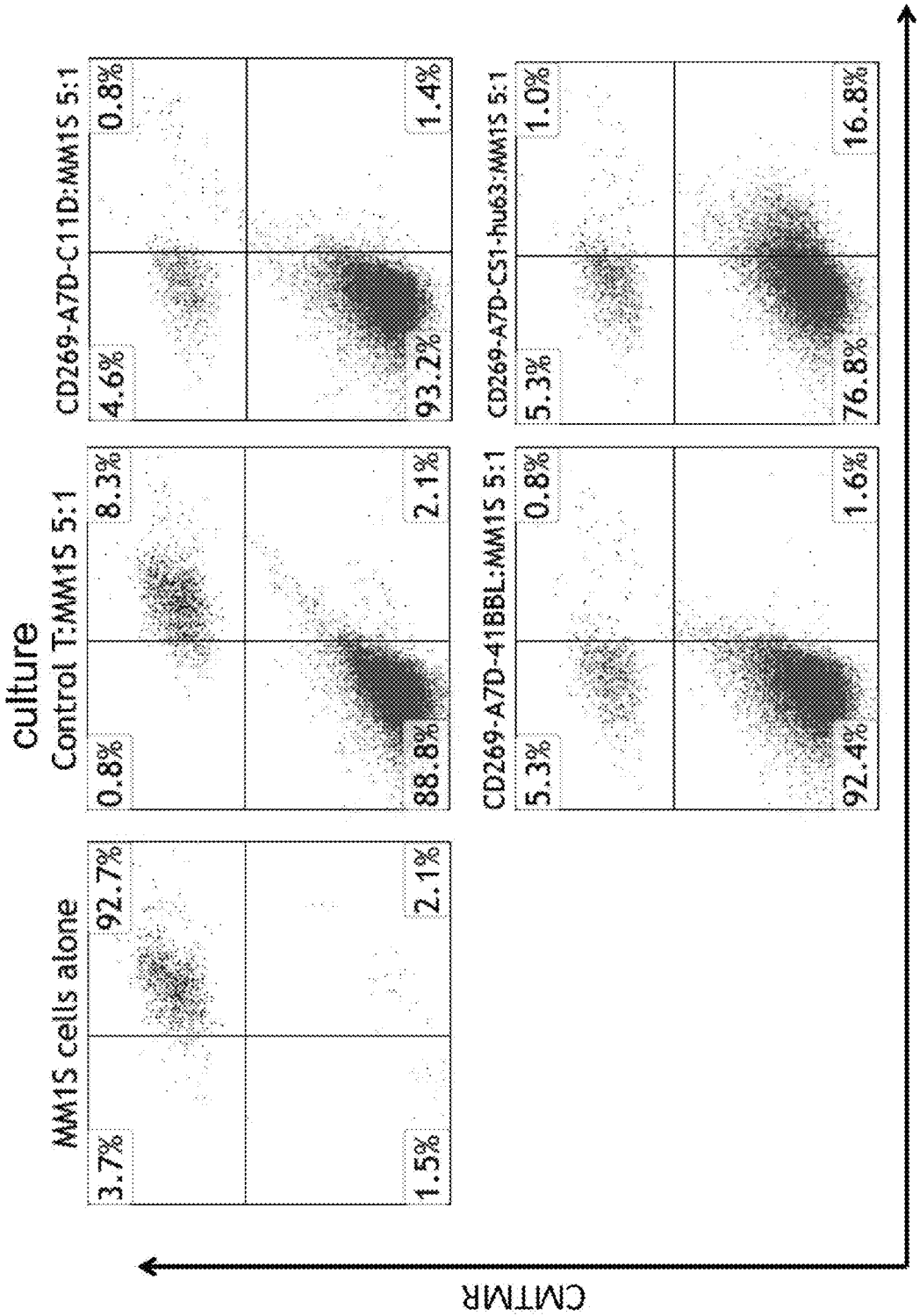

FIG. 30F. CD269-A7D cCAR T cells specifically lyse the MM1S tumor cell line in co-culture assays.

Co-culture experiments were performed at an effector to target ratio of 5:1 for 18 hours and were directly analyzed by flow cytometry for CD269 (BCMA) and CMTMR (Cell-Tracker). Each assay consists of MM1S target cells alone (left), control T cells (top center panel), CD269-A7D-41BBL (bottom center), CD269-A7D-C11D (top right) and CD269-A7D-CS1-hu63 cCAR T cells (bottom right). MM1S cells are represented by blue dots. (N=2).

Figure 30G:
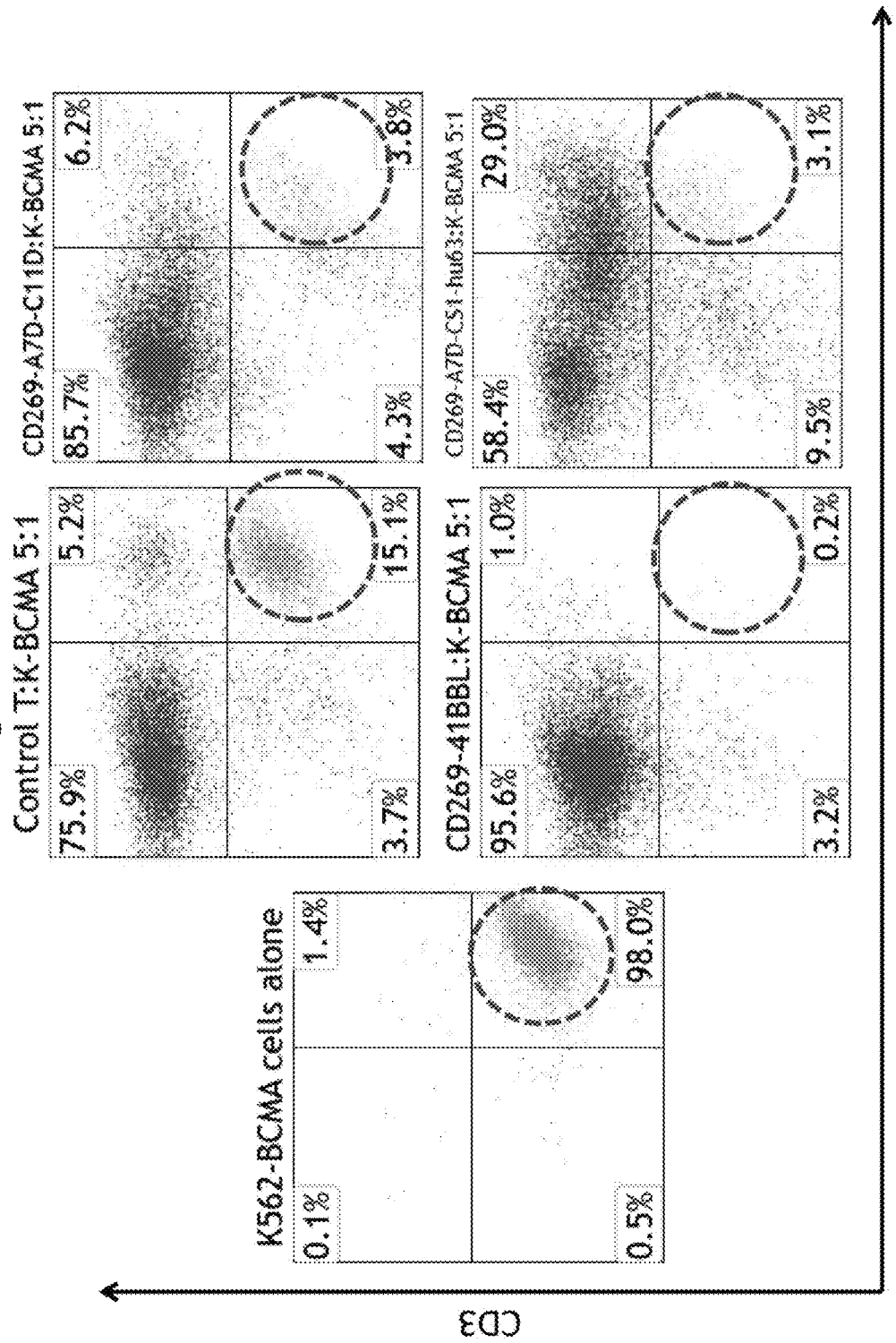

FIG. 30G. Different versions of CD269-CS1 cCAR or enhanced CD269 CAR T cells specifically lyse the K562-BCMA tumor cell line in co-culture assays.

Co-culture experiments were performed at an effector to target ratio of 5:1 for 18 hours and were directly analyzed by flow cytometry for CD269 and CD3. Each assay consists of MM1S target cells alone (left), control T cells (top center panel), CD269-A7D-41BBL (bottom center), CD269-A7D-C11D (a cCAR targeting two different epitopes of BCMA antigen) (top right) and CD269-A7D-CS1-hu63 CART cells (bottom right). K-BCMA cells are represented by green dots. (N=2).

Figure 30H:
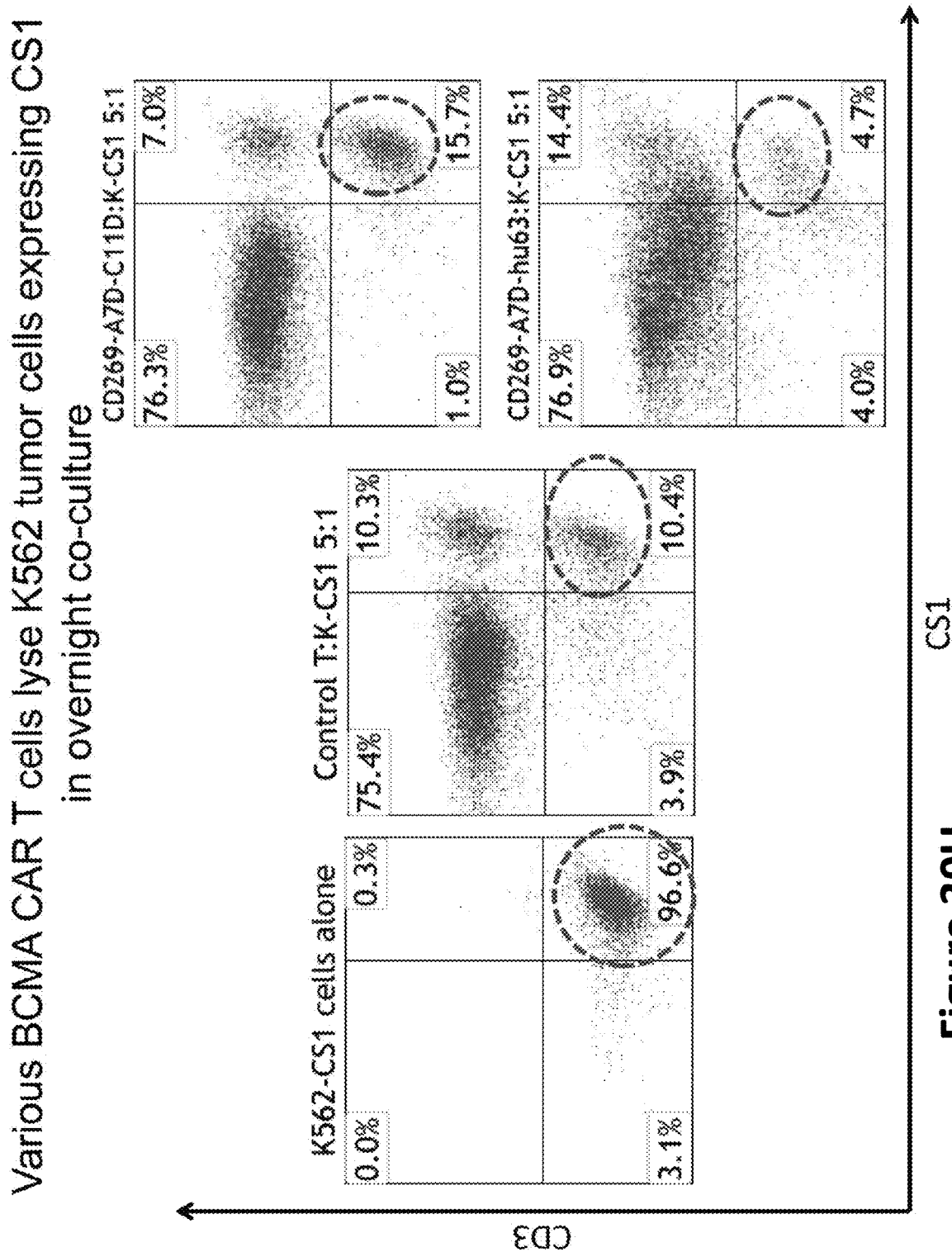

FIG. 30H. CD269-A7D-CS1-hu63 CAR T cells specifically lyse the K562-CS1 tumor cell line in co-culture assays, while CD269-A7D-C11D cCAR (a cCAR targeting different epitopes of BCMA antigen, without a CS1 CAR) do not. Co-culture experiments were performed at an effector to target ratio of 5:1 for 18 hours and were directly analyzed by flow cytometry for CD269 and CD3. Each assay consists of MM1S target cells alone (left), control T cells (center panel), CD269-A7D-C11D (top right) and CD269-A7D-CS1-hu63 CART cells (bottom right). K-CS1 cells are represented by dark green dots. (N=2).

Figure 30I:
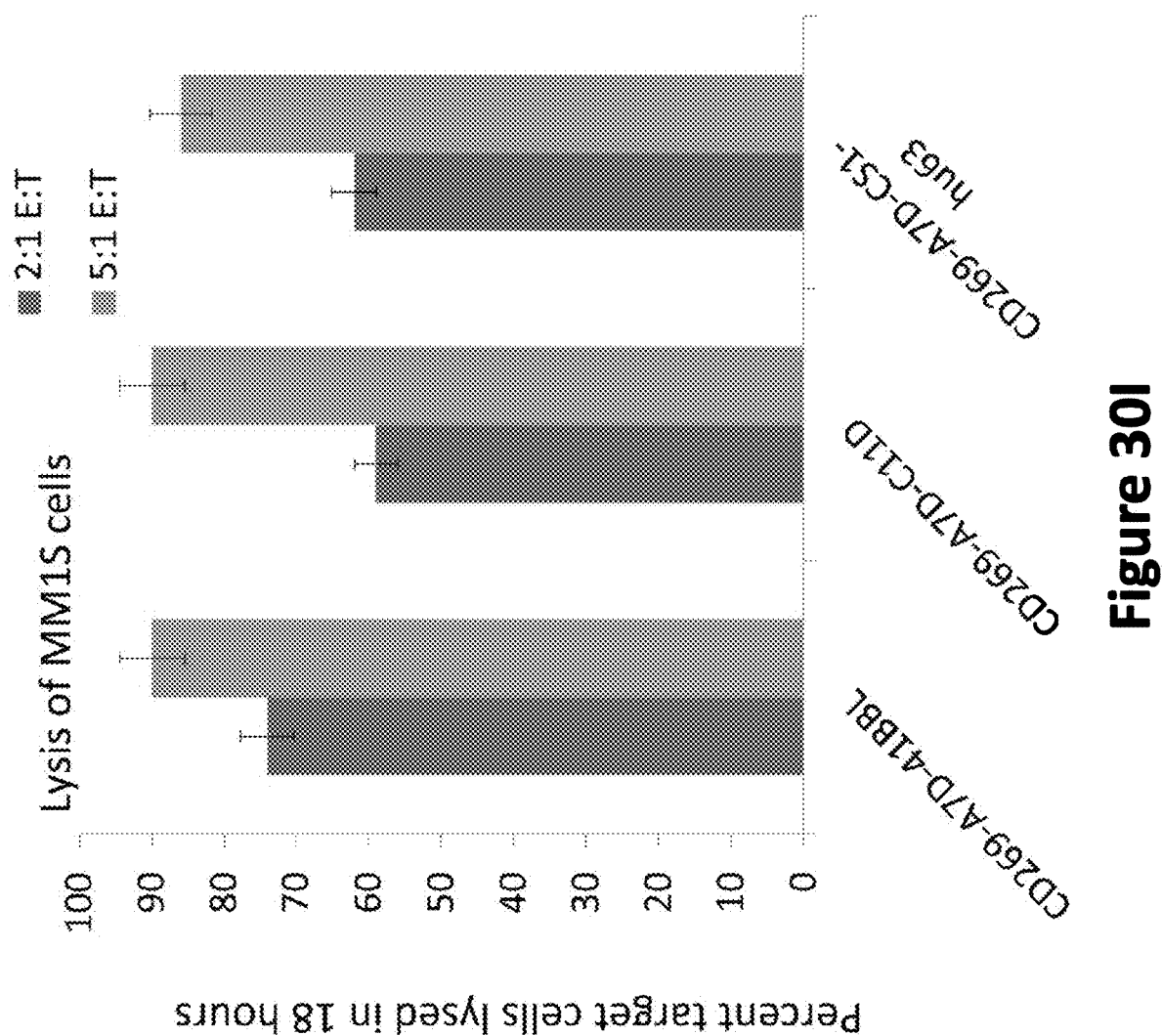

FIG. 30I. Summary lysis of MM1S myeloma cells by CD269-A7D-41BBL, CD269-A7D-C11D and CD269-CS1-hu63 CAR T cells.

Figure 30J:
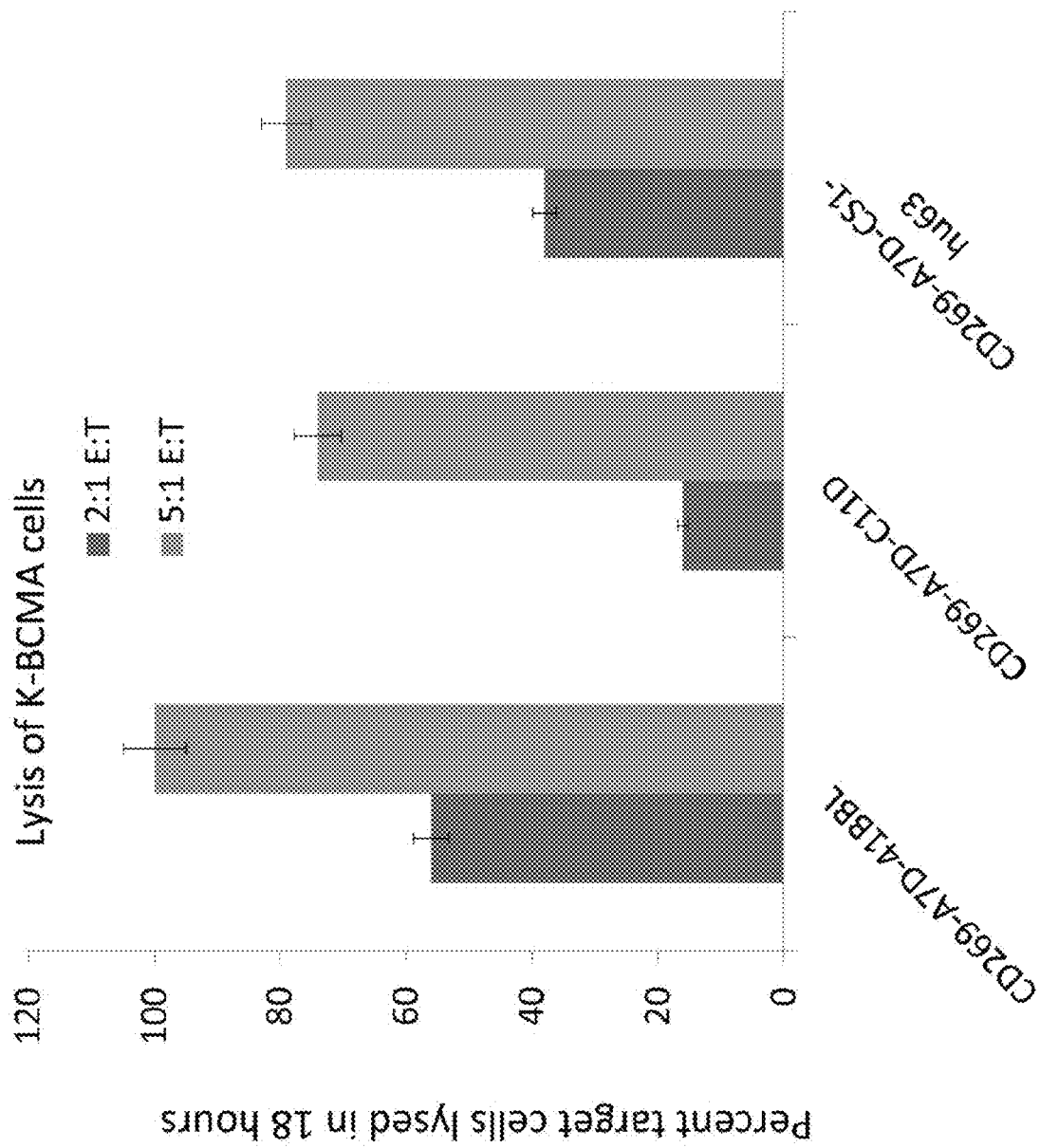

FIG. 30J. Summary lysis of K-BCMA (K562 expressing BCMA) cells by CD269-A7D-41BBL, CD269-A7D-C11D and CD269-CS1-hu63 CAR T cells.

Figure 30K:
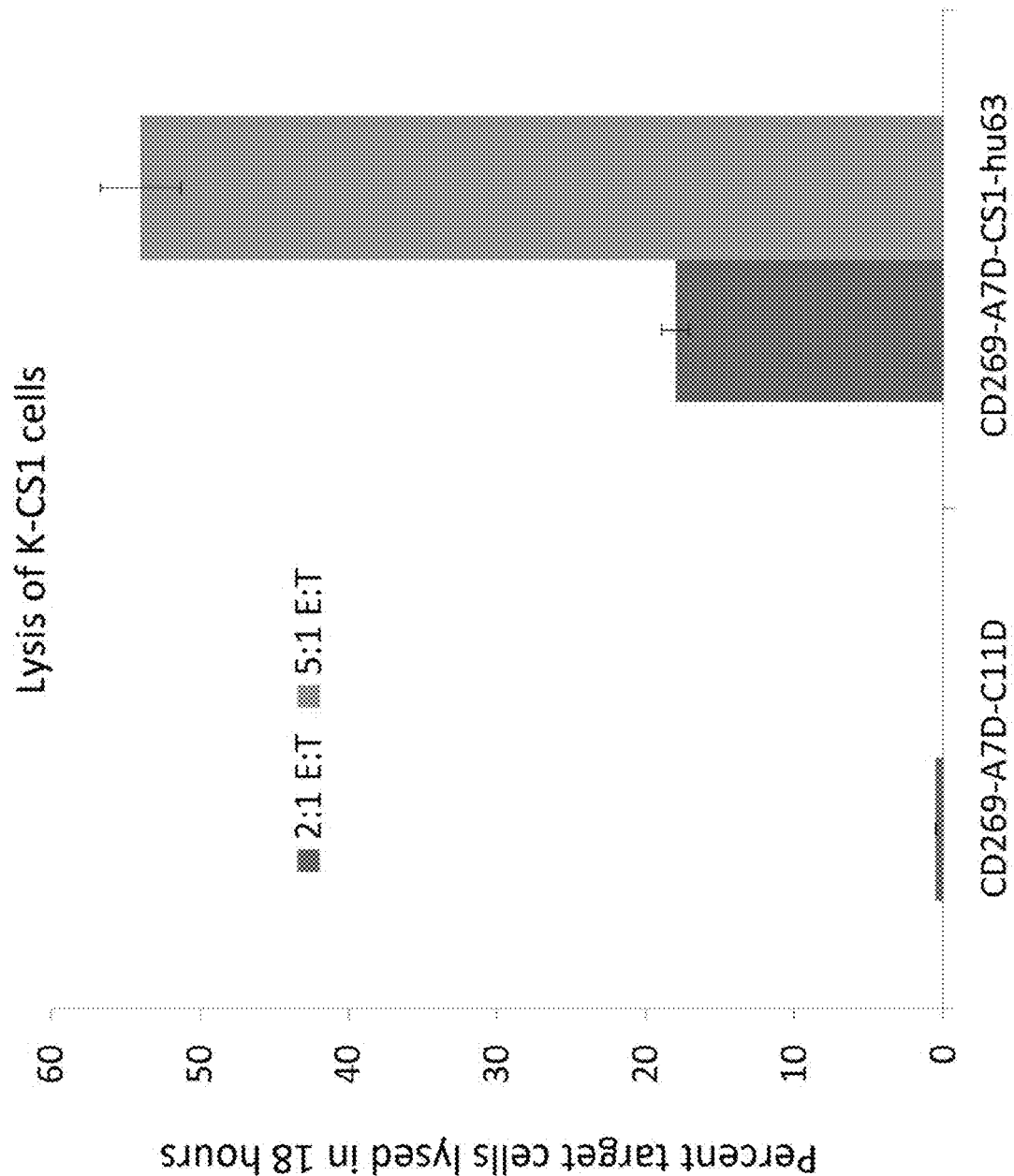

FIG. 30K. Summary lysis of K-CS1 (K562 expressing CS1) cells by CD269-A7D-C11D and CD269-CS1-hu63 cCAR T cells.

Figure 31:
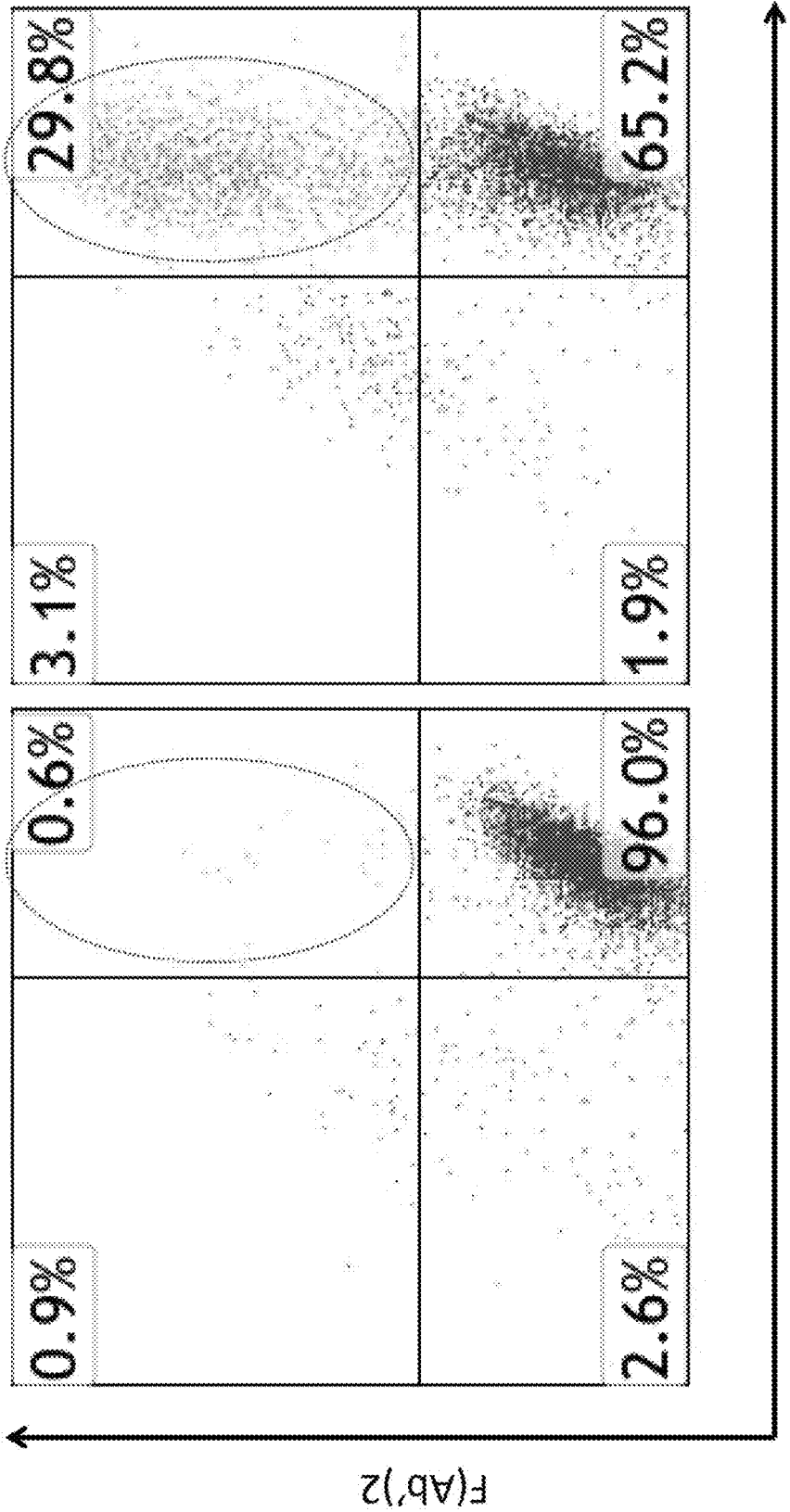

FIG. 31. Expression of CLL1–CD33b CAR T cells. Buffy coat cells were activated 3 days with anti-CD3 antibody.

Cells were transduced with either control vector (left) or CLL1–CD33b CAR (right) lentiviral supernatant. After 3 days of incubation, cells were harvested and labeled for flow cytometry.

Figure 32A:
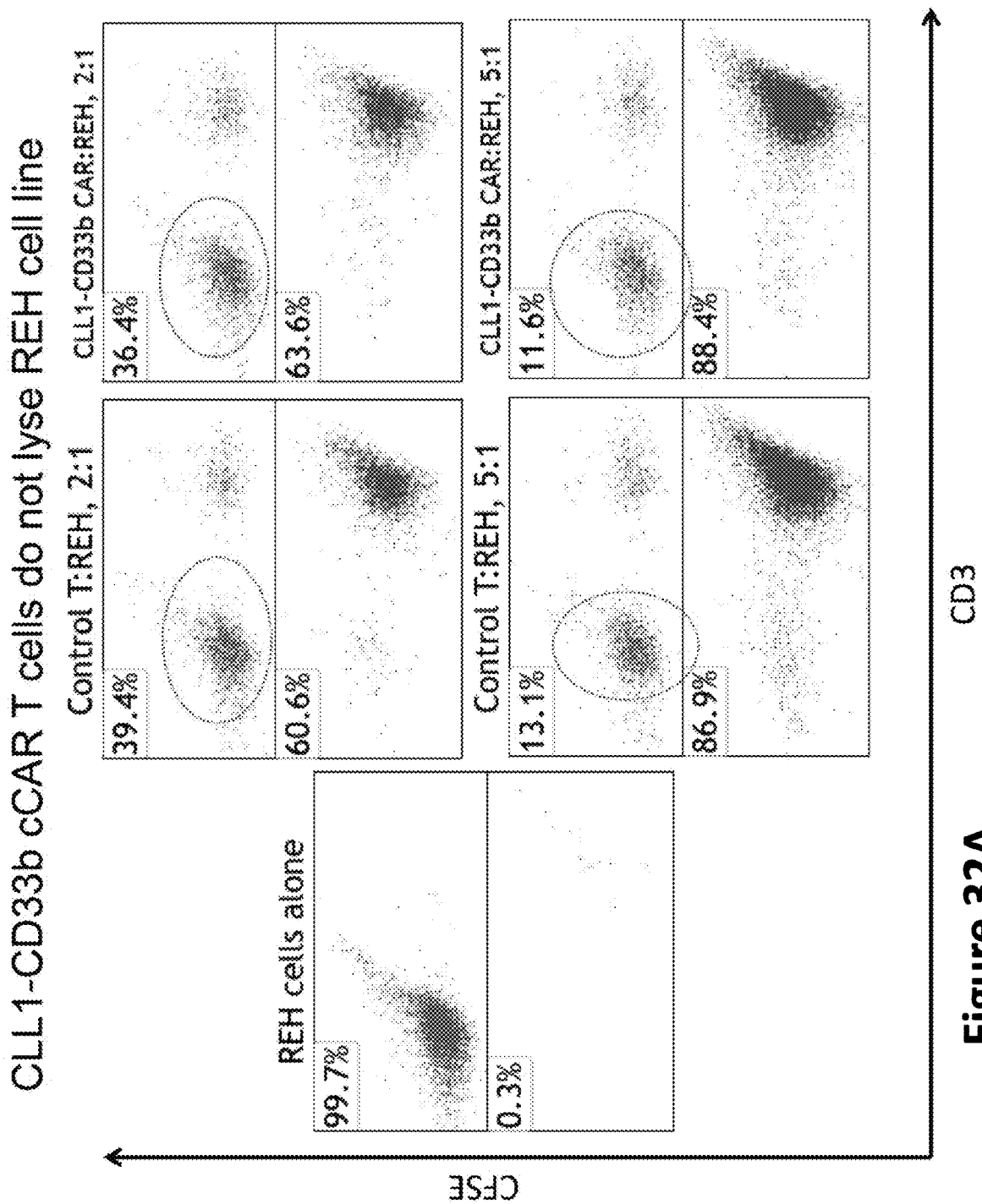

FIG. 32A. CLL1–CD33b CAR T cells do not lyse REH tumor cell line in co-culture assays.

Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of REH target cells alone (left), control T cells (center panels) and CLL1–CD33b CAR T cells (right panels). REH cells are represented as purple dots. Note: REH cells do not express CLL1 (CLL-1) or CD33.

Figure 32B:
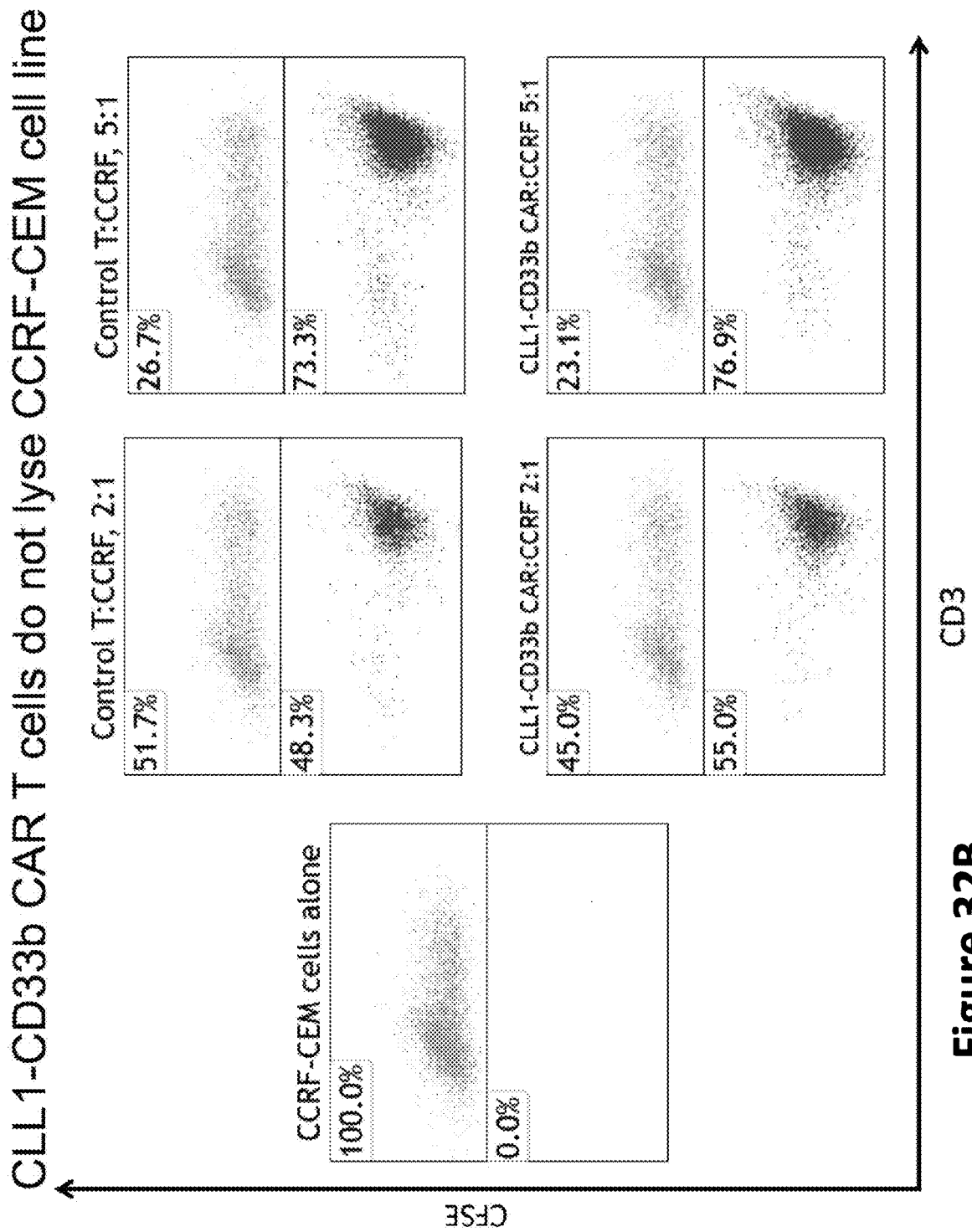

FIG. 32B. CLL1–CD33b CAR T cells do not lyse CCRF-CEM tumor cell line, in co-culture assays.

Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of CCRF-CEM target cells alone (left), control T cells (center panels) and CLL1–CD33b CAR T cells (right panels). CCRF-CEM cells are represented as orange dots. Note: CCRF-CEM cells do not express CLL1 or CD33 antigen.

Figure 32C:
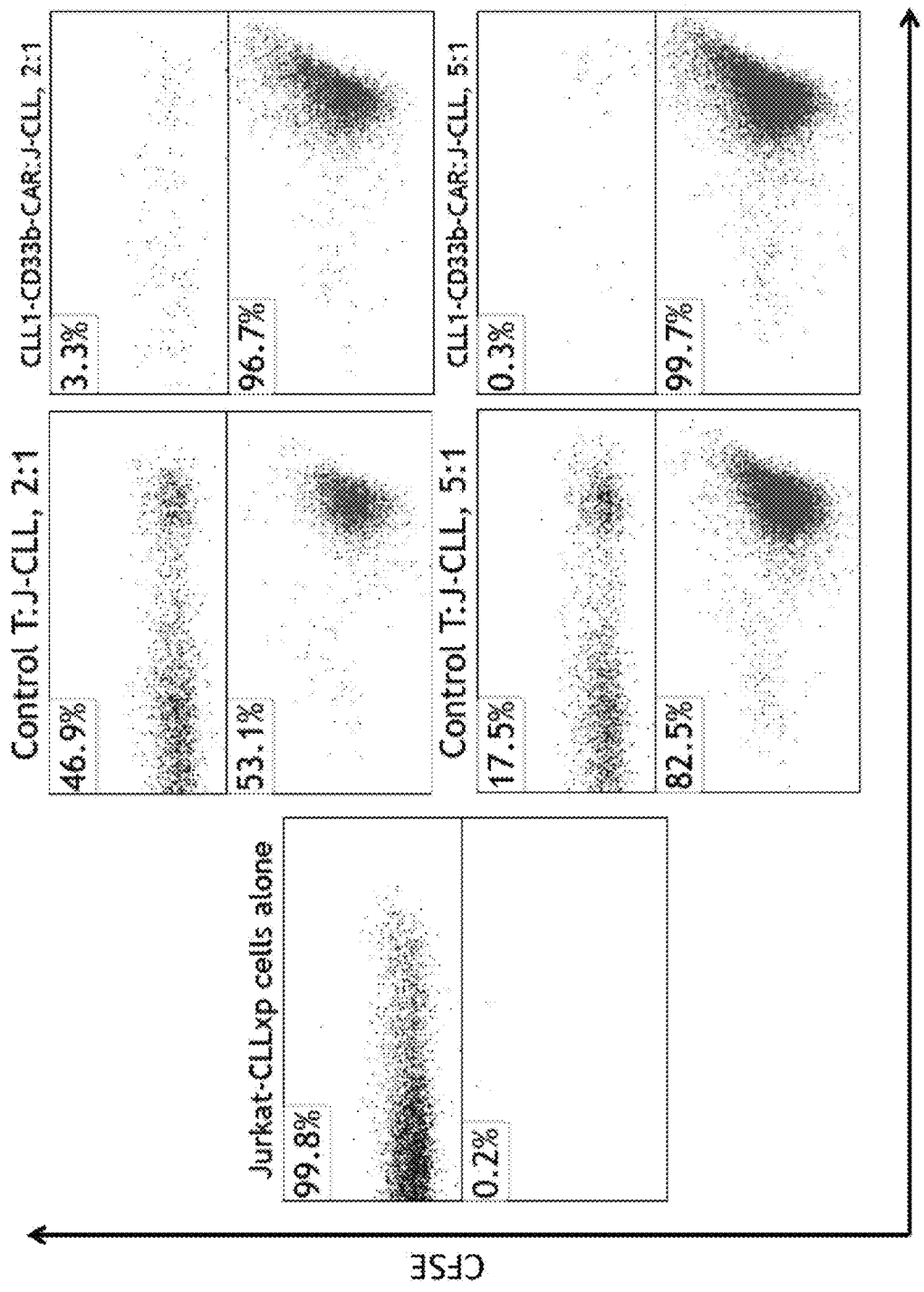

FIG. 32C. CLL1–CD33b CAR T cells specifically lyse the Jurkat tumor cell line, which is synthetically expressing CLL-1 surface antigen in co-culture assays.

Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of Jurkat-CLL1 (J-CLL) target cells alone (left), control T cells (center panels) and CLL1–CD33b CAR T cells (right panels). Jurkat-CLL cells are represented as blue dots.

Figure 32D:
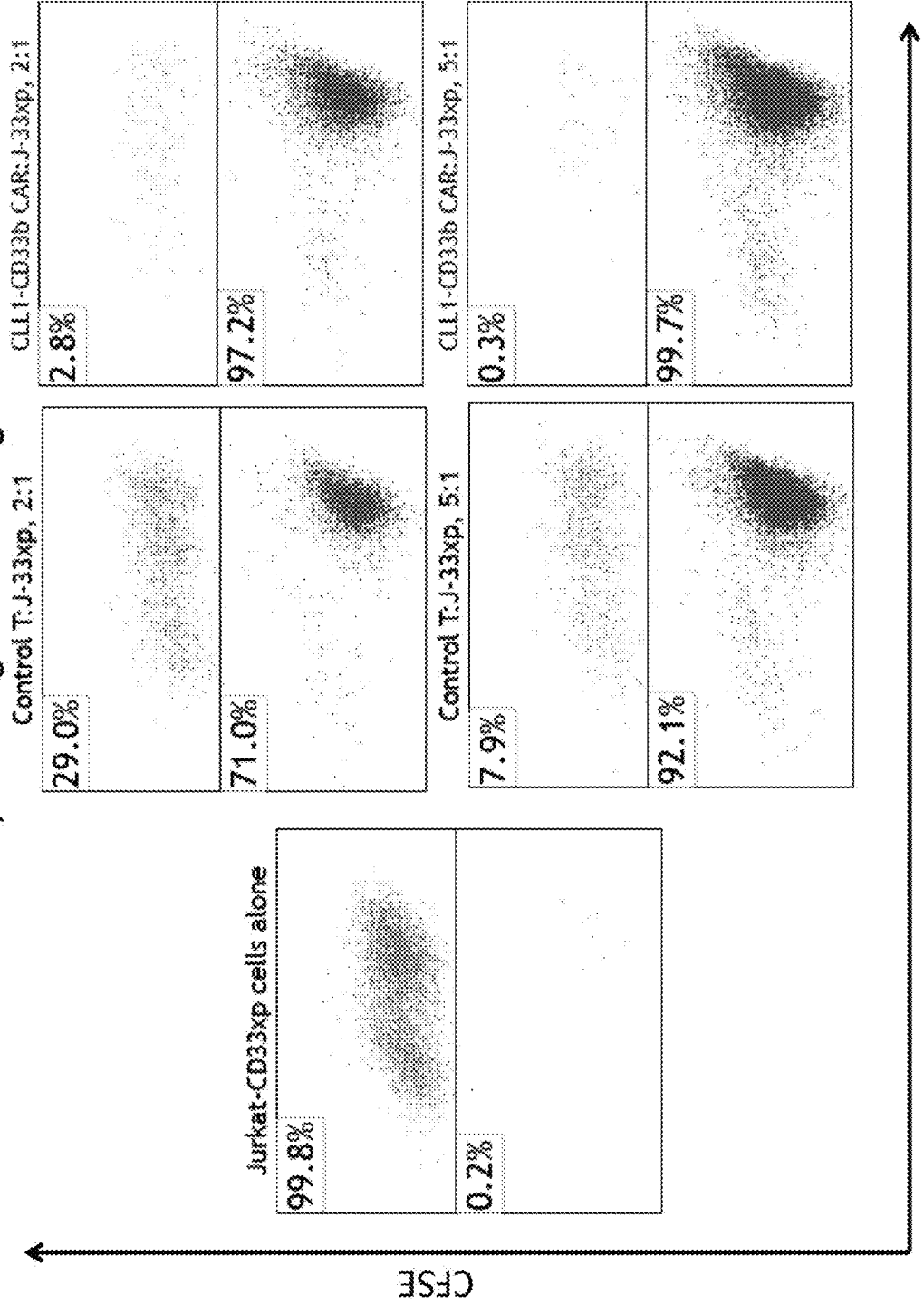

FIG. 32D. CLL1–CD33b CAR T cells specifically lyse the Jurkat tumor cell line, which is synthetically expressing CD33 surface antigen, in co-culture assays.

Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of Jurkat-CD33 (J-33xp) target cells alone (left), control T cells (center panels) and CLL1–CD33b CAR T cells (right panels). Jurkat-CD33 (J-33xp) cells are represented as light blue dots.

Figure 32E:
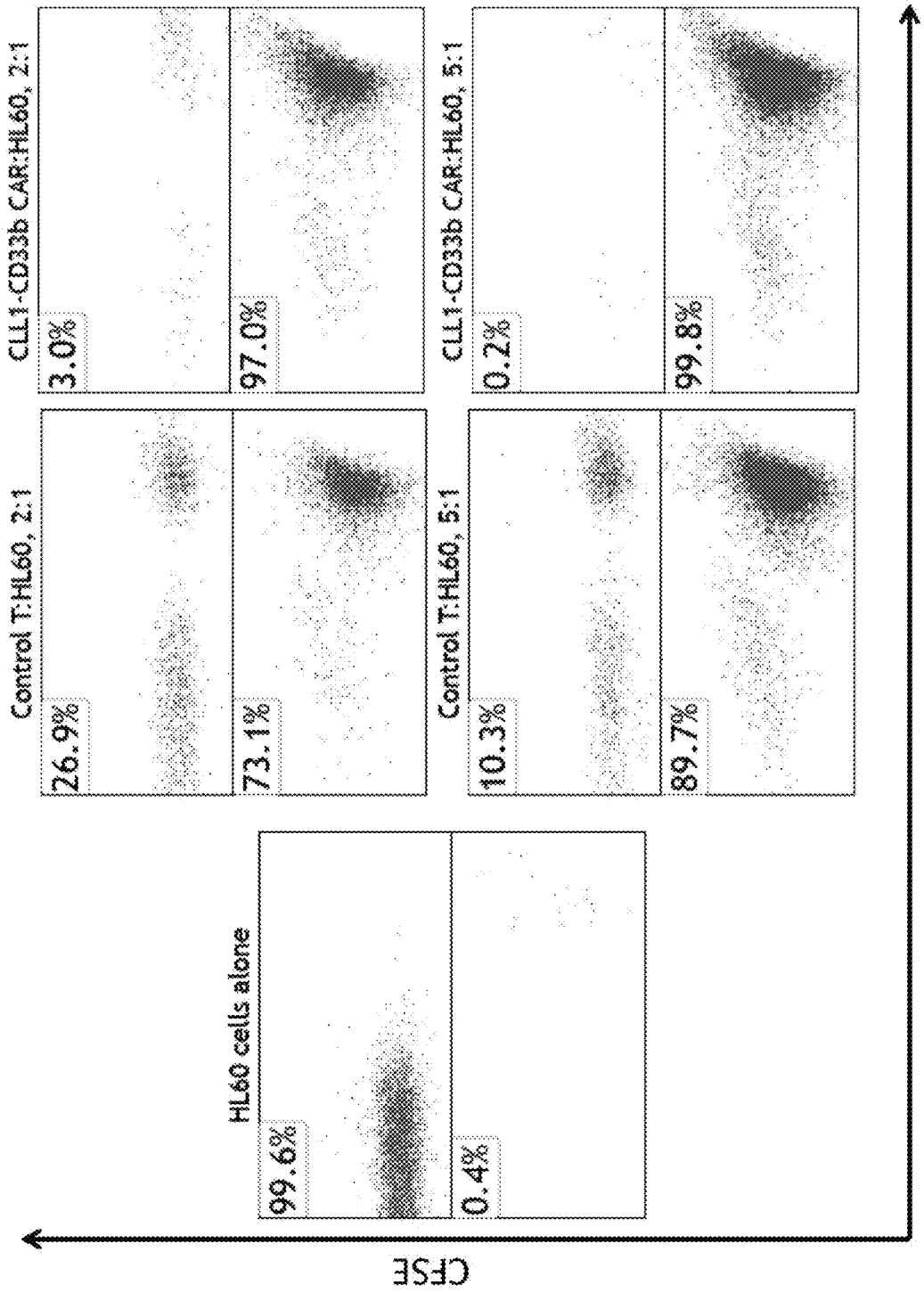

FIG. 32E. CLL1–CD33b cCAR T cells efficiently lyse HL60 tumor cell line in co-culture assays.

Target cells were prelabeled with CFSE dye to distinguish them from T cells. Co-culture experiments were performed at an effector to target ratio of 2:1 or 5:1 for 18 hours and were directly analyzed by flow cytometry for CFSE and CD3. Each assay consists of HL60 target cells alone (left), control T cells (center panels) and CLL1–CD33b CAR T cells (right panels). HL60 cells are represented as green dots.

Figure 32F:
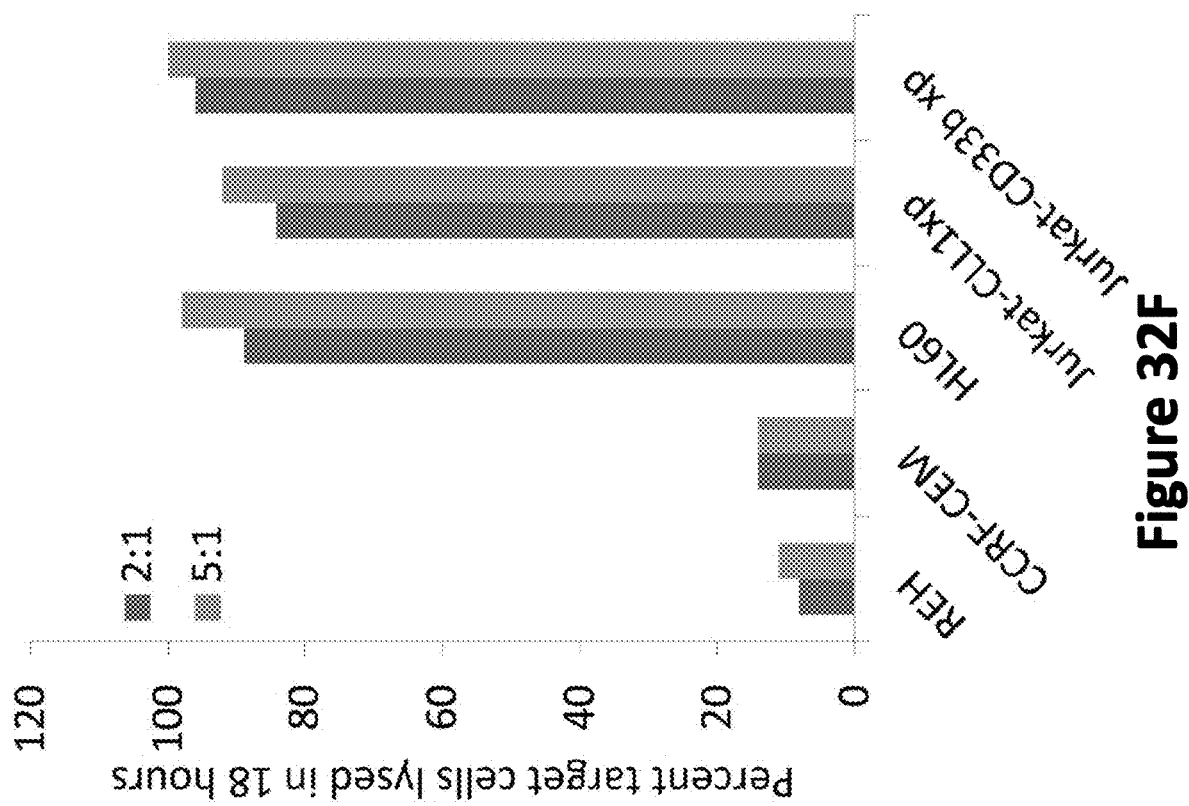

FIG. 32F. Summary of CLL1–CD33 cCAR (CLL-1–CD33 cCAR) lysis results in co-culture assays using different AML cell lines and Jurkat cells expressing either CLL-1 or CD33.

Figure 32G:
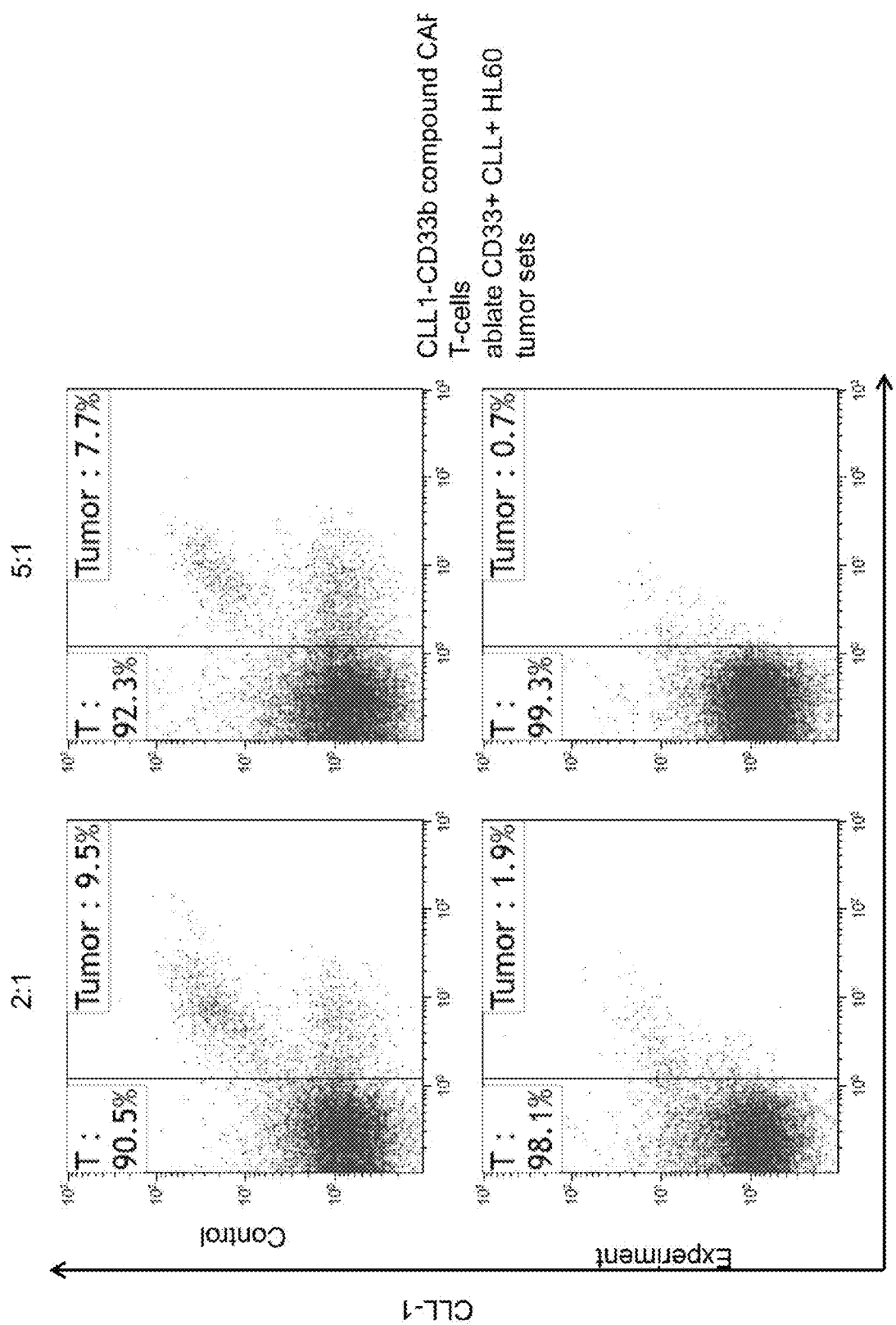

FIG. 32G—CLL1–CD33b compound CAR T cells ablate HL60 target tumor cells

Cocultures were carried out overnight at E:T ratios of 2:1 and 5:1. Target HL60 cells mostly double positive for CLL-1 and CD33 were prelabeled with CFSE membrane dye. Flow cytometry acquisition (FACS) was conducted the next day using CD3, CLL-1, and CD33 antibodies.

FIG. 32H—CLL1–CD33b compound CAR T cells ablate U937 target tumor cells

Cocultures were carried out overnight at E:T ratios of 2:1 and 5:1. Target U937 cells are highly positive for both CLL-1 and CD33 and were prelabeled with CFSE membrane dye. Flow cytometry acquisition (FACS) was conducted the next day using CD3, CLL-1, and CD33 antibodies.

Figure 32I:
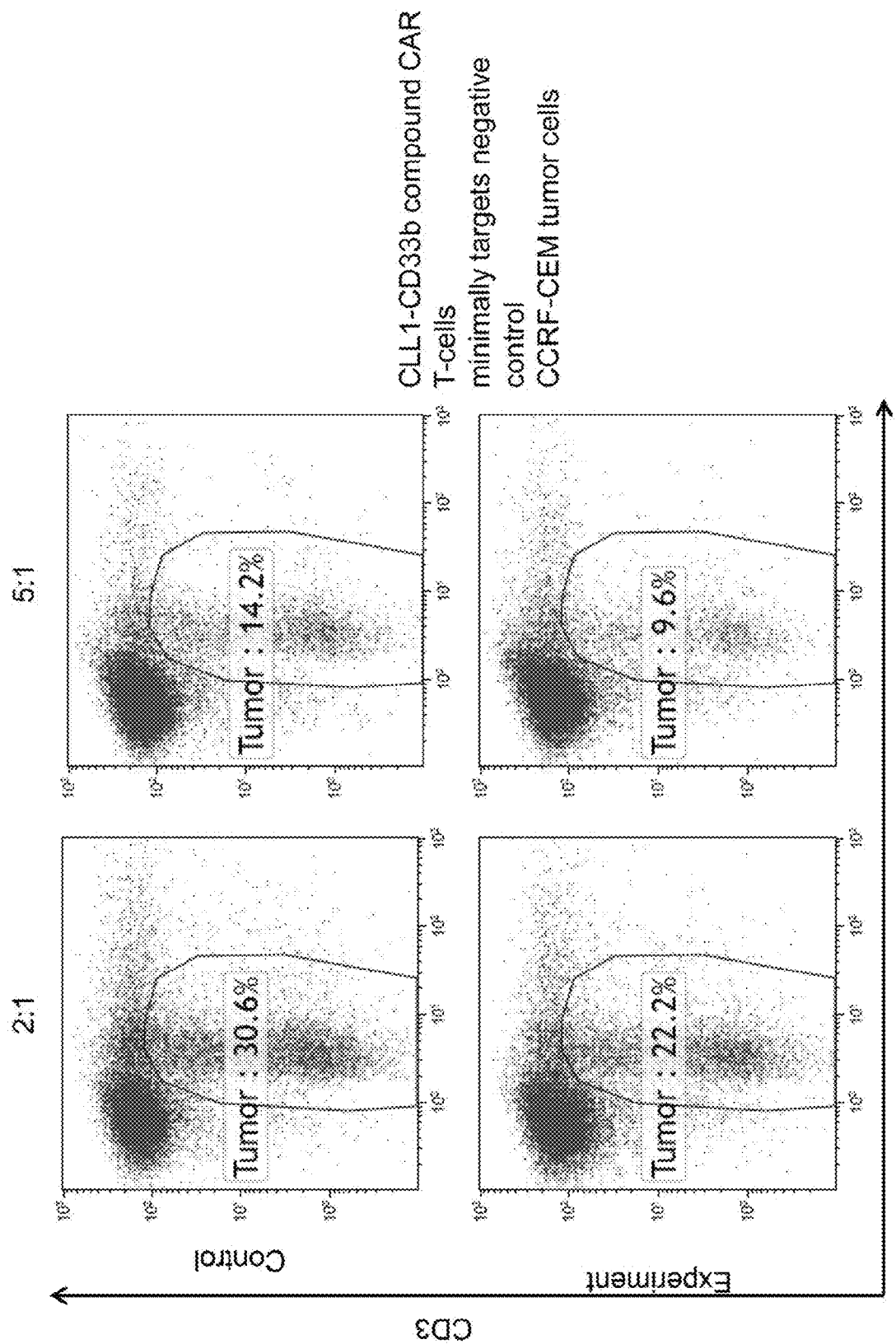

FIG. 32I—CLL1–CD33b compound CAR T cells minimally target negative control CCRF-CEM cells.

Cocultures were carried out overnight at E:T ratios of 2:1 and 5:1. CCRF-CEM cells are predominantly negative for CLL-1 and CD33 and were prelabeled with CFSE membrane dye. Flow cytometry acquisition (FACS) was conducted the next day using CD3, CLL-1, and CD33 antibodies.

Figure 32J:
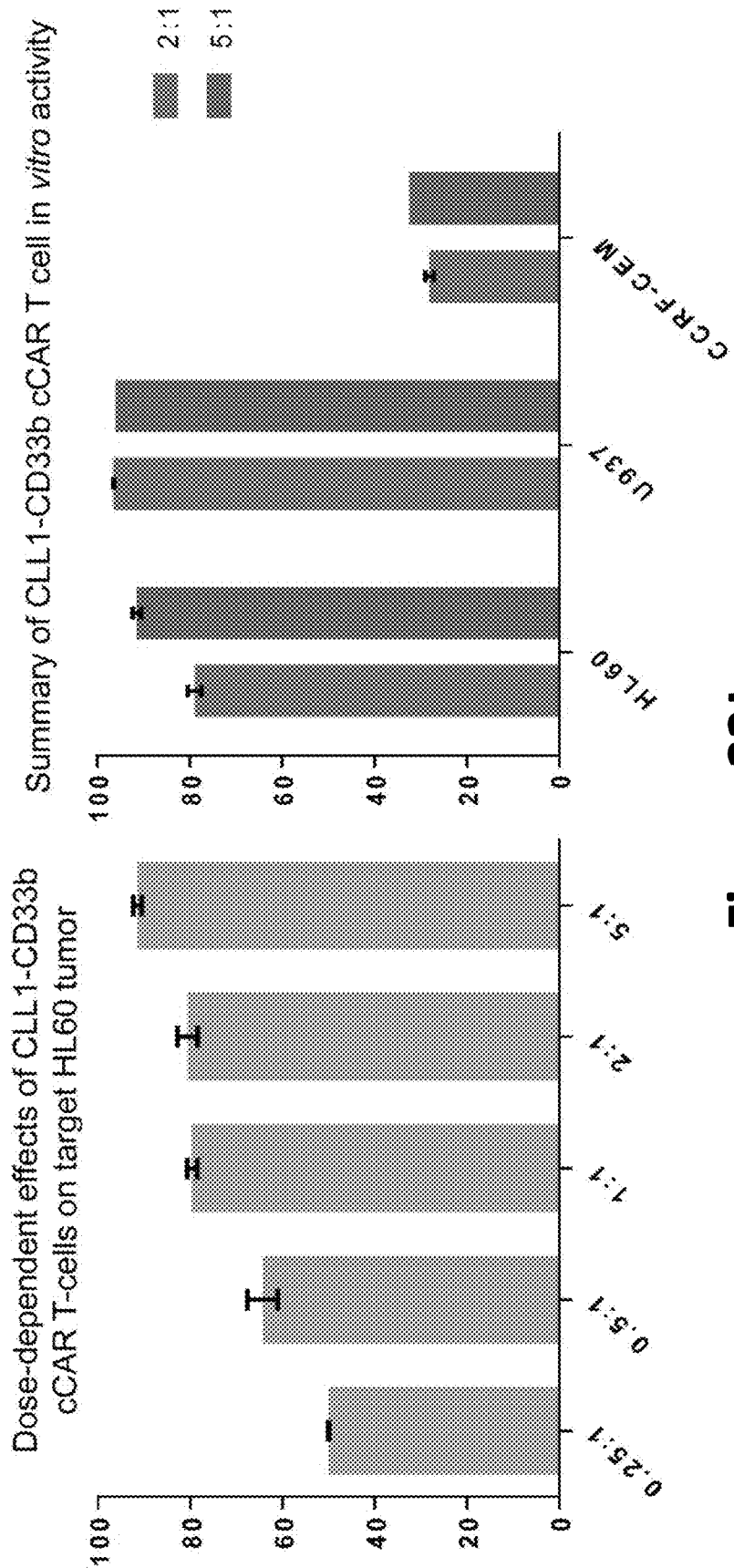

FIG. 32J—In vitro summary of CLL1–CD33b compound CAR T cells against target cell lines.

All co-cultures were carried out overnight and target cells were prelabeled with CFSE membrane dye. Flow cytometry acquisition (FACS) was conducted the next day using CD3, CLL-1, and CD33 antibodies for all samples. Dose dependent co-cultures using HL60 target cells were conducted in an escalating E:T ratio scheme under identical co-culture conditions.

Figure 32K:
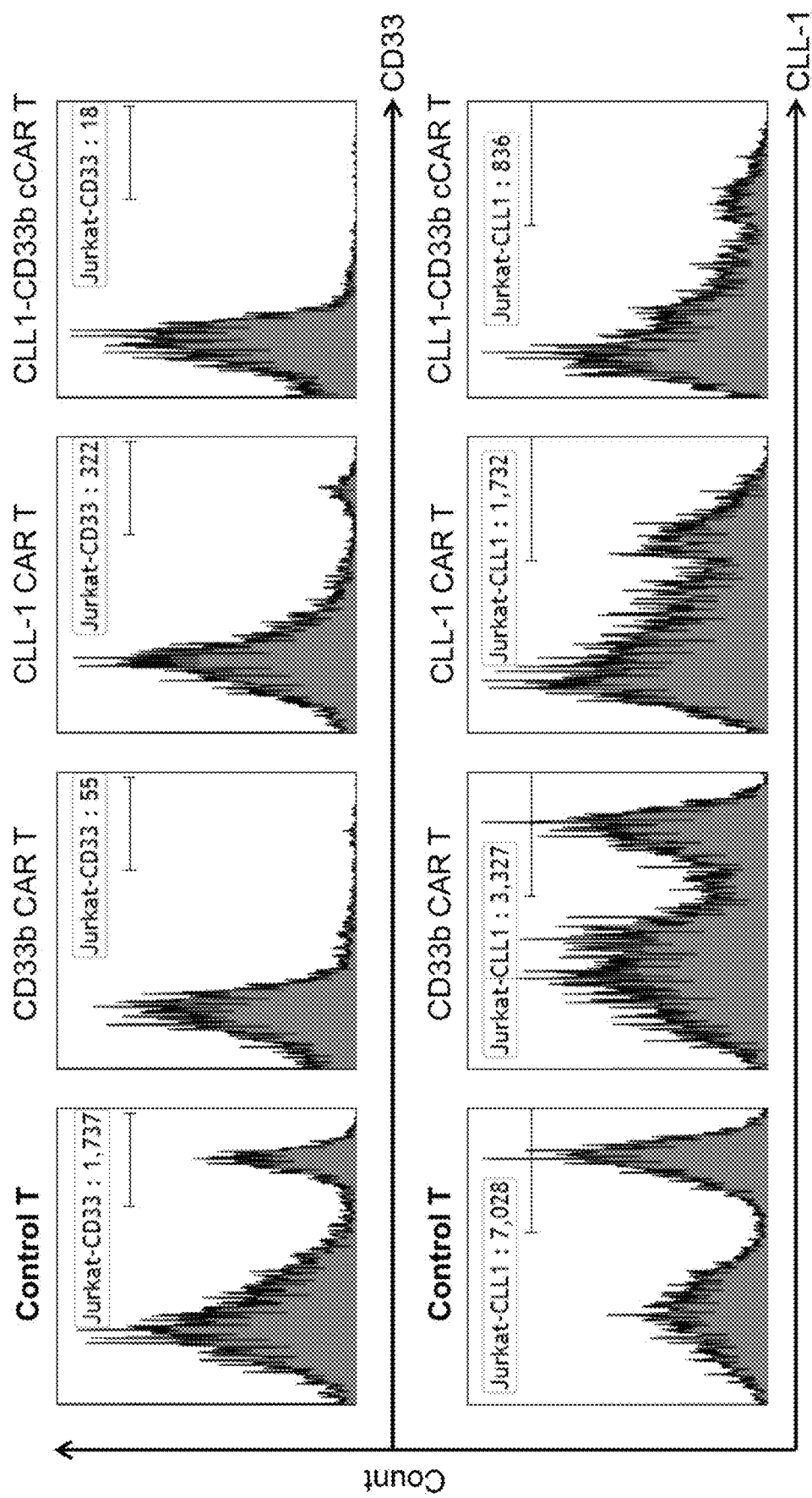

FIG. 32K—Antigen depletion by CLL1–CD33b compound CAR in relation to single CAR T cells in a mixed cell co-culture.

CD33 expressing and CLL-1 expressing Jurkat cells were produced by stable transfection of CD33 or CLL-1 expressing cDNA into wild type Jurkat cells. Jurkat cells were then sorted for expression to establish homogeneous stable cell lines expressing either CD33 or CLL-1. For mixed cell co-culture, Jurkat cells expressing CD33 (Jurkat-CD33) and Jurkat cells expressing CLL-1 (Jurkat-CLL1) were mixed together in an approximate 1:1 ratio totaling 200,000 cells. Effector cells were then added in a 1:2 ratio (effector: target), totaling 100,000 T-cells in an overnight culture. Flow cytometry acquisition (FACS) was conducted the next day using CD3, CLL-1, and CD33 antibodies for all samples. Histograms depicting antigen depletion under various CAR treatments are shown, with bars (left) depicting T-cell populations and antigen expressing Jurkat cells (right).

FIG. 32L—Summary of antigen depletion by CLL1–CD33b compound CAR in relation to single CAR T cells in a mixed cell co-culture.

Graphs summarizing histogram data of the previous figure. Overall, CLL1–CD33b compound CAR T cells exhibit potent and targeted cytotoxicity against both CD33 and CLL-1 expressing Jurkat cells with ablation rates of greater than 85% against both cell types. Furthermore, CLL1–CD33b compound CAR T cells were able to demonstrate superior cytotoxicity compared to a single anti-CD33b CAR T or a single anti-CLL-1 CAR T cell against their own respective antigen populations. The compound CAR was able to target CD33 60% better than a CD33 CAR T and CLL-1 40% better than a CLL-1 CAR T cell.

Figure 32M:
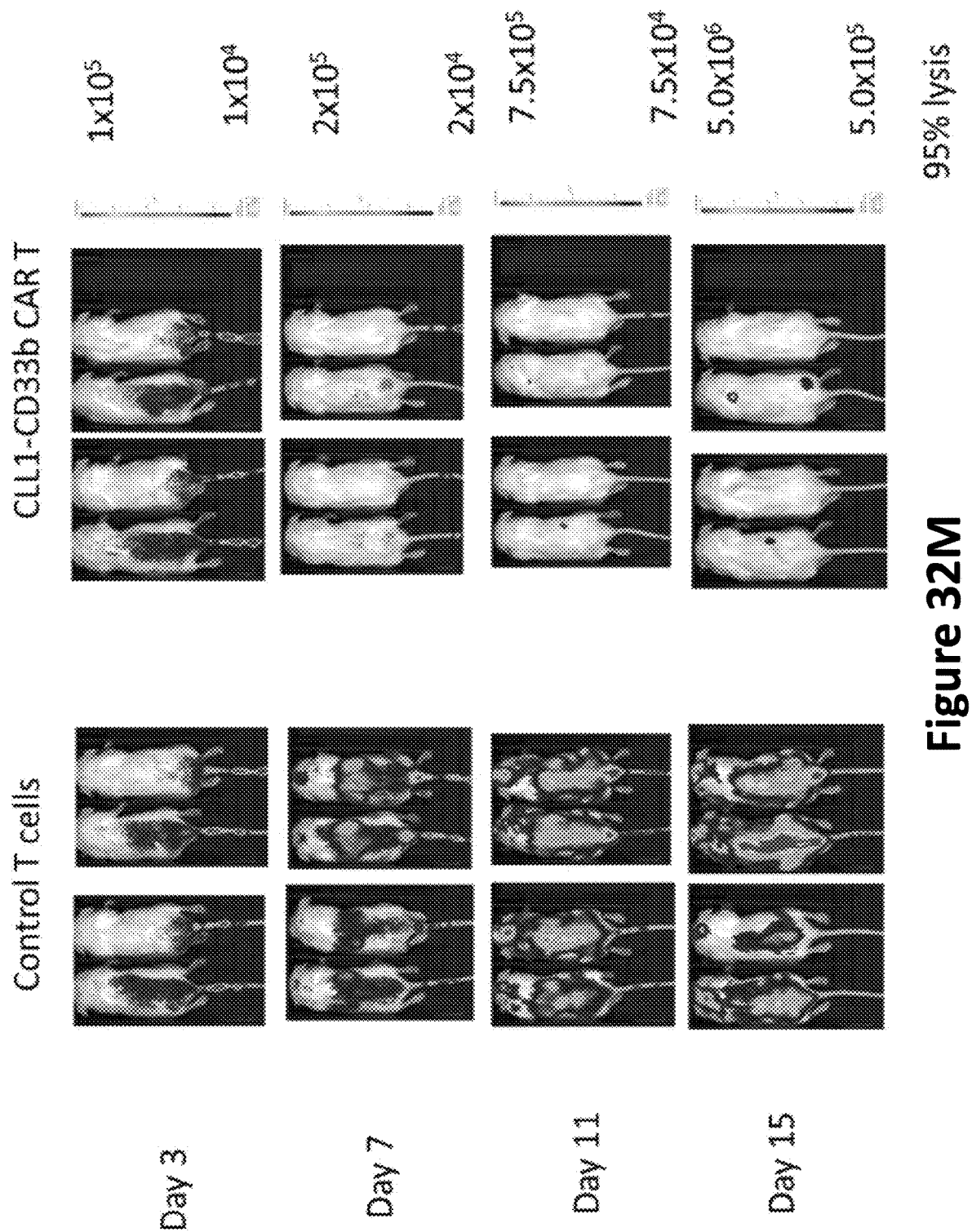

FIG. 32M. CLL1–CD33b CAR T cells demonstrate antitumor effects in vivo against cell line expressing CD33 antigen. NSG mice were sublethally irradiated and intravenously injected with $1.0 \times 10^6$ luciferase-expressing U937 cells (Day 0) to induce measurable tumor formation. Starting 3 days after injection of tumor cells, mice were intravenously injected with a course of $10 \times 10^6$ CLL1–CD33b CAR T cells or vector control T cells. On days 3, 7, 11 and 15, mice were injected subcutaneously with RediJect D-Luciferin and subjected to IVIS imaging.

Figure 32N:
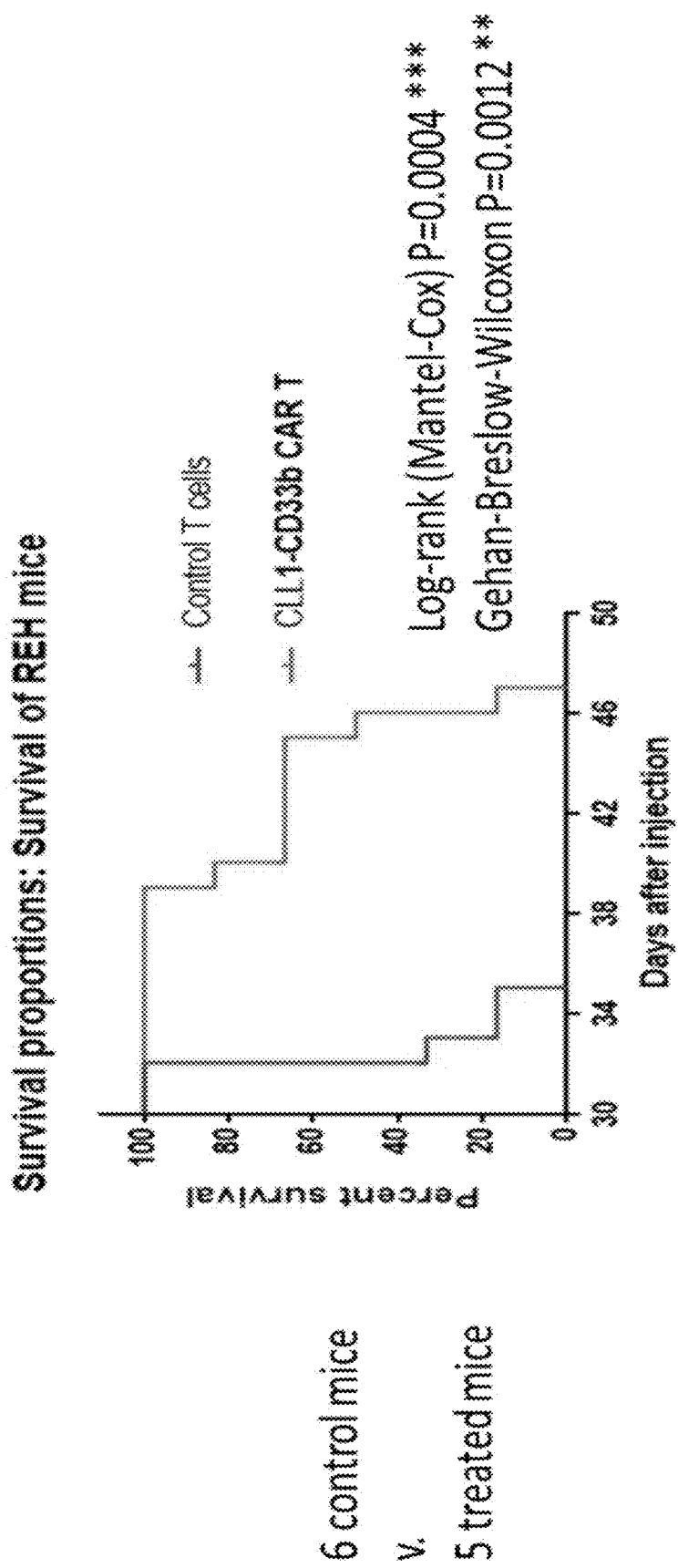

FIG. 32N. Kaplan-Meier survival analysis curve represents survival outcomes (Mantel-Cox log-rank test p=0.0004).

Figure 32O:
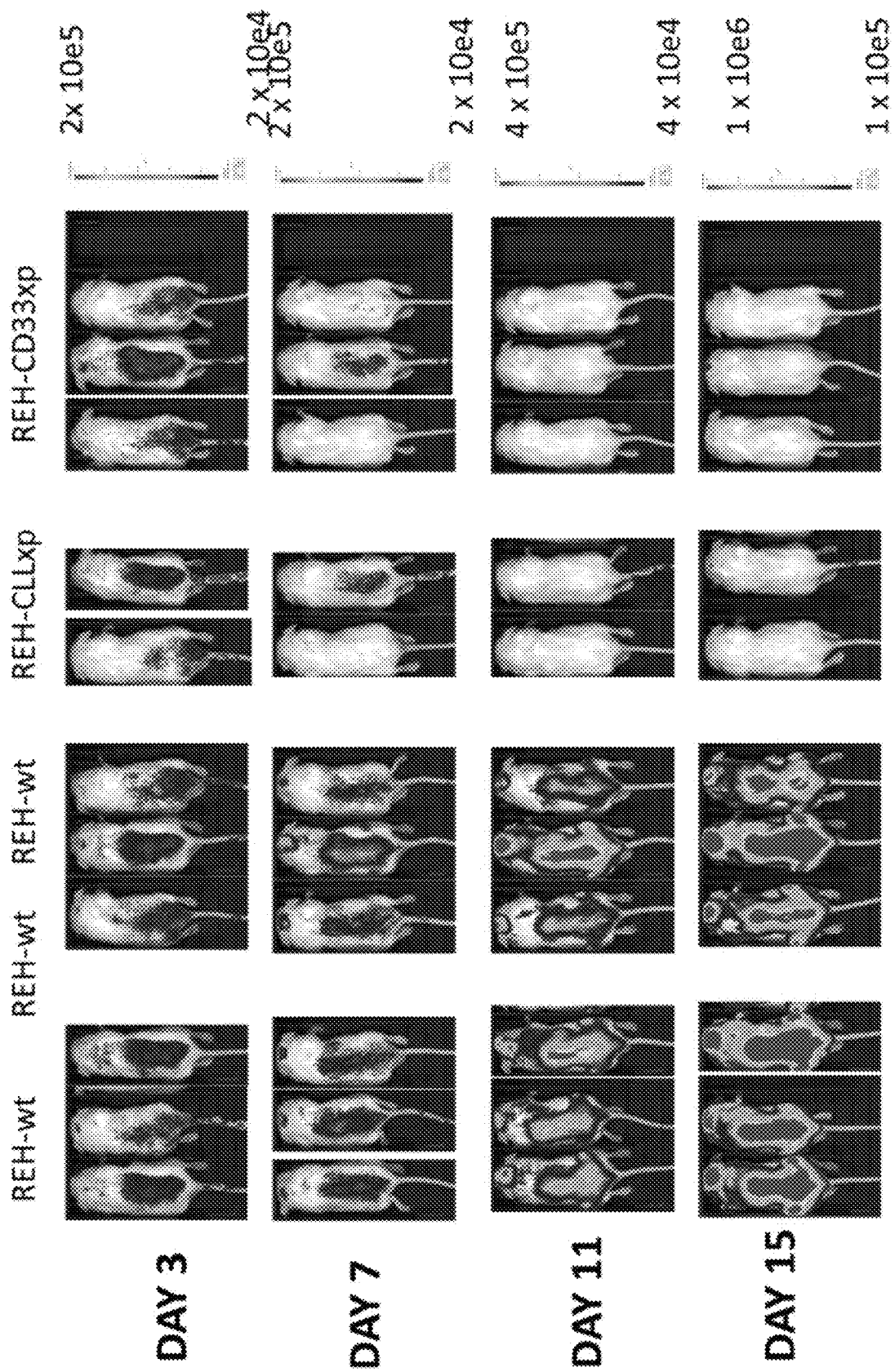

FIG. 32O. CLL1–CD33b CAR T cells demonstrate antitumor effects in vivo against cell line synthetically expressing CD33 antigen. NSG mice were sublethally irradiated and intravenously injected with $1.0 \times 10^6$ luciferase-expressing REH cells or REH expressing CLL1(REH-CLLxp) or REH expressing CD33 (REH-33xp) (Day 0) to induce measurable tumor formation. Starting 3 days after injection of tumor cells, mice were intravenously injected with a course of $10 \times 10^6$ CLL1–CD33b CAR T cells or vector control T cells. On days 3, 7, 11 and 15, mice were injected subcutaneously with RediJect D-Luciferin and subjected to IVIS imaging.

Figure 33A:
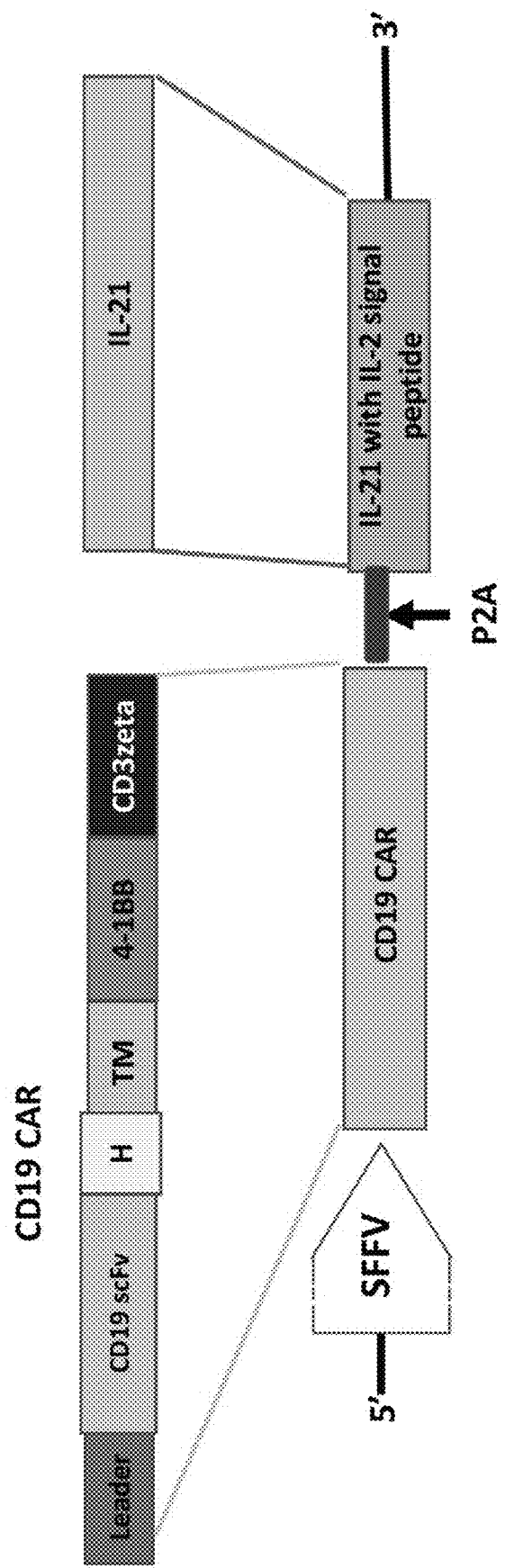

FIG. 33A. A Link by P2A schematic showing CD19 CAR and IL-21 in a single construct (Cd19 CAR co-expressing IL-21) and its expression in T or NK cells.

Figure 33B:
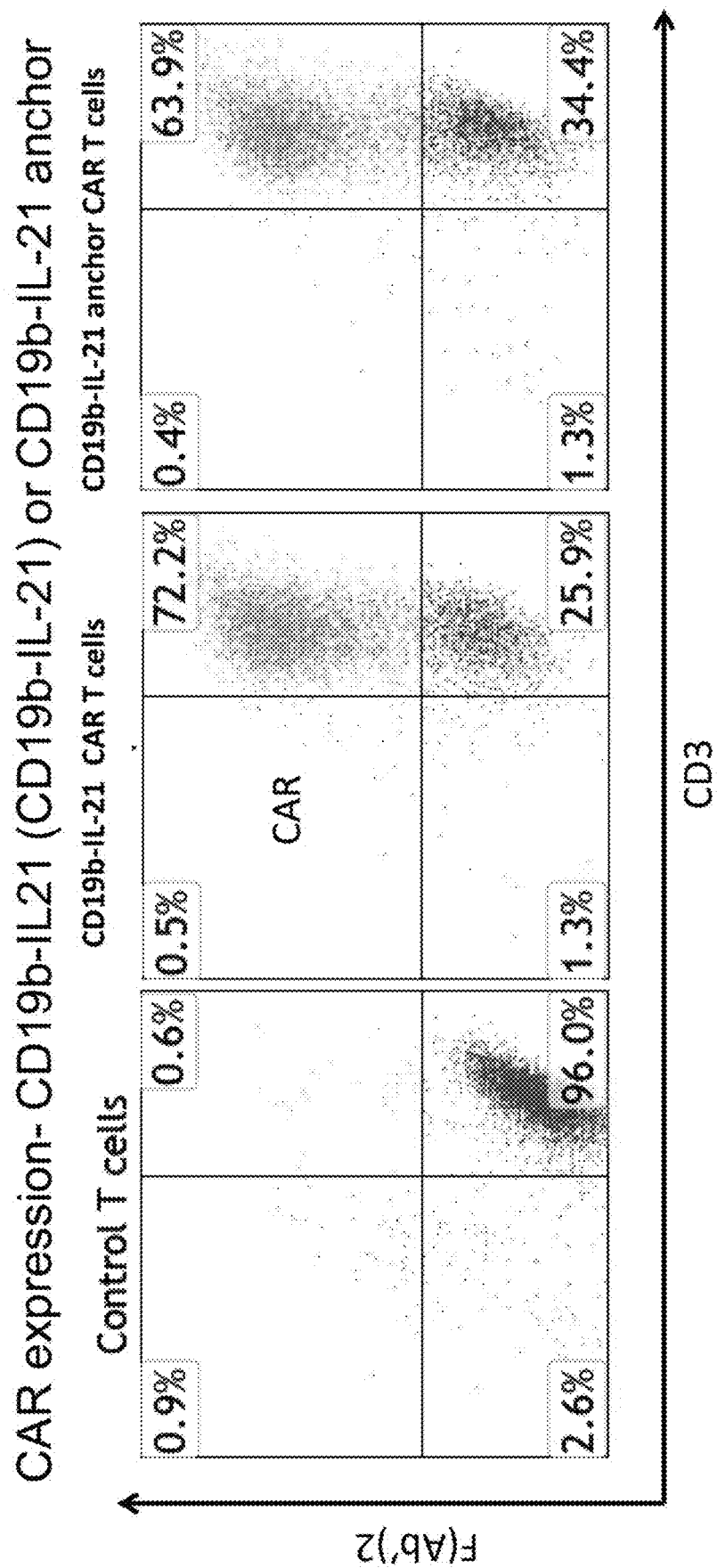

FIG. 33B. Expression of CD19b-IL-21 CAR T cells and CD19-IL-21 anchor. Buffy coat cells were activated 3 days with anti-CD3 antibody.

Cells were transduced with either control vector (left), CD19b-IL-21, or CD19b-IL21-anchor CAR (right) lentiviral supernatant. After 3 days of incubation, cells were harvested and labeled for flow cytometry.

Figure 34:
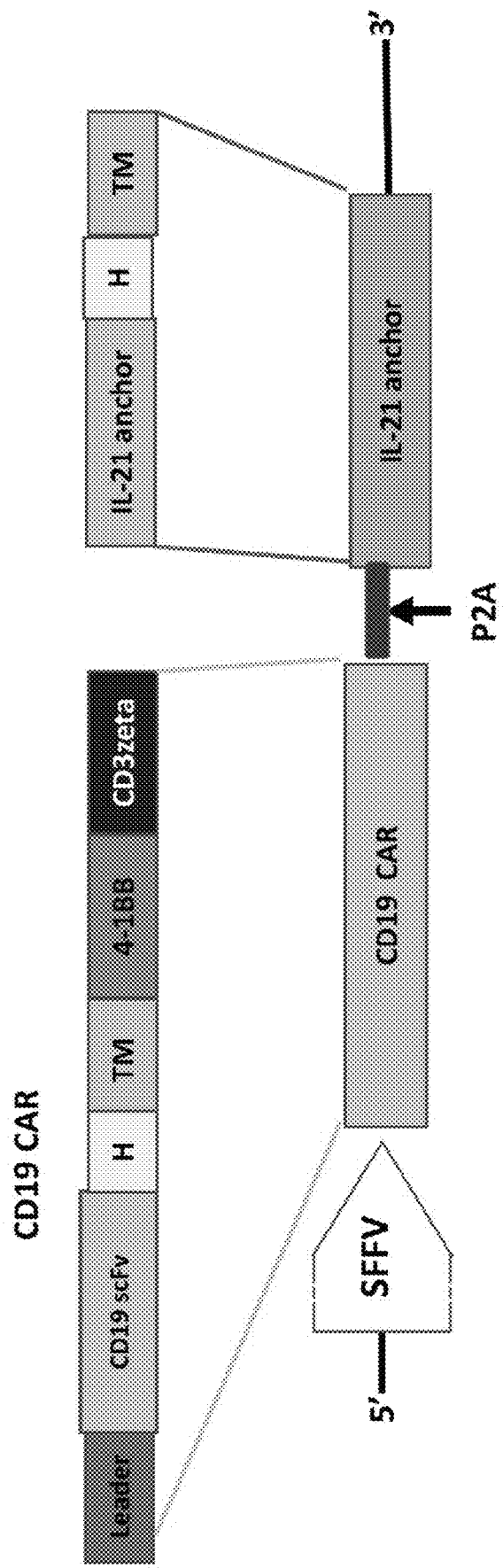

FIG. 34. Schematic diagram to elucidate the construct (CD19 CAR co-expressing IL-21 anchor) and its expression in T or NK cells.

CD19 CAR with IL-21 anchor is linked with the P2A self-cleaving sequence. The IL-21 anchor fusion is composed of IL-2 signal peptide fused to IL-21, and linked to CD8 hinge region and CD8 transmembrane domain. The combination of CD19 CAR and IL-21 fusion is assembled on an expression vector and their expression is driven by the SFFV promoter. The IL-21 signal peptide is replaced with IL-2 signal peptide for a better secretion of IL-21 and anchoring on the cell surface.

Figure 35:
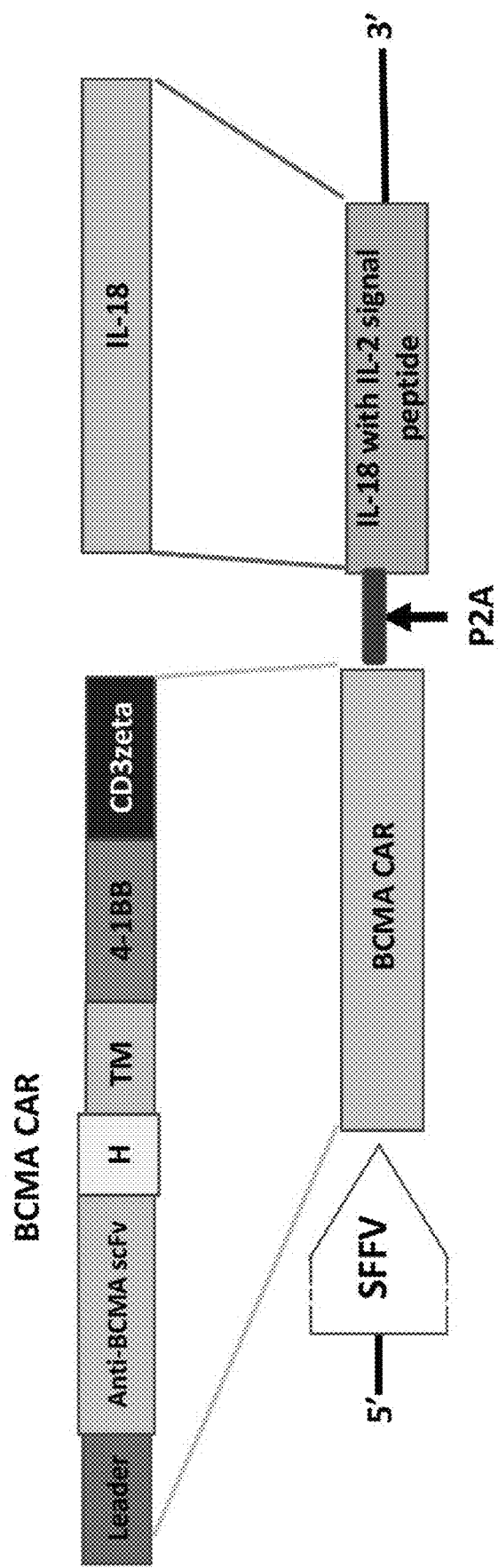

FIG. 35. A Link by P2A schematic showing BCMA CAR, and IL-18 in a single construct (BCMA CAR co-expressing IL-18) and its expression in T or NK cells.

The construct consists of a SFFV promoter driving the expression of CAR with costimulatory domain, 4-1BB). Upon cleavage of the linkers, BCMA CAR and IL-18 split and engage upon targets expressing antigen. CAR T cells received not only costimulation through the 4-1BB or CD28 but also 4-1BB ligand (4-1BBL or CD137L) or IL-18. The CD3-zeta signaling domain complete the assembly of this CAR-T. The IL-21 signal peptide is replaced with IL-2 signal peptide for a better secretion of IL-21. H, CD8a hinge region, TM, CD8a transmembrane domain.

Figure 36:
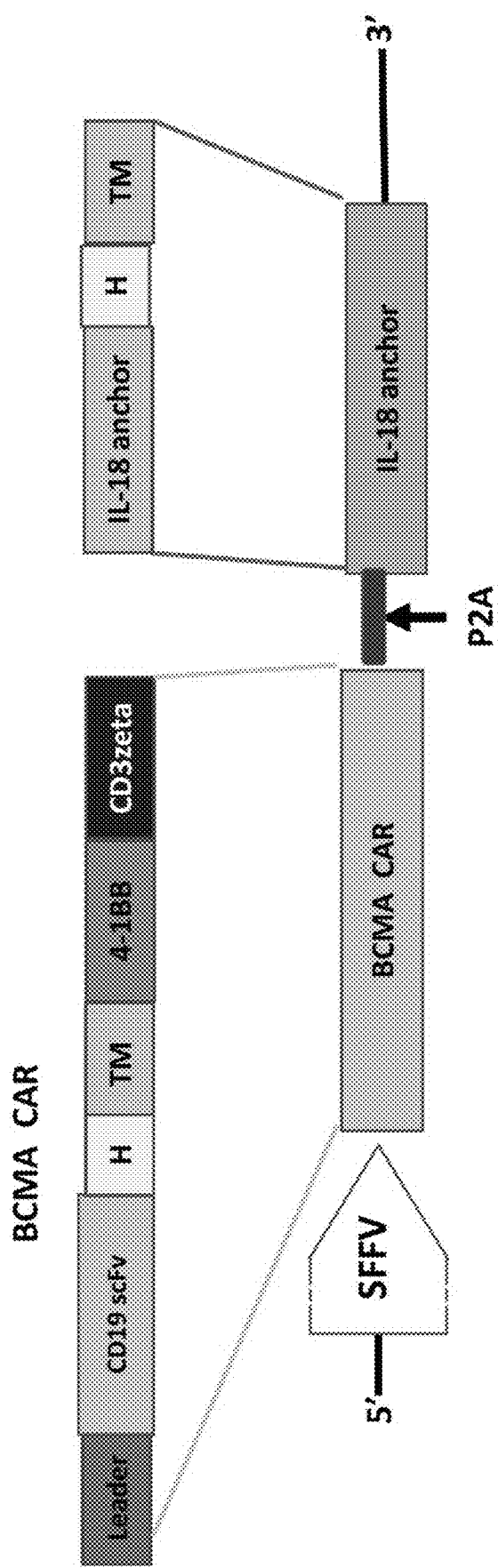

FIG. 36. Schematic diagram to elucidate the construct BCMA (CAR co-expressing IL-18 anchor) and its expression in T or NK cells.

A CAR with IL-18 anchor is linked with the P2A self-cleaving sequence. The IL-18 anchor fusion is composed of IL-2 signal peptide fused to IL-18, and linked to CD8 hinge region and CD8 transmembrane domain. The combination of BCMA CAR and IL-18 anchor fusion is assembled on an expression vector and their expression is driven by the SFFV promoter. The IL-18 signal peptide is replaced with IL-2 signal peptide for a better secretion of IL-18 and anchoring on the cell surface.

Figure 37:
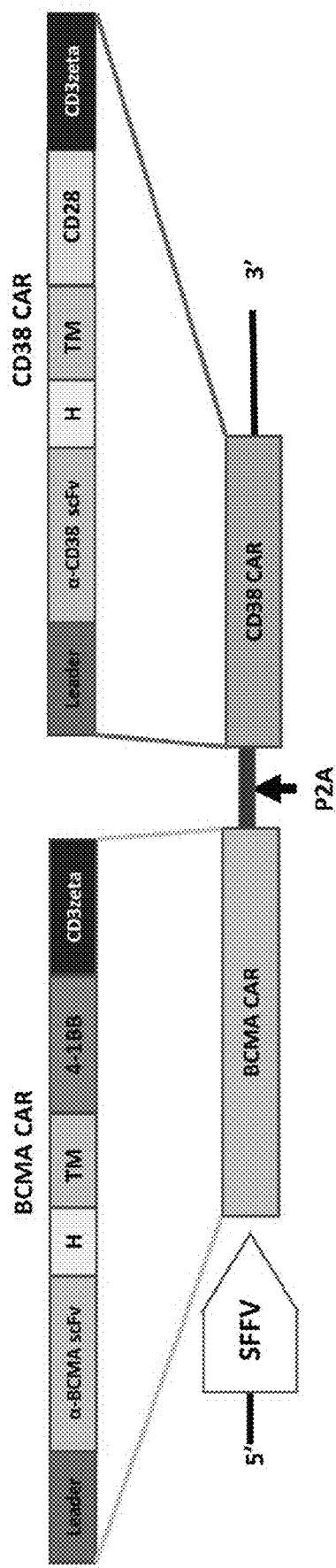

FIG. 37. A schematic representation of cCAR construct (BCMA–CD38 cCAR).

The construct comprises a SFFV promoter driving the expression of multiple modular units of CARs linked by a P2A cleavage peptide. Upon cleavage of the P2A linker, the cCARs split and engage upon targets expressing BCMA and/or CD38. Each unit of CAR bears a scFv against the antigen, a hinge domain (H), a transmembrane domain (TM), a co-stimulatory domain (including, but not limited to, CD28 or 4-1BB) and the intracellular signaling domain CD3 zeta chain. As a novel cCAR construct, the activation domains of the construct may include, but is not limited to, 4-1BB on the BCMA CAR segment and a CD28 region on the CD38 CAR.

Figure 38:
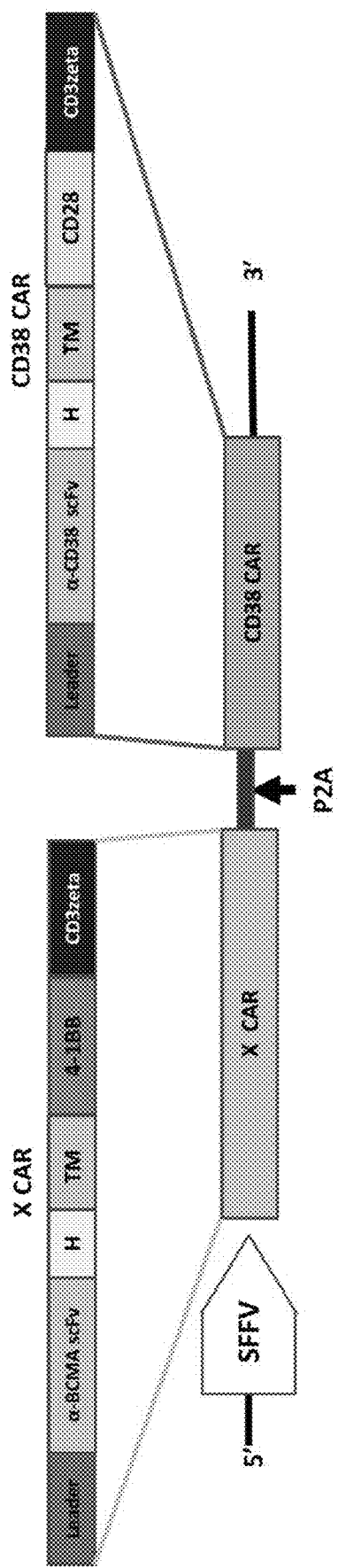

FIG. 38. A schematic representation of CD38 based cCAR construct.

The construct comprises a SFFV promoter driving the expression of multiple modular units of CARs linked by a P2A cleavage peptide. Upon cleavage of the P2A linker, the cCARs split and engage upon targets expressing X CAR and/or CD38. Each unit of CAR bears a scFv against the antigen, a hinge domain (H), a transmembrane domain (TM), a co-stimulatory domain (including, but not limited to, CD28 or 4-1BB) and the intracellular signaling domain CD3 zeta chain. As a novel cCAR construct, the activation domains of the construct may include, but is not limited to, 4-1BB or CD28 on the X CAR segment and a CD28 or 4-1BB region on the CD38 CAR. X CAR can be a CAR that can be selected from the group of, but not limited to, CD4, CD5, CD3, CD7, CD2, CD56, CD19, CD20, CD22, BCMA, CD138, CS1, CD123, CD33, CLL-1, BAFF receptor, April, and integrin.

Figure 39A:
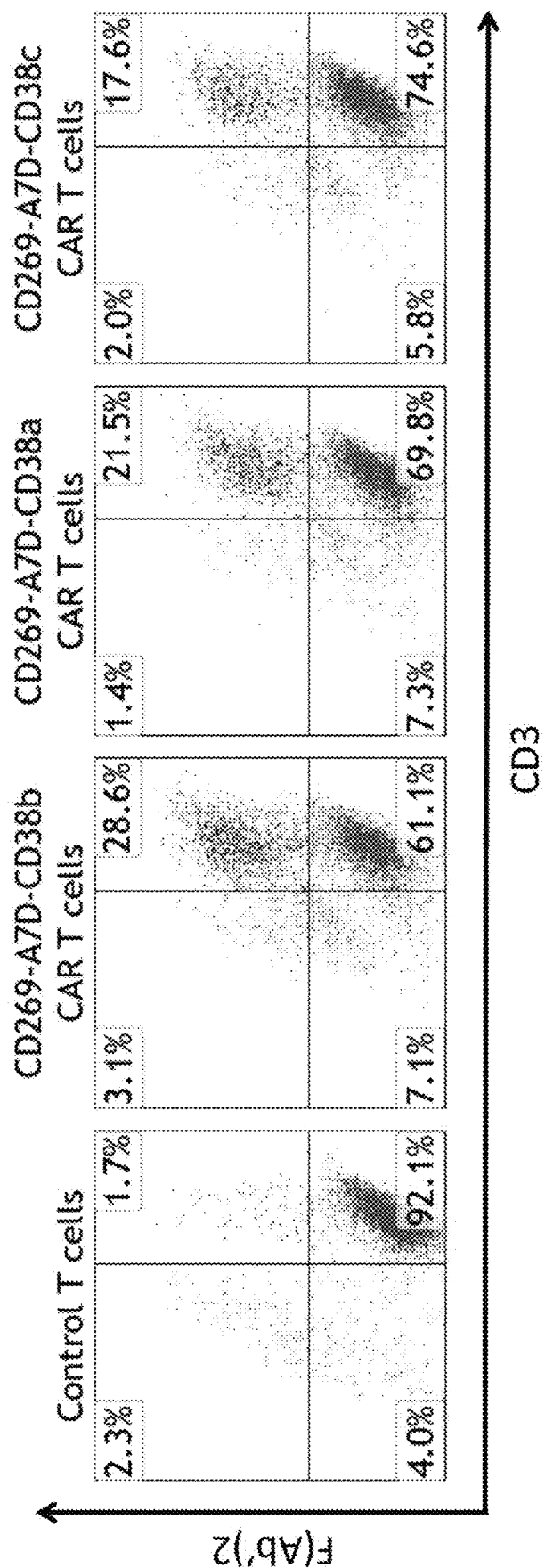

FIG. 39A. Expression of CD269-A7D-CD38 cCAR T cells. Buffy coat cells were activated 3 days with anti-CD3 antibody. Cells were transduced with either control vector (left), CD269-A7D-CD38a, CD269-A7D-CD38b, or CD269-A7D-CD38c CAR (right) lentiviral supernatant. After 3 days of incubation, cells were harvested and labeled for flow cytometry. There are three versions of CD269-A7D-CD38 cCAR T cells, CD269-A7D-CD38a, CD269-A7D-CD38b, CD269-A7D-CD38c CAR.

Figure 39B:
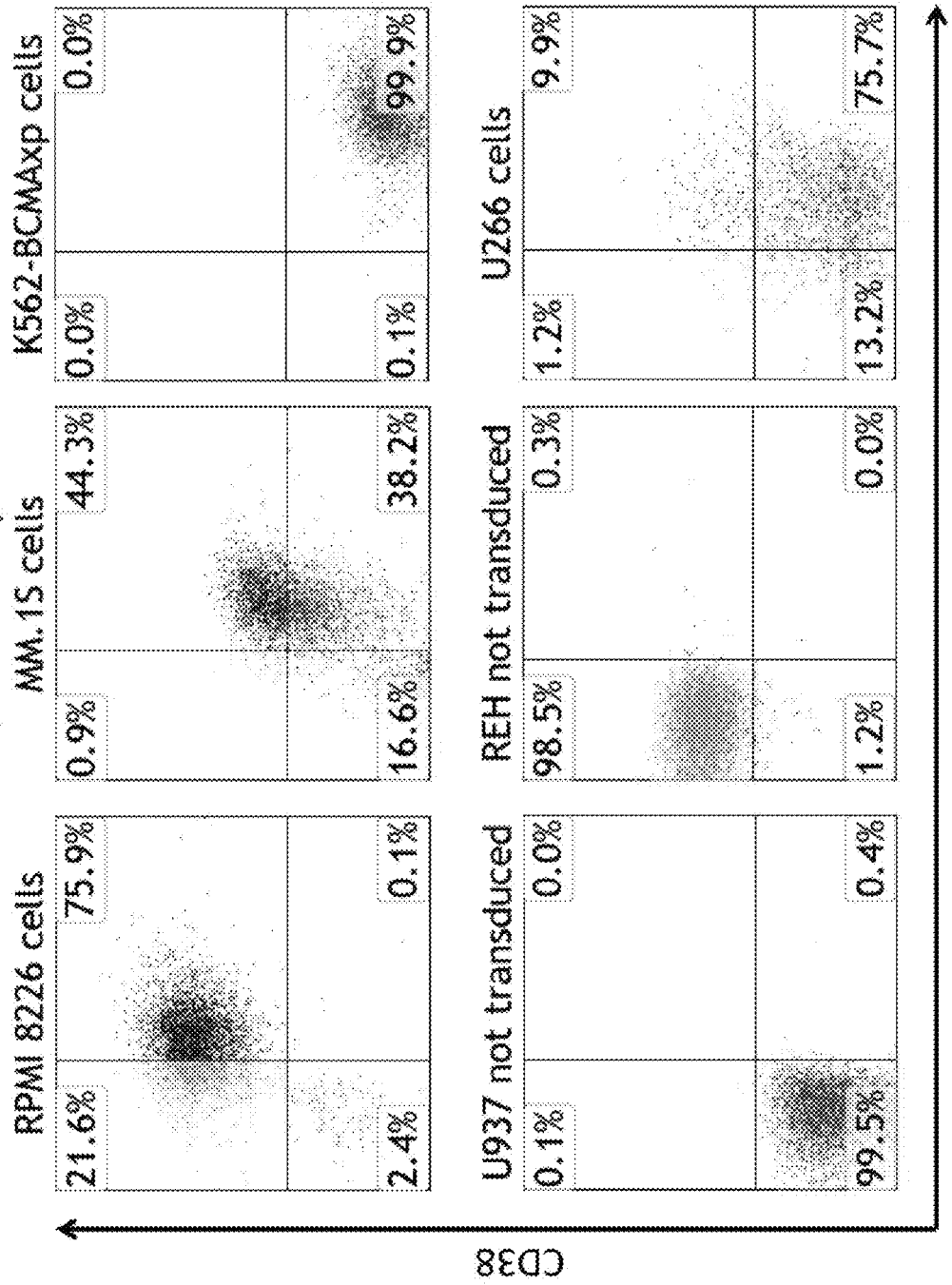

FIG. 39B. Six cell lines were analyzed for BCMA (CD269) and CD38 cell surface expression by flow cytometry. Cells were labeled with mouse anti-human CD269 (APC) and CD38 (PE). CD38 is expressed in myeloma cells, RPMI 8226 and MM1S. B-ALL cell line REH also expresses CD38. K562-BCMAxp cells is an AML cells (K562) and used to express BCMA using a lentiviral vector. K562-BCMAxp cells show all cells expressing BCMA.

Figure 39C:
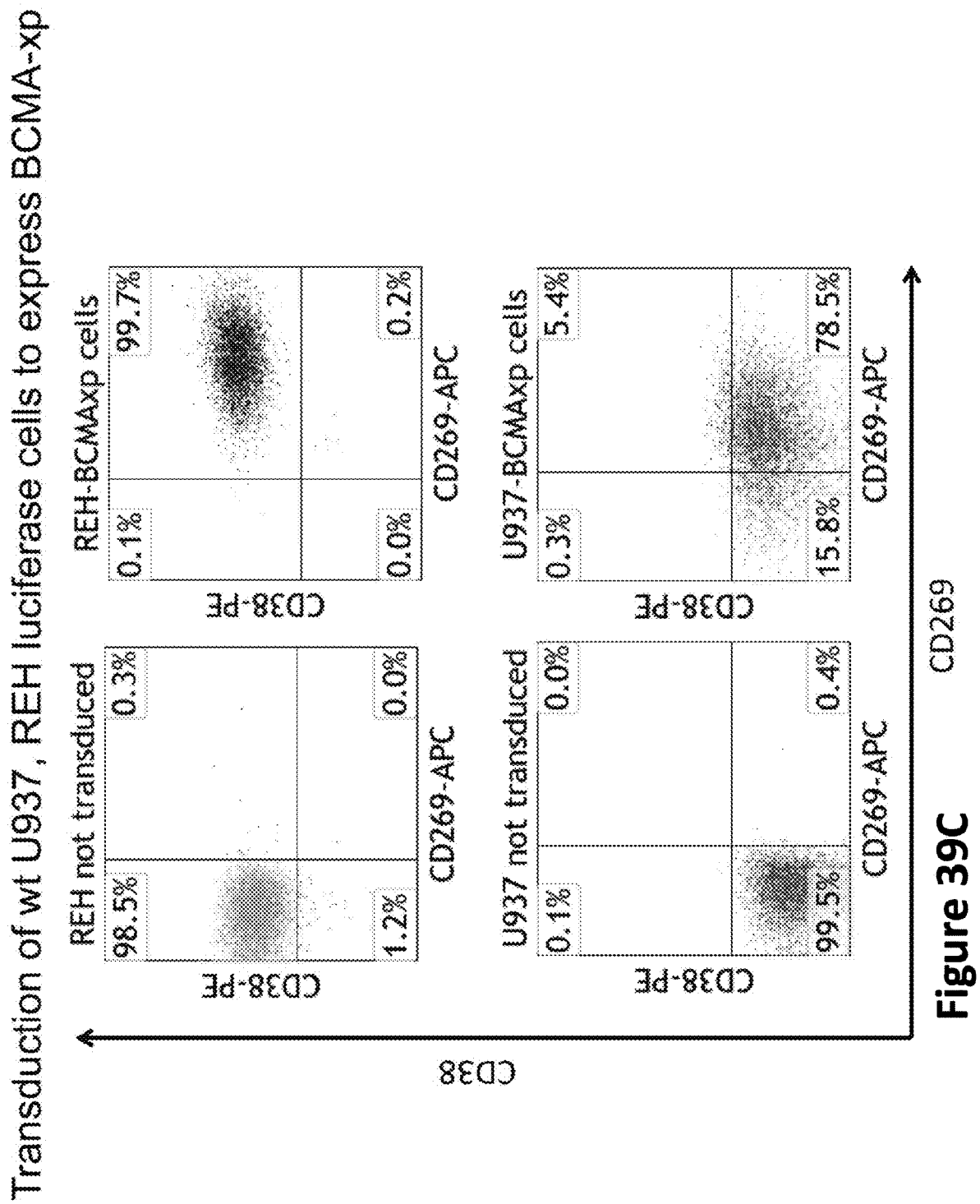

FIG. 39C. REH and U937 wild-type cell lines expressing luciferase were transduced with BCMA-xp lentiviral vector expressing BCMA. After recovery, non-transduced (left) and transduced cells (right) were labeled with mouse anti-human CD269 (BCMA) (APC) and CD38 (PE) and analyzed by flow cytometry. U937-BCMAxp and REH cell line express BCMA surface antigen while the wild type cell line, U937 or REH does not.

Figure 39D:
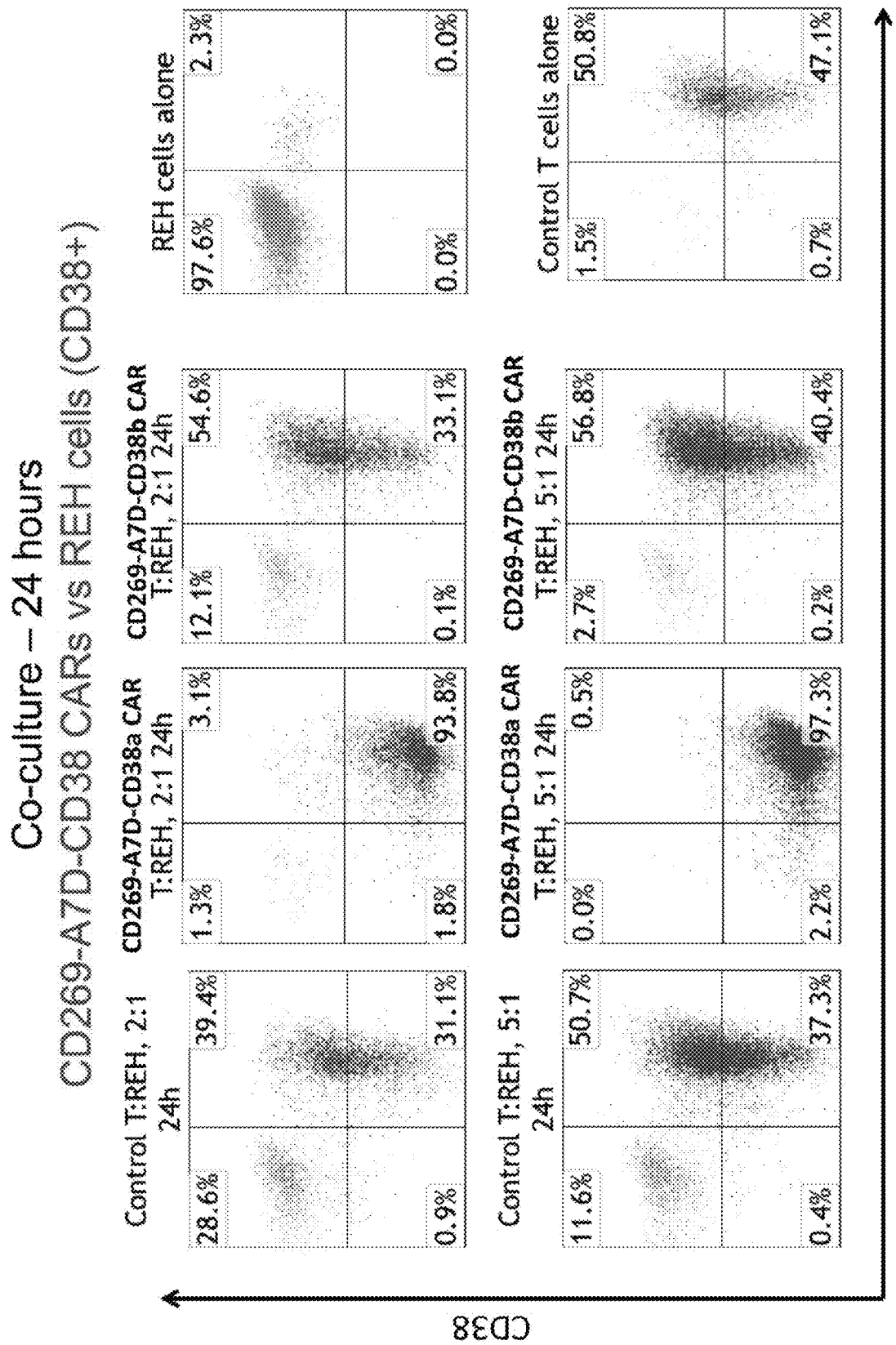

FIG. 39D. CD269-A7D-CD38 CAR T cells specifically lyse the CD38+ REH tumor cell line, which expresses CD38 surface antigen but not CD269 (BCMA), in co-culture assays. Co-culture experiments were performed at an effector to target ratio of 2:1 (top row) or 5:1 (bottom row) for 24 hours and were directly analyzed by flow cytometry for CD38 and CD3. Each assay consists of REH target cells incubated with control T cells (left panels), CD269-A7D-CD38a (center left panels) or CD269-A7D-CD38b CAR T cells (center-right panels), or cells alone (far right). REH cells are represented as blue dots.

Figure 39E:
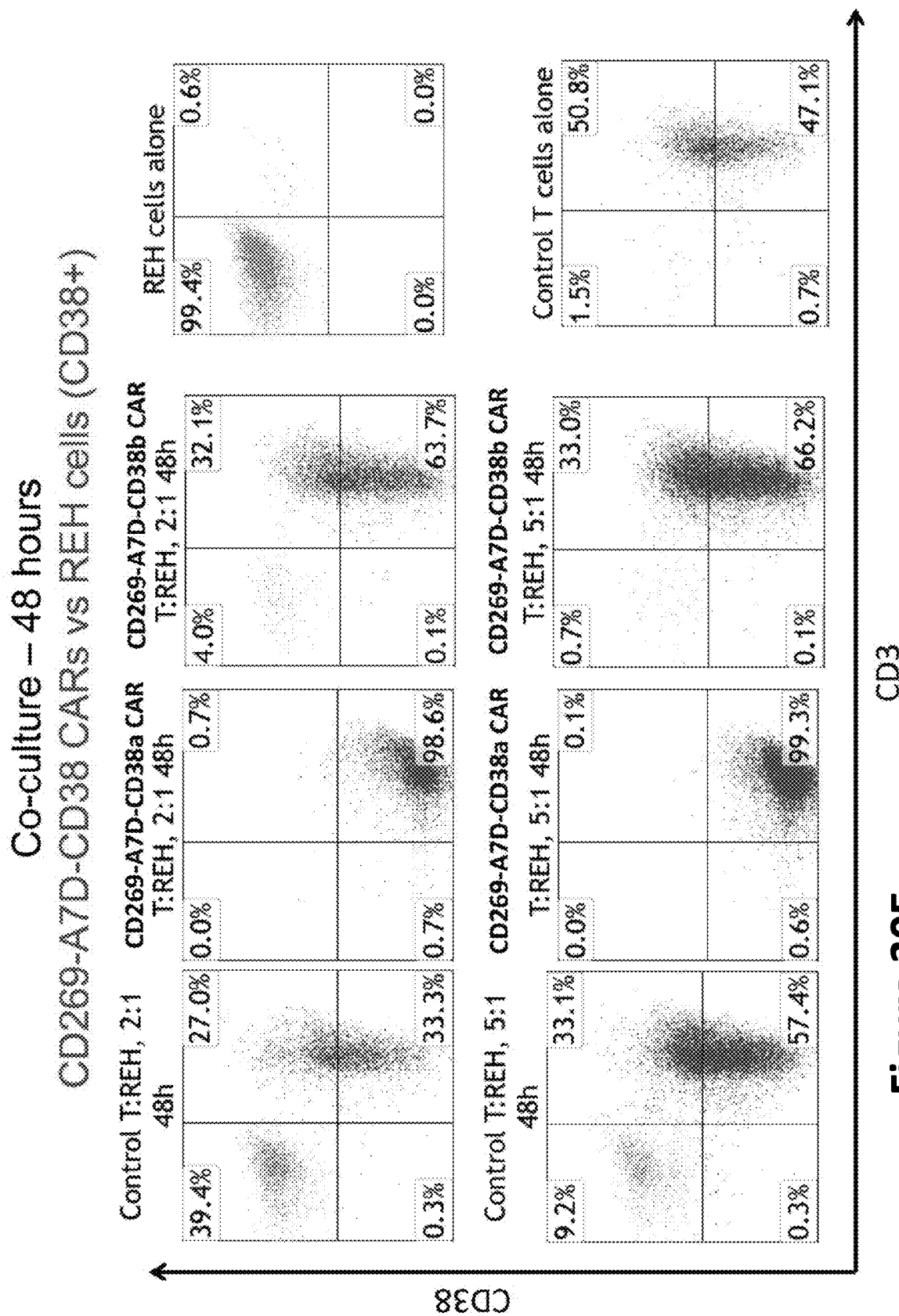

FIG. 39E. CD269-A7D-CD38 CAR T cells specifically lyse the REH tumor cell line, which expresses CD38 surface antigen but not CD269, in co-culture assays. Co-culture experiments were performed at an effector to target ratio of 2:1 (top row) or 5:1 (bottom row) for 48 hours and were directly analyzed by flow cytometry for CD38 and CD3. Each assay consists of REH target cells incubated with control T cells (left panels), CD269-A7D-CD38 (center left panels) or CD269-A7D-CD38b CAR T cells (center-right panels), or cells alone (far right). REH cells are represented as blue dots.

Figure 39F:
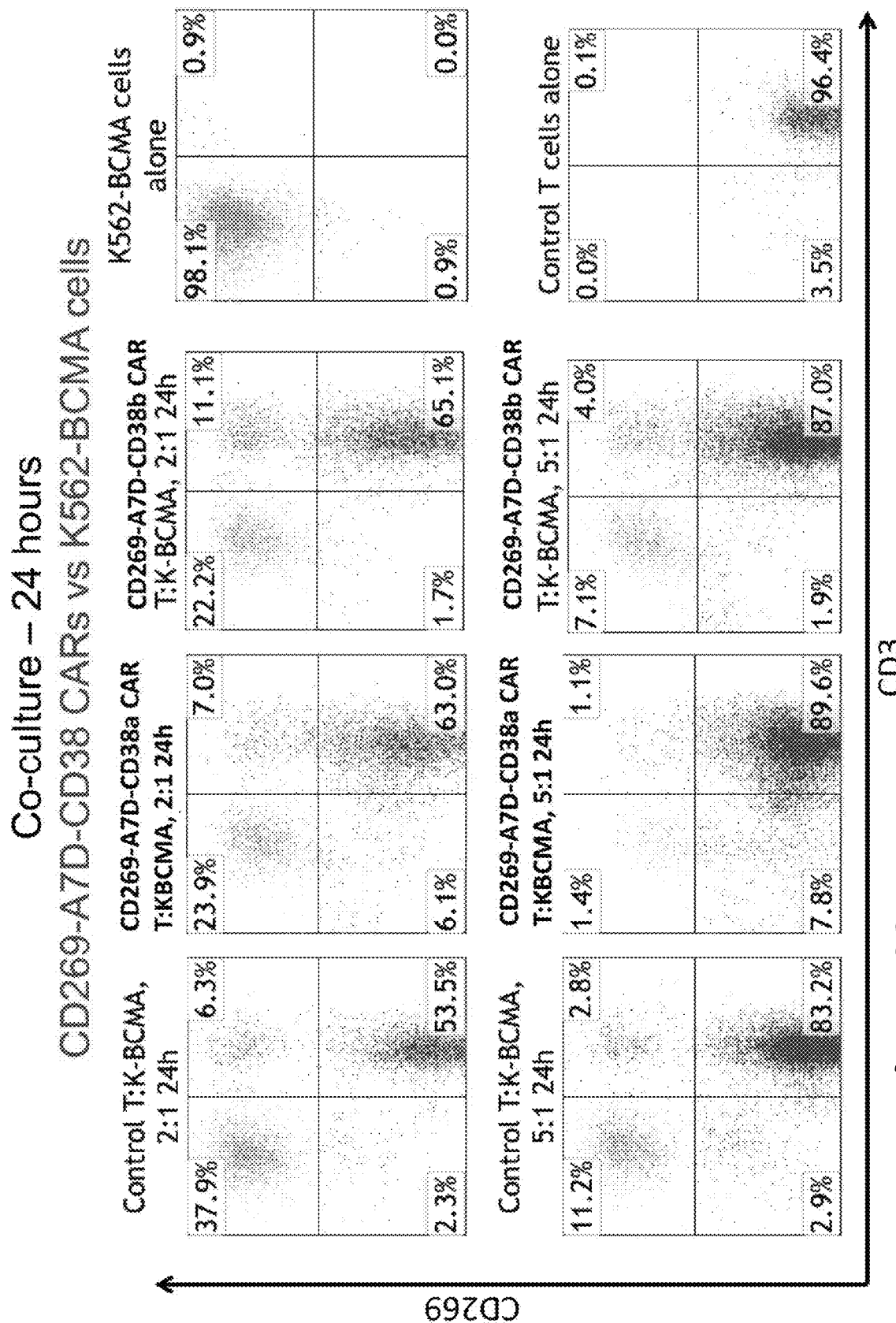

FIG. 39F. CD269-A7D-CD38 CAR T cells specifically lyse the K562 tumor cell line, which is synthetically expressing CD269 (BCMA) surface antigen but CD38, in co-culture assays. Co-culture experiments were performed at an effector to target ratio of 2:1 (top row) or 5:1 (bottom row) for 24 hours and were directly analyzed by flow cytometry for CD269 and CD3. Each assay consists of K562-BCMA (K-BCMA) target cells incubated with control T cells (left panels), CD269-A7D-CD38a (center left panels) or CD269-A7D-CD38b CAR T cells (center-right panels), or cells alone (far right). K-BCMA cells are represented as green dots.

Figure 39G:
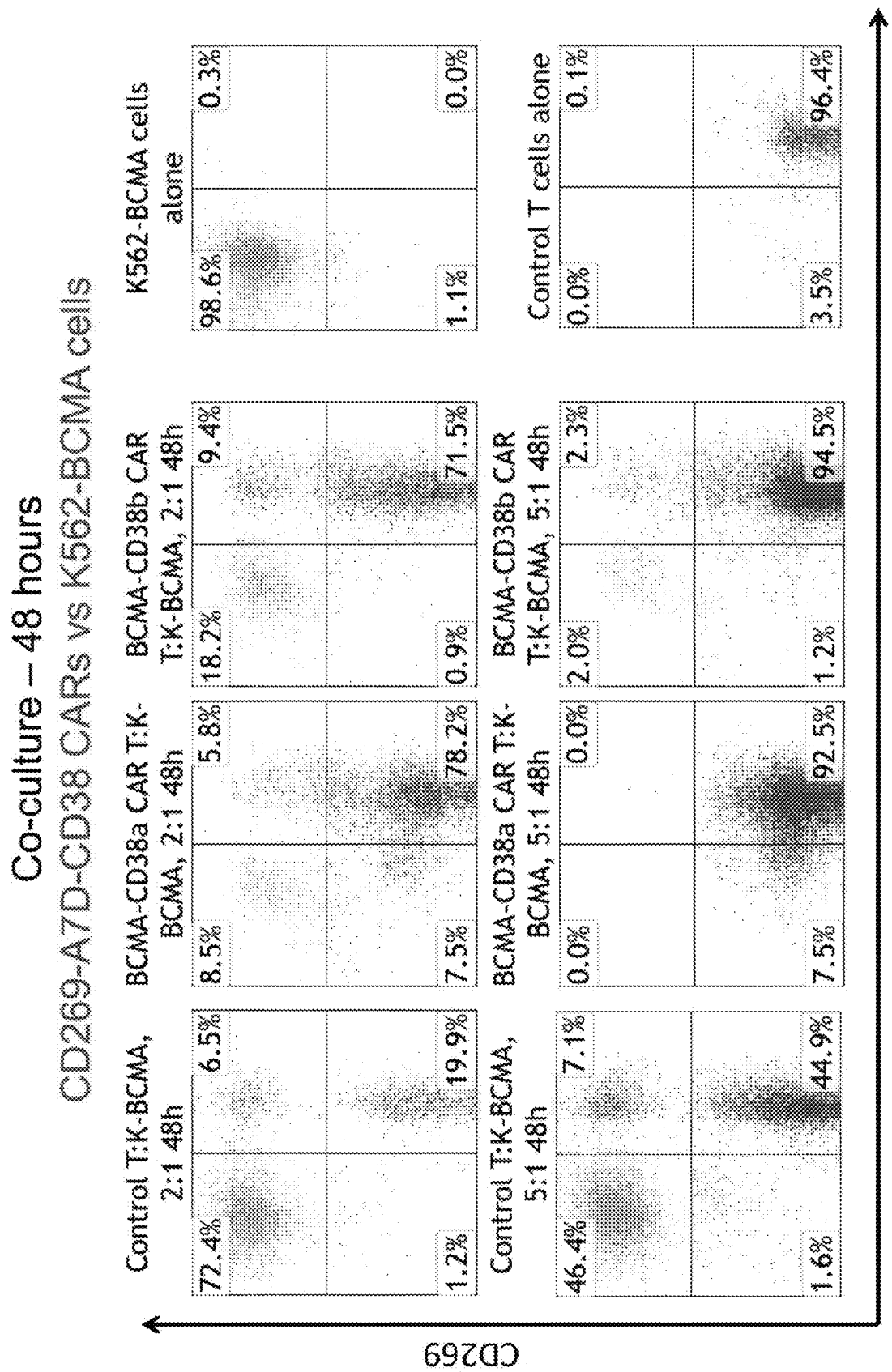

FIG. 39G. CD269-A7D-CD38 CAR T cells specifically lyse the K562 tumor cell line, which is synthetically expressing CD269 (BCMA) surface antigen, in co-culture assays. Co-culture experiments were performed at an effector to target ratio of 2:1 (top row) or 5:1 (bottom row) for 48 hours and were directly analyzed by flow cytometry for CD269 and CD3. Each assay consists of K562-BCMA target cells incubated with control T cells (left panels), CD269-A7D-CD38a (center left panels) or CD269-A7D-CD38b CAR T cells (center-right panels), or cells alone (far right). K-BCMA cells are represented as green dots.

Figure 40A:
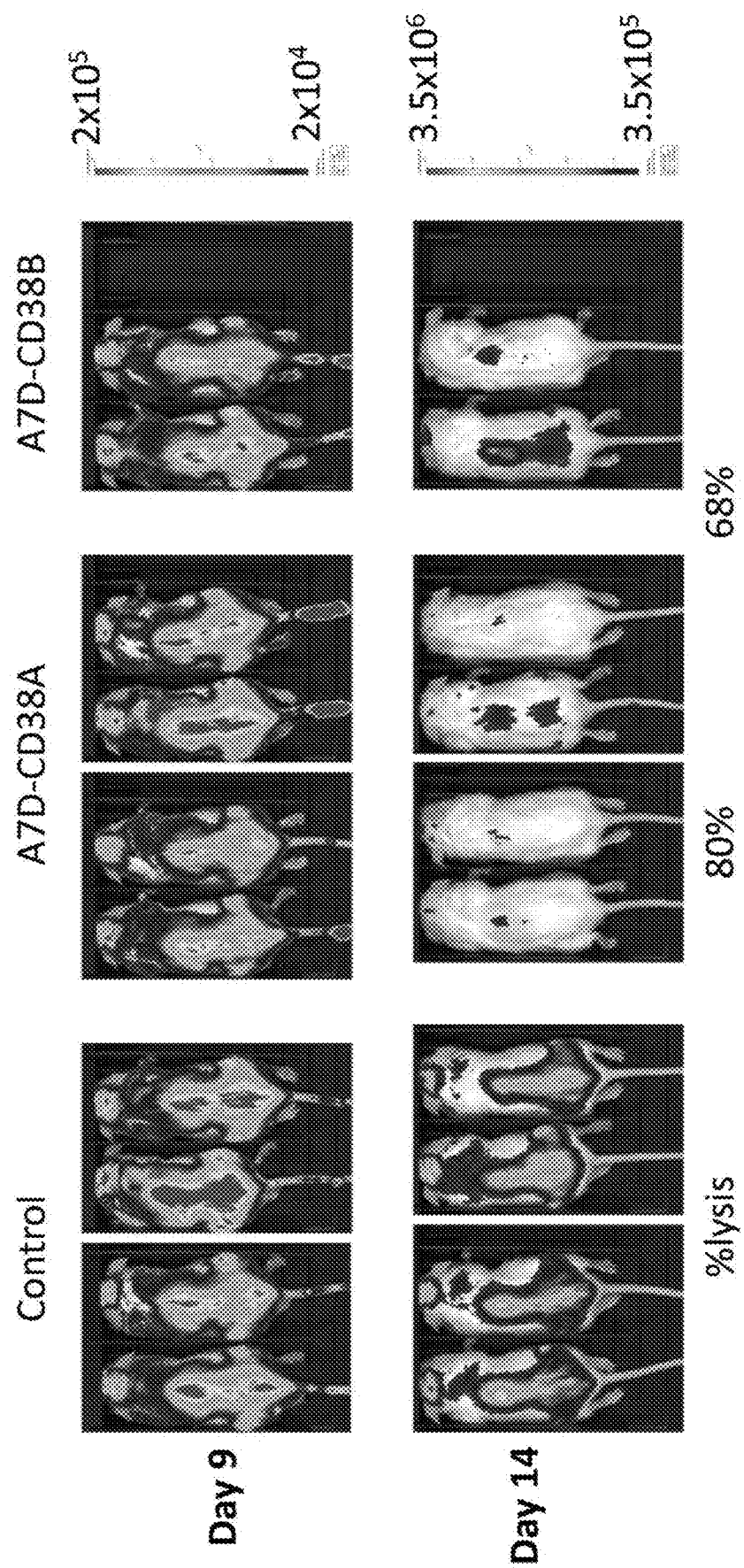

FIG. 40A. CD269-A7D-CD38a CAR T cells demonstrate stronger anti-tumor effects in vivo against MM.1S tumor cell line than CD269-A7D-CD38b CAR T cells (dorsal view). NSG mice were sublethally irradiated and intravenously injected with $4.0\times10^6$ luciferase-expressing MM.1S cells (Day 0) to induce measurable tumor formation. Starting 10 days after injection of tumor cells, mice were intravenously injected with a course of $10\times10^6$ either CD269-A7D-CD38a, CD269-A7D-CD38b, or vector control T cells. On days 9 and 12, mice were injected subcutaneously with RediJect D-Luciferin and subjected to IVIS imaging. Dorsal view is shown.

Figure 40B:
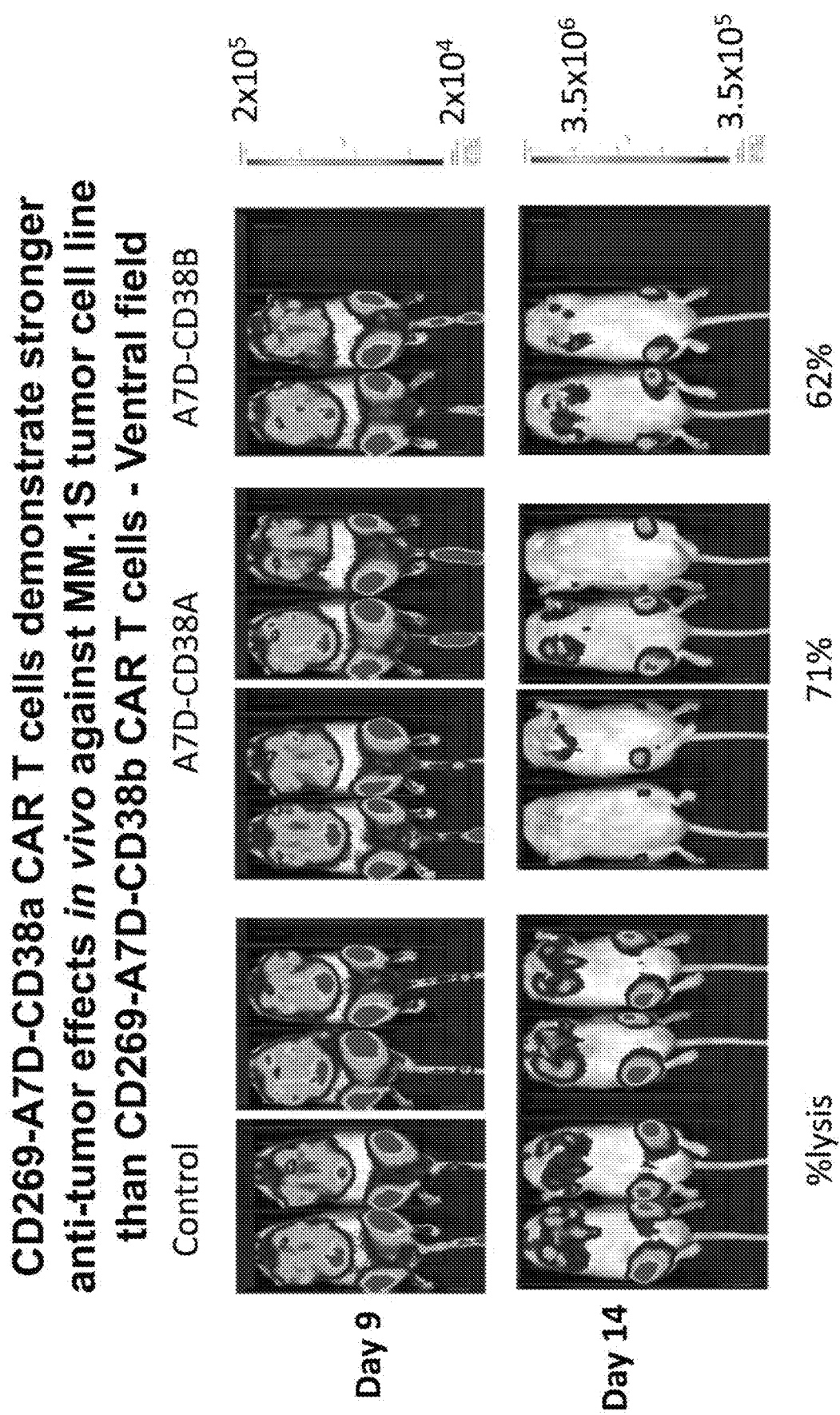

FIG. 40B. CD269-A7D-CD38a CAR T cells demonstrate stronger anti-tumor effects in vivo against MM.1S tumor cell line than CD269-A7D-CD38b CAR T cells (ventral view). NSG mice were sublethally irradiated and intravenously injected with $4.0\times10^6$ luciferase-expressing MM.1S cells (Day 0) to induce measurable tumor formation. Starting 10 days after injection of tumor cells, mice were intravenously injected with a course of $10\times10^6$ either CD269-A7D-CD38a, CD269-A7D-CD38b, or vector control T cells. On days 9 and 12, mice were injected subcutaneously with RediJect D-Luciferin and subjected to IVIS imaging. Ventral view is shown.

Figure 40C:
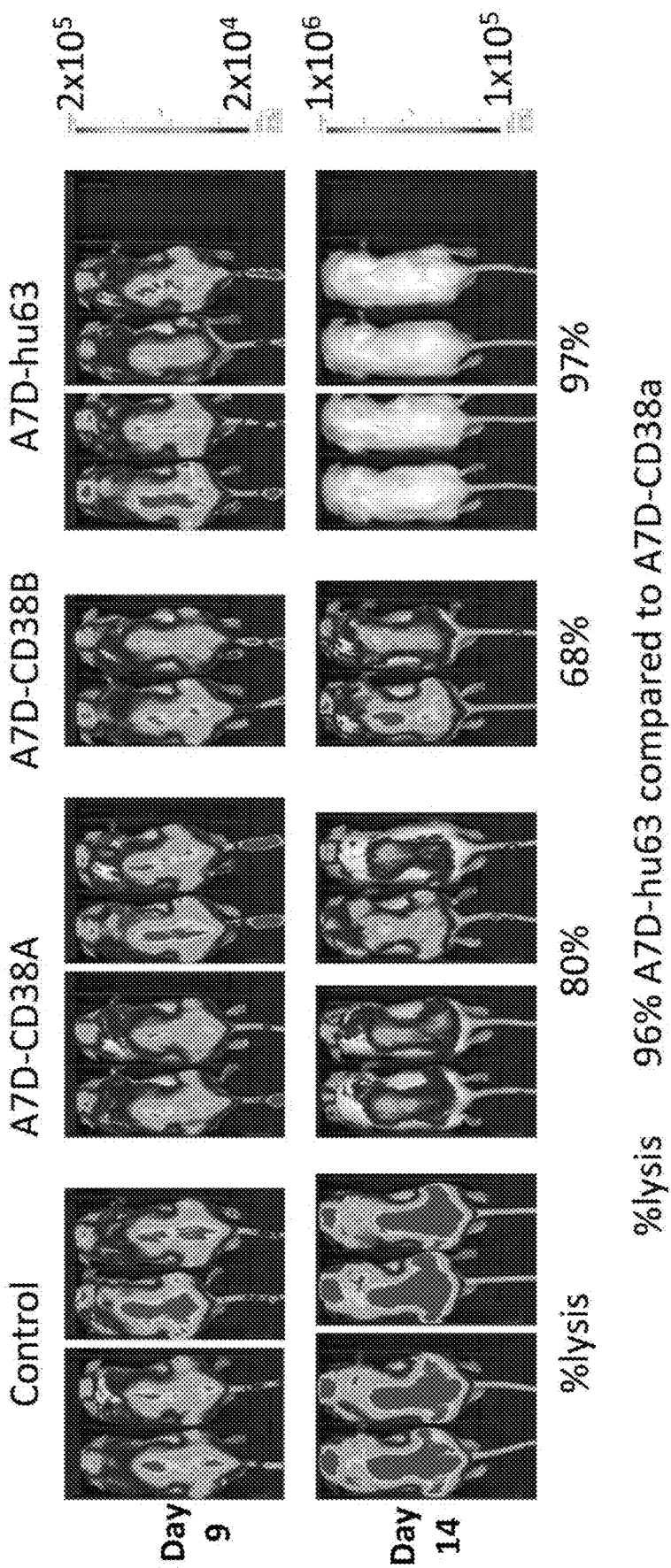

FIG. 40C. CD269-A7D-CS1-hu63 CAR T cells demonstrate stronger anti-tumor effects in vivo against MM.1S tumor cell line than either CD269-A7D-CD38a or CD269-A7D-CD38b CAR T cells (dorsal view). NSG mice were sublethally irradiated and intravenously injected with $4.0\times10^6$ luciferase-expressing MM.1S cells (Day 0) to induce measurable tumor formation. Starting 10 days after injection of tumor cells, mice were intravenously injected with a course of $10\times10^6$ either CD269-A7D-CD38a, CD269-A7D-CD38b, or CD269-A7D-hu63 CAR T cells, or vector control T cells. On days 9 and 12, mice were injected subcutaneously with RediJect D-Luciferin and subjected to IVIS imaging. Dorsal view is shown.

Figure 40D:
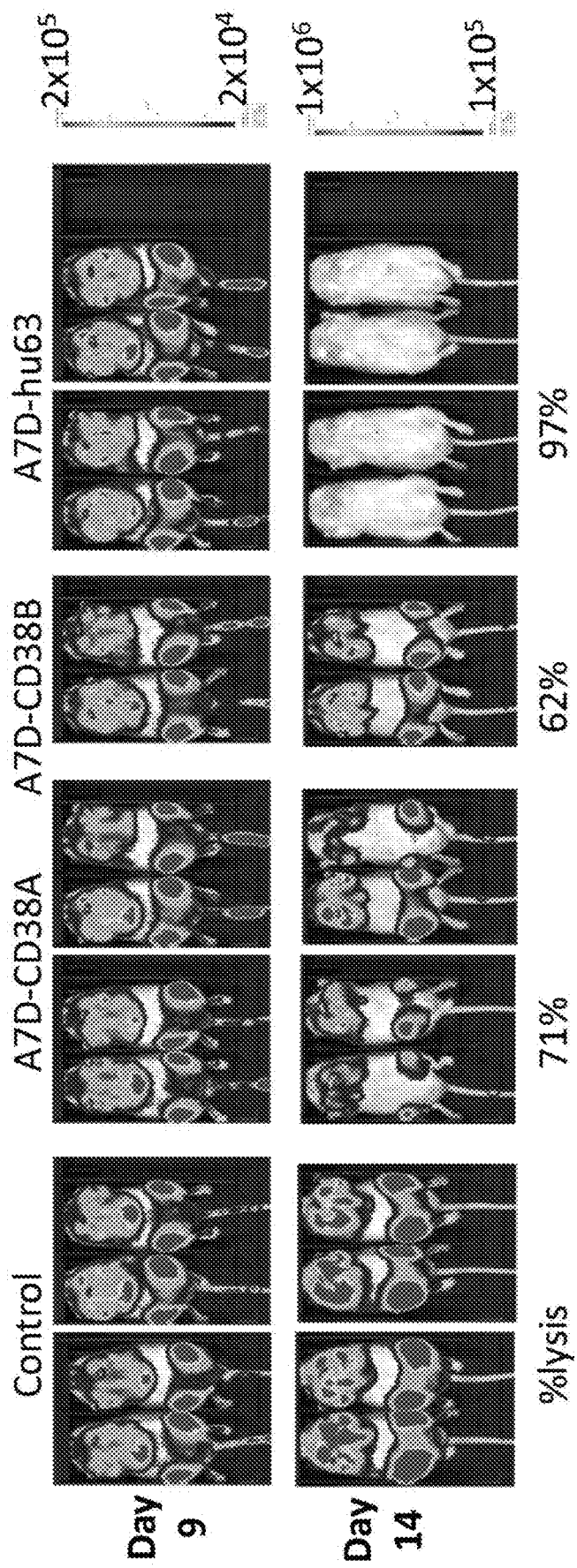

FIG. 40D. CD269-A7D-CS1-hu63 CAR T cells demonstrate stronger anti-tumor effects in vivo against MM.1S tumor cell line than either CD269-A7D-CD38a or CD269-A7D-CD38b CAR T cells (ventral view). NSG mice were sublethally irradiated and intravenously injected with $4.0\times10^6$ luciferase-expressing MM.1S cells (Day 0) to induce measurable tumor formation. Starting 10 days after injection of tumor cells, mice were intravenously injected with a course of $10\times10^6$ either CD269-A7D-CD38a, CD269-A7D-

CD38b, or CD269-A7D-hu63 CAR T cells, or vector control T cells. On days 9 and 12, mice were injected subcutaneously with RediJect D-Luciferin and subjected to IVIS imaging. Ventral view is shown.

Figure 41A:
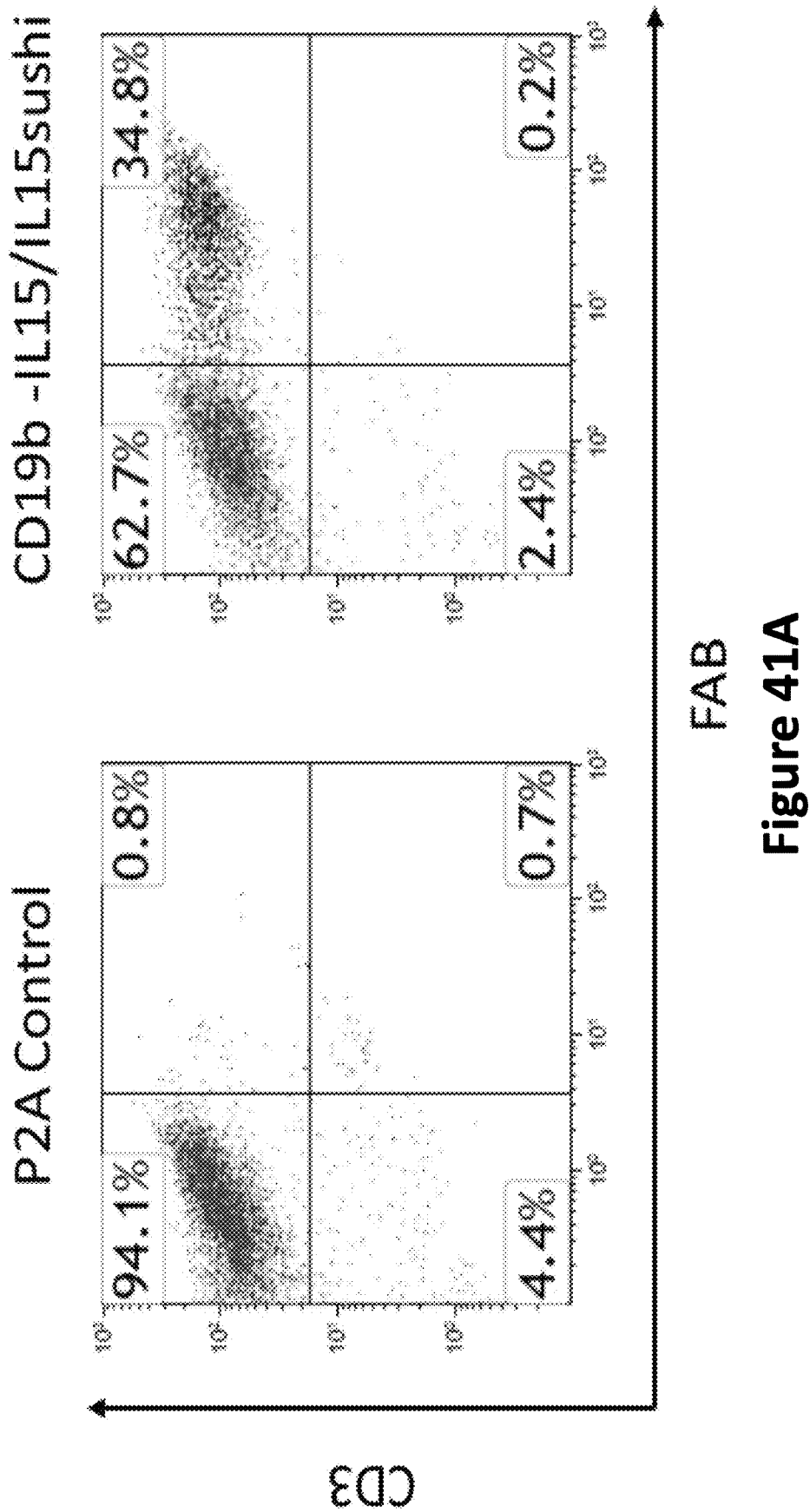

FIG. 41A. Expression of CD19b-IL-15/IL-15sushi (CD19b-IL-15/IL15sushi) CAR T cells.

Expression was measured by FACS against control T-cells. CD19b-IL-15/IL15sushi CAR T-cells were created by the viral transduction of patient or donor T-cells with the armored CAR gene construct. The translated anti-CD19b armored CAR proteins were then expressed on the surface of the CAR T-cells, where they can recognize and bind the CD19 target proteins on the surface of tumor cells. The pharmacologic effect and mechanism of CD19b-IL-15/IL15sushi CAR T-cells is mediated by CD19b CAR recognition of the antigen, which triggers CD3zeta/Zap70 canonical cytotoxic T-cell activity further enhanced by the incorporation of CD28 co-activation domains in the construct. FACS analysis showed that CD19b-IL-15/IL-15sushi CAR was able to be expressed on roughly 35% of the T cells and secret IL-15/IL-15sushi complexes; furthermore, the IL-15/IL-15sushi "armor" provides additional stimulation, proliferation, and potency enhancement to the CAR T cell when compared to a standard CAR cell. P2A, vector control.

Figure 41B:
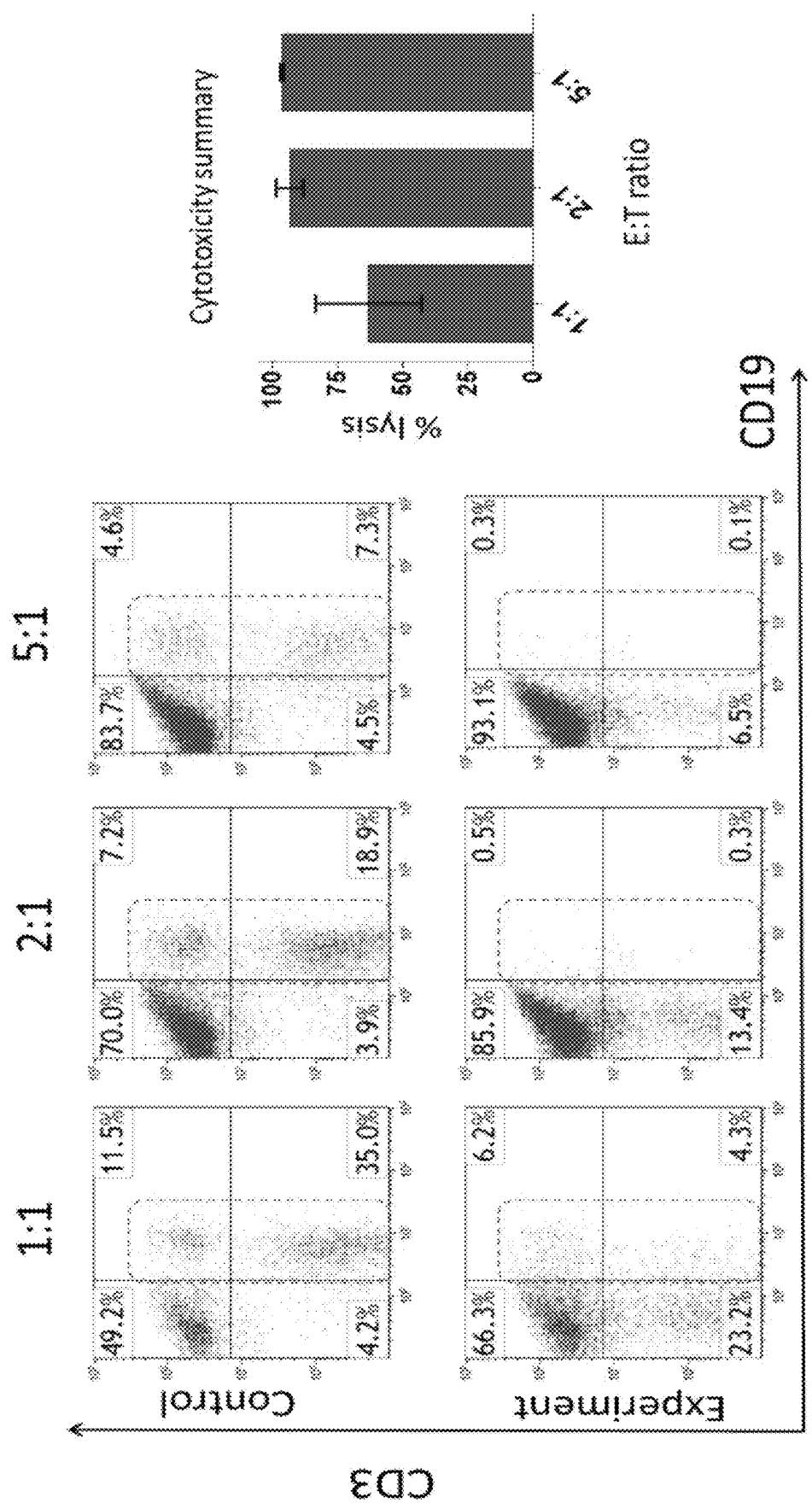

FIG. 41B. CD19b-IL15/IL-15sushi CAR T-cells potently lyse CD19+ SP53 cells. Co-culture experiments were performed at an effector to target (E:T) ratio of spanning from 1:1 to 5:1 for 24 hours and were directly analyzed by flow cytometry with mouse anti-human CD3pPerCp and mouse anti-human CD19-PE. Each assay consists of target cells (Sp53 all CD19+) incubated with either P2A vector control or CAR T-cells. Bar graph summarizing cytotoxic activity (right). N=2. This experiment reveals the dose-dependent nature of the CD19b-IL-15/IL-15sushi CART, where even at low E:T ratios such as 1:1, there is potent lysis of tumor cells of greater than 60%. At 2:1, saturation of killing ability is observed with virtually all tumor cells lysed.

Figure 41C:
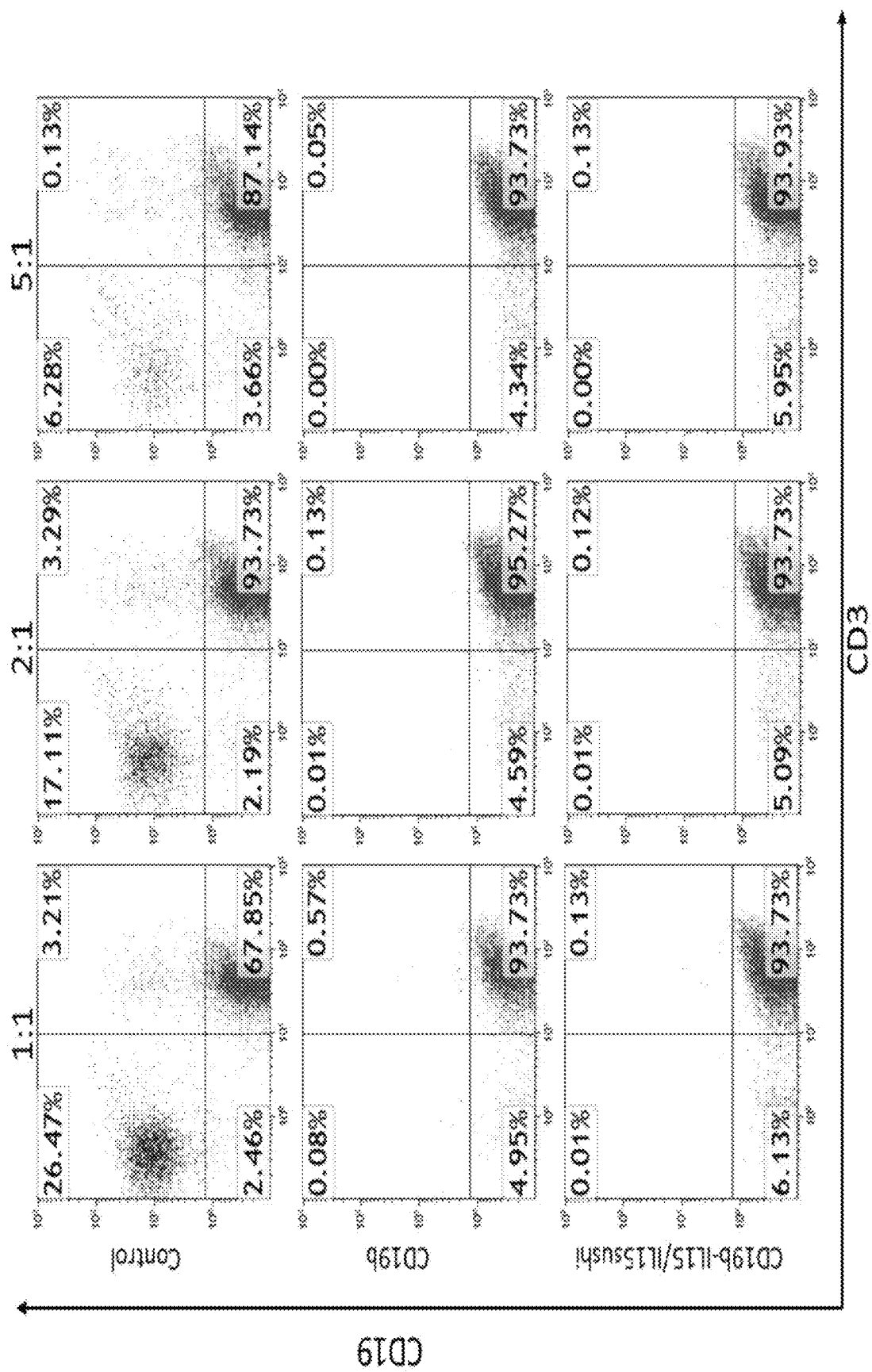

FIG. 41C. CD19b-IL-15/IL-15sushi CAR T-cells potently lyse CD19+ Sp53 cells (with comparison to CD19b CAR T cells). Similar co-cultures conditions were used as above (FIG. 41B). In this experimental scheme, armored CD19b (CD19b-IL-15/IL-15sushi CAR T cells were cultured against CD19 positive Reh cells, B-ALL cells and compared to both control P2A and anti-CD19b CART cells. Anti-CD19b CART cells were generated with the same methodology and expression on T cell surfaces was verified to be ~50% of all T cells (data not shown). The results here demonstrate that even at low E:T ratios such as 1:1, both CART treatments are equally effective, with potent and virtual deletion of all antigen-positive Reh cells. The "IL-15 armor" does not have a deleterious effect on the cytotoxicity of the CAR T cells.

Figure 42A:
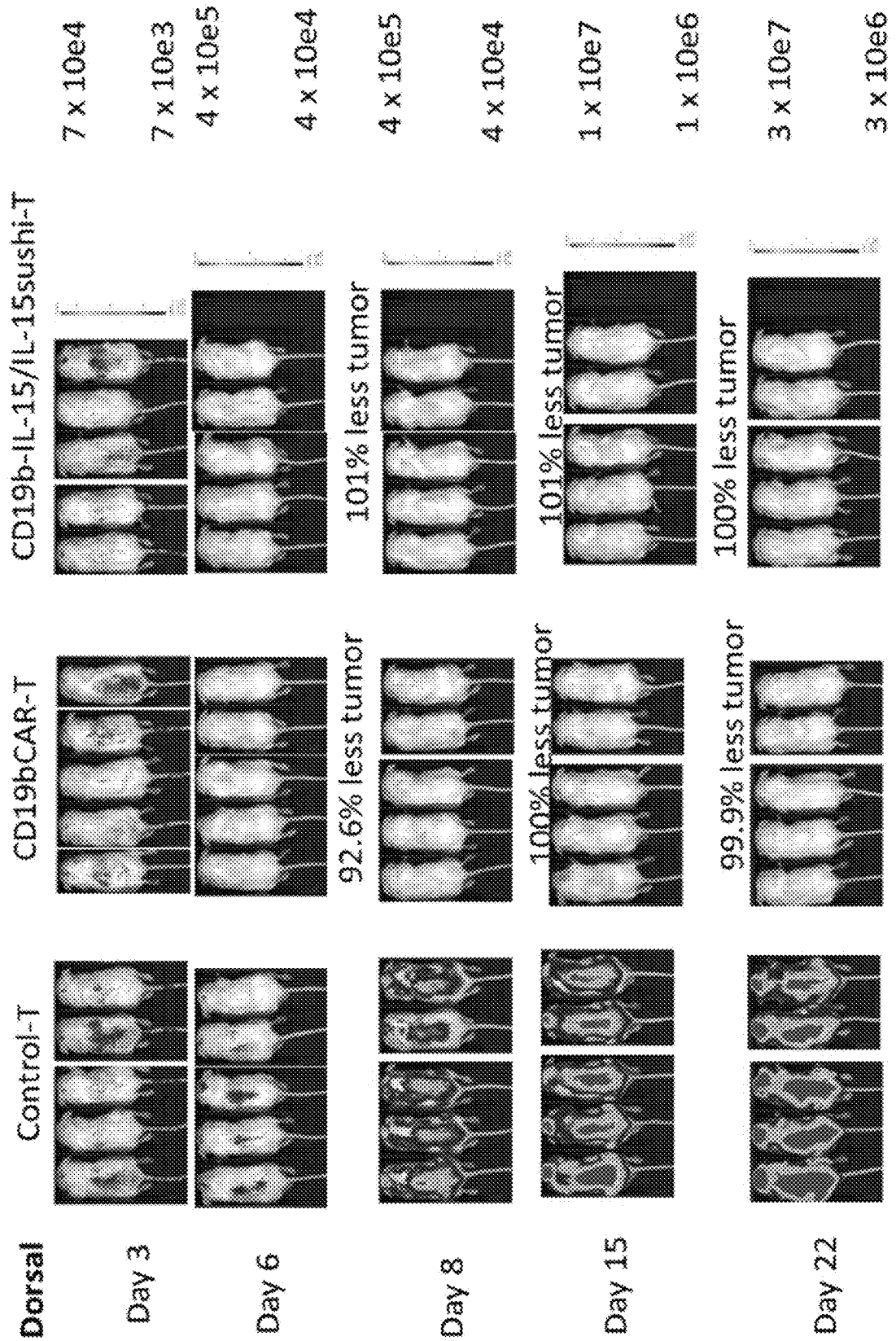

FIG. 42A. CD19 based CARs deplete Reh cells in vivo and co-expression of IL-15/IL-15sushi strongly enhances anti-tumor response. Mice were injected with Reh tumor cells ($0.5 \times 10^6$ cells/mouse) expressing luciferase on Day 1. On Day 3, IVIS was conducted to assay the appearance of Reh cells. On Day 4, control T-cells, CD19b CAR, and CD19b-IL15/IL15sushi CAR T-cells were injected ($7.5 \times 10^6$ total cells/mouse) and on day 6 through 22, IVIS imaging was conducted to assay semi-quantitative assessment of tumor burden and subsequent tumor depletion and control of cell growth by T-cells. Here, both CART treatments demonstrated similar efficacy, with the IL-15/IL-15sushi armored CAR demonstrating comparable or better control of the Reh tumor growth when compared to standard CART19 cells.

Figure 42B:
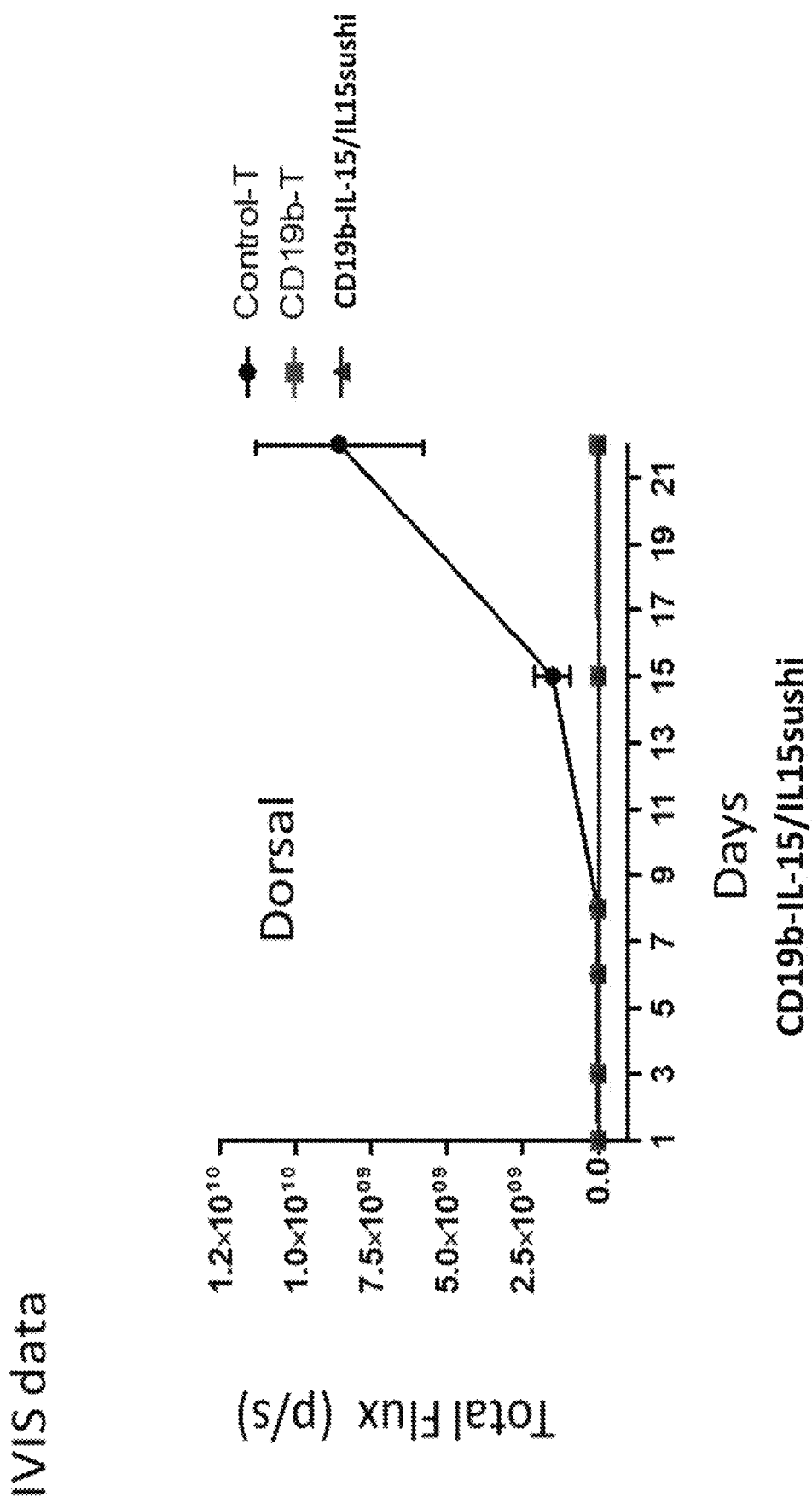

FIG. 42B. Line graph plotting IVIS values (estimation of tumor burden) against time for the treatment cohorts. As the tumor burden rises within the control group, both CART groups show steady maintenance of tumor suppression with significantly decreased tumor counts as measured by statistical analysis.

Figure 42C:
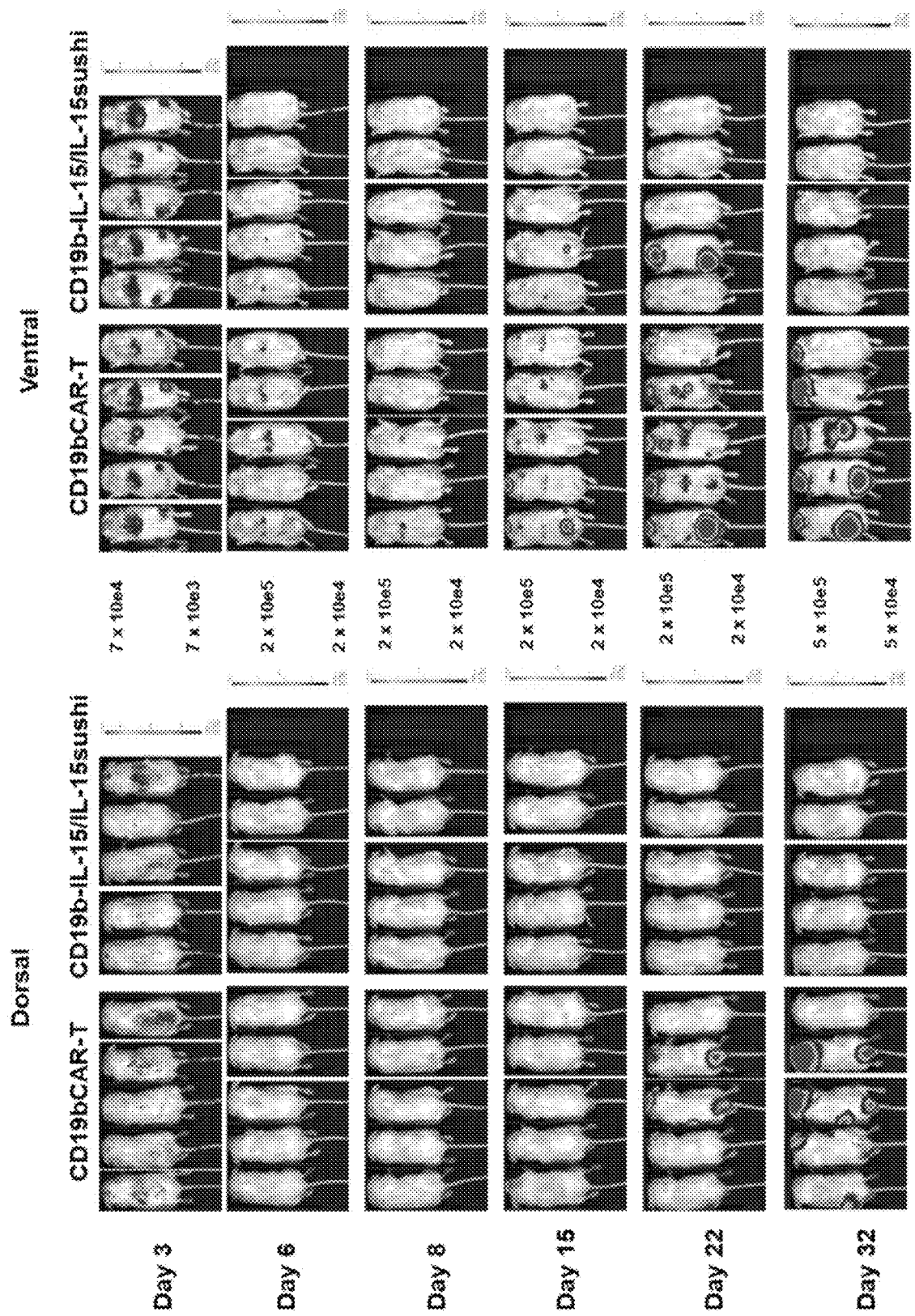

FIG. 42C. Comparison CD19b-CAR-T (CART19) vs CD19b-IL-15/IL15sushi CAR-T against REH cells over long term. Similar experimental scheme with identical IVIS methodology as above; however, mice were followed until signs of tumor relapse were seen. Here, after day 30, we observed that aggressive Reh tumor relapse began to occur in standard CART19 treated mice. Clusters of tumor (indicated by red regions on the IVIS imaged mice) were seen in most CART19 mice, with a single CD19b-IL-15/IL-15sushi CART treated mice also showing tumor growth by day 22. However, after day 30, all CART19 mice showed signs of severe tumor relapse, while CD19b-IL-15/IL-15sushi CART treated mice showed no sign of tumor. Even the relapsed mouse on day 22 was absolved of its tumor by day 32, signifying that CD19b-IL-15/IL-15sushi CART cells were still in effective circulation.

FIG. 42D. IL-15/IL-15sushi armor is able to prevent disease relapse after standard CAR T fails. Line graph summarizing IVIS trend values estimating tumor growth over time for each treatment cohort. Past day 30, the tumor burden for the standard CD19b CAR (CART19) treated mice rises precipitously, resulting in highly significant increases in tumor burden compared to the CD19b-IL-15/IL-15sushi armored CART treatment group which remained largely tumor free. Values are displayed for both views of the mice (ventral and dorsal image acquisition views).

Figure 42E:
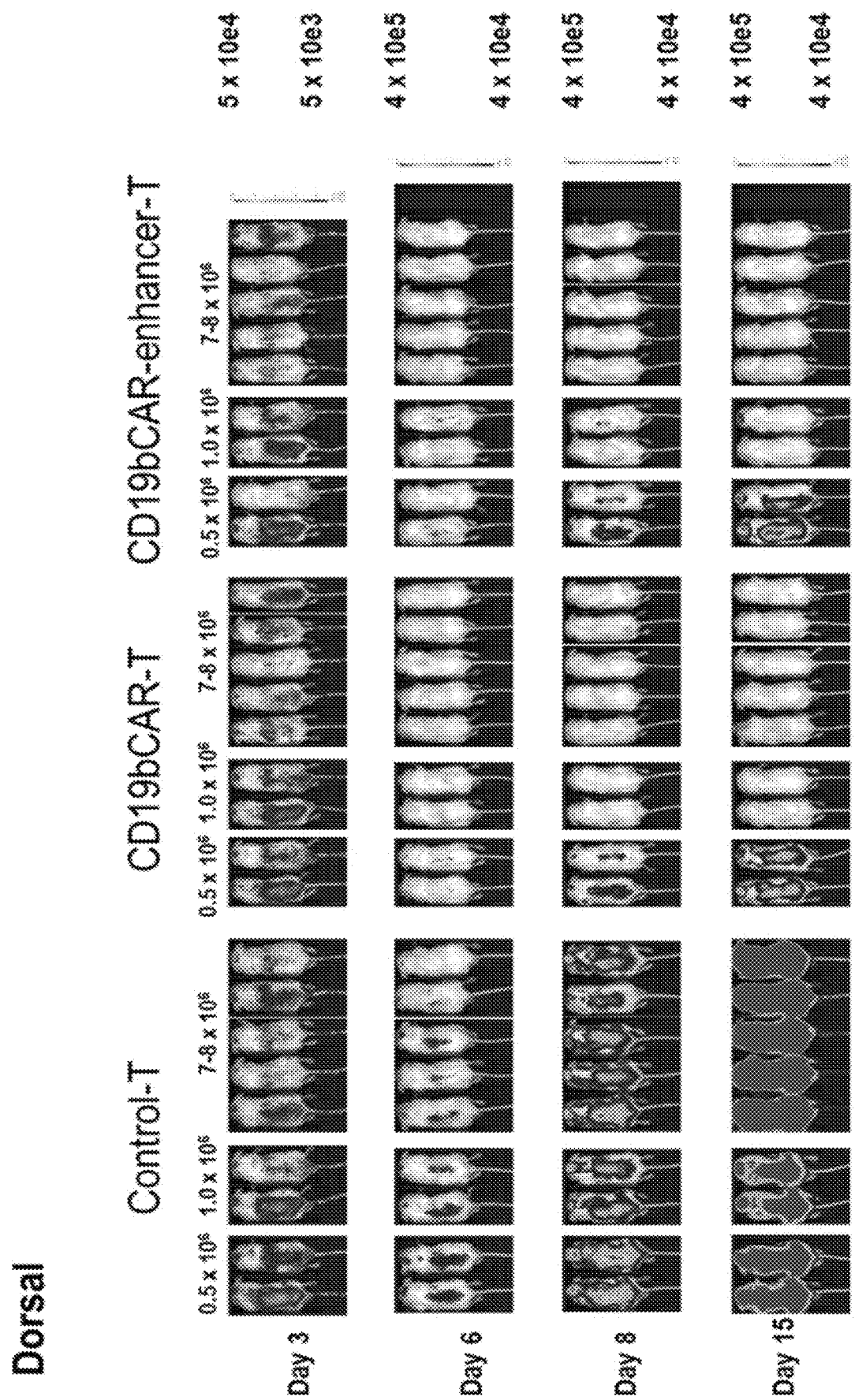

FIG. 42E. Lower doses of CAR T cells prevent cytokine storm. Mice were injected with Reh tumor cells ($0.5 \times 10^6$ total cells/mouse) expressing luciferase on Day 1. On Day 3, IVIS was conducted to assay the appearance of circulating Reh cells. The methodology remains the same as for FIG. 42C; however, only $0.5 \times 10^6$ and $1.0 \times 10^6$ CAR T or control cells were injected per mouse to assay for the lowest effective dose with regards to potential side-effects. This experiment was conducted because although the armored CAR (secreting IL-15/IL-15sushi) mice cohort in FIG. 42C showed robust elimination of tumor and impressive control of tumor growth when assayed by IVIS, ultimately, survival endpoints were reached as a result of untenable cytokine storm. As a result, it is necessary to titrate the dose of CAR T to find the lowest effective dose that could be administered with minimal risk of severe side effects. We found that while a dose of $0.5 \times 10^6$ total T cells per mouse was too low to control tumor burden in either standard CART19 or armored CAR T cohorts, a dosage of just $1.0 \times 10^6$ cells (10 fold less than a regular dose, which is 10 million CAR T cells in mice) was sufficient to control tumor growth without cytokine storm in both CAR T models. Hence, translation of armored CART therapy will require the administration of lower doses, as the increased potency and persistency of IL-15/IL-15sushi armored CARs may potentially also be associated with increased risk of cytokine release, leading to dangerous side effects.

Figure 43A:
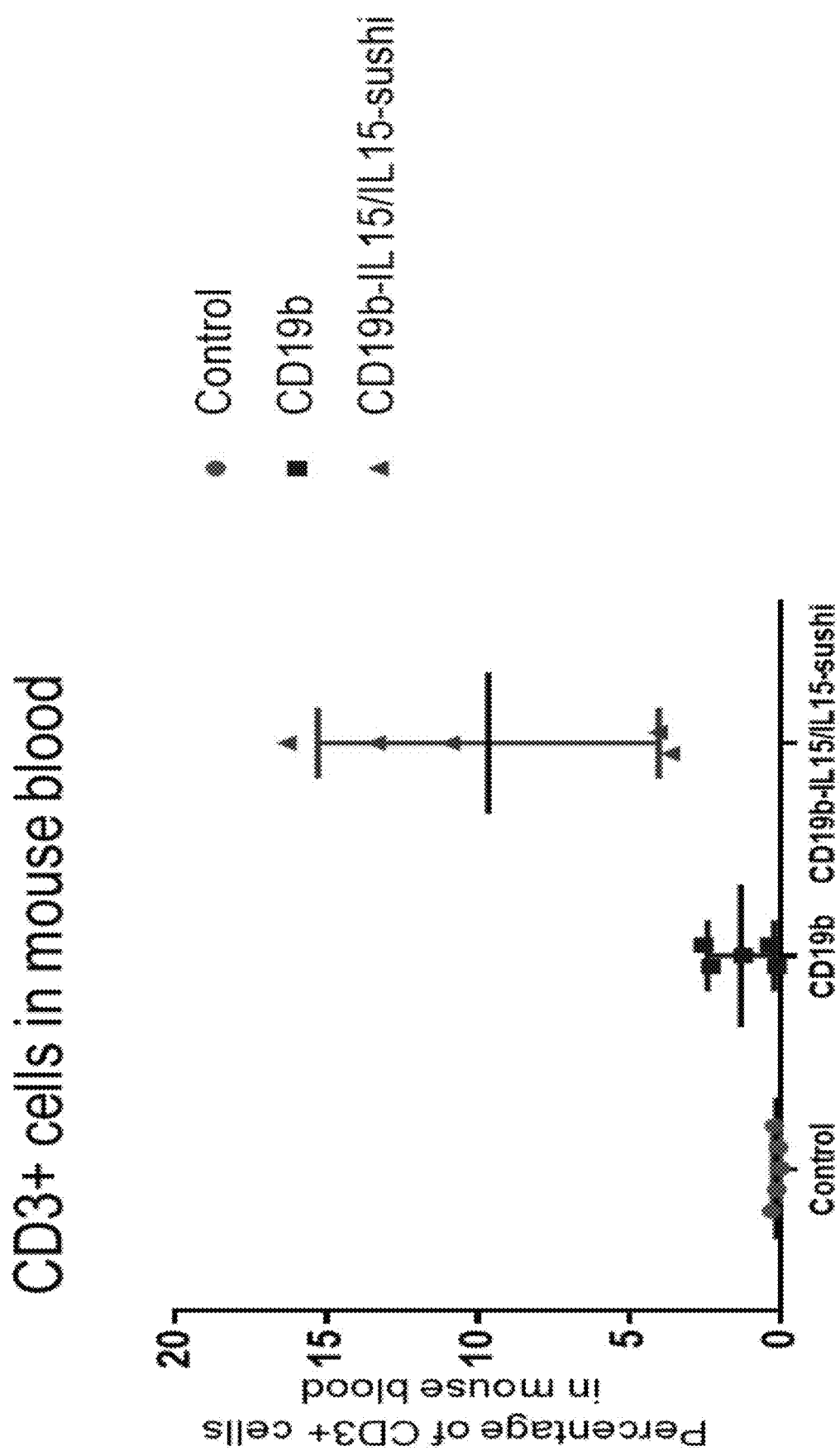

FIG. 43A. Overall summary of mice blood data (summarized persistency of CAR T cells in mice). The overall persistence of T cells in mouse blood from the model in FIG. 42C was assayed at survival endpoints and screened by flow cytometry using CD3 antibody for bulk T cell populations. To further dissect the persistency results of the CD19b-IL-15/IL-15sushi armored CAR, the collection of mouse blood is necessary to reveal the presence of durability of the engrafted human cells. Overall, we found by flow cytometry analysis that there was a higher average count of T cells in the armored CAR cohorts when compared to the standard CART19 groups. Control group T cells remained at baseline as expected due to minimal stimulation from circulating in vivo tumor.

Figure 43B:
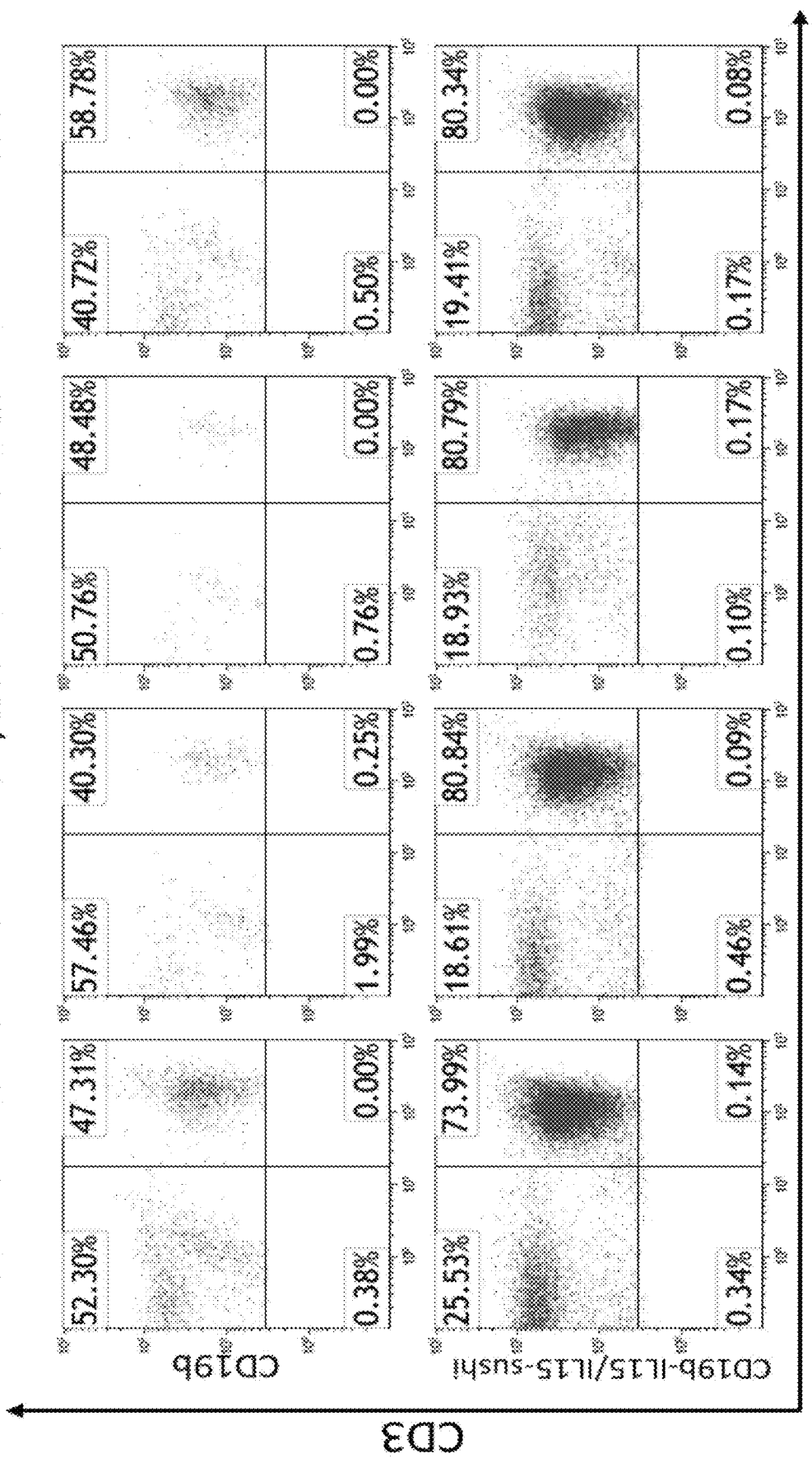

FIG. 43B. Phenotype characteristics of engrafted mouse blood (individual). Mouse blood from FIG. 42C was furthered analyzed by CD8 expression in CD3 positive subsets to reveal the degree of persistent cytotoxic T cells remaining in circulation at survival endpoints. Of particular note is the much higher amount of cytotoxic CD8+ T cells present in the armored CAR cohort mice blood, signifying that the expansion of tumor-killing T cells was greatly augmented, not just by signal transduction from standard target engagement, but also by the inclusion of the IL-15/IL-15sushi based cytokine secretory complex armor." Comparison to the standard CART19 cohort shows the standard response expected from CAR therapy with the expansion of cells solely accomplished by target engagement and subsequent signal response.

Figure 43C:
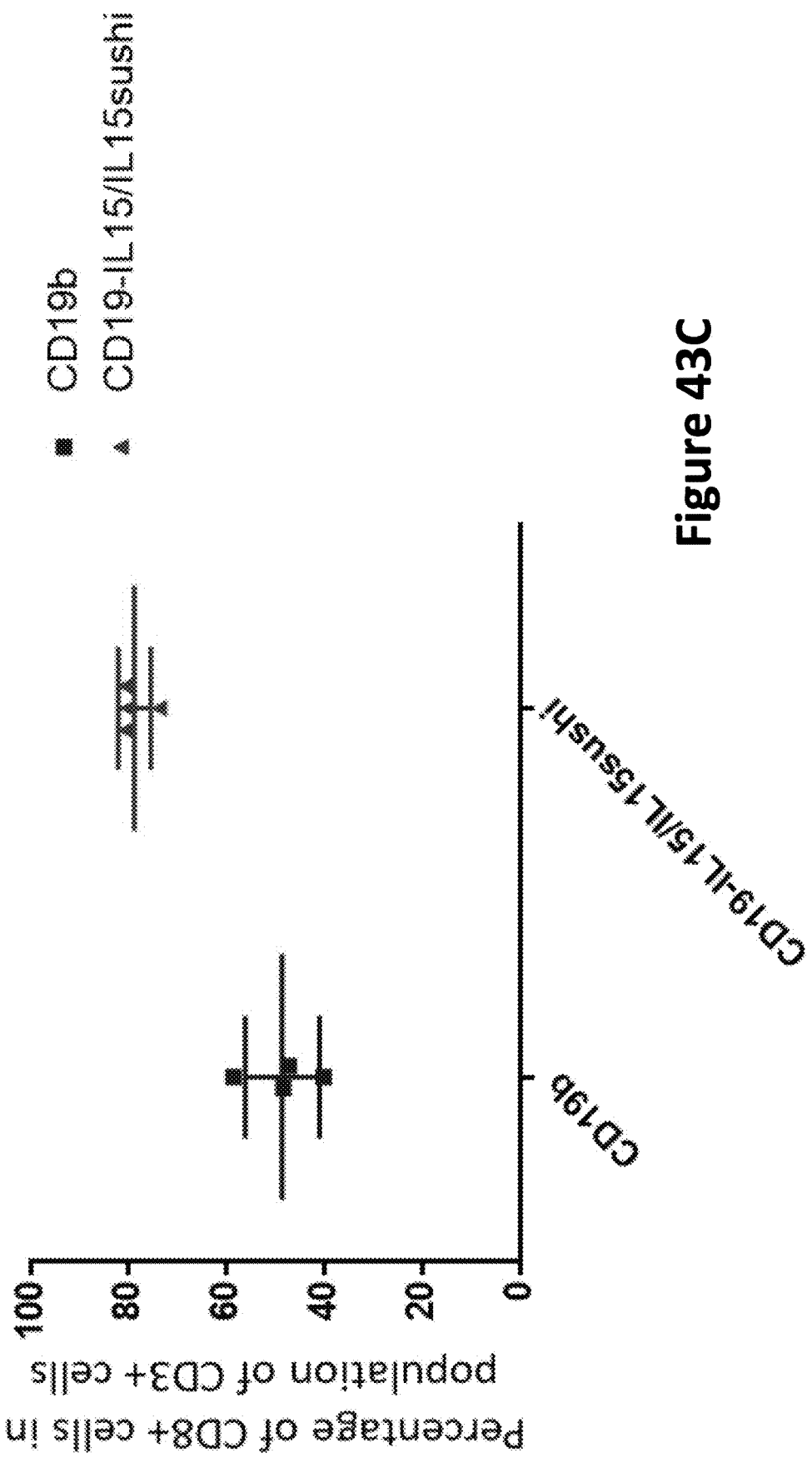

FIG. 43C. Further dissection of engrafted CAR T phenotype characteristics. Mouse blood characteristics from FIG. 42B between CD19b (CART19) and CD19b-IL-15/IL-15sushi CAR T cells were further compared by analyzing the CD4 and CD8 population subsets. In general, there were a higher amount of CD3+ cells in the armored CAR cohort, correlating with increased persistency, a higher average of CD8+ cells within the CD3+ effector T cell population in the armored CAR cohort, and increased ability of the armored CAR T cells to bear the central memory immune-phenotype, correlating with improved immune-surveillance.

Figure 43D:
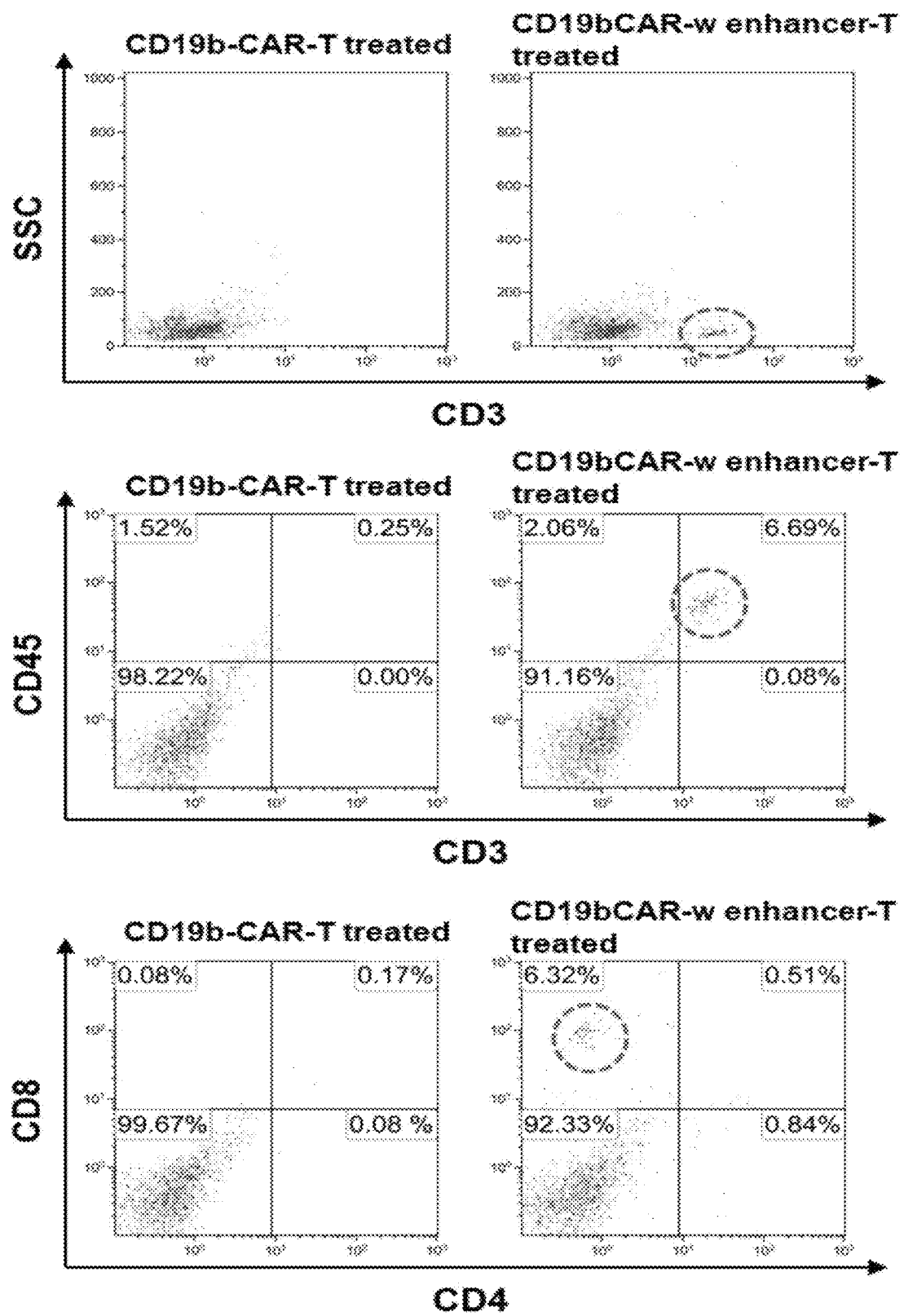

FIG. 43D. Transplantation of detected remaining CD19b-IL-15/IL-15sushi CAR T cells into new mice hosts. The rationale behind this experiment is to show that IL-15/IL-15sushi "armored" CAR T cells will not become immortalized as a result of the engineered cytokine scaffolding to enhance its own function. Reh tumor cells ($0.5 \times 10^6$ cells) were injected intravenously into each NSG mouse after sublethal irradiation. On the following day, $5.6 \times 10^6$ cells of CD19b-CAR-T-cells (CART19) or CD19b w/enhancer (CD19b-IL-15/IL-15sushi) CAR T-cells were injected via IV (intravenously) into each mouse. This condition serves as the first base, where injected CAR T cells will then bind to target tumor cells and expand in order to provide enough cellular material to collect for transplantation.

At Day 36, both groups of treated mouse were euthanized and then whole blood and spleen were collected to evaluate the persistency of CART19 cells or CD19b-IL-15/IL-15sushi T-cells using flow cytometry analysis. Red blood cells in blood and homogenized spleen were lysed using BD Pharm Lyse buffer (BD Biosciences). Flow cytometry analysis showed persistence of CD19b-IL-15/IL-15sushi T-cells (Blue dots circled in green) in mouse. We observed that there were more armored CAR T cells within circulating tissues for collection than CART19 cells. Homogenized spleen cells were labeled with CD3 and CD45 antibodies to detect either CAR T-cells. First, CAR T cells were gated by side scatter (SSC) and CD3 expression to distinguish from mouse cells (A.) and then CD3 positive cells were gated by CD45 and CD3 expression (B.). Left panel is Reh and CD19b-CAR-T-cells treated mouse. Right panels are Reh and CD19bCAR-w enhancer T-cells treated mouse. We only detected CD3-positive CAR T-cells from the armored CAR cohort mouse (Blue dots circled in green). To determine the immune-phenotype of CAR-T-cells, cells were labeled with CD8 and CD4 antibodies (C.) FACS data indicates that CD19b-IL-15/IL-15sushi T-cells are CD8-positive cells but not CD4-positive cells. Finally, we infused $0.5 \times 10^6$ total cells from each spleen homogenate into 2 of each NSG mouse to observe for autonomous growth of armored CAR T cells.

Figure 43E:
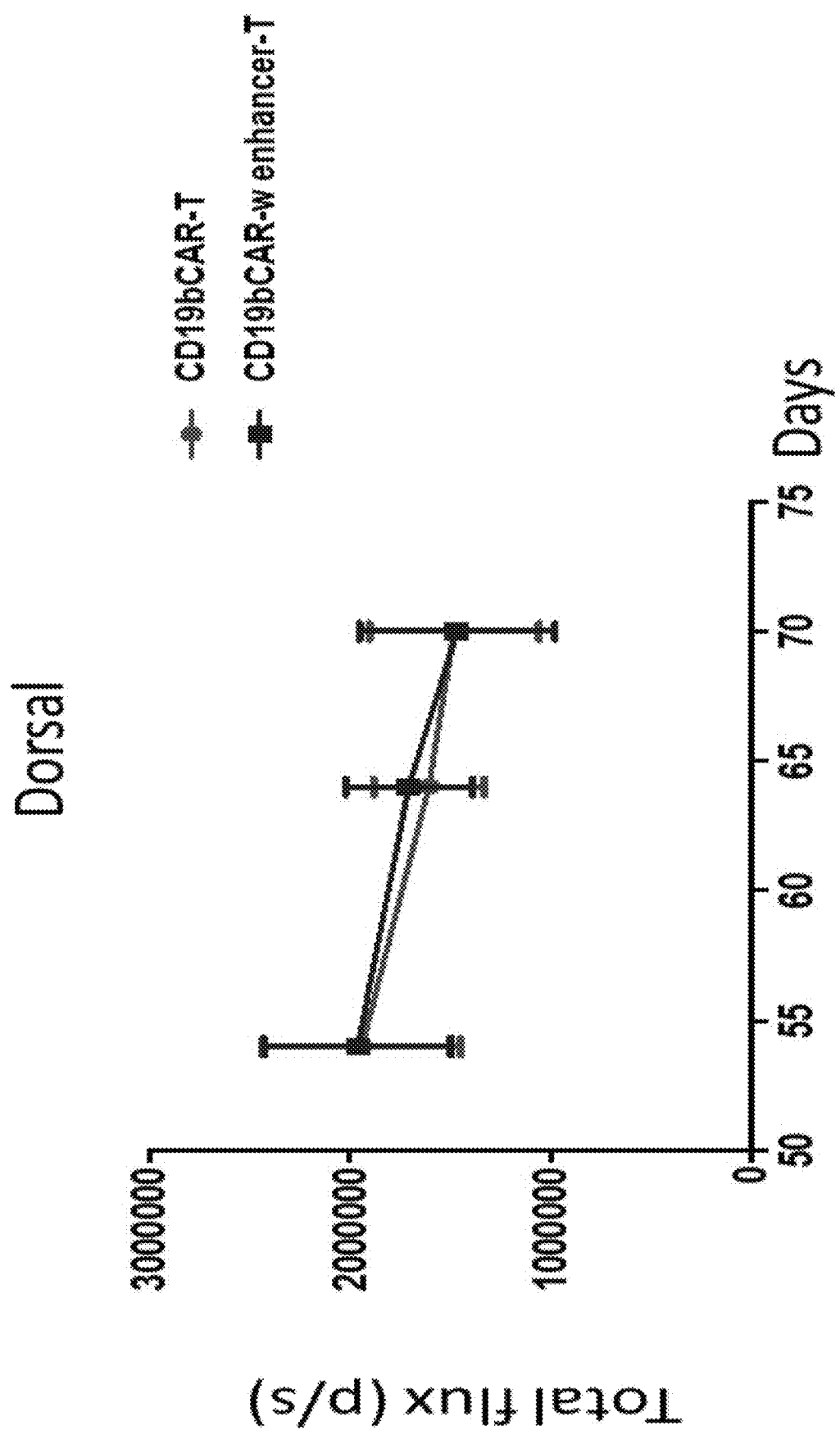

FIG. 43E. Comparison of total flux values (photons /sec) between CD19bCAR- and CD19b-IL-15/IL-15sushi T-cell transplanted mice over time. IVIS imaging of cell fluorescence in both mice groups over time. IVIS fluorescence here represents a semi-quantitative estimation of transplanted cell mass. In this case, auto fluorescence intensities remained around background levels and showed no detectable changes or increase in flux, thus demarcating limited cell growth or expansion of new cells. No growth of tumor or expansion of T cells was seen in transplanted mice.

Figure 43F:
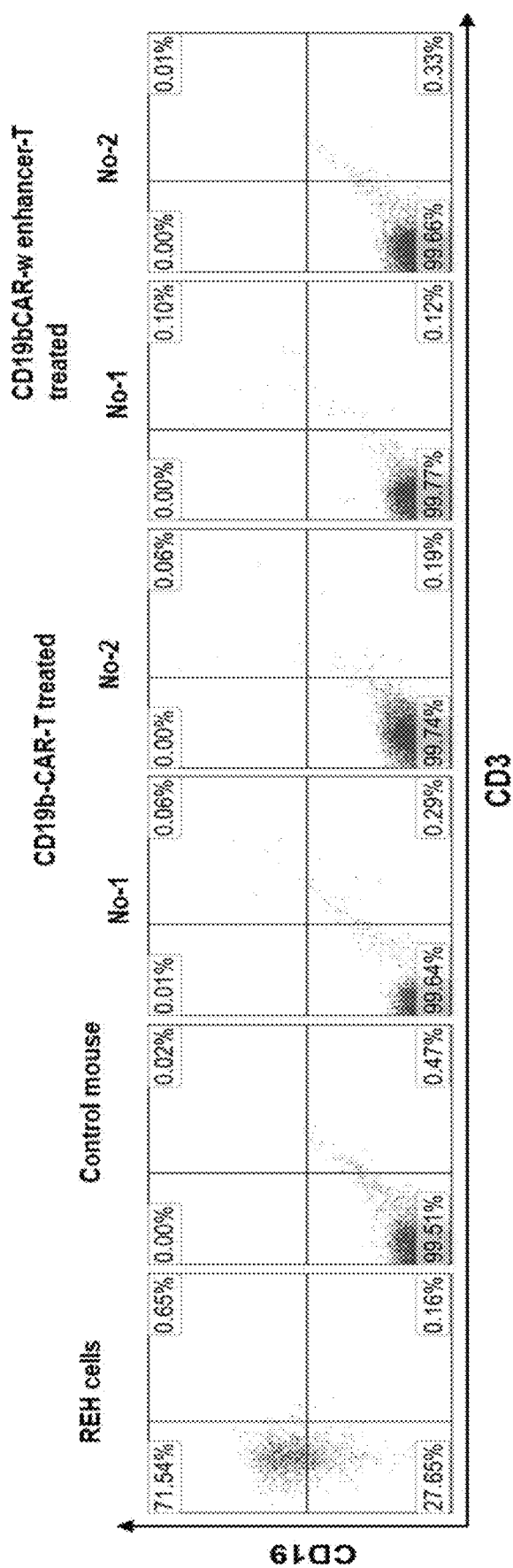

FIG. 43F. Undetectable T cell and tumor populations in transplanted mice on day 64. On day 64, we collected facial peripheral blood from each mouse and labeled using CD3 and CD19 antibodies to evaluate the presence of Reh tumor cells or CAR-T cells using FACS analysis. We could not detect Reh cells or CAR T cells in facial peripheral blood samples in any of the mice, signifying that after transplant, armored CAR T cells are not able to further survive and proliferate, or otherwise become immortalized cells in their own right. This may be of translational use in the clinic, where there may be concern that armored CAR T therapy may result in the expansion of tumor-like CAR T cells.

FIG. 44A. A schematic representation of a super1 CAR construct. Links by P2A and T2A schematic to generate a super1 CAR showing a CAR, GD2 CAR equipped with 4-1BBL and IL-15/IL-15sushi in a single construct. The construct consists of a SFFV promoter driving the expression of three segments, CAR, 4-1BBL and IL-15/IL-15sushi. Upon cleavage of the linkers (P2A and T2A), the CAR (GD2 CAR), 4-1BBL and IL-15/IL-15sushi split and engage upon a target (s). CAR has scFv, hinge region, transmembrane domain, costimulatory domain (including, but not limited to, CD28 or 4-1BB) and intracellular signaling, CD3 zeta chain. 4-1BBL or IL-15/IL-sushi or both provides a synergistic effect of T or NK cell activation and persistency or anti-tumor activity with CD28 or 4-1BB.

Figure 44B:
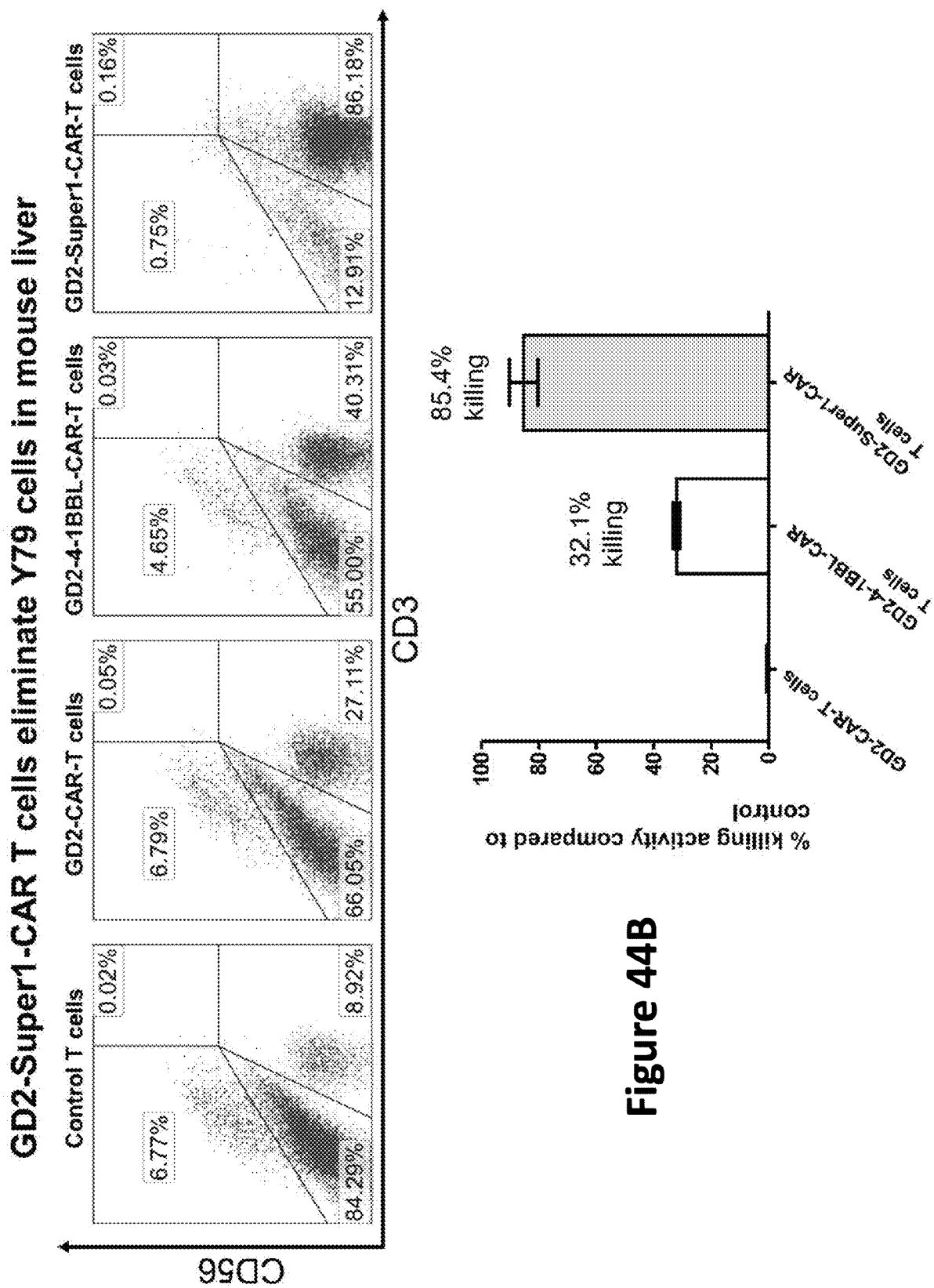

FIG. 44B. GD2-Super1-CAR-T cells virtually eliminate Y79 cells in mouse liver.

(A) Flow cytometry analysis shows persistence of Y79 tumor (Blue dots) in the livers of mice treated with different forms of anti-GD2 CAR T cells. Three days after Y79 cells ($1 \times 10^6$ cells) were injected mice via tail vein, CAR T-cells ($10 \times 10^6$ cells) were infused into mice by I.V.

injection. At day 30 after Y79 tumor injection, mice were euthanized and livers were homogenized to evaluate CAR T efficacy. Homogenized liver cells were labeled with mouse anti-human CD3 and CD56 antibodies to detect human T cells and Y79 tumor cells, respectively. A representation of a mouse given control T cells is shown on the left; mouse treated with GD2CAR (left center), GD2-4-1BBL CAR (right center), and GD2-Super1 CAR (right) T cells. Elimination of tumor cells was associated with high labels of T-cells. GD2-4-BBL CAR is a GD2 CAR co-expressing 4-1BBL ligand.

(B) Graph indicating percent killing activity against Y79 cells by each CAR treated mice compared to control mice (n=2). From these data, especially, only GD2 Super1 CAR T were able to virtually eliminate Y79 cells in liver.

Figure 44C:
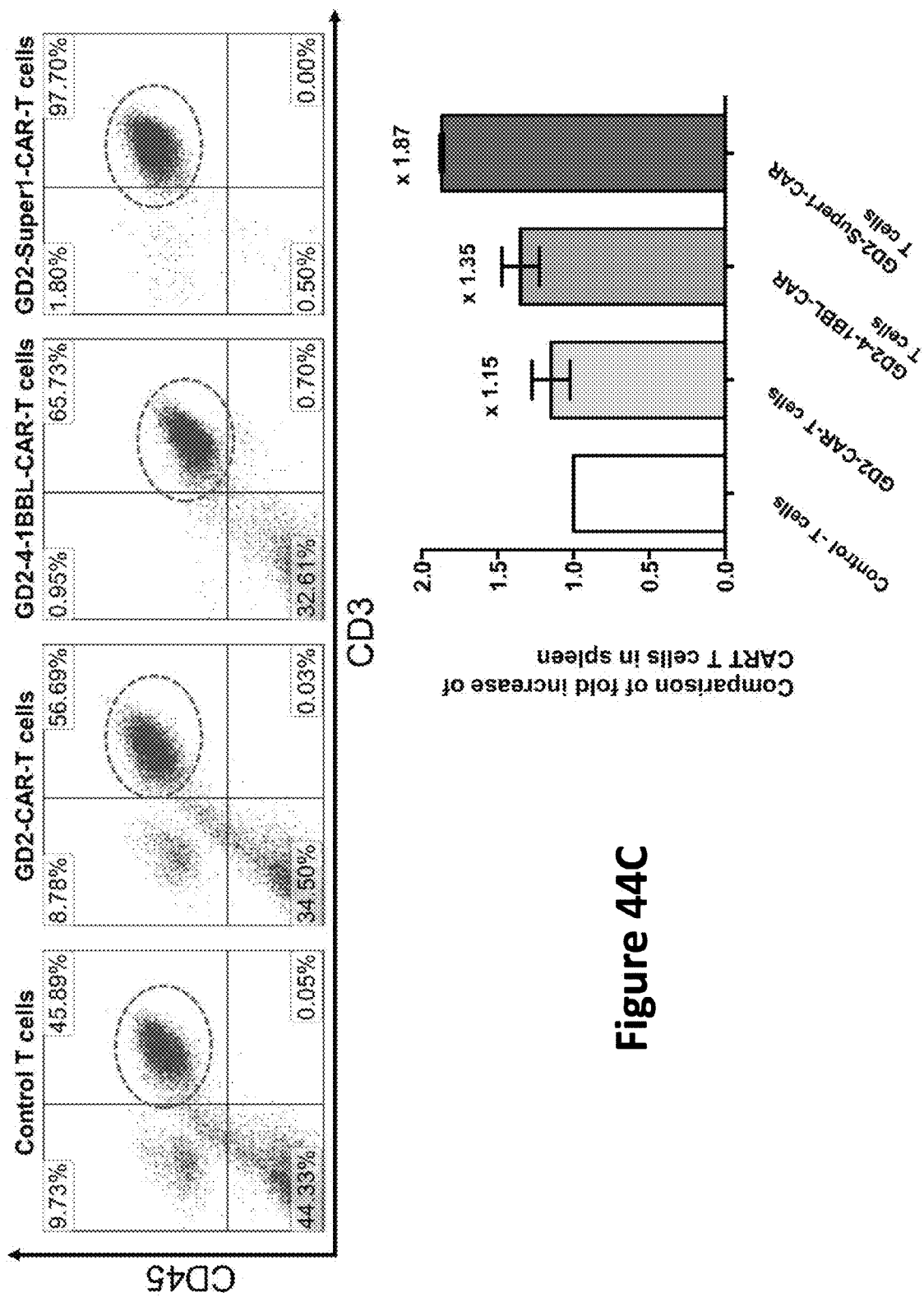

FIG. 44C. GD2-Super1-CAR T cells exhibit greater persistence in mouse spleen.

(A) Flow cytometry analysis shows persistence of CAR T cells (circled) in the livers of mice treated with different forms of anti-GD2 CAR T cells. Three days after Y79 cells ($1\times10^6$ cells) were injected mice via tail vein, CAR T-cells ($10\times10^6$ cells) were infused into mice by I.V. injection. At day 30 after Y79 tumor injection, mice were euthanized and spleens were homogenized to evaluate CAR T efficacy. Homogenized spleen cells were labeled with mouse anti-human CD3 and CD45 antibodies to detect human T cells. A representation of a mouse given control T cells is shown on the left; mouse treated with GD2CAR (left center), GD2-4-1BBL CAR (right center), and GD2-super1 CAR (right) T cells.

(B) Graph indicating fold-increase of CAR T cells in treated mice compared to control T mice (n=2). From these data, especially, GD2-Super CAR T cells were well expanded compared to control T-cells in total mouse spleen cells.

Figure 44D:
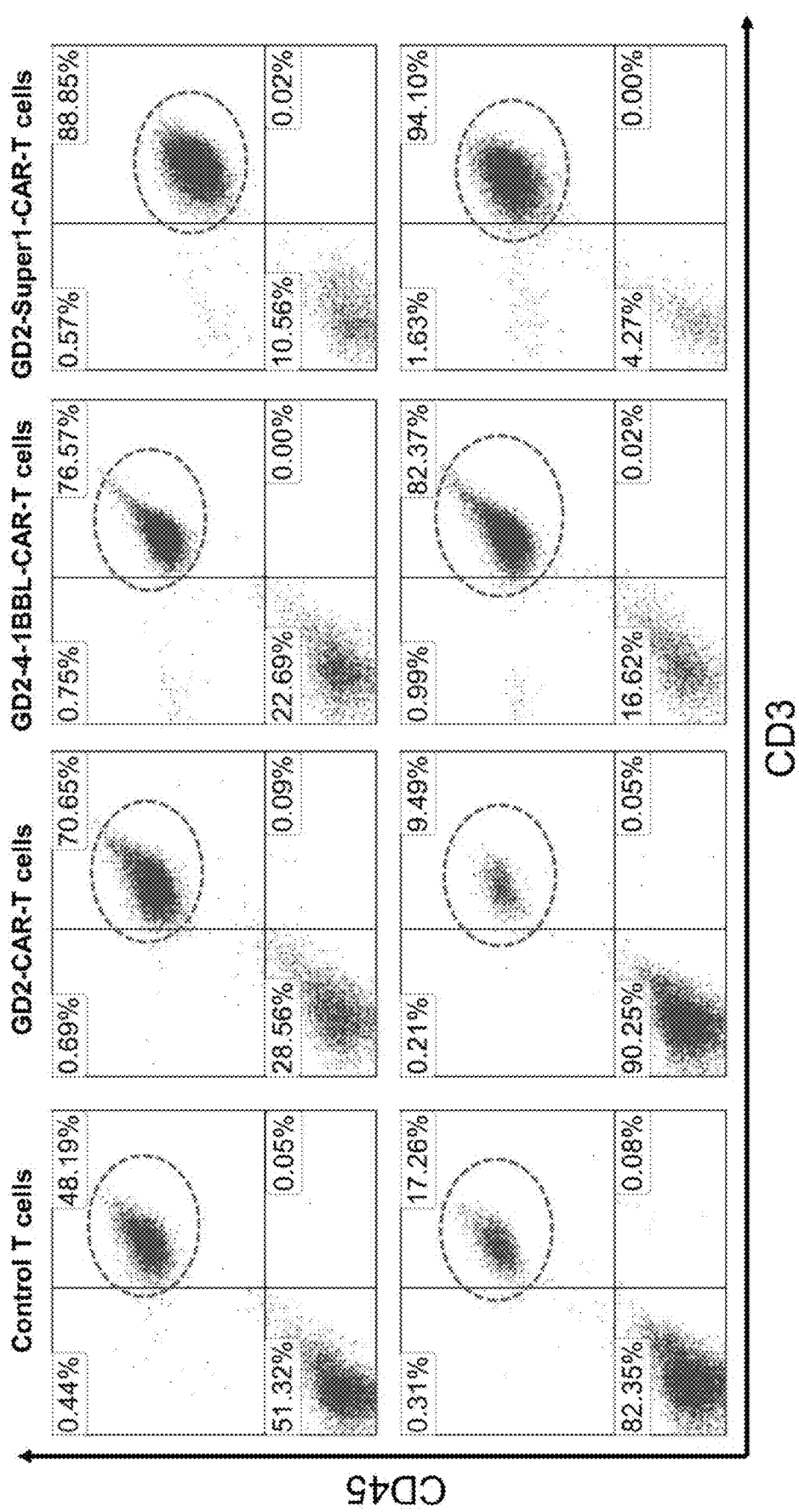

FIG. 44D. Persistence of CAR T cells in mouse blood.

(A) Flow cytometry analysis shows persistence of CAR T cells (circled) in the whole blood of mouse treated with different forms of anti-GD2 CAR T cells. Three days after Y79 cells ($1\times10^6$ cells) were injected mice via tail vein, CAR T-cells ($10\times10^6$ cells) were infused into mice by I.V. injection. At day 30 after Y79 tumor injection, mice were euthanized and whole blood was collected to evaluate CAR T persistence. Whole blood cells were labeled with mouse anti-human CD3 and CD45 antibodies, to detect human T cells. A representation of a mouse given control T cells is shown on the left; mice treated with GD2CAR (left center), GD2-4-1BBL CAR (right center), and GD2-Super1 CAR (right) T cells.

Figure 44E:
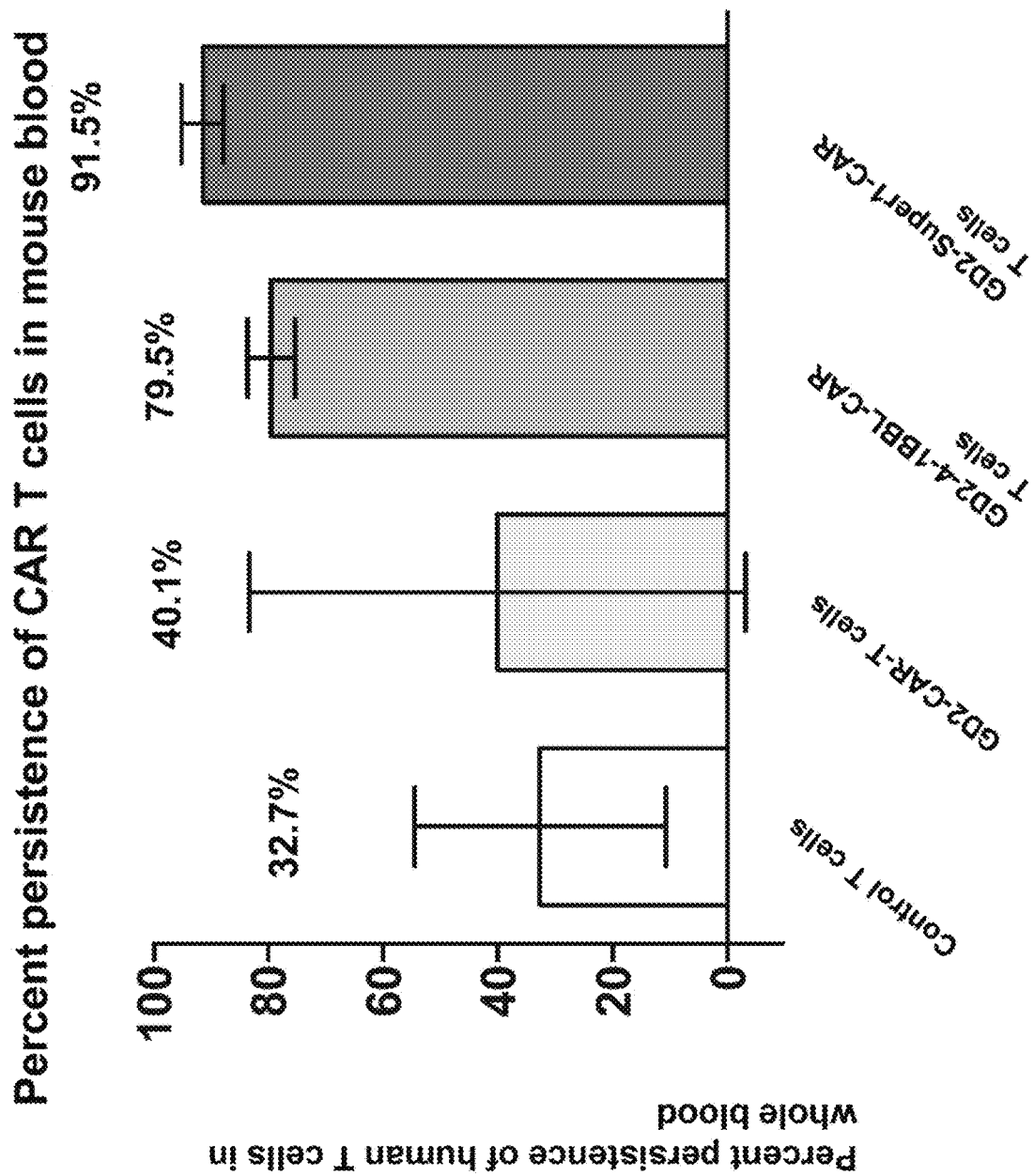

FIG. 44E. Bar graph representing the percent persistence of human T cells in whole blood samples, relative to the number of total cells analyzed by flow cytometry (n=2 each).

Figure 45:
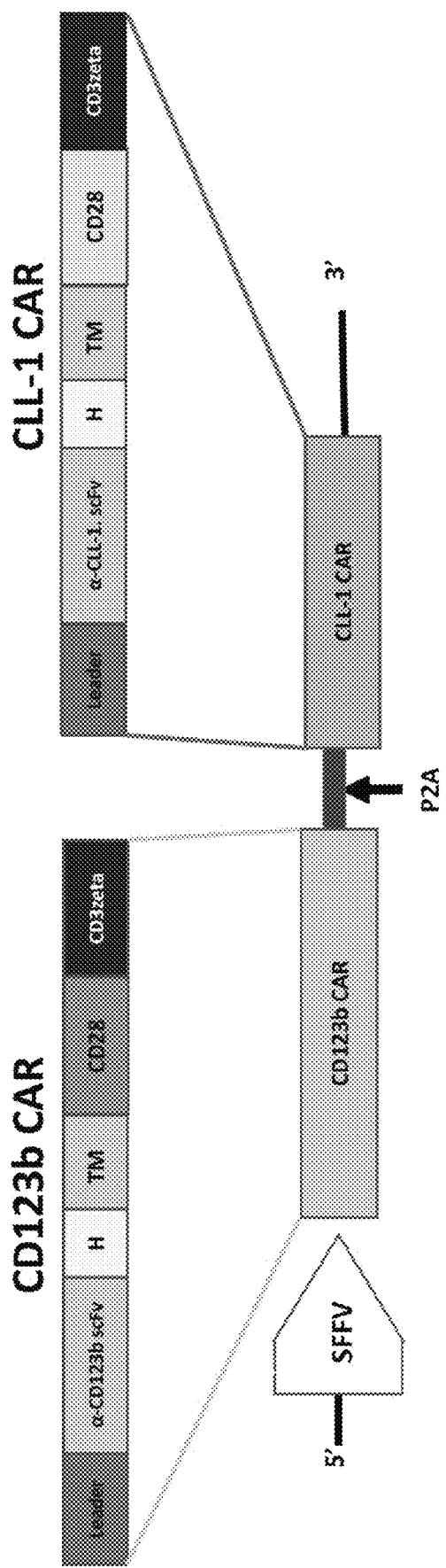

FIG. 45. A schematic representation of cCAR-T construct. The construct comprises a SFFV promoter driving the expression of multiple modular units of CARs linked by a P2A peptide. Upon cleavage of the linker, the cCARs split and engage upon targets expressing CD123b and/or CLL1. As a novel cCAR construct, the activation domains of the construct may include, but is not limited to, 4-1BB on the CD123 segment and a CD28

Figure 46A:
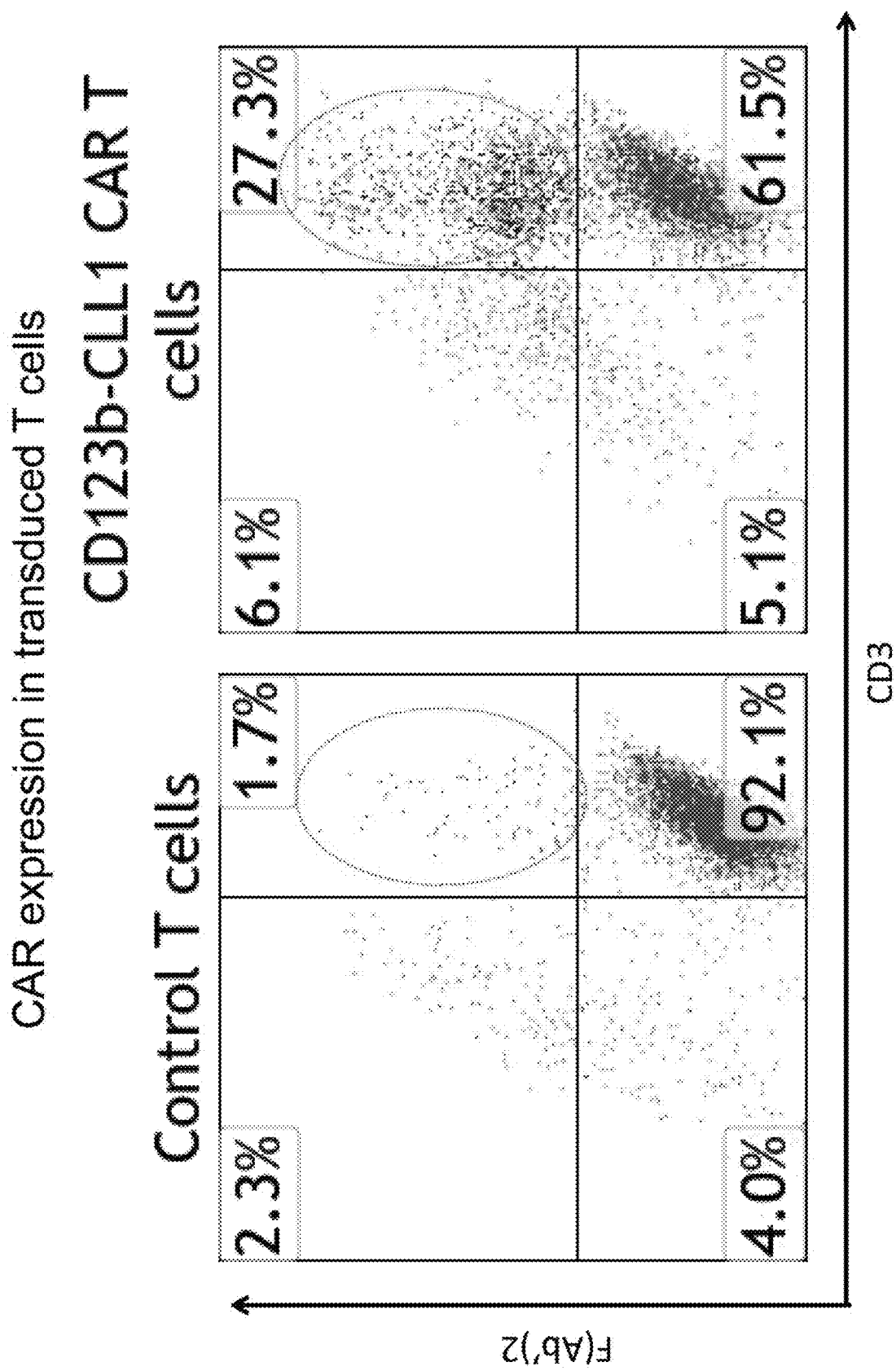

FIG. 46A. Expression of CD123b-CLL1 CAR T cells. Buffy coat cells were activated 3 days with anti-CD3 antibody. Cells were transduced with either control vector (left) or CD123b-CLL1 CAR (right) lentiviral supernatant. After 3 days of incubation, cells were harvested and labeled for flow cytometry.

Figure 46B:
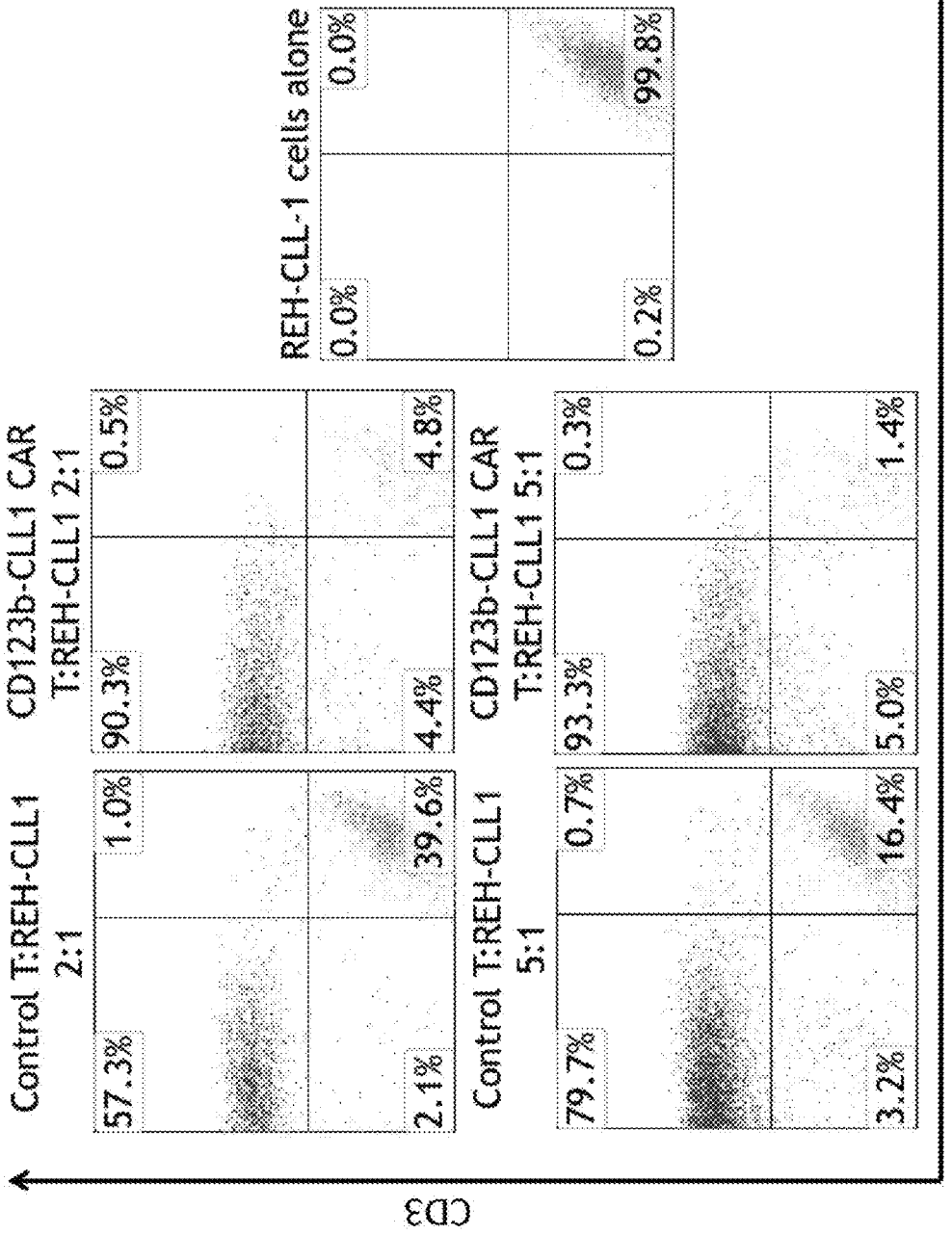

FIG. 46B. CD123b-CLL1 CAR T cells efficiently lyse REH tumor cell line, which is synthetically expressing CLL-1, in co-culture assays. Co-culture experiments were performed at an effector to target ratio of 2:1 or 5:1 for 24 hours and were directly analyzed by flow cytometry for CLL-1 and CD3. Each assay consisted of REH target cells alone (left), control T cells (center panels) and CLL1-CD33b CAR T cells (right panels). REH cells are represented as purple dots.

Figure 46C:
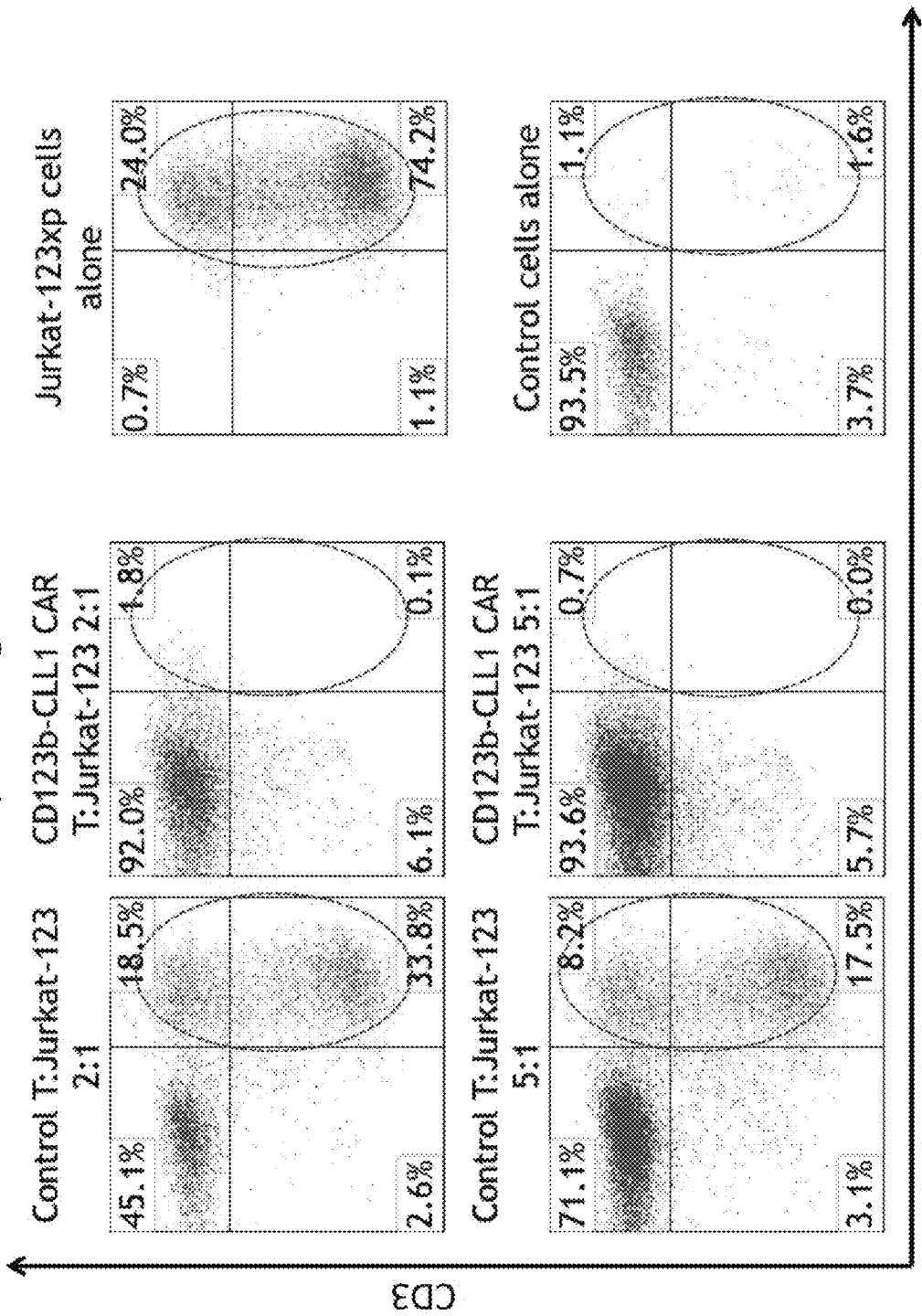

FIG. 46C. CD123bCLL1 CAR T cells efficiently lyse Jurkat tumor cell line, which is synthetically expressing CD123, in co-culture assays. Co-culture experiments were performed at an effector to target ratio of 2:1 or 5:1 for 24 hours and were directly analyzed by flow cytometry for CD123 and CD3. Each assay consisted of control T cells (left panels) and CD123bCLL1 CAR T cells (center panels). Target Jurkat cells expressing CD123 and control T cells alone, are shown on the right. Jurkat-123 cells, which partially express CD3, are circled and are represented as purple dots.

Figure 46D:
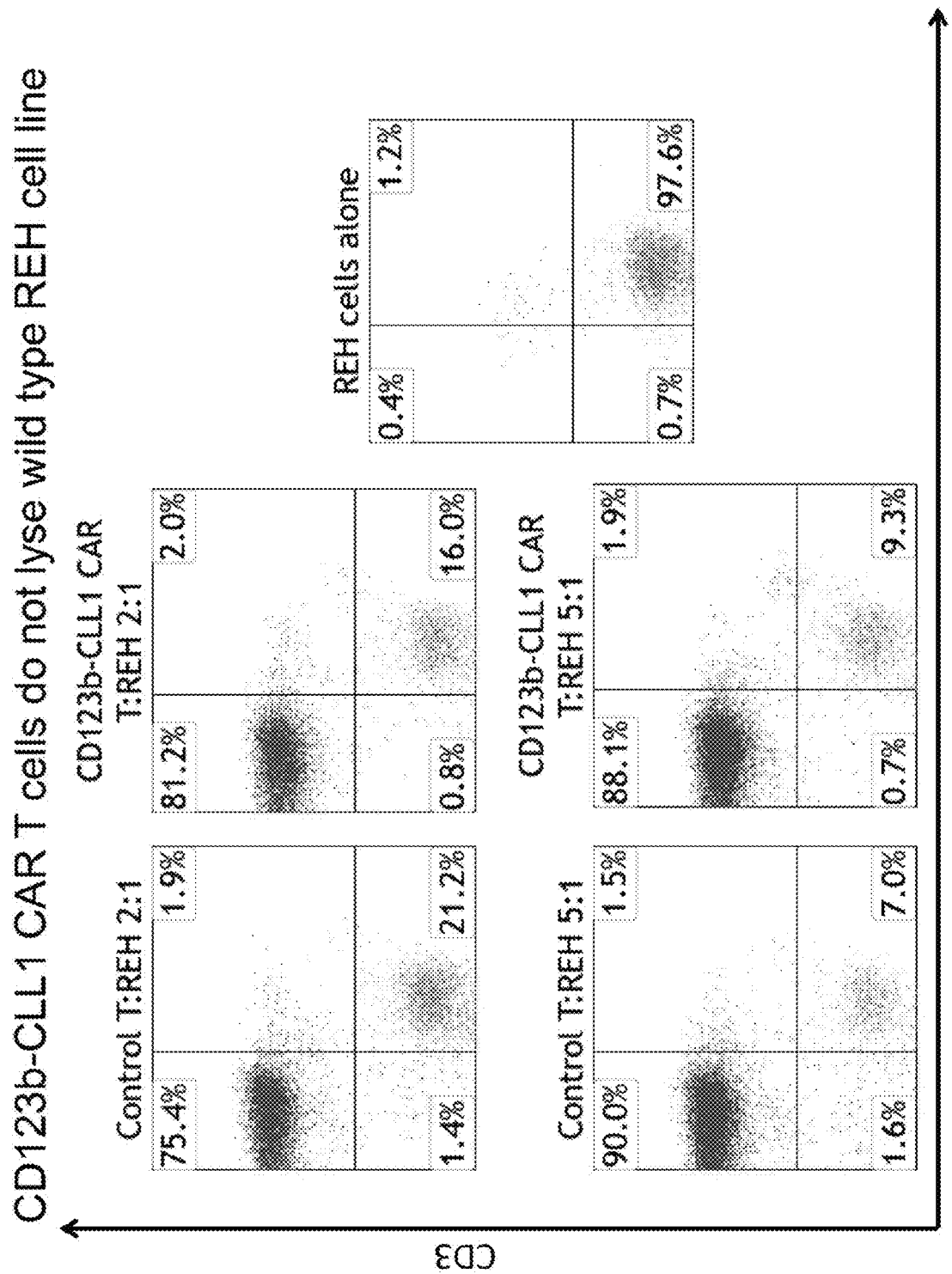

FIG. 46D. CD123b-CLL1 CAR T cells do not lyse wild type REH tumor cell line in co-culture assays. Co-culture experiments were performed at an effector to target ratio of 2:1 or 5:1 for 6 hours and were directly analyzed by flow cytometry for CD19 and CD3. Each assay consisted of control T cells (left panels) and CD123b-CLL1 CAR T cells (center panels). REH wild type cells alone, shown at the right, are represented as light blue dots.

Figure 46E:
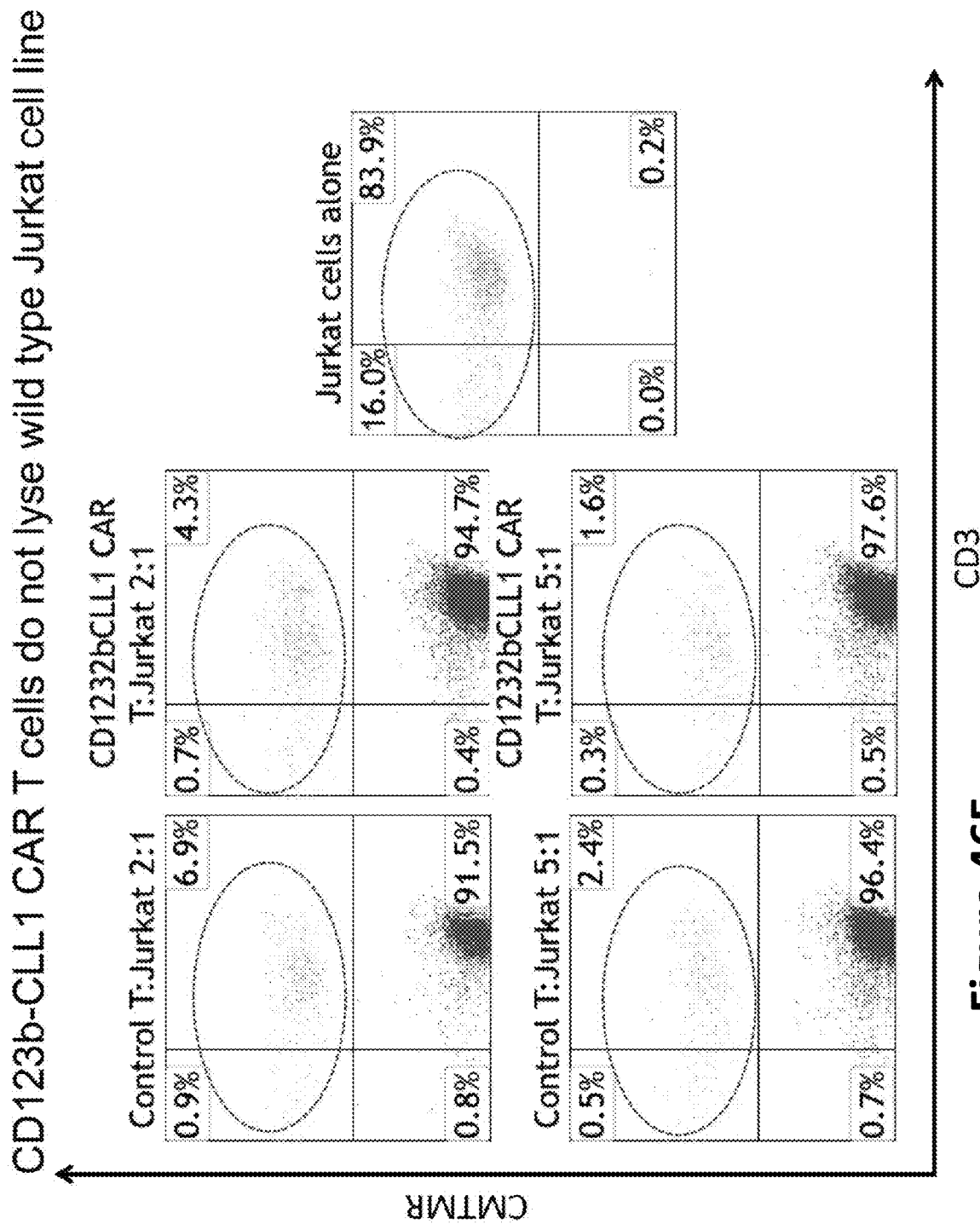

FIG. 46E. CD123bCLL1 CAR T cells do not lyse wild type Jurkat tumor cell line in co-culture assays. Jurkat cells were prestained with CMTMR membrane dye to distinguish them from T cells. Co-culture experiments were performed at an effector to target ratio of 2:1 or 5:1 for 6 hours and were directly analyzed by flow cytometry for CMTMR and CD3. Each assay consisted of control T cells (left panels) and CD123bCLL1 CAR T cells (center panels). Jurkat cells alone, are shown at the right. Jurkat cells, which partially express CD3, are circled and are represented as orange dots.

Figure 47:
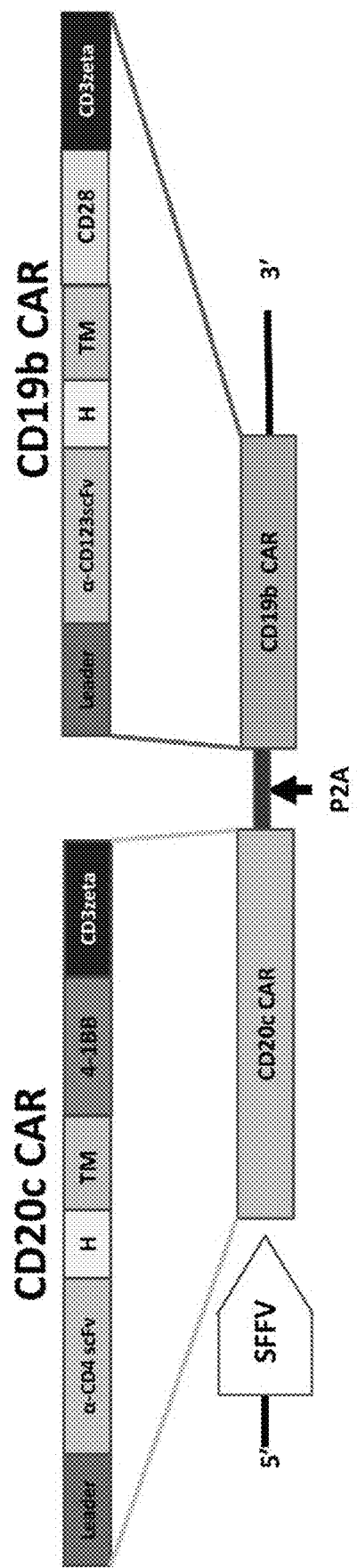

FIG. 47. A schematic representation of cCAR-T construct. The construct comprises a SFFV promoter driving the expression of multiple modular units of CARs linked by a P2A peptide. Upon cleavage of the linker, the cCARs, CD20c-CD19b cCAR split and engage upon targets expressing CD20 and/or CD19. As a novel cCAR construct, the activation domains of the construct may include, but is not limited to, 4-1BB on the CD20c CAR segment and a CD28 region on the CD19b CAR segment.

Figure 48A:
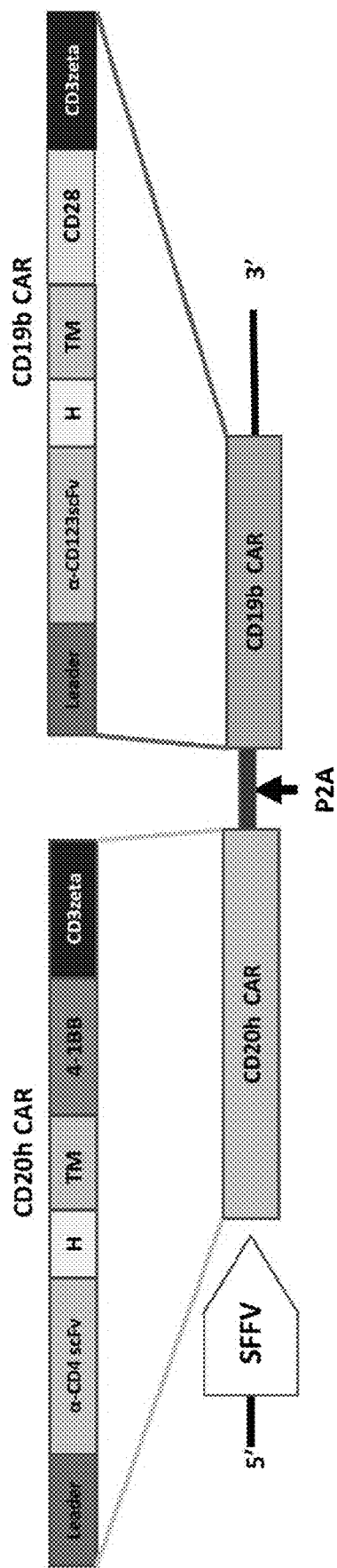

FIG. 48A. A schematic representation of cCAR-T construct. The construct comprises a SFFV promoter driving the expression of multiple modular units of CARs linked by a P2A peptide. Upon cleavage of the linker, the cCARs, CD20h-CD19b cCAR split and engage upon targets expressing CD20 and/or CD19. As a novel cCAR construct, the activation domains of the construct may include, but is not limited to, 4-1BB on the CD20h CAR segment and a CD28 region on the CD19b CAR segment. The CD20h CAR section in the cCAR contains a humanized anti-CD20 scFv targeting CD20 expressing cells.

Figure 48B:
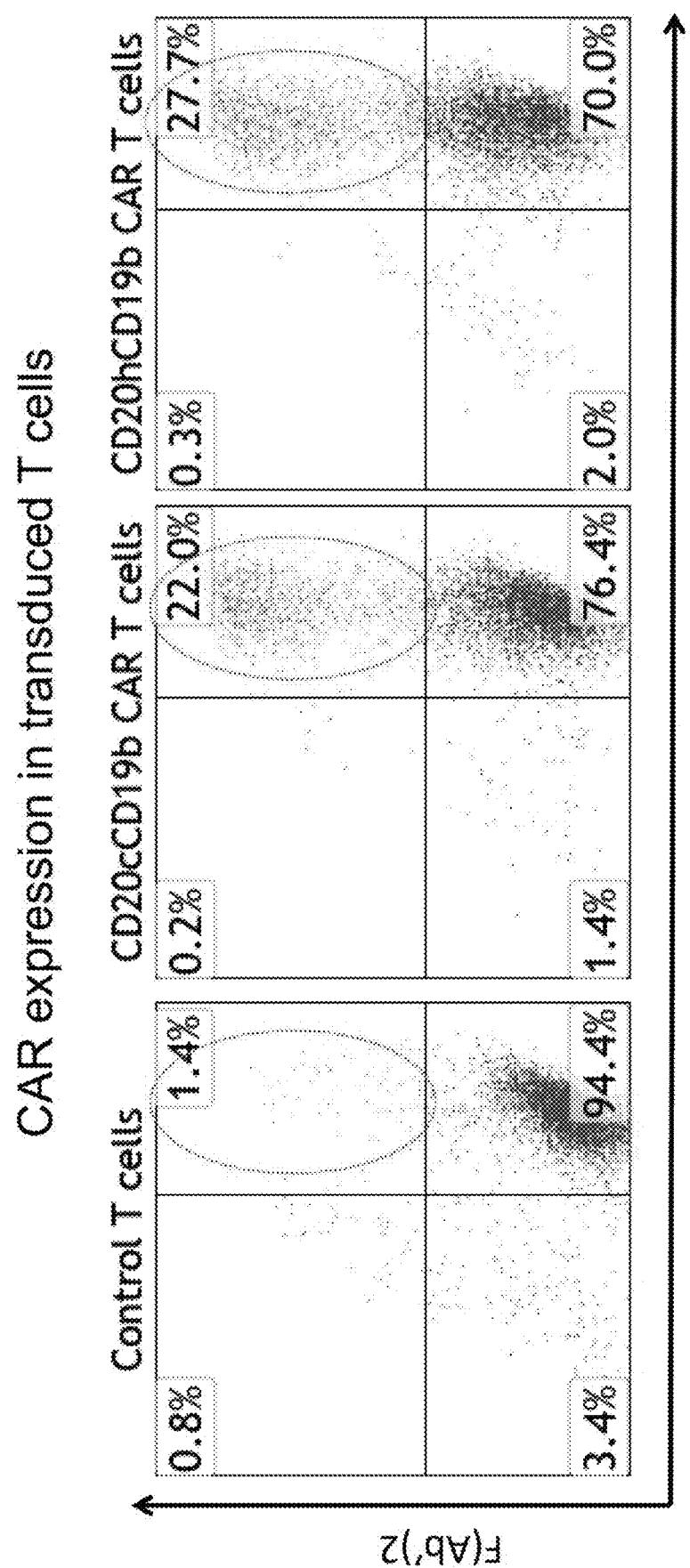

FIG. 48B. Expression of CD20cCD19b CAR T cells. Buffy coat cells were activated 3 days with anti-CD3 antibody. Cells were transduced with either control vector (left), CD20cCD19b or CD20hCD19b CAR (right) lentiviral supernatant. After 3 days of incubation, cells were harvested and labeled for flow cytometry.

Figure 48C:
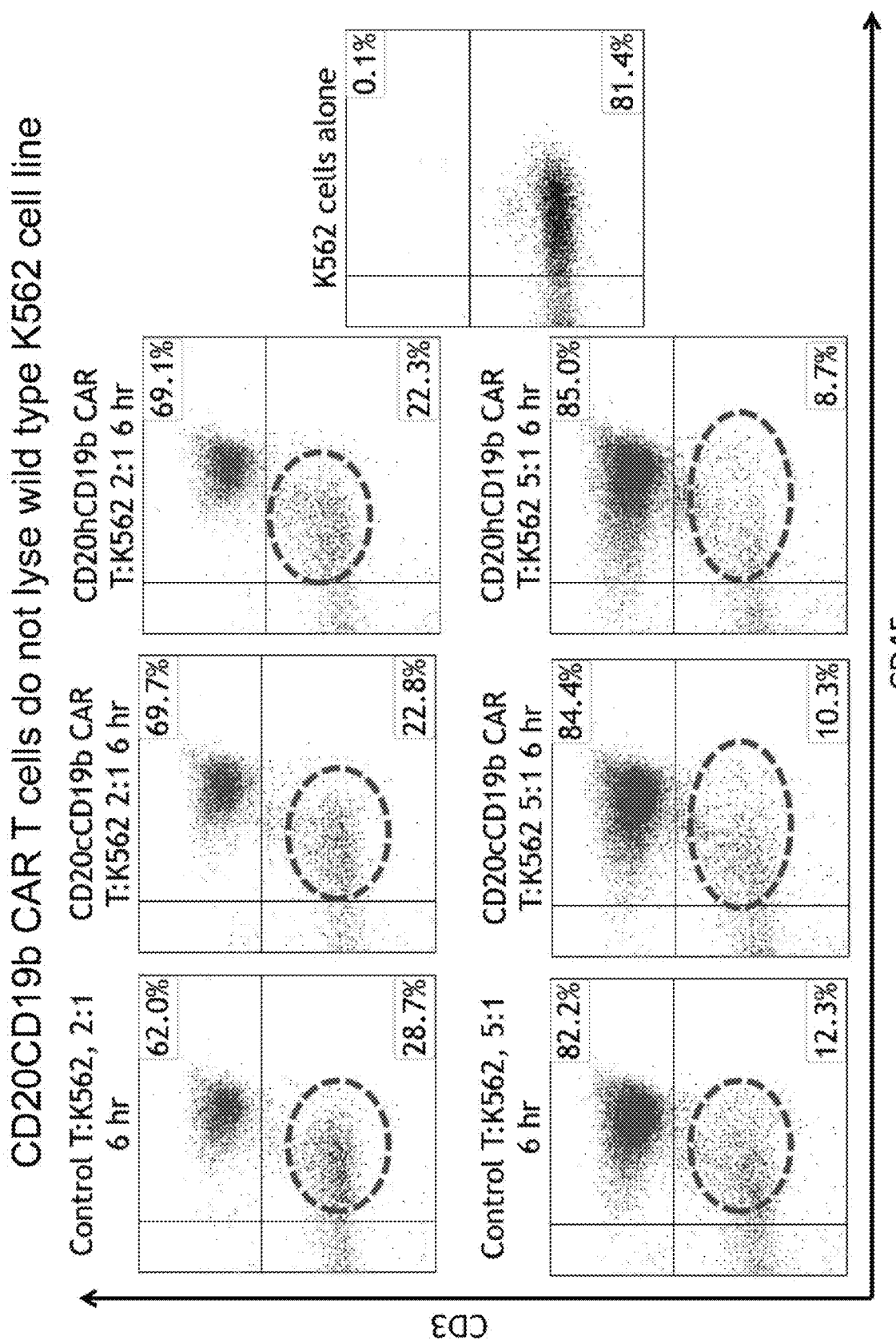

FIG. 48C. CD20cCD19b and CD20hCD19b CAR T cells do not lyse K562 tumor cell line in co-culture assays. Co-culture experiments were performed at an effector to target ratio of 2:1 or 5:1 for 6 hours and were directly analyzed by flow cytometry for CD3 and CD45. Each assay consists of K652 target cells alone (right), control T cells (left) and either CD20cCD19b or CD20hCD19b CAR T cells (center panels). Target cells are represented as blue dots. (N=2)

Figure 48D:
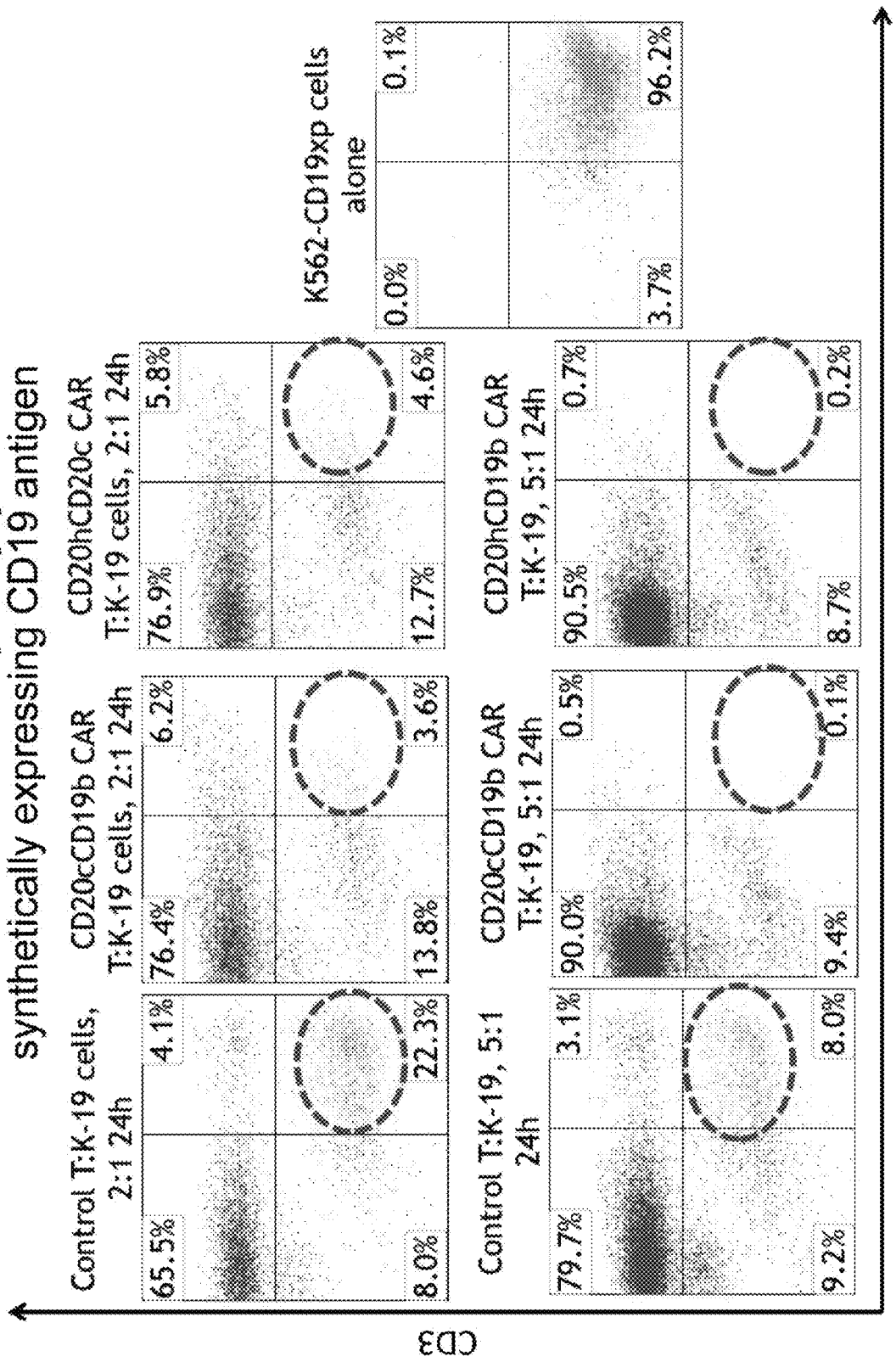

FIG. 48D. cCAR T cells lyse CD19 synthetically-expressing K562 tumor cell line in co-culture assays. Co-culture experiments were performed at an effector to target ratio of 2:1 or 5:1 for 24 hours and were directly analyzed by flow cytometry for CD19 and CD3. Each assay consists of K562-CD19xp target cells (K562 expressing CD19, K-19) alone (right side), control T cells (left panels) and either CD20cCD19b or CD20hCD19b CAR T cells (center panels). Target cells are represented as green dots.

Figure 48E:
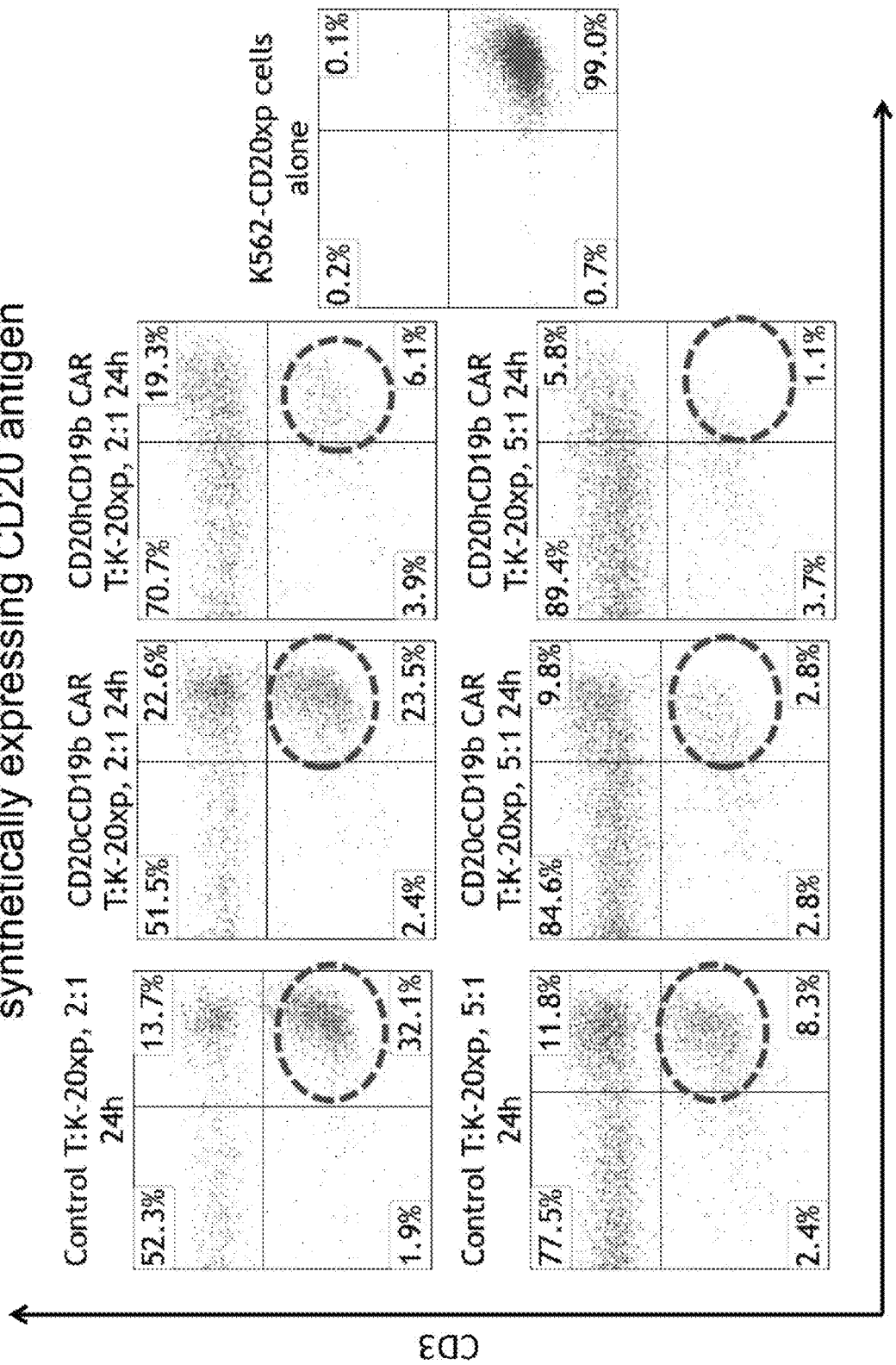

FIG. 48E. cCAR T cells lyse CD20 synthetically-expressing K562 tumor cell line (K-20) in co-culture assays. Coculture experiments were performed at an effector to target ratio of 2:1 or 5:1 for 24 hours and were directly analyzed by flow cytometry for CD20 and CD3. Each assay consists of K562-CD20xp target cells (K-20) alone (right side), control T cells (left panels) and either CD20cCD19b or CD20hCD19b CAR T cells (center panels). Target cells are represented as purple dots.

Figure 48F:
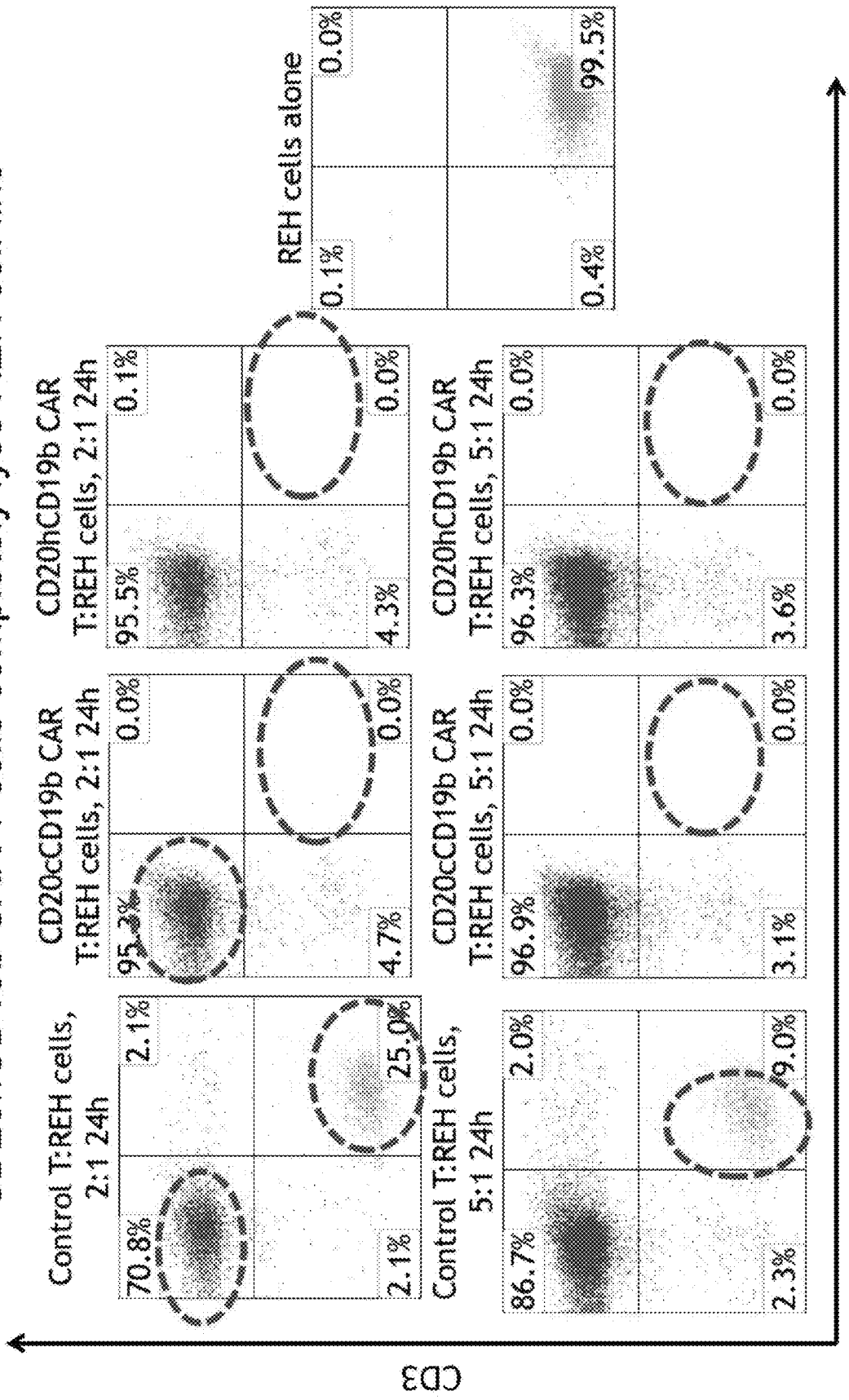

FIG. 48F. cCAR T cells completely lyse CD19-expressing REH tumor cell line in co-culture assays. Co-culture experiments were performed at an effector to target ratio of 2:1 or 5:1 for 24 hours and were directly analyzed by flow cytometry for CD19 and CD3. Each assay consists of REH target cells alone (right side), control T cells (left panels) and either CD20cCD19b or CD20hCD19b CAR T cells (center panels). Target cells are represented as orange dots.

Figure 48G:
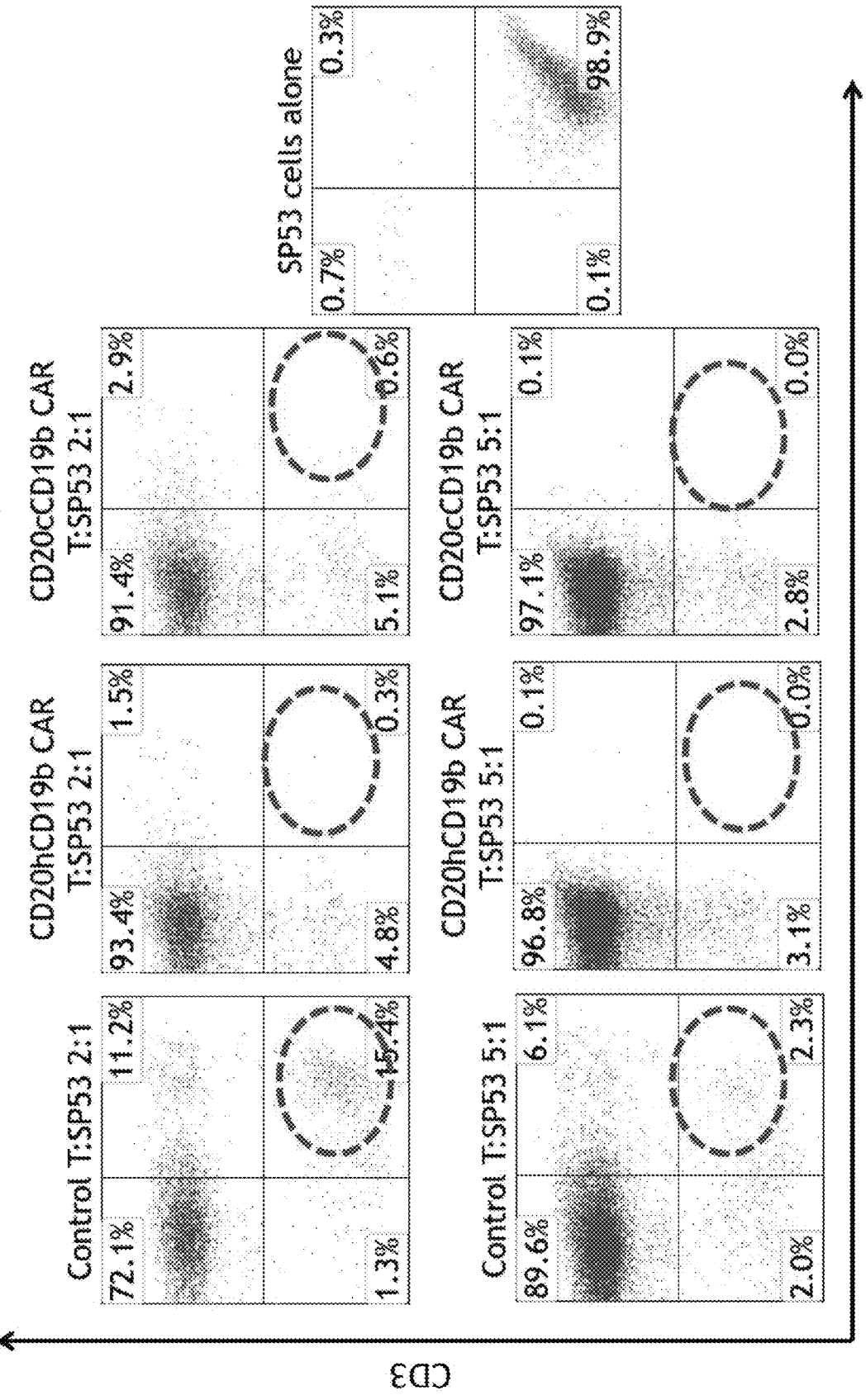

FIG. 48G. cCAR T cells completely lyse SP53 tumor cell line, which expresses both CD19 and CD20 antigens in co-culture assays. Co-culture experiments were performed at an effector to target ratio of 2:1 or 5:1 for 24 hours and were directly analyzed by flow cytometry for CD19 and CD3. Each assay consists of SP53 target cells alone (right side), control T cells (left panels) and either CD20cCD19b or CD20hCD19b CAR T cells (center panels). Target cells are represented as turquoise dots. (N=2)

Figure 48H:
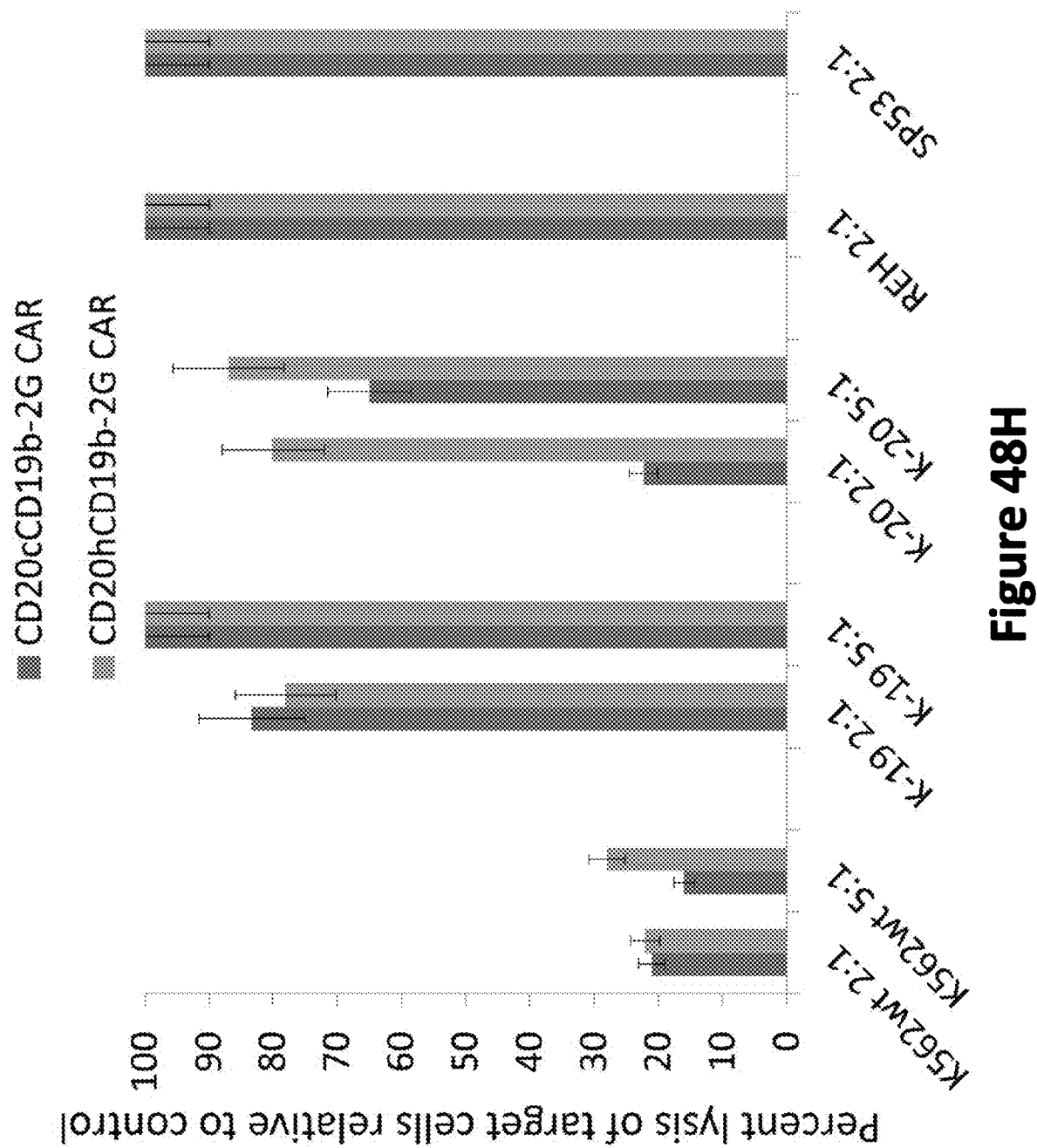

FIG. 48H. Summary of co-culture results. K562wt (wild type): 6 hour co-culture. All others, 24 hours. (N=2)

Figure 49A:
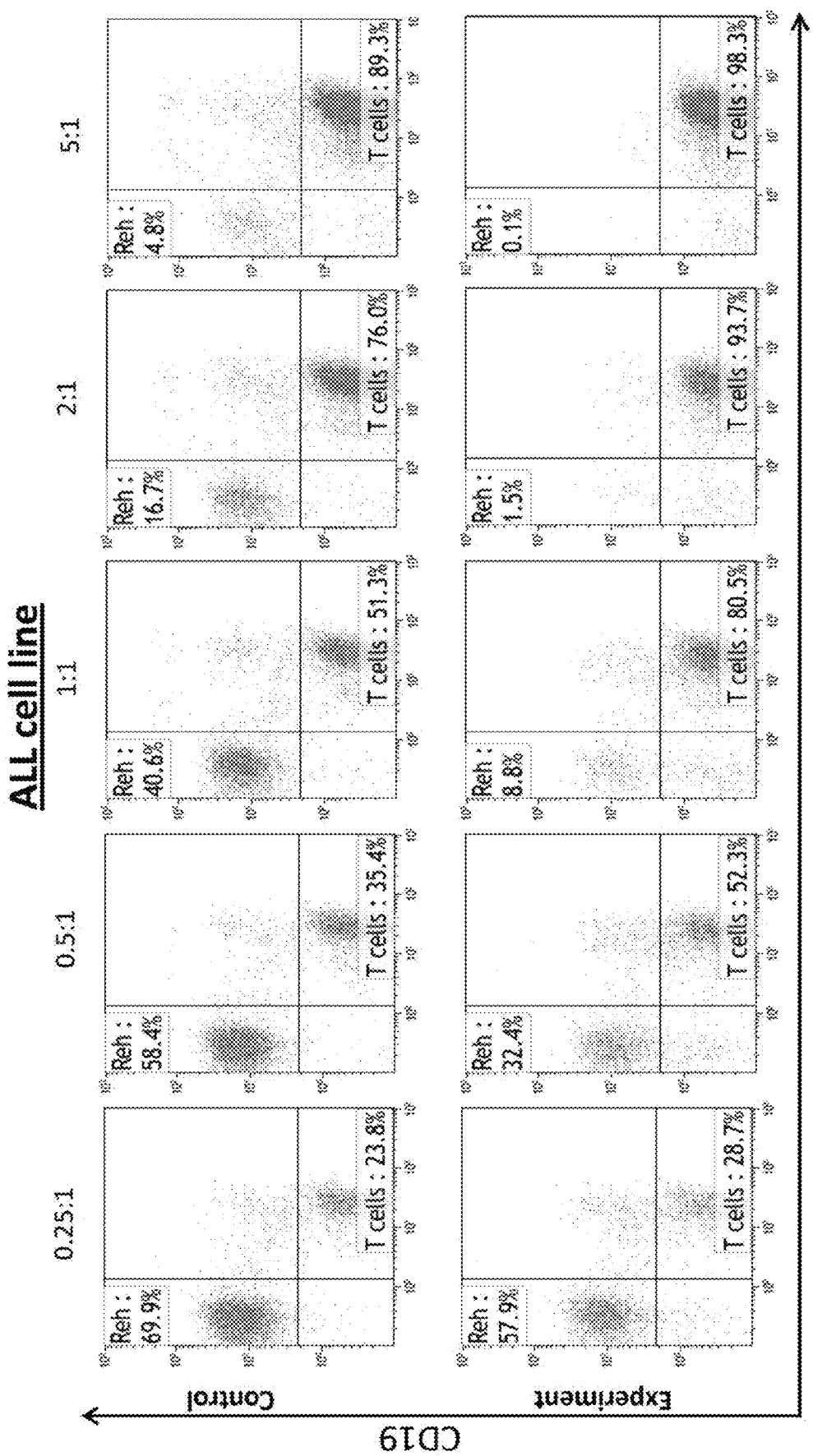

FIG. 49A. CD20h-CD19b cCAR T cells exhibit dose-dependent ablation of CD19+ Reh B-ALL cell line (FACS). In order to characterize the dose-dependent anti-tumor activity of the CD20h-CD19b CAR T cells, we conducted co-cultures against the CD19+ B-ALL tumor cell line at escalating E:T ratios from 0.25 to 1 (25 000 T cells to 100 000 Reh cells). Co-cultures were carried out overnight and labeled with CD3 and CD19 antibodies before FACS analysis was performed to analyze the extent of residual tumor cells. We found that generally, increased effector cell numbers corresponded with higher rates of observed target tumor cell lysis. Graph next slide.

Figure 49B:
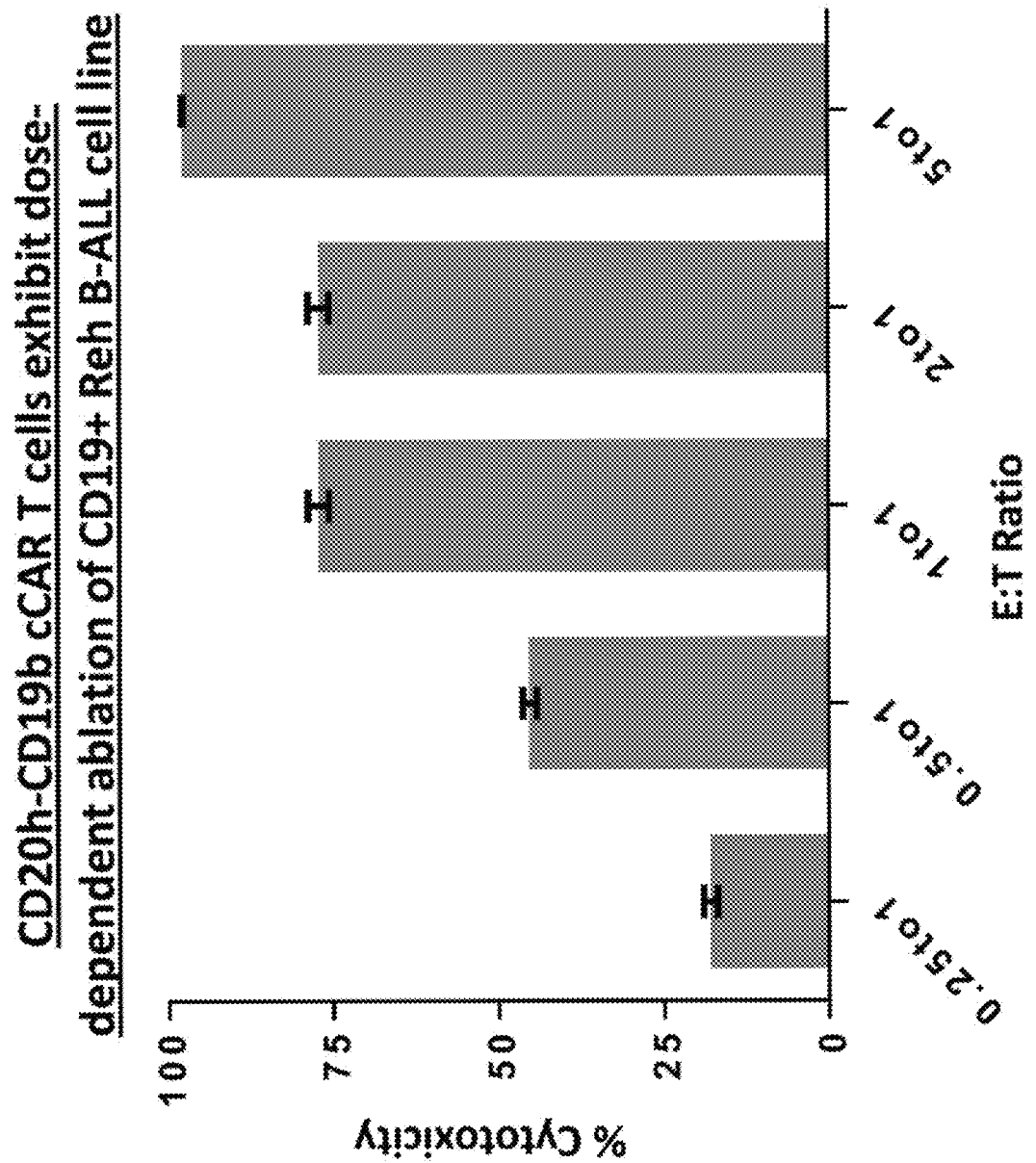

FIG. 49B. CD20h-CD19b cCAR T cells exhibit dose-dependent ablation of CD19+ Reh B-ALL cell line (graph). In order to characterize the dose-dependent anti-tumor activity of the CD20h-CD19b CAR T cells, we conducted co-cultures against the CD19+ B-ALL tumor cell line at escalating E:T ratios starting from 0.25 to 1 (25 000 T cells to 100 000 Reh cells). Co-cultures were carried out overnight and labeled with CD3 and CD19 antibodies before FACS analysis was performed to analyze the extent of residual tumor cells.

Figure 49C:
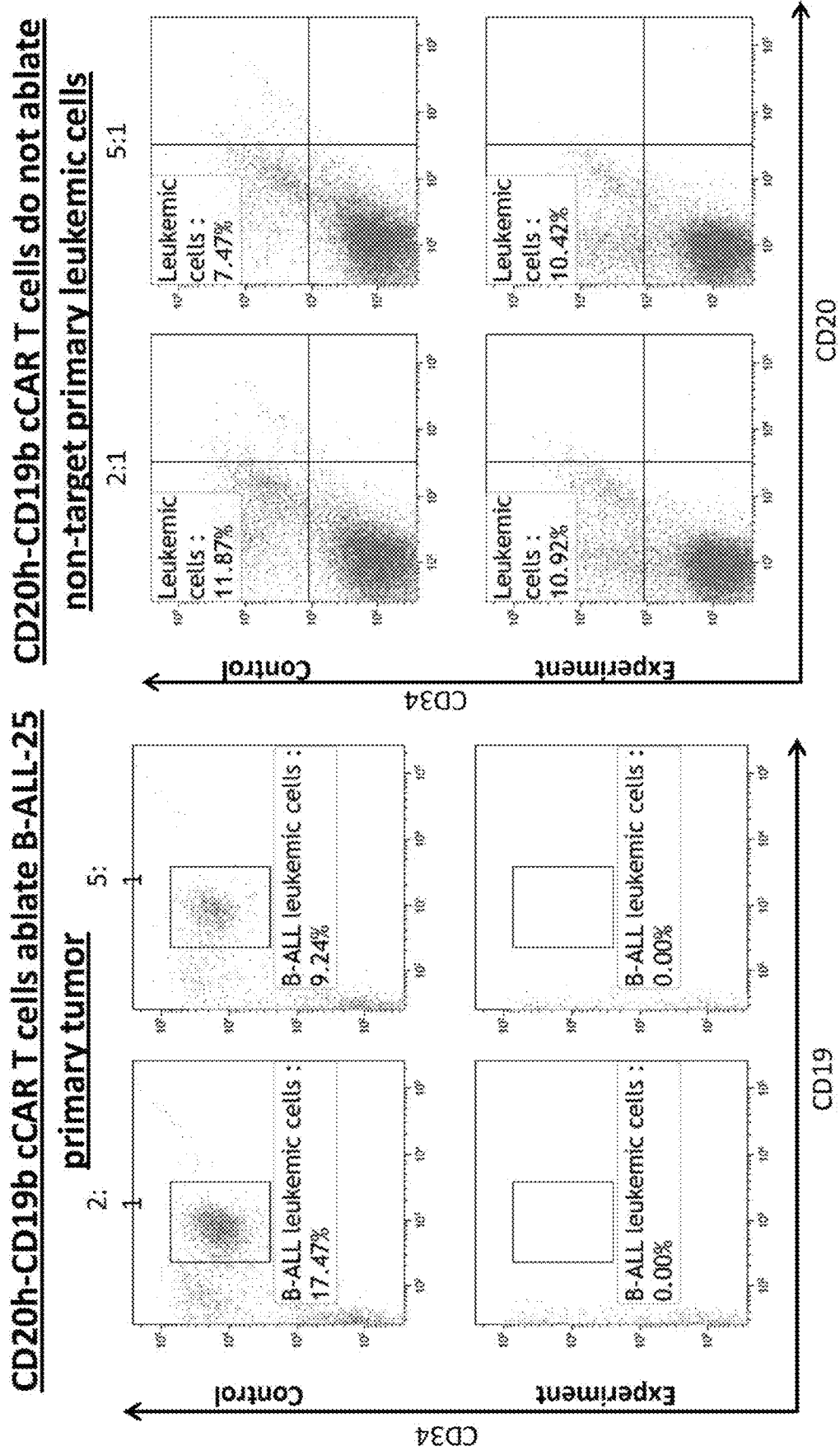

FIG. 49C. CD20h-CD19b cCAR T cells are able to ablate target primary B-ALL cells but cannot target off-target leukemic cells. In order to further characterize the anti-tumor activity of the CD20h-CD19b CAR T cells, we conducted co-cultures against primary CD19+ B-ALL leukemic blasts expressing CD19 and CD20 (B-ALL-25). To analyze the specificity of the CD20h-CD19b cCAR, we also conducted co-cultures against antigen negative primary leukemic cells negative for both CD19 and CD20, but positive for CD34. B-ALL-25 and negative control primary leukemic cells were both pre-labeled with a cell-tracking dye, CFSE, beforehand in order to separate effector T and target tumor populations. FACS analysis of co-cultures against B-ALL-25 (LEFT) shows profound ablation of the target primary leukemic blasts, showing total ablation even at E:T ratios of 2:1. Analysis of the negative control primary cell co-culture (RIGHT) shows that there was no effect by the cCAR on the bulk antigen-negative population.

Figure 50B:
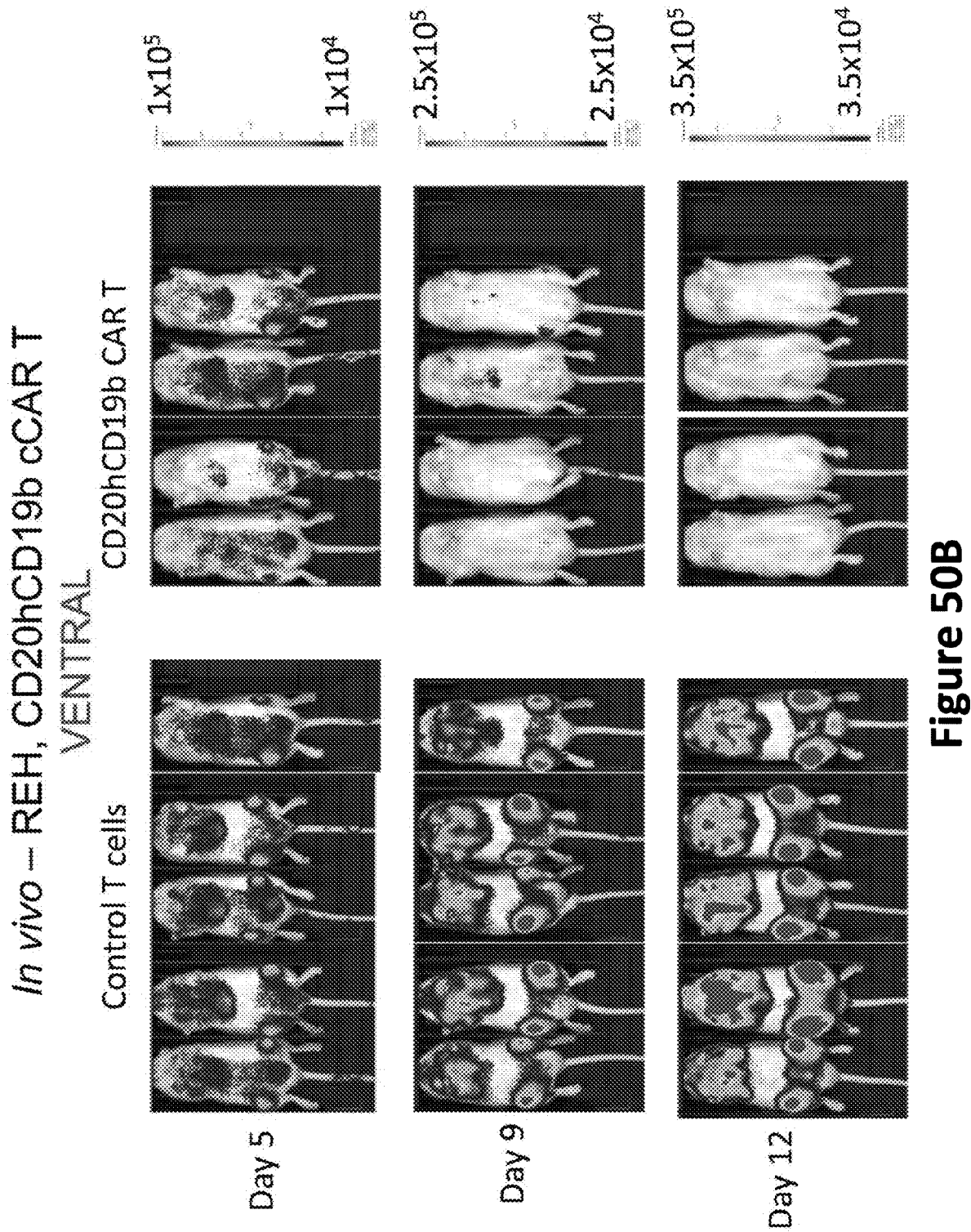

FIGS. 50A-50B. CD20hCD19b CAR T cells demonstrate anti-tumor effects in vivo against REH tumor cell line expressing CD19 antigen. NSG mice were sublethally irradiated and intravenously injected with $1.0 \times 10^6$ luciferase-expressing REH cells (Day 0) to induce measurable tumor formation. Starting 6 days after injection of tumor cells, mice were intravenously injected with a course of $10 \times 10^6$ CD20hCD19b CAR T cells or vector control T cells. On days 5, 9 and 12, mice were injected subcutaneously with RediJect D-Luciferin and subjected to IVIS imaging. (FIG. 50A) Dorsal view; (FIG. 50B) Ventral view.

Figure 51A:
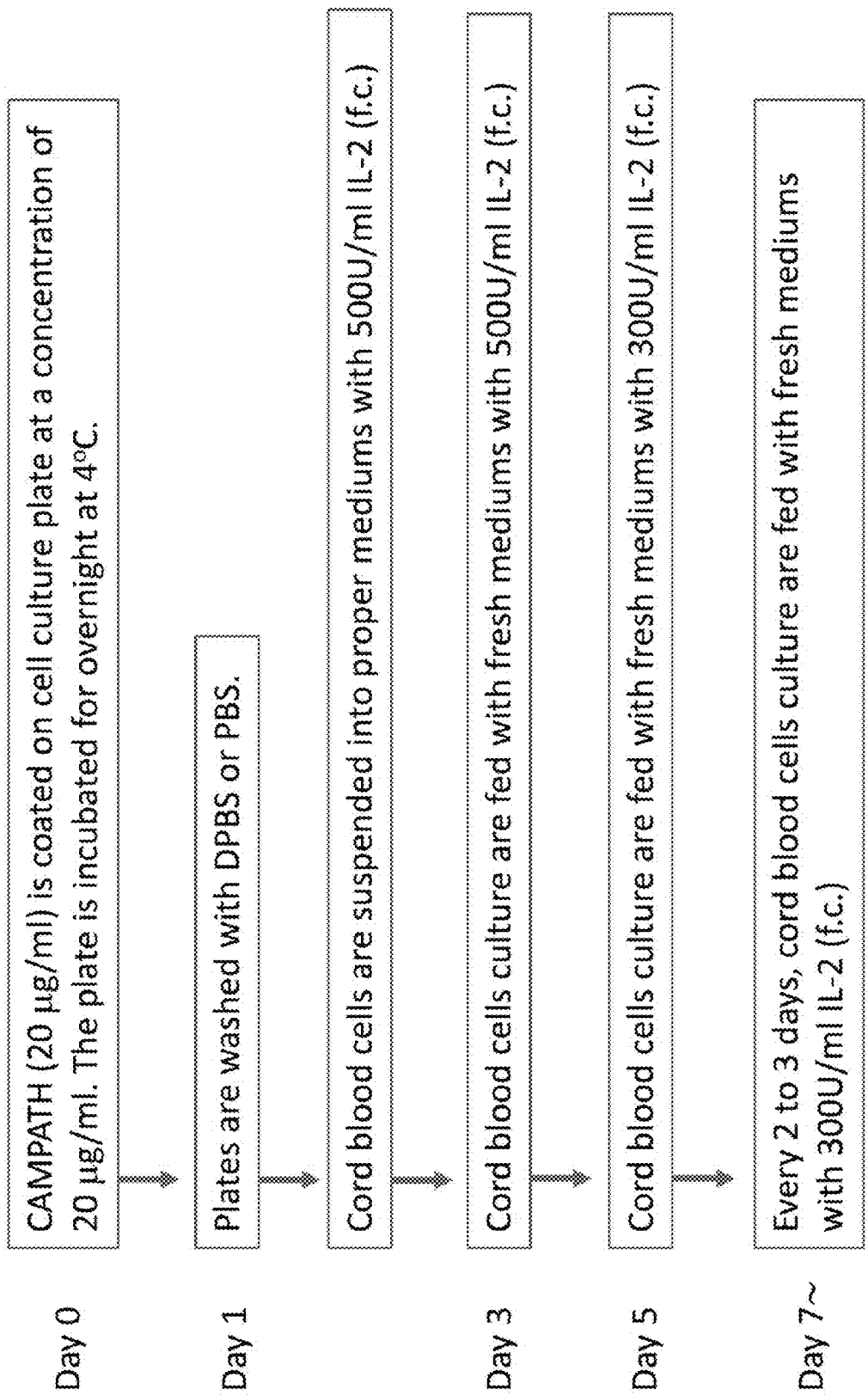

FIG. 51A. Steps of natural killer (NK) cell expansion from umbilical cord blood.

Figure 51B:
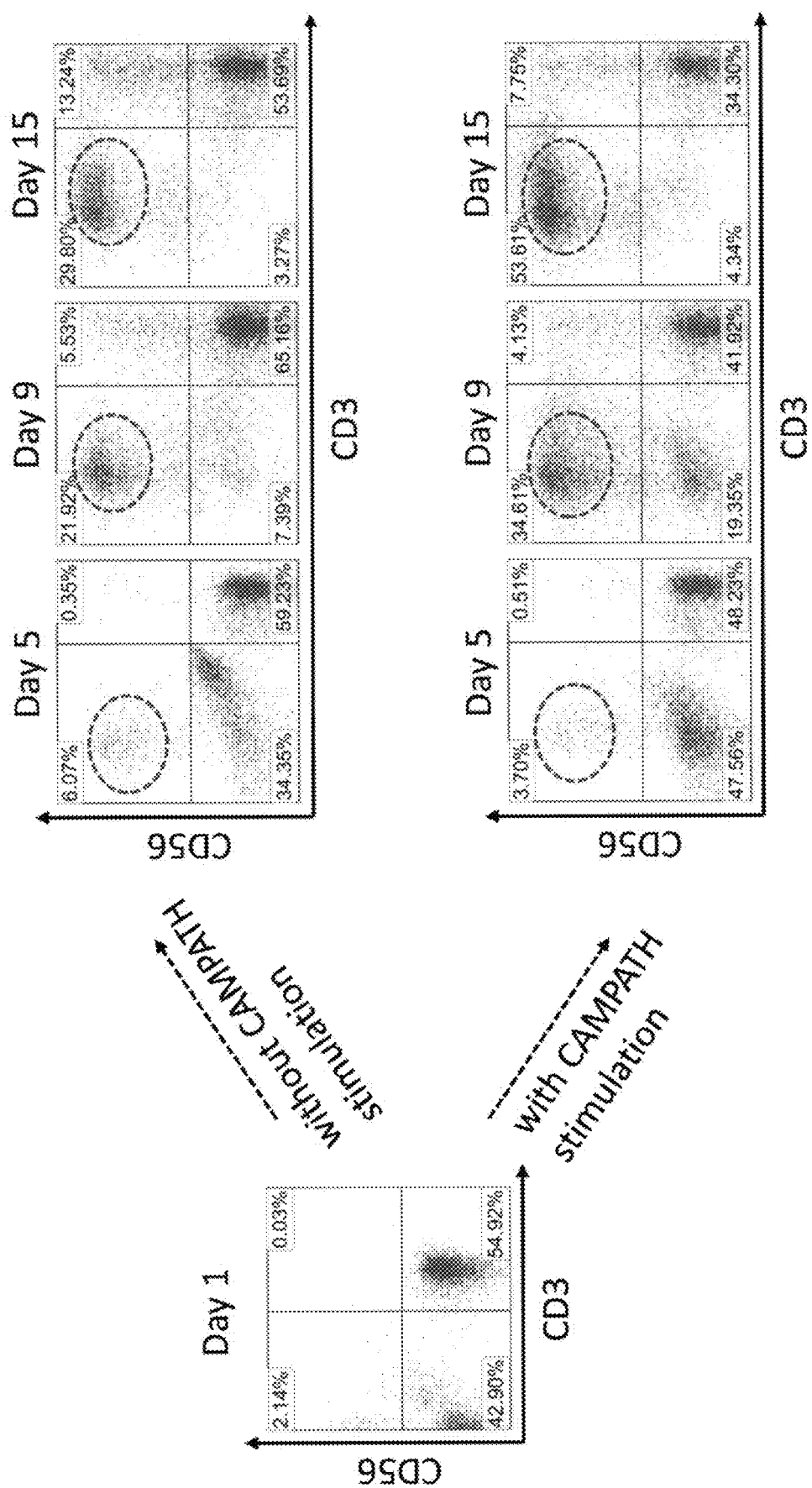

FIG. 51B. Comparison of natural killer (NK) cells expansion with or without CAMPATH stimulation. Cord blood cells were cultured in T-cell culture medium containing 10% FBS and IL-2 on CAMPATH coated cell culture flask or uncoated flask. The population of NK cells in total cells was determined by flow cytometry analysis using CD56 and CD3 antibodies (circled in blue). These data indicated that the population of NK cells increased more with CAMPATH stimulation in a day dependent manner.

Figure 52A:
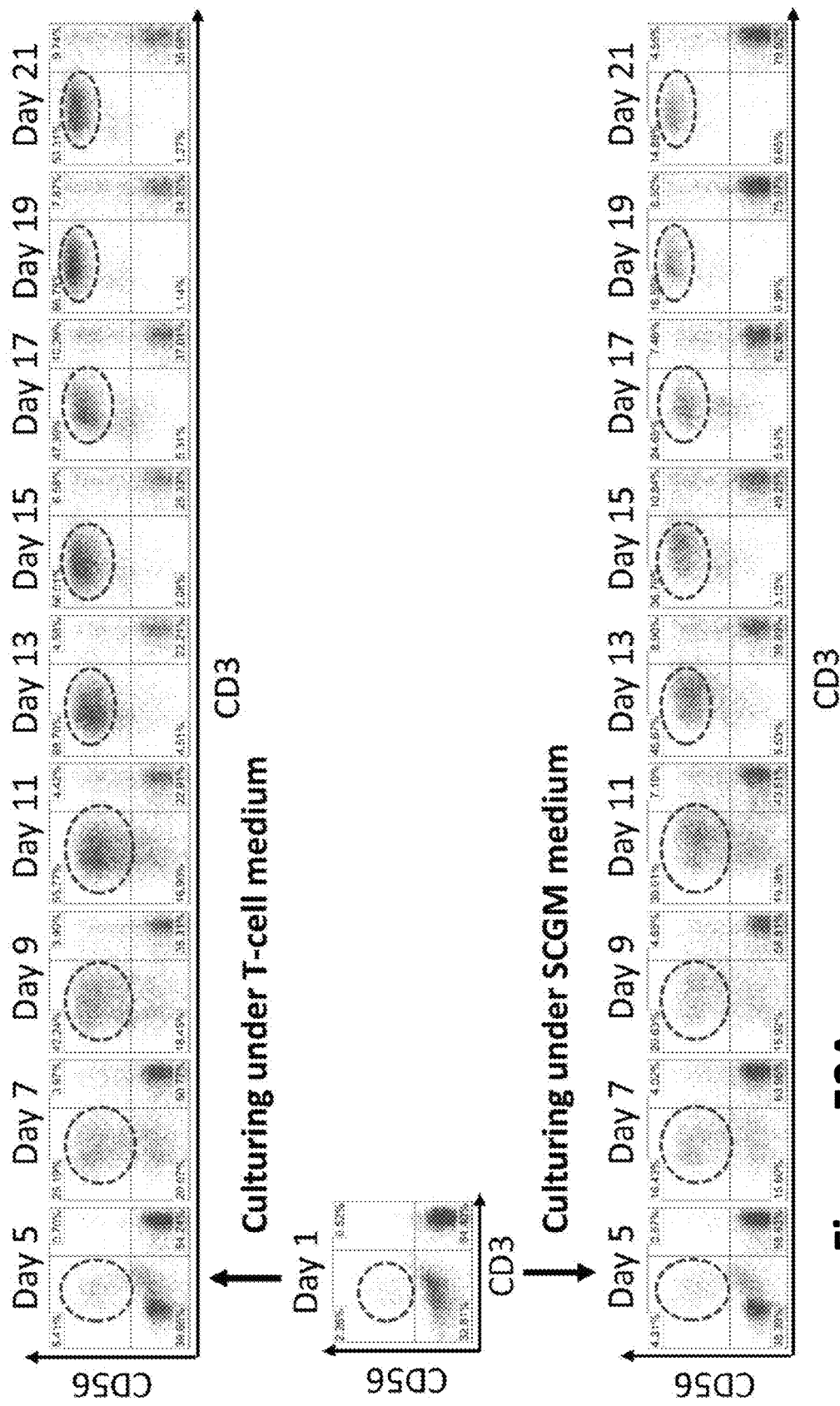

FIG. 52A. Comparison of natural killer (NK) cells expansion using different medium including 10% FBS and IL-2 with CAMPATH stimulation. Cord blood cells were cultured in T-cell culture medium or SCGM medium containing 10% FBS and IL-2 on CAMPATH coated cell culture flask. The population of NK cells in total cells were determined by flow cytometry analysis using CD56 and CD3 antibodies (circled in blue). These data indicated that the population of NK cells increased more in T-cell culture medium with CAMAPTH stimulation when compared to SCGM medium with CAMAPTH stimulation in a day dependent manner.

Figure 52B:
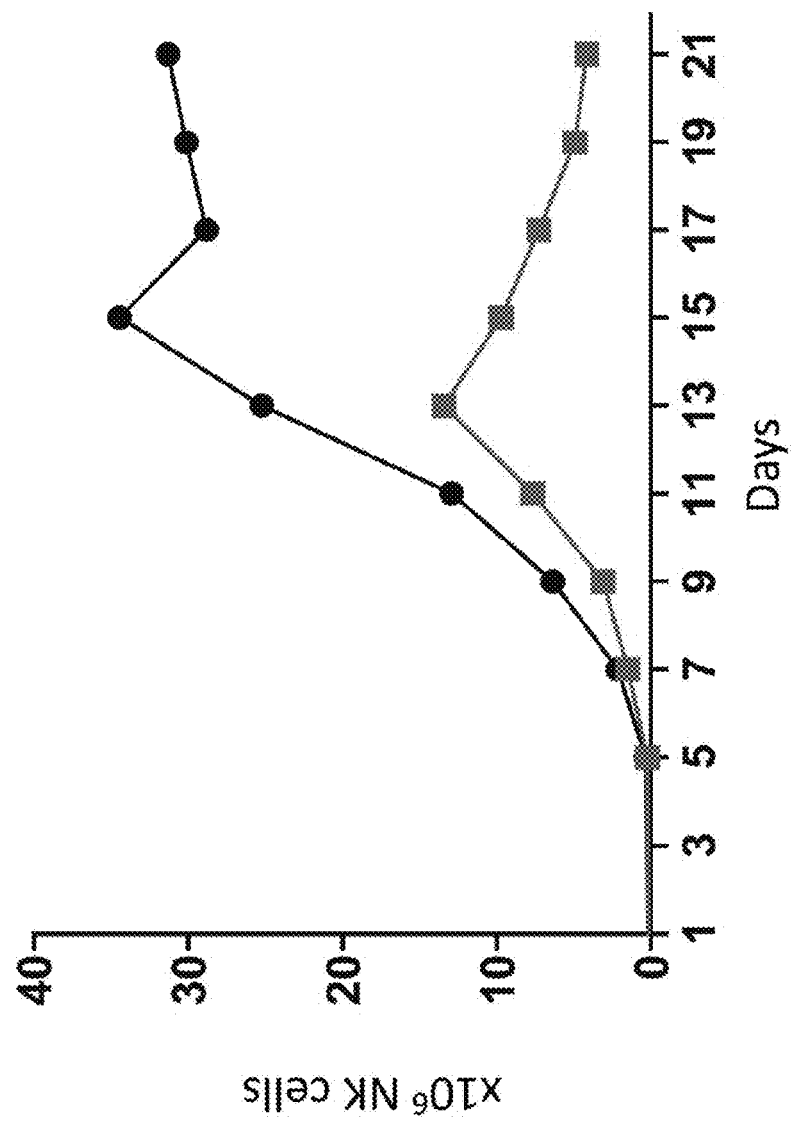

FIG. 52B. Cell growth curve of natural killer (NK) cells using different medium including 10% FBS and IL-2 with CAMPATH stimulation. The number of NK cells in T-cell media versus SCGM media was counted every other day. These data indicated that the use of T-cell culture medium with CAMAPTH stimulation is superior at expanding NK cells compared to the use of SCGM medium.

Figure 53A:
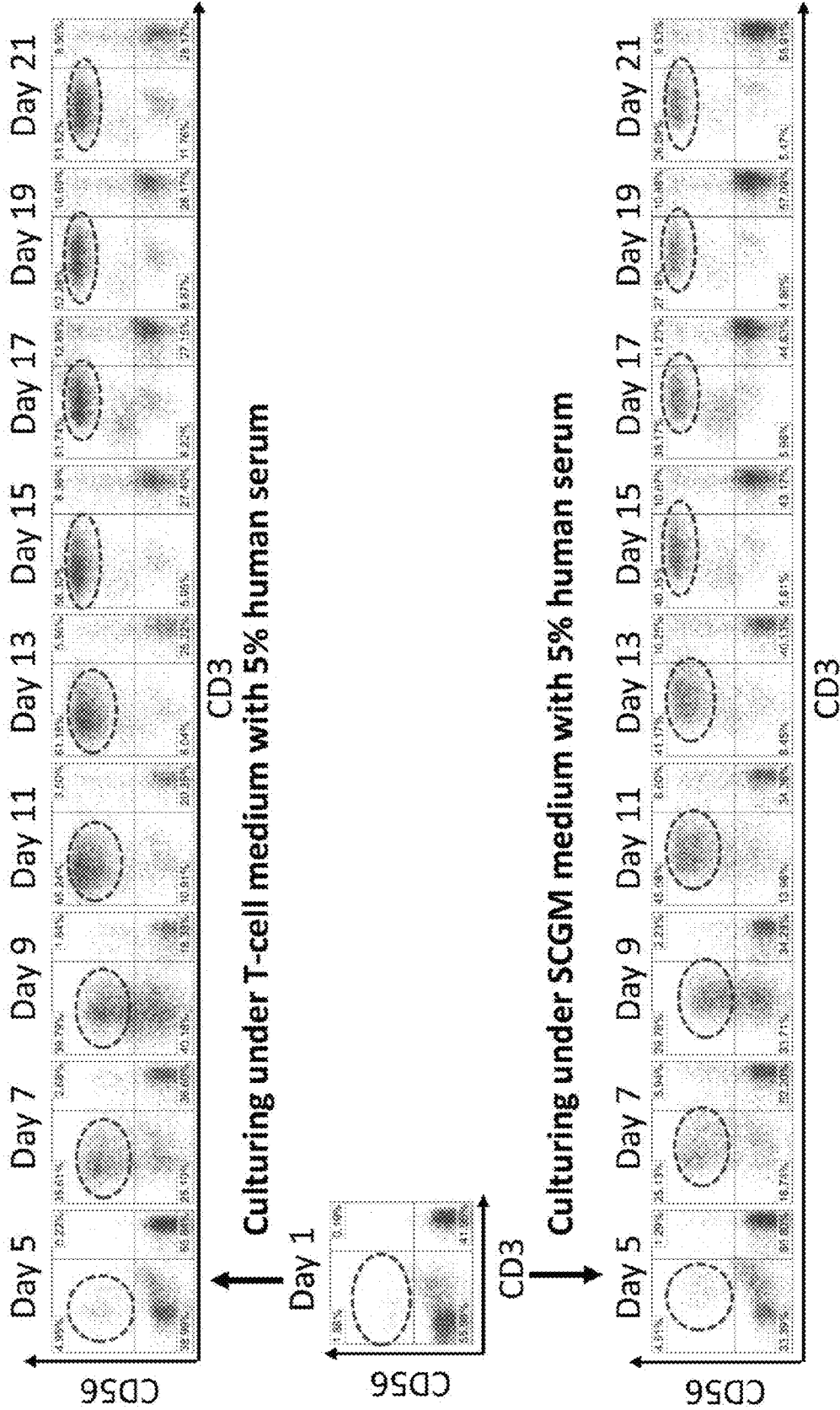

FIG. 53A. Comparison of natural killer (NK) cells expansion using different medium including 5% human serum and IL-2 with CAMPATH stimulation. Cord blood cells were cultured in T-cell culture medium or SCGM medium containing 5% human serum and IL-2 on CAMPATH coated cell culture flask. The population of NK cells in total cells was determined by flow cytometry analysis using CD56 and CD3 antibodies (circled in blue). These data indicated that the population of NK cells increased more in T-cell culture medium with CAMAPTH stimulation compared to SCGM medium with CAMAPTH stimulation in a day dependent manner.

Figure 53B:
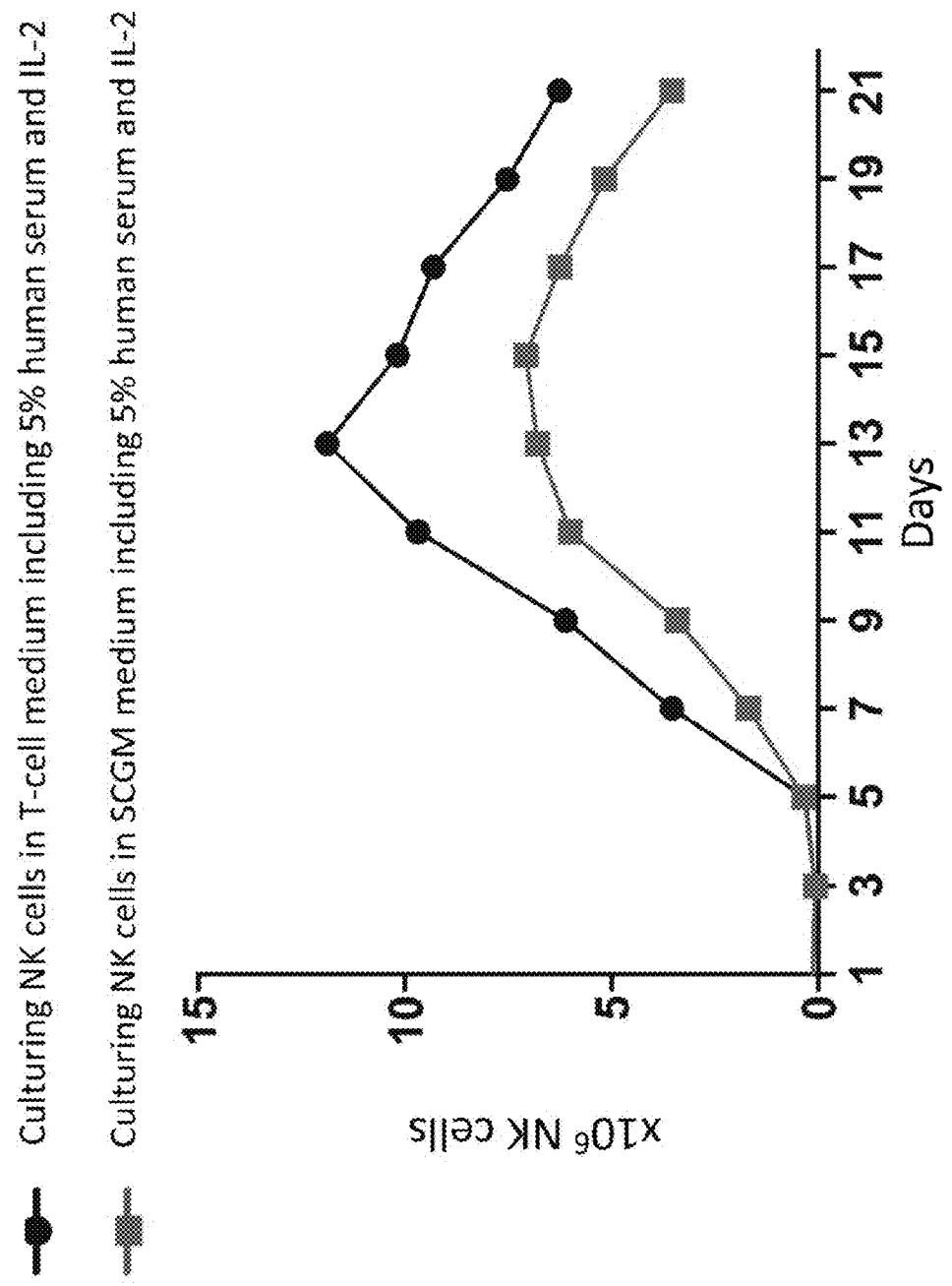

FIG. 53B. Cell growth curve of natural killer (NK) cells using different medium including 5% human serum and IL-2 with CAMPATH stimulation. To evaluate the effect of using different types of cell culture medium and human serum instead of FBS in cell culture medium for NK cells, the number of NK cells were counted every other day. These data indicated that T-cell culture medium with CAMAPTH stimulation improves NK cell expansion when compared to use SCGM medium.

Figure 54A:
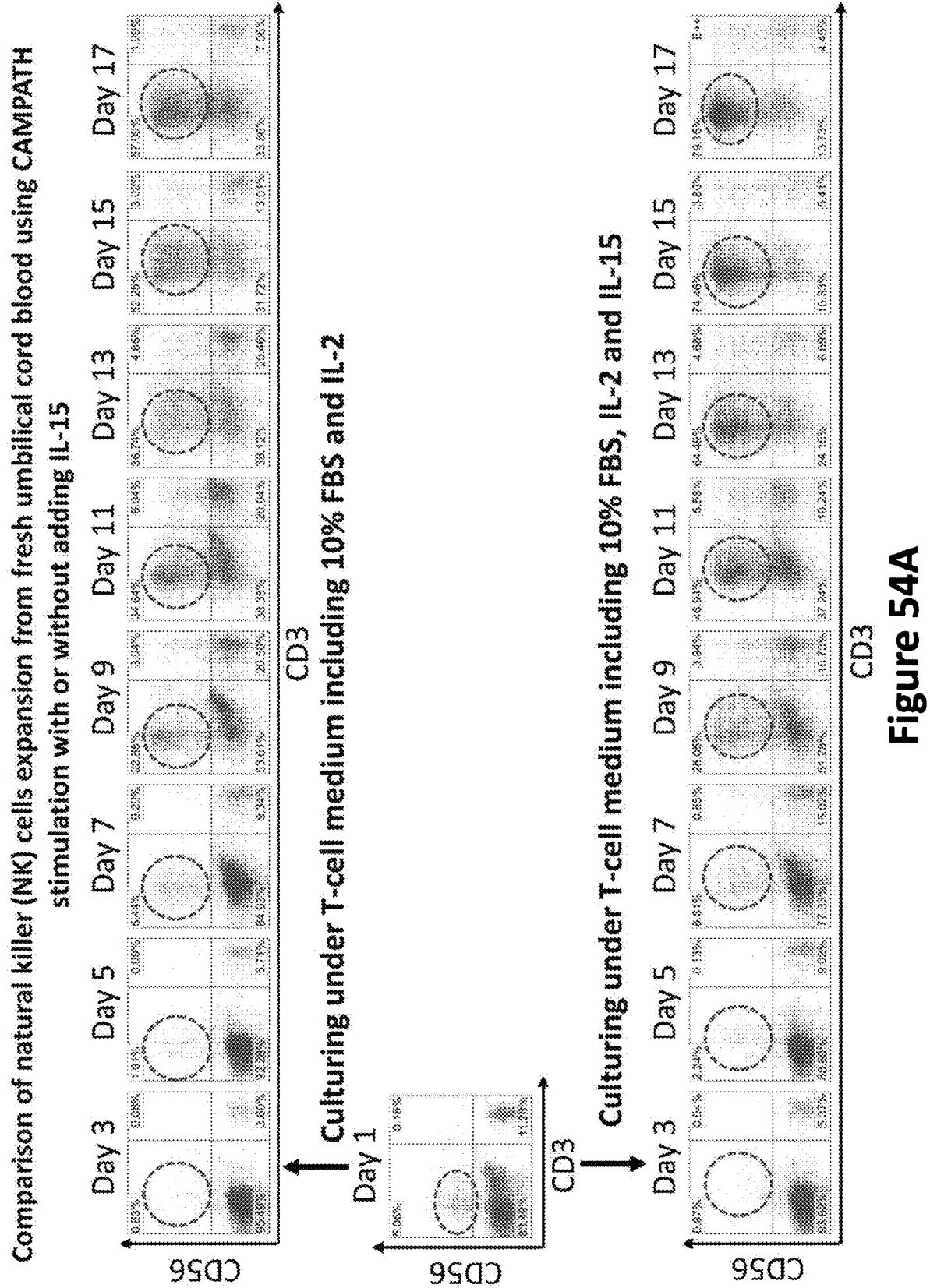

FIG. 54A. Comparison of natural killer (NK) cells expansion from fresh umbilical cord blood using CAMPATH stimulation with or without adding IL-15. To evaluate the effect of adding IL-15 in cell culture medium on NK cells expansion in fresh umbilical cord blood cells, fresh cord blood cells were cultured in T-cell culture medium containing 10% FBS and IL-2 on CAMPATH coated cell culture flask. The population of NK cells in total cells was determined by flow cytometry analysis using CD56 and CD3 antibodies (circled in blue). These data indicated that the population of NK cells increased more after adding IL-15 in T-cell culture medium with CAMAPTH in a day dependent manner.

Figure 54B:
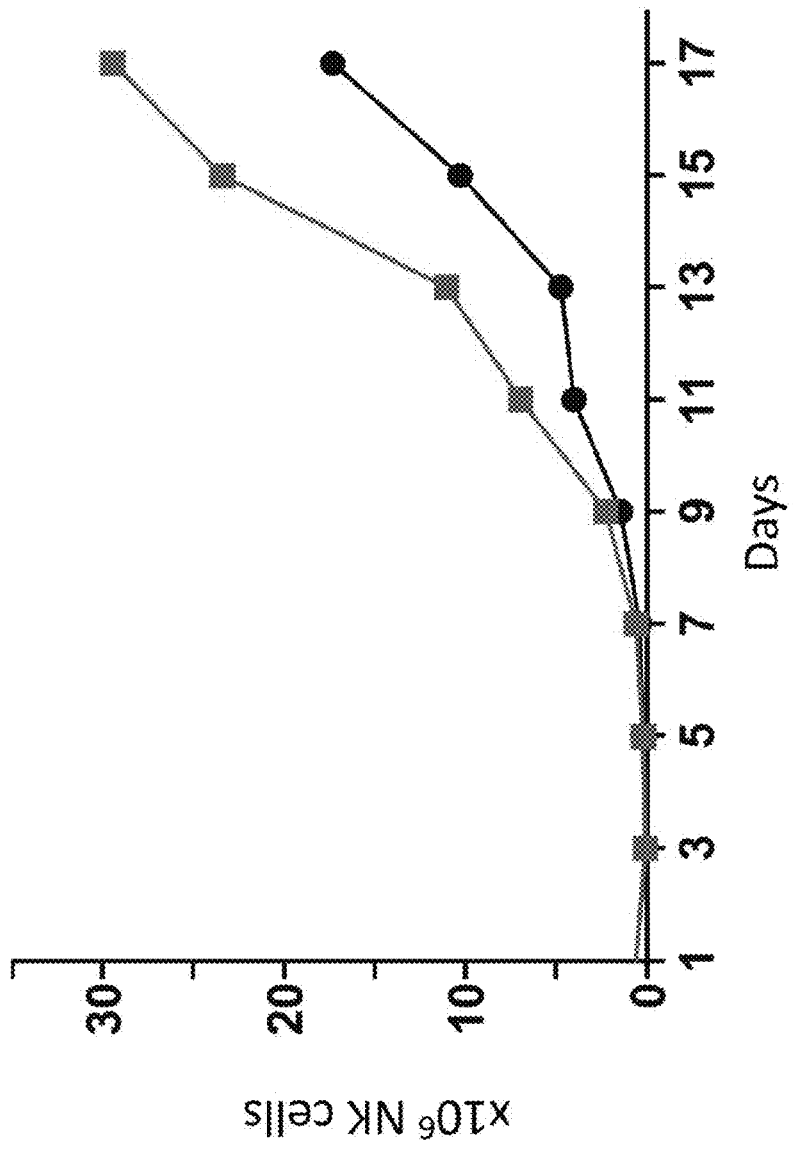

FIG. 54B. Cell growth curve of natural killer (NK) cells from fresh umbilical cord blood using CAMPATH stimulation with or without adding IL-15. To evaluate the effect of adding IL-15 in cell culture medium on NK cell proliferation in fresh umbilical cord blood cells, the number of NK cells was counted every other day. These data indicated that adding IL-15 in T-cell culture medium supported the expansion of NK cells when compared to not adding IL-15.

Figure 54C:
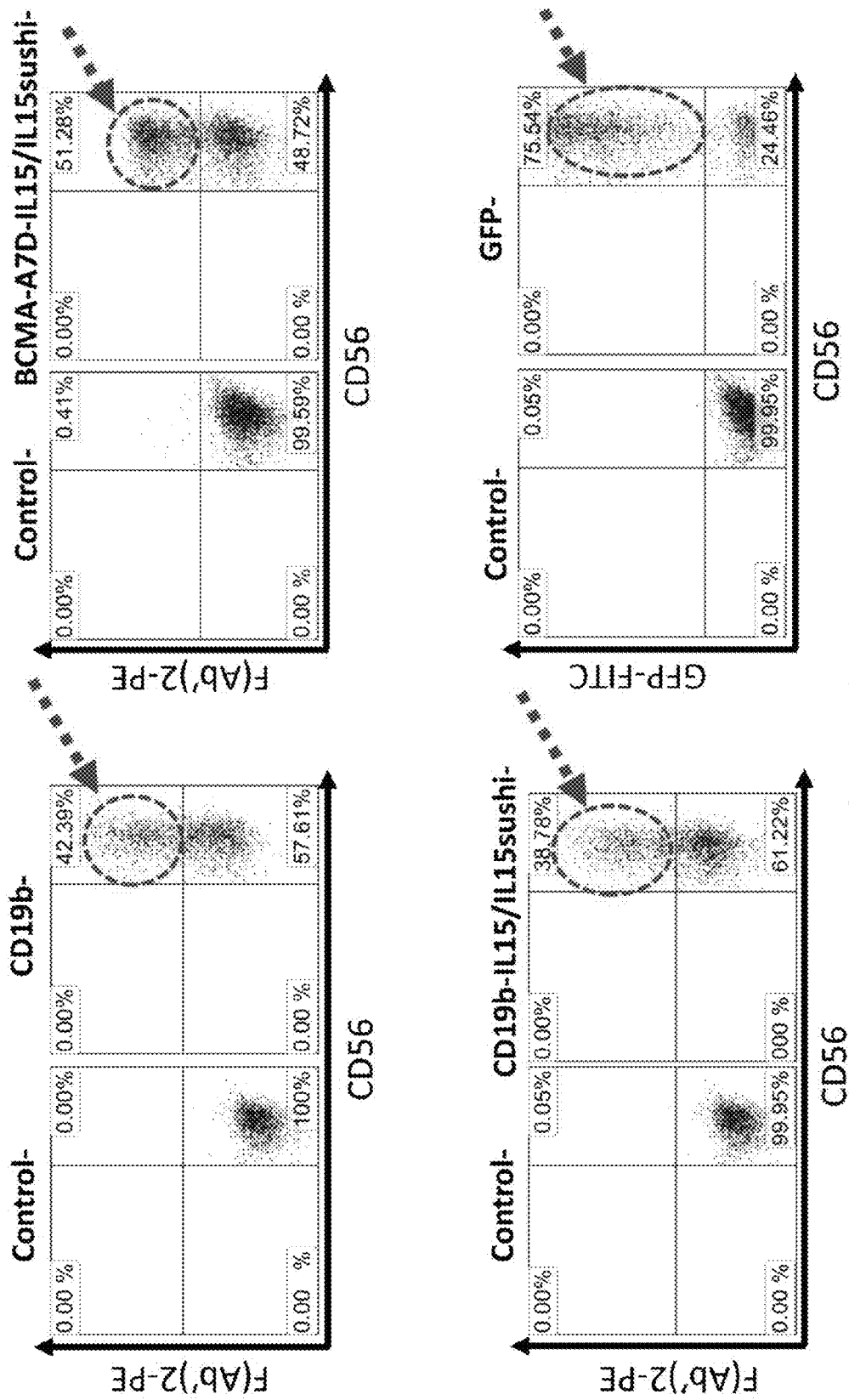

FIG. 54C. Transduction of CD19b-CAR-, CD19b-IL15/IL15sushi-CAR, BCMA-A7D-IL15/IL15sushi-CAR or GFP into NK cells. The expression levels of (A) CD19b-CAR-, (B) CD19b-IL15/IL-15sushi-CAR-, (C) BCMA-A7D-IL15/IL15sushi-CAR- or (D) GFP- on NK cells after CAR or GFP lentivirus transduction were determined by flow cytometry analysis (circled in reds) and compared to control NK cells (left panels). About 42% of CD19b-CAR-(A), 39% of CD19b-IL15/IL15sushi-CAR-(B), 51% of BCMA-A7D-IL15/IL15sushi-CAR- and (D) 76% of GFP- expression on cell surface were detected by flow cytometry analysis.

FIG. 55. This strategy can be applied for any cytokine release related CAR.

FIG. 56. Low dose of CD269-A7D-IL15/IL15sushi CAR T cells leads to tumor cell ablation similar to high dose T cells, but avoids cytokine release syndrome. Summary of two independent experiments. In both, NSG mice were sublethally irradiated and intravenously injected with 4.0× $10^6$ luciferase-expressing MM.1S cells (Day 0) to induce measurable tumor formation. Starting 9 days after injection of tumor cells, mice were intravenously injected with a course of 10×$10^6$ vector control T cells, and either 10×$10^6$ (experiment 1, left), or 2×$10^6$ CD269-A7D-IL15/IL15sushi (A7D-IL15/IL15sushi) CAR T cells (experiment 2, right). On days 7 or 8, 11 and 15, mice were injected subcutaneously with RediJect D-Luciferin and subjected to IVIS imaging. Dorsal view only.

DETAILED DESCRIPTION

The disclosure provides chimeric antigen receptor (CAR) compositions, methods and making thereof, and methods of using the CAR compositions.
Compositions
Chimeric Antigen Receptor Polypeptides In one embodiment, the disclosure provides a chimeric antigen receptor (CAR) polypeptide having a signal peptide, an antigen recognition domain, a hinge region, a transmembrane domain, at least one co-stimulatory domain, and a signaling domain.

As used herein, the terms "peptide," "polypeptide," and "protein" are used interchangeably, and refer to a compound having amino acid residues covalently linked by peptide bonds. A protein or peptide must contain at least two amino acids, and no limitation is placed on the maximum number of amino acids that can include a protein's or peptide's sequence. Polypeptides include any peptide or protein having two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "signal peptide" includes a peptide sequence that directs the transport and localization of the peptide and any attached polypeptide within a cell, e.g. to a certain cell organelle (such as the endoplasmic reticulum) and/or the cell surface.

The signal peptide is a peptide of any secreted or transmembrane protein that directs the transport of the polypeptide of the disclosure to the cell membrane and cell surface, and provides correct localization of the polypeptide of the present disclosure. In particular, the signal peptide of the present disclosure directs the polypeptide of the present disclosure to the cellular membrane, wherein the extracellular portion of the polypeptide is displayed on the cell surface, the transmembrane portion spans the plasma membrane, and the active domain is in the cytoplasmic portion, or interior of the cell.

In one embodiment, the signal peptide is cleaved after passage through the endoplasmic reticulum (ER), i.e. is a cleavable signal peptide. In an embodiment, the signal peptide is human protein of type I, II, III, or IV. In an embodiment, the signal peptide includes an immunoglobulin heavy chain signal peptide.

The "antigen recognition domain" includes a polypeptide that is selective for an antigen, receptor, peptide ligand, or protein ligand of the target; or a polypeptide of the target.

The target specific antigen recognition domain preferably includes an antigen binding domain derived from an antibody against an antigen of the target, or a peptide binding an antigen of the target, or a peptide or protein binding an antibody that binds an antigen of the target, or a peptide or protein ligand (including but not limited to a growth factor, a cytokine, or a hormone) binding a receptor on the target, or a domain derived from a receptor (including but not limited to a growth factor receptor, a cytokine receptor or a hormone receptor) binding a peptide or protein ligand on the target. The target includes GD2 and GD3. In another embodiment, the target includes any portion of GD2 and GD3. In another embodiment, the target is gangliosides GD2 with its structure, GD2=bDGalpNAc(1-4)[aNeu5Ac(2-8) aNeu5Ac(2-3)]bDGalp(1-4)bDGlcp(1-1)Cer. In another embodiment, the target is the gangliosides GD3 with its structure, GD3=aNeu5Ac(2-8)aNeu5Ac(2-3)bDGalp(1-4) bDGlcp(1-1)Cer.

In one embodiment, the antigen recognition domain includes the binding portion or variable region of a monoclonal or polyclonal antibody directed against (selective for) the target.

In one embodiment, the antigen recognition domain includes antigen-binding fragment (Fab). In another embodiment, the antigen recognition domain includes a single-chain variable fragment (scFv). scFv is a fusion protein of the variable regions of the heavy (VH) and light chains (VL) of immunoglobulins, connected with a short linker peptide.

In another embodiment, the antigen recognition domain includes Camelid single domain antibody, or portions thereof. In one embodiment, Camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001), and also includes an isolated VHH antibody of camelid, a recombinant VHH antibody of camelid, or a synthetic VHH antibody of camelid.

In another embodiment, the antigen recognition domain includes ligands that engage their cognate receptor. In another embodiment, the antigen recognition domain is humanized.

It is understood that the antigen recognition domain may include some variability within its sequence and still be selective for the targets disclosed herein. Therefore, it is contemplated that the polypeptide of the antigen recognition domain may be at least 95%, at least 90%, at least 80%, or at least 70% identical to the antigen recognition domain polypeptide disclosed herein and still be selective for the targets described herein and be within the scope of the disclosure.

In another embodiment, the antigen recognition domain is selective for gangliosides GD2 and gangliosides GD3.

The hinge region is a sequence positioned between for example, including, but not limited to, the chimeric antigen receptor, and at least one co-stimulatory domain and a signaling domain. The hinge sequence may be obtained including, for example, from any suitable sequence from any genus, including human or a part thereof. Such hinge regions are known in the art. In one embodiment, the hinge region includes the hinge region of a human protein including CD-8 alpha, CD28, 4-1BB, OX40, CD3-zeta, T cell receptor α or β chain, a CD3 zeta chain, CD28, CD3c, CD45, CD4, CD5, CD8, CD9, CD16, CD22, CD33, CD37, CD64, CD80, CD86, CD134, CD137, ICOS, CD154, functional derivatives thereof, and combinations thereof.

In one embodiment the hinge region includes the CD8a hinge region.

In some embodiments, the hinge region includes one selected from, but is not limited to, immunoglobulin (e.g. IgG1, IgG2, IgG3, IgG4, and IgD).

The transmembrane domain includes a hydrophobic polypeptide that spans the cellular membrane. In particular, the transmembrane domain spans from one side of a cell membrane (extracellular) through to the other side of the cell membrane (intracellular or cytoplasmic).

The transmembrane domain may be in the form of an alpha helix or a beta barrel, or combinations thereof. The transmembrane domain may include a polytopic protein, which has many transmembrane segments, each alpha-helical, beta sheets, or combinations thereof.

In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex.

For example, a transmembrane domain includes a transmembrane domain of a T-cell receptor α or β chain, a CD3 zeta chain, CD28, CD3c, CD45, CD4, CD5, CD8, CD9, CD16, CD22, CD33, CD37, CD64, CD80, CD86, CD134, CD137, ICOS, CD154, functional derivatives thereof, and combinations thereof.

The artificially designed transmembrane domain is a polypeptide mainly comprising hydrophobic residues such as leucine and valine. In one embodiment, a triplet of phenylalanine, tryptophan and valine is found at each end of the synthetic transmembrane domain.

In one embodiment, the transmembrane domain is the CD8 transmembrane domain. In another embodiment, the transmembrane domain is the CD28 transmembrane domain. Such transmembrane domains are known in the art.

The signaling domain and co-stimulatory domain include polypeptides that provide activation of an immune cell to stimulate or activate at least some aspect of the immune cell signaling pathway.

In an embodiment, the signaling domain includes the polypeptide of a functional signaling domain of CD3 zeta, common FcR gamma (FCER1G), Fc gamma Rlla, FcR beta (Fc Epsilon Rib), CD3 gamma, CD3 delta, CD3 epsilon, CD79a, CD79b, DNAX-activating protein 10 (DAP10), DNAX-activating protein 12 (DAP12), active fragments thereof, functional derivatives thereof, and combinations thereof. Such signaling domains are known in the art. In an embodiment, the CAR polypeptide further includes one or more co-stimulatory domains. In an embodiment, the co-stimulatory domain is a functional signaling domain (s) selected from at least a protein including, but not limited to, IL-15 receptor alpha; IL-15 receptor alpha cytoplasmic domain; B7-1/CD80; CD28; 4-1BB, 4-1BBL, B7-2/CD86; CTLA-4; B7-H1/PD-L1; ICOS; B7-H2; PD-1; B7-H3; PD-L2; B7-H4; PDCD6; BTLA; 4-1BB/TNFRSF9/CD137; CD40 Ligand/TNFSF5; 4-1BB Ligand/TNFSF9; GITR/TNFRSF18; BAFF/BLyS/TNFSF13B; GITR Ligand/TNFSF18; BAFF R/TNFRSF13C; HVEM/TNFRSF14; CD27/TNFRSF7; LIGHT/TNFSF14; CD27 Ligand/TNFSF7; OX40/TNFRSF4; CD30/TNFRSF8; OX40 Ligand/TNFSF4; Toll-like receptor ligands; Toll-like receptor 9 (TLR9) ligands; CD30 Ligand/TNFSF8; TACI/TNFRSF13B; CD40/TNFRSF5; 2B4/CD244/SLAMF4; CD84/SLAMF5; BLAME/SLAMF8; CD229/SLAMF3; CD2, CD27, CRACC/SLAMF7; CD2F-10/SLAMF9; NTB-A/SLAMF6; CD48/SLAMF2; SLAM/CD150; CD58/LFA-3; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR.

The present disclosure further provides a polynucleotide encoding the chimeric antigen receptor polypeptide described above. The polynucleotide encoding the CAR is easily prepared from an amino acid sequence of the specified CAR by any conventional method. A base sequence encoding an amino acid sequence can be obtained from the aforementioned NCBI RefSeq IDs or accession numbers of GenBenk for an amino acid sequence of each domain, and the nucleic acid of the present disclosure can be prepared using a standard molecular biological and/or chemical procedure. For example, based on the base sequence, a polynucleotide can be synthesized, and the polynucleotide of the present disclosure can be prepared by combining DNA fragments which are obtained from a cDNA library using a polymerase chain reaction (PCR).

In one embodiment, the polynucleotide disclosed herein is part of a gene, or an expression or cloning cassette.

The term "polynucleotide" as used herein is defined as a chain of nucleotides. Polynucleotide includes DNA and RNA. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and polymerase chain reaction (PCR), and the like, and by synthetic means.

Polynucleotide Vector

The polynucleotide described above can be cloned into a vector. A "vector" is a composition of matter which includes an isolated polynucleotide and which can be used to deliver the isolated polynucleotide to the interior of a cell. Numerous vectors are known in the art including, but not limited to, linear polynucleotides, polynucleotides associated with ionic or amphiphilic compounds, plasmids, phagemid, cosmid, and viruses. Viruses include phages, phage derivatives. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

In one embodiment, vectors include cloning vectors, expression vectors, replication vectors, probe generation vectors, integration vectors, and sequencing vectors.

In an embodiment, the vector is a viral vector. In an embodiment, the viral vector is a retroviral vector or a lentiviral vector. In an embodiment, the engineered cell is virally transduced to express the polynucleotide sequence.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Expression of chimeric antigen receptor polynucleotide may be achieved using, for example, expression vectors including, but not limited to, at least one of a SFFV (spleen focus-forming virus) or human elongation factor 11α (EF) promoter, CAG (chicken beta-actin promoter with CMV enhancer) promoter human elongation factor 1α (EF) promoter. Examples of less-strong/lower-expressing promoters utilized may include, but is not limited to, the simian virus 40 (SV40) early promoter, cytomegalovirus (CMV) immediate-early promoter, Ubiquitin C (UBC) promoter, and the phosphoglycerate kinase 1 (PGK) promoter, or a part thereof. Inducible expression of chimeric antigen receptor may be achieved using, for example, a tetracycline responsive promoter, including, but not limited to, TRE3GV (Tet-response element, including all generations and preferably, the 3rd generation), inducible promoter (Clontech Laboratories, Mountain View, Calif.) or a part or a combination thereof.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure should not be limited to the use of constitutive promoters, inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metalothionein promoter, a glucocorticoid promoter, a progesterone promoter, and a tetracycline promoter.

"Expression vector" refers to a vector comprising a recombinant polynucleotide expression control sequence operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Additional promoter elements, e.g., enhancers, regulate the frequency of transcriptional initiation. Typically, these are located in the region 30-100 bp upstream of the start site, although a number of promoters have recently been shown to contain functional elements downstream of the start site as well. The spacing between promoter elements frequently is flexible, so that promoter function is preserved when elements are inverted or moved relative to one another, in the thymidine kinase (tk) promoter, the spacing between promoter elements can be increased to 50 bp apart before activity begins to decline. Depending on the promoter, it appears that individual elements can function either cooperatively or independently to activate transcription.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors; in other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about $-20°$ C. Chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 19 1 Glycobiology 5; 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous polynucleotides into a host cell or otherwise expose a cell to the polynucleotide of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Engineered Cell

In another embodiment, the disclosure provides an engineered cell expressing the chimeric antigen receptor polypeptide described above or polynucleotide encoding for the same, and described above.

An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a chimeric antigen receptor or chimeric antigen receptor complex and express the chimeric receptor on the cell surface. Isolated host cells and engineered cells may be used, for example, for enhancing an NK cell activity or a T lymphocyte activity, treatment of cancer, and treatment of infectious diseases.

Any cell capable of expressing and/or capable of integrating the chimeric antigen receptor polypeptide, as disclosed herein, into its membrane may be used.

In an embodiment, the engineered cell includes immunoregulatory cells. Immunoregulatory cells include T-cells, such as CD4 T-cells (Helper T-cells), CD8 T-cells (Cytotoxic T-cells, CTLs), and memory T cells or memory stem cell T cells. In another embodiment, T-cells include Natural Killer T-cells (NK T-cells).

T cells comprise of CD4 and CD8 cells. CD4 is a glycoprotein present on the surface of immune cells such as T helper cells, important in T cell activation and receptor for HIV. Some monocytes or macrophages also express CD4. CD4 is also called OKT4. Cytotoxic T cells are also known as CD8+ T cells or CD8 T cells expressing CD8 glycoprotein at their surfaces. These CD8+ T cells are activated once they are exposed to peptide antigens presented by MHC class I.

In an embodiment, the engineered cell includes Natural Killer cells. Natural killer cells are well known in the art. In one embodiment, natural killer cells include cell lines, such as NK-92 cells. Further examples of NK cell lines include NKG, YT, NK-YS, HANK-1, YTS cells, and NKL cells.

NK cells mediate anti-tumor effects without the risk of GvHD and are short-lived relative to T-cells. Accordingly, NK cells would be exhausted shortly after destroying cancer cells, decreasing the need for an inducible suicide gene on CAR constructs that would ablate the modified cells.

As used herein, CDXCAR refers to a chimeric antigen receptor having a CDX antigen recognition domain. As used herein CDX may be any one of GD2 and GD3.

TCR Deficient T Cells Used to Carry CAR

In one embodiment, engineered cells, in particular allogeneic T cells obtained from donors can be modified to inactivate components of TCR (T cell receptor) involved in MHC recognition. As a result, TCR deficient T cells would not cause graft versus host disease (GVHD).

Sources of Cells

The engineered cells may be obtained from peripheral blood, cord blood, bone marrow, tumor infiltrating lymphocytes, lymph node tissue, or thymus tissue. The host cells may include placental cells, embryonic stem cells, induced pluripotent stem cells, or hematopoietic stem cells. The cells may be obtained from humans, monkeys, chimpanzees, dogs, cats, mice, rats, and transgenic species thereof. The cells may be obtained from established cell lines.

The above cells may be obtained by any known means. The cells may be autologous, syngeneic, allogeneic, or xenogeneic to the recipient of the engineered cells.

The term "autologous" refer to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "syngeneic" refers to an extremely close genetic similarity or identity especially with respect to antigens or immunological reactions. Syngeneic systems include for example, models in which organs and cells (e.g. cancer cells and their non-cancerous counterparts) come from the same individual, and/or models in which the organs and cells come from different individual animals that are of the same inbred strain.

In certain embodiments, T and NK cells are derived from human peripheral blood mononuclear cells (PBMC), leukapheresis products (PBSC), human embryonic stem cells (hESCs), induced pluripotent stem cells (iPSCs), bone marrow, or umbilical cord blood.

The potential disadvantages of using NK cells in CAR therapy include a lack of persistency that may reduce long-term efficacy.

Finding matching donor T cells for generating CAR T cells could be a challenge as un-matched T cells could attach to the recipient's tissues, resulting in graft vs. host disease (GVHD).

In one embodiment, the present disclosure comprises a method of generating chimeric antigen receptor (CAR)-modified NK cells with long-lived or long persistency in vivo potential for treating a disease. Surprisingly, it is found that CAR NK cells co-expressing IL-15/IL-15sushi or IL-15/IL-15 sushi anchor can extend survival for a long period of time.

In further embodiment, the extension of CAR NK cell survival can be achieved by co-expressing the IL-15/IL-15 anchor.

In some embodiments, CAR NK cells co-expressing IL-15/IL-15sushi or IL-15/IL-15sushi anchor can be scaled up and used as an off-the-shelf product.

In one embodiment, CAR NK cells co-expressing IL-15/IL-15 sushi or IL-15/IL-15sushi anchor are capable of continuing supportive cytokine signaling, which is critical to their survival post-infusion in a patient.

In further embodiment, the extension of CAR NK cell survival can be achieved by co-expressing a cytokine selected from a group of IL-7, IL-15, IL-15/IL-15 anchor, IL-15/IL-15RA, IL-12, IL-18 and IL-21.

Suicide and Safety Switch Systems

The engineered cells of the present disclosure may also include a suicide system. Suicide systems provide a mechanism whereby the engineered cell, as described above, may be deactivated or destroyed. Such a feature allows precise therapeutic control of any treatments wherein the engineered cells are used. As used herein, a suicide system provides a mechanism by which the cell having the suicide system can be deactivated or destroyed. Suicide systems are well known in the art.

In one embodiment, a suicide system includes a gene that can be pharmacologically activated to eliminate the containing cells as required. In specific aspects, the suicide gene is not immunogenic to the host harboring the polynucleotide or cell. In one example, the suicide system includes a gene that causes CD20 to be expressed on the cell surface of the engineered cell. Accordingly, administration of rituximab may be used to destroy the engineered cell containing the gene.

In some embodiments, the suicide system includes an epitope tag. Examples of epitope tags include a c-myc tag, CD52 streptavidin-binding peptide (SBP), and truncated EGFR gene (EGFRt). In this embodiment, the epitope tag is expressed in the engineered cell. Accordingly, administration of an antibody against the epitope tag may be used to destroy the engineered cell containing the gene.

In another embodiment, the suicide system includes a gene that causes truncated epidermal growth factor receptor to be expressed on the surface of the engineered cell.

Accordingly, administration of cetuximab may be used to destroy the engineered cell containing the gene.

In another embodiment, the suicide system includes CD52 to be expressed on the surface of the engineered cell. Accordingly, administration of anti-52 monoclonal antibody (CAMPATH, alemtuzumab) may be used to destroy the engineered cell containing the gene.

In another embodiment, the suicide system includes CAMPATH (alemtuzumab). Accordingly, administration of anti-52 monoclonal antibody (CAMPATH) may be used to destroy the engineered cell without expressing a tag or a gene as CAR T cells or T cells highly express CD52.

In another embodiment, the suicide gene may include caspase 8 gene, caspase 9 gene, thymidine kinase, cytosine deaminase (CD), or cytochrome P450.

Examples of further suicide systems include those described by Jones et al. (Jones B S, Lamb L S, Goldman F and Di Stasi A (2014) Improving the safety of cell therapy products by suicide gene transfer. Front. Pharmacol. 5:254. doi: 10.3389/fphar.2014.00254), which is herein incorporated by reference in its entirety.

Compound CAR (cCAR)

As used herein, a compound CAR (cCAR) or multiple CAR refers to an engineered cell having at least two complete and distinct chimeric antigen receptor polypeptides. As used herein, a "distinct chimeric antigen receptor polypeptide" has a unique antigen recognition domain, a signal peptide, a hinge region, a transmembrane domain, at least one costimulatory domain, and a signaling domain. Therefore, two unique chimeric antigen receptor polypeptides will have different antigen recognition domains. The signal peptide, hinge region, transmembrane domain, at least one costimulatory domain, and signaling domain may be the same or different between the two distinct chimeric antigen receptor polypeptides. As used herein, a chimeric antigen receptor (CAR) unit refers to a distinct chimeric antigen receptor polypeptide, or a polynucleotide encoding for the same.

As used herein, a unique antigen recognition domain is one that is specific for or targets a single target, or a single epitope of a target.

In some embodiments, the compound CAR targets the same antigen. For example, cCAR targets different epitopes or parts of a single antigen. In some embodiments, each of the CAR units present in the compound CAR targets different antigen specific to the same or different disease condition or side effects caused by a disease condition.

In some embodiments, the compound CAR targets two different antigens.

Creation of compound CARs bearing different CAR units can be quite challenging: (1) CAR-CAR interactions might have a deleterious effect and an appropriate CAR design is a key to offset this effect; (2) a compound CAR in a single construct could increase the length of the expression cassette, which may cause the reduction of the viral titer and level of protein expression; (3) an appropriate design to include various CAR body elements particularly to select a strategy to express multiple CARs in a single vector is required; (4) A strong promoter is particularly important for a compound CAR that bears additional units of CAR; (5) The hinge region in the CAR needs to be designed so that interaction of the hinge region between each CAR unit is avoided preferably; (6) two or more units of CARs expressing in a cell may cause toxic effects (CAR-CAR interaction). Applicants herein provide novel and surprising CAR compositions and methods to overcome these hurdles.

The transduction efficiency (percentage of CAR T cells) for cCARs is often lower than for a single-unit CAR. There are several ways to improve efficiency, at both the transfection and transduction steps. To improve viral titer for making cCARs, it is preferred to use LentiX™ 293 T (Clontech/Takara) packaging cell line, which is selected for high titer lentivirus production, instead of the commonly used HEK-293FT. It is also preferable to increase the amount of plasmid DNA (containing the cCAR construct) 1.5- to 2.0-fold when transfecting packaging cells, to increase transfection efficiency. The amount of viral packaging plasmids and transfection reagent remains the same during the forming of complexes. Transduction efficiency can be further enhanced by lowering the ratio of T cells to viral vector during the transduction step, to $0.3 \times 10^6$ cells per mL, and increasing the volume of lentiviral supernatant or lentiviruses.

In one embodiment, the present disclosure provides an engineered cell having multiple CAR units. This allows a single engineered cell to target multiple antigens. Targeting multiple surface markers or antigens simultaneously with a multiple CAR unit prevents selection of resistant clones and reduces tumor recurrence. Multiple CAR T cell immunotherapies, with each individual component CAR comprising various domains and activation sites has not yet been developed for any malignancies.

In one aspect of the present disclosure, cCAR includes multiple CAR units. In some embodiments, cCAR includes at least two CAR units. In another embodiment, the cCAR includes at least three CAR units. In another embodiment, the cCAR includes at least four units.

In one embodiment, the present disclosure provides an engineered cell having at least two distinct chimeric antigen receptor polypeptides, each having a different antigen recognition domain.

In one embodiment, he engineered cell having at least two distinct chimeric antigen receptor polypeptides is a T-cell. The T-cell may be engineered so that it does not express a cell surface antigen. For example, a may be engineered so that it does not express a CD45 cell surface antigen.

In a preferred embodiment, the engineered cell having at least two distinct chimeric antigen receptor polypeptides is a primary NK cell isolated from the peripheral blood or cord blood and NK-92 cells, such that it is administered "off-the-shelf" to any mammal with a disease or cancer.

In one embodiment, the engineered cell includes (i.) a first chimeric antigen receptor polypeptide comprising a first antigen recognition domain, a first signal peptide, a first hinge region, a first transmembrane domain, a first co-stimulatory domain, and a first signaling domain; and (ii.) a second chimeric antigen receptor polypeptide comprising a second antigen recognition domain, a second signal peptide, a second hinge region, a second transmembrane domain, a second co-stimulatory domain, and a second signaling domain. The first antigen recognition domain is different from the second antigen recognition domain.

In a preferred embodiment, each engineered CAR unit polynucleotide has different nucleotide sequences in order to avoid homologous recombination.

In one embodiment, the target of the first antigen recognition domain is selected from the group of, but not limited to, GD2, GD3, interleukin 6 receptor , ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, MMG49 epitope, CD30, EGFRvIII, CD33, CD123, CLL-1, NKG2D, NKG2D receptors, immunoglobin kappa and lambda, CD38, CD52, CD47, CD200, CD70, CD19, CD20, CD22, CD38, BCMA, CS1, BAFF receptor, TACI, CD3, CD4, CD8, CD5, CD7, CD2, and CD138; and the target of the second recognition domain is selected from the group consisting of GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, MMG49 epitope, NKG2D, NKG2D receptors, immunoglobin kappa and lambda, CD38, CD52, CD47, CD200, CD70, CD19, CD20, CD22, CD38, BCMA, CS1, BAFF, BAFF receptor, April receptor, TACI, CD3, CD4, CD8, CD5, CD7, CD2, and CD138.

In one embodiment, the target of the first antigen recognition domain is selected from the group of, but not limited to: GD2, GD3, CD19, CD20, CD22, CD38, CD138, BCMA, CS1, BAFF, BAFF receptor, TACI, April, April receptor, CD3, CD4, CD5, CD7, CD2, CLL-1, CD33, CD123, NKG2D receptors, MMG49 epitope and CD30; the target of the second recognition domain is selected from a group consisting of GD2, GD3, CD19, CD20, CD22, CD38, CD138, BCMA, CS1, BAFF, April, April receptor, BAFF receptor, TACI, CD3, CD4, CD5, CD7, CD2, CLL-1, CD33, CD123, MMG49 epitope, NKG2D receptors, and CD30.

In one embodiment, each CAR unit includes the same or different hinge region. In another embodiment, each CAR unit includes the same or different transmembrane region. In another embodiment, each CAR unit includes the same or different intracellular domain.

In one embodiment, each CAR unit includes the CD3 zeta chain signaling domain.

In one embodiment, each distinct CAR unit includes different co-stimulatory domains. For example, the first chimeric antigen receptor polypeptide includes a 4-1BB co-stimulatory domain; and the second chimeric antigen receptor polypeptide includes a CD28 co-stimulatory domain.

In one embodiment, each distinct CAR unit includes the same co-stimulatory domains. For example, the first chimeric antigen receptor polypeptide includes a 4-1BB co-stimulatory domain; and the second chimeric antigen receptor polypeptide includes a 4-1BB co-stimulatory domain.

In another embodiment, the hinge region is designed to exclude amino acids that may cause undesired intra- or intermolecular interactions. For example, the hinge region may be designed to exclude or minimize cysteine residues to prevent formation of disulfide bonds. In another embodiment, the hinge region may be designed to exclude or minimize hydrophobic residues to prevent unwanted hydrophobic interactions.

Compound CAR can perform killing independently or in combination. Multiple or compound CAR comprises same or different hinge region, same or different transmembrane, same or different co-stimulatory and same or different intracellular domains. Preferably, the hinge region is selected to avoid the interaction site.

The compound CAR of the present disclosure may target same or different tumor populations in T or NK cells. The first CAR, for example, may target the bulky tumor population and the next or the second CAR, for example, may eradicate cancer or leukemic stem cells, to avoid cancer relapses.

In accordance with the present disclosure, it was surprisingly found that the compound CAR in a T or NK cells targeting different or same tumor populations combat tumor factors causing cancer cells resistant to the CAR killing activity, thereby producing down regulation of the target antigen from the cancer cell surface. It was also surprisingly found that this enables the cancer cell to "hide" from the CAR therapy referred to as "antigen escape" and tumor heterogeneity, by which different tumor cells can exhibit distinct surface antigen expression profiles. As present disclosure below, it is surprisingly found that the compound CAR has significant advantages over single-CAR therapies due to its multi-targeting ability. While loss of a single antigen under antigen-specific selection pressure is possible, loss of two major antigens simultaneously is much less likely.

In one embodiment, the antigen recognition domain includes the binding portion or variable region of a humanized monoclonal or humanized polyclonal antibody directed against (selective for) the target.

In one aspect to the invention, an antigen recognition domain can be a bispecific tandem chimeric antigen receptor that includes two targeting domains. In further embodiment, there is a multispecific tandem chimeric antigen receptor that includes three or more targeting domains.

In certain aspects to the invention, an antigen recognition domain can be a bispecific chimeric antigen receptor (derived from a bispecific antibody) that includes two targeting domains.

In one embodiment, a bispecific tandem chimeric antigen receptor or a bispecific chimeric antigen receptor effectively offsets tumor escape or antigen loss and increases the sensitivity of antigen recognition.

In another embodiment, the antigen recognition domain includes camelid single domain antibody, or portions thereof. In one embodiment, camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001) and also includes an isolated VHH antibody of camelid, a recombinant VHH antibody of camelid, or a synthetic VHH antibody of camelid.

BCMA–CS1 Compound CAR (BCMA–CS1 cCAR)

Multiple myeloma (MM) is a blood cancer caused by the unusually rapid proliferation of plasma cells and accounts for 18% of all blood cancers in the United States. Treatment options for MM include chemotherapy, corticosteroid therapy, targeted therapy, high-dose chemotherapy with stem cell transplant, biological therapy, radiation therapy, monoclonal antibodies, proteasome inhibitors, and surgery. Even with these available treatments, the five-year survival rate for MM remains at 49.6%. However, there remains no cure for MM, and nearly all patients relapse after treatment Current CAR technology efforts in multiple myeloma involve the use of a BCMA (CD269) targeted CART-cell against bulk disease spearheaded by James Kochenderfer (NIH). Those patients in remission after BCMA CAR treatment eventually relapse and this may due to the fact that some myeloma cells are dim (weak) or negative expression for BCMA. Therefore, a single target for CAR based treatment may not be sufficient to prevent myeloma relapse. CS1 (SLAMF7) is another good target for myeloma as its expression is typically high and uniform in myeloma cells as well as being implicated in myeloma cell adhesion and tumorigenicity.

The present disclosure is composed of a single CAR T-cell expressing 2 discrete CAR units in a vector with independent signaling domains can be utilized as a novel approach for targeting multiple antigens and potentially avoiding tumor relapse. A compound CAR (cCAR) comprising of a BCMA CAR linked to a CS1 CAR via a self-cleaving P2A peptide and expressed both functional CAR molecules on the surface of a T cell.

In the present disclosure, it was surprisingly found that this BCMA–CS1 cCAR (BC1cCAR) T-cell exhibits potent and specific anti-tumor activity in vitro, as well as controlling significant tumor growth in vivo. We demonstrate, for the first time, a 2-unit discrete CAR is able to target effectively both antigens in vitro, with potential implications for more comprehensive clinical outcomes. It is unexpected that targeting multiple myeloma with a compound CAR targeting both BCMA and CS1 in combination is a very strong strategy. This novel approach circumvents the antigen escape (loss of a single antigen) from selection pressure of single CAR treatment due to combinatorial pressure from a compound design.

BCMA (B-cell maturation antigen) and CS1 (SLAMF7) were preferably chosen as targets for our compound CAR because the vast majority of myeloma cases express either or both surface antigens, and these antigens do not include hematopoietic stem cells. The use of two different targets widely expressed on plasma cells, BCMA and CS1, can increase coverage and efficaciously eradicate cancerous cells to prevent antigen escape In this disclosure, it is surprisingly found that the addition of CS1 as a target to the BCMA CAR enhanced the anti-tumor response by eliminating surviving BCMA$^-$CS1+ myeloma cells to reduce the risk of relapse. BCMA and CS1 (CD319) are both widely expressed on MM cells, and this high expression allows the BCMA–CS1 cCAR to have a comprehensive coverage of all potentially cancerous cells. This allows for a more complete elimination of cancerous cells to reduce antigen escape by hitting hard with multiple targets simultaneously before resistance develops.

In one embodiment, BCMA–CS1 directed BCMA–CS1cCAR (BC1cCAR) therapy is as a "bridge" to bone marrow transplant (BMT) or combination with a heavy chemotherapy plus BMT. BCMA–CS1 cCAR can offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, BCMA–CS1 cCAR therapy is able to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, BCMA–CS1 cCAR therapy can have further applications for patients with BCMA+ and/or CS1+ multiple myelomas beyond a bridge to bone marrow transplantation. BCMA–CS1cCAR therapy as a standalone therapy, or as a part of a patient-individualized immunochemotherapy regimen. For elderly patients, or for those with comorbidities who cannot tolerate highly intensive chemotherapy or BMT, this might be a promising strategy to prolong patient's survival time and reserve better life quality.

In some embodiments, BCMA–CS1cCAR T-cell therapy can be developed as a "bridge to transplant," a supplement to chemotherapy, or as a standalone therapy for patients with multiple myeloma.

In some embodiments, the present disclosure provides a compound CAR polypeptide engineered cell that targets cells expressing BCMA or CS1 antigens or both. The targeted cells may be cancer cells, such as, but not limited to, lymphomas, or leukemias or plasma cell neoplasms. In further embodiments, plasma cell neoplasms are selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

Without wishing to be bound by theory, it is believed that co-expression of IL-15/IL-15sushi or IL-15/IL-15sushi anchor or 4-1BBLwith BCMA–CS1 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with BCMA–CS1 cCAR provides long-term durable remission in patients by increasing the sensitivity of CAR recognition of target cancer cells or recruiting innate immune cells to cancer cells.

BCMA1-BCMA2 Compound CAR (BCMA1-BCMA2 cCAR)

Initial remission of most B-ALL can be seen in CD19 CAR T therapy but relapses with epitope loss occur in 10% to 20% of responders.

Current CAR technology efforts in multiple myeloma involve the use of a BCMA (CD269) targeted CAR T-cell against multiple myeloma spearheaded by James Kochenderfer (NIH). Those patients in initial remission after BCMA CAR treatment eventually relapse and this may due to the fact that some myeloma cells are dim (weak) or negative expression for BCMA. In addition, potency of a single CAR is also an issue for eliminating multiple myeloma cells in the patients. Therefore, a single target for CAR based treatment may not be sufficient to prevent myeloma relapse.

In one embodiment, the antibody recognition domain includes the binding variable region of a monoclonal antibody, single chain fragment variable (scFv). The scFv includes one light and heavy of antibody. In a particular embodiment, antigen recognition domain is composed of two different heavy chain domains (VHH). Each heavy chain domain binds to a different epitope of the same antigen or different antigen. A VHH antibody is more stable and robust than a whole antibody.

In some embodiments, the compound CAR targets the same antigen. For example, cCAR targets different epitopes or parts of a single antigen. In some embodiments, each of the CAR units present in the compound CAR targets different epitopes specific to the same antigen but different locations.

In some embodiments, a compound CAR targets different epitopes on one antigen.

The present disclosure is composed of a single CAR T-cell expressing two discrete CAR units in a vector with independent signaling domains can be utilized as a novel approach for targeting different epitopes on one antigen, and potentially avoiding tumor epitope skipping or epitope loss or epitope escape. A compound cCAR (BCMA1-BCMA2 cCAR) is comprising of one BCMA CAR (BCMA1 CAR) linked to another BCMA CAR (BCMA2 CAR) via a self-cleaving P2A peptide and expressed both functional CAR molecules on the surface of a T cell. Both units of CARs in cCAR target the same antigen, BCMA.

In one embodiment, the engineered cell includes a first chimeric antigen receptor polypeptide having a BCMA antigen recognition epitope and second chimeric antigen receptor polypeptide having a different BCMA recognition epitope. In one embodiment, this engineered cell includes a polypeptide of SEQ ID NO. 3 and corresponding polynucleotide of SEQ ID NO. 4.

In the present disclosure, it was surprisingly found that this BCMA1-BCMA2 cCAR T-cell exhibits potent and specific anti-tumor activity in vitro, as well as controlling significant tumor growth in vivo. We demonstrate, for the first time, a 2-unit discrete CAR is able to target effectively both different epitopes on one antigen, BCMA in vitro, with potential implications for more comprehensive clinical outcomes. It is unexpected that targeting multiple myeloma with a compound CAR targeting different epitopes in combination is a very strong strategy. This novel approach circumvents the epitope escape (loss of a single epitope or epitope skipping) from selection pressure of single CAR treatment due to combinatorial pressure from a compound design.

In this disclosure, it is surprisingly found that the addition of epitope as a target to the BCMA CAR enhances the anti-tumor response and reduces the risk of multiple myeloma relapse due to the loss of BCMA epitope.

In one embodiment, BCMA1-BCMA2 directed therapy is as a "bridge" to bone marrow transplant (BMT) or combination with a heavy chemotherapy plus BMT. BCMA1-BCMA2 cCAR can increase the sensitivity of recognition of BCMA antigen, and offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, BCMA1-BCMA2 cCAR therapy is able to bring down disease burden to the lowest possible level prior to transplant or thoroughly eliminate MRD, it can be expected that the relapse rate will decrease and long-term disease-free survival rate will increase, and patient outcomes will be dramatically improved.

In some embodiments, the present disclosure provides a compound CAR polypeptide engineered cell that targets two different epitopes on the BCMA antigen. The targeted cells may be cancer cells, such as, but not limited to, lymphomas, or leukemias or plasma cell neoplasms. In further embodiments, plasma cell neoplasms are selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

Without wishing to be bound by theory, it is believed that co-expression of IL-15/IL-15sushi or IL-15/IL-15sushi anchor or 4-1BBLwith BCMA1-BCMA2 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with BCMA1-BCMA2 cCAR provides long-term durable remission in patients by increasing the sensitivity of CAR recognition of target cancer cells or recruiting innate immune cells to cancer cells.

CD123-CD33 Compound CAR (CD123-CD33 cCAR)

Translating CAR success to AML requires a careful understanding of characteristics unique to the disease. AML is characterized by the presence of blast cells, which are highly aggressive and rapidly dividing cells that form the bulk of disease. Unlike B-cell malignancies, AML is uniquely challenging to treat due to the role of leukemic stem cells (LSCs). LSCs are a population of cells expressing markers of hematopoietic stem cells (CD34+CD38−) that are capable of initiating and maintaining hematopoietic malignancy, producing clonal cell populations that overtake healthy bone marrow. Since LSCs remain mostly in the quiescent phase of the cell cycle, chemotherapy directed against rapidly dividing tumor populations leaves LSCs untouched. Most often it is this elusive population that comprises minimal residual disease (MRD) and is responsible for inevitable relapse after AML treatment. Successful translation of CAR therapy to AML to completely eliminate disease and ensure no relapse requires careful antigen selection that will enable eradication of not just bulk leukemic disease, but also leukemic stem cells.

It is expected that a CD123-CD33 cCAR that will ablate both CD33+ and CD123+ cells without causing a CAR and CAR interaction. A useful analogy in this case would be to consider AML as a cancer tree with leaves and roots. While the leaves make up the majority/bulk of the disease (these are the CD33+ AML blast cells), trimming these leaves does not prevent the tree from growing further unless you also pull the tree from its root (these are the CD123+CD34+CD38− LSCs). A study of 319 AML patients and found that 87.8% of cases expressed CD33, so it follows that targeting CD33 might most leukemic cells. However, patients treated with gentuzumab ozogamicin, an anti-CD33 antibody therapy linked to calicheamicin, relapsed with CD33+ AML likely due to acquired chemoresistance to calicheamicin. Therefore, while targeting CD33 eliminates the majority of disease, the chemoresistant LSCs must also be targeted or relapse will occur. This can be achieved by targeting CD123, which is overexpressed on CD34+CD38− LSCs as compared to healthy hematopoietic stem cells. Considering that 97.2% of AML cases express at least one of the two targets, targeting both CD123 and CD33 would therefore eliminate all cancer cells in the majority of patients, increasing treatment efficacy and uprooting the cancer tree.

AML is a rapidly progressing blood cancer that accounts for about 15-20% of acute childhood leukemias and 80% of acute adult leukemia cases. Patients are nowadays still treated by high-dose multi-agent chemotherapy potentially followed by hematopoietic stem cell transplantation. Despite such intensive therapies, which are often associated with considerable toxicities and even death, about 60-70% of AML patients still relapse due to acquired therapy resistance or LSC re-emergence. Moreover, the five-year survival rate from AML remains at a dismal 27%. However, there are a limited number of clinical trials attempting the use of CARs to treat AM.

The present disclosure is composed of a single CAR T-cell expressing two discrete CAR units in a vector with independent signaling domains can be utilized as a novel approach for targeting multiple antigens and potentially avoiding tumor relapse. A compound CAR (cCAR) comprising of a CD123 CAR linked to a CD33 CAR via a self-cleaving P2A peptide and expressed both functional CAR molecules on the surface of a T cell.

In the present disclosure, it was surprisingly found that this CD123-CD33 cCAR T-cell exhibits potent and specific anti-tumor activity in vitro, as well as controlling significant tumor growth in vivo. We demonstrate, for the first time, a 2-unit discrete CAR is able to target effectively both antigens in vitro, with potential implications for more comprehensive clinical outcomes. It is unexpected that targeting AML with a compound CAR targeting both CD123 and Cd33 in combination is a very strong strategy. This novel approach circumvents disease relapses associated with LSCs, and antigen escape (loss of a single antigen) from selection pressure of single CAR treatment due to combinatorial pressure from a compound design.

In this disclosure, it is surprisingly found that the addition of CD123 as a target to the CD33 CAR enhanced the anti-tumor response by eliminating both leukemic blasts and its root, LSCs to reduce the risk of relapse. This allows for a more complete elimination of cancerous cells to reduce disease relapse by deleting both slowly growing LSCs and proliferative leukemic cells.

In this disclosure, it is surprisingly found that CD123-CD33 cCAR T-cells are able to eliminate regular leukemic cells and leukemic precursor cells to reduce the risk of relapse, and enhance anti-tumor activities.

In this disclosure, it is also surprisingly found that CD123-CD33 cCAR T-cells exhibit a more complete elimination of cancerous cells to reduce antigen escape by hitting hard with multiple targets simultaneously before resistance develops.

In one embodiment, CD123-CD33cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to, acute myeloid leukemia, myelodysplastic syndromes, chronic myeloid leukemia and chronic myeloproliferative disorders.

In another embodiment, CD123-CD33cCAR T-cell therapy can use to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, CD123-CD33cCAR T-cell therapy can have further applications for patients with Cd123+ and/or CD33+ leukemic patients beyond a bridge to bone marrow transplantation. CD123-CD33cCAR T-cell therapy as a standalone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

Without wishing to be bound by theory, it is believed that co-expression of IL-15/IL-15sushi or IL-15/IL-15sushi anchor or 4-1BBLwith CD123-CD33 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CD123-CD33 cCAR provides long-term durable remission in patients by increasing the sensitivity of CAR recognition of target cancer cells or recruiting innate immune cells to cancer cells.

In one embodiment, the disclosure provides a CD123-CD33-IL-15/IL-15sushi CAR engineered cell that includes secreting IL-15/IL-15sushi (SEQ ID NO. 24) and corresponding polynucleotide (SEQ ID NO. 25).

CLL-1-CD33 Compound CAR (CLL-1-CD33 cCAR)

A cCAR contains two units of CARs, CLL-1CAR and CD33 CAR targeting tumor cells expressing CLL-1 and CD33, respectively. CD33b CAR and CLL-1 CAR were used to construct a version of cCAR shown in FIG. 92. The construct comprises a SFFV promoter driving the expression of multiple modular units of CARs linked by a P2A peptide. Upon cleavage of the linker, the cCARs split and engage upon targets expressing CD33 and CLL-1. The activation domains of the construct included 4-1BB on the CD33b (CD33) CAR unit and a CD28 on the CLL-1 CAR unit. This CD33b-CLL-1 cCAR was designed to delete myeloid leukemic cells including leukemic stem cells.

At the present, therapies for MDS, MPN (chronic myeloproliferative neoplasms) and AML have focused on the leukemic blast cells because they are very abundant and clearly represent the most immediate problem for patients. Importantly, leukemic stem cells (LSCs) are quite different from most of the other leukemia cells ("blast" cells), and they constitute a rare subpopulation. While killing blast cells can provide short-term relief, LSCs, if not destroyed, will always re-grow, causing the patient to relapse. It is imperative that LSCs be destroyed in order to achieve durable cures for MDS disease. Unfortunately, standard drug regimens are not effective against MDS or MPN or AML LSCs. Therefore, it is critical to develop new therapies that can specifically target both the leukemic stem cell population and the bulky leukemic population. The compound CAR disclosed in the present disclosure target both populations and is embodied herein.

In one aspect of the present disclosure, CLL-1 antigen is one of the targets for cCAR therapy. C-type lectin-like-1 (CLL-1) is also known as MICL, CLEC12A, CLEC-1 and DCAL2. CLL-1 is a glycoprotein receptor and is expressed in hematopoietic cells. CLL-1 is absent on uncommitted CD34+/CD38- or CD34+/CD33- stem cells but present on subsets of CD34+/CD38+ or CD34+/CD33+ progenitor cells (Bakker et al, 2004). In addition, CLL-1 is not expressed in any other tissue.

CLL-1 expression is seen in acute myeloid leukemia (AML) blasts and leukemic stem cells. CLL-1 is expressed in a variety of leukemias including myelomonocytic leukemia (M4), acute monocytic leukemia (M5), acute promyelocytic leukemia (M3), chronic myeloid leukemia (CML), chronic myeloproliferative neoplasms and myelodysplastic syndromes (MDS).

CLL-1 is expressed on a subset of leukemic cells related to leukemic stem cells (LSCs), the ablation of which is essential in preventing disease refractoriness and relapse.

CD33 (Siglec-3) is a myeloid lineage-specific antigen expressed on early myeloid progenitors, most monocytic cells and approximately 90% of AML blasts, but absent on normal HSCs.

In one aspect of the present disclosure, CD33 antigen is one of the targets for cCAR therapy. CD33 is a transmembrane receptor expressed on 90% of malignant cells in acute myeloid leukemia. Thus, according to the present disclosure, CLL-1 and CD33 target antigens are particularly attractive from a safety standpoint.

In accordance with the present disclosure, the compound CLL-1-CD33 cCARs may be highly effective for therapeutic treatment of chronic myeloid leukemia (CML) population. In chronic myeloid leukemia (CML), there is a rare subset of cells that are CD34+CD38-. This population is considered as comprised of LSCs. Increased number of LSCs is associated with the progression of the disease. A small-molecule Bcr-Abl tyrosine kinase inhibitor (TKI) is shown to significantly improve the overall survival in CP-CML patients. However, LSCs are thought to be resistant to TKI therapy. A novel therapy targeting CML resistant LSCs is urgently needed for treatment of CML and the novel therapy is embodied in the compound CD33CLL-1 CAR disclosed in the present disclosure. CLL-1 expression is high in the CD34+CD38− population. In accordance with the present disclosure, the compound CD33CLL-1 CARs is highly effective for therapeutic treatment of this population.

In one embodiment of the present disclosure, leukemic cells expressing both CD33 and CLL-1 in the cCAR are used as a therapeutic treatment. CD33 is expressed on cells of myeloid lineage, myeloid leukemic blasts, and mature monocytes but not normal pluripotent hematopoietic stem cells. CD33 is widely expressed in leukemic cells in CML, myeloproliferative neoplasms, and MDS.

Since a significant number of patients with acute myeloid leukemia (AML) are refractory to standard chemotherapy regimens or experience disease relapse following treatment (Burnett 2012), the development of CAR T cell immunotherapy for AML has the potential to address a great clinical need. In the majority of these patients, leukemic cells express both CLL-1 and CD33, giving broad clinical applicability to the compound CLL-1–CD33 cCAR disclosed herein. Thus, the present disclosure discloses a novel multiple cCAR T/NK cell construct comprising multiple CARs targeting multiple leukemia-associated antigens, thereby offsetting antigen escape mechanism, targeting leukemia cells, including leukemic stem cells, by synergistic effects of co-stimulatory domain activation, thereby providing a more potent, safe and effective therapy.

In further embodiments, the present disclosure provides a method of eradicating or killing leukemic stem cells (LSCs) or bulk leukemic cells expressing CLL-1 or CD33, or both. In this embodiment, a T or NK engineered cell having a CD33 unit and a CLL-1 unit is administered to a patient in need thereof.

In further embodiments, a compound CAR in a T or NK cell may be used to eradicate or kill CD34+ CD38− leukemic stem cells or bulk leukemic cells expressing CLL-1 or CD33 or both.

The present disclosure further discloses a compound CAR construct with enhanced potency of anti-tumor activity against cells co-expressing target antigens, and yet retains sensitivity to tumor cells only expressing one antigen. In addition, each CAR of the compound CAR includes one or two co-stimulatory domains and exhibits potent killing capability in the presence of the specific target.

In this disclosure, it is surprisingly found that CLL-1–CD33 cCAR T-cells are able to eliminate regular leukemic cells and leukemic precursor cells to reduce the risk of relapse, and enhance anti-tumor activities.

In this disclosure, it is also surprisingly found that CLL-1–CD33 cCAR T-cells exhibit a more complete elimination of cancerous cells to reduce antigen escape by hitting hard with multiple targets simultaneously before resistance develops.

In this disclosure, it is also surprisingly found that compound CAR exhibits less toxicity when compared to single CAR. An unexpected finding from our recent clinical trial supported this notion that compound CAR exhibits less toxicity when compared to individual CAR and compared to what was previously thought in respect to off-target effects. In a further disclosure, compound CAR can increase the affinity or trafficking to the tumor cell expressing two target antigens rather than off-target cells that express only one target antigen. In this way, the compound CAR may elicit selectivity and prefer to target cells expressing both target antigens rather than cells expressing only one antigen, which could lead to increased off-target toxicity.

In one embodiment, CLL-1–CD33 cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to, acute myeloid leukemia, myelodysplastic syndromes, chronic myeloid leukemia and chronic myeloproliferative disorders.

In another embodiment, CLL-1–CD33cCAR T-cell therapy can use to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, CLL-1–CD33 cCAR T-cell therapy can have further applications for patients with CLL-1+ and/or CD33+ leukemic patients beyond a bridge to bone marrow transplantation. CLL-1–CD33cCAR T-cell therapy as a standalone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

Without wishing to be bound by theory, it is believed that co-expression of IL-15/IL-15sushi or IL-15/IL-15sushi anchor or 4-1BBLwith CLL-1–CD33 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CLL-1–CD33 cCAR provides long-term durable remission in patients by increasing the sensitivity of CAR recognition of target cancer cells or recruiting innate immune cells to cancer cells.

In one embodiment, the disclosure provides a CLL1–CD33b-IL-15/IL-15sushi CAR engineered cell that includes secreting IL-15/IL-15sushi (SEQ ID NO. 28) and corresponding polynucleotide (SEQ ID 29)

CD123-NKG2D cCAR or CLL-1–NKG2D cCAR or CD33-NKG2D cCAR or BCMA–NKG2D cCAR

NKG2D (NKG2D receptor) is considered a transmembrane protein belonging to the CD94/NKG2 family of C-type lectin-like receptors. NKG2D can bind to at least 8 different ligands that are naturally expressed in AML, multiple myeloma or other leukemias. NKG2D ligands are induced-self proteins which are virtually absent or present only at very low levels on surface of normal cells but are overexpressed in cancer cells, including AML and multiple myeloma. Therefore, they are good candidates for CAR targeting.

A cCAR contains two units of CARs, a CD123 CAR and NKG2D CAR that target tumor cells expressing CD123 and NKG2D ligands, respectively.

A cCAR contains two units of CARs, a CLL-1 CAR and NKG2D CAR that target tumor cells expressing CLL-1 and NKG2D ligands, respectively.

CD123-NKG2D cCAR or CLL-1–NKG2D cCAR or CD33-NKG2D cCAR are able to eliminate leukemias including AML, MDS, CML and MPN.

In the present disclosure, BCMA–NKG2D cCAR is able to eliminate multiple myeloma.

In this disclosure, the addition of NKG2D as a target to the CD123 CAR or CLL-1 CAR or CD33 CAR enhances the anti-tumor response and reduces the risk of antigen escape associated with disease relapse because NKG2D is widely expressed on AML, MDS, CML and MPN.

BCMA and NKG2D ligands are both widely expressed on multiple myeloma cells, and this high expression allows the BCMA-NKG2D cCAR to have a comprehensive coverage of all potentially cancerous cells. This allows for a more complete elimination of cancerous cells to reduce antigen escape by hitting hard with multiple targets simultaneously before resistance develops.

BCMA-CD38 Compound CAR (BCMA-CD38 cCAR)

Current CAR technology efforts in multiple myeloma involve the use of a BCMA (CD269) targeted CART-cell against bulk disease spearheaded by James Kochenderfer (NIH). Those patients in remission after BCMA CAR treatment eventually relapse and this may due to the fact that some myeloma cells are dim (weak) or negative expression for BCMA. Therefore, a single target for CAR based treatment may not be sufficient to prevent myeloma relapse.

CD38 also known as cyclic ADP ribose hydrolase is a glycoprotein is found on the surface of many immune cells including CD4+, CD8+, B lymphocytes, plasma cells, and natural killer cells.

CD38 is another good target for myeloma as its expression is typically high and uniform in myeloma cells and lymphoma cells.

The present disclosure is composed of a single CAR T-cell expressing 2 discrete CAR units in a vector with independent signaling domains can be utilized as a novel approach for targeting multiple antigens and potentially avoiding tumor relapse. A compound CAR (cCAR) comprising of a BCMA CAR linked to a CD38 CAR via a self-cleaving P2A peptide and expressed both functional CAR molecules on the surface of a T cell. This compound cCAR expression is controlled by a strong promoter, SFFV to ensure adequate CAR expression.

In the present disclosure, BCMA-CD38 cCAR T-cell can provide potent and specific anti-tumor activity in controlling myeloma (FIG. 37). Targeting multiple myeloma with a compound CAR targeting both BCMA and CD38 in combination is a very strong strategy. This novel approach circumvents the antigen escape (loss of a single antigen) from selection pressure of single CAR treatment due to combinatorial pressure from a compound design.

In this disclosure, the addition of CD38 as a target to the BCMA CAR enhanced the anti-tumor response by eliminating surviving BCMA$^-$CD38$^+$ myeloma cells to reduce the risk of relapse.

BCMA and CD38 are both widely expressed on multiple myeloma cells, and this high expression allows the BCMA-CD38 cCAR to have a comprehensive coverage of all potentially cancerous cells. This allows for a more complete elimination of cancerous cells to reduce antigen escape by hitting hard with multiple targets simultaneously before resistance develops.

In one embodiment, BCMA-CD38 directed BCMA-CD38 cCAR therapy is as a "bridge" to bone marrow transplant (BMT) or combination with a heavy chemotherapy plus BMT. BCMA-CD38 cCAR can offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, BCMA-CD38 cCAR therapy is able to bring down disease burden to the lowest possible level prior to transplant or thoroughly eliminate MRD, it can be expected that the relapse rate will decrease and long-term disease-free survival rate will increase, and patient outcomes will be dramatically improved.

In one embodiment, BCMA-CD38 cCAR therapy can have further applications for patients with BCMA+ and/or CD38+ multiple myelomas beyond a bridge to bone marrow transplantation. BCMA-CD38 cCAR therapy as a stand-alone therapy, or as a part of a patient-individualized immuno-chemotherapy regimen. For elderly patients, or for those with comorbidities who cannot tolerate highly intensive chemotherapy or BMT, this might be a promising strategy to prolong patient's survival time and reserve better life quality.

In some embodiments, the present disclosure provides a compound CAR polypeptide engineered cell that targets cells expressing BCMA or CD38 antigens or both. The targeted cells may be cancer cells, such as, but not limited to, lymphomas, or leukemias or plasma cell neoplasms. In further embodiments, plasma cell neoplasms are selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

Without wishing to be bound by theory, it is believed that co-expression of IL-15/IL-15sushi or IL-15/IL-15sushi anchor or 4-1BBLwith BCMA-CD38 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with BCMA-CD38 cCAR provides long-term durable remission in patients by increasing the sensitivity of CAR recognition of target cancer cells or recruiting innate immune cells to cancer cells.

Without wishing to be bound by theory, it is believed that BCMA-CD38 compound CAR engineered cells provide a better therapeutic outcome in patients suffering from an autoimmune disorder or organ rejection by depletion of B-cells and plasma cells associated with autoimmune disorders.

In some embodiments, a compound CAR (BCMA-CD38 cCAR) targets cells expressing BCMA or CD38 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plasmacytoma, monoclonal gammopathy of undetermined significance (MGUS) and smoldering multiple myeloma.

BCMA-CD38 cCAR targeted cells are B cells, immature B cells, memory B cells, plasmablasts, long lived plasma cells, or plasma cells in patients with autoimmune diseases. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, pulmonary alveolar proteinosis, granulomatosis and vasculitis, Addison's disease, antigen-antibody complex mediated diseases, and antiglomerular basement membrane disease.

In another embodiment, the present disclosure provides a method of treating an autoimmune disease. An autoimmune disorder is selected from a group of diseases including autoimmune disease comprises systemic lupus erythematosus (SLE), multiple sclerosis (MS), Inflammatory bowel disease (IBD), Rheumatoid arthritis, Sjogren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis, pemphigus vulgaris (PV) and pemphigus foliaceus (PF). Pemphigus vulgaris (PV) and pemphigus foliaceus (PF) are chronic and life-threatening blistering diseases caused by autoantibodies.

CD19-CD38 Compound CAR (CD19-CD38 cCAR)

While initial remission rates of approximately 90% are commonly seen in patients with B-ALL using CD19CAR, most patients relapse within a year. The relapse is at least in part due to antigen escape. Thus, more effective CAR T cell treatments to prevent relapse are urgently needed.

CD38 is another good target for lymphomas as its expression is typically high and uniform in lymphoma cells. CD38 is expressed in a variety of lymphomas including chronic lymphocytic lymphoma/small lymphocytic lymphoma, follicular lymphoma, primary effusion lymphoma, diffuse large cell lymphoma, lymphoplasmacytic lymphoma.

The present disclosure is composed of a single CAR T-cell expressing two discrete CAR units in a vector with independent signaling domains can be utilized as a novel approach for targeting multiple antigens and potentially avoiding tumor relapse. A compound CAR (cCAR) comprising of a CD19 CAR linked to a CD38 CAR via a self-cleaving P2A peptide and expressed both functional CAR molecules on the surface of a T cell. This compound cCAR expression is controlled by a strong promoter, SFFV to ensure adequate CAR expression.

In the present disclosure, CD19-CD38 cCAR T-cell can provide potent and specific anti-tumor activity in controlling lymphoma. Targeting multiple myeloma with a compound CAR targeting both BCMA and CD19 in combination is a very strong strategy. This novel approach circumvents the antigen escape (loss of a single antigen) from selection pressure of single CAR treatment due to combinatorial pressure from a compound design.

In this disclosure, the addition of CD38 as a target to the BCMA CAR enhanced the anti-tumor response by eliminating surviving BCMA$^-$CD38$^+$ lymphomas to reduce the risk of relapse.

CD19 and CD38 are both widely expressed on multiple myeloma cells, and this high expression allows the CD19-CD38 cCAR to have a comprehensive coverage of all potentially lymphoma cells. This allows for a more complete elimination of cancerous cells to reduce antigen escape by hitting hard with multiple targets simultaneously before resistance develops.

In one embodiment, CD19-CD38 directed BCMA-CD38 cCAR therapy is as a "bridge" to bone marrow transplant (BMT) or combination with a heavy chemotherapy plus BMT. CD19-CD38 cCAR can offer a path to a potentially curative BMT option to many patients that previously would have a residual disease. Current literature supports the idea that reducing the minimal residual disease burden (MRD) to an undetectable level could be associated with improved patient outcomes. This could be extremely beneficial in terms of prevention of relapse for the difficult to treat and highly aggressive malignancies.

In another embodiment, CD19-CD38 cCAR therapy is able to bring down disease burden to the lowest possible level prior to transplant or thoroughly eliminate MRD, it can be expected that the relapse rate will decrease and long-term disease-free survival rate for lymphoma will increase, and patient outcomes will be dramatically improved.

In one embodiment, CD19-CD38 cCAR therapy can have further applications for patients with CD19+ and/or CD38+ multiple myelomas beyond a bridge to bone marrow transplantation. CD19-CD38 cCAR therapy as a standalone therapy, or as a part of a patient-individualized immunochemotherapy regimen. For elderly patients, or for those with comorbidities who cannot tolerate highly intensive chemotherapy or BMT, this might be a promising strategy to prolong patient's survival time and reserve better life quality.

In some embodiments, the present disclosure provides a compound CAR polypeptide engineered cell that targets cells expressing CD19 or CD38 antigens or both. The targeted cells may be cancer cells, such as, but not limited to, lymphomas. In further embodiments, lymphomas are selected from without limiting, B-ALL, high grade B cell lymphoma, low grade B-cell lymphoma, diffuse large B cell lymphoma, Burkett lymphoma, mantle cell lymphoma, CLL, marginal zone B cell lymphoma and follicular lymphoma.

Without wishing to be bound by theory, it is believed that co-expression of IL-15/IL-15sushi or IL-15/IL-15sushi anchor or 4-1BBL with CD19-CD38 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CD19-CD38 cCAR provides long-term durable remission in patients by increasing the sensitivity of CAR recognition of target cancer cells or recruiting innate immune cells to cancer cells.

Without wishing to be bound by theory, it is believed that CD19-CD38 compound CAR engineered cells provide a better therapeutic outcome in patients suffering from an autoimmune disorder or organ rejection by depletion of B-cells and plasma cells associated with autoimmune disorders.

In one embodiment, the engineered cell includes a CD19 chimeric antigen receptor polypeptide (SEQ ID NO. 30), and corresponding nucleotides (SEQ ID NO. 31).

In some embodiments, a compound CAR (BCMA-CD38 cCAR) targets cells expressing BCMA or CD38 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plasmacytoma, monoclonal gammopathy of undetermined significance (MGUS) and smoldering multiple myeloma.

BCMA-CD38 cCAR targeted cells are B cells, immature B cells, memory B cells, plasmablasts, long lived plasma cells, or plasma cells in patients with autoimmune diseases. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, pulmonary alveolar proteinosis, granulomatosis and vasculitis, Addison's disease, antigen-antibody complex mediated diseases, and anti-glomerular basement membrane disease.

In another embodiment, the present disclosure provides a method of treating an autoimmune disease. An autoimmune disorder is selected from a group of diseases including autoimmune disease comprises systemic lupus erythematosus (SLE), multiple sclerosis (MS), Inflammatory bowel disease (IBD), Rheumatoid arthritis, Sjögren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis, pemphigus vulgaris (PV) and pemphigus foliaceus (PF). Pemphigus vulgaris (PV) and pemphigus foliaceus (PF) are chronic and life-threatening blistering diseases caused by autoantibodies.

BCMA–CD19 Compound CAR (BCMA–CD19 cCAR)

While killing multiple myeloma cells can provide short-term relief, LSCs (myeloma leukemic stem cells), if not destroyed, will always re-grow, causing the patient to relapse. It is imperative that LSCs be destroyed to achieve durable cures for multiple myeloma disease. Without wishing to be bound by theory, it is believed that a small subset of multiple myeloma cells is stem cells that are CD19 positive and associated with disease progression and relapses, and a bulky myeloma cell population is BCMA positive. Therefore, it is critical to develop new therapies that can specifically target both the myeloma stem cell population and the bulky myeloma population. A compound CAR in the present disclosure targets BCMA+ and/or CD19+ positive populations of multiple myeloma cells and is embodied herein.

In some embodiments, the present disclosure provides a method of eradicating or killing myeloma stem cells (LSCs) or bulk myeloma cells expressing CD19 and/or BCMA. In this embodiment, a T or NK engineered cell having a BCMA unit and a CD19 unit is administered to a patient in need thereof.

In some embodiments, the disclosed disclosure comprises methods and compositions of deleting both BCMA and CD19 populations in multiple myeloma to prevent relapses using a BCMA–CD19 cCAR. CAR is more powerful in eliminating myeloma cells when combination of two units of BCMA and CD19 (BCMA–CD19) together in a vector or a cell.

In further embodiments, a compound CAR, BCMA–CD19 cCAR in a T or NK cell may be used to eradicate or kill BCMA+CD19+ or BCMA+CD19– or BCMA–CD19+ populations.

In some embodiments, the disclosed disclosure comprises methods and compositions of deleting both BCMA and CD19 populations in multiple myeloma to prevent relapses using a BCMA–CD19 cCAR. CAR is more powerful in eliminating myeloma cells when combination of two units of BCMA and CD19 (BCMA–CD19) together in a vector or a cell.

In some embodiments, CD19+ populations can be early precursors for multiple myeloma cells, and CD19–BCMA+ cells can be more differentiated malignant multiple myeloma cells. In some embodiments, the disclosed invention comprises methods and compositions of deleting both early precursor of multiple myeloma cells and more differential malignant multiple myeloma cells using a BCMA–CD19b cCAR (a version of BCMA–CD19 cCAR) T or NK cell. In a further embodiment, the disclosed disclosure comprises methods and compositions of targeting both early precursor and more differential malignant cells to completely eliminate malignant clones for multiple myeloma using a BCMA–CD19b cCAR T or NK cell.

The present disclosure further discloses a compound CAR construct with enhanced potency of anti-myeloma cell activity against cells co-expressing target antigens, and yet retains sensitivity to tumor cells only expressing one antigen. In addition, each CAR of the compound CAR includes one or two co-stimulatory domains and exhibits potent killing capability in the presence of the specific target.

Without wishing to be bound by theory, it is believed that co-expression of IL-15/IL-15sushi or IL-15/IL-15sushi anchor or 4-1BBLwith BCMA–CD19 cCAR provides long-term durable remission in patients by increasing the sensitivity of CAR recognition of target myeloma cells or recruiting innate immune cells to myeloma cells.

In some embodiments, a compound CAR (BCMA–CD19 cCAR) targets cells expressing BCMA or CD19 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plasmacytoma, monoclonal gammopathy of undetermined significance (MGUS) and smoldering multiple myeloma.

Without wishing to be bound by theory, it is believed that co-expression of IL-21 or IL-IL-21 anchor with BCMA–CD19 cCAR provides long-term durable remission in patients by increasing the sensitivity of CAR recognition of target myeloma cells or recruiting innate immune cells to myeloma cells.

Without wishing to be bound by theory, it is believed that co-expression of IL-18 or IL-IL-18 anchor with BCMA–CD19 cCAR provides long-term durable remission in patients by increasing the sensitivity of CAR recognition of target myeloma cells or recruiting innate immune cells to myeloma cells.

In some embodiments, the disclosure provides a method of depleting B cells, immature B cells, memory B cells, plasmablasts, long lived plasma cells, or plasma cells in patients with an autoimmune disease by administering to patients CAR or compound CAR (BCMA–CD19 cCAR) T cells or NK cells.

BCMA–CD19 cCAR targeted cells are B cells, immature B cells, memory B cells, plasmablasts, long lived plasma cells, or plasma cells in patients with autoimmune diseases. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, pulmonary alveolar proteinosis, granulomatosis and vasculitis, Addison's disease, antigen-antibody complex mediated diseases, and anti-glomerular basement membrane disease.

In some embodiments, immune cells including B cells, immature B cells, memory B cells, plasmablasts, long lived plasma cells, or plasma cells in patients with autoimmune diseases can be eliminated by a BCMA and CD19 bispecific CAR T cell or bispecific antibody.

In another embodiment, the present disclosure provides a method of treating an autoimmune disease. An autoimmune disorder is selected from a group of diseases including autoimmune disease comprises systemic lupus erythematosus (SLE), multiple sclerosis (MS), Inflammatory bowel disease (IBD), Rheumatoid arthritis, Sjögren syndrome, dermatomyosities, autoimmune hemolytic anemia, Neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis, Pemphigus vulgaris (PV) and pemphigus foliaceus (PF). An organ transplant represents a new life for a person and organs that can be transplanted could include the kidneys, heart, lungs, pancreas and intestine. However, many patients are unable to receive a potentially life-saving organ because of pre-existing or developing donor-specific antibody against the donor's antigens such human leukocyte antigens (HLA). Thus, patients may lose the donated organ. Currently there are few treatment options available for antibody mediated rejection, and an enormous unmet need in the field for efficacious treatment of antibody mediated rejection. Deletion of B cells or plasma cells or both using CAR T/NK cell provide a therapy for antibody-mediated rejection.

BCMA–CD19 cCAR or CD19–CD38 cCAR or BCMA–CD38 cCAR targeted cells are B cells, immature B cells, memory 13 cells, plasmablasts, long lived plasma cells, or plasma cells in patients with the antibody-mediated rejection associated with organ rejections.

Engineered Cell Having CAR Polypeptide and Enhancer

In another embodiment, the present disclosure provides an engineered cell having at least one chimeric antigen receptor polypeptide and an enhancer.

In another embodiment, the present disclosure provides an engineered cell having at least one chimeric antigen receptor polypeptide and at least one enhancer.

In one embodiment, the present disclosure provides an engineered cell having at least two distinct chimeric antigen receptor polypeptides and an enhancer.

In one embodiment, the present disclosure provides an engineered cell having at least two distinct chimeric antigen receptor polypeptides and at least one enhancer.

As used herein, an enhancer includes a biological molecule that promotes or enhances the activity of the engineered cell having the chimeric antigen receptor polypeptide. Enhancers include cytokines. In another embodiment, enhancers include IL-2, IL-7, IL-12, IL-15, IL-18, IL-21, IL-21 anchor, PD-1, PD-L1, CSF1R, CTAL-4, TIM-3, and TGFR beta, receptors for the same, and functional fragments thereof.

Enhancers may be expressed by the engineered cell described herein and displayed on the surface of the engineered cell or the enhancer may be secreted into the surrounding extracellular space by the engineered cell. Methods of surface display and secretion are well known in the art. For example, the enhancer may be a fusion protein with a peptide that provides surface display or secretion into the extracellular space.

The effect of the enhancer may be complemented by additional factors such as enhancer receptors and functional fragments thereof. The additional factors may be co-expressed with the enhancer as a fusion protein, or expressed as a separate polypeptide and secreted into the extracellular space.

Enhancers can be cytokines secreted from engineered CAR cells and are designed to co-express with the CAR polypeptide. A massive release occurs upon CAR engagement of cognate antigen. Inflammatory cells surrounding tumor cells have a significant correlation with cancer cell progression and metastasis. Inflammatory cells could include T cells and innate immune response cells, such as NK cells, macrophages, and dendritic cells and their proliferation and anti-tumor activity are regulated by cytokines. CAR cells such as CAR T or NK cells bind to targeted cancer cells and trigger massive secretion of enhancers from the expansion of CAR T/NK cells. The secreted enhancers efficiently promote survival, differentiation and activation of immune response cells against cancer cells. The co-expression of an enhancer(s) with CAR can supplement the defect that CAR T or NK cells are unable to eliminate non-targeting cancer cells CAR cells can be a carrier of cytokines, and cytokines can be delivered to targeted cancer sites by CAR cells to reduce systemic toxicity with high-dose exogenous cytokines.

To improve sustained survival or long-lived persistence of CAR cells, a membrane bound enhancer (s) can be co-expressed with CAR to improve CAR persistency In one embodiment, the enhancer is IL-15. In this instance, the additional factor described above is the IL-15 receptor, and functional fragments thereof. Functional fragments include the IL-15 receptor, IL-15RA, and the sushi domain of IL-15RA (IL-15sushi). Soluble IL-15RA or IL15sushi profoundly potentiates IL-15 functional activity by prevention of IL-15 degradation. Soluble IL-15/IL-15RA or IL-15/IL-15sushi complexes are stable and much more stimulatory than IL-15 alone in vivo.

In one embodiment, IL-15 is co-expressed as a fusion protein with at least one of IL-15 receptor, IL-15RA, and the sushi domain of IL-15RA (IL-15sushi). In one embodiment, the IL-15 receptor, IL-15RA, or the sushi domain of IL-15RA (IL-15sushi) is at the N-terminus of IL-15. In another embodiment, the IL-15 receptor, IL-15RA, or the sushi domain of IL-15RA (IL-15sushi) is at the C-terminus of IL-15. As used herein, IL-15/IL-15 sushi denotes that IL-15 sushi is at the C-terminus of IL-15 in a fusion protein; and IL-15sushi/i1-15 denotes that IL-15 sushi is at the N-terminus of IL-15 in a fusion protein.

In some embodiments, IL-15 and the IL-15 receptor or functional fragments thereof polypeptide is on a single polypeptide molecule and is separated by a peptide linker, the peptide linker may be 1-25 amino acid residues in length, 25-100 amino acid residues in length, or 50-200 amino acid residues in length. This linker may include a high efficiency cleavage site described herein.

Interleukin (IL)-15 and its specific receptor chain, IL-15Ra (IL-15-RA) play a key functional role in various effector cells, including NK and CD8 T cells. CD8+ T cells can be modified to express autocrine growth factors including, but not limited to, IL-2, 11-7, IL-21 or IL-15, to sustain survival following transfer in vivo. Without wishing to be bound by theory, it is believed that IL-15 overcomes the CD4 deficiency to induce primary and recall memory CD8T cells. Overexpression of IL-15-RA or an IL-15 IL-RA fusion on CD8 T cells significantly enhances its survival and proliferation in-vitro and in-vivo. In some embodiments, CD4CAR or CD19 CAR or CD45 CAR or BCMA CAR or any CAR is co-expressed with at least one of IL-15, IL15RA and IL-15/IL-15RA or IL15-RA/IL-15 or IL-15/IL-15sush, or a part or a combination thereof, to enhance survival or proliferation of CAR T or NK, and to improve expansion of memory CAR CD8+ T cells or NK cells.

CD4CAR or CD19 CAR or CD45 CAR or BCMA CAR or any CAR is co-expressed with at least one of IL-15/IL-15sushi or a part or a combination thereof, to enhance survival or proliferation of CAR NK, and to improve expansion of memory CAR CD8+ T cells.

It is surprisingly found that CAR co-expression of IL-15/IL-15sushi is important for the longer persistence and enhanced activity of the T cells and NK cells targeting tumor cells.

It is surprisingly found that CAR co-expression of IL-15/IL-15sushi is important for the T cells and NK cells targeting tumor cells and preventing cancer relapses.

It is surprisingly found that CAR NK cells or NK cells can extend survival when co-expressing with IL-15/IL-15sushi.

The present disclosure provides an engineered cell having a CAR polypeptide as described herein and at least one of IL-15, IL-15RA, IL-15sushi, IL-15/IL-15RA, IL-15-RA/IL-15, IL-15/IL-15sushi, IL15sushi/IL-15, fragment thereof, a combination thereof, to enhance survival or persistence or proliferation of CAR T or NK for treating cancer in a patient.

In another embodiment, the present disclosure provides an engineered cell having at least one of recombinant IL-15, IL-15RA, IL-15sushi, IL-15/IL-15RA, IL15-RA/IL-15, IL-15/IL-15sushi, IL15sushi/IL-15, functional fragment thereof, and combination thereof; and at least one distinct CAR polypeptide wherein the antigen recognition domain includes GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, immunoglobin kappa and lambda, CD38, CD52, CD47, CD200, CD70, CD19, CD20, CD22, CD38, BCMA, CS1, BAFF receptor, TACI, CD3, CD4, CD8, CD5, CD7, CD2, and CD138.

Without wishing to be bound by theory, it is believed that IL-15/IL-15sushi and other types of IL-15 or IL-15RA proteins or protein fragments thereof provide synergistic efficacy of a CAR polypeptide when combined with checkpoint inhibitors or modulators (e.g. anti-PD-1).

In one embodiment, the present disclosure provides a method of providing long-term durable remission in patients suffering from cancer by administering a CAR engineered cell that co-expresses IL-21 or IL-12 anchor to a patient in need thereof (FIGS. 24 and 25). Without wishing to be bound by theory, it is believed that co-expression of IL-21 or IL-21 anchor with a CAR provides long-term durable remission in patients by increasing the persistence of CAR engineered cells.

Without wishing to be bound by theory, it is also believed that co-expression of secreting IL-21 with a CAR polypeptide provides long-term durable remission in patients by affecting tumor micro-environment resulting in reduction of immunosuppression and promotion of innate cell proliferation or functions.

Without wishing to be bound by theory, it is believed that CAR co-expression of secreting IL-21 or IL-21 anchor is important for the longer persistence and enhanced activity of the T cells and NK cells targeting tumor cells. CAR NK cells or NK cells can extend survival when co-expressing with IL-21 or IL-21 anchor.

In one embodiment, the present disclosure provides a method related to that CAR T or NK cells targeting tumor cells can be a carrier to delivery an enhancer, IL-21 to the tumor micro-environment. CAR T or NK cells are engineered to co-express a secretory IL-21. Engineered CAR T or NK cells in tumor microenvironment, target tumor cells, binding to the CAR targeting antigen, and triggering lysis of tumor cells and massive secretion of soluble IL-21 from the expansion of CAR T or NK cells.

In particular embodiments, elimination of tumor can be achieved by combination of at least one or more of the following steps:
(1) binding of an CAR engineered T cell or NK cell disclosed herein to a portion of tumor cells by targeting CAR or NK antigen(s);
(2) Triggering of a massive secretion of IL-21 from expansion of CAR T/NK cells, which co-express this molecule;
(3) Recruiting and stimulating a variety of innate and adaptive immune cells against tumor;
(4) Reducing tumor suppression that is present in tumor by administration of a checkpoint blockage such as PD-L1 and CTLA-4 inhibitor.

Without wishing to be bound by theory, it is believed that the combination of steps described above provide potent anti-tumor effects via a concerted innate and adaptive immune response.

In another embodiment, the present disclosure provides an engineered cell having IL-21 or IL-21 anchor, functional fragment thereof, and combination thereof; and at least one distinct CAR polypeptide wherein the antigen recognition domain includes GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, CD30, EGFRvIII, CD33, CD123, CLL-1, immunoglobin kappa and lambda, CD38, CD52, CD19, CD20, CD22, CD38, BCMA, CS1, BAFF receptor, TACI, CD3, CD4, CD8, CD5, CD7, CD2, and CD138.

In one embodiment, the present disclosure provides a method of providing long-term durable remission in patients suffering from cancer by administering a CAR engineered cell that co-expresses IL-18 or IL-18 anchor to a patient in need thereof (FIGS. 26 and 27). Without wishing to be bound by theory, it is believed that co-expression of IL-18 or IL-18 anchor with a CAR provides long-term durable remission in patients by increasing the persistence of CAR engineered cells.

Without wishing to be bound by theory, it is also believed that co-expression of secreting IL-18 with a CAR polypeptide provides long-term durable remission in patients by affecting tumor micro-environment resulting in reduction of immunosuppression and promotion of innate cell proliferation or functions.

Without wishing to be bound by theory, it is believed that CAR co-expression of secreting IL-18 or IL-18 anchor is important for the longer persistence and enhanced activity of the T cells and NK cells targeting tumor cells. CAR NK cells or NK cells can extend survival when co-expressing with IL-18 or IL-18 anchor.

In one embodiment, the present disclosure provides a method related to that CAR T or NK cells targeting tumor cells can be a carrier to delivery an enhancer, IL-18 to the tumor micro-environment. CAR T or NK cells are engineered to co-express a secretory IL-18. Engineered CAR T or NK cells in tumor microenvironment, target tumor cells, binding to the CAR targeting antigen, and triggering lysis of tumor cells and massive secretion of soluble IL-18 from the expansion of CAR T or NK cells.

In particular embodiments, elimination of tumor can be achieved by combination of at least one or more of the following steps:
(1) binding of an CAR engineered T cell or NK cell disclosed herein to a portion of tumor cells by targeting CAR or NK antigen(s);
(2) Triggering of a massive secretion of IL-18 from expansion of CAR T/NK cells, which co-express this molecule;
(3) Recruiting and stimulating a variety of innate and adaptive immune cells against tumor;
(4) Reducing tumor suppression that is present in tumor by administration of a checkpoint blockage such as PD-L1 and CTLA-4 inhibitor.

Without wishing to be bound by theory, it is believed that the combination of steps described above provide potent anti-tumor effects via a concerted innate and adaptive immune response.

In another embodiment, the present disclosure provides an engineered cell having IL-18 or IL-18 anchor, functional fragment thereof, and combination thereof; and at least one distinct CAR polypeptide wherein the antigen recognition domain includes GD2, GD3, interleukin 6 receptor, ROR1, PSMA, PSCA (prostate stem cell antigen), MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, MMG49 epitope, CD30, EGFRvIII, CD33, CD123, CLL-1, immunoglobin kappa and lambda, CD38, CD52, CD47, CD200, CD70, CD19, CD20, CD22, CD38, BCMA, CS1, BAFF receptor, TACI, CD3, CD4, CD8, CD5, CD7, CD2, and CD138.

In some embodiments, targeting more than one different antigen can be achieved by pooled CAR engineered cells, which are generated by at least two separate CAR T or NK cells. As used herein, pooled CAR engineered cells include a population of engineered cells having more than one distinct CAR polypeptide unit. By way of example, pooled engineered cells include a population of engineered cells with a distinct CAR polypeptide and a population of engineered cells with a different and distinct CAR polypeptide. Furthermore, the pooled CAR engineered cells include engineered cells having cCAR polypeptides.

Methods of Generating Engineered Cells

Any of the polynucleotides disclosed herein may be introduced into an engineered cell by any method known in the art.

In one embodiment, CAR polynucleotides are delivered to the engineered cell by any viral vector as disclosed herein.

In one embodiment, to achieve enhanced safety profile or therapeutic index, the any of the engineered cells disclosed herein be constructed as a transient RNA-modified "biodegradable" version or derivatives, or a combination thereof. The RNA-modified CARs of the present disclosure may be electroporated into T cells or NK cells. The expression of the compound CAR may be gradually diminished over few days.

In some embodiments of the present disclosure, any of the engineered cells disclosed herein may be constructed in a transponson system (also called a "Sleeping Beauty"), which integrates the CAR DNA into the host genome without a viral vector.

In some embodiments of the present disclosure, any of the engineered cells disclosed herein may be introduced by two vectors, and each vector bears a unit of CAR or an enhancer.

Methods of Generating an Engineered Cell Having Multiple CAR Units

In another embodiment, the present disclosure provides a method making an engineered cell having at least two CAR units.

In some embodiments, multiple units of CAR are expressed in a T or NK cell using bicistronic or multicistronic expression vectors. There are several strategies which can be employed to construct bicistronic or multicistronic vectors including, but not limited to, (1) multiple promoters fused to the CARs' open reading frames; (2) insertion of splicing signals between units of CAR; fusion of CARs whose expressions are driven by a single promoter; (3) insertion of proteolytic cleavage sites between units of CAR (self-cleavage peptide); and (4) insertion of internal ribosomal entry sites (IRESs); (5) separate two vectors to express different units of CAR.

In a preferred embodiment, multiple CAR units are expressed in a single open reading frame (ORF), thereby creating a single polypeptide having multiple CAR units. In this embodiment, an amino acid sequence or linker containing a high efficiency cleavage site is disposed between each CAR unit.

As used herein, high cleavage efficiency is defined as more than 50%, more than 70%, more than 80%, or more than 90% of the translated protein is cleaved. Cleavage efficiency may be measured by Western Blot analysis, as described by Kim 2011.

Furthermore, in a preferred embodiment, there are equal amounts of cleavage product, as shown on a Western Blot analysis.

Examples of high efficiency cleavage sites include porcine teschovirus-1 2A (P2A), FMDV 2A (abbreviated herein as F2A); equine rhinitis A virus (ERAV) 2A (E2A); and Thoseaasigna virus 2A (T2A), cytoplasmic polyhedrosis virus 2A (BmCPV2A) and flacherie Virus 2A (BmIFV2A), or a combination thereof. In a preferred embodiment, the high efficiency cleavage site is P2A. High efficiency cleavage sites are described in Kim J H, Lee S-R, Li L-H, Park H-J, Park J-H, Lee K Y, et al. (2011) High Cleavage Efficiency of a 2A Peptide Derived from Porcine Teschovirus-1 in Human Cell Lines, Zebrafish and Mice. PLoS ONE 6(4): e18556, the contents of which are incorporated herein by reference.

In embodiments, wherein multiple CAR units are expressed in a single open reading frame (ORF), expression is under the control of a strong promoter. Examples of strong promoters include the SFFV promoter, and derivatives thereof.

When designing longer gene constructs, the level of protein expression drops significantly with each 1 kb of additional length. Therefore, an initial screen of several antigen recognition sequences is preferred to find the combination that yields both the highest transduction efficiency along with highest target cell lysis. Additionally, it is preferred to avoid very high CAR expression which leads to tonic effects and poor lysis caused by single chain aggregation on the cell surface.

In embodiments, wherein multiple CAR units are expressed in a cell, CAR-CAR interaction between the hinge region of each individual CAR is preferred to be avoided. The interaction site of the hinge is preferred to be excluded or each unit of CARs uses different hinge regions to avoid their interaction.

In some embodiments, wherein multiple CAR units are expressed in a cell, different nucleotide sequences for each domain in common, such as leader sequence, hinge and transmembrane regions, and CD3zeta region, are preferred to avoid homologous recombination, while maintaining the same amino acid sequence.

In some embodiments, wherein multiple CAR units are created, the choice of target antigen is preferred based on which will give the best therapeutic effect, based on medical knowledge and background.

In some embodiments, targeting more than one different antigen can be achieved by pooled CAR engineered cells, which are generated by at least two separate CAR T or NK cells.

It is preferred that co-culture lysis experiments be performed on both on-target cell lines, and off-target cell lines using CAR T or NK cells, to test specificity. Additionally, it is preferred that cell lines expressing only one targeted antigen each be used to demonstrate the ability of each component CAR to lyse. To do this, it is preferred that an off-target cell line be made to synthetically express the desired antigen(s).

In some embodiments, targeting more than one different antigen can be achieved by pooled CAR engineered cells, which are generated by at least two separate CAR T or NK cells.

As used herein, pooled CAR engineered cells include a population of engineered cells having more than one distinct CAR polypeptide unit. By way of example, pooled engineered cells include a population of engineered cells with a distinct CAR polypeptide and a population of engineered cells with a different and distinct CAR polypeptide. Furthermore, the pooled CAR engineered cells include engineered cells having cCAR polypeptides.

Engineered Cell Having CAR Polypeptide and Enhancer

In another embodiment, the present disclosure provides a method making an engineered cell that expresses at least one CAR unit and an enhancer.

In some embodiments, at least one CAR unit and enhancer is expressed in a T or NK cell using bicistronic or multicistronic expression vectors. There are several strategies which can be employed to construct bicistronic or multicistronic vectors including, but not limited to, (1) multiple promoters fused to the CARs' open reading frames; (2) insertion of splicing signals between units of CAR; fusion of CARs whose expressions are driven by a single promoter; (3) insertion of proteolytic cleavage sites between units of CAR (self-cleavage peptide); and (4) insertion of internal ribosomal entry sites (IRESs).

In some embodiments, at least one CAR and an enhancer (s) expressing in a T cell or NK cell can be achieved by two separate vectors or viruses.

In a preferred embodiment, at least one CAR unit and an enhancer are expressed in a single open reading frame (ORF), thereby creating a single polypeptide having at least one CAR unit and an enhancer. In this embodiment, an amino acid sequence or linker containing a high efficiency cleavage site is disposed between each CAR unit and between a CAR unit and enhancer. In this embodiment, the ORF is under the control of a strong promoter. Examples of strong promoters include the SFFV promoter, and derivatives thereof.

Furthermore, in a preferred embodiment, there are equal amounts of cleavage product, as shown on a Western Blot analysis.

CD123–CLL-1

Unlike B-cell and plasma cell malignancies, AML is uniquely challenging to treat due to the role of leukemic stem cells (LSCs). LSCs are a population of cells expressing markers of hematopoietic stem cells (CD34+CD38−) that are capable of initiating and maintaining hematopoietic malignancy, producing clonal cell populations that overtake healthy bone marrow. Since LSCs remain mostly in the quiescent phase of the cell cycle, chemotherapy directed against rapidly dividing tumor populations leaves LSCs untouched. Most often it is this elusive population that comprises minimal residual disease (MRD) and is responsible for inevitable relapse after AML treatment. The successful translation of CAR therapy to AML to completely eliminate disease and ensure no relapse occurs will require careful antigen selection to enable the eradication of not just bulk leukemic disease, but also leukemic stem cells.

Single-CAR therapy has recently made breakthroughs in achieving high remission rates in the treatment of previously refractory and relapsed B cell malignancies. Conversely, new treatment approaches for AML are lacking, and CAR therapy offers a beacon of hope. In particular, the application of a compound CAR therapy to AML has the potential to transform its treatment entirely.

CD123 and C-type lectin-like molecule-1 (CLL-1) are present on AML CD34+ CD38− cells in the majority of AML patients. Without wishing to be bound by theory, it is believed that a compound CAR presents the idea in which a single T-cell encoding two discrete CAR units can simultaneously and more broadly target and eradicate LSCs, preventing disease relapse.

The present disclosure is composed of a single CAR T-cell expressing two discrete CAR units in a vector with independent signaling domains that can be utilized as a novel approach for targeting multiple antigens and potentially avoiding tumor relapse. A compound CAR (cCAR) is comprised of a CD123 CAR linked to a CLL-1 CAR via a self-cleaving P2A peptide and expressed both functional CAR molecules on the surface of a T cell.

In one embodiment, CD123–CLL-1 cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to: acute myeloid leukemia, myelodysplastic syndromes, chronic myeloid leukemia and chronic myeloproliferative disorders.

In another embodiment, CD123–CLL-1 cCAR T-cell therapy can be used to thoroughly eliminate MRD. It can be expected that the relapse rate will decrease and long-term disease-free survival rate will increase, and patient outcomes will be dramatically improved.

In one embodiment, CD123–CLL1 cCAR T-cell therapy can have further applications for patients with CD123+ and/or CLL-1+ leukemic patients beyond a bridge to bone marrow transplantation. CD123–CLL-1 cCAR T-cell therapy can be used as a standalone therapy or as a part of a patient-individualized immuno-chemotherapy regimen. For elderly patients or for those with comorbidities who cannot tolerate highly intensive chemotherapy or BMT, this might be a promising strategy to prolong patients' survival time and reserve a better quality of life.

Without wishing to be bound by theory, it is believed that co-expression of IL-15/IL-15sushi or IL-15/IL-15sushi anchor or 4-1BBLwith CD123–CDLL-1 cCAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with CD123–CLL-1 cCAR provides long-term durable remission in patients by increasing the sensitivity of CAR recognition of target cancer cells or by recruiting innate immune cells to cancer cells.

In one embodiment, the disclosure provides a CD123-CLL1 CAR engineered cell that includes secreting IL-15/IL-15sushi (SEQ ID NO. 28) and corresponding polynucleotide (SEQ ID NO. 29).

CD123-CLL-1

EXAMPLE

An engineered CD123-CLL-1 CAR cell was prepared in accordance with the present disclosure (FIG. 45). CD123-CLL-1 CAR lyses leukemia/lymphoma expressing CD123+ and/or CLL-1+ antigens.

Cell killing assay is performed and targeted cells expressing CD123+ and/or CLL-1+ are lysed by CD123-CLL-1 CAR.

In vivo anti-tumor activities and cell killing are performed in a xenogeneic mouse model, and targeted cells expressing CD123 and/or CLL-1 are eliminated or suppressed by CD123-CLL-1 CAR T or NK cells using methods described in PCT/US2016/019953 and PCT/US2016/039306

Compound CD38 CARs and CD19-CD38 CAR CD38 (cluster of differentiation 38), also known as cyclic ADP ribose hydrolase, is a glycoprotein. CD38 has been used as a prognostic marker in a variety of leukemia/lymphoma. CD38 is expressed in B-NHL (non-Hodgkin lymphoma) including CLL/SLL, diffuse large cell lymphoma, follicular lymphoma, plasmablastic lymphoma, plasma cell neoplasms, and primary effusion lymphoma. CD38 is also expressed in transient myeloproliferative disorder in Down syndrome, T cell lymphoma, AML, T-ALL and B-ALL. CD38 expression is known to be associated with a poor prognosis.

On the basis of these expression profiles, CD38 is considered an ideal and nearly universal target for malignancies. However, single-CAR, CD38 CAR therapy may not be sufficient to completely eliminate leukemia cells and achieve high remission rates because CD38 is not expressed in all leukemic cells. Targeting at least two markers, with one including CD38 (CD38-based compound CAR), can offer some distinct benefits. A compound CAR targeting of leukemia by at least two antigens (or two surface markers including CD38) can overcome the pitfalls of single-antigen therapy by preventing relapse due to antigen loss. While loss of a single antigen under antigen-specific selection pressure is possible, loss of two antigens simultaneously is much less likely. A compound CAR targeting two antigens, with one including CD38, increases effector cell efficacy and persistency as described in studies with our other compound CAR systems.

In one embodiment, the target of the first antigen recognition domain is selected from the group of, but not limited to: GD2, GD3, CD19, CD20, CD22, CD138, BCMA, CS1, BAFF, BAFF receptor, TACI, April, April receptor, CD3, CD4, CD5, CD7, CD2, CLL-1, CD33, CD123, NKG2D receptors, MMG49 epitope, CD30, CD3, CD4, CD5, CD7 and CD2; the target of the second recognition domain is CD38.

In one embodiment, the target of the first antigen recognition domain is CD38; the target of the second recognition domain is selected from the group of, but not limited to: GD2, GD3, CD19, CD20, CD22, CD138, BCMA, CS1, BAFF, BAFF receptor, TACI, April, April receptor, CD3, CD4, CD5, CD7, CD2, CLL-1, CD33, CD123, NKG2D receptors, MMG49 epitope, CD30, CD3, CD4, CD5, CD7 and CD2.

In another embodiment, the present disclosure provides methods using a CD38-based compound CAR for treating B-cell lymphoma, T-cell lymphoma/leukemia, blastic plasmacytoid dendritic cells (BPDC), multiple myeloma, acute myeloid leukemia, chronic myeloid leukemia, acute myeloma leukemia, myelodysplastic syndromes, chronic myeloproliferative neoplasms, B-cell acute lymphoblastic leukemia (B-ALL), and cell proliferative diseases by administering any of the engineered cells described above to a patient in need thereof.

In another embodiment, the present disclosure provides methods using a CD38-based compound CAR for treating Burkett's lymphoma or Burkett like lymphoma.

In another embodiment, the present disclosure provides methods using a CD38-based compound CAR for treating CLL/SLL, diffuse large cell lymphoma, follicular lymphoma, mantle cell lymphoma, marginal zone lymphoma, plasmablastic lymphoma, plasma cell neoplasms, and primary effusion lymphoma.

In another embodiment, the present disclosure provides a method using a CD38-based compound CAR for treating an autoimmune disease; wherein said autoimmune disease comprises systemic lupus erythematosus (SLE), multiple sclerosis (MS), inflammatory bowel disease (IBD), rheumatoid arthritis, Sjogren syndrome, dermatomyosities, autoimmune hemolytic anemia, neuromyelitis optica (NMO), NMO Spectrum Disorder (NMOSD), idiopathic thrombocytopenic purpura (ITP), antineutorphil cytoplasmic autoantibodies (ANCAs) associated with systemic autoimmune small vessel vasculitis syndromes or microscopic polyangiitis (MPA), granulomatosis with polyangiitis (GPA, Wegener's granulomatosis), or eosinophilic granulomatosis with polyangiitis (EGPA, Churg-Strauss syndrome) and TTP (thrombotic thrombocytopenic purpura)

The present disclosure is composed of a single T-cell expressing two discrete CAR units in a vector with independent signaling domains that can be utilized as a novel approach for targeting multiple antigens and potentially avoiding tumor relapse. A compound CAR (cCAR) is comprised of a CD19 CAR linked to a CD38 CAR via a self-cleaving P2A peptide and expresses both functional CAR molecules on the surface of a T cell.

Without wishing to be bound by theory, it is believed that CD19-CD38 cCAR T-cells are able to eliminate regular leukemic cells and leukemic precursor cells to reduce the risk of relapse and enhance anti-tumor activities.

Without wishing to be bound by theory, it is believed that CD19-CD38 cCAR T-cells are able to eliminate Non-Hodgkin lymphomas to reduce the risk of relapse and enhance anti-tumor activities.

Without wishing to be bound by theory, it is believed that CD19-CD38 cCAR T-cells exhibit a more complete elimination of cancerous cells to reduce antigen escape by hitting hard with multiple targets simultaneously before resistance develops.

In one embodiment, CD19-CD38 cCAR T-cell therapy could be developed as a "bridge to transplant", a supplement to chemotherapy, or a checkpoint blockage (including, but not limited to PD-L1, CTLA-4 inhibitor) or as a standalone therapy for patients with diseases including, but not limited to: lymphoma, acute myeloid leukemia, myelodysplastic syndromes, chronic myeloid leukemia and chronic myeloproliferative disorders.

In another embodiment, CD19-CD38 cCAR T-cell therapy can be used to thoroughly eliminate MRD. It can be expected that the relapse rate will decrease and long-term disease-free survival rate will increase, and patient outcomes will be dramatically improved.

In one embodiment, CD19-CD38 cCAR T-cell therapy can have further applications for patients with CD19+ and/or CD38+ leukemic patients beyond a bridge to bone marrow transplantation. CD19-CD38 cCAR T-cell therapy can be used as a standalone therapy or as a part of a patient-individualized immuno-chemotherapy regimen. For elderly patients or for those with comorbidities who cannot tolerate highly intensive chemotherapy or BMT, this might be a promising strategy to prolong patients' survival time and reserve better quality of life.

Without wishing to be bound by theory, it is believed that co-expression of IL-15/IL-15sushi or IL-15/IL-15sushi anchor or 4-1BBLwith CD19-CD38 cCAR provides long-term durable remission in patients by increasing the sensitivity of CAR recognition of target cancer cells or by recruiting innate immune cells to cancer cells.

Without wishing to be bound by theory, it is believed that co-expression of IL-21 or IL-21 anchor with CD19-CD38 cCAR provides long-term durable remission in patients by increasing the sensitivity of CAR recognition of target cancer cells or by recruiting innate immune cells to cancer cells.

Compound CD38 CARs for T Cell Malignancies

The present disclosure is composed of a single T-cell expressing two discrete CAR units in a vector with independent signaling domains that can be utilized as a novel approach for targeting multiple antigens and potentially avoiding tumor relapse. A CD38-based compound CAR (cCAR) includes a CD4 CAR or CD5 CAR or CD3 CAR or CD7 CAR linked to a CD38 CAR via a self-cleaving P2A peptide and expresses both functional CAR molecules on the surface of a T cell.

The present disclosure is composed of a single NK-cell expressing two discrete CAR units in a vector with independent signaling domains that can be utilized as a novel approach for targeting multiple antigens and potentially avoiding tumor relapse. A CD38-based compound CAR (cCAR) includes a CD4 CAR or CD5 CAR or CD3 CAR or CD7 CAR linked to a CD38 CAR via a self-cleaving P2A peptide and expresses both functional CAR molecules on the surface of a T cell.

Without wishing to be bound by theory, it is believed that the CD38-based compound cCAR T or NK-cells are able to eliminate T cell lymphoma/leukemic cells to reduce the risk of relapse due to the antigen escape and enhance anti-tumor activities.

A CD4-CD38 compound CAR (cCAR) comprising of a CD4 CAR is linked to a CD38 CAR via a self-cleaving P2A peptide and expresses both functional CAR molecules on the surface of a T cell.

A CD5-CD38 compound CAR (cCAR) comprising of a CD5 CAR is linked to a CD38 CAR via a self-cleaving P2A peptide and expresses both functional CAR molecules on the surface of a T cell.

In one embodiment, the engineered cell includes a CD5-CD38 chimeric antigen receptor polypeptide (SEQ ID NO. 18), and corresponding nucleotides (SEQ ID NO. 19).

A CD7-CD38 compound CAR (cCAR) comprising of a CD4 CAR is linked to a CD38 CAR via a self-cleaving P2A peptide and expresses both functional CAR molecules on the surface of a T cell.

CD56-CD38 CARs for Lymphoma/Leukemia

CD56 is a glycoprotein and functions as the neural cell adhesion molecule. The antigen is expressed on NK cells. CD56 or CD38 is usually present in most cases of 1) aggressive NK cells leukemia/lymphoma, 2) extranodal NK/T lymphoma (nasal type), hepatopleenic T cell lymphoma, and 4) chronic NK cell lymphocytosis.

Like CD38, CD56 is also expressed in non-hematologic cells, such as brain cells. The off-target effects would be severe for a patient administered CD56 or CD38 CAR T cells alone.

Without wishing to be bound by theory, it is believed that compound cCAR T cells bearing two CARs and targeting different antigens have a higher affinity of binding to a cell bearing two antigens targeted by cCAR than that of a cell carrying a single cCAR targeted antigen. As a result, it is believed that the compound CAR T cells have a higher capability of trafficking to the tumor than a single CAR T cells. Thus, applicants surprisingly discovered that there was significantly reduced concern of off-target effects when a compound CAR cell based therapy was used.

CD56 is a glycoprotein and functions as the neural cell adhesion molecule. The antigen is expressed on NK cells. Like CD38, CD56 is also expressed in non-hematologic cells, such as brain cells. The off-target effects would be severe for a patient administered CD56 CAR or CD38 CAR T cells. Thus, the invention disclosure provides a method of generating CD56-CD38 cCAR to reduce concerns of off-target effects associated with using CD56 CAR or CD38 CAR alone.

The present invention is composed of a single T-cell expressing two discrete CAR units in a vector with independent signaling domains that can be utilized as a novel approach for targeting CD56 and CD38 simultaneously and potentially avoiding tumor relapse. A CD56-CD38 compound CAR (cCAR) bears CD56 CAR linked to a CD38 CAR via a self-cleaving P2A peptide and expresses both functional CAR molecules on the surface of a T cell.

The present invention is composed of a single T-cell expressing two discrete CAR units in a vector with independent signaling domains that can be utilized as a novel approach for targeting CD56 and CD38 simultaneously and potentially avoiding tumor relapse. A CD56-CD38 compound CAR (cCAR) bears CD56 CAR linked to a CD38 CAR via a self-cleaving P2A peptide and expresses both functional CAR molecules on the surface of a NK cell.

CD19-CD38 cCAR

EXAMPLE

An engineered CD19b-CD38a (a version of CD19-CD38 cCAR) cell was prepared in accordance with the present disclosure. A compound CAR (cCAR) is comprised of a CD19b CAR (a version of CD19 CAR) linked to a CD38a CAR (a version of CD38 CAR) via a self-cleaving P2A peptide and expresses both functional CAR molecules on the surface of a T cell.

Peripheral blood mononuclear buffy coat cells were activated for two or three days and transduced with either CD19b-CD38a cCAR or control vector. Expression of CD19b-CD38a cCAR on the T-cell surface was determined by flow cytometry three days after transduction by staining transduced T cells with goat anti-mouse Fab antibody and mouse anti-human CD3.

Cell killing assay was performed and targeted cells expressing CD19 and/or CD38 were lysed by CD19b-CD38a cCAR.

In vivo anti-tumor activities and cell killing were performed in a xenogeneic mouse model, and targeted cells expressing CD19 and/or CD38 were eliminated or suppressed by CD19b–CD38a cCAR T or NK cells using the methods described in PCT/US2016/019953 and PCT/US2016/039306.

Ovarian Cancer

Ovarian cancer is the leading cause of mortality from gynecological cancer in women and is commonly seen in postmenopausal woman. The majority of women with ovarian cancer are diagnosed late when cancer has spread beyond the ovaries. The lack of specific symptoms and reliable early detection procedures are attributed to this phenomenon. The follicle-stimulating hormone receptor (FSHR) appears to be selectively expressed in women with ovarian epithelial ovarian cancer and ovarian granulosa cells while the level of FSHR expression in the normal ovarian epithelial cells is low. Overexpression of FSHR has been shown to play a role in ovarian cancer development. Therefore, the FSHR could be an appropriate target for ovarian cancer, as the oophorectomy is a surgical standard procedure used to treat ovarian cancer and targeting the FSHR may not cause a severe health problem.

The gonadotropin hormone family is distinguished by its heterodimeric structure in which the members share a common α subunit and a β hormone-specific subunit. Subunit assembly is essential for the function of these hormones, and only the dimers are bioactive. The secretion efficiency of the dimer is determined by the β subunit.

In some embodiments, FSHR binding domain or polypeptide is a biologically active fusion gene encoding the follicle-stimulating hormone β subunit and the common a subunit. In a further embodiment, FSHR binding domain or polypeptide comprises the FSH (follicle-stimulating hormone) heterodimer linked to a single chain by genetically fusing the carboxyl end of the FSH β subunit to the amino end of the a subunit in the presence or absence of a linker sequence.

The secretion efficiency of the heterodimer is considered to be determined by the β subunit.

In some embodiments, a FSHR CAR can be comprised of: 1) FSHR binding domain or a scFv against FSHR; 2) a hinge region; 3) co-stimulatory domain (s) and intracellular signaling domain.

In some embodiments, the target for FSHR can comprise FSHR binding domain. In a further embodiment, FSHR binding domain can be a ligand or hormone or scFv against FSHR.

Some ovarian cells are dim (weak) or negative for FSHR. To increase the sensitivity of FSHR recognition, it is critical to target multiple recognition sites or antigens. In a further embodiment, a compound CAR, cCAR, bears multiple units of CARs that can be used to target multiple recognition sites or antigens in ovarian cancers.

In some embodiments, a unit of CAR in a cCAR can be comprised of: 1) FSHR binding domain or a scFv against MUC16; 2) a hinge region; 3) co-stimulatory domain (s) and intracellular signaling domain.

In some embodiments, the disclosure provides a method of generating a compound cCAR comprising of FSHR and MU16 CARs to complement some ovarian cancer cells that cannot be eliminated by a FSHR CAR.

In some embodiments, a unit of CAR in a cCAR can be comprised of: 1) FSHR binding domain or a scFv against Folate receptor-α (FRα); 2) a hinge region; 3) co-stimulatory domain (s) and intracellular signaling domain.

In some embodiments, the disclosure provides a method of generating a compound cCAR comprising of FSHR and FRα CARs to complement some of ovarian cancer cells that cannot be eliminated by a FSHR CAR. FRα CAR bears FRα-specific scFv antigen recognition domain.

In some embodiments, a unit of CAR in a cCAR can be comprised of: 1) FSHR binding domain or a scFv against HER2; 2) a hinge region; 3) co-stimulatory domain (s) and intracellular signaling domain.

In some embodiments, the disclosure provides a method of generating a compound cCAR comprising of FSHR and HER2 CARs to complement some of ovarian cancer cells that cannot be eliminated by a FSHR CAR. HER2 CAR bears HER2-specific scFv antigen recognition domain.

Without wishing to be bound by theory, it is believed that co-expression of IL-15/IL-15sushi or IL-15/IL-15sushi anchor or 4-1BBLwith FSHR CAR provides long-term durable remission in patients by increasing the sensitivity of CAR recognition of target cancer cells or recruiting innate immune cells to cancer cells.

Without wishing to be bound by theory, it is believed that co-expression of IL-21 or IL-21 anchor with FSHR CAR provides long-term durable remission in patients by increasing the sensitivity of CAR recognition of target cancer cells or by recruiting innate immune cells to cancer cells.

Peripheral blood mononuclear buffy coat cells are activated for two or three days and transduced with either FSHR or control vector. Expression of FSHR CAR on the T-cell surface will be demonstrated three days after transduction by staining transduced T cells with goat anti-mouse Fab antibody and mouse anti-human CD3.

Cell killing assay is performed and targeted cells expressing FSHR are lysed by FSHR CAR or FSHR CAR equipped with IL-15/IL-15sushi or IL-15/IL-15sushi anchor or 4-1BBL.

In vivo anti-tumor activities and cell killing is performed in a xenogeneic mouse model and targeted cells expressing FSHR CAR or FSHR CAR equipped with IL-15/IL-15sushi or IL-15/IL-15sushi anchor or 4-1BBL are eliminated or suppressed by FSHR CAR equipped with IL-15/IL-15sushi or IL-15/IL-15sushi anchor or 4-1BBL T or NK cells using the methods described in PCT/US2016/019953 and PCT/US2016/039306.

Human Vascular Tumors

Human vascular tumors could include infantile hemangioma and vascular malformations. Vascular malformations can include capillary, lymphatic, venous, and arteriovenous malformation. FSHR is found in the endothelium of vascular anomalies but not in the normal endothelial cells.

The mechanism for the growth of infantile hemangioma and vascular malformations is unknown. However, follicle-stimulating hormone secretion provides a clue related to the life-cycle of infantile hemangioma and increases during adolescence when vascular malformations often progress. It has been shown that the secretion of FSH correlates with the growth pattern of infantile hemangioma and vascular malformations, indicating that FSH might be involved in the pathogenesis of these vascular lesions. FSHR expression is seen in stem/progenitor cells for infantile hemangioma and vascular malformation. Therefore, the FSHR could be an appropriate target for these diseases.

In some embodiments, FSHR CAR engineered cells are used to deplete stem/progenitor cells for infantile hemangioma or vascular malformation.

In a further embodiment, FSHR CAR cells may be used for post-treatment of patients after removal of tumor to prevent disease relapse.

In some embodiments, the present disclosure comprises a method of selectively depleting or ablating an endogenous stem/progenitor population, where the endogenous stem/progenitor cells expresses FSHR, by contacting said cells with FSHR CAR engineered cells that specifically target FSHR expressing stem/progenitor cells for infantile hemangioma and vascular malformation.

In some embodiments, FSHR CAR cells are utilized for treating or preventing a residual disease after surgical therapy.

In one embodiment, the disclosure provides a FSHR CAR engineered cell that includes polynucleotide FSHR CAR (SEQ ID NO. 32) and corresponding polynucleotide (SEQ ID NO. 33).

In one embodiment, the disclosure provides a FSHR super1 CAR engineered cell that includes secreting IL-15/IL-15sushi (SEQ ID NO. 34) and corresponding polynucleotide (SEQ ID NO. 35).

Universal CAR (uCAR) NK Cells

The majority of current clinical trials or therapies infuse autologous CAR T cells, as allogeneic CAR T cells are capable of inducing GVHD (graft-versus-host disease) in recipients. Although this autologous approach achieved remarkable clinical successes, the process of manufacturing a patient-specific T cell product is both time-consuming and expensive. Furthermore, it is not always possible to collect enough T cells from a heavily pretreated patient to successfully generate sufficient doses of CAR T cells. There is great demand for the development of an off-the-self allogeneic CAR product. NK cells are similar to T cells in that they are highly cytotoxic immune effectors. In contrast to T cells, NK cells bear the property of killing their targets through an on-specific manner. NK cells can be used as an off-the-self allogeneic product because they usually lack the potential to cause GVHD. The major disadvantage of using NK cells is their lack of persistence in vivo, with a half-life of only about a week.

In some embodiments, the present invention discloses a form of universal CAR-expressing NK cells from a healthy donor that can be stored and then infused into an individual on demand. In further embodiments, the invention comprises a method of generating of off-the-self universal CAR NKs from allogeneic healthy donors that can be infused to any patient without causing GVHD.

In some embodiments, NK cell is obtained from an umbilical cord blood bank and a peripheral blood bank. In a further embodiment, NK is an induced pluripotent stem cell or embryonic stem cell or NK-92 cell.

In some embodiments, the present disclosure comprises a method for having a CAR or compound CAR (cCAR) co-expressing IL-15/IL-15sushi in a NK cell. These engineered NK cells are called uCAR NK cells.

In some embodiments, uCAR NK cells have CAR or cCAR co-expressing IL-15/IL-15sushi. In further embodiments, uCAR NK cells is capable of persisting for more than one week in vivo.

In some embodiments, the present disclosure comprises a method for a uCAR NK cell with a vector expressing a CAR or cCAR with IL-15/IL-15sushi.

In some embodiments, co-expression of IL-15/IL-15sushi with a CAR or cCAR provides long-term persistence for a NK cell in a subject.

In some embodiments, co-expression of IL-15/IL-15sushi with a CAR or cCAR provides long-term durable remission in patients by increasing the sensitivity of CAR recognition of target cancer cells or by recruiting innate immune cells to cancer cells.

In some embodiments, the present disclosure comprises a method for generating a NK cell with one CAR or cCARs co-expressing IL-15/IL-15sushi. In further embodiments, a particular tumor antigen targeted by an antigen recognition domain in a CAR can be selected from the group of, but not limited to: GD2, GD3, interleukin 6 receptor, FSHR, ROR1, PSMA, PSCA (prostate stem cell antigen), MAGE A3, Glycolipid, glypican 3, F77, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, MMG49 epitope, CD30, EGFRvIII, CD33, CD123, CLL-1, NKG2D, NKG2D receptors, immunoglobin kappa and lambda, CD38, CD52, CD47, CD200, CD70, CD56, CD19, CD20, CD22, CD38, BCMA, CS1, BAFF receptor, TACI, CD3, CD4, CD8, CD5, CD7, CD2, and CD138.

In some embodiments, the present disclosure comprises a method for the treatment of a disorder or disease by the infusion of a therapeutically effective amount of NK cells that are genetically engineered to express IL-15/IL-15sushi and/or a CAR with an antigen recognition domain for a particular tumor antigen. In further embodiments, a particular tumor antigen targeted by an antigen recognition domain can be selected from the group of, but not limited to: GD2, GD3, interleukin 6 receptor, FSHR, ROR1, PSMA, PSCA (prostate stem cell antigen), MAGE A3, Glycolipid, glypican 3, F77, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, MUC1, MUC2, MUC3, MUC4, MUC5, MMG49 epitope, CD30, EGFRvIII, CD33, CD123, CLL-1, NKG2D, NKG2D receptors, immunoglobin kappa and lambda, CD38, CD52, CD47, CD200, CD70, CD56, CD19, CD20, CD22, CD38, BCMA, CS1, BAFF receptor, TACI, CD3, CD4, CD8, CD5, CD7, CD2, and CD138.

In some embodiments, the administration of a high dose of uCAR NK cells can cause cytokine release syndrome (CRS). In present disclosure comprises a method of reduction or avoidance of CRS by providing a subject with a lower doses or split doses of uCAR NK cells. Below is the strategy to avoid CRS caused by the administration of a high dose of uCAR NK cells.

Liver Cancer

Hepatocellular carcinoma (HCC) is an aggressive tumor and the third most common cause of cancer-related deaths. There is an unmet medical need to develop a new approach to address this aggressive disease. Glypican-3 (GPC3) is a member of heparin sulfate proteoglycans and highly expressed in HCC. GPC3 is not detected in normal liver tissue or benign liver lesions.

In one embodiment, the disclosure provides an engineered chimeric antigen receptor polynucleotide that encodes for a chimeric antigen receptor polypeptide with an antigen recognition domain selective for GPC3.

In one embodiment, the disclosure provides a GPC3 CAR engineered cell that includes polynucleotide GPC3 CAR (SEQ ID NO. 36, 42) and corresponding polynucleotide (SEQ ID NO. 37, 43).

In one embodiment, the disclosure provides a GPC3-IL-15/IL-15sushi CAR engineered cell that includes secreting IL-15/IL-15sushi (SEQ ID NO. 38, 44) and corresponding polynucleotide (SEQ ID NO. 39,45).

In one embodiment, the disclosure provides a GPC3 super1 CAR engineered cell that includes secreting (SEQ ID NO. 40, 46) and corresponding polynucleotide (SEQ ID NO. 41,47).

The large volume of some HCC can make it difficult for CAR T cells to eradicate the whole tumor. In addition, the immunosuppressive microenvironment needs to be overcome, as CAR T cells may end up simply being inactivated or suppressed when contacting tumor.

On this basis, the present disclosure provides a method of providing long-term durable remission in patients by administering an engineered cell containing a GPC3 CAR polypeptide disclosed herein and co-expression of IL-15/IL-15sushi to increase the sensitivity of GPC3CAR recognition of target cancer cells or recruit innate immune cells to cancer cells.

In some embodiments, the present disclosure provides a method of co-expressing secretory IL-15/IL-15sushi and a chimeric antigen receptor polypeptide in an engineered cell.

In some embodiments, the present disclosure provides a method of increasing the half-life of GPC3 CAR engineered cell in vivo through the co-expression of secretory IL-15/IL-15sushi in said engineered cell. Without wishing to be bound by theory, it is believed that the secreted complexes of IL-15/IL-15sushi are functionally stable and efficiently promote survival of the GPC3 CAR-containing engineered cell.

In some embodiments, the present disclosure provides a method of delivering IL-15/IL-15sushi to targeted cancer sites using GCP3 CAR as a carrier to promote the proliferation of innate immune response cells against HHC cells, prevent tumor microenvironment suppression of immune functions, and reduce systemic toxicity with high-dose exogenous cytokines.

In some embodiments, the present disclosure provides a method of delivering IL-15/IL-15sushi to targeted cancer sites using GCP3 CAR as a carrier to recruit other effector immune cells to the site and help them kill HCC cells.

In some embodiments, the present disclosure provides a method of delivering IL-15/IL-15sushi to targeted cancer sites using GCP3 CAR as a carrier to activate bystander immunity to eradicate cancer cells that lose the antigen targeted by GCP3 CAR T/NK cells.

In one embodiment, the engineered cell includes GPC3 CAR super (super CAR) linked to 4-1BBL and IL-15/IL-15sushi via the P2A and T2A cleavage sequences. A polypeptide providing this embodiment includes SEQ ID No. 40, 46 and corresponding polynucleotide sequence SEQ ID No. 41, 47.

Without wishing to be bound by theory, it is believed that GPC3 super CAR (super CAR) becomes more powerful when incorporating both 4-1BBL and IL-15/IL-15sushi.

Combination Therapy

The compositions and methods of this disclosure can be used to generate a population of CAR T lymphocyte or NK cells that deliver both primary and co-stimulatory signals for use in immunotherapy in the treatment of cancer. In further embodiments, the present invention for clinical aspects are combined with other agents effective in the treatment of hyperproliferative diseases, such as anti-cancer agents. Anti-cancer agents are capable of reduction of tumor burdens in a subject. Anti-cancer agents include chemotherapy, radiotherapy and immunotherapy.

More than 50% of persons with cancer will undergo surgery of some type. Curative surgery includes resection in which all or part of cancerous tissue is physically removed, excised, and/or destroyed.

The compositions and methods described in the present disclosure may be utilized in conjunction with other types of therapy for cancer, such as chemotherapy, surgery, radiation gene therapy, and so forth.

In accordance with the present disclosure, natural killer (NK) cells represent alternative cytotoxic effectors for CAR driven killing. Unlike T-cells, NK cells do not need pre-activation and constitutively exhibit cytolytic functions. Further expression of cCARs in NK cells allow NK cells to effectively kill cancers, particularly cancer cells that are resistant to NK cell treatment.

Further, NK cells are known to mediate anti-cancer effects without the risk of inducing graft-versus-host disease (GvHD).

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure Administration of any of the engineered cells described herein may be supplemented with the co-administration of a CAR enhancing agent. Examples of CAR enhancing agents include immunomodulatory drugs that enhance CAR activities, such as, but not limited to agents that target immune-checkpoint pathways, inhibitors of colony stimulating factor-1 receptor (CSF1R) for better therapeutic outcomes. Agents that target immune-checkpoint pathways include small molecules, proteins, or antibodies that bind inhibitory immune receptors CTLA-4, PD-1, and PD-L1, and result in CTLA-4 and PD-1/PD-L1 blockades. As used herein, enhancing agent includes enhancer as described above.

As used herein, "patient" includes mammals. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human. A patient includes subject.

In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

The terms "effective amount" and "therapeutically effective amount" of an engineered cell as used herein mean a sufficient amount of the engineered cell to provide the desired therapeutic or physiological or effect or outcome. Such, an effect or outcome includes reduction or amelioration of the symptoms of cellular disease. Undesirable effects, e.g. side effects, are sometimes manifested along with the desired therapeutic effect; hence, a practitioner balances the potential benefits against the potential risks in determining what an appropriate "effective amount" is. The exact amount required will vary from patient to patient, depending on the species, age and general condition of the patient, mode of administration and the like. Thus, it may not be possible to specify an exact "effective amount". However, an appropriate "effective amount" in any individual case may be determined by one of ordinary skill in the art using only routine experimentation. Generally, the engineered cell or engineered cells is/are given in an amount and under conditions sufficient to reduce proliferation of target cells.

Following administration of the delivery system for treating, inhibiting, or preventing a cancer, the efficacy of the therapeutic engineered cell can be assessed in various ways well known to the skilled practitioner. For instance, one of ordinary skill in the art will understand that a therapeutic engineered cell delivered in conjunction with the chemo-adjuvant is efficacious in treating or inhibiting a cancer in a patient by observing that the therapeutic engineered cell reduces the cancer cell load or prevents a further increase in cancer cell load. Cancer cell loads can be measured by methods that are known in the art, for example, using polymerase chain reaction assays to detect the presence of certain cancer cell nucleic acids or identification of certain cancer cell markers in the blood using, for example, an antibody assay to detect the presence of the markers in a sample (e.g., but not limited to, blood) from a subject or patient, or by measuring the level of circulating cancer cell antibody levels in the patient.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

As used herein, a XXXX antigen recognition domain is a polypeptide that is selective for XXXX. "XXXX" denotes the target as discussed herein and above. For example, a CD38 antigen recognition domain is a polypeptide that is specific for CD38.

As used herein, CDXCAR refers to a chimeric antigen receptor having a CDX antigen recognition domain.

EXAMPLES

Figure 1A:
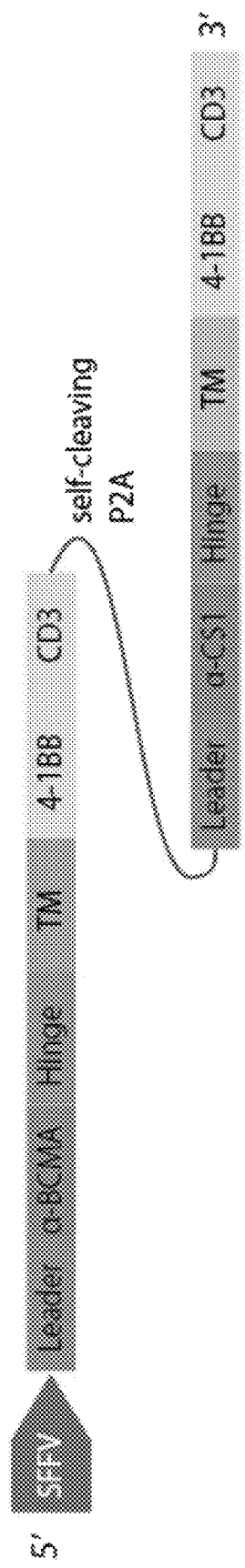
FIGS. 1A-1B: CAR construction and expression (1A) Two discrete CAR units: an anti-BCMA CAR comprised of: a CD8-derived hinge (H) and transmembrane (TM) regions, and 4-1BB co-activation domains linked to the CD3t signaling domain is fused to a complete anti-CS1 CAR by a self-cleaving P2A peptide. A strong spleen focus forming virus promoter (SFFV) and a CD8 leader sequence were used for efficient expression of the BC1cCAR (BCMA–CS1 cCAR) molecule on the T-cell surface. (1B) Expression of BC1cCAR was measured by FACS against control T-cells. BCMA also called CD269.
Figure 1B:
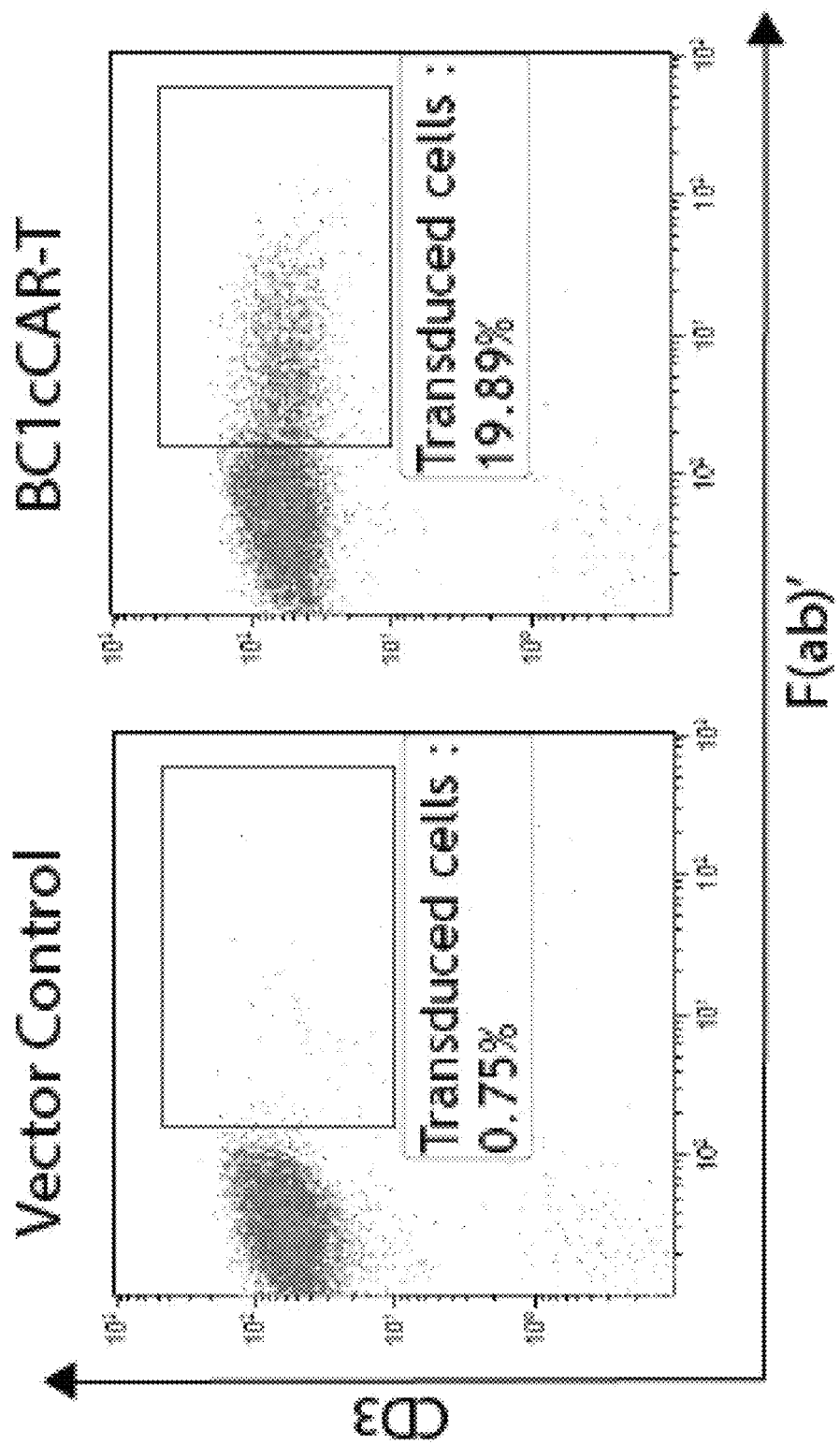

BCMA–CS1 cCAR Targeting Plasma Cell Diseases Such as Multiple Myeloma Generation of BCMA–CS1 cCAR (BC1cCAR) T-Cells The BC1cCAR construct is a 2-unit CAR composed of a complete BCMA–CAR fused to a complete CS1–CAR by a self-cleaving P2A peptide, enabling independent expression of both CAR receptors separately on the T-cell surface (FIG. 1A). Expression assayed by FACS revealed distinct transduced cells (FIG. 1B). A leader, a scFv, a hinge domain (H), a transmembrane domain (TM), a co-stimulatory domain (CD28 or 4-1BB) and the intracellular signaling domain CD3 zeta (CD3) are included in each CAR unit. A strong spleen focus forming virus promoter (SFFV) and a CD8 leader sequence were used for efficient expression of the BCMA–CS1 cCAR molecule on the T-cell surface.

BC1cCAR T-Cells Specifically Lyse BCMA$^+$ and CS1$^+$ Myeloma Cell Lines

Figure 2A:
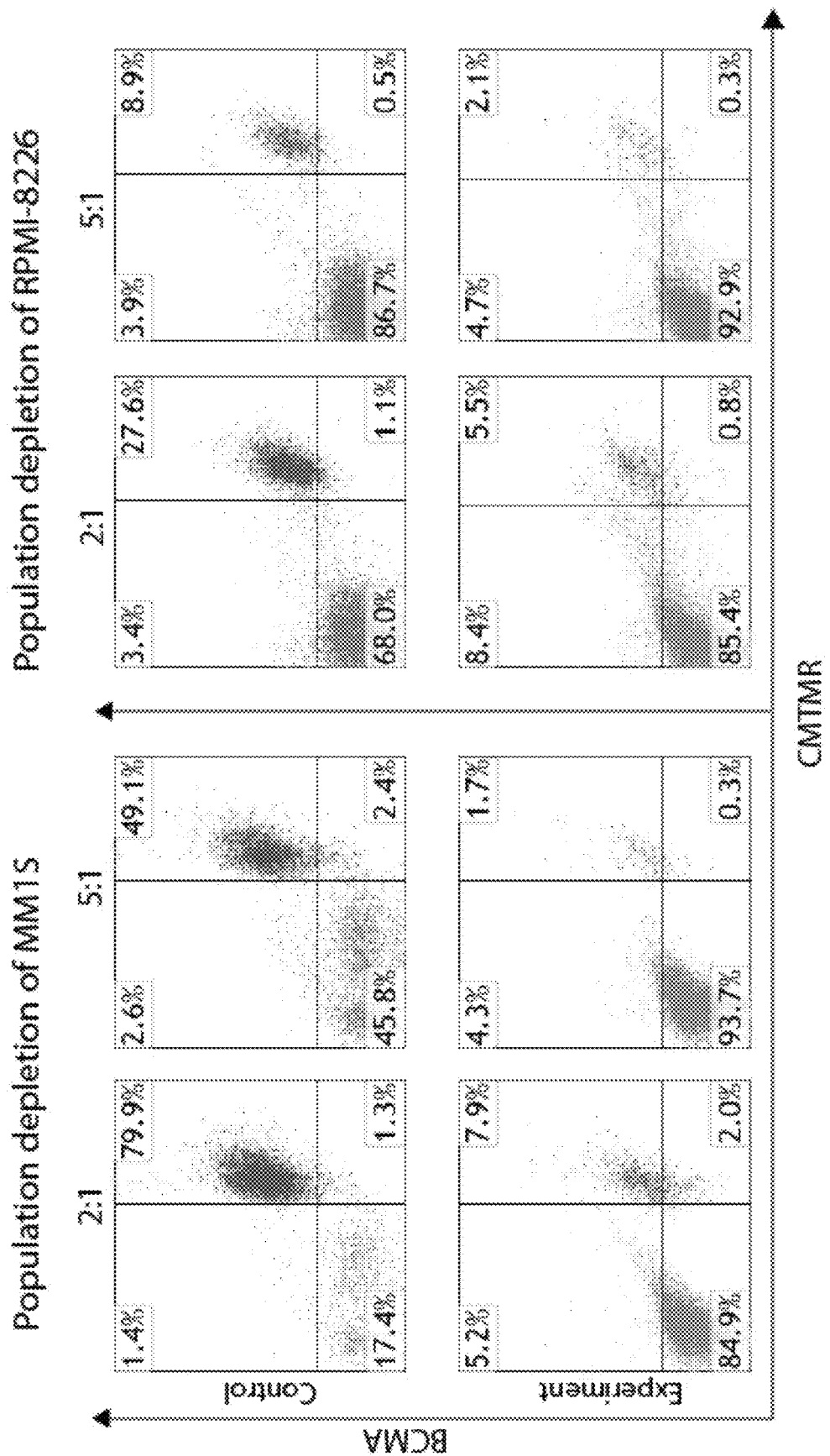
FIGS. 2A-2C: In vitro evaluation of BC1cCAR T-cells against myeloma cell lines. (2A) BC1cCAR and control T-cells cultured with MM1S and RPMI-8226 cells for 24 hours at E:T ratios of 2:1 and 5:1. Target cells were stained by Cytotracker dye (CMTMR) to distinguish them from effector T-cells, and are indicated in red. Populations were gated by BCMA, CS1, and CMTMR. (2B) BC1cCAR and control T-cells were incubated with U266 (BCMA$^+$CS1$^{dim}$) cells under similar conditions. (2C) Graphical summary of BC1cCAR T-cell in vitro cytotoxicity against various myeloma cell lines.
Figure 2B:
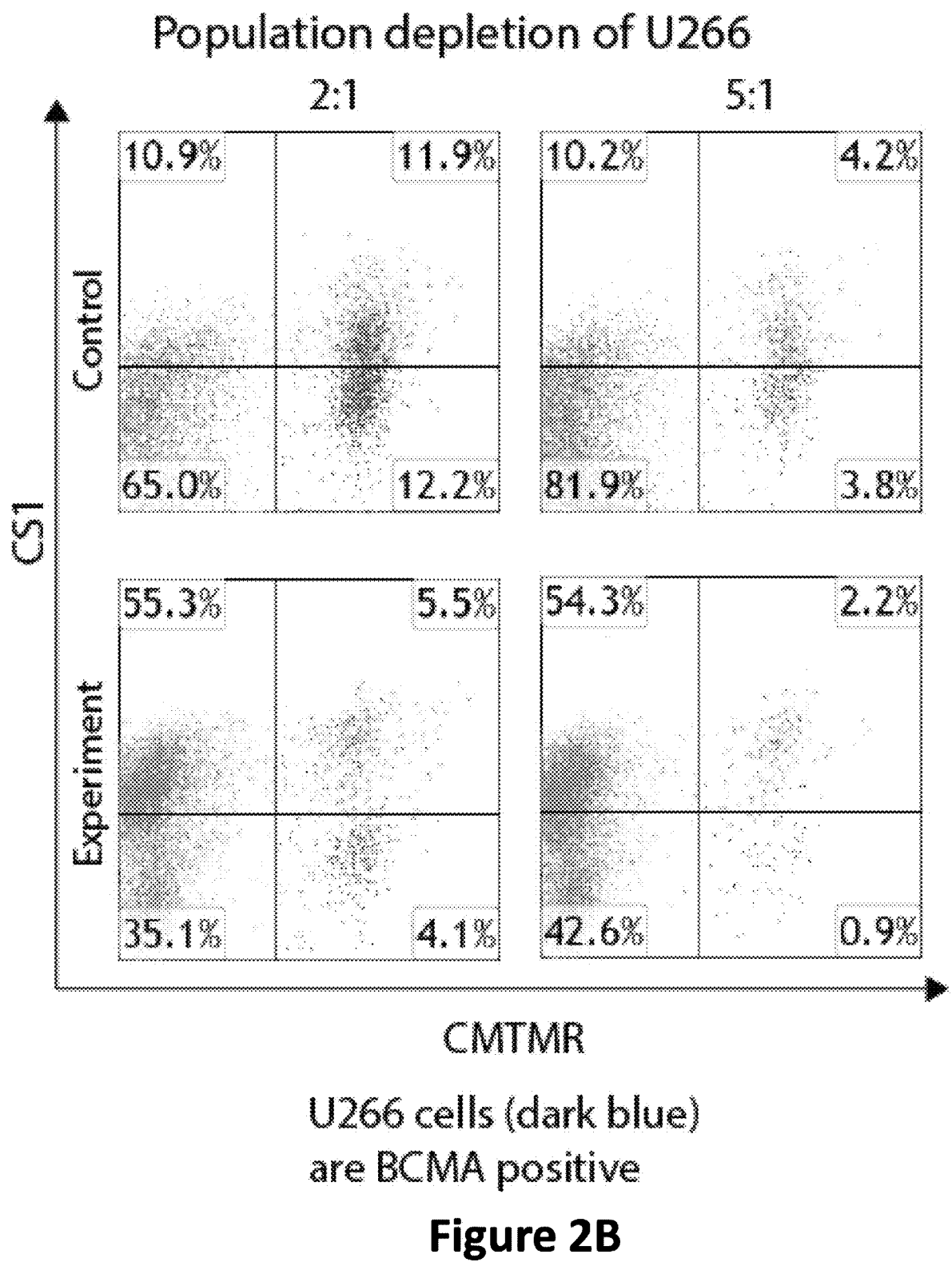
Figure 2C:
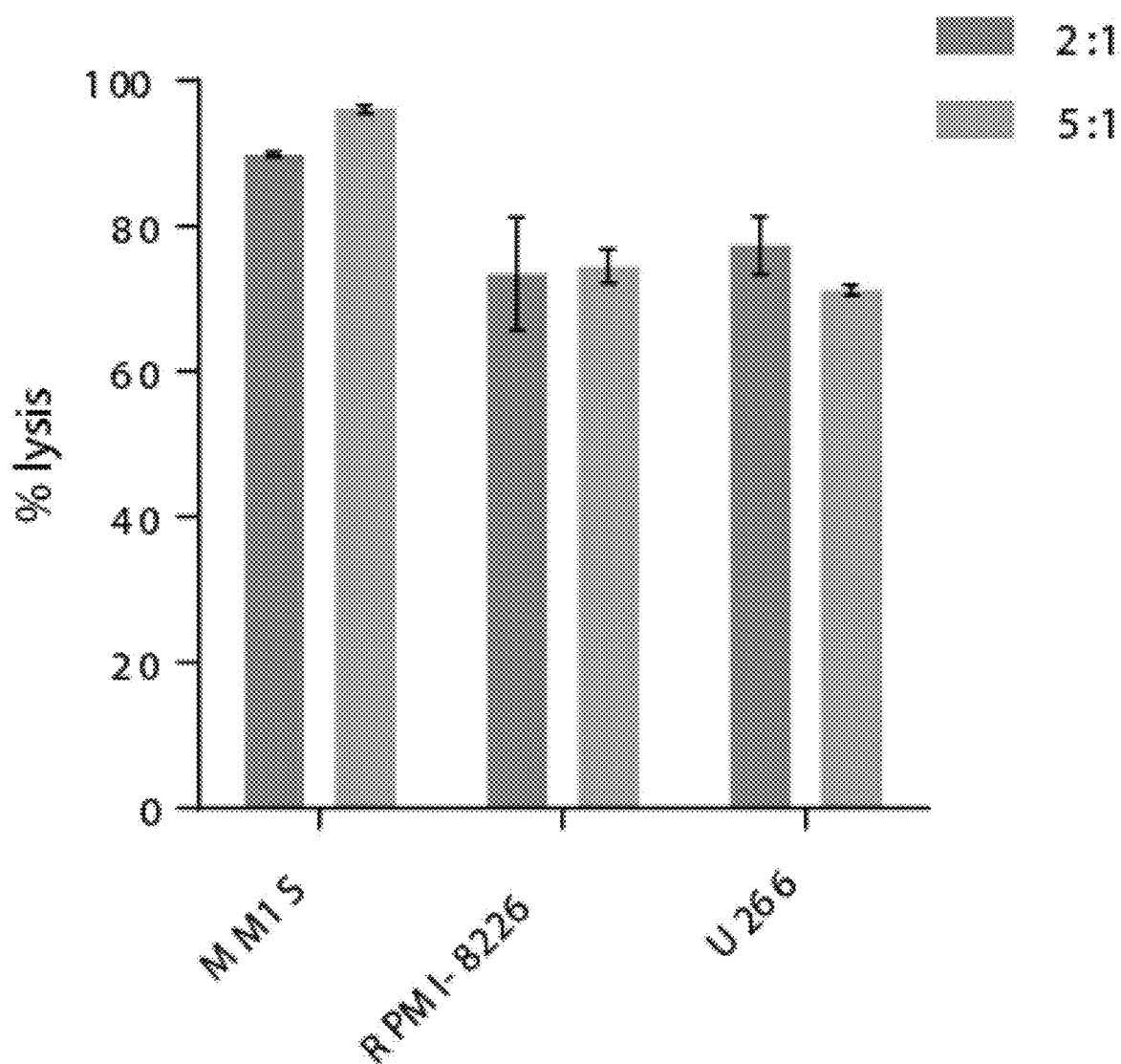

To assess the cytotoxicity of BC1cCAR T-cells, we conducted co-culture assays against myeloma cell lines: MM1S (BMCA$^+$ CS1$^+$), RPMI-8226 (BCMA$^+$ CS1$^{dim}$), and U266 (BCMA$^+$ CS1$^{dim}$). FACS analysis of BC1cCAR cytotoxicity in 24 hour co-cultures show virtually complete lysis of MM1S cells (>90%) at all E:T ratios (FIG. 2A). Similar trends were observed against RPMI-8226 and U266 cells in culture (FIGS. 2A, 2B), demonstrating effective bulk cytotoxicity against target populations with varying levels of antigen expression (FIG. 2C).

Figure 3:
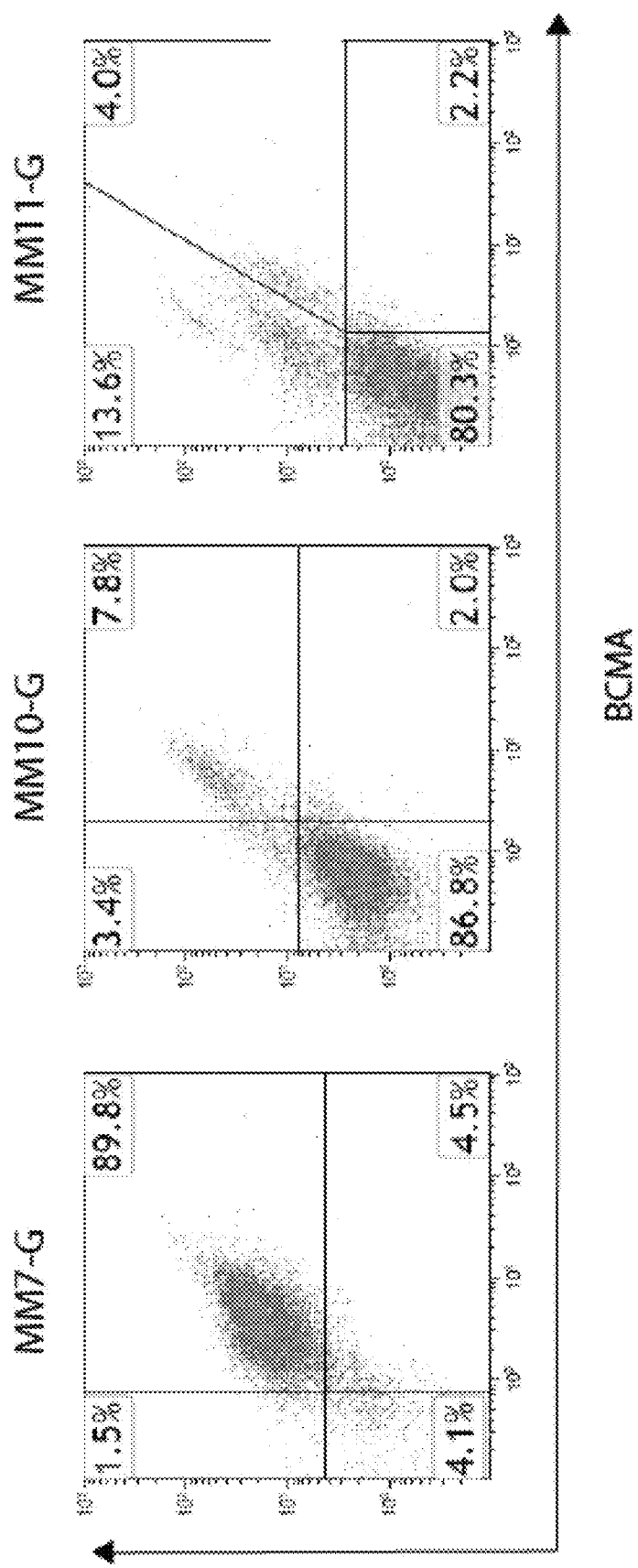
FIG. 3: Primary patient cell phenotypes.
Figure 4A:
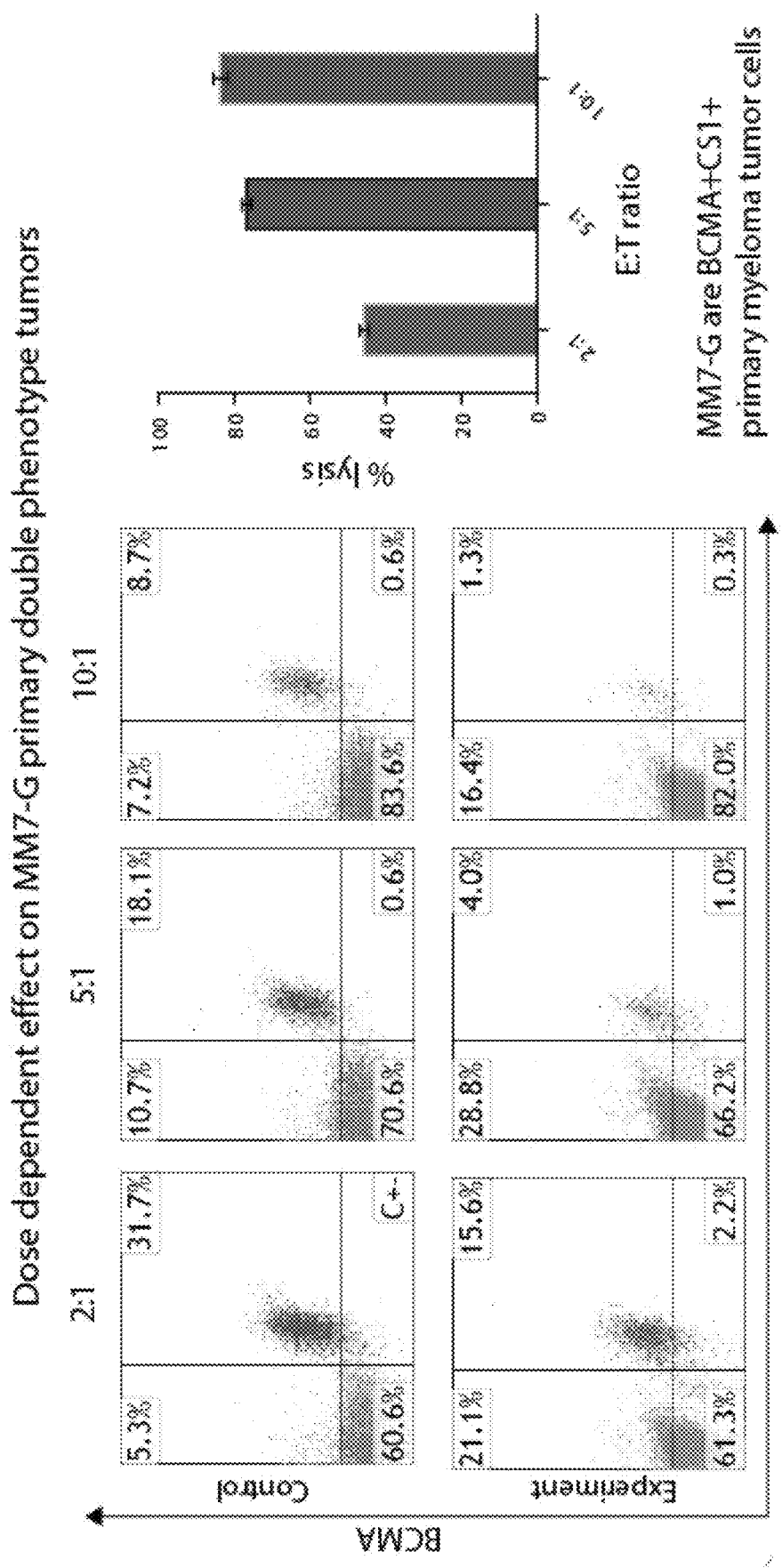

BC1cCAR T-Cells Specifically Target BCMA$^+$ and CS1$^+$ Populations in Primary Myeloma Samples To further evaluate the BC1cCAR's ability to kill diverse primary myeloma cell types, primary samples were chosen to exhibit a spectrum of target antigen expression (FIG. 3). Flow cytometry analysis of the MM10-G sample revealed a mixed tumor with double positive BCMA$^+$ CS1$^+$ as well as CS1$^+$ only population subsets. MM7-G sample showed a complete BCMA CS1$^+$ phenotype while bone marrow aspirate MM11-G exhibited a noisy BCMA$^{dim}$ CS1$^{dim}$ phenotype. BC1cCAR T-cells showed robust (>80%) dose-dependent ablation of the MM7-G primary patient sample (FIG. 4A).

Figure 4B:
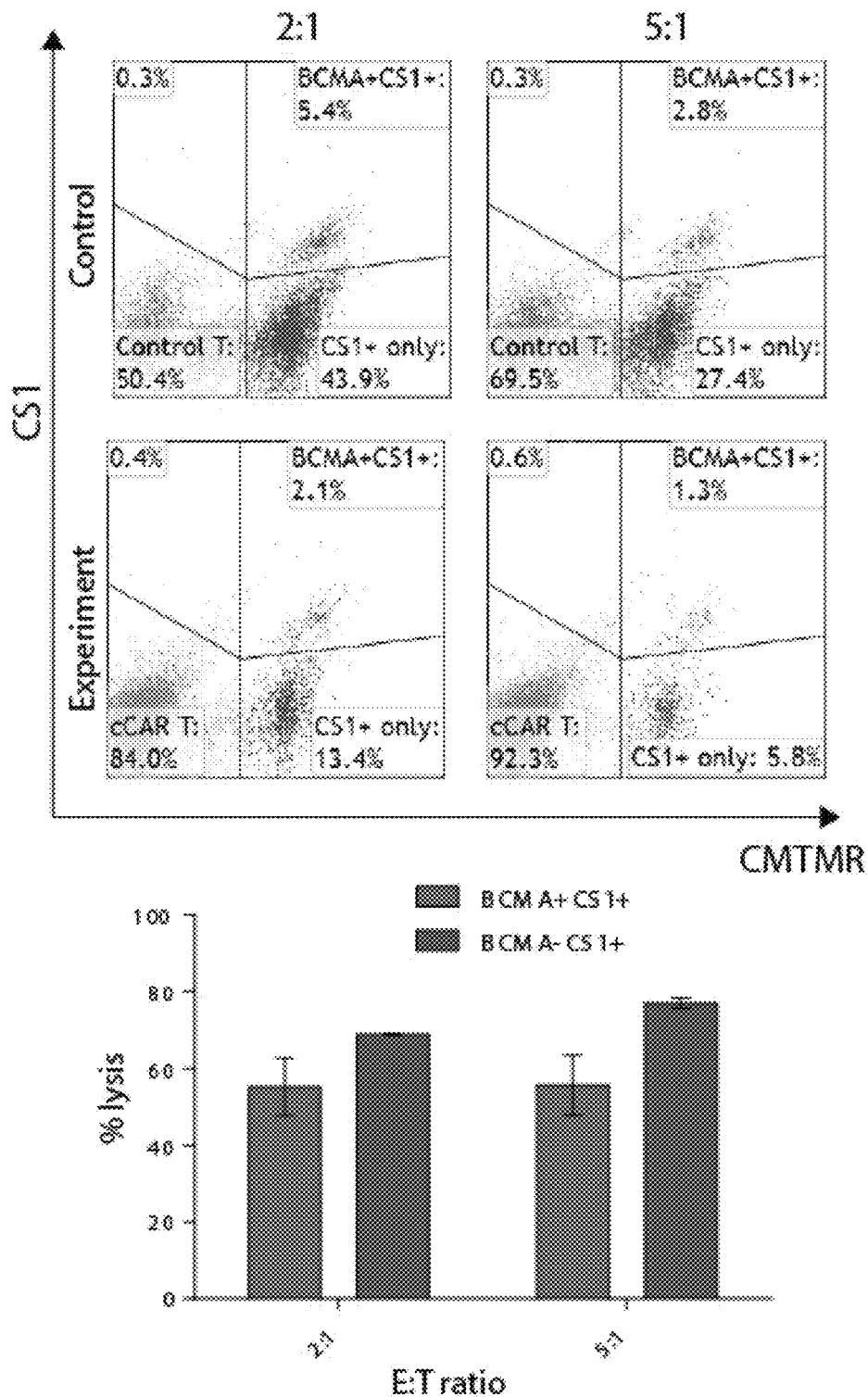
Figure 4C:
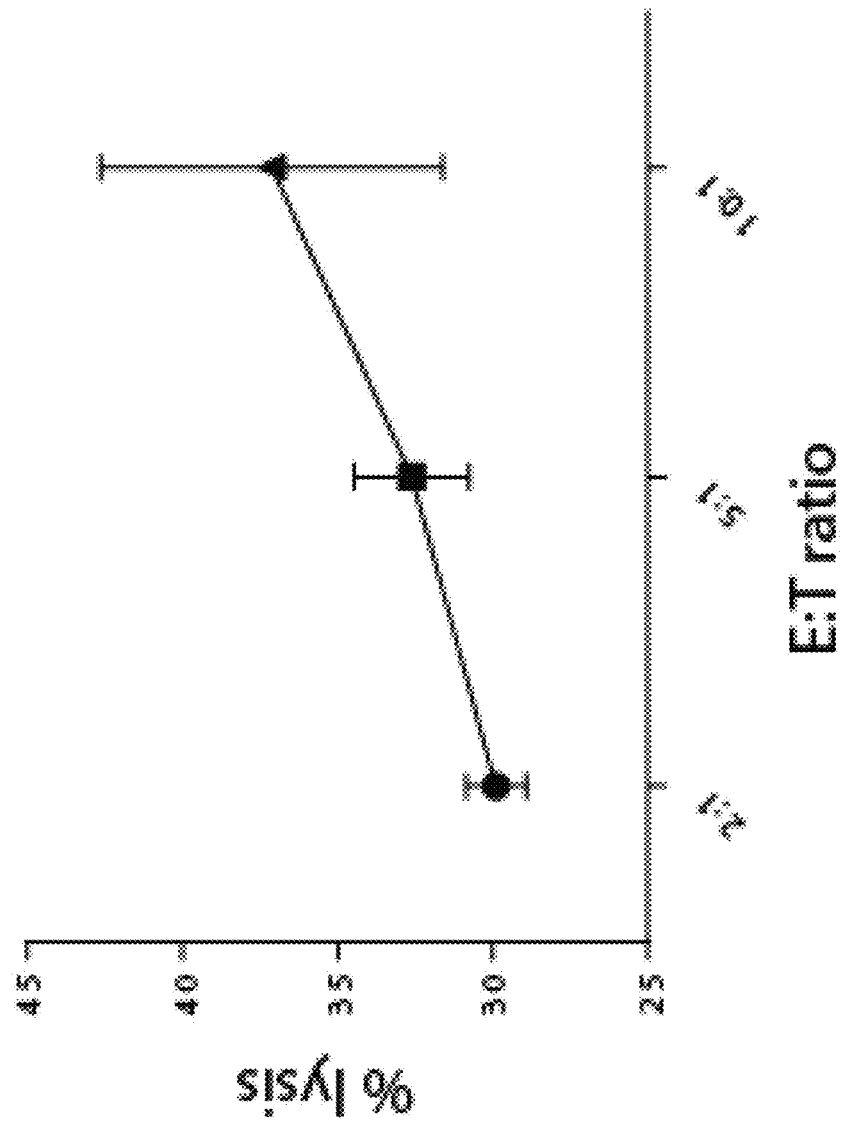
Figure 4D:
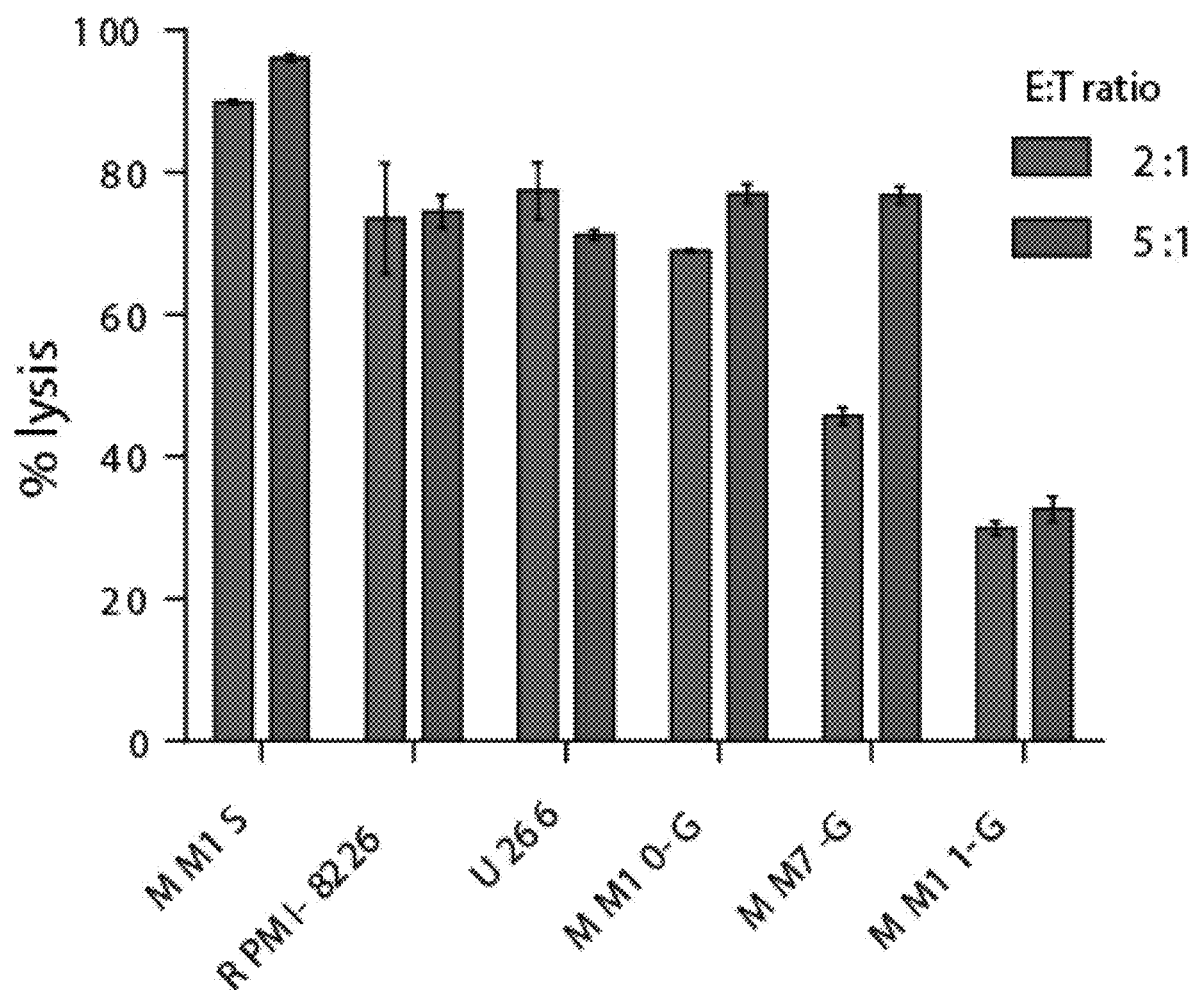

BC1cCAR also showed targeted and specific lysis ability, by significantly ablating both BCMA$^+$ CS1$^+$ and BCMA$^-$ CS1$^+$ population subsets in MM10-G co-cultures. At an E:T ratio of 2:1, BC1cCAR T-cells ablated over 60% of the BCMA$^+$ CS1$^+$ population, and 70% of the CS1$^+$ only population with slight dose dependent increases (FIG. 4B). BC1cCAR T-cells were also able to demonstrate dose-dependent cytotoxic activity against the MM11-G cells (FIG. 4C). Across the cytotoxicity screening, BC1cCAR T cells exhibited robust anti-tumor activity against both myeloma cell lines and primary tumor cells expressing different combinations of BCMA and CS1 (FIG. 4D)

Functional Evaluation of BC1cCAR Antigen Specific Activity

We established a model that allowed us to test the BC1cCAR scFv functionality independently. A CML cell line, K562, negative for myeloma markers was overexpressed with either CS1 (CS1-K562) or BCMA (BCMA-K562). After confirming independent antigen expression in each cell line (FIG. 5A), we determined BC1cCAR T-cell targeting functionality through co-culture experiments.

In short-term cultures (overnight), BC1cCAR T-cells exhibited cytotoxic activity against BCMA-K562 cells. There were no off-target effects against wild-type K562 cells negative for either antigen (FIG. 5B). Short-term cultures against CS1-K562 cells also showed similar responses against CS1-expressing target cells. In addition, BC1cCAR T-cells appeared to have a stronger cytotoxic effect than a CS1-specific CAR against CS1-K562 cells (FIG. 5B).

Residual tumor populations possessing a non-target antigen may lead to relapse in patients who have undergone treatment using a single-antigen CAR. Thus, to model more clinically relevant mixed antigen-expressing cell populations, we conducted combined co-culture experiments. BCMA-K562 and CS1-K562 cells were mixed in 1:1 ratios in a sustained (48 h) culture to assay for residual antigen positive populations. Next, histograms were constructed that represented populations of T-cells and target tumor cells with residual gated target tumor populations marked (FIG. 5C). We found that compared to control T-cells, BCMA-specific CAR and CS1-specific CAR had profound cytotoxic effects against their respective target populations. However, CS1-CAR left a significant residual BCMA$^+$ population, whereas BCMA-CAR achieved a high degree of cytotoxicity but left a small CS1$^+$ population. In contrast, the BC1cCAR T-cells effectively depleted both target populations (FIG. 5C).

Tumor Re-Challenge Demonstrates Sequential Killing Ability of BC1cCAR T-Cells

We next investigated the ability of BC1cCAR T-cells to kill tumor cells in a sequential manner under unfavorable microenvironments caused by cell lysis, debris, and tumor re-challenge. Using the scheme in FIG. 6A, we conducted long-term co-cultures using MM1S cells as a model myeloma tumor and periodically re-challenged BC1cCAR T-cells and single BCMA-CAR and CS1-CAR T-cells with fresh MM1S cells to simulate tumor expansion or relapse. Even without exogenous cytokines, we found that all CAR treatments depleted target antigens after 48 hours, with significant clustering and T-cell proliferation (FIG. 6B). In contrast, control T-cells showed no response or proliferation, and yielded a tumor cell population twice its initial size. After re-challenging all treatment wells with fresh MM1S cells we found that all CARs still retained a high degree of cytotoxicity. By 108 hours, new MM1S cells were virtually depleted by both BCMA-CAR and the BC1cCAR, while the CS1-CAR displayed incomplete killing of the new MM1S cells (FIG. 6C). All CAR-mediated tumor lysis and cytotoxicity stopped after 168 hours, however, BCMA-CAR and BC1cCAR still showed detectable minority T-cell populations while control T-cells and CS1-CAR T-cells were virtually undetectable (data not shown).

BC1cCAR T-Cells Exhibit Significant Control and Reduction of Tumor In Vivo

In order to evaluate the in vivo activity of BC1cCAR T-cells, we developed a myeloma mouse model with luciferase-expressing MM1S cells to induce fluorescence visible tumor formation. The BC1cCAR T-cells significantly reduced tumor burden and prolonged survival in MM1S-injected mice when compared to control T-cells. Mice were given a single dose of BC1cCAR or control T-cells and tumor burden assayed by IVIS imaging (FIG. 7A). There was a highly significant difference (P<0.0003) in IVIS measurement of tumor burdens between the control group and the BC1cCAR treatment group from Day 6 onwards (FIG. 7B). CAR injected mice also had significantly more favorable survival outcomes (FIG. 7C).

Mixed Antigen Population Mouse Models Demonstrate Superior Tumor Burden Control by cCAR Expressing Cells vs Single CAR Expressing Cells To model heterogeneous cell populations and potential antigen escape, we injected mice with a 4:1 mix of BCMA:CS1-expressing K562 cells and treated on day 3 with $7.5 \times 10^6$ of either control, BCMA-CAR, or BC1cCAR T-cells. CS1-CAR T-cells were excluded on the basis of inferior in vitro efficacy. On day 3, two control mice died as a result of the injection procedure and were excluded from analysis. Tumor burden was visualized by fluorescence (FIG. 8A). At day 10, both CARs exhibited over 50% tumor reduction compared to GFP control, increasing to over 60% by day 12 (FIG. 8A—right). By day 10, BC1cCAR outpaced BCMA-CAR in tumor suppression by 6% and this spread increased to 17% by day 12, potentially modeling the inability of BCMA-CAR to lyse residual CS1-K562 cells (20% of tumor injected). Survival outcomes for all CAR T-cell treated mice were significantly improved over the control group. There was also a significant improvement (p<0.05) in survival for the BC1cCAR group versus the BCMA-CAR group (FIG. 8B). While both CARs were efficacious in controlling tumor growth, the BC1cCAR demonstrates more robust control compared to a single target option.

Enhanced T-Cell Persistency and Maintenance of Tumor Depletion by Compound CAR T-Cells in Independent Antigen Mouse Models To assay specific BCMA and CS1 antigen-expressing cell depletion and verify compound scFv efficacy, a third mouse model was constructed in which 4 groups consisting of 5 mice each were injected with either BCMA-K562 or CS1-K562 cells, with control and BC1cCAR T-cells administered to each tumor group (n=19 as a result of an early spontaneous mouse death). At times of sacrifice (various: day 30-80+), mice whole blood and liver tissues were screened for T-cell and tumor populations. Both hematological tissue types show consistent tumor presence in control groups when compared to cCAR groups (FIGS. 9A, 9B, 10, 11). Aggregate tissue analysis of averaged tumor cell populations in both tissues show consistent trends of depleted tumor burden in cCAR treated mice groups (FIG. 9B). In both the blood and liver, control T-cells were unable to persist beyond the 30 day mark and exhibited significant tumor burden in both tissue types (FIGS. 9B, 9C). In contrast, cCAR treated mice showed significant T-cell expansion and persistency compared to control T-cells across all mice even at day 30+ (FIG. 9C), correlating with observed increased anti-tumor activity and supporting overall improved survival.

Examples for Targeting CD123+ and/or CD33+ Leukemia/Lymphomas by CD123b–CD33b cCAR (a Version of CD123–CD33 cCAR) T Cells Generation of CD123b–CD33b cCAR T-Cells Lentivirus transfected cytotoxic effector T-cells were engineered to express two complete units of CAR linked by a self-cleaving P2A peptide (FIG. 12A). The resulting compound CAR (CD123b–CD33b cCAR) is capable of targeting CD123+ and/or CD33+ leukemic cells (FIG. 12B). A leader, a scFv, a hinge domain (H), a transmembrane domain (TM), a co-stimulatory domain (CD28 or 4-1BB) and the intracellular signaling domain CD3 zeta (CD3) are included in each CAR unit. A strong spleen focus forming virus promoter (SFFV) and a CD8 leader sequence were used for efficient expression of the CD123b–CD33b cCAR molecule on the T-cell surface.

CD123b–CD33b cCAR T-Cell Transduction Efficiency

To evaluate CD123b–CD33b cCAR expression levels on the T-cell surface after transduction, flow cytometry analysis was used (FIG. 13). The transduction efficiency was determined to be 25%.

CD123b–CD33b cCAR T-Cells Effectively Lyse Acute Myeloid Leukemia Cell Lines

Figure 14A:
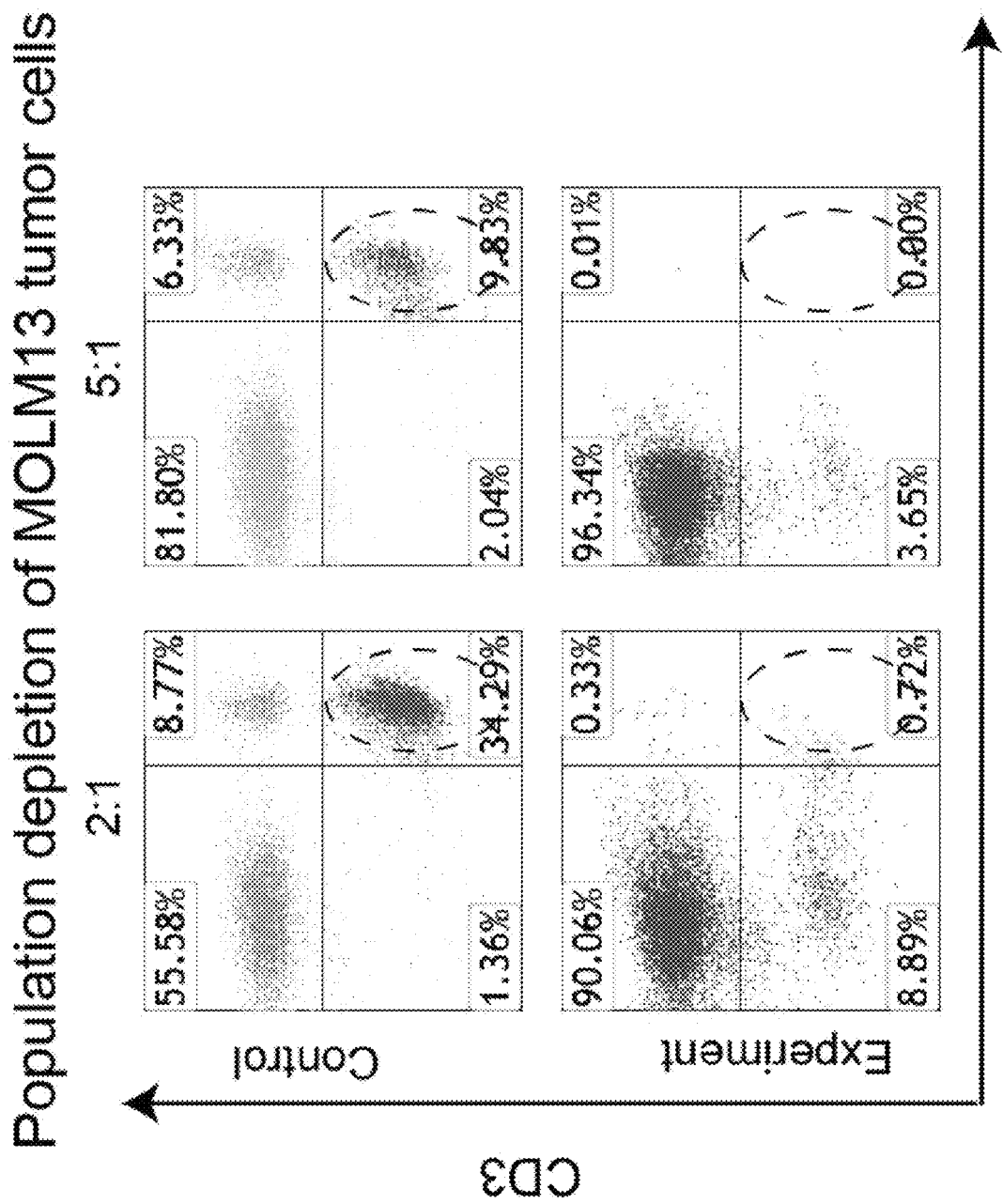
Figure 14B:
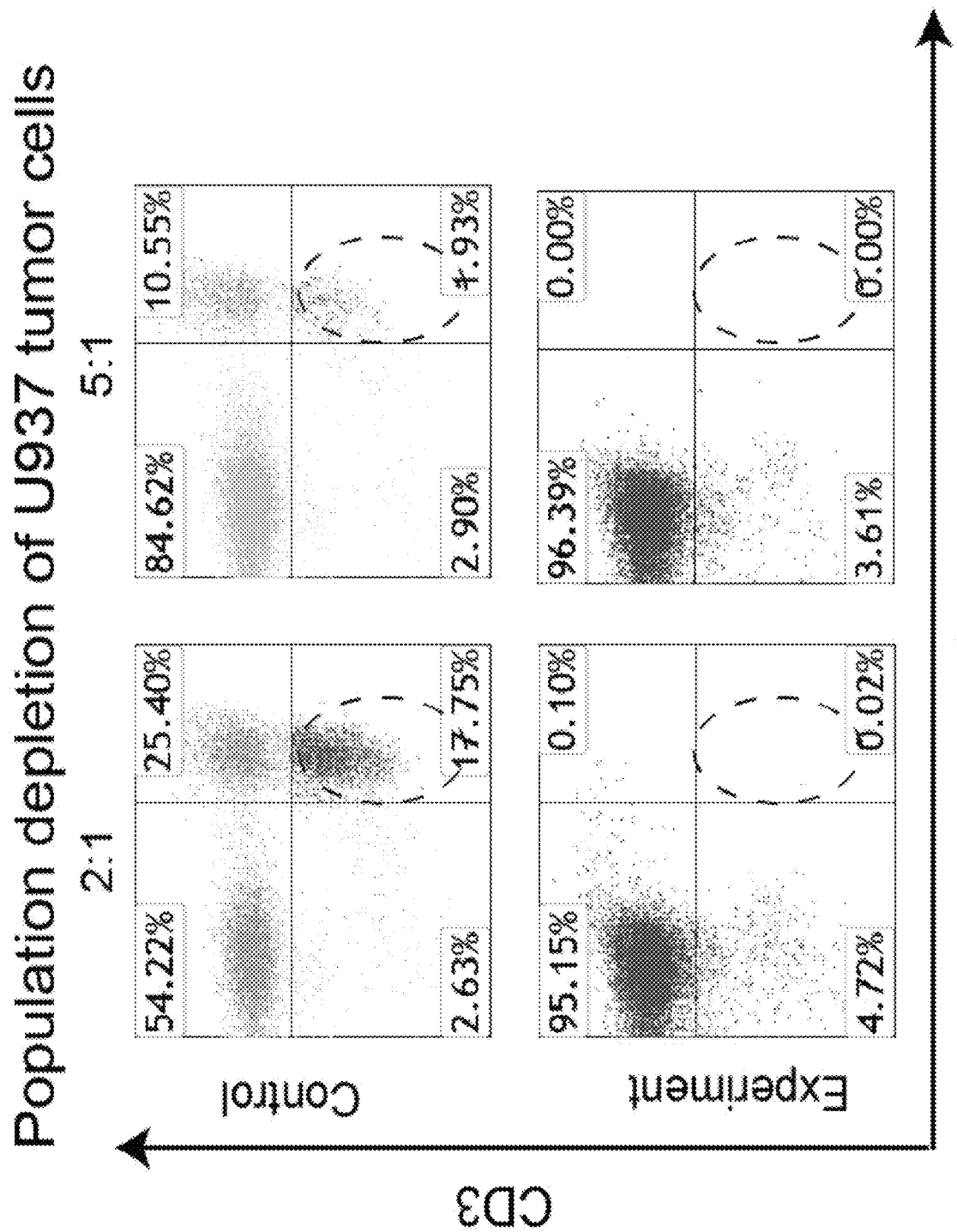
Figure 14C:
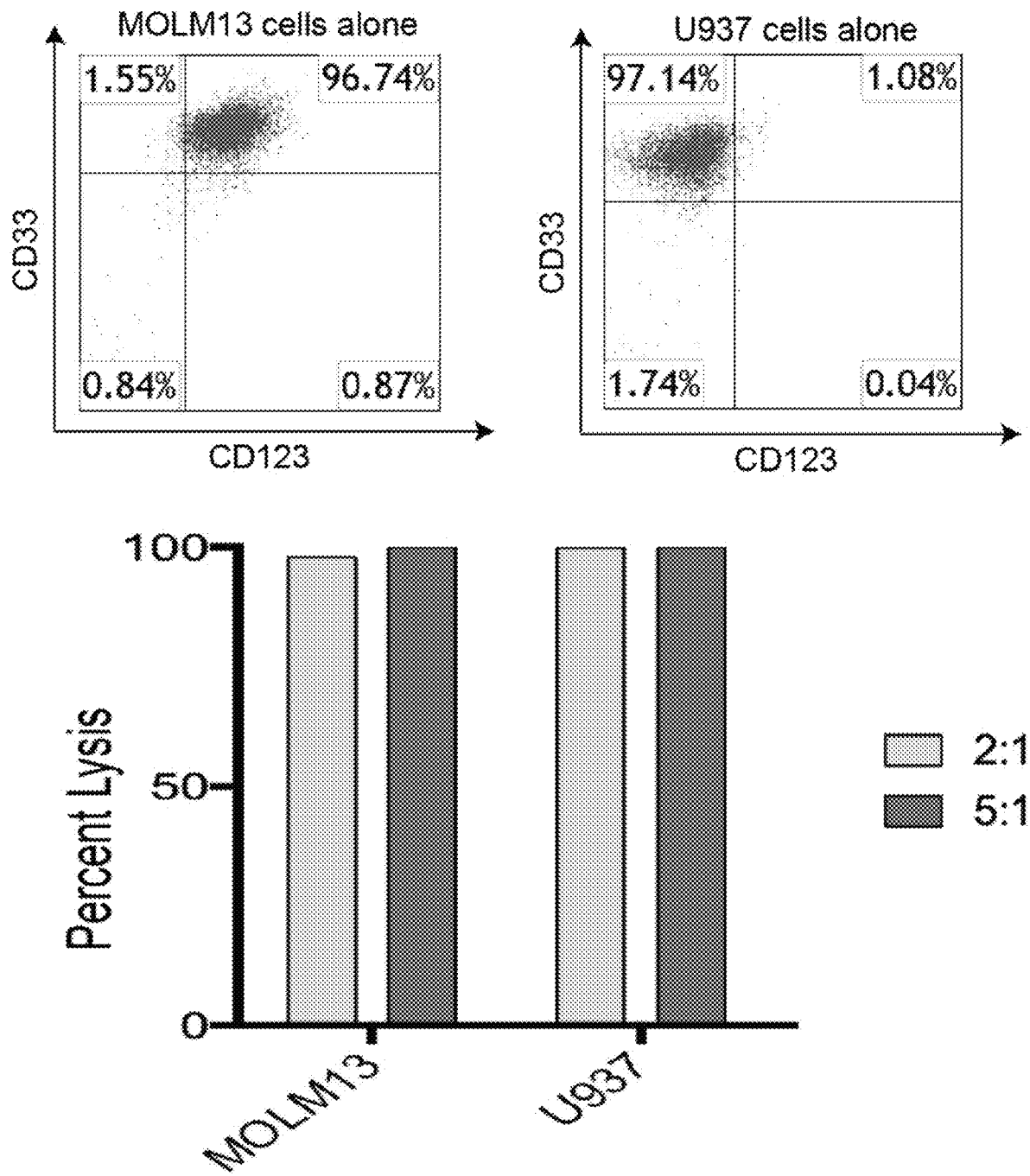

To evaluate the anti-tumor activity of the CD123b–CD33b cCAR (CD123b–CD33b cCAR) T-cells, we performed co-cultures using the AML cell line MOLM13 (CD33+CD123+) and the promonocytic U937 cell line (CD33+CD123−). To distinguish between the target leukemia calls (MOLM13 and U927; both are CD3−) and effector T-cells (CD3+) during flow cytometry, cells were stained with CD3. Co-culture assays were performed at effector to target (E:T) ratios of 2:1 and 5:1 for 24 hours, and flow cytometry analysis was used to determine cell lysis rates by CD123b–CD33b cCAR T-cells or control T-cells (FIGS. 14A, 14B). At the 2:1 E:T ratio, CD123b–CD33b cCAR T-cells were able to lyse around 98% of CD123+CD33+ MOLM13 cells and 99.9% of CD33+ U937 cells when compared to control T-cells. Furthermore, at the 5:1 ratio, 100% lysis of both cell lines was observed (FIG. 14C). We also validated the surface markers expressed on both the MOLM13 and U937 cell lines (FIG. 14C). Overall, these results suggest that CD123b–CD33b cCAR T-cells specifically and robustly eliminate tumor cells expressing either or both antigens. Moreover, the finding that the CD123b–CD33b cCAR T-cells effectively ablated U937 cells expressing only CD33 and not CD123 supports the fact that each discrete unit of the compound CAR can independently target its antigen and eliminate a target expressing only one antigen or both antigens.

Figure 14D:
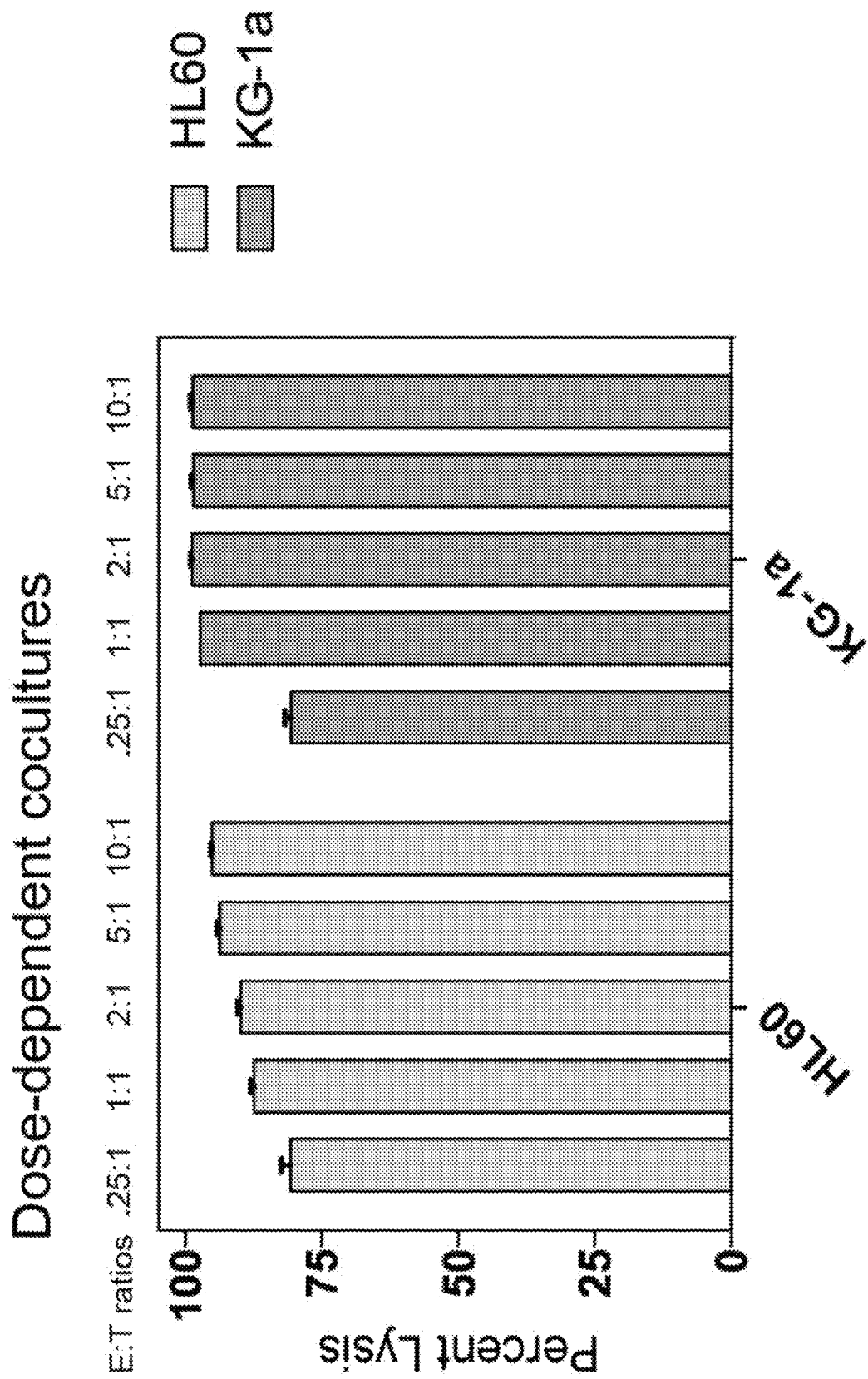

We further evaluated the dose-dependent tumor lysis ability of the CD123b–CD33b cCAR T-cells by varying and decreasing the E:T ratio against two other cell lines: KG1a (CD123dimCD33+) and HL60 (CD123dimCD33+). CD123b–CD33b cCAR T-cells were cultured against KG1a and HL60 cell lines in 0.25:1, 0.5:1, 1:1, 2:1, 5:1, and 10:1 E:T ratios, showing over 75% tumor lysis ability at even a 0.25:1 ratio. Overall, there was a strong correlation between dose and tumor-lysis until saturation at the 5:1 ratio (FIG. 14D).

CD123b–CD33b cCAR T-Cells Effectively Lyse Primary Myeloid Leukemia Tumor Cells

We next established the anti-tumor properties of the CD123b–CD33b cCAR T-cells against primary tumor cells. Cells were stained with CD3 to distinguish the CAR T-cells from the CD3− leukemia samples. Different primary patient leukemia samples including two CD123+CD33+ AML and two CD123+ B-ALL samples (PT1:AML, PT2:B-ALL, PT3:AML, and PT4:B-ALL) were assayed in this panel and flow cytometry analysis was performed to verify tumor lysis with depleted target populations encircled (FIG. 15). Compared to the previous anti-tumor cytotoxicity results for AML cell lines (FIG. 14), CD123b–CD33b cCAR T-cells showed similarly positive results against all patient samples, with over 80% tumor lysis at the 2:1 ratio and more than 98% tumor lysis at the 5:1 E:T ratio (FIG. 15). Moreover, similarly to our cell lines, the finding that the CD123b–CD33b cCAR T-cells effectively ablated PT2 cells expressing only CD123 and not CD33 supports the fact that each discrete unit of the compound CAR can independently target its antigen and eliminate a cell expressing only one of its target antigens (as seen against CD33+ U937 and CD123+ PT2 cells) or both target antigens (as seen against CD123+ CD33+ MOLM13 and PT1 cells). Overall, these results suggest that CD123b–CD33b cCAR T-cells display high killing efficacy against patient tumor cells expressing either or both antigens.

Figure 15A:
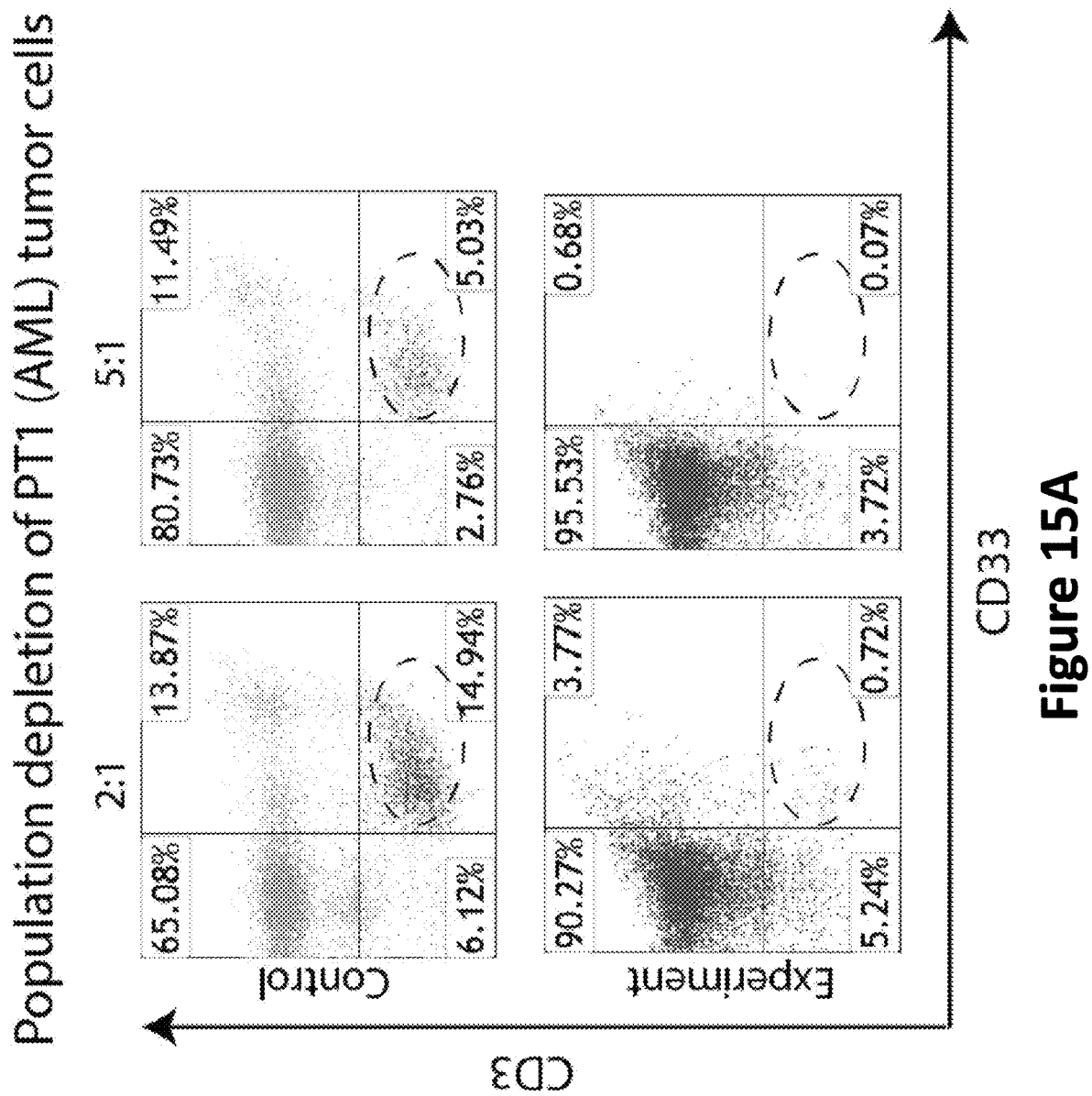
Figure 15B:
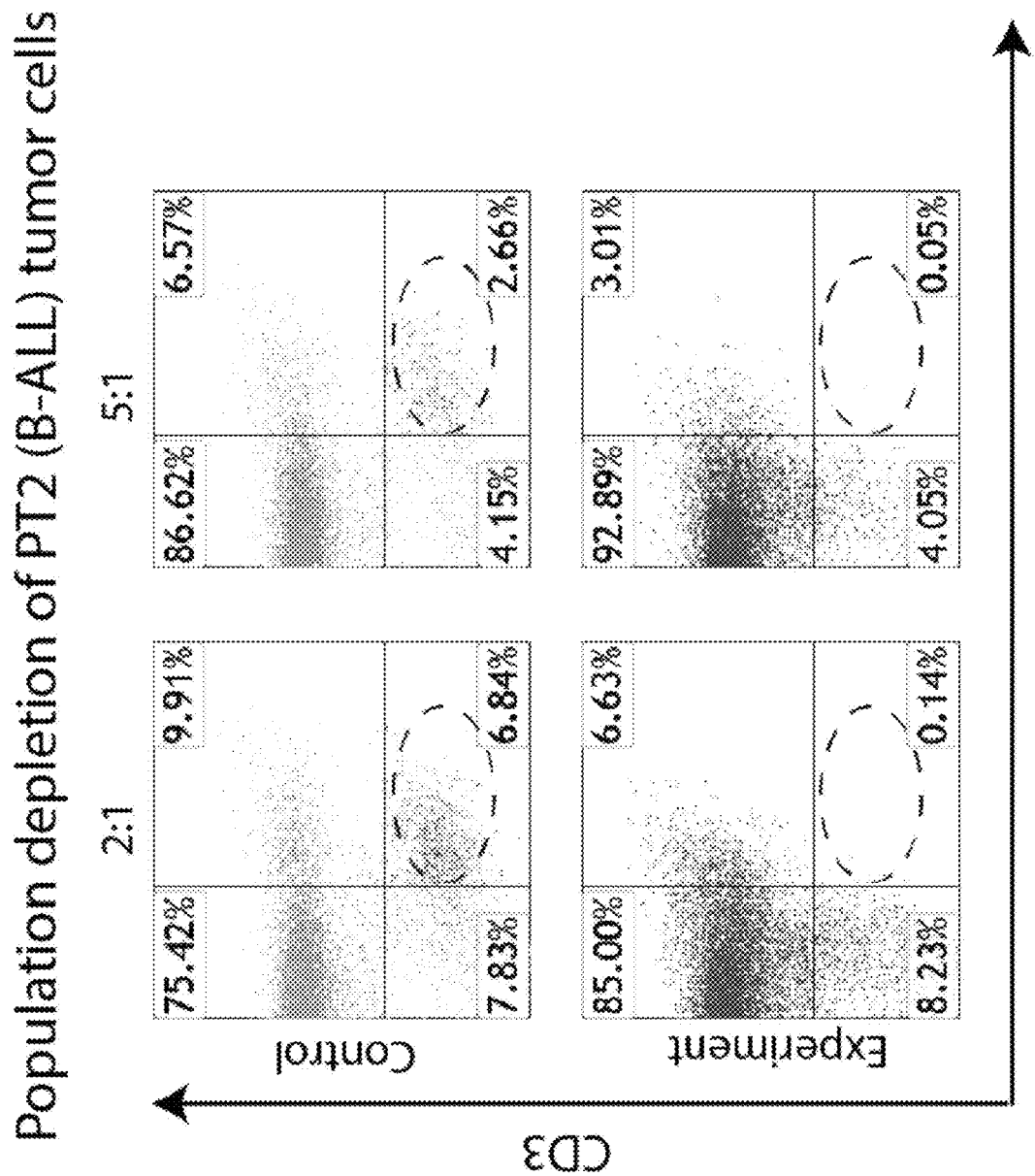
Figure 15C:
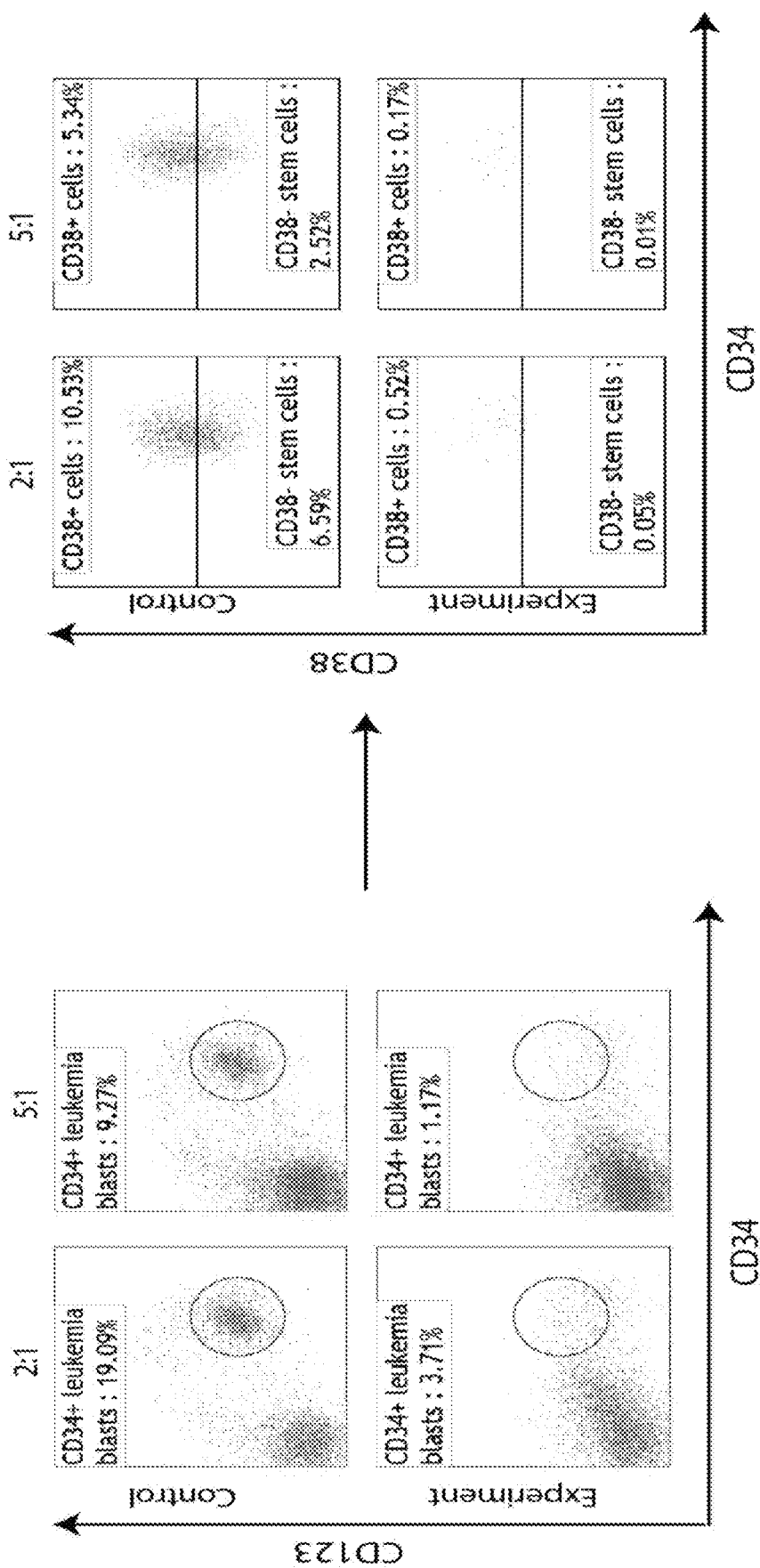
Figure 15D:
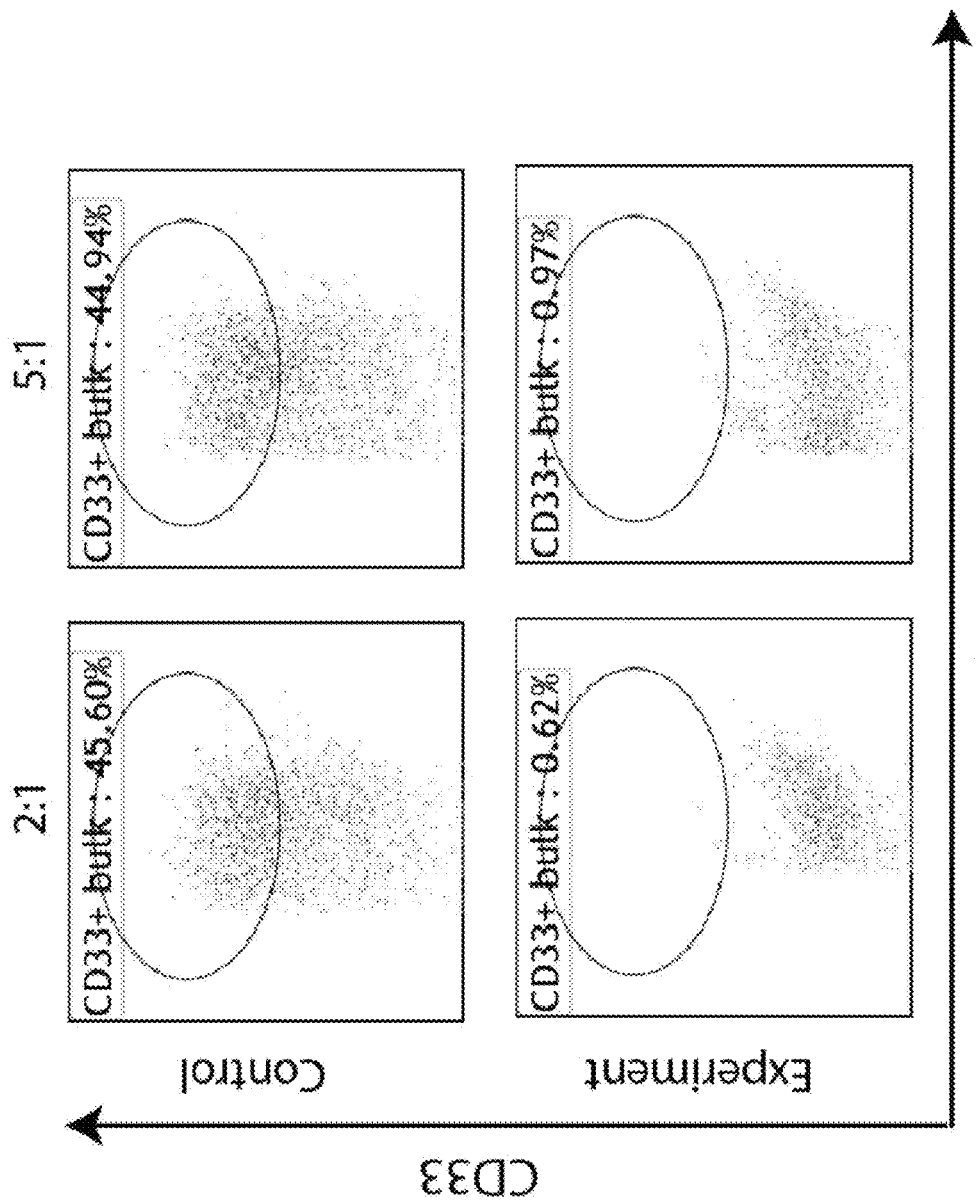
Figure 15E:
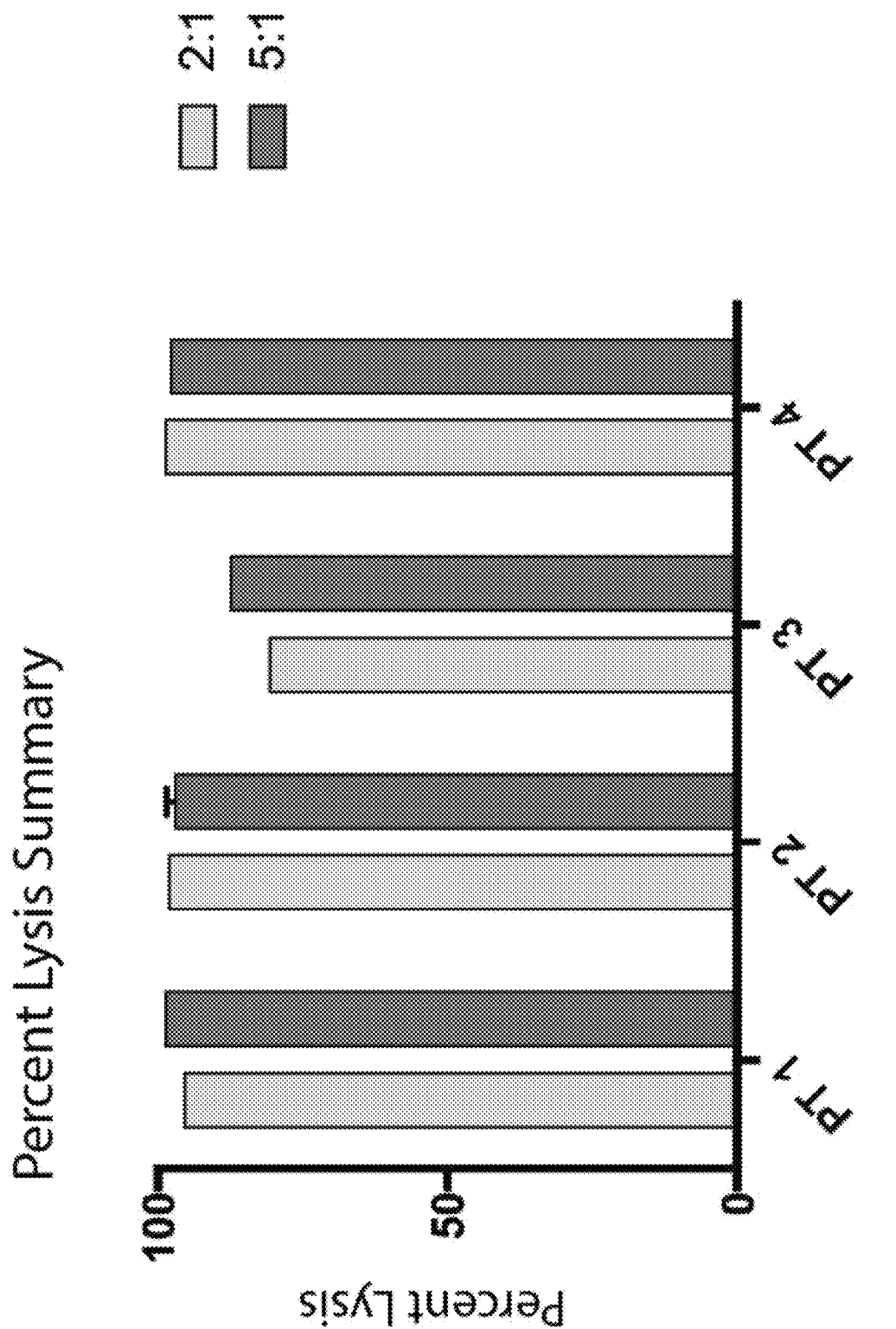

We also specifically examined the ability of our CD123b–CD33b cCAR to eliminate specific cell populations including leukemic stem cells (CD123+CD34+CD38−) in the PT3 sample and myeloid leukemia bulk disease (CD34variableCD33+) in the PT4 sample (FIGS. 15C, 15D). We found that CD123b–CD33b cCAR T-cells successfully ablated both LSCs and bulk disease cells.

CD123b–CD33b cCAR T-Cells' Discrete Receptor Units Independently Lyse Target Cells in an Antigen-Specific Manner To further confirm our cCAR's independent antigen targeting ability, we generated Jurkat artificial cell lines expressing either CD123 or CD33 and tested CD123b–CD33b cCAR T-cells against these cells in addition to wild-type Jurkat cells expressing neither antigen (FIG. 16). We found that the CD123b–CD33b cCAR T-cells specifically and potently ablated cells expressing either the CD123 or CD33 antigen when compared to wild-type Jurkat cells expressing neither antigen (FIGS. 16A, 16B and 16C). Overall, we conclude that the our CD123b–CD33b cCAR T-cells can act via stimulation of either CAR receptor, and are able to target cells expressing only one target antigen or both equally well, and eliminate targets with high efficacy.

CD123b–CD33b cCAR T-Cells Exhibit Profound Anti-Tumor Activity in Two Xenograft Mouse Models of AML Using MOLM13 and U937 Cells In order to evaluate the in vivo anti-tumor activity of CD123b–CD33b cCAR T-cells as a predictor of their therapeutic efficacy in patients, we developed two xenograft mouse models (FIG. 17). NSG mice were sublethally (2.0 Gy) irradiated and intravenously injected with either $1.0\times10^6$ firefly luciferase-expressing MOLM13 cells or $1.0\times10^6$ firefly luciferase-expressing U937 cells. On day 4 following MOLM13 or U937 engraftment, mice were intravenously injected with a $10\times10^6$ cells of either CD123b–CD33b cCAR or control T-cells. To evaluate tumor burden in mice, RediJect D-Luciferin (Perkin-Elmer) was injected intraperitoneally on days 6, 9, and 13, and mice were subjected to IVIS imaging to quantify the luciferase activity (Caliper LifeSciences) (FIGS. 17A, 17B). As observed by IVIS imaging, total flux levels continually increased in control mice with drastic tumor burden growth. In contrast, CD123b–CD33b cCAR treated mice significantly suppressed tumor burden as early as day 3. By day 6, mice treated with the cCAR had over 80% reduction in tumor burden in both models (FIGS. 17A, 17B). This tumor suppression was maintained and increased in potency through day 13, as total flux in CD123b–CD33b cCAR treated mice remained near background null values with statistically significant differences from control T-cell treated mice.

We also evaluated tumor cell and CAR T-cell persistency at the time of sacrifice. Peripheral blood was collected from each experimental mouse at the time of sacrifice along with control mice, and analyzed via flow cytometry for the presence of transplanted tumor (MOLM13 or U937 cells) and T-cells (cCAR or control). MOLM13 and U937 cells are CD3− cells, allowing them to be distinguished from CD3+ CAR or control T-cells. Murine peripheral blood cells were gated by side scatter and human CD45 antibody, and then broken down into CD3 vs. CD33. While control treated mice showed significant residual tumor populations (~75-87%) in the peripheral blood, CD123b–CD33b cCAR treated mice showed virtual depletion of all tumor comparable to control mice (FIG. 17C). In addition, CD123b–CD33b cCAR treated mice showed significant T cell expansion with virtually all human cells in the peripheral blood that were CAR T cells. This confirms the potency and persistency of our cCAR T-cells in maintaining long-term responses. Furthermore, CD123b–CD33b cCAR treated mice showed significantly increased survival outcomes as compared to control treated mice (FIGS. 17A, 17B).

In Vivo Depletion of Infused cCAR T-Cells Following Treatment with CAMPATH

For clinical treatment using CAR T-cells against acute myeloid leukemias, establishment of safety methods to eliminate CAR T-cells from patients may be necessary after tumor depletion or in emergency cases due to unexpected side effects caused by CAR therapy. T-cells and B-cells express CD52 on the cell surface and a CD52 specific antibody, CAMPATH (alemtuzumab), can eliminate CD52+ cells from circulation. To assess the effect of CAR elimination by CAMPATH treatment, we conducted in vivo procedures as described (FIG. 18A). We intravenously injected 10×10$^6$ cCAR T-cells into irradiated mice. On the next day, we administered 0.1 mg/kg of either CAMPATH or PBS via IP injection to 3 mice of each group. At 6 and 24 hours following CAMPATH treatment, we collected peripheral blood and determined the presence of cCAR T-cells by FACS analysis. cCAR T-cells were gated by side scatter (SSC) and CD3 expression and CD3 and CD45 expression to distinguish them from mouse cells. CAMPATH injection depleted cCAR T-cells in blood at both 6 h and 24 h (FIGS. 18B, 18C). These findings support the use of CAMPATH as a safety switch to rapidly deplete CAR-T cells from the circulation.

Examples for Targeting B-ALL and Other Leukemias by CD19b–CD123 cCAR (a Version of CD19–CD123 cCAR)

Generation of CD19b–CD123 cCAR T Cells

Lentivirus transfected cytotoxic effector cells, namely T cells, are engineered to express an anti-CD19 single-chain variable fragment (scFv1, CD19b) region fused to an anti-CD123 fragment (scFv2, CD123) by a self-cleaving P2A peptide. These antibody domains are linked by CD8-derived hinge (H) and transmembrane (TM) regions to 4-1BB and CD28 co-activation domains and a CD3ζ signaling domain (FIG. 19). A strong spleen focus forming virus promoter (SFFV) and a CD8 leader sequence were used for efficient expression of the CD19b–CD123 cCAR molecule on the T-cell surface.

CD19b–CD123 cCAR T-Cell Transduction Efficiency

T-cells isolated from umbilical cord blood (UCB) buffy coats were transduced with CD19b–CD123 cCAR lentivirus after 2 days of activation. The CD19b–CD123 cCAR transduction efficiency was determined to be 26% by flow cytometry (FIG. 20).

Figure 21A:
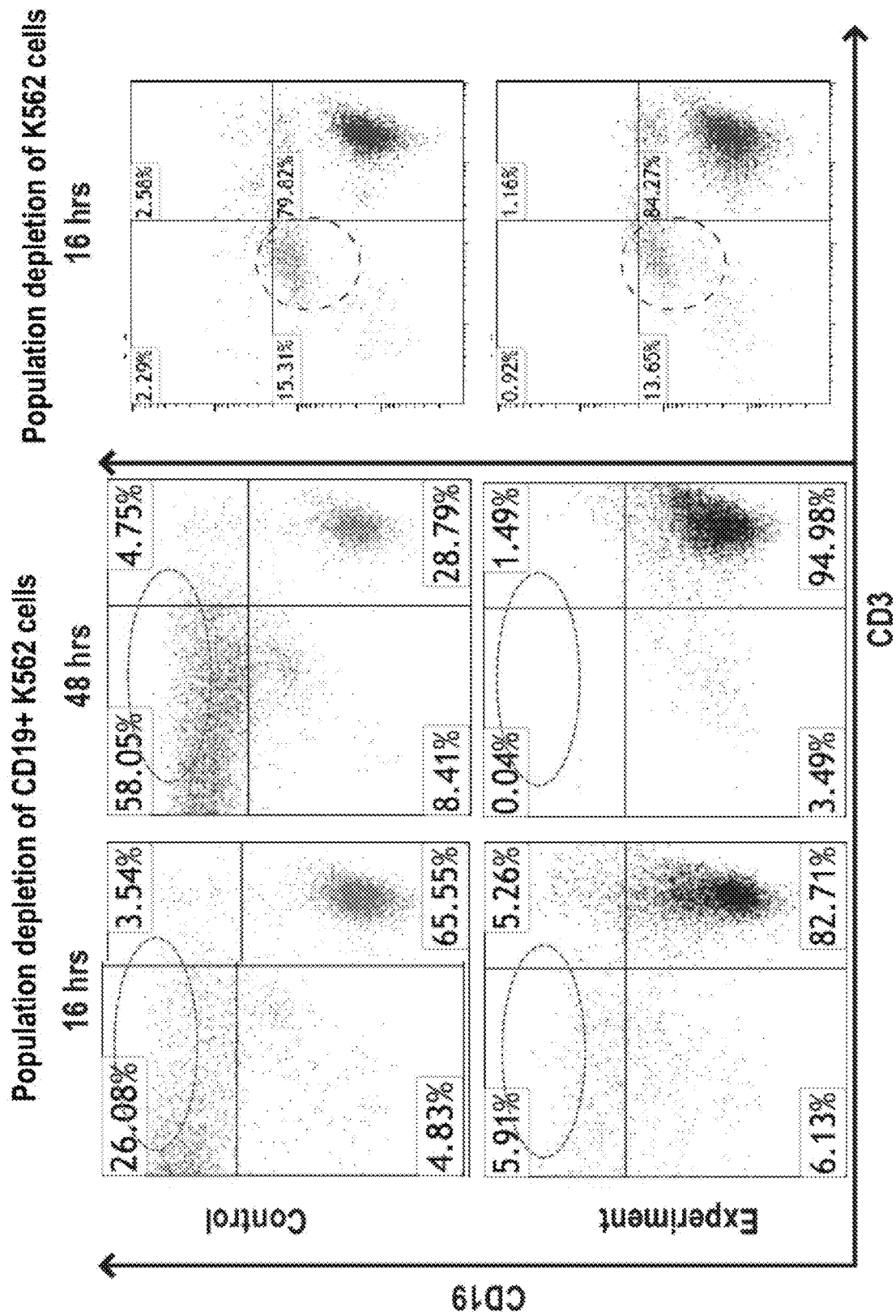
Figure 21B:
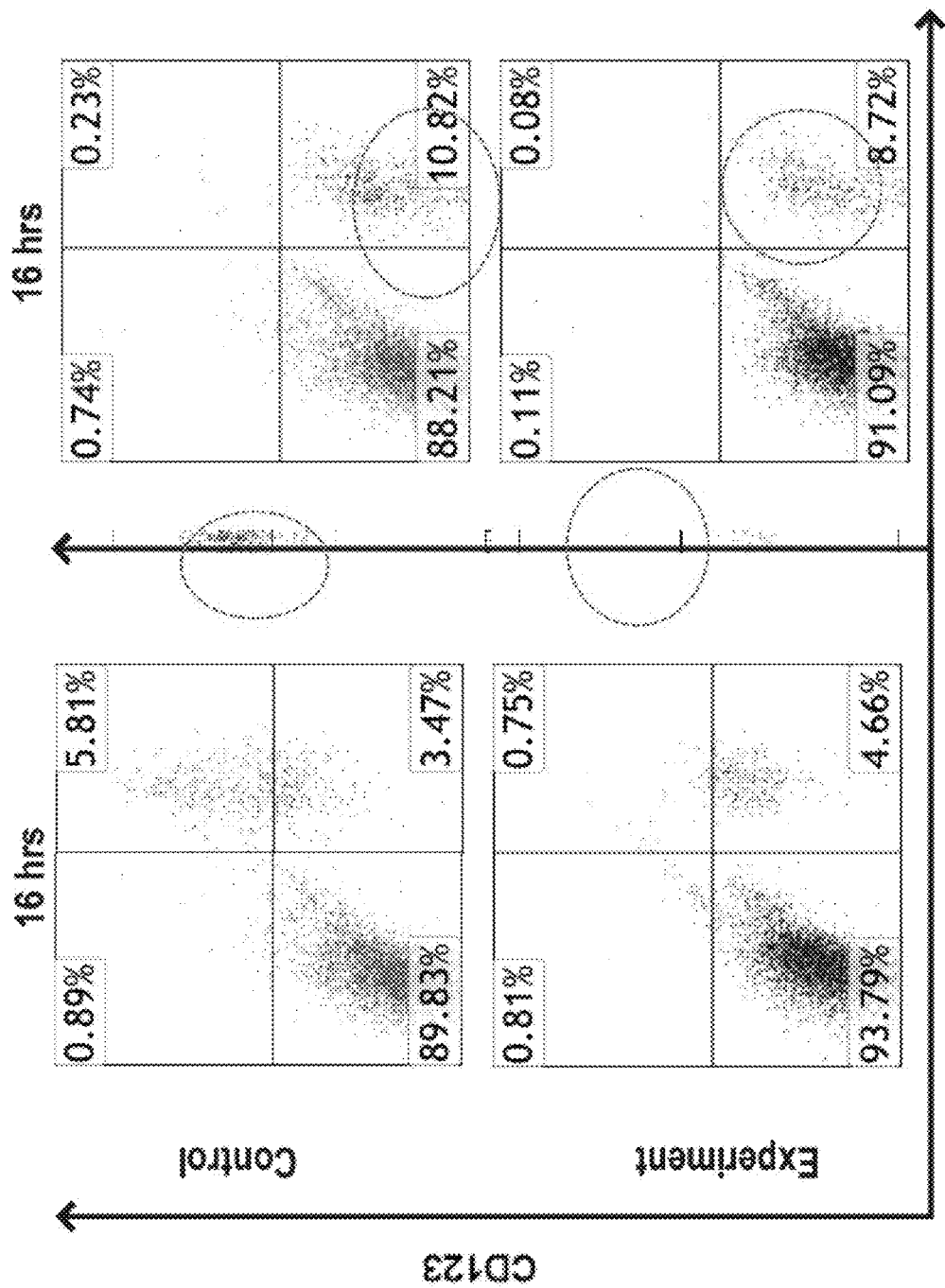
Figure 21C:
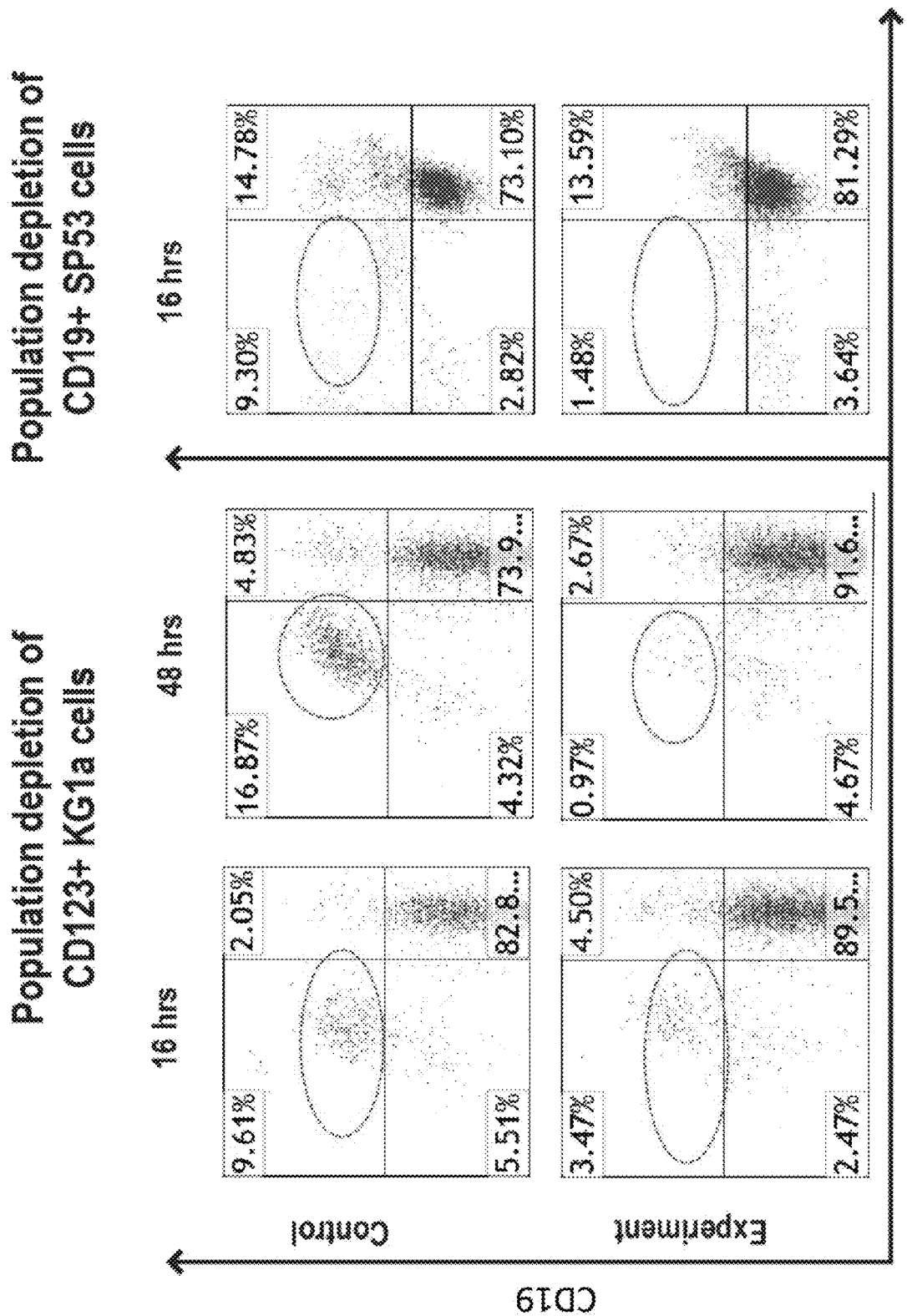
Figure 21D:
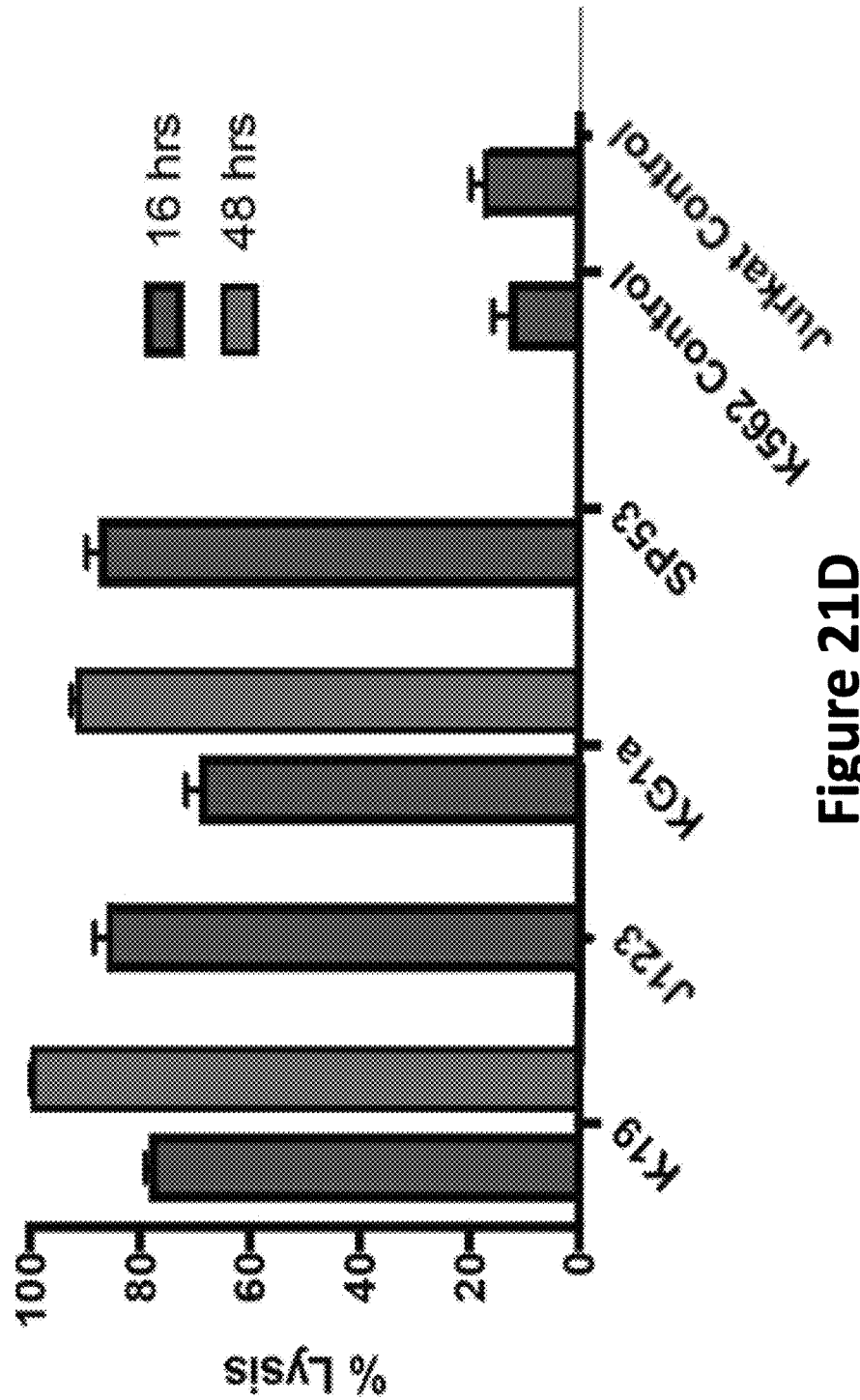

CD19b–CD123 cCAR-2G T-Cells Effectively Lyse CD19-Positive and CD123-Positive Leukemic Cell Lines To assess the cytotoxicity of CD19b–CD123 cCAR T-cells, we conducted co-culture assays at a 5:1 effector:target (E:T) ratio against leukemia/lymphoma cell lines with artificially expressing CD19 and CD123. K562 cells (a myeloid leukemia cell line) were used to express CD19 antigen by lentiviral infection (named K19), and wild type K562 cell line was used as a control. Jurkat cells were similarly used to express CD123 antigen (named J123), and wild-type Jurkat cells were used as a control. CD19b–CD123 cCAR T-cells lysis of target cells was quantified by flow cytometry. In 16 hour co-cultures, CD19b–CD123 cCAR T-cells lysed over 66% of K19 cells at 16 hours, and over 99% at 48 hours (FIG. 21A). Over 88% of J123 cells were lysed at 16 hours, reaching saturation (FIGS. 21B and 21D). Control K562 and control Jurkat cells were not significantly lysed, with less than 20% lysis. The finding that the CD19b–CD123 cCAR T-cells effectively ablate both artificially-induced singly-positive CD19 and CD123 cells supports the idea that each discrete unit of the compound CAR can independently target its antigen and eliminate a target expressing only one antigen or both antigens. Furthermore, the lack of cell lysis of control K562 and Jurkat cells demonstrates that CD19b–CD123 cCAR T-cells exhibit antigen-specific cytotoxicity.

We next assessed the ability of CD19b–CD123 cCAR T-cells to target leukemia/lymphoma cell lines with naturally occurring CD19/CD123 antigen expression: human mantle cell lymphoma SP53 (CD19$^+$ CD123$^−$) and human acute myeloid leukemia KG1a (CD19$^−$ CD123$^+$). In 16 hour co-cultures, the CD19b–CD123 cCAR exhibited virtually complete lysis of SP53 cells, with 86% depletion of target cells, reaching saturation (FIG. 21C). In KG1a, CD19b–CD123 cCAR lysed over 69% of CD123$^+$ target cells at 16 hours, and over 94% at 48 hours (FIGS. 21C and 21D). Overall, CD19b–CD123 cCAR T-cells specifically and effectively lysed target populations expressing either antigen target, displaying effective bulk cytotoxicity.

Figure 22A:
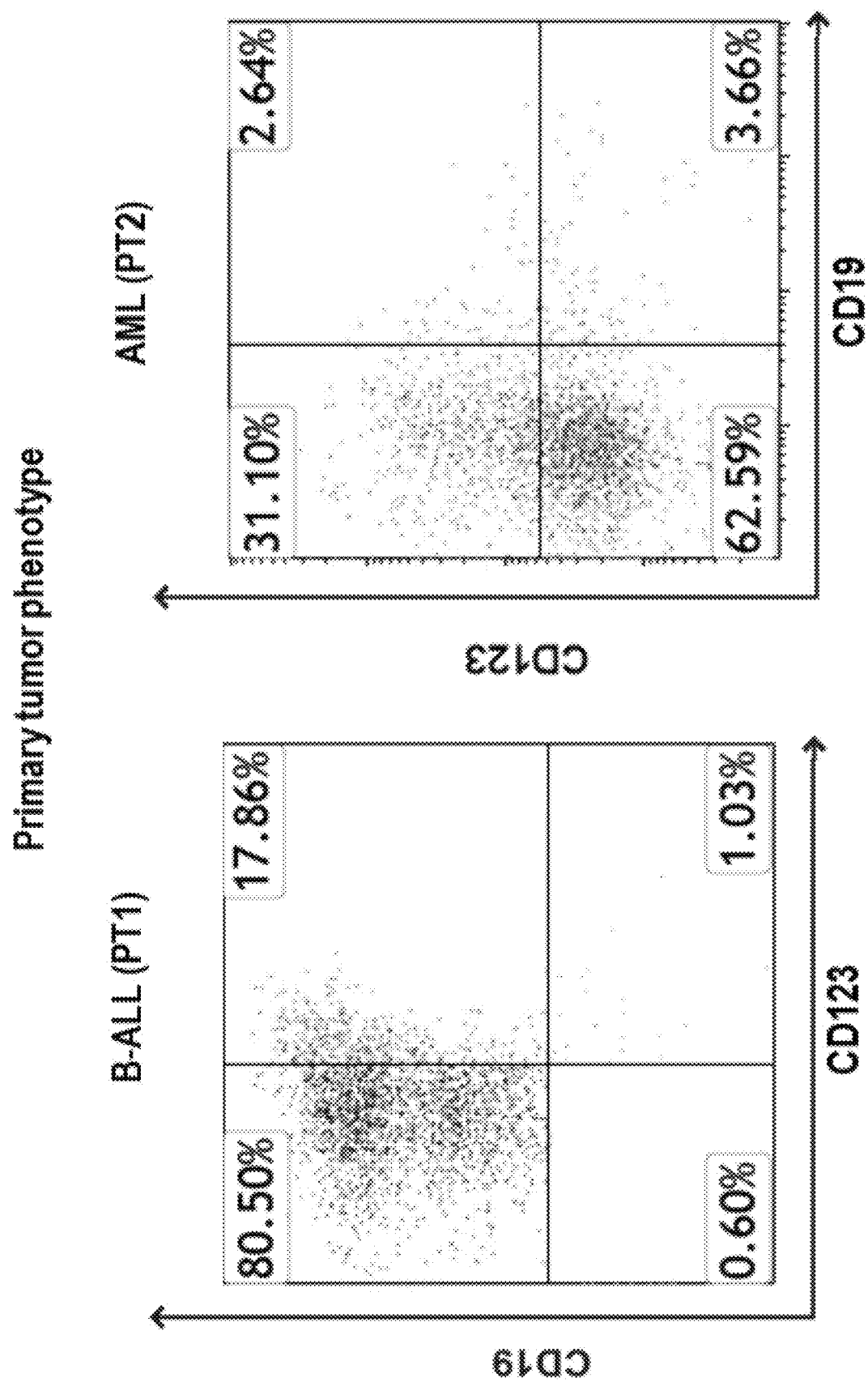
Figure 22B:
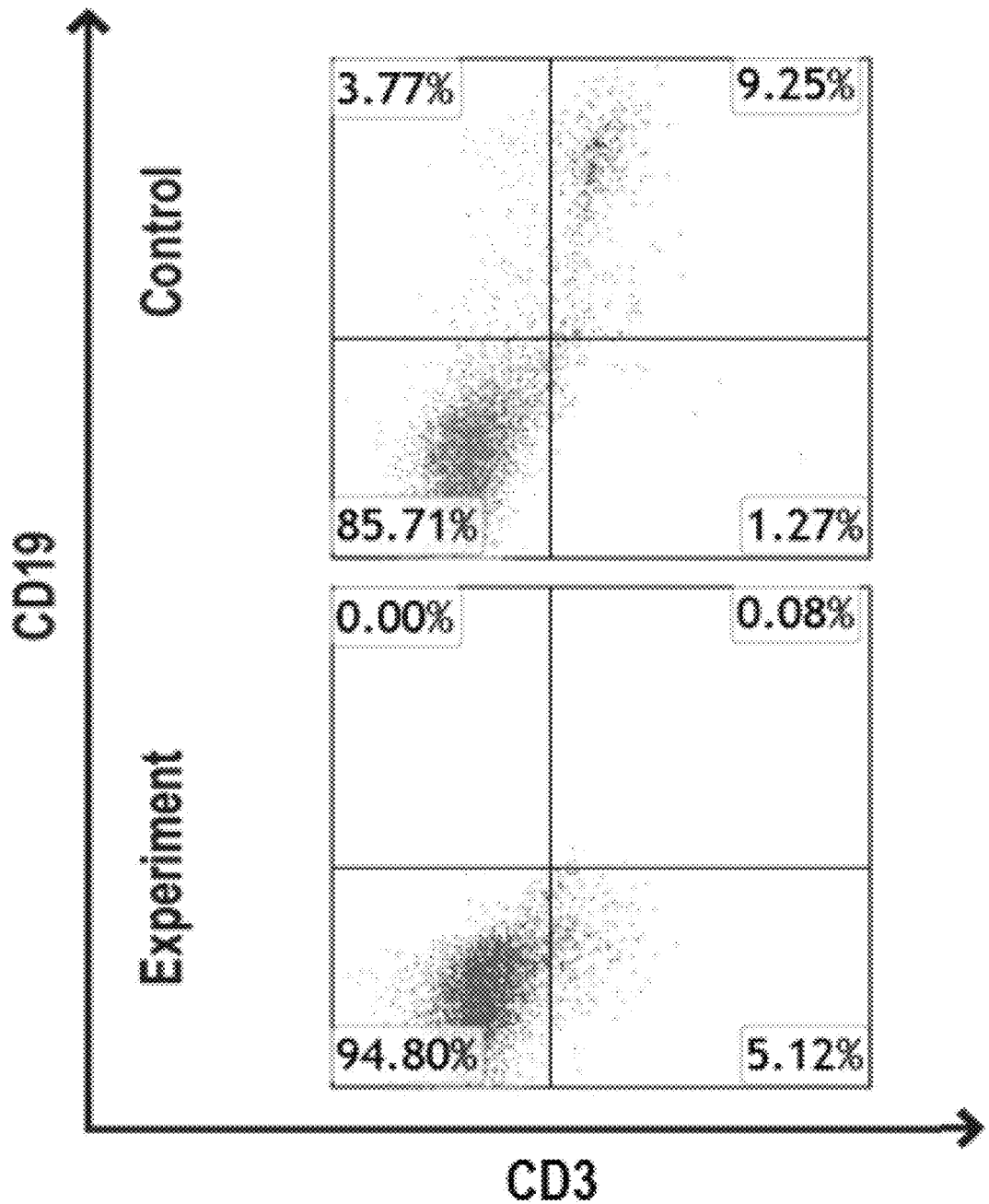
Figure 22C:
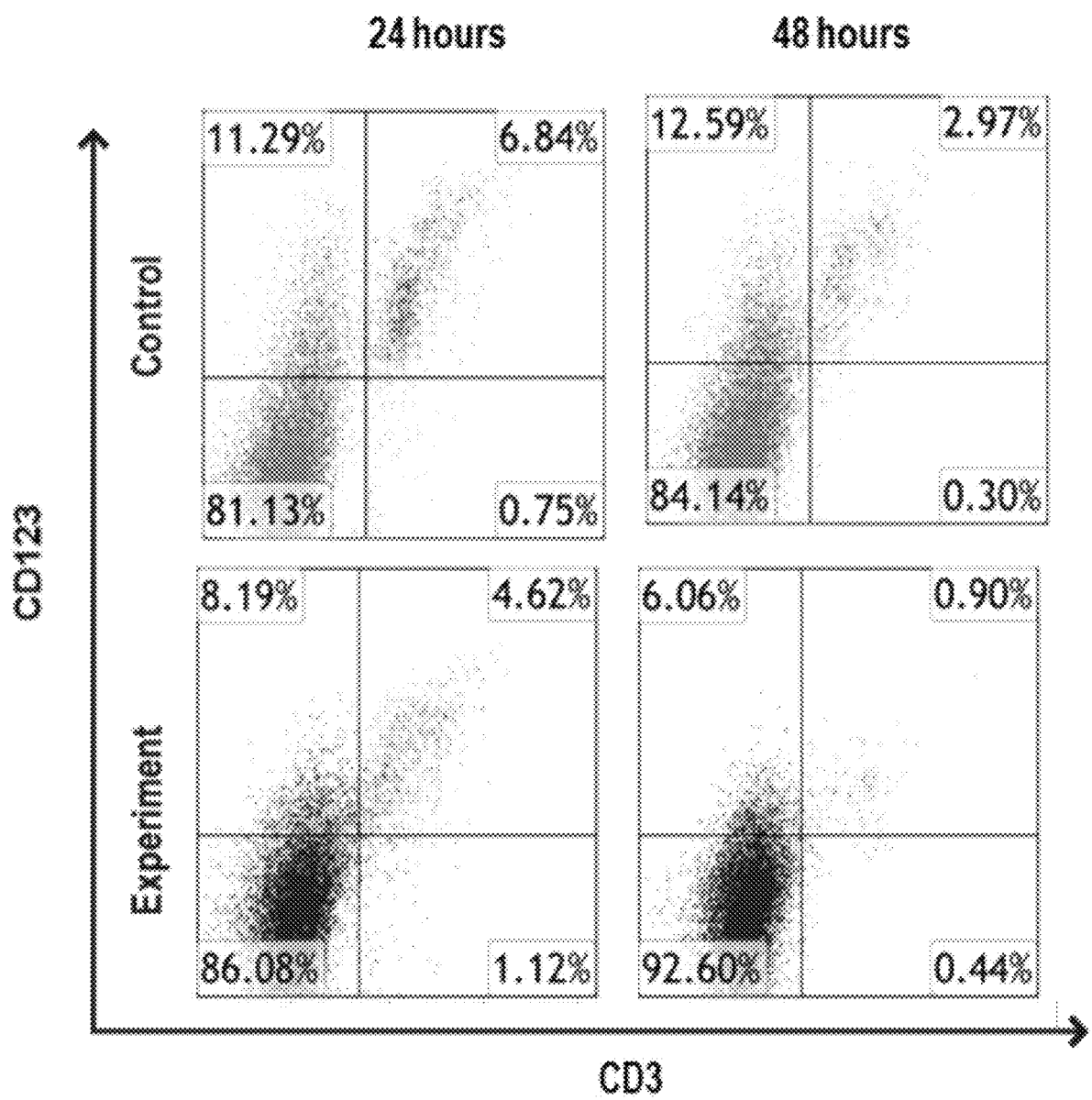
Figure 22D:
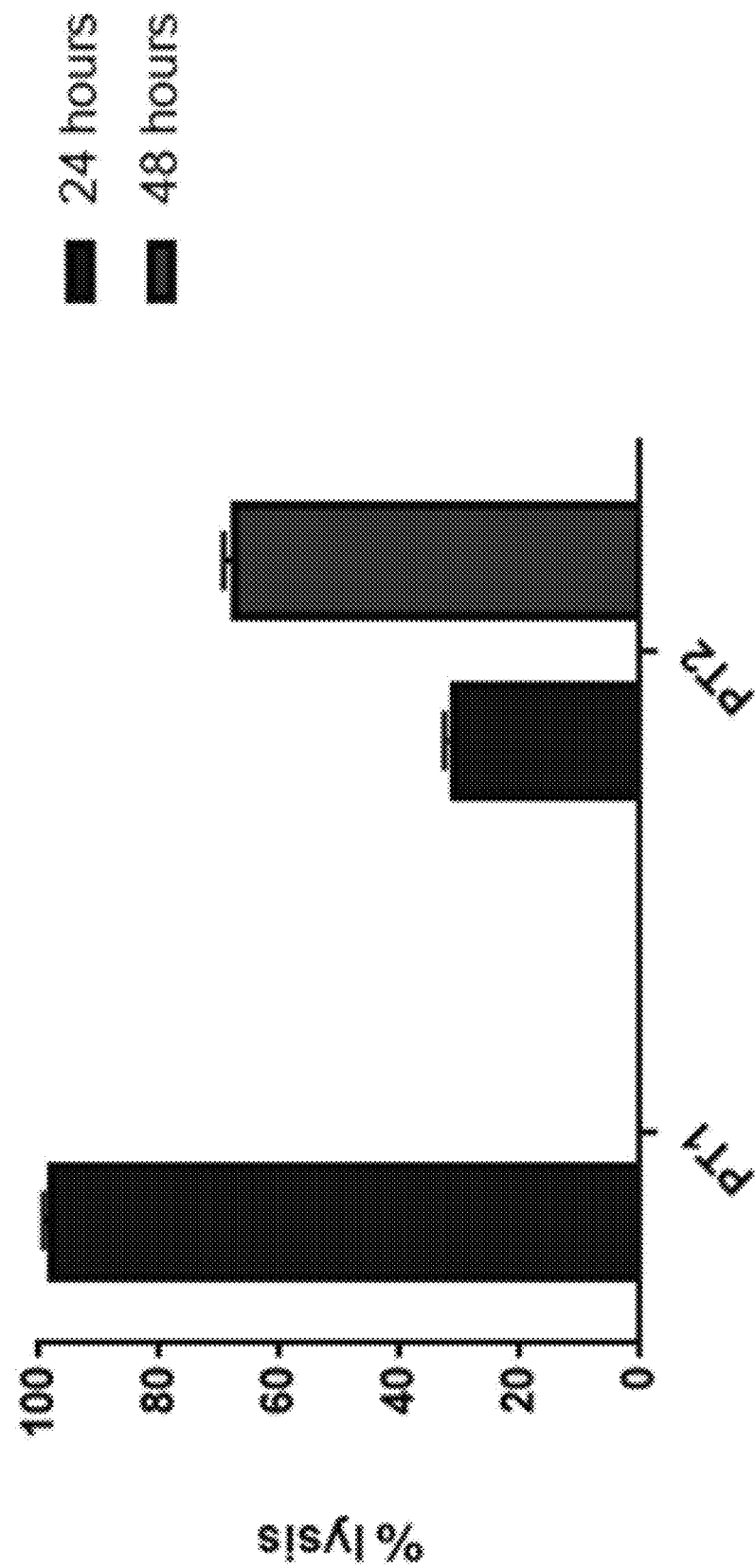

CD19b–CD123 cCAR-2G T-Cells Effectively Lyse Primary B-Cell Acute Lymphoblastic Leukemia (B-ALL) and Acute Myeloid Leukemia (AML) Tumor Cells We conducted co-cultures using CD19b–CD123 cCAR T-cells against primary tumor cells to evaluate their ability to kill diverse primary leukemia cell types. Patient samples were stained with CMTMR Cytotracker Dye to distinguish primary tumor cells from CAR T-cells. Co-cultures were performed with two samples, PT1:B-ALL and PT2:AML, and flow cytometry was performed to verify tumor-lysis. Flow cytometry analysis of the PT1 sample showed a near complete CD19+ phenotype, with a distinct CD19+ CD123+ population. The PT2 sample showed a mixed tumor phenotype with a partial CD123+ CD19− phenotype (FIG. 22A). CD19b–CD123 cCAR T-cells showed robust ablation of the PT1 primary B-ALL sample, with near complete lysis at an E:T ratio of 5:1 at 24 hours (FIGS. 22B and 22D). CD19b–CD123 cCAR T-cells also ablated the PT2 primary AML sample, with 31% lysis at 24 hours and 67% lysis at 48 hours (FIGS. 22C and 22D). In summary, CD19b–CD123 cCAR T cells exhibited robust anti-tumor activity against both leukemia cell lines and primary tumor cells expressing different combinations of CD19 and CD123 (FIG. 22D).

CD19b–CD123 cCAR-3G T-Cells Exhibit Profound Anti-Tumor Activity in Two Xenograft Mouse Models of AML and B-ALL Using MOLM-13 and REH Cells.

Figure 23A:
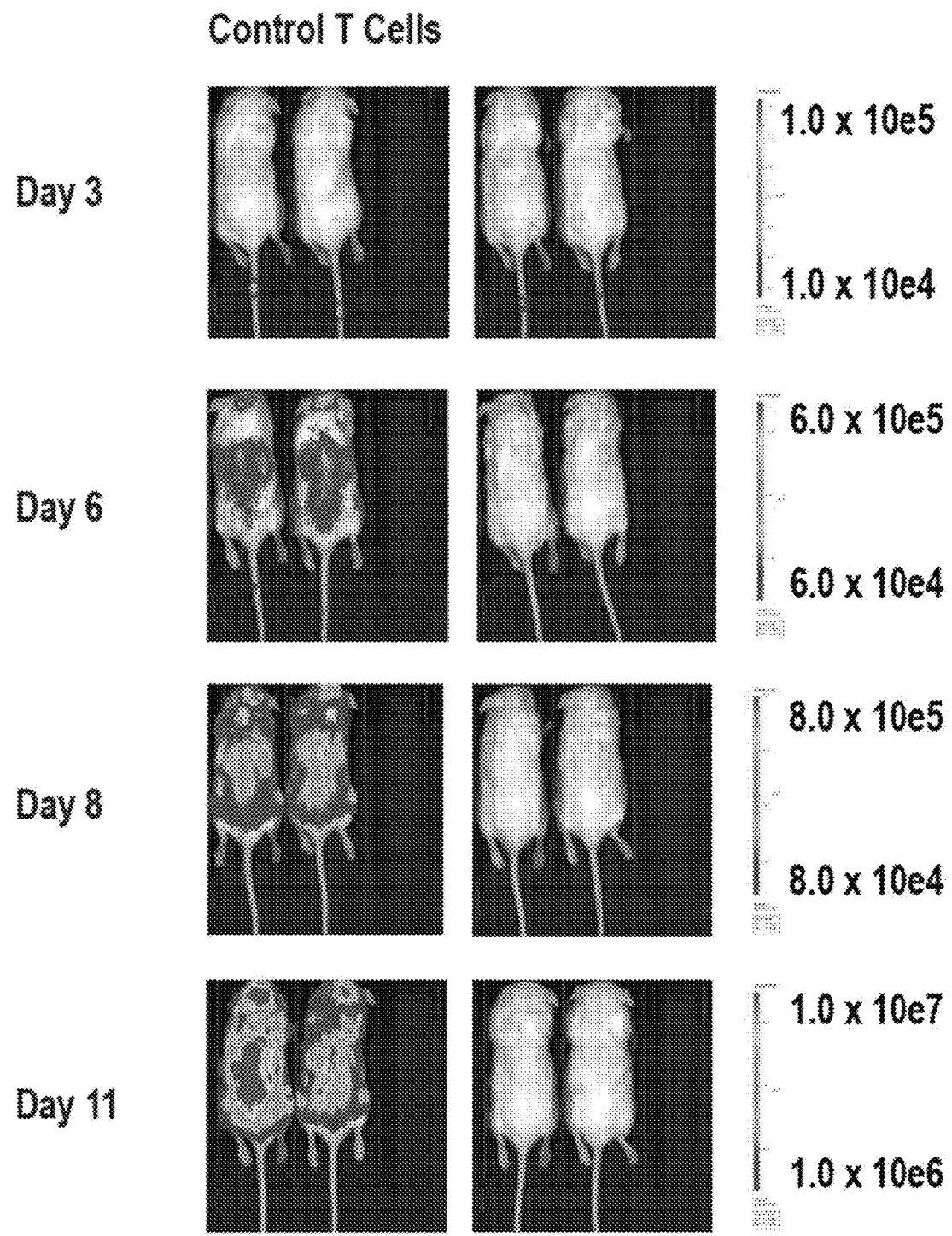
Figure 23B:
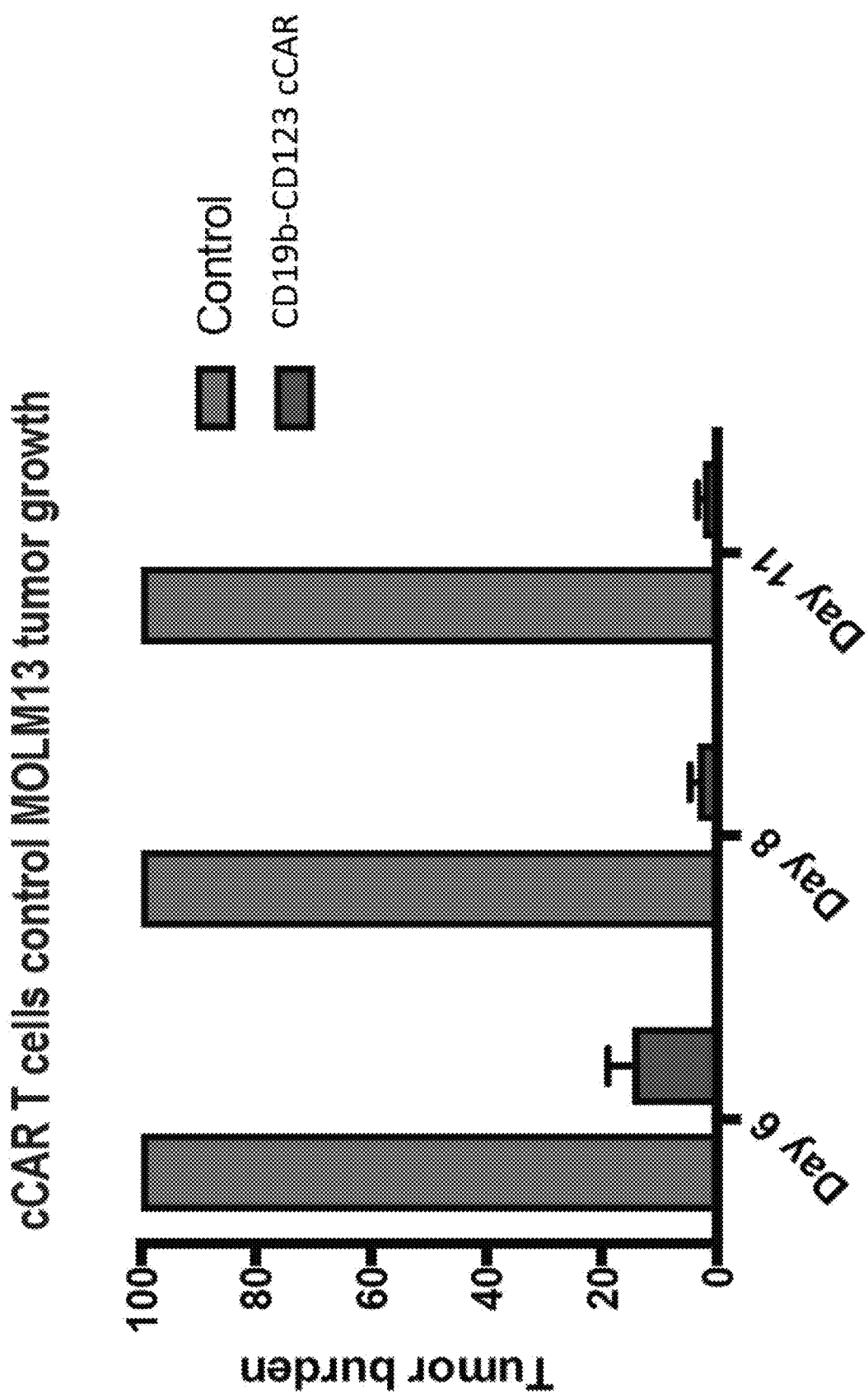
Figure 23C:
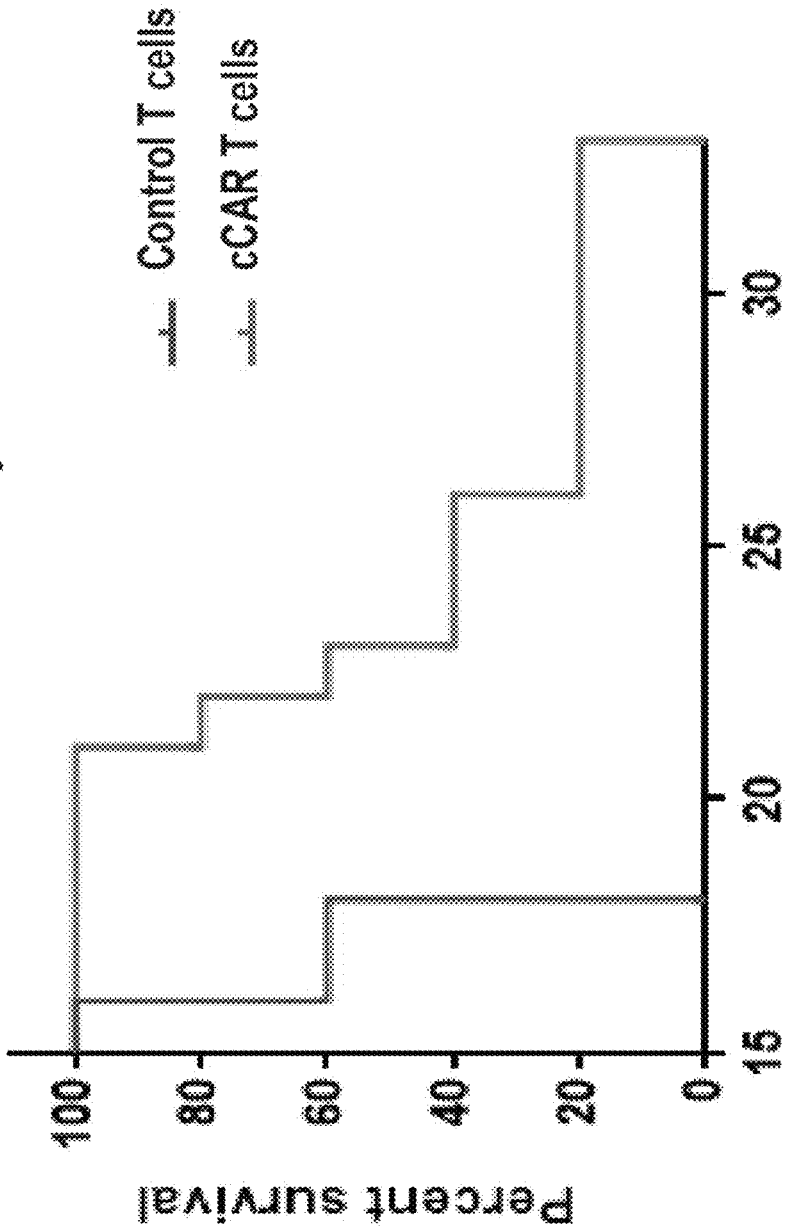

In order to evaluate the in vivo anti-tumor activity of CD19b–CD123 cCAR T-cells, we developed two models, one with luciferase-expressing MOLM13 cells (CD123+ CD19−), and one with luciferase-expressing REH cells (CD19+ CD123−) to induce measurable tumor formation. Mice were given a single dose of CD19b–CD123 cCAR T-cells or control GFP cells, and tumor burden was measured on days 3, 6, 8, and 11 (FIG. 23A). In the MOLM13 model, there was a significant difference (P<0.01) between the cCAR treated and control groups by day 6, with less light intensity and thus less tumor burden in the CD19b–CD123 cCAR T-cell injected group compared to control (FIG. 23B). Mice injected with CD19b–CD123 CAR T-cells had 99% less tumor burden than control mice by day 11. Next, we compared mouse survival across the two groups. Following the IVIS imaging experiments previously described, mice were observed every day for symptoms of severe illness and were sacrificed once movement was greatly impaired. All control mice died by day 18, while the CD19b–CD123 CAR T treated mice survived longer than control mice by up to 15 days (p=0.0031) (FIG. 23C).

Figure 23D:
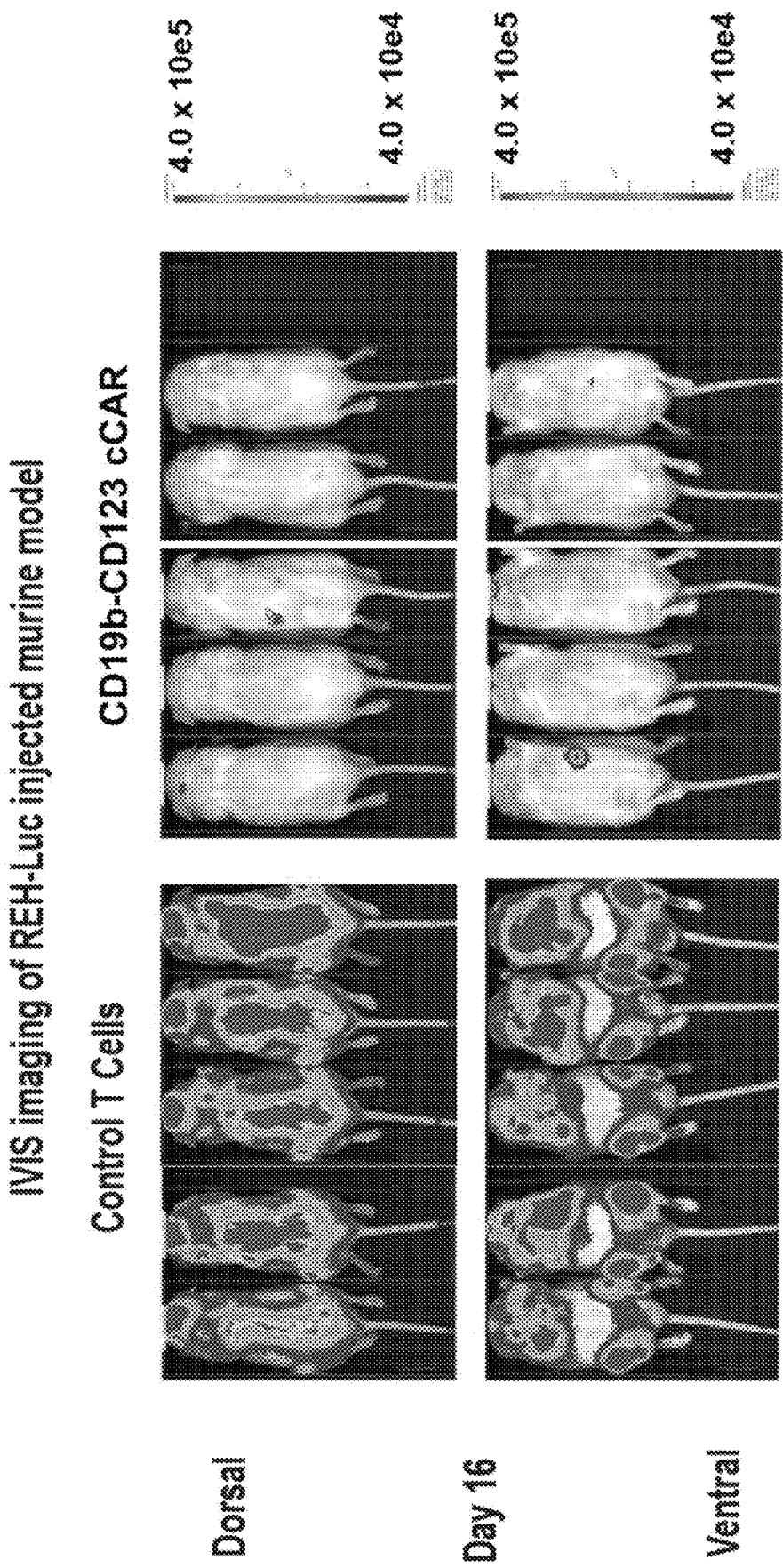
Figure 23E:
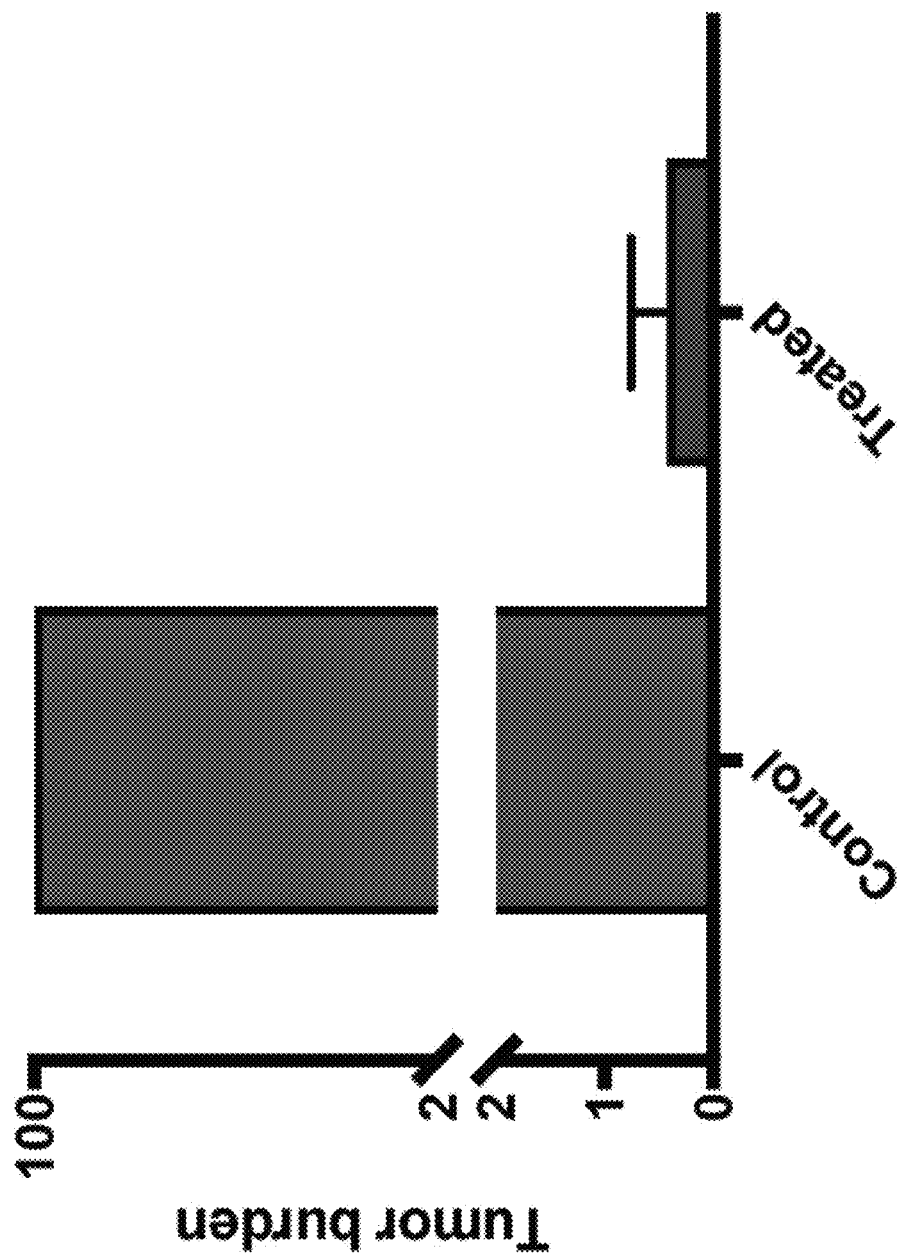
Figure 23F:
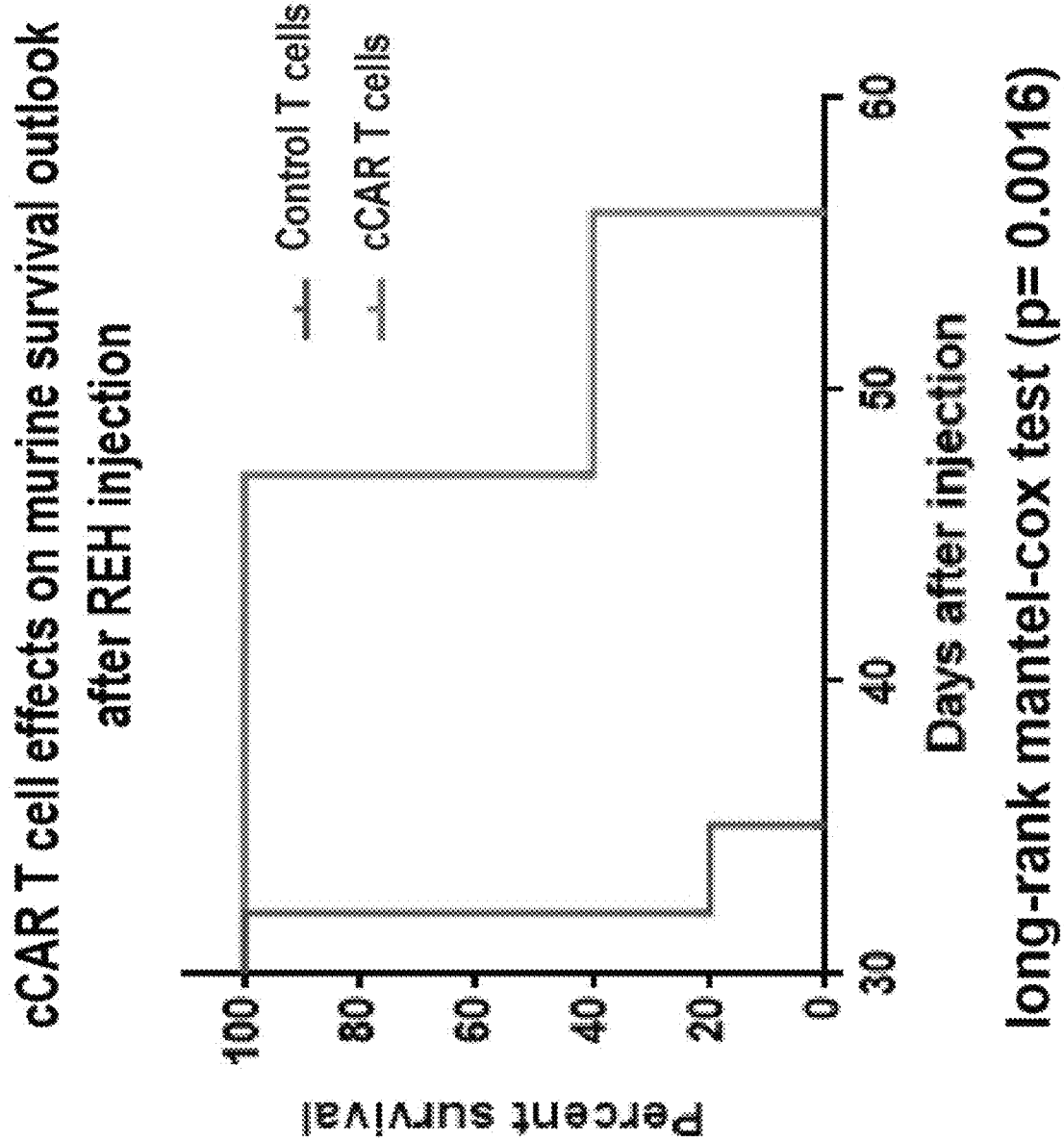

A similar result was seen in the REH mouse model (FIG. 23D). REH leukemic mice injected with CD19b–CD123 cCAR T cells had 99% less tumor burden than control mice on day 16 (FIG. 23E). When comparing mouse survival across cCAR and control treated groups, CD19b–CD123 cCAR T injected mice survived much longer than control mice (FIG. 23F)(p=0.0031). In summary, these in vivo data indicate that CD19b–CD123 cCAR T-cells significantly reduce tumor burden and prolong survival in MOLM13-injected and REH-injected NSG mice when compared to control T-cells.

Screening and Evaluation of Several Versions of cCARs Targeting BCMA+ and/or CS1+ Leukemic Cells, Particularly Multiple Myeloma Cells Using Co-Culture Killing Assays.

1. Generations of Different Versions of BCMA (CD269)-CS1 cCARs.

As described above, creation of compound CARs bearing different CAR units can be quite challenging. We selected various CAR body elements to express multiple units of CARs in a single vector using a strong promoter and P2A self-cleaving site. The hinge region in the CAR was chosen so that interaction of the hinge region between each CAR unit could be avoided. Lentivirus transfected cytotoxic effector cells, namely T cells, were engineered to express an anti-BCMA (CD269) single-chain variable fragment (scFv1) region fused to an anti-CS1 fragment (scFv2) by a self-cleaving P2A peptide. These scFv domains are linked by CD8-derived hinge (H) and transmembrane (TM) regions to 4-1BB and CD28 co-activation domains and a CD3 (CD3) signaling domain (FIG. 30). A strong spleen focus forming virus promoter (SFFV) and a CD8 leader sequence were used for efficient expression of the compound CAR molecule on the T-cell surface. Finally, the generated constructs were screened and evaluated for their expression and functions. scFv1 represents different scFv versions (A7D or C11D) against BCMA antigen. scFv 2 represents different scFv versions (hu63 or mu34 or mu90) against CS1 antigen.

2. Varied Level of CAR Expression in T Cells Transduced with Various Versions of BCMA–CS1 cCAR Lentiviruses.

Peripheral blood mononuclear buffy coat cells were activated for three days and transduced with the lentiviral vector for 6 different sequence variations cCARs comprised of CD269 (A7D or C11D) combined with CS1 (hu63, mu34, or mu90) CAR, or control vector. Expression of CAR on the T-cell surface was demonstrated three days after transduction by staining transduced T cells with goat anti-mouse Fab antibody and mouse anti-human CD3. FIG. 30A shows surface expression for each of the CD269-CS1 CARs: for A7D-mu34, 11.2%; A7D-mu90, 23.1%; A7D-hu63, 28.5%; C11D-mu34, 28.0%; C11Dmu90 13.6%; and C11Dhu63, 42%. This demonstrates the need to find a pairing of CAR units that result in the highest level of CAR expression. A high efficiency lentiviral packaging cell line is critical for generation of a high titer for these constructs (FIG. 30B). We used lenti-X 293 T cell line as a packaging system to generate high viral titers for compound CAR constructs. Lenti-X 293T packaging cell line clearly outperformed the other cell lines and produced over 2 to 6-times as many viruses as 293 FT cells.

The transduction efficiency (percentage of CAR T cells) for cCARs is often lower than for a single-unit CAR. There are several ways to improve efficiency, at both the transfection and transduction steps. To improve viral titer for making cCARs, it is preferred to use LentiX™ 293 T (Clontech/Takara) packaging cell line, which is selected for high titer lentivirus production, instead of the commonly used HEK-293FT. It is also preferable to increase the amount of plasmid DNA (containing the cCAR construct) 1.5- to 2.0-fold when transfecting packaging cells, to increase transfection efficiency. The amount of viral packaging plasmids and transfection reagent remains the same during the forming of complexes. Transduction efficiency can be further enhanced by lowering the ratio of T cells to viral vector during the transduction step, to $0.3 \times 10^6$ cells per mL, and increasing the volume of lentiviral supernatant or lentiviruses.

3. Testing CAR Expression in T Cells Transduced with Various Anti-BCMA Lentiviral Vectors.

Based on the above studies, CD269-A7D (also called A7D) and CS1-hu63 (also called hu63) were chose as good candidates for generation of enhanced CARs or compound CAR (cCAR). We also generated a cCAR (CD269-A7D-C11D-2G) targeting two epitopes on the same antigen, BCMA. In this cCAR, each unit of CARs bears different scFv targeting different epitopes of BCMA. Enhanced CARs are CD269-A7D-IL15/IL15sushi and CD269-A7D-41BBL-2G targeting BCMA antigen. Compound CARs are CD269-A7D-CD19b-2G targeting BCMA and CD19 antigens, and CD269-A7D-CS1-hu63 or CD269-C11D-CS1-hu63-BB targeting BCMA and CS1 antigens.

Peripheral blood mononuclear buffy coat cells were activated for three days and transduced with the anti-BCMA lentiviral vectors for single CARs (CD269-A7D-2G, CD269-A7D-IL15/IL15sushi, CD269-A7D-41BBL-2G) and cCARs (CD269-A7D-C11D-2G, CD269-A7D-CD19b-2G, CD269-A7D-CS1-hu63, CD269-C11D-CS1-hu63-BB) or control vector (FIG. 30B). Expression of CAR on the T-cell surface was demonstrated three days after transduction by staining transduced T cells with goat anti-mouse Fab antibody and mouse anti-human CD3. FIG. 30B shows surface expression for each of the lentiviral CARs: for CD269-A7D-2G, 48.4%; CD269-A7D-IL15/IL15sushi, 32.2%; CD269-A7D-41BBL-2G, 36%; CD269-A7D-C11D-2G, 27.4%; CD269-A7D-CD19b-2G, 30.6%; CD269-A7D-CS1-hu63, 28.5%; and CD269-C11D-CS1-hu63-BB, 42.0%.

4. CD269-A7D-CD19b cCAR T Cells Efficiently Lyse Both BCMA and/or CD19-Expressing Tumor Cell Lines The CD269-A7D-CD19b cCAR T cells were tested for their ability to lyse individual target cell lines in in vitro co-culture assays (FIGS. 30C and 30D). K562 cells were modified to synthetically express either BCMA (CD269) (called K-BCMA) or CD19 (called K-19) on the cell surface. After 18-hour co-incubation, cells were labeled with anti-human CD3 and either anti-human CD269 or CD19, and analyzed by flow cytometry (FIG. 30C and CD30E). CD269-A7D-CD19b cCAR T cells were able to lyse 31% of the target K-BCMA cells at the 2:1 E:T ratio, and 65% at 5:1 ratio. CD269-A7D-CD19b cCAR T cells were also able to lyse 60% of the target K-CD19 cells at the 2:1 E:T ratio, and nearly all at 5:1 ratio (FIG. 30D and CD30E). These results confirm that each CAR unit—CD269 and CD19b CAR—effectively lyses its specific target cells.

5. CD269-A7D-41BBL, CD269-A7D-CS1-hu63, and CD269-A7D-C11D cCAR T Cells Efficiently Lyse MM1S Tumor Cell Line Various versions of BCMA-CS1 cCAR T cells generated above were tested for their ability to lyse specific target cell lines in in vitro co-culture assays. The human multiple myeloma cell line, MM1S, was co-cultured with CD269-A7D-41BBL CAR, CD269-A7D-CS1-hu63 cCAR, CD269-A7D-C11D cCAR T cells, or control T cells, at 2:1 and 5:1 E:T ratios (FIG. 30F). After 18-hour co-incubation, cells were labeled with CMTMR (Cell Tracker) and anti-human CD269 and analyzed by flow cytometry. CD269-A7D-41BBL CAR T cells were able to lyse 74% of the target MM1S cells at the 2:1 E:T ratio, and 90% at 5:1 ratio, while CD269-A7D-CS1-hu63 cCAR T cells lysed 59% and 90%, and CD269-A7D-C11D CART cells lysed 62% and 86% of the MM1S cells at 2:1 and 5:1 ratios, respectively (FIG. 30F). These compound CARs did not appeared to show any evidence of the CAR to CAR interaction. In vivo anti-tumor activities, cell killing is performed in a xenogeneic mouse model and targeted cells expressing BCMA or CS1 or both are eliminated or suppressed by cCAR T or NK cells using methods described in PCT/US2016/019953 and PCT/US2016/039306

6. CD269-A7D-41BBL, CD269-A7D-CS1-hu63, and CD269-A7D-C11D CAR T Cells Efficiently Lyse the Cell Line K562 Synthetically Expressing BCMA or CS1

Various versions of BCMA-CS1 cCAR T cells generated above were tested for their ability to lyse specific target cell lines in in vitro co-culture assays. K562 cells were modified to synthetically express either BCMA (CD269) or CS1 on the cell surface, and were subsequently co-cultured with CD269-A7D-41BBL, CD269-A7D-CS1-hu63, CD269-A7D-C11D cCAR T cells, or control T cells, at 2:1 and 5:1 E:T ratios. After 18 hour co-incubation, cells were labeled with anti-human CD3 and anti-human CD269 (or CS1) and analyzed by flow cytometry. CD269-A7D-41BBL CART cells were able to lyse 56% of the target K-BCMA cells at the 2:1 E:T ratio, and completely eliminated all target cells at 5:1 ratio, while CD269-A7D-CS1-hu63 cCAR T cells lysed 38% and 79%, and CD269-A7D-C11D CART cells lysed 16% and 74% of the K-BCMA cells at 2:1 and 5:1 ratios, respectively (FIG. 30G). Only CD269-A7D-CS1-hu63, CD269-A7D-C11D cCAR T cells were tested in co-culture against the K-CS1 cells (FIG. 30H. CD269-A7D-CS1-hu63 cCAR T cells lysed 18% and 54%, of the K-562 cells at 2:1 and 5:1 ratios, respectively, while the CD269-A7D-C11D cCAR T cells, a compound CARs targeting two different epitopes on the BCMA antigen, showed no ability to lyse the K-CS1 cells at either ratio, which was expected, due to the absence of a CS1 CAR unit. (FIG. 30H). These results demonstrate the ability of each CAR unit to specifically lyse its target population.

Examples for Targeting CLL1+ and/or CD33+ Leukemic Cells by CLL1-CD33b cCAR (a Version of CLL1-CD33)

Transduced T Cells Efficiently Express the CLL1-CD33b cCAR (CLL1-CD33b CAR)

Peripheral blood mononuclear buffy coat cells were activated for two or three days and transduced with either CLL1-CD33b cCAR or control vector. Expression of CLL1-CD33b cCAR on the T-cell surface was demonstrated three days after transduction by staining transduced T cells with goat anti-mouse Fab antibody and mouse anti-human CD3. FIG. 31 shows that 29.7% of cells transduced with the CLL1-CD33b cCAR viruses were positive for both F(ab')2 and CD3 as determined by flow cytometry.

CLL1-CD33b cCAR T Cells Specifically Target Both CLL1 (CLL-1) and CD33-Expressing Tumor Cell Lines T cell coculture killing assays were performed to determine the ability of CLL1-CD33b cCAR T cells to effectively and specifically lyse CLL1 (CLL-1) and CD33-expressing cell lines: the acute myeloid leukemia cell line HL60, which expresses both antigens on the cell surface naturally; and Jurkat cells which were modified to synthetically express either CLL1 (called Jurkat-CLL-1xp) or CD33 (called Jurkate-CD33xp). In addition, CLL1-CD33b cCAR T cells were co-cultured against the REH and CCRF-CEM cell lines, which are negative for CLL1 and CD33 (FIGS. 32A and 32B). All target cells were pre-labeled with CFSE membrane dye to distinguish them from T cells. After 18 hour co-incubation, cells were labeled with anti-human CD3 and analyzed by flow cytometry. At the low 2:1 effector:target ratio, CLL1-CD33b cCAR T cells were able to effectively lyse HL60 cells (89%), Jurkat-CLL-lxp cells (84%) and Jurkat—CD33xp cells (96%) (FIGS. 32C, 32D and 32E); at the 5:1 E:T ratio, nearly all target cells were depleted (FIG. 2a-d). However, the REH (8%) and CCRF-CEM cells (14%), both off-target, showed very little cell lysis (FIGS. 32A and 32B). This demonstrates remarkable potency and specificity of the CLL1-CD33b cCAR T lysis. The results are summarized in the bar graph (FIG. 32F).

CLL1-CD33b Compound CAR T Cells are Able to Demonstrate Potent and Directed Cytotoxicity In Vitro.

We conducted co-culture assays using target AML cell lines HL60 and U937 expressing high amounts of both CLL-1 and CD33. We found that the CLL-1 CART cell was able to potently ablate both of these cell types at high efficiency >90% (FIGS. 32G and 32H). Furthermore, the compound CAR exhibited minimal targeting of negative control cell line CCRF-CEM with basal levels of activity (FIG. 32I).

In addition, the CLL1-CD33b cCAR demonstrated potent dose dependent cytotoxicity in an escalating dosage scheme, with ~50% activity even at the lowest dose threshold of 0.25:1 (effector:target) cell ratio (FIG. 32J).

Compared to single CAR T Options, the CLL1-CD33b cCAR T Cells Demonstrate Superior Anti-Tumor Activity Jurkat cells expressing either CLL-1 or CD33 were combined in a 1:1 ratio and incubated with 100,000 effector cells for a final effective E:T ratio of 1:2. The results show that the compound CAR exhibited highly specific and potent cytotoxicity against either CLL-1 or CD33 expressing sets of Jurkat cells (>85%) while demonstrating increased cytotoxicity over single CAR options for their respective antigens (FIG. 32K and 32L).

CD19b-IL-21 CAR (a Version of CD19-IL-21 CAR)

EXAMPLE

An engineered CD19b-IL-21 (CD19b-IL21) CAR cell was prepared in accordance with the present disclosure (FIG. 33A). CD19b CAR is equipped with secreting IL-2 to lyse leukemia/lymphoma expressing CD19 antigen.

Peripheral blood mononuclear buffy coat cells were activated for two or three days and transduced with either CD19b-IL-21 or control vector. Expression of CD19b-IL-21 on the T-cell surface was demonstrated three days after transduction by staining transduced T cells with goat anti-mouse Fab antibody and mouse anti-human CD3. FIG. 33B shows that 63.9% of cells transduced with the CD19b-IL-21 CAR viruses were positive for both F(ab')2 and CD3 as determined by flow cytometry.

Cell killing assay is performed and targeted cells expressing CD19 are lysed by IL-19-IL-21 CAR.

In vivo anti-tumor activities, cell killing is performed in a xenogeneic mouse model and targeted cells expressing CD19 are eliminated or suppressed by CD19b-IL-21 CAR T or NK cells using methods described in PCT/US2016/019953 and PCT/US2016/039306

Similar assays can be used for BCMA-IL-18 CAR (FIG. 35)

In one embodiment, the engineered cell includes a CD19 chimeric antigen receptor polypeptide and IL-21 (SEQ ID NO. 16), and corresponding nucleotides (SEQ ID NO. 17).

In one embodiment, the engineered cell includes a CD19 chimeric antigen receptor polypeptide and IL-21 anchor (SEQ ID NO. 1), and corresponding nucleotides (SEQ ID NO. 2).

In one embodiment, the engineered cell includes a BCMA chimeric antigen receptor polypeptide and IL-18 (SEQ ID NO. 11), and corresponding nucleotides (SEQ ID NO. 12).

In one embodiment, the engineered cell includes a BCMA chimeric antigen receptor polypeptide and IL-18 anchor (SEQ ID NO. 13), and corresponding nucleotides (SEQ ID NO. 14).

CD19b-IL-21 Anchor CAR (a Version of CD19-IL-21 Anchor)

EXAMPLE

An engineered CD19b-IL-21 anchor (CD19b-IL21) CAR cell was prepared in accordance with the present disclosure (FIG. 34). CD19b-IL-21 anchor CAR is to lyse leukemia/lymphoma expressing CD19 antigen.

Cell killing assay is performed and targeted cells expressing CD19 are lysed by IL-19-IL-21 anchor CAR.

In vivo anti-tumor activities, cell killing is performed in a xenogeneic mouse model and targeted cells expressing CD19 are eliminated or suppressed by CD19b-IL-21 anchor CAR T or NK cells using methods described in PCT/US2016/019953 and PCT/US2016/039306

Similar assays can be used for BCMA-IL-18 anchor CAR (FIG. 36)

Examples for targeting multiple myeloma by BCMA-CD38 cCAR

EXAMPLE

An engineered BCMA-CD38 cCAR cell was prepared in accordance with the present disclosure (FIG. 37). Lentivirus transfected cytotoxic effector T or NK -cells were engineered to express two complete units of CAR linked by a self-cleaving P2A peptide. The resulting compound CAR) is capable of targeting BCMA+ and /or CD38+ multiple myeloma cells or abnormal plasma cells (FIG. 37). A leader, a scFv, a hinge domain (H), a transmembrane domain (TM), a co-stimulatory domain (CD28 or 4-1BB) and the intracellular signaling domain CD3 zeta (CD3) are included in each CAR unit. A strong spleen focus forming virus promoter (SFFV) and a CD8 leader sequence were used for efficient expression of the BCMA-CD38 cCAR molecule on the T or NK-cell surface.

BCMA-CD38 cCAR is to lyse multiple myeloma cells or abnormal plasma cells expressing BCMA and/or CD38 antigen.

Cell killing assay is performed and targeted cells expressing BCMA and/or CD38 antigen are lysed by BCMA-CD38 cCAR.

In vivo anti-tumor activities, cell killing is performed in a xenogeneic mouse model and targeted cells expressing BCMA and/or CD38 antigen are eliminated or suppressed by BCMA-CD38 cCAR T or NK cells using methods described in PCT/US2016/019953 and PCT/US2016/039306.

In one embodiment, the CD38 antigen recognition domain includes SEQ ID NO. 15.

In one embodiment, the engineered cell includes a first chimeric antigen receptor polypeptide having a BCMA antigen recognition domain and second chimeric antigen receptor polypeptide having a CD38 recognition domain. In one embodiment, this engineered cell includes a polypeptide of SEQ ID NO. 5, 7, 9 and corresponding polynucleotide of SEQ ID NO. 6, 8, 10.

CD38 Based cCAR

Schematic representation of CD38 based cCAR constructs are shown in FIG. 38.

CD269-A7D-CD38 CAR

EXAMPLE

For generation of a high level of cCAR expression, the Lenti-X 293T cell line was used as packaging cells to generate lentiviruses. Activated human peripheral blood T cells were transduced with the lentiviral vector from BCMA-CD38 CARs comprised of 3 different antigen recognition sequences for CD38. FIG. 39A shows the transduction efficiency between activated T cells transduced with either control lentiviruses, CD269-A7D-CD38a, CD269-A7D-CD38b, or CD269-A7D-CD38c CAR lentiviruses, as determined by labeling with goat anti-mouse F(Ab') 2 antibody. Activated T cells transduced with the CAR viruses resulted in 28.6%, 21.5% and 17.6% F(Ab')2 positive cells for CD269-A7D-CD38a, CD269-A7D-CD38b, or CD269-A7D-CD38c, respectively. These CAR T cells were used in the following in vitro killing assay.

Analysis of Tumor Cell Line Phenotypes

Flow cytometry was used to analyze the phenotypes of six different cell lines (FIG. 39B). Analysis showed that CD38 is expressed in myeloma cells, RPMI 8226, and MM1S. B-ALL cell line REH also expresses CD38. K562-BCMAxp cells is in AML cells (K562) and used to express BCMA using a lentiviral vector expressing BCMA. K562-BCMAxp cells show all cells expressing BCMA.

Transduction of wt U937, REH Luciferase Cells to Express BCMA-xp

REH and U937 wild-type cell lines expressing luciferase were transduced with BCMA-xp lentiviral vector expressing BCMA. Flow cytometry analysis confirmed that U937-BCMAxp and REH cell line expressed BCMA surface antigen while the wild type cell line, U937 or REH did not (FIG. 39C).

CD269-A7D-CD38-2G CAR T Cells Efficiently Lyse CD38-Expressing REH Tumor Cells or CD269 (BCMA)-Expressing K562 Cells in an In Vitro Assay The CD269-A7D-CD38a or CD269-A7D-CD38b CAR T cells were assayed for their comparative ability to lyse REH (B-ALL) and K562-BCMA cells. Target cells were pre-stained with CMTMR to more easily distinguish them from the T cells in co-culture. Co-cultures were set up at 2:1 and 5:1 effector cell:target cell ratios, for 24 hours. Assays with REH cells were stained with mouse anti-human CD3 and CD38, and analyzed by flow cytometry (FIG. 39D). Assays with K562-BCMA cells were stained with mouse anti-human CD3 and CD269, and analyzed by flow cytometry (FIG. 39F). Co-culture result showed that CD269-A7D-CD38 CAR T cells specifically lyse the CD38+ REH tumor cell line expressing CD38 surface antigen but not CD269 in addition to the K562 tumor cell line synthetically expressing CD269 in co-culture. Results after a 48-hour co-culture for REH cells (FIG. 39E) and for K562-BCMA cells (FIG. 39G) are also shown. While lysis of REH target cells by each of the 2 CARs (cCAR) was robust, results indicated that CD269-A7D-CD38a CAR T cells alone were able to completely eliminate their target cells at the 2:1 ratio. These results demonstrate the robust lysis of CD269+ and CD38+ target cells by both individual CAR domains (CD269 and CD38, a-b) of the compound CARs, and that CD269-A7D-CD38a CAR T cells exhibit the best in vitro killing.

To evaluate the in vivo lysis of target tumor cells by CD269-A7D-CD38a CAR T cells versus CD269-A7D-CD38b CAR T cells, NSG mice were sublethally irradiated and intravenously injected with $4.0 \times 10^6$ luciferase-expressing MM.1S cells (Day 0) to induce measurable tumor formation (FIGS. 40A, B). Starting 10 days after injection of tumor cells, mice were intravenously injected with a course of $10 \times 10^6$ either CD269-A7D-CD38a, CD269-A7D-CD38b, or vector control T cells. On days 9 and 12, mice were injected subcutaneously with RediJect D-Luciferin and subjected to IVIS imaging. CD269-A7D-CD38a CAR T cells demonstrated greater anti-tumor effects, with 80% lysis of target MM.1S tumor cells compared to 68% lysis by CD269-A7D-CD38b CAR T cells.

To compare in vivo lysis of target MM.1S tumor cell line by CD269-A7D-CS1-hu63, CD269-A7D-CD38a, or CD269-A7D-CD38b CAR T cells, NSG mice were sublethally irradiated and intravenously injected with $4.0 \times 10^6$ luciferase-expressing MM.1S cells (Day 0) to induce measurable tumor formation (FIGS. 40C, D). Starting 10 days after injection of tumor cells, mice were intravenously injected with a course of $10 \times 10^6$ either CD269-A7D-CD38a, CD269-A7D-CD38b, or CD269-A7D-hu63 CAR T cells, or vector control T cells. On days 9 and 12, mice were injected subcutaneously with RediJect D-Luciferin and subjected to IVIS imaging. CD269-A7D-CS1-hu63 CART cells achieved 97% lysis, compared to 80% by CD269-A7D-CD38a CART cells and 68% by CD269-A7D-CD38b CART cells. CD269-A7D-CS1-hu63 CAR T cells demonstrated stronger anti-tumor effects in vivo against MM.1S tumor cell line than either CD269-A7D-CD38a or CD269-A7D-CD38b CAR T cells.

CD19b-IL15/IL-15sushi CAR

EXAMPLE

Expression of the CD19b-IL15/IL-15sushi CAR was measured by FACS against control T-cells (FIG. 41A). CD19b-IL-15/IL15sushi CAR T-cells are created by the viral transduction of patient or donor T-cells with the armored CAR gene construct. The translated anti-CD19b armored CAR proteins are then expressed on the surface of the CAR T-cells, where they can recognize and bind the CD19 target proteins on the surface of tumor cells. The pharmacologic effect and mechanism of CD19b-IL-15/IL15sushi CAR T-cells is mediated by CD19b CAR recognition of the antigen, which triggers CD3zeta/Zap70 canonical cytotoxic T-cell activity further enhanced by the incorporation of CD28 co-activation domains in the construct. FACS analysis shows that CD19b-IL15/IL-15sushi CAR is able to be expressed on roughly 35% of the T cells, furthermore, the IL-15/IL-15sushi "armor" provides additional stimulation, proliferation, and potency enhancement to the CAR T cell when compared to a standard CAR cell. P2A, vector control is also shown. This CD19b-IL-15/IL15suhsi CAR was designed to change tumor microenvironment and enhance anti-tumor cytotoxicity, and CAR potency and persistency by virtue of the IL-15/IL-15sushi secretion from CAR T cells.

Co-culture killing assays, in which target tumor cell lines that express the CD19+ cell surface phenotype were incubated with CD19b-IL-15/IL15sushi CAR or P2A control T cells and employed to determine anti-tumor function of CART cells in vitro against bulk CD19+ disease. Co-culture experiments were performed at an effector to target (E:T) ratio of spanning from 1:1 to 5:1 for 24 hours and were directly analyzed by flow cytometry with mouse anti-human CD3pPerCp and mouse anti-human CD19–PE. Each assay consisted of target cells (Sp53 all CD19+) incubated with either P2A control or CAR T-cells (FIG. 41B). Sp52 is a mantle cell lymphoma cell line. Bar graph summarizing cytotoxic activity is shown on the right. N=2. This experiment reveals the dose-dependent nature of the CD19b-IL-15/IL-15sushi CAR T, where even at low E:T ratios such as 1:1, there is potent lysis of tumor cells of greater than 60%. At 2:1, saturation of killing ability is observed with virtually all tumor cells lysed.

Similar cocultures conditions were used as above (FIG. 41B). In this experimental scheme, armored CD19b (CD19b-IL-15/IL-15sushi CAR T cells were cultured against CD19 positive Reh cells in comparison to both control P2A and single anti-CD19b CAR T cells. Anti-CD19b CAR T cells were generated with the same methodology and expression on T cell surfaces was verified to be ~50% (of all T cells, data not shown). The results here demonstrate that even at low E:T ratios such as 1:1, both CAR T treatments are equally effective, with potent and virtual deletion of all antigen-positive Reh cells. The "IL-15/IL-15sushi armor" does not have a deleterious effect on the cytotoxicity of the CAR T cells. Through dose dependent co-cultures, we show that the ablation of CD19+ Reh cells is robust, even at low E:T ratios, and is strictly comparable to its single unarmored CAR version, the single CD19b CAR T.

To test CD19b-IL-15/IL-15sushi CAR function in vivo, we established xenogeneic mouse models. Mice were injected with Reh tumor cells ($0.5 \times 10^6$ cells/mouse) expressing luciferase on Day 1 (FIG. 42A). On Day 3, IVIS was conducted to assay the appearance of circulating Reh cells. On Day 4, control T-cells, CD19b CAR, and CD19b-IL15/IL15sushi CAR T-cells were injected ($7.5 \times 10^6$ total cells/mouse) and on day 6 through 22, IVIS imaging was conducted to assay semi-quantitative assessment of tumor burden and subsequent tumor depletion and control of cell growth by T-cells. Here, both CAR T treatments demonstrated similar efficacy, with the IL-15 armored CAR demonstrating comparable or better control of the Reh tumor growth when compared to standard CART19 cells. It was found that CD19 based CARs deplete Reh cells in vivo and IL15/IL15sushi conjugates augment anti-tumor response. A line graph was then constructed, plotting IVIS values (estimation of tumor burden) against time for the treatment cohorts (FIG. 42B). As the tumor burden rises within the control group, both CAR T groups show steady maintenance of tumor suppression with significantly decreased tumor counts as measured by statistical analysis.

We then performed a long-term comparison CD19b-CAR-T vs CD19b-IL-15/IL15sushi CAR-T against REH cells using a similar experimental scheme with identical IVIS methodology as described in FIG. 42A; however, mice were followed until signs of tumor relapse were seen (FIG. 42C). Here, after day 30, we observed that aggressive Reh tumor relapse began to occur in standard CART19 treated mice. Clusters of tumor (indicated by red regions on the IVIS imaged mice) are seen in most CART19 mice, with a single CD19b-IL-15/IL-15sushi CART treated mice also showing tumor growth by day 22. However, after day 30, all CART19 mice showed signs of severe tumor relapse, while CD19b-IL-15/IL-15sushi CAR T treated mice showed no sign of tumor. Even the relapsed mouse on day 22 was absolved of its tumor by day 32, signifying that CD19b-IL-15/IL-15sushi CAR T cells were still in effective circulation. A line graph was then created to summarize IVIS trend values estimating tumor growth over time for each treatment cohort (FIG. 42D). Past day 30, the tumor burden for the standard CD19b CAR (CART19) treated mice rises precipitously resulting in highly significant increases in tumor burden compared to the CD19b-IL-15/IL-15sushi armored CAR T treatment group which remained largely tumor free. Values are displayed for both views of the mice (ventral and dorsal image acquisition views). As time passed, Reh tumor relapsed in standard CAR T treatment; however, the armored CAR persisted and depleted relapsed tumor, keeping mice disease free.

However, mice injected with a total number of $10 \times 10^6$ CD19b-IL-15/IL-15sushi CART cells ultimately were sacrificed at survival endpoints due to cytokine storm toxicity. As a result, we decreased the dosage of T cells to $0.5 \times 10^6$ and $1.0 \times 10^6$ cells per treatment group. To assess the effect of lower doses of armored and non-armored CAR T cells as compared to controls, mice were injected with Reh tumor cells ($0.5 \times 10^6$ total cells/mouse) expressing luciferase on Day 1 (FIG. 42E). On Day 3, IVIS was conducted to assay the appearance of circulating Reh cells. The methodology remains the same as for FIG. 42A; however, only $0.5 \times 10^6$ and $1.0 \times 10^6$ CAR T or control cells were injected per mouse to assay for lowest effective dose with regards to potential side-effects. This experiment was conducted because although the armored CAR mice cohort in FIG. 42C showed robust elimination of tumor and impressive control of tumor growth when assayed by IVIS, ultimately, survival endpoints were reached as a result of untenable cytokine storm. As a result, it is useful to titrate the dose of CART to find the lowest effective dose that could be administered with minimal risk of severe side effects. We found that while $0.5 \times 10^6$ T cells were generally too few to control tumor growth, a dose of $1.0 \times 10^6$ cells was able to control tumor growth in the CD19b-IL-15/IL-15sushi cohort without complications from cytokine toxicity. Due to gene-transfer efficiencies ~30%, the actual dose of CAR T cells administered to this low dose population numbered only around 300 000 CAR+ cells per mouse. Hence, translation of armored CAR T therapy will require the administration of lower doses as the increased potency and persistency of IL-15 armored CARs may potentially also relate with increased risk of cytokine release leading to dangerous side effects. Our results indicate that lower doses of CAR T cells may help prevent cytokine storm.

The overall persistence of T cells in mouse blood from the model in FIG. 42C was assayed at survival endpoints and screened by flow cytometry using CD3 antibody for bulk T cell populations (FIG. 43A). To further dissect the persistency results of the CD19b-IL-15/IL-15sushi armored CAR, the collection of mouse blood is necessary to reveal the presence of durability of the engrafted human cells. Overall, we found by flow cytometry analysis that there was a higher average count of T cells in the armored CAR cohorts when compared to the standard CART19 groups. Control group T cells remained at baseline as expected due to minimal stimulation from circulating in vivo tumor.

Mouse blood from FIG. 42C was furthered analyzed in FIG. 43B by CD8 expression in CD3 positive subsets to reveal the degree of persistent cytotoxic T cells remaining in circulation at survival endpoints. Of particular note is the much higher amount of cytotoxic CD8+ T cells present in the armored CAR cohort mice blood, signifying that the expansion of tumor-killing T cells was greatly augmented not just by signal transduction from standard target engagement, but also by the inclusion of the IL-15 based cytokine secretory complex "armor." Comparison to the standard CART19 cohort shows the standard response expected from CAR therapy with the expansion of cells solely accomplished by target engagement and subsequent signal response.

Mouse blood characteristics from FIG. 42C between CD19b (CART19) and CD19b-IL-15/IL-15sushi CAR T cells were further compared by analyzing the CD8 and CD3 population subsets (FIG. 43C). In general, there were a higher amount of CD3+ cells in the armored CAR cohort, correlating with increased persistency, a higher average of CD8+ cells within the CD3+ effector T cell population in the armored CAR cohort, and increased ability of the armored CART cells to bear the central memory immune-phenotype, correlating with improved immune-surveillance.

Detected remaining CD19b-IL-15/IL-15sushi CAR T cells were then transplanted into new mice hosts (FIG. 43D). The rationale behind this experiment was to show that "IL-15 armored" CAR T cells will not become immortalized as a result of the engineered cytokine scaffolding to enhance its own function. Reh tumor cells ($0.5 \times 10^6$ cells) were injected intravenously into each NSG mouse after sublethal irradiation. On the following day, $5.6 \times 10^6$ cells of CD19b-CAR-T-cells (CART19) or CD19b w/enhancer (CD19b-IL-15/IL-15sushi) CAR T-cells were injected via IV (intravenously) into each mouse. This condition serves as the first base, where injected CAR T cells will then bind to target tumor cells and expand in order to provide enough cellular material to collect for transplantation. At Day 36, both groups of treated mice were euthanized and then whole blood and spleen were collected to evaluate the persistency of CART19 cells or CD19b-IL-15/IL-15sushi T-cells using flow cytometry analysis. Red blood cells in blood and homogenized spleen were lysed using BD Pharm Lyse buffer (BD Biosciences). Flow cytometry analysis showed persistence of CD19b-IL-15/IL-15sushi T-cells (Blue dots circled in green) in mouse. We observed that there were more armored CAR T cells within circulating tissues for collection than CART19 cells. Homogenized spleen cells were labeled with CD3 and CD45 antibodies to detect either CAR T-cells. First, CAR T cells were gated by side scatter (SSC) and CD3 expression to distinguish from mouse cells (43D, A.) and then CD3 positive cells were gated by CD45 and CD3 expression (43D, B.). Left panel is Reh and CD19b-CAR-T-cells treated mouse. Right panels are Reh and CD19bCAR-w enhancer T-cells treated mouse. We only detected CD3-positive CAR T-cells from the armored CAR cohort mouse (Blue dots circled in green). To determine the immune-phenotype of CAR-T-cells, cells were labeled with CD8 and CD4 antibodies (43D, C.) FACS data indicates that most CD19b-IL-15/IL-15sushi T-cells are CD8-positive cells. Finally, we infused $0.5 \times 10^6$ total cells from each spleen homogenate into 2 of each NSG mouse to observe for autonomous growth of armored CAR T cells. This transplantation revealed detectable CD19b-IL-15sushi CD8 T-cells in mouse spleen at Day 36 when compared to CART19.

In a comparison of total flux values (photons/sec) between CD19bCAR- and CD19b-IL-15/IL-15sushi T-cell transplanted mice over time, no growth of tumor or expansion of T cells was found in transplanted mice (FIG. 43E). IVIS imaging of cell fluorescence in both mice groups over time was conducted. IVIS fluorescence here represents a semi-quantitative estimation of transplanted cell mass. In this case, auto fluorescence intensities remained around background levels and showed no detectable changes or increase in flux, thus demarcating limited cell growth or expansion of new cells. On day 64, we collected facial peripheral blood from each mouse and labeled using CD3 and CD19 antibodies to evaluate the presence of Reh tumor cells or CAR-T cells using FACS analysis (FIG. 43F). We could not detect Reh cells or CAR-T cells in facial peripheral blood samples in any of the mice, signifying that after transplant, armored CAR T cells are not able to further survive and proliferate, or otherwise become immortalized cells in their own right. This may be of translational use in the clinic, where there may be concern that armored CAR T therapy may result in the expansion of tumor-like CAR T cells. T cell and tumor populations were undetectable in transplanted mice on day 64. Although IL-15/IL-15sushi armor provides enhanced potency and persistency, these cells were not able to survive upon implantation into new mice, demonstrating that the armor does not result in self-proliferating, immortalized cytotoxic T cells.

GD2-Super1-CAR

EXAMPLE

The structural organization of GD2 super1 CAR shown in FIG. 44A. Links by P2A and T2A schematic to generate a super1 CAR showing a CAR, GD2 CAR equipped with 4-1BBL and IL-15/IL-15sushi in a single construct. The construct consists of a SFFV promoter driving the expression of three segments, CAR, 4-1BBL and IL-15/IL-15sushi. Upon cleavage of the linkers (P2A and T2A), the CAR, 4-1BBL and IL-15/IL-15sushi split and engage upon a target (s). CAR has scFV, hinge region, transmembrane domain, costimulatory domain (including, but not limited to, CD28 or 4-1BB) and intracellular signaling, CD3 zeta chain. 4-1BBL or IL-15/IL-sushi or both provides a synergistic effect of T or NK cell activation and persistency or anti-tumor activity with CD28 or 4-1BB.

In order to evaluate the in vivo anti-tumor activity of various GD2-targeting CAR constructs, we developed a xenogeneic mouse model using NSG mice sublethally irradiated and intravenously injected with luciferase-expressing Y79 retinoblastoma cells to induce measurable tumor formation. Three days following tumor cell injection, mice were intravenously injected with a course of $10 \times 10^6$ of either GD2-CAR, GD2-4-1BBL CAR, or GD2-super1 CAR, or vector control T cells. To determine the persistence of CAR T cells, mice were euthanized on Day 30. Liver, spleen and whole blood was collected from each mouse.

Flow cytometry analysis shows persistence of Y79 tumor (blue dots) in the livers of mice treated with different forms of anti-GD2 CAR T cells (FIG. 44B). Homogenized liver cells were labeled with mouse anti-human CD3 and CD56 antibodies, to detect human T cells and Y79 tumor cells, respectively. A representation of a mouse given control T cells is shown on the left; mouse treated with GD2CAR (left center), GD2-4-1BBL CAR (right center), and GD2-super1 CAR (right) T cells. FIG. 44B shows that GD2CAR T cells were unable to eliminate Y79 cells from the liver, relative to the mouse given control T cells, while mice treated with GD2-4-1-BBL CAR T cells had 32% fewer tumor cells. By contrast, the GD2-super1 CAR treated mice had 85% less tumor cells in the liver. A graph was then constructed to indicate percent killing activity against Y79 cells by each CAR treated mice compared to control mice (n=2) (FIG. 44B). From these data, especially, GD2-Super CAR eliminates Y79 cells in liver. Analysis of mice spleen showed a 1.87-fold increase in human T cells in GD2-super1 treated mice compared to control mice (FIG. 44C), and higher than GD2CAR (1.15×) and GD2-4-1BBL (1.35). This increase in GD2-super1 T cells is even more pronounced in the analysis of mouse whole blood, where there is a nearly 3-fold increase over control mice, and more than double the percentage of GD2CAR (FIG. 44D). A graph was then created to indicate the persistence of human T cells in whole blood samples, relative to the number of total cells analyzed by flow cytometry (n=2 each) (FIG. 44E). These data strongly suggest that GD2-super1 CAR, with both secreted IL-15/IL-15sushi and 4-1BBL domains, lyses GD2-expressing tumor cells and exhibits greater persistence than GD2CAR or GD2-41BBL CAR T cells.

CD123b–CLL1 CAR

EXAMPLE

The percent expression of CD123bCLL1 CAR T cells on transduced T-cells was approximately 27%, shown in FIG. 46A. Buffy coat cells were activated after 3 days with anti-CD3 antibody. Cells were transduced with either control vector (left) or CD123b-CLL1 CAR (right) lentiviral supernatant. After 3 days of incubation, cells were harvested and labeled for flow cytometry.

CD123b-CLL1-2G CAR T cells were assayed for their ability to specifically lyse both REH cells synthetically expressing CLL-1 antigen (FIG. 46B) and Jurkat cells synthetically expressing CD123 antigen (FIG. 46C) in co-cultures. Wild-type REH or Jurkat cells were transduced with lentiviral vector for either CLL-1 or CD123 antigen expression and positively selected by FACS (FACS-Aria, BD). Co-cultures with synthetic expression cells were set up at 2:1 and 5:1 effector cell:target cell ratios for 24 hours. Following these incubations, cells were stained using mouse anti-human CD3 antibody (in all cases) and either CLL-1 for REH-CLL-1 expression cells or CD123 for Jurkat CD123 expression cells, and analyzed by flow cytometry. For Jurkat cells expressing CD123 for both ratios, including the low 2:1 ratio, lysis was complete after 24 hours (FIG. 46C). REH cells expressing the CLL-1 phenotype were lysed at 89% and 92% at the 2:1 and 5:1 ratios, respectively (FIG. 46B). These results demonstrate that each CAR component of the CD123b—CLL1-2G CAR T cell is able to lyse its intended target cells.

To assess the specificity of target lysis by CD123b-CLL1-2G CART cells on non-target cells, co-culture experiments were also performed with wild type REH (FIG. 46D) and Jurkat cells (FIG. 46E), which do not express CLL-1 or CD123 antigens. Wild-type Jurkat cells were pre-stained with CMTMR membrane dye to distinguish them from T cells. Co-cultures with target cells were set up at 2:1 and 5:1 effector cell:target cell ratios, for 6 hours. Following this incubation, cells were labeled using mouse anti-human CD3 antibody and CD19 (for wild-type REH cells), and analyzed by flow cytometry. Lysis of REH wild-type cells by CD123bCLL-1 CAR T cells was limited (24% at the 2:1 ratio, but 0% at 5:1; FIG. 46D), while lysis of wild-type Jurkat cells remained at approximately 33% at both 2:1 and 5:1 ratios (FIG. 46E), which was well below the extent of lysis by CAR T cells against Jurkat cells expressing CD123 (FIG. 46C). These data show that CD123b-CLL-1 CAR T cells do not lyse off-target Jurkat and REH tumor cells.

In one embodiment, the engineered cell includes a Cd123b–CLL-1 polypeptide (SEQ ID NO. 26), and corresponding nucleotides (SEQ ID NO. 27).

CD20cCD19b and CD20hCD19b CAR

EXAMPLE

The organization of CD20cCD19b or CD20hCD19b CAR are seen in the FIG. 47 and FIG. 48A. The percent expression of two compound CARs, CD20cCD19b and CD20hCD19b CAR on transduced T cells was found to be 22% and 28%, respectively (FIG. 48B). Buffy coat cells were activated after 3 days with anti-CD3 antibody. Cells were transduced with either control vector (left), CD20cCD19b or CD20hCD19b CAR (right) lentiviral supernatant. After 3 days of incubation, cells were harvested and labeled for flow cytometry.

To assess the specificity of CD20cCD19b and CD20hCD19b CAR T cells on non-target wild-type K562 cells, co-culture experiments were performed at an effector to target ratio of 2:1 or 5:1 for 6 hours and were directly analyzed by flow cytometry for CD3 and CD45 (FIG. 48C). Each assay included K652 target cells alone (right), control T cells (left) and either CD20cCD19b or CD20hCD19b CAR T cells (center panels). Target cells are represented as blue dots (N=2). CD20cCD19b and CD20hCD19b CAR T cells did not lyse K562 tumor cell line that did not expressing either CD20 or CD19 in co-culture assays.

To assess the ability of CD20cCD19b and CD20hCD19b CAR T cells to lyse target cells expressing CD19, co-culture experiments were then performed with target K562 cell line synthetically expressing the CD19 antigen (K-19) at an effector to target ratio of 2:1 or 5:1 for 24 hours and were directly analyzed by flow cytometry for CD19 and CD3 (FIG. 48D). Each assay included K562-CD19xp target cells alone (right side), control T cells (left panels) and either CD20cCD19b or CD20hCD19b CAR T cells (center panels). Target cells are represented as green dots. Both types of compound CAR T cells lysed CD19 synthetically-expressing K562 tumor cell line in co-culture assays.

To assess CD20cCD19b and CD20hCD19b CAR T cells' ability to lyse on-target cells expressing CD20, co-culture experiments were performed with target K562 cell line synthetically expressing the CD20 antigen at an effector to target ratio of 2:1 or 5:1 for 24 hours and were directly analyzed by flow cytometry for CD20 and CD3 (FIG. 48E). Each assay consisted of K562-CD20xp target cells (K-20) alone (right side), control T cells (left panels) and either CD20cCD19b or CD20hCD19b CAR T cells (center panels). Target cells are represented as purple dots. Both types of compound CAR T cells lysed CD19 or CD20 synthetically-expressing K562 tumor cell line in co-culture assays (FIGS. 48D and 48E).

To assess the specificity of CD20cCD19b and CD20hCD19b CAR T cells on-target REH cells expressing CD19, co-culture experiments were performed with CD19-expressing REH cell lines at an effector to target ratio of 2:1 or 5:1 for 24 hours and were directly analyzed by flow cytometry for CD19 and CD3 (FIG. 48F). Each assay consisted of REH target cells alone (right side), control T cells (left panels) and either CD20cCD19b or CD20hCD19b CAR T cells (center panels). Target cells are represented as orange dots. Both types of compound CAR T cells were found to completely lyse CD19-expressing REH tumor cell line in co-culture assays (FIG. 48F).

To assess the ability of CD20cCD19b and CD20hCD19b CART cells to lyse on-target cells expressing both CD19 and CD20 antigens, co-culture experiments were also performed with the CD19- and CD20-expressing SP53 B-cell lymphoma cell line at an effector to target ratio of 2:1 or 5:1 for 24 hours and were directly analyzed by flow cytometry for CD19 and CD3 (FIG. 48G). Each assay consisted of SP53 target cells alone (right side), control T cells (left panels) and either CD20cCD19b or CD20hCD19b CAR T cells (center panels). Target cells are represented as turquoise dots (N=2). Both types of compound CAR T cells completely lysed SP53 tumor cell line, which expresses both CD19 and CD20 antigens, in co-culture assays.

A summary of the co-culture results is shown in FIG. 48H, with K562wt (Wild type) performed at a 6 hour co-culture and the others at 24 hours (N=2). Both compound CAR types exhibited superior on-target lysis relative to the control T cells, with CD20hCD19b-2G CAR T cells demonstrating more robust killing of target K562 cells synthetically expressing the CD20 antigen when compared to CD20cCD19b-2G CAR T cells.

In regard to CD20hCD19b cCAR, we analyzed the ablation of the Reh B-ALL cell line using a co-culture to characterize the dose-dependent anti-tumor activity of the CD20h-CD19b CAR T cells. (FIG. 49A). Co-cultures against the CD19+ B-ALL tumor cell line were performed at escalating E:T ratios starting from 0.25 to 1 (25 000 T cells to 100 000 Reh cells). Co-cultures were carried out overnight and labeled with CD3 and CD19 antibodies before FACS analysis was performed to analyze the extent of residual tumor cells. A bar graph representation of these results was also created (FIG. 49B). We found that generally, increased effector cell numbers corresponded with higher rates of observed target tumor cell lysis.

In order to further characterize the anti-tumor activity of the CD20h-CD19b CAR T cells, we conducted co-cultures against primary CD19+ B-ALL leukemic blasts expressing CD19 and CD20 (B-ALL-25) (FIG. 49C). To analyze the specificity of the CD20h-CD19b cCAR, we also conducted co-cultures against antigen negative primary leukemic cells negative for both CD19 and CD20, but positive for CD34. B-ALL-25 and negative control primary leukemic cells were both pre-labeled with a cell-tracking dye, CFSE, beforehand in order to separate effector T and target tumor populations. FACS analysis of co-cultures against B-ALL-25 (LEFT) showed profound ablation of the target primary leukemic blasts, showing total ablation even at E:T ratios of 2:1. Analysis of the negative control primary cell co-culture (RIGHT) showed that there was no effect by the cCAR on the bulk antigen-negative population. CD20h-CD19b cCAR T cells were able to ablate target primary B-ALL cells but did not target off-target leukemic cells.

To characterize anti-tumor activity of CD20h-CD19 CAR T cells in vivo, NSG mice were sublethally irradiated and intravenously injected with $1.0 \times 10^6$ luciferase-expressing REH cells (Day 0) to induce measurable tumor formation (FIGS. 50A, B). Starting 6 days after injection of tumor cells, mice were intravenously injected with a course of $10 \times 10^6$ CD20hCD19b CAR T cells or vector control T cells. On days 5, 9 and 12, mice were injected subcutaneously with RediJect D-Luciferin and subjected to IVIS imaging. By day 12, CD20h-CD19 CAR T cells achieved 98% lysis of tumor cells for both dorsal and ventral sides. These results demonstrate that CD20h-CD19 CAR T cells exhibit robust lysis of REH cells expressing the CD19 antigen.

In one embodiment, the engineered cell includes a CD20-CD19 chimeric antigen receptor polypeptide (SEQ ID NO. 20,22), and corresponding nucleotides (SEQ ID NO. 21,23).

In one embodiment, the engineered cell includes a CD20h-CD19b cCAR and a humanized chimeric antigen receptor polypeptide targeting CD20 (SEQ ID NO. 22), and corresponding nucleotides (SEQ ID NO. 23).

Expansion of Natural Killer (NK) Cells from Umbilical Cord Blood

EXAMPLE

Natural killer cells were expanded using the steps described (FIG. 51A). To determine the role of CAMPATH stimulation for NK cells expansion in umbilical cord blood cells, cord blood cells were cultured in T-cell culture medium containing 10% FBS and IL-2 on CAMPATH coated cell culture flask or uncoated flask (FIG. 51B). The population of NK cells in total cells was determined by flow cytometry analysis using CD56 and CD3 antibodies (circled in blue). These data indicated that the population of NK cells increased more with CAMPATH stimulation in a day dependent manner.

To evaluate the effect of using different types of cell medium for NK cell expansion in umbilical cord blood cells, cord blood cells were cultured in T-cell culture medium or SCGM medium containing 10% FBS and IL-2 on CAMPATH coated cell culture flask (FIG. 52A). The population of NK cells in total cells were determined by flow cytometry analysis using CD56 and CD3 antibodies (circled in blue). The number of NK cells were counted every other day, and a growth curve was created (FIG. 52B). These data indicated that the population of NK cells increased more in T-cell culture medium with CAMAPTH stimulation when compared to SCGM medium with CAMAPTH stimulation in a day dependent manner.

To evaluate the effect of using human serum instead of FBS in cell culture medium for NK cells expansion in umbilical cord blood, cord blood cells were cultured in T-cell culture medium or SCGM medium containing 5% human serum and IL-2 on CAMPATH coated cell culture flask (FIG. 53A). The population of NK cells in total cells was determined by flow cytometry analysis using CD56 and CD3 antibodies (circled in blue). The number of NK cells were then counted every other day, and a growth curve was formed (FIG. 53B). These data indicated that the population of NK cells increased more in T-cell culture medium with CAMAPTH stimulation compared to SCGM medium with CAMAPTH stimulation in a day dependent manner.

To evaluate the effect of adding IL-15 in cell culture medium on NK cells expansion in fresh umbilical cord blood cells, fresh cord blood cells were cultured in T-cell culture medium containing 10% FBS and IL-2 on CAMPATH coated cell culture flask (FIG. 54A). The population of NK cells in total cells was determined by flow cytometry analysis using CD56 and CD3 antibodies (circled in blue). The number of NK cells was then counted every other day, and a growth curve was created (FIG. 54B). These data indicated that the population of NK cells increased more after adding IL-15 in T-cell culture medium with CAMAPTH in a day dependent manner.

To measure expression levels of CD19b, CD19b-IL15/IL15sushi, and BCMA-A7D-IL15/IL15sushi CAR on the surface of NK cells after transduction when compared to GFP, flow cytometry was performed (FIG. 54C). About 42% of CD19b-CAR (A), 39% of CD19b-IL15/IL-15sushi-CAR (B), 51% of BCMA-A7D-IL15/IL15sushi-CAR and (D) 76% of GFP-expression on cell surface were detected by flow cytometry analysis.

CD19b-IL15/IL15sushi or BCMA-A7D-IL15/IL15sushi CAR NK cells can be used as uCAR NK cells for lysing targeted cells.

In vivo persistent assays, CD19b-IL15/IL15sushi or BCMA-A7D-IL15/IL15sushi CAR NK cells are performed in a xenogeneic mouse model. CD19b-IL15/IL15sushi or BCMA-A7D-IL15/IL15sushi CAR NK cells can persist for more than two weeks or one or two months in mice using methods described in PCT/US2016/019953 and PCT/US2016/039306. In vivo anti-tumor activities, cell killing is performed in a xenogeneic mouse model and targeted cells expressing targeted antigen are eliminated or suppressed by CAR NK cells using methods described in PCT/US2016/019953 and PCT/US2016/039306.

Strategy for IL-15/IL-15sushi Secreting CAR T Therapy

The strategy for IL15/IL-15sushi secreting CAR T cell therapy is described in FIG. 55.

Limiting Dose of CD269-A7D-IL15/IL15RA CAR T Cells Avoids Cytokine Release Syndrome but Does Not Decrease Ablation of MM.1S Tumor Cells in Xenogeneic Mouse Model In order to evaluate the in vivo anti-tumor activity of CD269-A7D-IL-15/IL-15sushi (CD269-A7D-IL15/IL15sushi) CAR T cells, we developed a xenogeneic mouse model using NSG mice sublethally irradiated and intravenously injected with $4 \times 10^6$ luciferase-expressing MM.1S multiple myeloma cells to induce measurable tumor formation. Eight days following tumor cell injection, two mice per group were intravenously injected with a course of $10 \times 10^6$ of either CD269-A7D-IL15/IL15sushi (A7D-IL15/IL15sushi) CAR, or vector control T cells. On days 7, 11 and 15, mice were injected subcutaneously with RediJect D-Luciferin and subjected to IVIS imaging. By Day 11, CD269-A7D-IL15/IL15sushi CAR T cell-treated mice had 97% less tumor than control mice, and 99% less on Day 15. (FIG. 56, Exp.1).

However, both treated mice developed later symptoms of cytokine release syndrome (CRS). One mouse died and another mouse recovered after treatment with CAMPATH antibody in order to reduce CAR T cell population. The second experiment was performed as above, but using an injection of one-fifth the dose of CAR T cells ($2\times10^6$) on Day 9 to determine if CRS could be avoided. On days 8, 12 and 15 mice were injected subcutaneously with RediJect D-Luciferin and subjected to IVIS imaging. As expected, tumor lysis was slower with the lower dose. By Day 11, CD269-A7D-IL15/IL15sushi CART cell-treated mice had only 54% less tumor than control mice, but by Day 15, it had risen to 93% less tumor, very similar to the first experiment. (FIG. 56, Exp. 2). Neither mouse was observed to have symptoms of CRS at any point during the experiment, and both survived for more than two months before the experiment was ended. These data show that a lower dose of CAR T cells led to an equivalent amount of tumor cell ablation, but with no adverse effects.

It is also unexpected that the low split dose can reach a remarkable efficacy of killing cancer cells, but with no severe CRS in our clinical trial study.

INCORPORATION OF SEQUENCE LISTING

Incorporated herein by reference in its entirety is the Sequence Listing for the above-identified Application. The Sequence Listing is disclosed on a computer-readable ASCII text file titled "2541_3CIP_ST25.txt", created on Feb. 10, 2018. The sequence.txt file is XX KB in size.

The invention claimed is:

1. An ex vivo engineered T cell or NK cell co-expressing two distinct chimeric antigen receptor (CAR) units at the cell surface, wherein the engineered T cell or NK cell comprises a nucleotide sequence comprising from 5' to 3' a first polynucleotide encoding a first chimeric antigen receptor polypeptide (CAR), a second polynucleotide encoding a second chimeric antigen receptor polypeptide (CAR), a nucleotide encoding a viral self-cleavage peptide disposed between the first CAR and second CAR, under the transcriptional control of a single promoter, wherein:
   (i) the first CAR comprises a first signal peptide, a first antigen recognition domain, a first hinge region, a first transmembrane domain, a first 4-1BB or CD28 co-stimulatory domain, and a first CD3ζ signaling domain that form a first fusion protein; and
   (ii) the second CAR comprises a second signal peptide, a second antigen recognition domain, a second hinge region, a second transmembrane domain, a second 4-1BB or CD28 co-stimulatory domain, and a second CD3ζ signaling domain that form a second fusion protein; and
wherein the first antigen recognition domain and the second antigen recognition domain are different and each bind to a different target, wherein when the target of one of the first antigen recognition domain or second antigen recognition domain is an scFv of CD33 or an scFv of CD123, then the target of the other antigen recognition domain is an scFv of C-type lectin-like molecule-1(CLL-1), wherein the first and second co-stimulatory domains are intracellular, and wherein the cleavage site is selected from the group consisting of porcine teschovirus-1 2A (P2A), thoseaasigna virus 2A (T2A), equine rhinitis A virus (ERAV) 2A (E2A), and FMDV 2A (F2A).

* * * * *

UNITED STATES PATENT AND TRADEMARK OFFICE
CERTIFICATE OF CORRECTION

PATENT NO. : 11,173,179 B2
APPLICATION NO. : 15/893629
DATED : November 16, 2021
INVENTOR(S) : Yupo Ma et al.

It is certified that error appears in the above-identified patent and that said Letters Patent is hereby corrected as shown below:

In the Specification

Column 4, Line 46: now reads "CD3t"
should read --CD3ζ--

Column 11, Line 45: now reads "CART cells"
should read --CAR T cells--

Column 17, Line 21: now reads "secret"
should read --secrete--

Column 20, Line 42: now reads "IL-15/IL-sushi"
should read --IL-15/IL-15sushi--

Column 27, Line 30: now reads "ICD3c"
should read --CD3ε--

Column 27, Line 59: now reads "CD3c"
should read --CD3ε--

Column 47, Line 16: now reads "CART-cell"
should read --CAR T cell--

Column 48, Line 29: now reads "plamacytoma"
should read --plasmacytoma--

Column 54, Line 52: now reads "IL-15Ra"
should read --IL-15Rα--

Signed and Sealed this
Eleventh Day of April, 2023

Katherine Kelly Vidal
*Director of the United States Patent and Trademark Office*

CERTIFICATE OF CORRECTION (continued)
U.S. Pat. No. 11,173,179 B2

| | |
|---|---|
| Column 54, Line 64: | now reads "IL-15/IL-15sush" |
| | should read --IL-15/IL-15sushi-- |
| Column 72, Line 58: | now reads "BCMACS1$^+$" |
| | should read --IBCMA$^+$CS1$^+$-- |
| Column 79, Line 54: | now reads "CD3(CD3)" |
| | should read --CD3$\zeta$(CD3)-- |
| Column 90, Line 19: | now reads "10×106" |
| | should read --10 × 10$^6$-- |